(12) United States Patent
Chen

(10) Patent No.: US 8,840,889 B2
(45) Date of Patent: Sep. 23, 2014

(54) METHODS OF MODULATING IMMUNE FUNCTION

(75) Inventor: Lieping Chen, Sparks Glencoe, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/390,054

(22) PCT Filed: Aug. 13, 2010

(86) PCT No.: PCT/US2010/045479
§ 371 (c)(1),
(2), (4) Date: May 18, 2012

(87) PCT Pub. No.: WO2011/020024
PCT Pub. Date: Feb. 17, 2011

(65) Prior Publication Data
US 2012/0219559 A1    Aug. 30, 2012

Related U.S. Application Data

(60) Provisional application No. 61/233,650, filed on Aug. 13, 2009, provisional application No. 61/289,951, filed on Dec. 23, 2009.

(51) Int. Cl.
*A61K 39/395* (2006.01)
*C07K 16/28* (2006.01)
*C07K 14/705* (2006.01)

(52) U.S. Cl.
CPC ......... *C07K 16/2827* (2013.01); *C07K 2316/95* (2013.01); *C07K 2316/96* (2013.01); *C07K 2319/30* (2013.01); *C07K 2317/74* (2013.01); *C07K 14/70532* (2013.01); *C07K 16/2818* (2013.01); *C07K 14/70521* (2013.01)
USPC ..................................... 424/139.1; 424/173.1

(58) Field of Classification Search
None
See application file for complete search history.

(56) References Cited

U.S. PATENT DOCUMENTS

| | | | |
|---|---|---|---|
| 4,676,980 A | 6/1987 | Segal et al. | |
| 4,816,567 A * | 3/1989 | Cabilly et al. | |
| 5,434,131 A * | 7/1995 | Linsley et al. | 424/133.1 |
| 5,521,288 A * | 5/1996 | Linsley et al. | 530/387.3 |
| 5,552,391 A | 9/1996 | Coutts et al. | |
| 5,565,332 A | 10/1996 | Hoogenboom et al. | |
| 5,580,717 A | 12/1996 | Dower et al. | |
| 5,656,444 A | 8/1997 | Webb et al. | |
| 5,733,743 A | 3/1998 | Johnson et al. | |
| 5,807,715 A | 9/1998 | Morrison et al. | |
| 5,866,692 A | 2/1999 | Shitara et al. | |
| 5,997,867 A | 12/1999 | Waldmann et al. | |
| 6,054,297 A | 4/2000 | Carter et al. | |
| 6,054,561 A | 4/2000 | Ring | |
| 6,180,377 B1 | 1/2001 | Morgan et al. | |
| 6,265,150 B1 | 7/2001 | Terstappen et al. | |
| 6,331,415 B1 | 12/2001 | Cabilly et al. | |
| 6,416,999 B1 | 7/2002 | Li et al. | |
| 6,429,303 B1 | 8/2002 | Green et al. | |
| 6,436,704 B1 | 8/2002 | Roberts et al. | |
| 6,441,163 B1 | 8/2002 | Chari et al. | |
| 6,521,749 B1 * | 2/2003 | Ling et al. | 536/23.5 |
| 6,803,039 B2 * | 10/2004 | Tsuji et al. | 424/144.1 |
| 6,965,018 B2 | 11/2005 | Mikesell et al. | |
| 7,279,567 B2 | 10/2007 | Mikesell et al. | |
| 2003/0039999 A1 | 2/2003 | Yoshinaga et al. | |
| 2003/0134283 A1 | 7/2003 | Peterson et al. | |
| 2003/0162186 A1 | 8/2003 | Bejanin et al. | |
| 2003/0208058 A1 * | 11/2003 | Fiscella et al. | 536/23.5 |
| 2004/0077043 A1 | 4/2004 | Watarai et al. | |
| 2004/0162236 A1 | 8/2004 | Alsobrook, II et al. | |
| 2004/0236088 A1 | 11/2004 | Heuer et al. | |
| 2005/0202536 A1 | 9/2005 | Chen | |
| 2006/0154313 A1 | 7/2006 | Anderson et al. | |
| 2006/0275287 A1 | 12/2006 | St Croix et al. | |
| 2007/0053903 A1 * | 3/2007 | Gao et al. | 424/144.1 |
| 2007/0292885 A1 | 12/2007 | Bejanin et al. | |

FOREIGN PATENT DOCUMENTS

| | | |
|---|---|---|
| EP | 0519596 | 12/1992 |
| EP | 1292619 | 3/2003 |
| EP | 1327638 | 7/2003 |
| EP | 1514933 | 3/2005 |
| EP | 1892251 | 2/2008 |
| WO | WO 99/46281 | 9/1999 |
| WO | WO 00/68266 | 11/2000 |

(Continued)

OTHER PUBLICATIONS

UniProtKB/Swiss-Prot Accession No. Q96BF3.2 (2003).*

(Continued)

*Primary Examiner* — Ilia Ouspenski
(74) *Attorney, Agent, or Firm* — Pabst Patent Group LLP

(57) ABSTRACT

Presented herein are therapeutic agents that modulate one or more immune functions and uses of such therapeutic agents in the prevention, treatment and management of diseases. In one aspect, the therapeutic agents modulate one or more signal transduction pathways induced by the binding of B7-H7 to B7-H7CR, or the binding of B7-H2 to either ICOS, CD28, or CTLA-4. In another aspect, the therapeutic agents modulate the binding of B7-H7 to B7-H7CR, or the binding of B7-H2 to either ICOS, CD28, or CTLA-4. The therapeutic agents can be used in the prevention, treatment and/or management of diseases in which it might be useful to modulate one or more immune functions (e.g., cancer, infectious disease, autoimmune disease, and transplantation rejection). In another aspect, presented herein are methods for identifying receptor-ligand interactions.

7 Claims, 72 Drawing Sheets

(56) References Cited

FOREIGN PATENT DOCUMENTS

Figure 1:
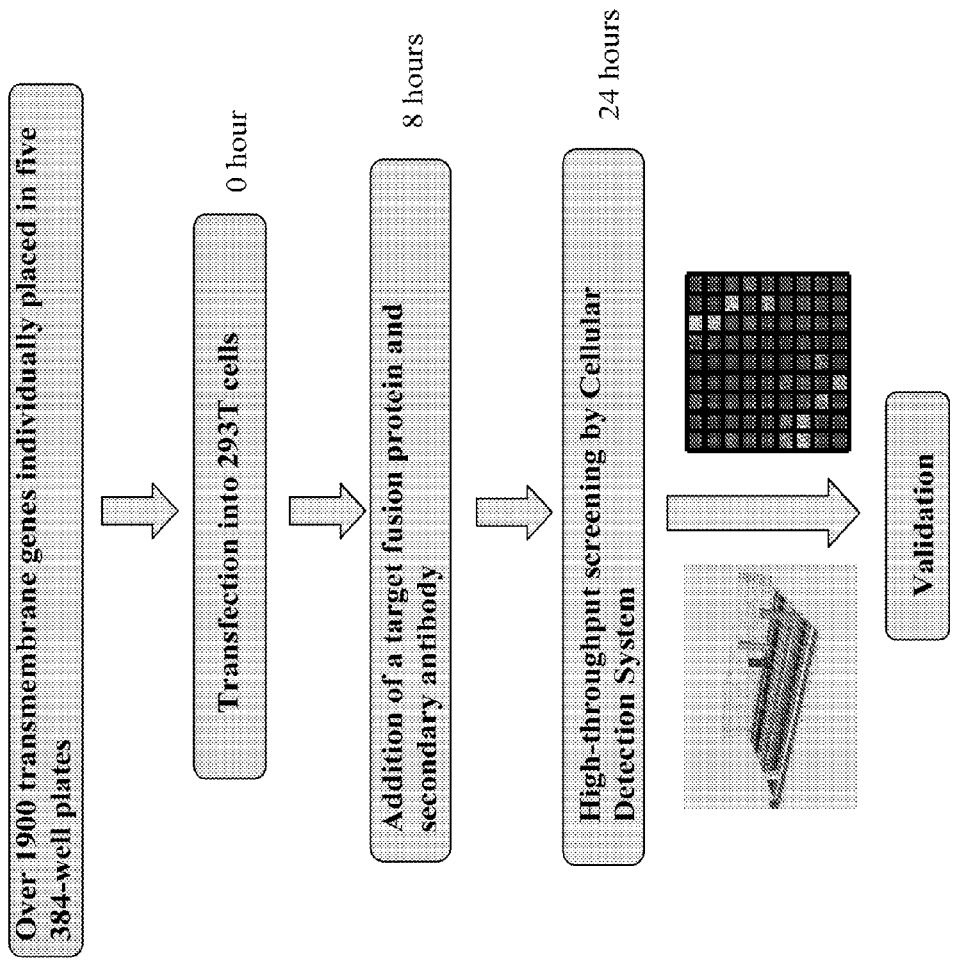

| | | |
|---|---|---|
| WO | WO 01/14557 | 3/2001 |
| WO | WO 01/18021 | 3/2001 |
| WO | WO 01/18204 | 3/2001 |
| WO | WO 01/77303 | 10/2001 |
| WO | WO 01/89567 | 11/2001 |
| WO | WO 01/94413 | 12/2001 |
| WO | WO 02/08279 | 1/2002 |
| WO | WO 02/10187 | 2/2002 |
| WO | WO 02/32375 | 4/2002 |
| WO | WO 02/099119 | 12/2002 |
| WO | WO 03/068938 | 8/2003 |
| WO | WO 04/000221 | 12/2003 |
| WO | WO 04/001381 | 12/2003 |
| WO | WO 2007/149067 | 12/2007 |
| WO | WO 2008/083228 | 7/2008 |
| WO | WO 2009/089149 | 7/2009 |

OTHER PUBLICATIONS

GenBank Accession No. AAD48396.1 (1999).*
"B7-H7CR" Pubmed search summary, Aug. 3, 2013, 1 page.*
Lederman et al. (Molecular Immunology, 1991, 28: 1171-1181.*
Colman P.M. (Research in Immunology, 1994, 145: 33-36.*
Boon et al. (Annu. Rev. Immunol., 2006, 24: 175-208.*
Nielsen et al., 2000, Cancer Chemother. Pharmacol., 46 (Suppl.): S62-S66.*
Lee et al., 1999, J. Immunol., 163: 6292-6300.*
Wadman M., Nature, 2006, 440: 388-389.*
Hopkin M., Nature, 2006, 440: 855-856.*
Mehrishi et al., Vaccine, 2007, 25: 3517-3523.*
Abrams, J.R. et al. (1999) "*CTLA4Ig-Mediated Blockade of T-Cell Costimulation in Patients With Psoriasis Vulgaris*," J. Clin Invest. 103(9):1243-1252.
Agarwal, A. et al. (2008) "The role of positive costimulatory molecules in transplantation and tolerance," Curr. Opin. Organ Transplant. 13:366-372.
Albino, A.P. et al. (1983) "Biochemical Analysis of a 130,000 Molecular Weight Glycoprotein on Human Melanoma Cells," J. Immunol. 131(3):1595-1599.
Anonymous, (2000) "*New Products for Molecular Biotechnology*," Molec. Biol. 16:293-294.
Arrufo, A. and Seed, B. (1987). "Molecular Cloning of a CD28 cDNA by a High Efficiency COS Cell Expression System," Proc. Natl. Acad. Sci. U.S.A. 84:8573-8577.
Banki et al. (1994) "Cloning and Expression of the Human Gene for Transaldolase," J. Biol. Chem. 269(4)2847-2851.
Bendayan et al. (1995) "Possibilities of False Immunochemical Results Generated by the Use of Monoclonal Antibodies: The Example of the Anti-proinsulin Antibody," J. Histochem. Cytochem. 43(9):881-886.
Bernard, A. et al. (2005) "T and B Cell Cooperation: A Dance of Life and Death," Transplantation 79:S8-S11.
Bertram, E.M. (2004) "Role of T Cell Costimulation in Anti-Viral Immunity," Seminars in Immunol. 16:185-196.
Blazar, B.R. et al. (1999) "*Opposing Roles of CD28:B7 and CTLA-4:B7 Pathways in Regulating In Vivo Alloresponses in Murine Recipients of MHC Disparate T Cells*," J. Immunol. 162(11):6368-6377.
Bodey et al. (2000) "Failure of Cancer Vaccines: The Significanct Limitations of this Approach to Immunotherapy," Anticancer Res. 20:2665-2676.
Boon (1992) "Toward an Genetic Analysis of Tumor Rejection Antigens," Adv. Canc. Res. 58:177-210.
Brown, B.A. et al. (1987). "Tumor-Specific Genetically Engineered Murine/Human Chimeric Monoclonal Antibody," Cancer Res. 47:3577-3583.
Brunet, J.F. et al. (1987) "*A New Member of the Immunoglobulin Superfamily—CTLA-4*," Nature 328(6127):267-270.
Carter et al., "Humanization of an anti-p185HER2 antibody for human cancer therapy," Proc. Natl. Acad. Sci. USA 89:4285-4289, 1992.

Castriconi, R. et al. (2004) "*Identification of 4Ig-B7-H3 as a Neuroblastoma-Associated Molecule That Exerts a Protective Role From an NK Cell-Mediated Lysis*," Proc. Natl. Acad. Sci. (U.S.A.) 101(34):12640-5. Epub Aug. 16, 2004.
Chapoval, A.I. et al. (2001) "*B7-H3: A Costimulatory Molecule for T Cell Activation and IFN-Gamma Production*," Nature Immunology. 2 (2001). 269-274.
Chen, S. et al. (2000) "Surface Antigen Expression and Complement Susectibility of Differentiated Neuroblastoma Clones,"Amer. J. Pathol. 156(3):1085-1091.
Clauser, K.R. et al. (1999). "Role of Accurllte Mass Measurement (±10 ppm) in Protein Identification Strategies Employing MS or MSIMS and Database Searching," *Analytical Chemistry* 71(4):2871-2882.
Co, M.S. et al. (1992). "Chimeric and Humanized Antibodies with Specificity for the CD33 Antigen," *J.Immunol.* 148(4):1149-1154.
Co, M.S. et al. (1991). "Humanized Antibodies for Antiviral Therapy," *Proc. Natl Acad Sci. US.A.* 88:2869-2873.
Collins, M. et al. (2005) "The B7 Family of Immune-Regulatory Ligands," Genome Biol. 6:223.1-223.7.
Coyle, A.J. et al. (2001) "The Expanding B7 Superfamily: Increasing Complexity in Costimulatory Signals Regulating T Cell Function," Nature Immunol. 2(3):203-209.
Crispen, P.L. et al. (2008) "*Tumor Cell and Tumor Vasculature Expression of B7-H3 Predict Survival in Clear Cell Renal Cell Carcinoma*," Clin Cancer Res. 14(16):5150-5157 Epub Aug. 11, 2008.
Daugherty, B.L. et al. (1991). Polymerase:Chain Reaction Facilitates the Cloning, CDR-Grafting, and Rapid Expression ofa Murine Monoclonal Antibody Directed Against the CD18 Component of Leukocyte Integrins, a Nucl. Acids Res. 19(9):2471-2476.
Dermer (1994) "*Another Anniversary fo the War on Cancer*,"Bio/Technology 12:320.
Dillman, R.O. et al. (1988). "Superiority of an Acid-Labile Daunorubicin-Monoclonal Antibody Immunoconjugate Comarec,i to Free Drug," *Cancer Res.* 48:6097-6102.
Dong, C. et al. (2003) "Immune Regulation by Novel Costimulatory Molecules," Immunolog. Res. 28(1):39-48.
Dong, H. et al. (1999) "*B7-H1, A Third Member of the B7 Family, Co-Stimulates T-Cell Proliferation and Interleukin-10 Secretion*," Nat Med. 5(12):1365-1369.
Emamaullee, J. et al. (2009) "*Costimulatory Blockade With Belatacept in Clinical and Experimental Transplantation—A Review*," Expert Opin Biol Ther. 9(6):789-796.
Flies, D.B. et al. (2007) "The New B7s: Playing a Pivotal Role in Tumor Immunity," J. Immunother. 30(3):251-260.
Gennaro, A.R. ed. (2000). Remington: The Science and Practice of Pharmacy; Twentieth Edition, Lippincott Williams & Wilkins: Philadelphia, PA pp. xiv-xv (Table of Contents Only).
Gharahdaghi, F. et al. (1999)."Mass Spectrometric Identification of Proteins From Silver-Stained Polyacrylamide Gel: A Method for the Removal of Silver Ions to Enhance Sensitivity," *Electrophoresis* 20:601-605.
Goldenberg, D.M. ed. (1995). Cancer Therapy With Radiolabeled Antibodies CRC Press: Boca Raton, FL, four pages (Table of Contents Only).
Gorman, S.D. et al. (1991). "Reshaping a Therapeutic CD4 Antibody," *Proc. Natl. Acad. Sci. U.S.A.* 88:4181-4185.
Greenwald, R.J. et al. (2005) "The B7 Family Revisited," Ann. Rev. Immunol. 23:515-548.
Hashiguchi, M. et al. (2008) "*Triggering Receptor Expressed on Myeloid Cell-Like Transcript 2 (TLT-2) Is a Counter-Receptor for B7-H3 and Enhances T Cell Responses*," Proc. Natl. Acad. Sci. (U.S.A.) 105(30):10495-10500.
Henry, J. et al. (1999) "*Structure and Evolution of the Extended B7 Family*," Immunol Today. 20(6):285-288.
Hofmeyer, K. et al. (2008) "The Contrasting Role of B7-H3," Proc. Natl. Acad. Sci. (U.S.A.) 105(30):10277-10278.
International Search report for PCT/US03/19819 (May 19, 2005) (5 pages).
Jones, P.T. et at. (1986). "Replacing the Complementarity-Determining Regions in a Human Antibody With Those From a Mouse," *Nature* 321:522-525.

(56) References Cited

OTHER PUBLICATIONS

Kettleborough, C.A. et al. (1991). "Humanization of a Mouse Monoclonal Antibody by CDR Grafting: The Importance of Framework Residues on Loop Conformation," *Protein Engineering* 4:(7)773-783.
Khawli, L.A. et al. (2008) "Cytokine, Chemokine, and Co-Stimulatory Fusion Proteins for the Immunotherapy of Solid Tumors," Exper. Pharmacol. 181:291-328.
Kirk, A.D. et al. (1997) "*CTLA4-Ig and Anti-CD40 Ligand Prevent Renal Allograft Rejection in Primates*," Proc. Natl. Acad. Sci. (U.S.A.) 94(16):8789-8794.
Kirkin et al. "Melanoma-Associated Antigens Recognized by Cytotoxic T Lymphocytes," (1998) APMIS 106:665-679.
Kohler, G. and Milstein, C. (1975). "Continuous Cultures of Fused Cells Secreting Antibody of Predefined Specificity," *Nature* 256:495-497.
Korman, A.J. et al. (2007) "Checkpoint Blockade in Cancer Immunotherapy," Adv. Immunol. 90:297-339.
Kristiansen, O.P. et al. (2000) "*CTLA-4 in Autoimmune Diseases—A General Susceptibility Gene to Autoimmunity?*" Genes Immun. 1(3):170-184.
Larsen, C.P. et al. (1996) "*Long-Term Acceptance of Skin and Cardiac Allografts After Blocking CD40 and CD28 Pathways*," Nature 381(6581):434-438.
Leach, D.R. et al. (1996) "*Enhancement of Antitumor Immunity by CTLA-4 Blockade*," Science. 271(5256):1734-1736.
Lee et al. (1999) "*Increased Vaccine-Specific T Cell Frequency After Peptide-Based Vaccination Correlates with Increased Susceptibility to In Vitro Stimulation but Does Not Lead to Tumor Regression*" J. Immunol. 163:6269-6300.
Linsley, P.S. et al. (2009) "The Clinical Utility of Inhibiting CD28-Mediated Co-Stimulation," Immunolog. Rev. 229:307-321.
LoBuglio, A.F. et al. (1989). "Mouse/Human Chimeric Monoclonal Antibody in Man: Kinetics and Immune Response," *Proc. Natl. Acad. Sci. U.S.A.* 86:4220-4224.
Loke, P. et al. (2004) "Emerging Mechanisms of Immune Regulation: The Extended B7 Family and Regulatory T Cells." Arthritis Res. Ther. 6:208-214.
Lonberg, N. and Huszar, D. (1995). "Human Antibodies From Transgenic Mice," *Int. Rev. Immunol.* 13:65-93.
Maeda, H. et al. (1991). "Construction of Reshaped Human Antibodies with UN-Neutralizing Activity," *Human Antibodies Hybridoma* 2:124-134.
Mahato, R.I. et al. (1991). "Cationic Lipid-Based Gene Delivery Systems: Pharmaceutical Perspectives," *Pharm. Res.* 14(7):853-859.
Mahnke, K. et al. (2007) "*Induction of Immunosuppressive Functions of Dendritic Cells In Vivo by CD4+CD25+ Regulatory T Cells: Role of B7-H3 Expression and Antigen Presentation*." Eur J Immunol. Aug. 2007;37(8):2117-26.
Mangham, D.C. and Isaacson, P.G. (1999). "A Novel Immunohistochemical Detection System Using Mirror Image Complementary Antibodies (MICA)," *Histopathology* 35(2): 129-133.
Martin-Orozco, N. et al. (2007) "Inhibitory Costimulation and Anti-Tumor Immunity," Semin. Cancer Biol. 17(4):288-298.
Modak, S. et al. (1998) "*Novel Tumor-Associated Surface Antigen: Broad Distribution Among Neuroectodermal, Mesenchymal and Epithelial Tumors, With Restricted Distribution in Normal Tissues*," Program/Proceedings, American Society of Clinical Oncology, 34th Annual Meeting, May 16-19, 1998, p. 445a; Abstract 1716.
Modak, S. et al. (2001) "*Monoclonal Antibody 8H9 Targets a Novel Cell Surface Antigen Expressed by a Wide Spectrum of Human Solid Tumors*," Cancer Res. 61(10):4048-4054.
Modak, S. et al. (Mar. 1999) "*Disialoganglioside GD2 and Antigen 8H9: Potential Targets for Antibody-Based Immunotherapy Against Desmoplastic Small Round Cell Tumor (DSRCT) and Rhabdomyosarcoma (RMS)*," Proceedings of the American Association for Cancer Research Annual Meeting, vol. 40:474 (90th Annual Meeting of the American Association for Cancer Research; Philadelphia, Pennsylvania, US; Apr. 10-14, 1999.

Modak, S. et al. (Mar. 2000) "*Radioimmunotargeting to Human Rhabdomyosarcoma Using Monoclonal Antibody 8H9*," Proc. Am. Assoc. Cancer Res.41:724.
Paul, William E, (1993) "Fundamental Microbiology, 3 Ed." p. 242-243.
Peeters, K. et al. (2001). "Production of Antibodies and Antibody Fragments in Plants," *Vaccine* 19:2756-2761.
Pollock, D.P. et al. (1999). "Transgenic Milk as a Method for the Production of Recombinant Antibodies," *J. Immunol. Methods* 231:147-157.
Prasad, D.V. et al. (2004) "*Murine B7-H3 Is a Negative Regulator of T Cells*," J. Immunol. 173:2500-2506.
Riechmann, L. et al. (1988). "Reshaping Human Antibodies for Therapy," *Nature* 332:323-327.
Sato, K. et al. (1993). "Reshaping a Human Antibody to Inhibit the Interleukin 6-Dependent Tumor Cell Growth," *Cancer Res.* 53:851-856.
Sharpe, A.H. et al. (2002) "The B7-CD28 Superfamily," Nature Rev. Immunol. 2:116-126.
Shaw, D.R. et al. (1987). "Characterization of a MouselHuman Chimeric Monoclonal Antibody (17-IA) to a Colon Cancer Tumor-Associated Antigen," *J. Immunol.* 138(12):4534-4538.
Shen, W-C. and Ryser, H. J-P. (1981). "CIS-Aconityl Spacer Between Daunomycin and Macromolecular Carriers: A Model of ph-Sensitive Linkage Releasing Drug from a Lysosomotropic Conjugate," *Biochem. Biophys. Res. Commun.* 102(3):1048-1054.
Smith, R.T. (1994) "Cancer and the Immune System," Clin. Immunol. 41(4):841-849.
Steinberger, P. et al. (2004) "*Molecular Characterization of Human 4Ig-B7-H3, A Member of the B7 Family With Four Ig-Like Domains*," Am Assoc Immunol, 172(4):2352-9.
Stephan, J-P. et al. (1999). "Distribution and Function of the Adhesion Molecule BEN During Rat Development," *Dev. Biol.* 212:264-277.
Stephan, J-P. et al. (1999). "Selective Cloning of Cell Surface Proteins Involved in Organ Development: Epithelial Glycoprotein is Involved in Normal Epithelial Differentiation," *Endocrinology.* 140(12):5841-5854.
Subudhi, S.K. et al. (2005) "The Balance of Immune Responses: Costimulation Verse Coinhibition," J. Mol. Med. 83:193-202.
Suh, W.K. et al. (2003) "*The B7 Family Member B7-H3 Preferentially Down-Regulates T Helper Type 1-Mediated Immune Responses*," Nat Immunol. 4(9):899-906. Epub Aug. 17, 2003.
Sun, M. et al. (2000). "Characterization of Mouse and Human B7-H3 Genes," *J. Immunol.* 168:6294-6297.
Supplemental Partial European Search Report (Mar. 12, 2007) for EP 03761281.9 (5 pages).
Tempest, P.R. et at. (1991). "Reshaping a Human Monoclonal Antibody to Inhibit Human Respiratory Syncytial Virus Infection in Vivo," *Bio/Technoiogy* 9:266-271.
Tivol, E.A. et al. (1995) "*Loss of CTLA-4 Leads to Massive Lymphoproliferation and Fatal Multiorgan Tissue Destruction, Revealing a Critical Negative Regulatory Role of CTLA-4*," Immunity 3(5):541-547.
Tran, C.N. et al. (2008) "*Interactions of T Cells With Fibroblast-Like Synoviocytes: Role of the B7 Family Costimulatory Ligand B7-H3*," J Immunol, 180(5):2989-2998.
Trouet, A. et al. (1982). "A Covalent Linkage Between Daunorubicin and Proteins that is Stable in Serum and Reversible by Lysosomal Hydrolases, as Required for a Lysosomotropic Drug-Carrier Conjugate: In vitro and in vivo Studies," *Proc. Natl. Acad. Sci. USA.* 79:626-629.
Vandenborre, K. et al. (1999) "*Interaction of CTLA-4 (CD152) With CD80 or CD86 Inhibits Human T-Cell Activation*," Immunology 98(3):413-421.
Verhoeyen, M. et al. (1988). "Reshaping Human Antibodies: Grafting an Antilysozyme Activity," *Science* 239:1534-1536.
Viglietta, V. et al. (2007) "Modulating Co-Stimulation," Neurotherapeutics 4:666-675.
Wang, S. et al. (2004) "Co-Signaling Molecules of the B7-CD28 Family in Positive and Negative Regulation of T Lymphocyte Responses," Microbes Infect. 6:759-766.

(56) References Cited

OTHER PUBLICATIONS

Weiner, L.M. et al. (2001), "Therapeutic Monoclonal Antibodies: General Principles," Section 5, Chapter 20; In Cancer: Principles and Practice of Oncology Sixth Edition Lippincott Williams & Wilkins: Philadelphia, PA, pp. 495-508.

Wheatley, S.P. and Wang, Y-L. (1998). "Indirect Immunofluorescence Microscopy in Cultured Cells," Chapter 18 in Methods in Cell Biology Mather, J.P. and Barnes, D. eds. Academic Press vol. 57, pp. 313-332.

White et al. (2001) "Antibody-Targeted Immunotherapy for Treatment of Malignancy," Ann. Rev. Med. 52:125-145.

Winter, G. and Milstein, C. (1991). "Man-Made Antibodies," *Nature* 349:293-299.

Winter, G. et al. (1994). "Making Antibodies by Phage Display Technology," *Annu. Rev. Immunol.* 12:433-455.

Woodruff, T.K. (1998). "Cellular Localization of mRNA and Protein: In Situ Hybridization Histochemistry and in Situ Ligand Binding," Chapter 19 in Methods in Cell Biology Mather, J.P. and Barnes, D. eds. Academic Press vol. 57, pp. 333-351.

Xu, H. et al. (2006) "*Soluble Mouse B7-H3 Down-Regulates Dendritic Cell Stimulatory Capacity to Allogenic T Cell Proliferation and Production of IL-2 and IFN-Gamma*," Cell Mol Immunol. 3(3):235-240.

Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281.

Yang, H.M. and Reisfeld, R.A. (1988). "Pharmacokinetics and Mechanism of Action of a Doxorubicon-Monoclonal Antibody 9.2.27 Conjugate Directed to a Human Melanoma Proteoglycan," *J. Natl. Canc, Inst.* 80:1154-1159.

Yi. K.H. et al. (2009) "Fine Tuning the Immune Response Through B7-H3 and B7-H4," Immunol. Rev, 229:145-151.

Zang, X. et al. (2007) "*B7-H3 and B7x Are Highly Expressed in Human Prostate Cancer and Associated With Disease Spread and Poor Outcome*," Proc. Natl. Acad. Sci. (U.S.A.) 104(49):19458-19463 Epub Nov. 27, 2007.

Zang, X. et al. (2007) "*The B7 Family and Cancer Therapy: Costimulation and Coinhibition*," Clin. Cancer Res. 13:5271-5279.

Zips et al. (2005) "*New Anti-Cancer Agents: In Vitro and In Vivo Evaluation*," In Vivo 19:1-8.

UNIPROT accession No. Q96BF3, "Transmembrane and immunoglobulin domain-containing protein 2", 6 pages, retrieved from EBI accession No. UNIPROT:Q96BF3, Last Modified Nov. 30, 2010. Version 79.

Zou, et al., "Inhibitory B7-family molecules in the tumor microenvironment", Nature Rev., 8(6):467-77 (2008).

Seliger, et al., "The complex role of B7 molecules in tumor immunology", Trends in Molecular Med., 14(12):550-9 (2008).

Gerhard, et al., "The status, quality, and expansion of the NIH full-length cDNA project: the Mammalian Gene Collection (MGC)", Genome Res., 14(10B):2121-7 (2004).

UNIPROT accession No. Q9UM44, "HERV-H LTR-associating protein 2; AltName: Full=Human endogenous retrovirus-H long terminal repeat-associating protein 2", 6 pages, retrieved from EBI accession No. UNIPROT:Q9UM44, Last Modified Nov. 30, 2010. Version 71.

Dong, et al., "Costimulating aberrant T cell responses by B7-H1autoantibodies in rheumatoid arthritis", J Clin. Invest., 111(3):363-70 (2003b), (2003).

International Search Report for Corresponding PCT application PCT/UD2010/045479 mailed May 6, 2011.

* cited by examiner

Figure 3A:
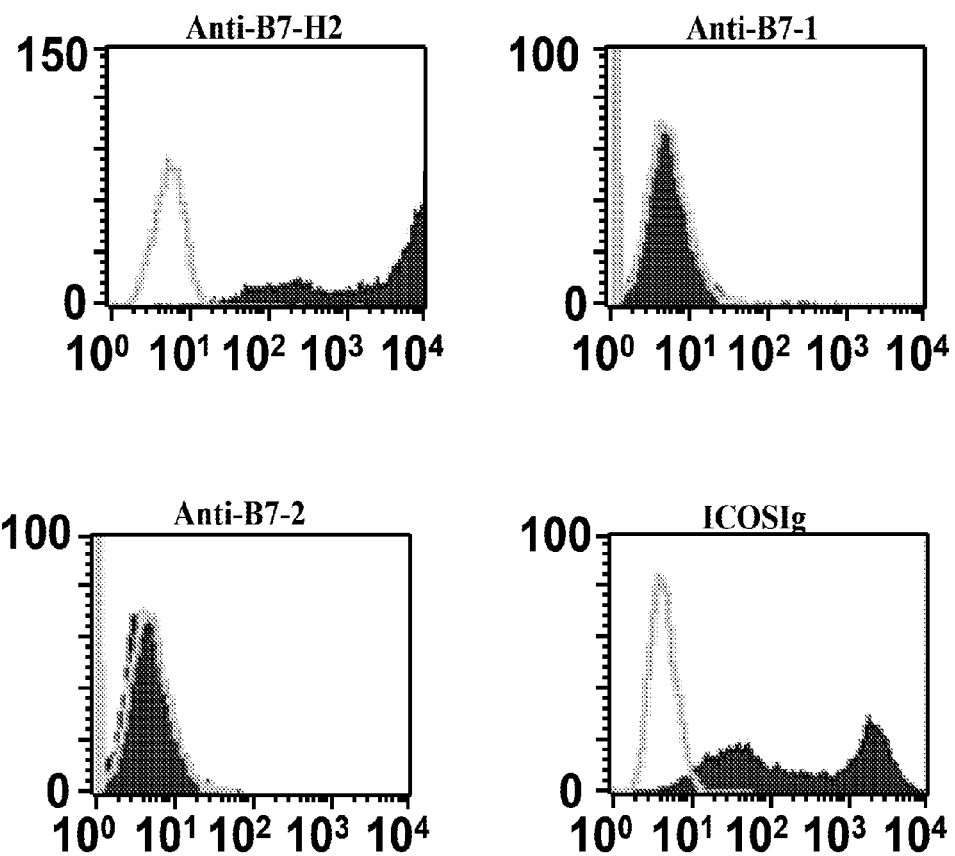
Figures 3B, 3C:
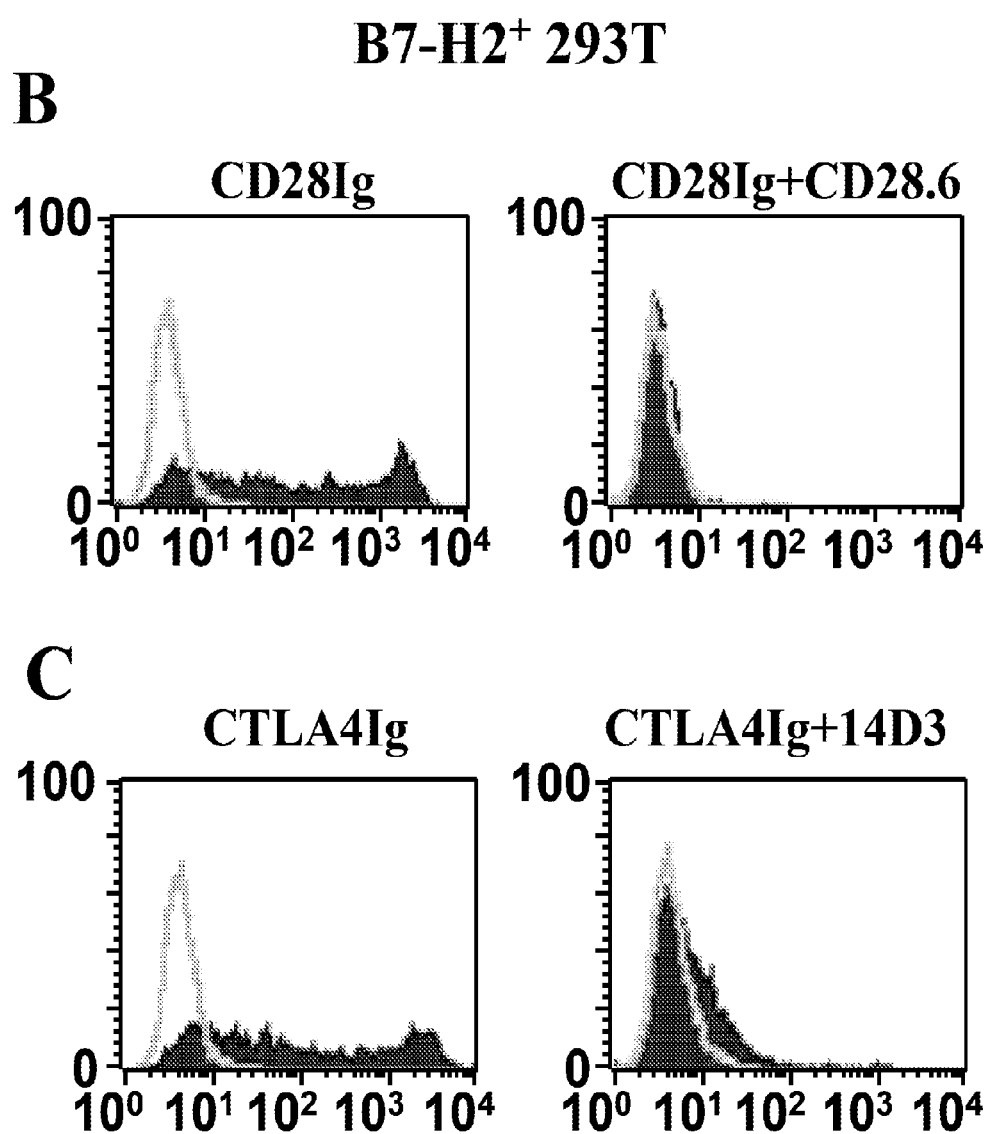

H CD28⁺ 293T
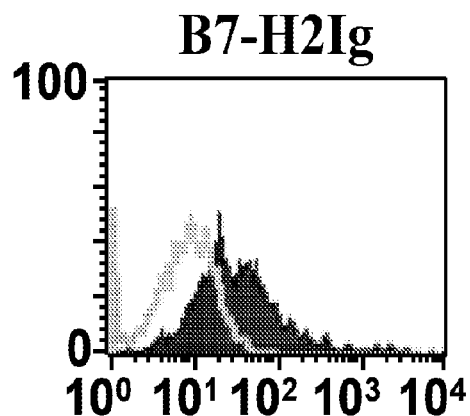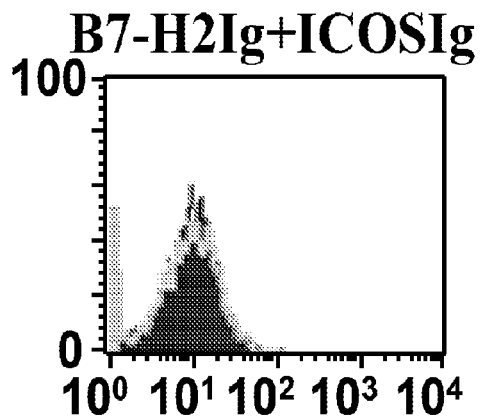
I CTLA-4⁺ 293T
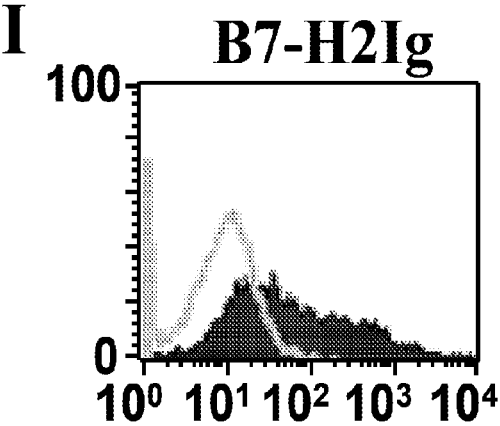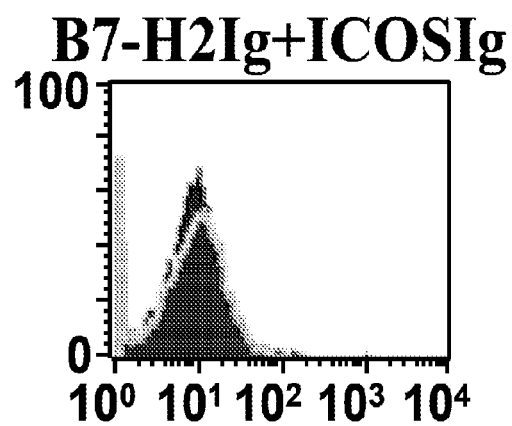
FIG. 3H-3I

|          |                                                              | 40 |
|----------|--------------------------------------------------------------|-----|
| CD28     | - - - - - - - - - - M L R L L L A L N L F P S - - - - - - - I Q V T G N K I L V |  |
| CTLA-4   | M A C L G F Q R H K A Q L N L A T R T W P C T L L F F L L F I P V F C K A M H V |  |
| ICOS     | - - - - - - M K S G L W Y F F L F C L R - - - - - - I K V L T G E I N G |  |
| PD-1     | M Q I P Q A P W P V V W A V L Q L G W R P G - - - - W F L D S P D R P W N P P T |  |
| B7-H7CR  | - - - - M G S P G M V L G L L V Q I W A L - - - - - - - Q E A S S L S V Q |  |

|          |                                                              | 80 |
|----------|--------------------------------------------------------------|-----|
| CD28     | K Q S P M L V A Y D N A V N - L S C K Y S Y N L F S R E F R A S L H K G L D S A |  |
| CTLA-4   | A Q P A V V L A S S R G I A S F V C E Y A S P G K A T E V R V T V L R Q A D S Q |  |
| ICOS     | S A N Y E M F I F H N G G V Q I L C K Y P - D I V Q Q F K M Q L L K G G - - - |  |
| PD-1     | F S P A L L V V T E G D N A T F T C S F S - - N T S E S F V L N W Y R M S P S N |  |
| B7-H7CR  | Q G P N L L Q V R Q G S Q A T L V C Q V D Q A T A W E R L R V K W T K D G - - - |  |

|          |                                                              | 120 |
|----------|--------------------------------------------------------------|-----|
| CD28     | V - E V C V V Y G N Y S Q Q L Q V Y S K T G F N C D G K L G N E S V T F Y L Q N |  |
| CTLA-4   | V T E V C A A T Y M M G N E L T F L D D S - - I C T G T S S G N Q V N L T I Q G |  |
| ICOS     | - Q I L C D L T K T G S G N T V S I K S L K F C H S Q L S N N S V S F F L Y N |  |
| PD-1     | Q T D K L A A F P E - - D R S Q P G Q D C R F R V T Q L P N G R D F H M S V V R |  |
| B7-H7CR  | - - A I L C Q P Y I T N G S L S L G V C G P Q G R L S W Q A P S H L T L Q L D P |  |

FIG. 7

FIG. 7 cont.

```
                          260                    280
CD28      M N M T P R R P G P T R K H Y Q P Y A P P R D F A A Y R S - - - - - - - - - -
CTLA-4    V K M P P T E P - E C E K Q F Q P Y F I P I N - - - - - - - - - - - - - - - -
ICOS      G E Y M F M R A V N T A K K S R L T D V T L - - - - - - - - - - - - - - - - -
PD-1      R E K T P E P P V P C V P E Q T E Y A T I V F P S G M G T S S P A R R G S A D G
B7-H7CR   G Q S I Y S T S F P Q A P R Q P H L A S R P C P S P R P C P S P R P G H P V S
                          300                    320
CD28      - - - - - - - - - - - - - - - - - - - - -
CTLA-4    - - - - - - - - - - - - - - - - - - - - -
ICOS      - - - - - - - - - - - - - - - - - - - - -
PD-1      P R S A Q P L R P E D G H C S W P L - - - -
B7-H7CR   M V R V S P - R P S P T Q Q P R P K G F P K V G E E
```

```
                              260                                 280
human B7-1    L I K Y G H L R V N - - - - - - - - - - - - - - - - - - - -
human B7-2    I L E T D K T R L L S - - - - - - - - - - - - - - - - - - -
human B7-DC   V F W N T H V R E - - - - - - - - - - - - - - - - - - - - -
human B7-H1   T F R R L D P E E - - - - - - - - - - - - - - - - - - - - -
human B7-H2   C I E N V L Q Q N L T - - - - - - - - - - - - - - - - - - -
human B7-H3   L V R N P V L Q Q - - - - - - - - - - - - - - - - - - - - -
human B7-H4   M I E N D I A K A - - - - - - - - - - - - - - - - - - - - -
human B7-H7   T I E N S L K Q T W T G R W T M K D G L H K M Q S E H V S L S C Q P V N D Y F 300                                 320
human B7-1    - - - - - - - - - - - - - - - - - - - - - - - - - - - - - -
human B7-2    - - - - - - - - - - - - - - - - - - - - - - - - - - - - - -
human B7-DC   - - - - - - - - - - - - - - - - - - - - - - - - - - - - - -
human B7-H1   - - - - - - - - - - - - - - - - - - - - - - - - - - - - - -
human B7-H2   - - - - - - - - - - - - - - - - - - - - - - - - - - - - - -
human B7-H3   - - - - - - - - - - - - - - - - - - - - - - - - - - - - - -
human B7-H4   - - - - - - - - - - - - - - - - - - - - - - - - - - - - - -
human B7-H7   S P N Q D F K V T W S R M K S G T F S V L A Y Y L S S S Q N T I I N E S R F S W
```

FIG 9. cont.

FIG 9. cont.

```
                          420                                                440
human B7-1    E R L R R E S V R P V - - - - - - - - - - - - - - - - - - - - - - - - - - - -
human B7-2    K C G T N T M E R E E S E Q T K K R E K I H I P E R S D E A Q R V F K S S K T S
human B7-DC   Y S S K D T T K R P V - - - - - - - - - - - - - - - T T K R F V N S A I - - -
human B7-H1   D V K K C G I Q D T N - - - - - - - - - - - - - - - S K K Q S D T H L E E T - -
human B7-H2   Y A G A W A V S P E T - - - - - - - - - - - - - - - - - - E L T G H V - - - -
human B7-H3   E E E N A G A E D Q D G E G - - - - - - S K T A L Q P L K H S D S K E D D G Q E I A
human B7-H4   - L K - - - - - - - - - - - - - - - - - - - - - - - - - - - - - - - - - - - -
human B7-H7   Q L E A R R S R H P A D G A Q Q E R C C V P P G E R C P S A P D N G E E N V P L
                                  460                                          480 human B7-1    - - - - - - - - - -
human B7-2    S C D K S D T C F - -
human B7-DC   - - - - - - - - - -
human B7-H1   - - - - - - - - - -
human B7-H2   - - - - - - - - - -
human B7-H3   - - - - - - - - - -
human B7-H4   - - - - - - - - - -
human B7-H7   S G K V - - - - - -
```

FIG 9. cont.

Figure 16A:
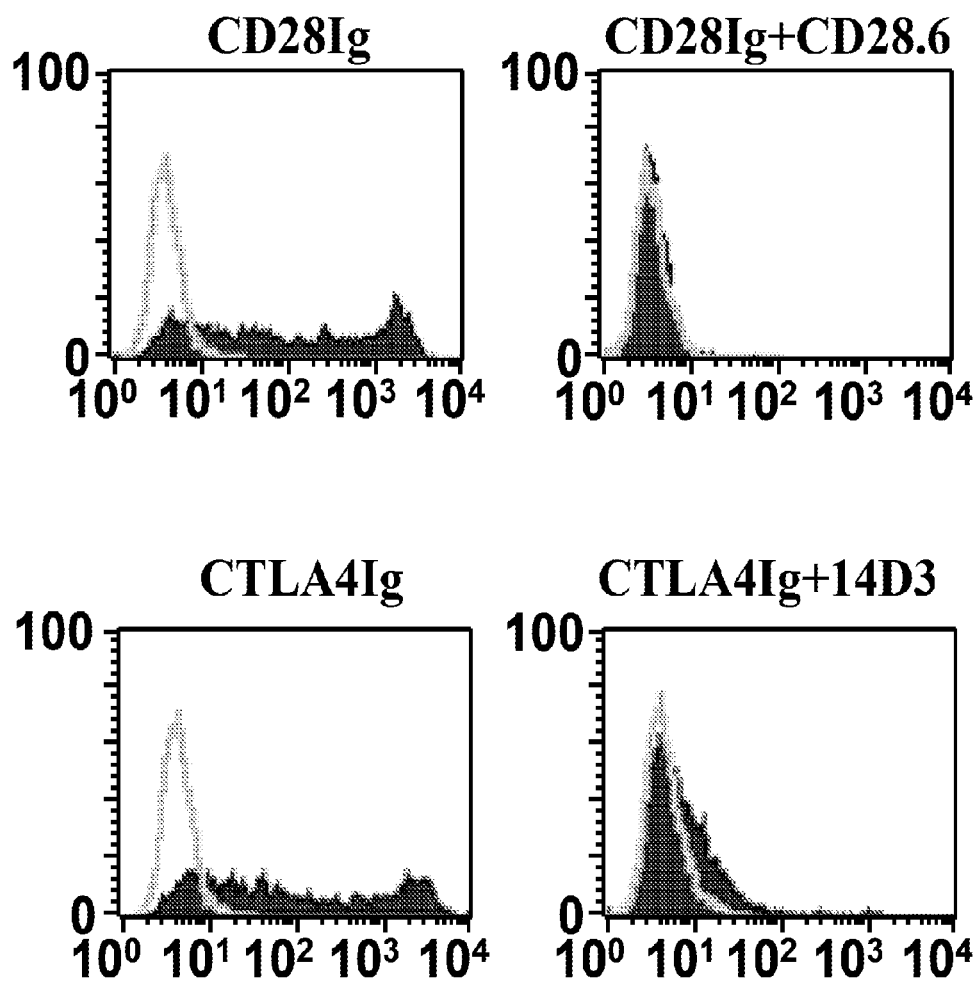

A B7-H2⁺ 293T
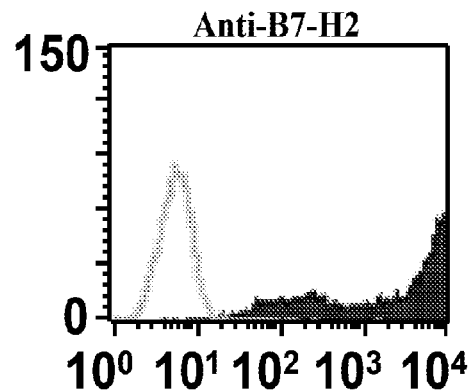
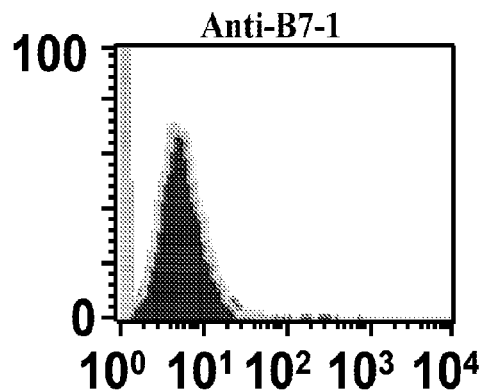
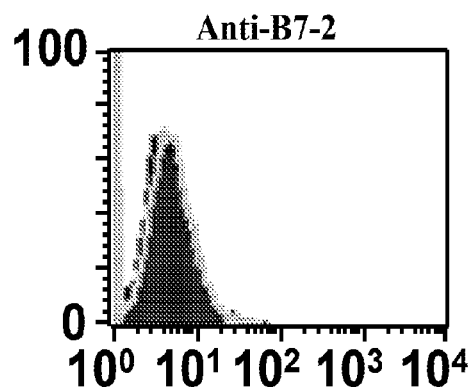
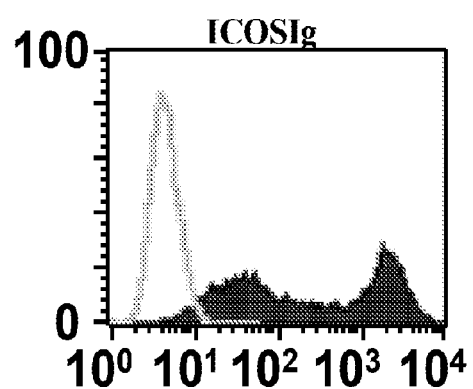
FIG. 16A

Figure 20A:
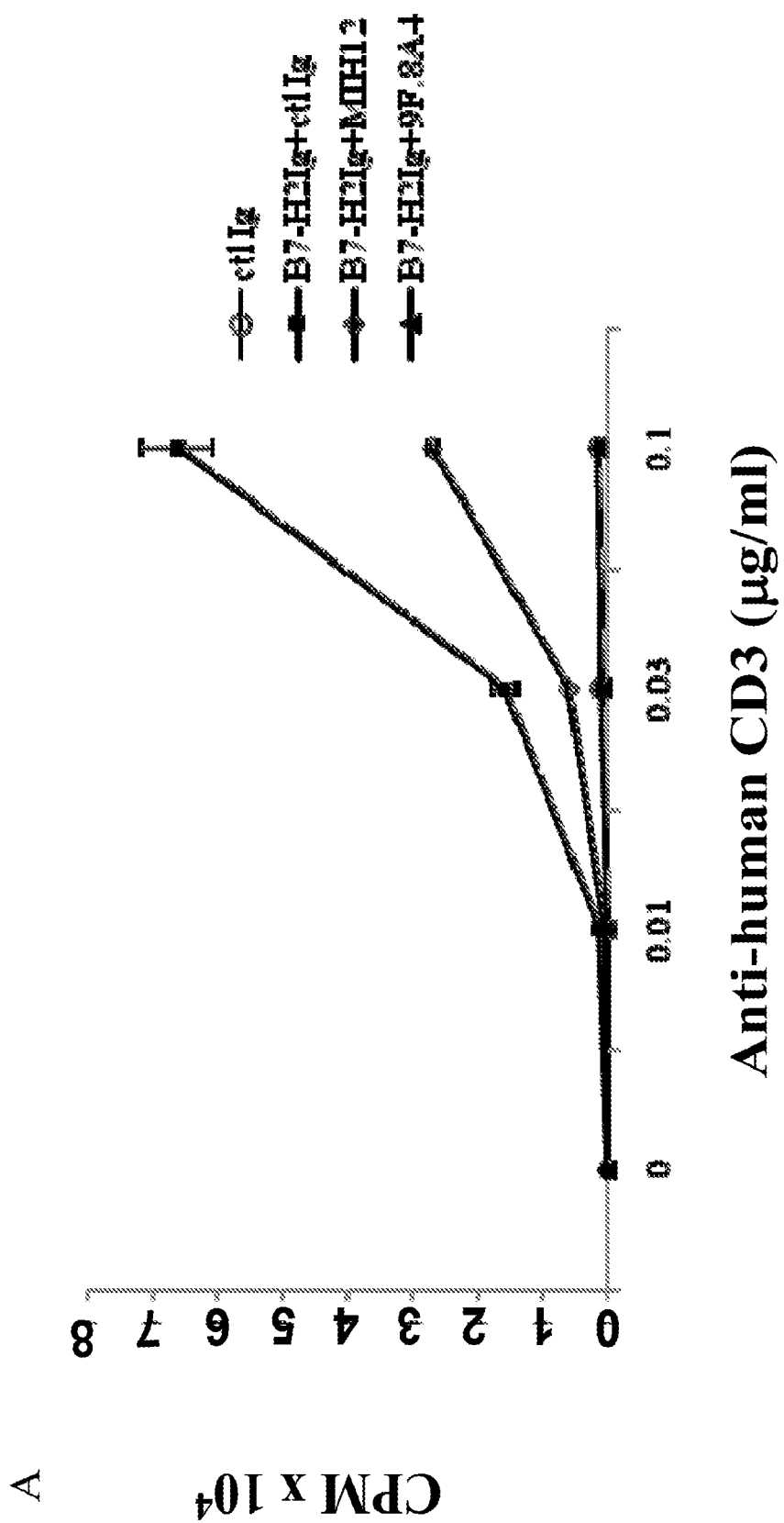
Figure 20B:
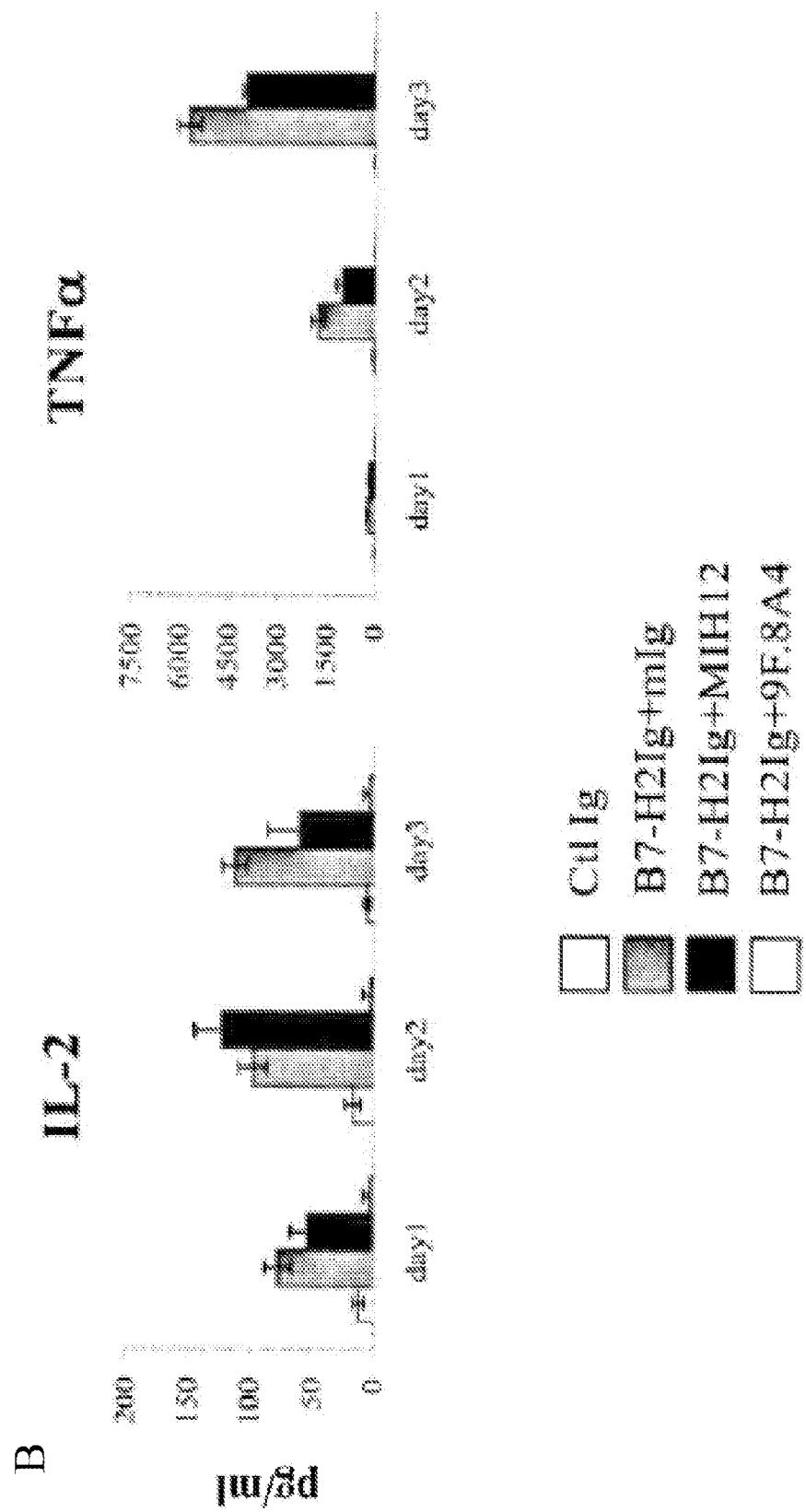
Figure 20B:
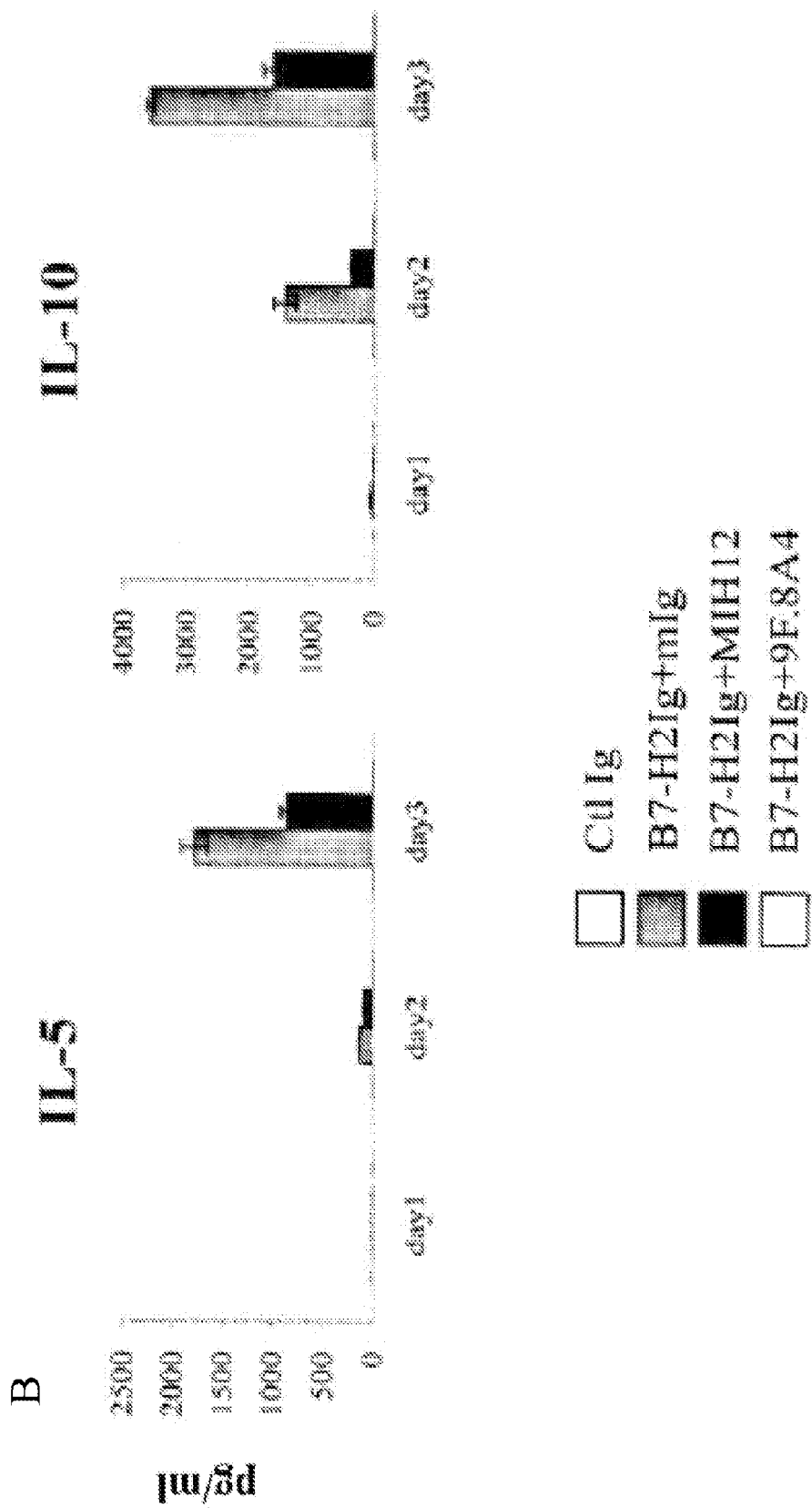
Figure 20B:
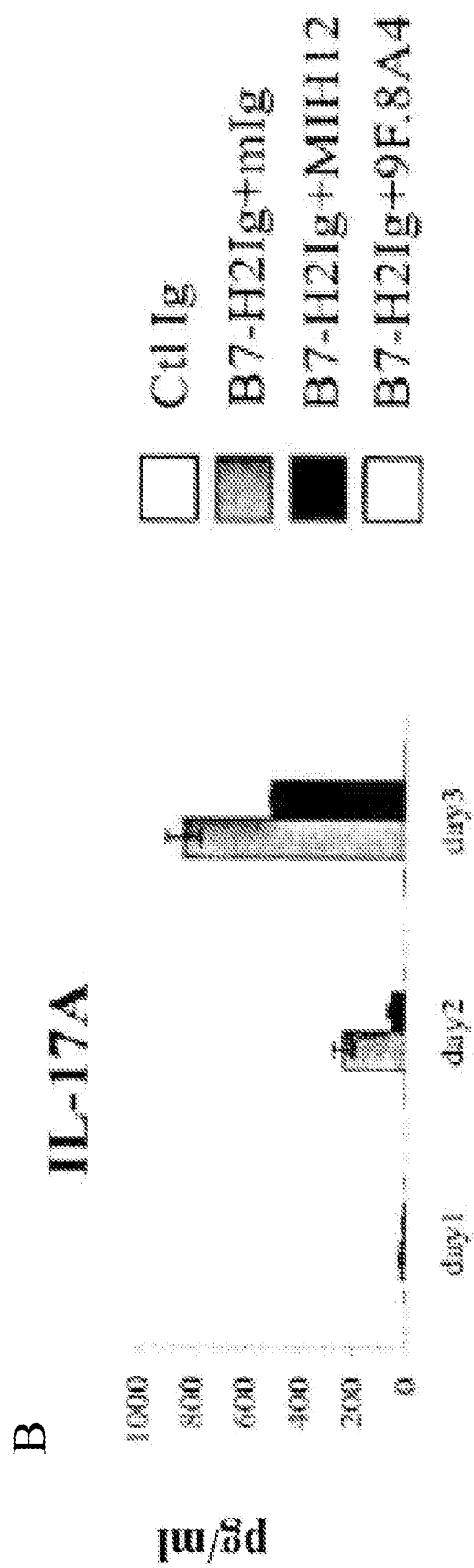

B
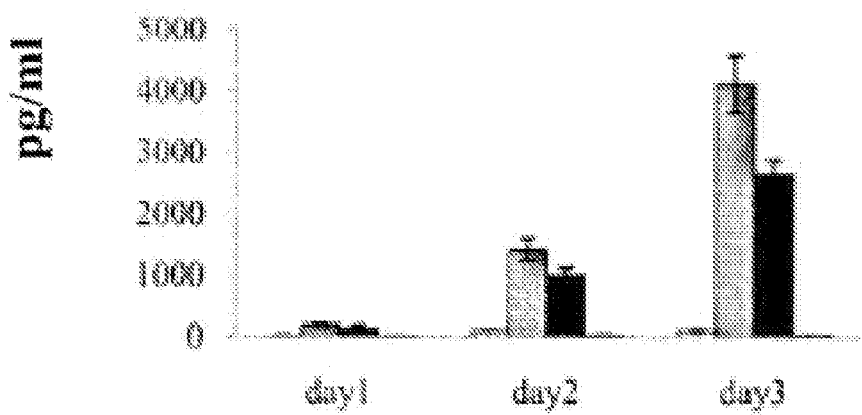
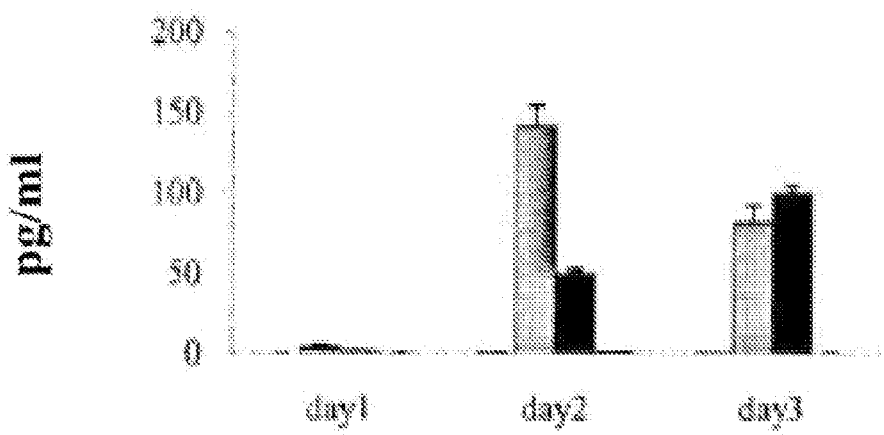
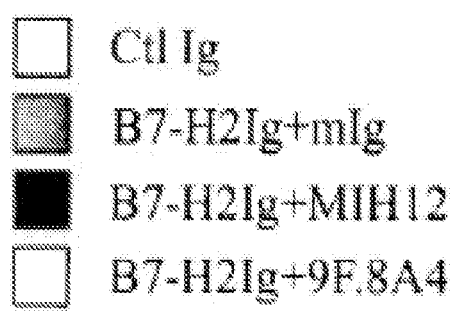
FIG. 20B cont.

Sequence View: Similarity Format, Color areas of high matches at same base position

```
hB7-H7 protein.t    1  mkaqtaisffliiltslagsqgifplaffiyypmaeqivigrldedilpssfergsevvlhwkyqpl---syrvhsyykgsdhlesqdpryanrtslfyneiqnquaslffrrvslldegiytccyvgrai
rheesus B7-H7 pro   1  mkaqt--sfflliisslagsqgiflsafftvyrpmaeqiligrldedilpssfergsevvlhwkyqdsynayrvhsyykqsqrlesqdtryanrtslfyneiqnquaslffrrlslldegiytccyvgrai
chimp B7-H7 prot    1  mkakqtaisffliiltslagsqgalfpmafstyrpvnaeqivigrldedilpssfergsevvlhwkyqpl---syrvhsyykgsdhlesqdprthrtslfyneiq-gnaslfsprvslldegiytccyvgrai hB7-H7 protein.t  128  qvitakvrlkvgvfltpvmkyekrntnafllcsvlsvyprpiitwkndurpiseunmeetgsldsfsinsplnltqsnasyecrienstikqtnrgwrnkdglhknqsenvslseqpvndyfspnqdfk
rheesus B7-H7 pro 129  gaitakvrlkvgvfllcmvlsvyprpiltwkndurpiseunmqetgslpfsinerlnltqsnasyecrienstikqtnrgwrnkdglhknqsenvslacelvndyfspnqdfk
chimp B7-H7 prot  127  qvitakvrlkvgvfltpvmkyekrntnafllcsvlsvyprpiitwkndurpiseunmeetgsldsfsinsplnltqsnasyecrienstikqtnrgwrnkdglhknqsenvslseqpvndyfspnqdfk hB7-H7 protein.t  258  vtwsrmksgtfsvlayylsssqntilnesrfsunkelingsdfsmnlmdlnlsdagevlcnlssdeyllt-lhrvhvepsqetashnkglwllvpsailaaf-l--linsvkccraqlearsrhpadgaq
rheesus B7-H7 pro 259  vtwsrmeegiasllayylsssqqttfyesrfsunkelkngsdfsmnirdlsldsdagevlcnlssdeyllt-lhrvhvpsqgetasdnkglwlvaslivlcllwliwvkcstaqleasrsrypadgaq
chimp B7-H7 prot  257  vtwsrmksgtfsilayylsssqntilnesrfsunkelingsdfsmnlmdlnlsdagevlcnlssdeyllt-lhrvhvepsqgetashnkglwllvpsvlaaf-l--lintvkrcraqpearsrhpadgaq hB7-H7 protein.t  386  qerycvpngercpsapdngeenv-plsqkv
rheesus B7-H7 pro      -----------------------------
chimp B7-H7 prot  385  qerycvpngehcpsapdngeenvsvsqkv
```

METHODS OF MODULATING IMMUNE FUNCTION

This application is the U.S. national stage entry of international patent application No. PCT/US2010/045479, filed Aug. 13, 2010, which claims priority to U.S. provisional patent application No. 61/233,650, filed Aug. 13, 2009 and U.S. provisional patent application No. 61/289,951, filed Dec. 23, 2009, each of which is incorporated herein by reference in its entirety.

This invention was made, in part, with United States Government support under award numbers R01 CA97085 and R01 AI72592 from the National Institutes of Health (NIH). The United States Government may have certain rights in this invention.

1. INTRODUCTION

Presented herein are therapeutic agents that modulate one or more immune functions and uses of such therapeutic agents in the prevention, treatment and management of diseases. In one aspect, the therapeutic agents modulate one or more signal transduction pathways induced by the binding of B7-H7 to B7-H7CR, or the binding of B7-H2 to either ICOS, CD28, or CTLA-4. In another aspect, the therapeutic agents modulate the binding of B7-H7 to B7-H7CR, or the binding of B7-H2 to either ICOS, CD28, or CTLA-4. The therapeutic agents can be used in the prevention, treatment and/or management of diseases in which it might be useful to modulate one or more immune functions (e.g., cancer, infectious disease, autoimmune disease, and transplantation rejection). In another aspect, presented herein are methods for identifying receptor-ligand interactions.

2. BACKGROUND

Activation of T cells is an important aspect of the immune system. T cell activation is required for specific immune responses against infectious agents. T cell activation also plays an important role in tumor immunity and in autoimmune and inflammatory disorders. T cell activation is initiated when T cell antigen receptors (TCR) of T cells recognize their specific antigen (Ag) in the context of major histocompatibility complex (MHC) molecules. Although TCR signal transduction is required for naive T cell activation, TCR activation alone is not sufficient to generate an immune response. A secondary signal, known as costimulation, is needed for optimal activation of naive T cells. In particular, signal transduction through the TCR and CD28, known as a costimulatory receptor, are required for activation of naive T cells. B7-1 (CD80) and B7-2 (CD86), known as costimulatory molecules, are two ligands for CD28. B7-1 and B7-2 are typically expressed on professional antigen-presenting cells (APCs). In addition to binding CD28, B7-1 and B7-2 also bind to the co-stimulatory receptor known as CTLA-4 (CD152) on T cells. Another co-stimulatory receptor found on T cells is ICOS.

B7 molecules mediate both positive and negative signals to T cells by binding to costimulatory receptors on T cells. CD28 is the most extensively studied receptor that accepts a secondary signal from B7-1(CD80) and B7-2(CD86, B70) to costimulate naive T cells to full activation in the presence of T cell receptor signaling (Linsley et all, 1990, PNAS USA 87: 5031-5035). On the other hand, CTLA-4, a CD28 homolog expressed on activated T cells and interacting with the same set of ligands, attenuates T cell responses (Krummel et al., 1995, J. Exp. Med. 182: 469-465; Walnus et al., 1994, Immunity 1: 405-413). ICOS, another CD28 homolog, is expressed on activated T cells and costimulates 1 cell activation upon binding of a distinct ligand B7-H2 (ICOSLG, GL50, B7RP1, CD275, ICOSL, LICOS) (Hutloff et al., 1999, Nature 397: 263-266; Yoshinaga et al., 1999, Nature 402: 827-832). CD28, CTLA-4 and ICOS form a tight gene cluster on human chromosome 2q33 and on mouse chromosome 1, suggesting they originated by gene duplication during evolution (Swallow et al., 1999, Immunity 11: 423-432). Although CD28 and ICOS have distinct ligands, they share significant functional redundancy including their capacity in costimulating growth, survival and differentiation of T cells as well as their requirement for antibody response (Ling et al., 2000, J. Immunol. 164: 1653-1657; Ling et al., 2001, Genomics 78: 155-168; Dong et al., 2001, Nature 409: 97-101; McAdam et al., 2001, Nature 409: 102-105; Tafuri et al., 2001, Nature 409: 105-109; Linterman et al., 2009, Immunity 30: 228-241). Both CD28 and ICOS signals have been shown to costimulate an array of cytokines. However, only CD28 signal induces high level of IL-2, while ICOS preferentially stimulates IL-10 (Hutloff et al., 1999, Nature 397: 263-266).

Modulation of costimulatory molecules and their receptors permits the modulation of various immune functions. Agents that modulate the interaction between costimulatory molecules and their receptors may have beneficial use in a variety of applications, including, e.g., therapeutic and prophylactic uses and vaccinations. The present invention fulfills these and other needs.

3. SUMMARY

Presented herein is the discovery of the interaction between the orphan proteins B7-H7 and B7-H7CR. Also presented herein is the discovery that B7-H2 is a ligand for CD28 as well as CTLA-4. Various embodiments presented herein are based, in part, on the discovery of these interactions and that modulation of such interactions can used to modulate immune function or response.

In one aspect, described herein are antibodies the specifically bind to B7-H7, B7-H7CR, or the complex of B7-H7 and B7-HCR. In another aspect, presented herein are methods for modulating the interaction between B7-H7 and its receptor or the interaction between B7-H2 and one or more of its receptors. In a specific embodiment, presented herein are methods for modulating the interaction between B7-H7 and B7-H7CR. In another embodiment, presented herein are methods for modulating the interaction between B7-H2 and one or more of the following receptors: ICOS, CD28 or CTLA-4.

In another aspect, presented herein are methods for modulating one or more signal transduction pathways induced by the binding of B7-H7CR to one or more of its ligands. In a specific embodiment, presented herein are methods for modulating one or more signal transduction pathways induced by the binding of B7-H7CR to B7-H7.

In another aspect, presented herein are methods for modulating one or more signal transduction pathways induced by B7-H7 binding to its receptor or B7-H2 binding to one or more of its receptors. In a specific embodiment, presented herein are methods for modulating one or more signal transduction pathways induced by B7-H7 binding to B7-H7CR. In another embodiment, presented herein are methods for modulating one or more signal transduction pathways induced by B7-H2 binding to one or more of the following receptors: ICOS, CD28 or CTLA-4.

Presented herein are Therapeutic Agents that are based, in part, on the discovery of the receptor-ligand interaction between B7-H7 and B7-H7CR and the receptor-ligand interactions between B7-H2 and ICOS, CD28, and CTLA-4. The Therapeutic Agents or compositions thereof can be used in cell culture to modulate immune cell functions (e.g., lymphocyte proliferation, cytokine production, or antibody production). In particular, a cell may be contacted with a Therapeutic Agent to modulate one or more immune cell functions. In addition, Therapeutic Agents can be administered to a subject to prevent, treat or manage certain diseases, such as cancer, an infectious disease, an autoimmune disease, an inflammatory disease, and transplant rejection.

In certain embodiments, presented herein are pharmaceutical compositions comprising a Therapeutic Agent, and pharmaceutically acceptable carrier. In specific embodiments, the Therapeutic Agent is present in the pharmaceutical composition in an amount effective to modulate T lymphocyte proliferation, modulate one or more immune functions, or to prevent, treat or manage cancer, an infectious disease, an autoimmune disorder, an inflammatory disorder, graft versus host disease, or organ transplant rejection. In some embodiments, presented herein are methods for modulating T lymphocyte proliferation, modulating one or more immune functions, or preventing, treating or managing cancer, an infectious disease, an autoimmune disorder, an inflammatory disorder, graft versus host disease, or organ transplant rejection utilizing an effective amount of Therapeutic Agent.

In one embodiment, the Therapeutic Agent is an antibody that specifically binds to B7-H7CR, an antibody that specifically binds to B7-H7, an antibody that specifically binds to a B7-H7CR/B7-H7 complex, a B7-H7CR derivative, or a B7-H7 derivative. In another embodiment, the Therapeutic Agent is a fusion protein comprising: (i) the extracellular domain of B7-H7 or a fragment thereof and the Fc domain of an immunoglobulin or a constant region thereof; or (ii) the extracellular domain of B7-H7CR or a fragment thereof and the Fc domain of an immunoglobulin or a constant region thereof. In certain embodiments, the therapeutic agent modulates one or more signal transduction pathways mediated by the interaction of B7-H7CR with one or more of its ligands (e.g., B7-H7).

In another embodiment, the Therapeutic Agent is an antibody that specifically binds to ICOS, an antibody that specifically binds to B7-H2, an antibody that specifically binds to a B7-H2/ICOS complex, an ICOS derivative, a B7-H2 derivative, a fusion protein comprising the extracellular domain of ICOS or a fragment thereof and the Fc domain of an immunoglobulin or a constant region thereof, or a fusion protein comprising the extracellular domain of B7-H2 or a fragment thereof and the Fc domain of an immunoglobulin or a constant region thereof. In another embodiment, the Therapeutic Agent is an antibody that specifically binds to CD28, an antibody that specifically binds to CTLA-4, an antibody that specifically binds to a CD28/B7-H2 complex, an antibody that specifically binds to a CTLA-4/B7-H2 complex, a CD28 derivative, a CTLA-4 derivative, a fusion protein comprising the extracellular domain of CD28 or a fragment thereof and the Fc domain of an immunoglobulin or a constant region thereof, or a fusion protein comprising the extracellular domain of CTLA-4 or a fragment thereof and the Fc domain of an immunoglobulin or a constant region thereof. In certain embodiments, the Therapeutic Agent selectively modulates one or more signal transduction pathways induced by B7-H2 binding to one or more of its receptors (e.g., ICOS, CD28 or CTLA-4). In some embodiments, the Therapeutic Agent selectively modulates the binding of B7-H2 to one or more of its receptors (e.g., ICOS, CD28 or CTLA-4).

In another aspect, described herein are methods of identifying receptor-ligand interactions. Such methods can be used to identify interactions between ligands and receptors, such as costimulatory ligands and costimulatory receptors.

3.1 TERMINOLOGY

As used herein, the term "abnormal" in the context of expression of a proteinaceous agent refers to a proteinaceous agent for which the expression is increased or decreased by at least 5%, 10%, 20%, 25%, 50%, 75%, 85%, 90%, or 95%, or 5% to 10%, 5% to 25%, 10% to 25%, 10% to 50%, 25% to 75%, 50% to 75%, 50% to 95%, of 75% to 95% to the expression of the proteinaceous agent by a normal subject or population (e.g., 5 or more normal subjects).

As used herein, the terms "about" and "approximately," when used to modify a numeric value or numeric range, indicate that deviations of 5% to 15% above and 5% to 15% below the value or range remain within the intended meaning of the recited value or range.

As used herein, the term "agonist(s)" refers to a molecule(s) that binds to another molecule and induces a biological reaction. In a specific embodiment, an agonist is a molecule that binds to a receptor on a cell and triggers one or more signal transduction pathways. For example, an agonist includes an antibody or ligand that binds to a receptor on a cell and induces one or more signal transduction pathways. In certain embodiments, the antibody or ligand binds to a receptor on a cell, induces one or more signal transduction pathways, and blocks or prevents a native ligand of the receptor from binding to the receptor. In certain embodiments, a Therapeutic Agent is an agonist of signal transduction normally mediated by binding of a native ligand (e.g., B7-H7) to B7-HCR. In other embodiments, a Therapeutic Agent is an agonist of signal transduction normally mediated by binding of a native ligand (e.g., B7-H2) to one, two or all of the following receptors: ICOS, CD28, or CTLA-4.

As used herein, the term "Immunostimulating Therapeutic Agent(s)" refers to a Therapeutic Agent(s) that induces, activates or enhances one or more immune functions or responses.

As used herein, the term "antagonist(s)" refers to a molecule(s) that inhibits the action of another molecule without provoking a biological response itself. In a specific embodiment, an antagonist is a molecule that binds to a receptor on a cell and blocks or dampens the biological activity of an agonist. For example, an antagonist includes an antibody or ligand that binds to a receptor on a cell and blocks or dampens binding of the native ligand to the cell without inducing one or more signal transduction pathways. Another example of an antagonist includes an antibody or soluble receptor that competes with the native receptor on cells for binding to the native ligand, and thus, blocks or dampens one or more signal transduction pathways induced when the native receptor binds to the native ligand. In certain embodiments, a Therapeutic Agent is an antagonist of signal transduction normally mediated by binding of a native ligand (e.g., B7-H7) to B7-HCR. In other embodiments, a Therapeutic Agent is an antagonist of signal transduction normally mediated by binding of a native ligand (e.g., B7-H2) to one, two or all of the following receptors: ICOS, CD28, or CTLA-4.

As used herein, the term "Inhibitory Therapeutic Agent(s)" refers to a Therapeutic Agent(s) that suppresses or reduces one or more immune functions or responses.

As used herein, the terms "antibody" and "antibodies" refer to molecules that contain an antigen binding site, e.g., immunoglobulins. Antibodies include, but are not limited to, monoclonal antibodies, bispecific antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. In a specific embodiment, an antibody is a human or humanized monoclonal antibody.

As used herein and unless otherwise specified, the term "B7-H2" refers to either a native B7-H2, a B7-H2 derivative, or both.

As used herein and unless otherwise specified, the term "B7-H2 polypeptide" refers to either a native B7-H2, a B7-H2 derivative, or both.

As used herein and unless otherwise specified, the terms "B7-H2/CD28 complex" and "CD28/B7-H2 complex" refer to complexes formed as a result of the interaction between a native B7-H2 and a native CD28, a native B7-H2 and a CD28 derivative, a B7-H2 derivative and a native CD28, or a B7-H2 derivative and a CD28 derivative.

As used herein and unless otherwise specified, the term "B7-H2/CTLA-4 complex" and "CTLA-4/B7-H2 complex" refer to complexes formed as a result of the interaction between a native B7-H2 and a native CTLA-4, a native B7-H2 and a CTLA-4 derivative, a B7-H2 derivative and a native CTLA-4, or a B7-H2 derivative and a CTLA-4 derivative.

As used herein and unless otherwise specified, the term "B7-H2/ICOS complex" and "ICOS/B7-H2 complex" refer to complexes formed as a result of the interaction between a native B7-H2 and a native ICOS, a native B7-H2 and an ICOS derivative, a B7-H2 derivative and a native ICOS, or a B7-H2 derivative and an ICOS derivative.

As used herein and unless otherwise specified, the term "B7-H7" refers to either a native B7-H7, a B7-H7 derivative, or both.

As used herein and unless otherwise specified, the term "B7-H7 polypeptide" refers to either a native B7-H7, a B7-H7 derivative, or both.

As used herein and unless otherwise specified, the term "B7-H7CR" refers to either a native B7-H7CR, a B7-H7CR derivative, or both.

As used herein and unless otherwise specified, the term "B7-H7CR polypeptide" refers to either a native B7-H7CR, a B7-H7CR derivative, or both.

As used herein and unless otherwise specified, the terms "B7-H7/B7-H7CR complex" and "B7-H7CR/B7-H7 complex" refer to complexes formed as a result of the interaction between a native B7-H7 and a native B7-H7CR, a native B7-H7 and a B7-H7CR derivative, a B7-H7 derivative and a native B7-H7CR, or a B7-H7 derivative and a B7-H7CR derivative.

As used herein and unless otherwise specified, the term "CD28" refers to either a native CD28, a CD28 derivative (e.g., a CD28 polypeptide), or both.

As used herein and unless otherwise specified, the term "CTLA-4" refers to either a native CTLA-4, a CTLA-4 derivative (e.g., a CTLA-4 polypeptide), or both.

As used herein, the term "derivative" in the context of proteins or polypeptides refers to: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native polypeptide; (d) a polypeptide encoded by nucleic acid sequence that can hybridize under high, moderate or typical stringency hybridization conditions to a nucleic acid sequence encoding a native polypeptide; (e) a polypeptide encoded by a nucleic acid sequence that can hybridize under high, moderate or typical stringency hybridization conditions to a nucleic acid sequence encoding a fragment of a native polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, at least 150 contiguous amino acids, or 20 to 50, to 75, 25 to 100, 25 to 150, 50 to 75, 50 to 100, 75 to 100, 50 to 150, 75 to 150, 100 to 150, or 100 to 200 contiguous amino acids; or (f) a fragment of a native polypeptide. Derivatives also include a polypeptide that comprises the amino acid sequence of a naturally occurring mature form of a mammalian polypeptide and a heterologous signal peptide amino acid sequence. In addition, derivatives include polypeptides that have been chemically modified by, e.g., glycosylation, acetylation, pegylation, phosphorylation, amidation, derivitization by known protecting/blocking groups, proteolytic cleavage, linkage to a cellular ligand or other protein moiety, etc. Further, derivatives include polypeptides comprising one or more non-classical amino acids. In one embodiment, a derivative is isolated or purified. In specific embodiments, a derivative retains one or more functions of the native polypeptide from which it was derived.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wis.). Information regarding hybridization conditions (e.g., high, moderate, and typical stringency conditions) have been described, see, e.g., U.S. Patent Application Publication No. US 2005/0048549 (e.g., paragraphs 72-73).

As used herein, the terms "disease" and "disorder" are used interchangeably to refer to a condition, in particular, a pathological condition.

As used herein, the term "elderly human" refers to a human 65 years or older.

As used herein, the term "effective amount" in the context of the administration of a therapy to a subject refers to the amount of a therapy that achieves a desired prophylactic or therapeutic effect. Examples of effective amounts are provided in Section 5.8.2, infra.

As used herein, the term "fragment" in the context of a nucleotide sequence refers to a nucleotide sequence comprising an nucleic acid sequence of at least 5 contiguous nucleic acid bases, at least 10 contiguous nucleic acid bases, at least 15 contiguous nucleic acid bases, at least 20 contiguous nucleic acid bases, at least 25 contiguous nucleic acid bases, at least 40 contiguous nucleic acid bases, at least 50 contiguous nucleic acid bases, at least 60 contiguous nucleic acid bases, at least 70 contiguous nucleic acid bases, at least 80 contiguous nucleic acid bases, at least 90 contiguous nucleic acid bases, at least 100 contiguous nucleic acid bases, at least 125 contiguous nucleic acid bases, at least 150 contiguous nucleic acid bases, at least 175 contiguous nucleic acid bases, at least 200 contiguous nucleic acid bases, at least 250 contiguous nucleic acid bases, at least 300 contiguous nucleic acid bases, at least 400 contiguous nucleic acid bases, or at least 500 contiguous nucleic acid bases, or in the range of between 5 to 25 contiguous nucleic acid bases, 5 to 50 contiguous nucleic acid bases, 5 to 100 contiguous nucleic acid bases, 25 to 50 contiguous nucleic acid bases, 25 to 75 contiguous nucleic acid bases, 25 to 100 contiguous nucleic acid bases, 25 to 150 contiguous nucleic acid bases, 25 to 200 contiguous nucleic acid bases, 25 to 250 contiguous nucleic acid bases, 50 to 250 contiguous nucleic acid bases, 50 to 300 contiguous nucleic acid bases, 50 to 500 contiguous nucleic acid bases, 100 to 250 contiguous nucleic acid bases, 100 to 500 contiguous nucleic acid bases, or 250 to 500 contiguous nucleic acid bases of the nucleotide sequence of the gene of interest, e.g., the B7-H2, B7-H7, ICOS, B7-H7CR, CD28 or CTLA-4 gene or coding region thereof. The nucleic acid may be RNA, DNA, or a chemically modified variant thereof. In a specific embodiment, the fragment is a fragment of the B7-H2, B7-H7, ICOS, B7-H7CR, CD28 or CTLA-4 gene. In another specific embodiment, the fragment is a fragment of the coding region of the B7-H2, B7-H7, ICOS, B7-H7CR, CD28 or CTLA-4 gene. In certain embodiments, the fragment of the nucleic acid sequence of interest encodes a polypeptide that retains one or more functions of the polypeptide encoded by the nucleic acid sequence of interest—in other words, it is a functional fragment. For example, the polypeptide retains the ability to interact with another protein or to induce one or more signal transduction pathways.

As used herein, the term "fragment" is the context of a fragment of a proteinaceous agent (e.g., a protein) refers to a fragment that is 8 or more contiguous amino acids, 10 or more contiguous amino acids, 15 or more contiguous amino acids, 20 or more contiguous amino acids, 25 or more contiguous amino acids, 50 or more contiguous amino acids, 75 or more contiguous amino acids, 100 or more contiguous amino acids, 150 or more contiguous amino acids, 200 or more contiguous amino acids, or in the range of between 10 to 300 contiguous amino acids, 10 to 200 contiguous amino acids, 10 to 250 contiguous amino acids, 10 to 150 contiguous amino acids, 10 to 100 contiguous amino acids, 10 to 50 contiguous amino acids, 50 to 100 contiguous amino acids, 50 to 150 contiguous amino acids, 50 to 200 contiguous amino acids, 50 to 250 contiguous amino acids, 50 to 300 contiguous amino acids, 25 to 50 contiguous amino acids, 25 to 75 contiguous amino acids, 25 to 100 contiguous amino acids, or 75 to 100 contiguous amino acids of a proteinaceous agent, e.g., B7-H7, B7-H7CR, B7-H2, ICOS, CD28 or CTLA-4 polypeptides. In a specific embodiment, a fragment of a proteinaceous agent retains one or more functions of the proteinaceous agent—in other words, it is a functional fragment. For example, a fragment of a proteinaceous agent retains the ability to interact with another protein or to induce one or more signal transduction pathways.

As used herein, the term "functional fragment," in the context of a proteinaceous agent, refers to a portion of a proteinaceous agent that retains one or more activities or functions of the proteinaceous agent. For example, a functional fragment of a B7-H7 polypeptide may retain the ability to bind one or more of its receptors (e.g., B7-H7CR) and/or induce or activate one or more signal transduction pathways mediated by the B7-H7 polypeptide binding to one or more of its receptors (e.g., B7-H7CR).

As used herein, the term "heterologous" refers an entity not found in nature to be associated with another entity.

As used herein, the term "human adult" refers to a human that is 18 years or older.

As used herein, the term "human child" refers to a human that is 1 year to 18 years old.

As used herein, the term "human infant" refers to a newborn to 1 year old human.

As used herein and unless otherwise specified, the term "ICOS" refers to either a native ICOS, an ICOS derivative, or both.

As used herein and unless otherwise specified, the term "ICOS polypeptide" refers to either a native ICOS, an ICOS derivative, or both.

As used herein, the terms "immunospecifically binds," "immunospecifically recognizes," "specifically binds," and "specifically recognizes" are analogous terms in the context of antibodies and refer to molecules that specifically bind to an antigen (e.g., epitope or immune complex) as understood by one skilled in the art. A molecule that specifically binds to an antigen may bind to other peptides or polypeptides with lower affinity as determined by, e.g., immunoassays (e.g., ELISA), surface plasmon resonance (e.g., BIAcore®), a KinEx assay (using, e.g., a KinExA 3000 instrument (Sapidyne Instruments, Boise, Id.)), or other assays known in the art. In a specific embodiment, molecules that specifically bind to an antigen bind to the antigen with a dissociation constant (i.e., $K_a$) that is at least 2 logs, 2.5 logs, 3 logs, 3.5 logs, 4 logs or greater than the $K_a$ when the molecules bind to another antigen. In a another specific embodiment, molecules that specifically bind to an antigen do not cross react with other proteins.

As used herein, the term "in combination" refers to the use of more than one therapies (e.g., one or more prophylactic and/or therapeutic agents). The use of the term "in combination" does not restrict the order in which therapies are administered to a subject with a disease or disorder, or the route of administration. A first therapy (e.g., a prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disease or disorder or a symptom thereof.

As used herein, the terms "manage," "managing," and "management," in the context of the administration of a therapy to a subject, refer to the beneficial effects that a subject derives from a therapy, which does not result in a cure of a disease. In certain embodiments, a subject is administered one or more therapies to "manage" a disease or disorder so as to prevent the progression or worsening of symptoms associated with a disease.

As used herein, the term "native B7-H2" in the context of proteins or polypeptides refers to any naturally occurring B7-H2 amino acid sequences, including immature or precursor and mature forms. Non-limiting examples of Accession Nos. for the amino acid sequence of native mammalian B7-H2 include: O75144-1 (*homo sapiens*), O75144-2 (*homo sapiens*), NP_056074.1 (GI:27477039; *homo sapiens*), Q9JHJ8-1 (mouse), Q9JHJ8-2 (mouse), and NP_056605.1

(GI:7657220; mouse). A representative amino acid sequence of the immature/precursor form of native human B7-H2 isoform 1, which comprises the signal peptide (underlined) and the mature human native B7-H2 (italicized), is provided:

```
                                            (SEQ ID NO: 1)
MRLGSPGLLF LLFSSLRADT QEKEVRAMVG SDVELSCACP

EGSRFDLNDV YVYWQTSESK TVVTYHIPQN SSLENVDSRY

RNRALMSPAG MLRGDFSLRL FNVTPQDEQK FHCLVLSQSL

GFQEVLSVEV TLHVAANFSV PVVSAPHSPS QDELTFTCTS

INGYPRPNVY WINKTDNSLL DQALQNDTVF LNMRGLYDVV

SVLRIARTPS VNIGCCIENV LLQQNLTVGS QTGNDIGERD

KITENPVSTG EKNAATWSIL AVLCLLVVVA VAIGWVCRDR

CLQHSYAGAW AVSPETELTG HV.
```

Human B7-H2 isoform 2 differs from isoform 1 as follows: 300-302 GHV to ESWNLLLLLS. In some embodiments, native B7-H2 is the immature or precursor form of a naturally occurring mammalian B7-H2. In other embodiments, native B7-H2 is the mature form of a naturally occurring mammalian B7-H2. In a specific embodiment, native B7-H2 is the precursor form of naturally occurring human B7-H2. In another embodiment, native B7-H2 is the mature form of naturally occurring human B7-H2. In one embodiment, the native B7-H2 protein/polypeptide is isolated or purified.

The human B7-H2 polypeptide is otherwise referred to as ICOS ligand, B7RP1, ICOSL, and KIAA0653 in the literature. At least one isoform of human B7-H2 polypeptide is 302 amino acids in length and has been reported to contain the following: a signal sequence, an extracellular domain, an Ig-like V-type domain, an Ig-like C2-type domain, a transmembrane domain, and a cytoplasmic domain. In particular, at least one form of human B7-H2 isoform 1 has been reported to contain the following: a signal sequence at amino acid residues 1 to 18 of the sequence at Accession No. O75144-1, an Ig-like V-type domain at amino acid residues 19 to 129 of the sequence at Accession No. O75144-1, an Ig-like C-2 type domain at amino acid residues 141 to 227 of the sequence at Accession No. O75144-1, an extracellular domain from amino acid residues 19 to 256 of the sequence at Accession No. O75144-1, a transmembrane domain at amino acid residues 257 to 302 of the sequence at Accession No. O75144-1, and a cytoplasmic domain at amino acids 278 to 302 of Accession No. O75144-1. Other isoforms may exist in nature and the specific positions of domains may vary, but can be identified by those skilled in the art using standard techniques. Such other isoforms are encompassed herein.

As used herein, the term "native B7-H2" in the context of nucleic acids refers to any naturally occurring nucleic acid sequences encoding B7-H2, including the immature or precursor and mature forms. Non-limiting examples of Accession Nos. for the nucleotide sequence of native mammalian B7-H2 include: AF289028.1 (GI:9858866; *homo sapiens*) and BC029227.1 (GI:22137738; mouse). A representative nucleotide sequence encoding the immature/precursor form of native human B7-H2, which comprises the nucleotide sequence encoding the signal peptide (underlined) and the nucleotide sequence encoding the mature human native B7-H2 (italicized), is provided:

```
                                                           (SEQ ID NO: 2)
   1 gagtagagcc gatctcccgc gccccgaggt tgctcctctc cgaggtctcc cgcggcccaa 61 gttctccgcg ccccgaggtc tccgcgcccc gaggtctccg cggcccgagg tctccgcccg 121 caccatgcgc ctgggcagtc ctggactgct cttcctgctc ttcagcagcc ttcgagctga 181 tactcaggag aaggaagtca gagcgatggt aggcagcgac gtggagctca gctgcgcttg 241 ccctgaagga agccgttttg atttaaatga tgtttacgta tattggcaaa ccagtgagtc 301 gaaaaccgtg gtgacctacc acatcccaca gaacagctcc ttggaaaacg tggacagccg 361 ctaccggaac cgagccctga tgtcaccggc cggcatgctg cggggcgact tctccctgcg 421 cttgttcaac gtcaccccc aggacgagca gaagtttcac tgcctggtgt tgagccaatc 481 cctgggattc caggaggttt tgagcgttga ggttacactg catgtggcag caaacttcag 541 cgtgcccgtc gtcagcgccc cccacagccc ctcccaggat gagctcacct tcacgtgtac 601 atccataaac ggctacccca ggcccaacgt gtactggatc aataagacgg acaacagcct 661 gctggaccag gctctgcaga atgacaccgt cttcttgaac atgcggggct gtatgacgt 721 ggtcagcgtg ctgaggatcg cacggacccc cagcgtgaac attggctgct gcatagagaa 781 cgtgcttctg cagcagaacc tgactgtcgg cagccagaca ggaaatgaca tcggagagag 841 agacaagatc acagagaatc cagtcagtac cggcgagaaa aacgcggcca cgtggagcat 901 cctggctgtc ctgtgcctgc ttgtggtcgt ggcggtggcc ataggctggg tgtgcaggga 961 ccgatgcctc caacacagct atgcaggtgc ctgggctgtg agtccggaga cagagctcac 1021 tggccacgtt tgaccggagc tcaccgccca gagcgtggac agggcttcca tgagacgcca 1081 ccgtgagagg ccaggtggca gcttgagcat ggactcccag actgcagggg agcacttggg 1141 gcagccccca gaaggaccac tgctggatcc cagggagaac ctgctggcgt tggctgtgat
```

```
1201  cctggaatga ggccctttca aaagcgtcat ccacaccaaa ggcaaatgtc cccaagtgag 1261  tgggctcccc gctgtcactg ccagtcaccc acaggaaggg actggtgatg ggctgtctct 1321  acccggagcg tgcgggattc agcaccaggc tcttcccagt accccagacc actgtgggt 1381  cttcccgtgg gatgcgggat cctgagaccg aagggtgttt ggtttaaaaa gaagactggg 1441  cgtccgctct tccaggacgg cctctgtgct gctggggtca cgcgaggctg tttgcagggg 1501  acacggtcac aggagctctt ctgccctgaa cgcttccaac ctgctccggc cggaagccac 1561  aggacccact ca.
```

In a specific embodiment, the nucleic acid is an isolated or purified nucleic acid. In some embodiments, nucleic acids encode the immature or precursor form of a naturally occurring mammalian B7-H2. In other embodiments, nucleic acids encode the mature form of a naturally occurring mammalian B7-H2. In a specific embodiment, nucleic acids encoding native B7-H2 encode the precursor form of naturally occurring human B7-H2. In another embodiment, nucleic acids encoding native B7-H2 encode the mature form of naturally occurring human B7-H2.

As used herein, the term "native B7-H7" in the context of proteins or polypeptides refers to any naturally occurring B7-H7 amino acid sequences, including immature or precursor and mature forms. Non-limiting examples of Accession Nos. for the amino acid sequence of native mammalian B7-H7 include: O9UM44-1 (*homo sapiens*), NP_009003 (GI: 5901964, *homo sapiens*), and AAD48396 (GI: 15726285, *homo sapiens*). A representative amino acid sequence of the immature/precursor form of native human B7-H7, which comprises the signal peptide (underlined) and the mature human native B7-H7 (the amino acid sequence after the signal peptide), is provided:

cellular domain, 3 immunoglobulin-like (Ig-like) domains, a transmembrane domain, and a cytoplasmic domain. In particular, the human B7-H7 polypeptide has been reported to contain an Ig-like V-type 1 domain, an Ig-like C-1 type domain, and an Ig-like V-type 2 domain. The human B7-H7 has been reported to contain the following: a signal sequence at amino acid residues 1 to 22 of the sequence at Accession No. O9UM44-1, an Ig-like V-type 1 domain at amino acid residues 61 to 131 of the sequence at Accession No. O9UM44-1, an Ig-like C-1 type domain at amino acid residues 138 to 222 of the sequence at Accession No. O9UM44-1, an Ig-like V-type 2 domain at amino acid residues 235 to 328 of the sequence at Accession No. O9UM44-1, and a transmembrane domain at amino acid residues 345 to 365 of the sequence at Accession No. O9UM44-1. The predicted dimer interface for human B7-H7 polypeptide is amino acid residues 141-144, 156, 158, 160, 162, 193-196, 198, 200, 201, 224, and 225. The predicted N-linked glycosylation sites for human B7-H7 polypeptide are at amino acid residues 90, 103, and 318. Natural variations of human B7-H7 polypeptide include I30T, N344K, and S346R (UniProt Q9UM44). With respect to SEQ ID NO:3 above, the reported signal peptide is (SEQ ID NO: 3)

MKAQTALSFFLILITSLSGSQGIFPLAFFIYVPMNEQIVIGRLDEDIILPSSFERGSEVVI

HWKYQDSYKVHSYYKGSDHLESQDPRYANRTSLFYNEIQNGNASLFFRRVSLLD

*EGIYTCYVGTAIQVITNKVVLKV*GVFLTPVMKYEKRNTNSFLICSVLSVYPRPIITWKMD

NTPISENNMEETGSLDSFSINSPLNITGSNSSYECTIENSLLKQTWTGRWTMKDGLH

KMQSEHVSLSCQPVNDYFSPNQDFKVTWSRMKSGTFSVLAYYLSSSQNTIINESR

FSWNKELINQSDFSMNLMDLNLSDSGEYLCNISSDEYTLLTIHTVHVEPSQETASH

NKGLWILVPSAILAAFLLIWSVKCCRAQLEARRSRHPADGAQQERCCVPPGERCPS

APDNGEENVPLSGKV.

In some embodiments, native B7-H7 is the immature or precursor form of a naturally occurring mammalian B7-H7. In other embodiments, native B7-H7 is the mature form of a naturally occurring mammalian B7-H7. In a specific embodiment, native B7-H7 is the precursor form of naturally occurring human B7-H7. In another embodiment, native B7-H7 is the mature form of naturally occurring human B7-H7. In one embodiment, the native B7-H7 protein/polypeptide is isolated or purified.

The human B7-H7 polypeptide is otherwise referred to as human endogenous retrovirus-H long terminal repeat-associating protein 2 (HHLA2) in the literature/databases but the function of B7-H7 was not previously identified. Human B7-H7 polypeptide is 414 amino acids in length and has been reported to contain the following: a signal sequence, an extraunderlined (signal peptide), the IgV domains are in bold (IgV domains), the IgC domain is italicized and in bold (IgC domain), the IgV/IgC domain overlap is italicized (IgV/IgC overlap), the transmembrane domain is underlined and in bold (transmembrane domain). The Ig domains of human B7-H7 comprise a pair of conserved cysteines that may form a disulphide bond. Cys residues at positions 159 and 210 of the IgC domain may form such disulphide bonds. Cys residues at positions 243 and 317 of the second IgV domain may form such disulphide bonds.

A representative amino acid sequence of the immature/precursor form of native *pan troglodytes* B7-H7, which comprises the signal peptide (underlined) and the mature *pan troglodytes* native B7-H7 (the amino acid sequence after the signal peptide), is provided:

```
                                                        (SEQ ID NO: 17)
MKAQTALSFFLILITSLSGSQAIFPMAFSTYVPVNEQIVIGRLDEDIILPSSFERGSEVV

IHWKYQDSYKVHSYYKGSDHLESQDPRYTNRTSLFYNEIQGNASLFSPRVSLLDE

GIYTCYVGTAIQVITNKVVLKVGVFLTPVMKYEKRNTNSFLICSVLSVYPRPITWKMDN

TPISENNMEETGSLDSFSINSPLNITGSNSSYECTIENSLLKQTWTGRWTMKDGLHK

MQSEHVSLSCQPVNDYFSPNQDFKVTWSRMKSGTFSILAYYLSSSQNTIINESRFS

WNKELINQSDFSMNLMDLNLSDSGEYLCNISSDEYTLLTIHTVHVEPSQETASHN

KGLWILVPSVILAAFLLIWTVKRCRAQPEARRSRHPADGAQQERYCVPPGEHCPSA

PDNGEENVRSVSGKV
```

With respect to SEQ ID NO:17, the reported signal is underlined (signal peptide), the IgV domains are in bold (IgV domains), the IgC domain is italicized and in bold (IgC domain), the IgV/IgC overlap is italicized (IgV/IgC overlap), and the transmembrane domain is underlined and in bold (transmembrane domain).

A representative amino acid sequence of the immature/precursor form of native *macaca mulatta* B7-H7, which comprises the signal peptide (underlined) and the mature *macaca mulatta* native B7-H7 (the amino acid sequence after the signal peptide), is provided:

```
                                                        (SEQ ID NO: 18)
MKAQTSFFLILISSLSGSQGIFLSAFFTYVPMNEQIIIGRLGEDIILPSSFERGSEVVIH

WKYQDSYNSYNVHSYYKGSGRLESQDTRYANRTSLFYNEIQNGNASLFFRRLSL

LDEGIYTCYVGTAIQAITNKVVLKVGVFLTPMMKYEKRNTNSFLICNVLSVYPRPIITWK

MDNTPISENNMQETGSLGPFSINSTLNITGSNSSYECTIENSLLKQTWTGRWTMKDG

LHKMQSEHVSLSCELVNDYFSPNQDFKVTWSRMESGISSILAYYLSSSQNTTFYE

SRFSWNKELKNQSDFSMNLTDLSLSDSGEYLCNISSDEYTLLTIHTVHVEPSQETA

SDNKGLWILVASLILVLCLIWLIWKVKCSTAQIEARRSRYPADGAQ
```

With respect to SEQ ID NO:18, the reported signal is underlined (signal peptide), the IgV domains are in bold (IgV domains), the IgC domain is italicized and in bold (IgC domain), the IgV/IgC overlap is italicized (IgV/IgC overlap), and the transmembrane domain is underlined and in bold (transmembrane domain).

A representative amino acid sequence comprising a partial sequence of the native bovine B7-H7 is provided:

```
                                                        (SEQ ID NO: 19)
MNEQIVTGRLGEDVILPCSFESGPNVVIHWKNQDTNVYSYYRDSDQLEKQDPRYVN

RISLFHGEIHNGNASLSFRRLTLQDEGIYVCYVGTSLGKITKKIVLKVGAFVTPVMKY

EKNTTNSFLICNVLSVFPYPIITWKVDNNTSISENNGKEVGSLGPFHINSRVNITGSNSS

YQCEIENPLLKQTWTGRWTRKDKERNTKRKEMHLQSSLEVKQIFSVNLHTVDLQYY

FSIK
```

FIG. 23 shows an alignment of the amino acid sequences of representative native human B7-H7, native *pan troglodytes* B7-H7 and native *macaca mulatta* B7-H7.

As used herein, the terms "native B7-H7" in the context of nucleic acids refer to any naturally occurring nucleic acid sequences encoding B7-H7, including the immature or precursor and mature forms. Non-limiting examples of Accession Nos. for the nucleotide sequence of native mammalian B7-H7 include: BC035971 (GI:23272002; *homo sapiens*) and AK126162 (GI:5726284; *homo sapiens*). A representative nucleotide sequence encoding the immature/precursor form of native human B7-H7, which comprises the nucleotide sequence encoding the signal peptide (underlined) and the nucleotide sequence encoding the mature human native B7-H7 (italicized), is provided:

```
                                                      (SEQ ID NO: 4)
   1 agttctcttc aagtcatgta atcgactttt ttgaattagt tttcagtttc attttgtttt
  61 ccctaattca agttgggaac acttcattt ccccaattca agttgggaac acttccttgg
 121 tatttccttg ctacatggac tttagcaaat gctactttac tctccttcca gctactcagg
 181 aggctgaggc aggagaatcg cttgaacccg ggaggcggag gttacagtga gccttttcct
 241 agttttactg ttggaagcct aactcacagg agagattatg caatacagtc ctgaagtcaa
 301 ggaaggagag catgtaggag aatactaacc ctgcacagat tgtgatggtg atgtggaata
 361 tactaaagcc tagaacgcac ctcctctgca tgactaatat gttctgcaca agacatgaag
 421 gcacagacag cactgtcttt cttcctcatt ctcataacat ctctgagtgg atctcaaggc
 481 atattccctt tggctttctt catttatgtt cctatgaatg aacaaatcgt cattggaaga
 541 cttgatgaag atataattct cccttcttca tttgagaggg gatccgaagt cgtaatacac
 601 tggaagtatc aagatagcta taaggttcat agttactaca aaggcagtga ccatttggaa
 661 agccaagatc ccagatatgc aaacaggaca tccctttttct ataatgagat tcaaaatggg
 721 aatgcgtcac tatttttcag aagagtaagc cttctggacg aaggaattta cacctgctat
 781 gtaggaacag caattcaagt gattacaaac aaagtggtgc taaaggtggg agttttctc
 841 acaccgtga tgaagtatga aaagaggaac acaaacagct tcttaatatg cagcgtgtta
 901 agtgtttatc ctcgtccaat tatcacgtgg aaaatggaca acacacctat ctctgaaaac
 961 aacatggaag aaacagggtc tttggattct ttttctatta acagcccact gaatattaca
1021 ggatcaaatt catcttatga atgtacaatt gaaaattcac tgctgaagca acatggaca
1081 gggcgctgga cgatgaaaga tggccttcat aaaatgcaaa gtgaacacgt ttcactctca
1141 tgtcaacctg taaatgatta ttttttcacca aaccaagact tcaaagttac ttggtccaga
1201 atgaaaagtg ggactttctc tgtcctggct tactatctga gctcctcaca aaatacaatt
1261 atcaatgaat cccgattctc atggaacaaa gagctgataa accagagtga cttctctatg
1321 aatttgatgg atcttaatct ttcagacagt ggggaatatt tatgcaatat ttcttcggat
1381 gaatatactt tacttaccat ccacacagtg catgtagaac cgagccaaga aacagcttcc
1441 cataacaaag gcttatggat tttggtgccc tctgcgattt tggcagcttt tctgctgatt
1501 tggagcgtaa aatgttgcag agcccagcta gaagccagga ggagcagaca ccctgctgat
1561 ggagcccaac aagaaagatg ttgtgtccct cctggtgagc gctgtcccag tgcacccgat
1621 aatggcgaag aaaatgtgcc tctttcagga aaagtatagg aaatgagaga agactgtgac
1681 aactcatgac ctgcatcctt aatatccagt gacttcatct ccccttttctt caccacaatt
1741 ccaggcaatg gcctgtcgga ccagacaatt ctaccactgc aaagagttgt aaccatttc
1801 tggtatcaca tttatttttc aagacatact tttcaagaca tcattcactg acccactacc
1861 tgcattgagt ataaatgcct ggatgttaag gattccaatt taactttgaa aagaactgtc
1921 tcattcattt acatttctgt tacagtcagc ccaggaggtt acagtgagct ctccactaag
1981 aatctggaag aaatgcatca ctaggggttg attcccaatc tgatcaactg ataatgggtg
2041 agagagcagg taagagccaa agtcaccta gtggaaaggt taaaaccag agcctggaaa
2101 ccaagatgat tgatttgaca aggtatttta gtctagtttt atatgaacgg ttgtatcagg
2161 gtaaccaact cgatttggga tgaatcttag ggcaccaaag actaagacag tatctttaag
```

Another representative nucleotide sequence encoding the native human B7-H7 is provided:

(SEQ ID NO: 13)
ATGAAGGCACAGACAGCACTGTCTTTCTTCCTCATTCTCATAACATCTCT
GAGTGGATCTCAAGGCATATTCCCTTTGGCTTTCTTCATTTATGTTCCTA
TGAATGAACAAATCGTCATTGGAAGACTTGATGAAGATATAATTCTCCCT
TCTTCATTTGAGAGGGGATCCGAAGTCGTAATACACTGGAAGTATCAAGA
TAGCTATAAGGTTCACAGTTACTACAAAGGCAGTGACCATTTGGAAAGCC
AAGATCCCAGATATGCAAACAGGACATCCCTTTTCTATAATGAGATTCAA
AATGGGAATGCGTCGCTATTTTTCAGAAGAGTAAGCCTTCTGGACGAAGG
AATTTACACCTGCTATGTAGGAACAGCAATTCAAGTGATTACAAACAAAG
TGGTGCTAAAGGTGGGAGTTTTTCTCACACCCGTGATGAAGTATGAAAAG
AGGAACACAAACAGCTTCTTAATATGCAGCGTGTTAAGTGTTTATCCTCG
TCCAATTATCACGTGGAAAATGGACAACACACCTATCTCTGAAAACAACA
TGGAAGAAACAGGGTCTTTGGATTCTTTTTCTATTAACAGCCCACTGAAT
ATTACAGGATCAAATTCATCTTATGAATGTACAATTGAAAATTCACTGCT
GAAGCAAACATGGACAGGGCGCTGGACGATGAAAGATGGCCTTCATAAAA
TGCAAAGTGAACACGTTTCACTCTCATGTCAACCTGTAAATGATTATTTT
TCACCAAACCAAGACTTCAAAGTTACTTGGTCCAGAATGAAAAGTGGGAC
TTTCTCTGTCCTGGCTTACTATCTGAGCTCCTCACAAAATACAATTATCA
ATGAATCCCGATTCTCATGGAACAAAGAGCTGATAAACCAGAGTGACTTC
TCTATGAATTTGATGGATCTTAATCTTTCAGACAGTGGGGAATATTTATG
CAATATTTCTTCGGATGAATATACTTTACTTACCATCCACACAGTGCATG
TAGAACCGAGCCAAGAAACAGCTTCCCATAACAAAGGCTTATGGATTTTG
GTGCCCTCTGCGATTTTGGCAGCTTTTCTGCTGATTTGGAGCGTAAAATG
TTGCAGAGCCCAGCTAGAAGCCAGGAGGAGCAGACACCCTGCTGATGAG
CCCAACAAGAAAGATGTTGTGTCCCTCCTGGTGAGCGCTGTCCCAGTGCA
CCCGATAATGGCGAAGAAAATGTGAGGTCTGTTTCTGGGAAAGTG

A representative nucleotide sequence encoding *pan troglodytes* is provided:

(SEQ ID NO: 14)
ATGAAGGCACAGACAGCACTGTCTTTCTTCCTCATTCTCATAACATCTCT
GAGTGGATCTCAAGCCATATTCCCTATGGCTTTCTCCACTTATGTTCCTG
TGAATGAACAAATCGTCATTGGAAGACTTGATGAAGATATAATTCTCCCT
TCTTCATTTGAGAGGGGATCGGAAGTCGTAATACACTGGAAGTATCAAGA
TAGCTATAAGGTTCACAGTTACTACAAAGGCAGTGACCATTTGGAAAGCC
AAGATCCCAGATATACAAACAGGACATCCCTTTTCTATAATGAGATTCAA
GGGAATGCGTCGCTATTTTCCCCAAGAGTAAGCCTTCTGGACGAAGGAAT
TTACACCTGCTATGTAGGAACAGCAATTCAAGTGATTACAAACAAAGTGG
TGCTAAAGGTGGGAGTTTTTCTCACACCCGTGATGAAGTATGAAAAGAGG
AACACAAACAGCTTCTTAATATGCAGCGTGTTAAGTGTTTATCCTCGTCC
AATTATCACGTGGAAAATGGACAACACACCTATCTCTGAAAACAACATGG
AAGAAACAGGGTCTTTGGATTCTTTTTCTATTAACAGCCCACTGAATATT
ACAGGATCAAATTCATCTTATGAATGTACAATTGAAAATTCACTGCTGAA
GCAAACATGGACAGGGCGCTGGACAATGAAAGATGGCCTTCATAAAATGC
AAAGTGAACACGTTTCACTCTCATGTCAACCTGTAAATGATTATTTTTCA
CCAAACCAAGACTTCAAAGTTACTTGGTCCAGAATGAAAAGTGGGACTTT
CTCTATCCTGGCTTACTATCTGAGCTCCTCACAAAATACAATTATCAATG
AATCCCGATTCTCATGGAACAAAGAGCTGATAAACCAGAGTGACTTCTCT
ATGAATTTGATGGATCTTAATCTTTCAGACAGTGGGGAATATTTATGCAA
TATTTCTTCAGATGAATATACTTTACTTACCATCCACACAGTGCATGTAG
AACCAAGCCAAGAAACAGCTTCCCATAACAAAGGCTTATGGATTTTGGTG
CCCTCTGTGATTTTGGCAGCTTTTCTGCTGATTTGGACAGTAAAACGTTG
CAGAGCCCAGCCAGAAGCCAGGAGGAGCAGACACCCTGCTGATGGAGCCC
AACAAGAAAGATATTGTGTCCCTCCTGGTGAGCACTGTCCCAGTGCACCC
GATAATGGCGAAGAAAATGTGAGGTCTGTTTCTGGGAAAGTG

A representative nucleotide sequence encoding *macaca mulatta* is provided:

(SEQ ID NO: 15)
ATGAAGGCACAGACGTCTTTCTTCCTCATTCTCATATCATCTCTGAGTGG
ATCTCAAGGCATATTCCTTTCAGCTTTCTTCACTTACGTTCCTATGAATG
AACAAATCATCATTGGAAGACTTGGTGAAGATATAATTCTCCCTTCTTCA
TTTGAGAGGGGATCCGAAGTTGTAATACACTGGAAGTATCAAGACAGCTA
CAATAGCTACAATGTTCACAGTTACTACAAAGGCAGTGGCCGTTTGGAAA

-continued

```
GCCAAGATACCAGATATGCAAACAGGACATCCCTTTTCTATAATGAGATT

CAAAATGGGAATGCGTCTCTATTTTTCAGAAGATTAAGCCTTCTGGATGA

AGGAATTTATACCTGCTATGTAGGAACAGCAATTCAAGCGATTACAAACA

AAGTGGTGCTAAAGGTGGGAGTTTTTCTCACACCCATGATGAAGTATGAA

AAGAGGAACACAAACAGCTTCTTAATATGCAACGTGTTAAGTGTTTATCC

TCGTCCAATTATCACGTGGAAAATGGACAACACACCTATCTCTGAAAACA

ATATGCAAGAAACAGGGTCTTTGGGTCCTTTTTCGATTAACAGCACGCTG

AATATTACAGGATCAAATTCATCTTATGAATGTACAATTGAAAATTCACT

TCTGAAGCAAACATGGACAGGGCGCTGGACAATGAAAGATGGCCTTCATA

AAATGCAAAGTGAACATGTTTCACTCTCATGTGAACTTGTAAATGATTAT

TTTTCACCAAACCAAGACTTCAAAGTTACTTGGTCCAGAATGGAAAGTGG

GATTTCCTCTATCCTGGCTTACTATCTGAGCTCCTCACAAAATACAACTT

TCTATGAATCCCGATTCTCATGGAACAAAGAGCTGAAAAACCAGAGTGAC

TTCTCTATGAATTTGACGGATCTTAGTCTTTCAGACAGTGGGGAATATTT

GTGCAATATTTCTTCGGATGAATATACTTTACTCACCATACACACGGTGC

ACGTAGAACCAAGCCAAGAAACAGCTTCCGATAACAAAGGCTTATGGATT

TTGGTGGCCAGTCTGATTTTGGTGCTCTGTCTGATTTGGCTGATTGGAA

AGTAAAATGTTCCACAGCCCAAATAGAAGCCAGGAGGAGCAGATACCCTG

CTGATGGAGCCCAA
```

A representative nucleotide sequence encoding bovine is provided:

```
                                       (SEQ ID NO: 16)
ATGAATGAGCAAATCGTCACTGGAAGACTAGGTGAAGATGTCATTCTCCC

TTGCTCATTTGAGAGTGGACCCAATGTCGTAATTCACTGGAAGAACCAAG

ATACCAATGTTTACTCATACTACAGAGACAGCGACCAGTTGGAAAAGCAA

GATCCCAGATATGTAAACAGGATATCCCTCTTCCATGGTGAGATTCACAA

TGGGAATGCCTCCCTGTCTTTCAGAAGATTAACCCTTCAGGATGAAGGAA

TCTACGTATGCTATGTGGGAACATCACTTGGAAAAATCACAAAGAAAATA

GTCCTAAAAGTGGGAGCTTTTGTCACACCTGTGATGAAGTATGAAAAGAA

TACCACCAACAGCTTCTTAATATGCAATGTGTTAAGTGTTTTTCCTTATC

CAATTATCACATGGAAAGTGGATAATAATACATCTATCTCTGAAAACAAT

GGGAAAGAAGTTGGATCTTTGGGTCCTTTTCATATAAACAGCAGAGTAAA

TATTACAGGATCAAATTCATCATATCAGTGTGAAATTGAAAACCCACTGC

TGAAGCAAACATGGACAGGAAGATGGACAAGGAAAGATAAAGAAAGGAAT

ACAAAAAGGAAGGAAATGCATTTGCAGAGTTCACTAGAAGTAAAGCAAAT

TTTTTCTGTAAATCTCCATACAGTGGACTTACAATATTATTTCAGTATAA

AA
```

In a specific embodiment, the nucleic acid is an isolated or purified nucleic acid. In some embodiments, nucleic acids encode the immature or precursor form of a naturally occurring mammalian B7-H7. In other embodiments, nucleic acids encode the mature form of a naturally occurring mammalian B7-H7. In a specific embodiment, nucleic acids encoding native B7-H7 encode the precursor form of naturally occurring human B7-H7. In another embodiment, nucleic acids encoding native B7-H7 encode the mature form of naturally occurring human B7-H7.

As used herein, the term "native B7-H7CR" in the context of proteins or polypeptides refers to any naturally occurring B7-H7CR amino acid sequences, including immature or precursor and mature forms. Non-limiting examples of Accession Nos. for the amino acid sequence of native mammalian B7-H7CR include: Q96BF3-1 (*homo sapiens*), Q96BF3-2 (*homo sapiens*), and NP_653216.1 (GI: 21389429; *homo sapiens*). A representative amino acid sequence of the immature/precursor form of one isoform of native human B7-H7CR, which comprises the signal peptide (underlined) and the mature human native B7-H7CR (italicized), is provided:

```
                                       (SEQ ID NO: 5)
MGSPGMVLGL LVQIWALQEA SSLSVQQGPN LLQVRQGSQA

TLVCQVDQAT AWERLRVKWT KDGAILCQPY ITNGSLSLGV

CGPQGRLSWQ APSHLTLQLD PVSLNHSGAY VCWAAVEIPE

LEEAEGNITR LFVDPDDPTQ NRNRIASFPG FLFVLLGVGS

MGVAAIVWGA WFWGRRSCQQ RDSGNSPGNA FYSNVLYRPR

GAPKKSEDCS GEGKDQRGQS IYSTSFPQPA PRQPHLASRP

CPSPRPCPSP RPGHPVSMVR VSPRPSPTQQ PRPKGFPKVG EE.
```

The amino acid sequence of a second isoform of native human B7-H7CR differs from this first isoform in that amino acid residues 186 to 189 of SEQ ID NO:5 are missing in the second isoform.

Another representative amino acid sequence of native human B7-H7CR is provided:

```
                                       (SEQ ID NO: 20)
MGSPGMVLGLLVQIWALQEASSLSVQQGPNLLQVRQGSQATLVCQVDQAT

AWERLRVKWTKDGAILCQPYITNGSLSLGVCGPQGRLSWQAPSHLTLQLD

PVSLNHSGAYVCWAAVEIPELEEAEGNITRLFVDPDDPTQNRNRIASFPG

FLFVLLGVGSMGVAAIVWGAWFWGRRSCQQRDSGNSPGNAFYSNVLYRPR

GPPKKSEDCSGEGKDQRGQSIYSTSFPQPAPRQPHLASRP

CPSPRPCPSPRPGHPVSMVRVSPRPSPTQQPRPKGFPKVGEE
```

A representative amino acid sequence of native *pan troglodytes* B7-H7CR is provided:

```
                                       (SEQ ID NO: 21)
MGSPGMVLGLLVQIWALQEASSLSVQQGPNLLQVRQGSQATLVCQVDQAP

AWERLRVKWTKDGAILCQPYITNGSLSLGVCGPQGRLSWQAPSHLTLQLD

PVNLNHSGAYVCWAAVEIPELEEAESNITRLFVDPDDPTQNRNRITSFPG

FLFVLLGVGSGAVAAIVLGAWFWGRRSCQQRDSGNSPGNAFYSNVLYRPR

GAPKKSEDCSGEGKDQRGQSIYSTSFPQPATRQPHLAPRPCPSPRPCPSP

RPGHPVSMVRVSPRPSPTQQPRPKGFPKVG EE
```

A representative amino acid sequence of native *bos taurus* B7-H7CR is provided:

(SEQ ID NO: 22)
MGSPGTVLVLLVQFWVLQGVTGLTVQQAPKLLQVRQDSQVTLACQVMHAQ

AWEWLRVEWIKDADIFCQTHIINGSLSKDVCGPQGWLSWQPPGNLTLQLN

HVSLNDSGLYVCGATVEIPVWEEAQGNGTQLLVERGVWLQDHSFSGLYFA

PLVTGAVAVAVFALGAGIWGRRRCRNGDAGSPIYSNVLYRPRRAARKKAW

PVERKVLDSEDQKGQSFYSISFPQRPKSHMAPKFCPSPRPIHPISAVRIS

PGPGSSGQPRSRGFLEVGREIRTAGEPEKTYPQRLYKDVTYS

Figure 24:
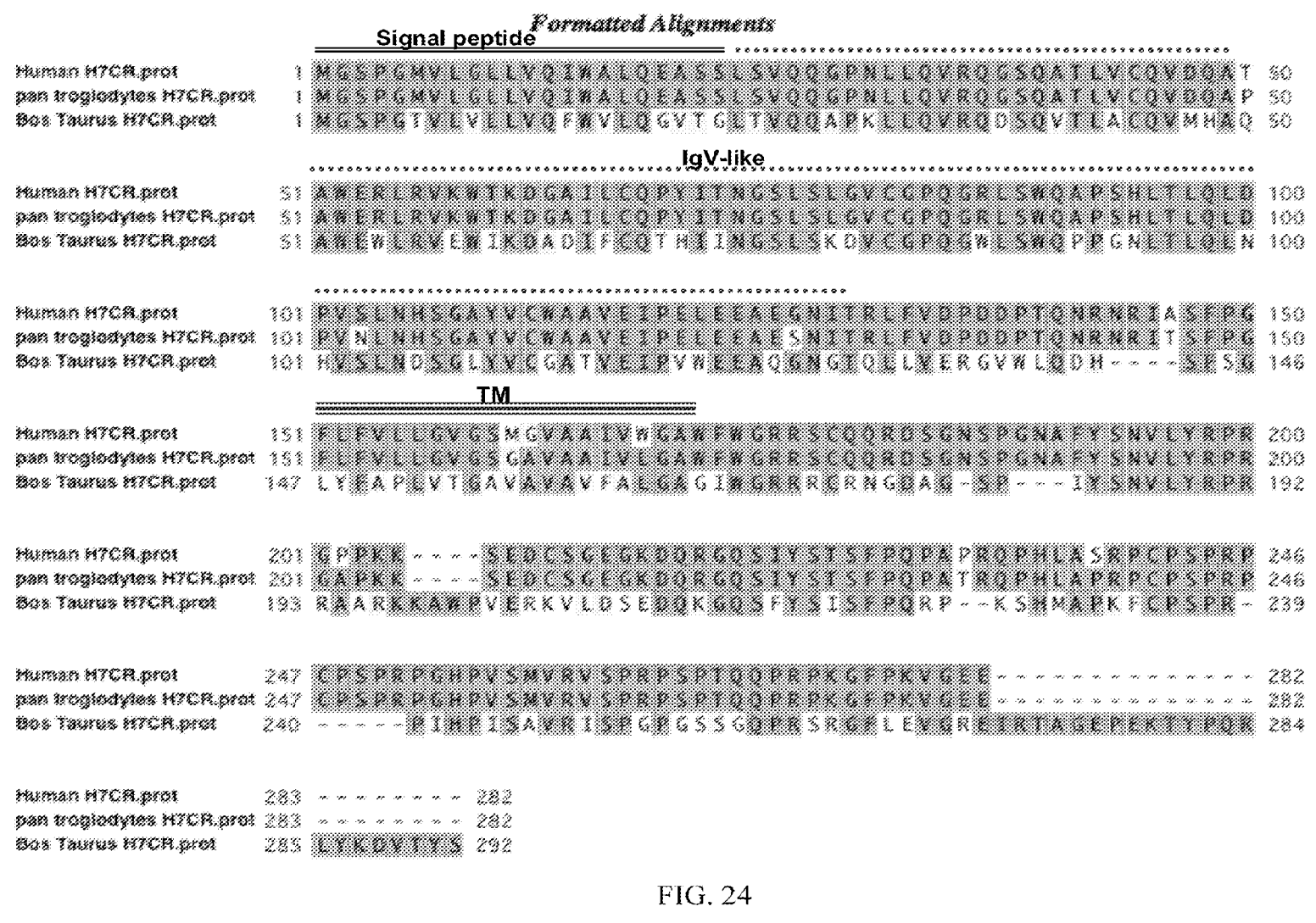

FIG. 24 shows an alignment of the amino acid sequences of representative native human B7-H7CR, native *pan troglodytes* B7-H7CR, and native *bos taurus* B7-H7CR.

In some embodiments, native B7-H7CR is the immature or precursor form of a naturally occurring mammalian B7-H7CR. In other embodiments, native B7-H7CR is the mature form of a naturally occurring mammalian B7-H7CR. In a specific embodiment, native B7-H7CR is the precursor form of naturally occurring human B7-H7CR. In another embodiment, native B7-H7CR is the mature form of naturally occurring human B7-H7CR. In one embodiment, the native B7-H7CR protein/polypeptide is isolated or purified.

The human B7-H7CR polypeptide is otherwise referred to as transmembrane and immunoglobulin domain containing 2 (TMIGD2) in the literature/databases but the function of B7-H7CR was not previously elucidated. At least one isoform of human B7-H7CR polypeptide is 282 amino acids in length and has been reported to contain the following: a signal sequence, an immunoglobulin-like (Ig-like) domain, a transmembrane domain, and a cytoplasmic domain. In particular, at least one isoform of human B7-H7CR has been reported to contain the following: a signal sequence at amino acid residues 1 to 22 of the sequence at Accession No. Q96BF3-1, an Ig-like domain at amino acid residues 23 to 129 of the sequence at Accession No. Q96BF3-1, an extracellular domain at amino acid residues 23 to 150 of the sequence at Accession No. Q96BF3-1, a transmembrane domain at amino acid residues 151 to 171 of the sequence at Accession No. Q96BF3-1, and a cytoplasmic domain at amino acid residues 172 to 282 of the sequence at Accession No. Q96BF3-1. The cytoplasmic domain of human B7-H7CR includes a proline rich region (amino acid residues 227-277), which may be involved in binding to SH3 domain-containing adaptor proteins. The cytoplasmic domain of human B7-H7CR includes a serine residue (S220), which may be phosphorylated. Human B7-H7CR is also predicted to have N-linked glycosylation sites at amino acid residues 73, 105, and 127. The IgV domain of human B7-H7CR comprises a pair of conserved cysteines at positions 44 and 112 that may form a disulphide bond. Cys residues at positions 67 and 81 may also form structurally important disulphide bonds. In addition, tyrosine residues of importance are found at positions 192, 197, and 222 of native human B7-H7CR (e.g., SEQ ID NO:5).

Two splices of human B7-H7CR have been predicted with the difference between the splice forms being the presence or absence of amino acid residues 186-189. There are two known naturally occurring variants of human B7-H7CR (W168L and A202P).

As used herein, the term "native B7-H7CR" in the context of nucleic acids refers to any naturally occurring nucleic acid sequences encoding B7-H7CR, including the immature or precursor and mature forms. Non-limiting examples of Accession Nos. for the nucleotide sequence of native mammalian B7-H7CR include: AK358964 (*homo sapiens*) and BC015655 (*homo sapiens*). A representative nucleotide sequence encoding the immature/precursor form of native human B7-H7CR, which comprises the nucleotide sequence encoding the signal peptide (underlined) and the nucleotide sequence encoding the mature human native B7-H7CR (italicized), is provided:

```
                                                        (SEQ ID NO: 6)
        ggaagtctgt caactgggag ggggagaggg gggtgatggg ccaggaatgg ggtccccggg    60
catggtgctg ggcctcctgg tgcagatctg ggccctgcaa gaagcctcaa gcctgagcgt   120
gcagcagggg cccaacttgc tgcaggtgag gcagggcagt caggcgaccc tggtctgcca   180
ggtggaccag gccacagcct gggaacggct ccgtgttaag tggacaaagg atggggccat   240
cctgtgtcaa ccgtacatca ccaacggcag cctcagcctg ggggtctgcg ggccccaggg   300
acggctctcc tggcaggcac ccagccatct caccctgcag ctggaccctg tgagcctcaa   360
ccacagcggg gcgtacgtgt gctgggcggc cgtagagatt cctgagttgg aggaggctga   420
gggcaacata acaaggctct ttgtggaccc agatgacccc acacagaaca gaaaccggat   480
cgcaagcttc ccaggattcc tcttcgtgct gctgggggtg ggaagcatgg gtgtggctgc   540
gatcgtgtgg ggtgcctggt tctggggccg ccgcagctgc cagcaaaggg actcaggtaa   600
cagcccagga aatgcattct acagcaacgt cctataccgg cccgggggc ccccaaagaa   660 gagtgaggac tgctctggag aggggaagga ccagaggggc cagagcattt attcaacctc   720
cttcccgcaa ccggcccccc gccagccgca cctggcgtca agaccctgcc ccagcccgag   780
accctgcccc agcccaggc ccggccaccc cgtctctatg gtcagggtct ctcctagacc   840
aagccccacc cagcagccga ggccaaaagg gttccccaaa gtgggagagg agtgagagat   900
cccaggagac ctcaacagga ccccacccat aggtacacac aaaaaagggg ggatcgaggc   960
cagacacggt ggctcacgcc tgtaatccca gcagtttggg aagccgaggc gggtggaaca  1020
```

-continued

```
cttgaggtca ggggtttgag accagcctgg cttgaacctg ggaggcggag gttgcagtga    1080
gccgagattg cgccactgca ctccagcctg ggcgacagag tgagactccg tctcaaaaaa    1140
aacaaaaagc aggaggattg ggagcctgtc agccccatcc tgagacccccg tcctcatttc   1200 tgtaatgatg gatctcgctc ccactttccc ccaagaacct aataaaggct tgtgaagaaa    1260
aaaaaaaaaa aaaaaa.
```

Another representative nucleotide sequence encoding a native human B7-H7CR is provided:

(SEQ ID NO: 23)
```
  1 atggggtccc cgggcatggt gctgggcctc ctggtgcaga tctgggccct gcaagaagcc
 61 tcaagcctga gcgtgcagca ggggcccaac ttgctgcagg tgaggcaggg cagtcaggcg
121 accctggtct gccaggtgga ccaggccaca gcctgggaac ggctccgtgt taagtggaca
181 aaggatgggg ccatcctgtg tcaaccgtac atcaccaacg gcagcctcag cctgggggtc
241 tgcggccccc aggacggct ctcctggcag gcacccagcc atctcaccct gcagctggac
301 cctgtgagcc tcaaccacag cggggcgtac gtgtgctggg cggccgtaga gattcctgag
361 ttggaggagg ctgagggcaa cataacaagg ctctttgtgg acccagatga ccccacacag
421 aacagaaacc ggatcgcaag cttcccagga ttcctcttcg tgctgctggg ggtgggaagc
481 atgggtgtgg ctgcgatcgt gtggggtgcc tggttctggg gccgccgcag ctgccagcaa
541 agggactcag gtaacagccc aggaaatgca ttctacagca acgtcctata ccggccccgg
601 gggcccccaa agaagagtga ggactgctct ggagagggga aggaccagag gggccagagc
661 atttattcaa cctccttccc gcaaccggcc ccccgccagc cgcacctggc gtcaagaccc
721 tgccccagcc cgagaccctg ccccagcccc aggcccggcc accccgtctc tatggtcagg
781 gtctctccta gaccaagccc cacccagcag ccgaggccaa aagggttccc caaagtggga
841 gaggagtga
```

A representative nucleotide sequence encoding native *pan troglodytes* is provided:

(SEQ ID NO: 24)
```
  1 atggggtccc cgggcatggt gctgggcctc ctggtgcaga tctgggccct gcaagaagcc
 61 tcaagcctga gcgtgcagca ggggcccaac ttgctgcagg tgaggcaggg cagtcaggcg
121 accctggtct gccaggtgga ccaggcccca gcctgggaac ggctccgtgt taagtggaca
181 aaggatgggg ccatcctgtg tcaaccgtac atcaccaacg gcagcctcag cctgggggtc
241 tgcggccccc aggacggct ctcctggcag gcacccagcc atctcaccct gcagctggac
301 cctgtgaacc tcaaccacag cggggcgtac gtgtgctggg cggccgtaga gattcctgag
361 ttggaggagg ctgagagcaa cataacaagg ctctttgtgg acccagatga ccccacacag
421 aacagaaacc ggatcacaag cttcccagga ttcctcttcg tgctgctggg ggtgggaagc
481 ggggctgtgg ccgcgatcgt gttgggtgcc tggttctggg gccgccgcag ctgccagcaa
541 agggactcag gtaacagccc aggaaatgca ttctacagca acgtcctata ccggccccgg
601 gggcccccaa agaagagtga ggactgctct ggagagggga aggaccagag gggccagagc
661 atttattcaa cctccttccc gcaaccgcc accgccagc cgcacctggc gccaagaccc
721 tgccccagcc cgagaccctg ccccagcccc aggcccggcc accccgtctc tatggtcagg
```

A representative nucleotide sequence encoding native *bos taurus* is provided:

(SEQ ID NO: 25)
```
  1 atggggtccc cgggcacagt gctggtcctc ctggtgcagt tctgggtcct acaaggagtc 61 acaggcctga ctgtgcagca ggcaccgaag ttgctgcagg tgagacagga cagccaggtg 121 actttggcct gccaggtgat gcacgcccag gcctgggagt ggctccgtgt cgagtggatc 181 aaggatgctg acatcttttg ccagacacac atcatcaatg gcagtctgag caaggatgtc 241 tgtgggcctc agggatggct atcctggcag ccgcctggca acctcaccct gcagctgaac 301 cacgtgagcc tcaatgacag tggactctat gtgtgtgggg caaccgtgga gatccctgtt 361 tgggaggagg cccagggcaa cgggacgcag ctcctggtgg agagaggtgt ctggctgcag 421 gaccacagct tctcaggcct ctacttcgcg ccgctggtga cggggccgt ggccgttgcc 481 gttttcgctc tgggcgctgg gatctggggc cgccgccgct gccggaacgg ggatgcaggc 541 agtccaatct acagcaacgt cctataccgg ccccggagag ccgcaaggaa gaaggcatgg 601 cctgtggaaa ggaaggtgct ggacagtgag gatcagaagg gccaaagctt ctactcgatc 661 tctttccccc agcgcccaa gtcgcatatg gctcccaaat tttgccccag tcccagaccc 721 attcacccca tctctgcagt cagaatctct cctggcccag gctcctctgg gcagccaagg 781 tcaagagggt tccttgaagt gggaagagaa atcagaaccg caggagagcc agagaagacc 841 taccccagc gactatataa agatgtgact tattcctag
```

Figure 25:
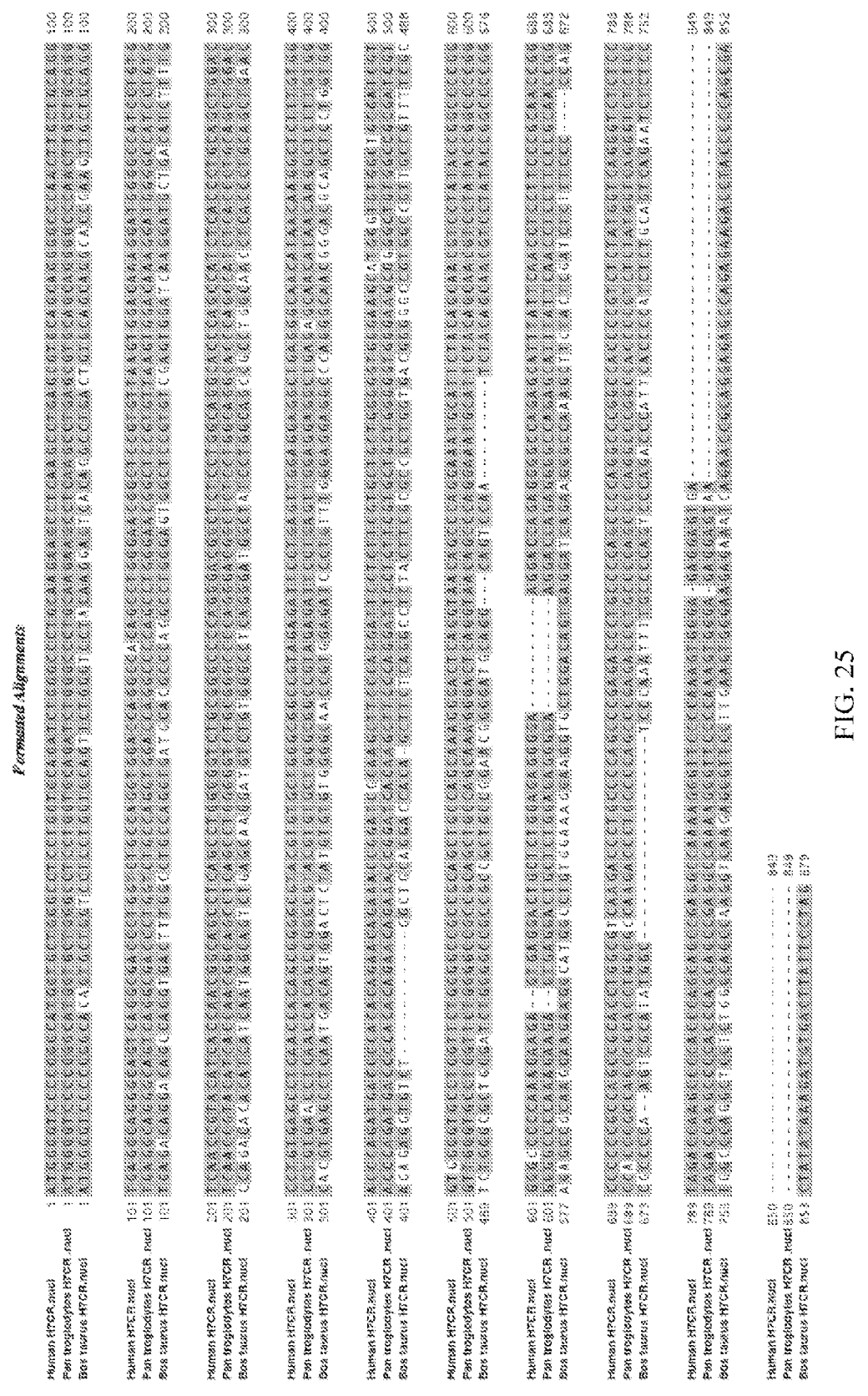

A nucleic acid alignment of representative native human B7-H7CR, native *pan troglodytes* B7-H7CR, and native *bos taurus* B7-H7CR is included as FIG. 25.

In a specific embodiment, the nucleic acid is an isolated or purified nucleic acid. In some embodiments, nucleic acids encode the immature or precursor form of a naturally occurring mammalian B7-H7CR. In other embodiments, nucleic acids encode the mature form of a naturally occurring mammalian B7-H7CR. In a specific embodiment, nucleic acids encoding native B7-H7CR encode the precursor form of naturally occurring human B7-H7CR. In another embodiment, nucleic acids encoding native B7-H7CR encode the mature of naturally occurring human B7-H7CR.

As used herein, the term "native CD28" in the context of proteins or polypeptides refers to any naturally occurring CD28 amino acid sequences, including immature or precursor and mature forms. Non-limiting examples of Accession Nos. for the amino acid sequence of various species of native mammalian CD28 include: P10747-1 (*homo sapiens*), P10747-2 (*homo sapiens*), P10747-3 (*homo sapiens*), P10747-4 (*homo sapiens*), P10747-5 (*homo sapiens*), P10747-6 (*homo sapiens*), NP_006130.1 (GI:5453611; *homo sapiens*), P31041-1 (mouse), and Q28071-1 (bovine). A representative amino acid sequence of one isoform of the immature/precursor form of native human CD28, which comprises the signal peptide (underlined) and the mature human native CD28 (italicized), is provided:

(SEQ ID NO: 7)
MLRLLLALNL FPSIQVTGNK ILVKQSPMLV AYDNAVNLSC

KYSYNLFSRE FRASLHKGLD SAVEVCVVYG NYSQQLQVYS

KTGFNCDGKL GNESVTFYLQ NLYVNQTDIY FCKIEVMYPP

PYLDNEKSNG TIIHVKGKHL CPSPLFPGPS KPFWVLVVVG

GVLACYSLLV TVAFIIFWVR SKRSRLLHSD YMNMTPRRPG

PTRKHYQPYA PPRDFAAYRS.

There are a number of isoforms of CD28 that have been reported (see, e.g., Accession Nos. P10747-1 to P10747-6 for various isoforms of human CD28). In some embodiments, native CD28 is the immature or precursor form of a naturally occurring mammalian CD28. In other embodiments, native CD28 is the mature form of a naturally occurring mammalian CD28. In a specific embodiment, native CD28 is the precursor form of naturally occurring human CD28. In another embodiment, native CD28 is the mature form of naturally occurring human CD28. In a specific embodiment, the native CD28 is not a naturally occurring mouse CD28. In one embodiment, the native CD28 protein/polypeptide is isolated or purified.

At least one isoform of human CD28 polypeptide is 220 amino acids in length and has been reported to contain the following: a signal sequence, an immunoglobulin-like (Ig-like) V-type domain, an extracellular domain, a transmembrane domain, and a cytoplasmic domain. In particular, a human CD28 isoform has been reported to contain the following: a signal sequence at amino acid residues 1 to 18 of the sequence at Accession No. P10747-1, an Ig-like V-type domain at amino acid residues 28 to 137 of the sequence at Accession No. P10747-1, an extracellular domain at amino acid residues 19 to 152 of the sequence at Accession No. P10747-1, a transmembrane domain at amino acid residues 153 to 179 of the sequence at Accession No. P10747-1, and a cytoplasmic domain at amino acid residues 180 to 220 of the sequence at Accession No. P10747-1.

As used herein, the term "native CD28" in the context of nucleic acids refers to any naturally occurring nucleic acid sequences encoding CD28, including the immature or pre- cursor and mature forms. Non-limiting examples of Accession Nos. for the amino acid sequence of various species of native mammalian CTLA-4 include: P16410-1 (*homo sapiens*), NP_001032720.1 (GI:83700231; *homo sapiens*), NP_005205.2 (GI:21361212; *homo sapiens*), P09793-1 (mouse), NP_033973.2 (mouse), and Q28090-1 (bovine). A representative amino acid sequence of the immature/precursor form of native human CTLA-4, which comprises the signal peptide (underlined) and the mature human native CTLA-4 (italicized), is provided:

```
                                                          (SEQ ID NO: 9)
         MACLGFQRHK AQLNLATRTW PCTLLFFLLF IPVFCKAMHV AQPAVVLASS RGIASFVCEY

ASPGKATEVR VTVLRQADSQ VTEVCAATYM MGNELTFLDD SICTGTSSGN QVNLTIQGLR

AMDTGLYICK VELMYPPPYY LGIGNGTQIY VIDPEPCPDS DFLLWILAAV SSGLFFYSFL

LTAVSLSKML KKRSPLTTGV YVKMPPTEPE CEKQFQPYFI PIN.
``` cursor and mature forms. Non-limiting examples of Accession Nos. for the nucleotide sequence of various species of native mammalian CD28 include: J02988.1 (GI:338444; *homo sapiens*), BC093698.1 (GI:62739452; *homo sapiens*), M34563.1 (GI:19248; mouse), and X93304.1 (GI:1369933; bovine). A representative nucleotide sequence encoding the immature/precursor form of native human CD28, which comprises the nucleotide sequence encoding the signal peptide (underlined) and the nucleotide sequence encoding the mature human native CD28 (italicized), is provided:

In some embodiments, native CTLA-4 is the immature or precursor form of a naturally occurring mammalian CTLA-4. In other embodiments, native CTLA-4 is the mature form of a naturally occurring mammalian CTLA-4. In a specific embodiment, native CTLA-4 is the precursor form of naturally occurring human CTLA-4. In another embodiment, native CTLA-4 is the mature form of naturally occurring human CTLA-4. In one embodiment, the native CTLA-4 protein/polypeptide is isolated or purified.

```
                                                          (SEQ ID NO: 8)
    1 ggaggagggg ctggaaccct agcccatcgt caggacaaag atgctcaggc tgctcttggc 61 tctcaactta ttcccttcaa ttcaagtaac aggaaacaag attttggtga agcagtcgcc 121 catgcttgta gcgtacgaca atgcggtcaa ccttagctgc aagtattcct acaatctctt 181 ctcaagggag ttccgggcat cccttcacaa aggactggat agtgctgtgg aagtctgtgt 241 tgtatatggg aattactccc agcagcttca ggtttactca aaaacggggt tcaactgtga 301 tgggaaattg ggcaatgaat cagtgacatt ctacctccag aatttgtatg ttaaccaaac 361 agatatttac ttctgcaaaa ttgaagttat gtatcctcct ccttacctag acaatgagaa 421 gagcaatgga accattatcc atgtgaaagg gaaacacctt tgtccaagtc ccctatttcc 481 cggaccttct aagccctttt gggtgctggt ggtggttggt ggagtcctgg cttgctatag 541 cttgctagta acagtggcct ttattatttt ctgggtgagg agtaagagga gcaggctcct 601 gcacagtgac tacatgaaca tgactccccg ccgcccgggg cccacccgca agcattacca 661 gccctatgcc ccaccacgcg acttcgcagc ctatcgctcc tgacacggac gcctatccag 721 aagccagccg gctggcagcc cccatctgct caa.
```

In a specific embodiment, the nucleic acid is an isolated or purified nucleic acid. In some embodiments, nucleic acids encode the immature or precursor form of a naturally occurring mammalian CD28. In other embodiments, nucleic acids encode the mature form of a naturally occurring mammalian CD28. In a specific embodiment, nucleic acids encoding native CD28 encode the precursor form of naturally occurring human CD28. In another embodiment, nucleic acids encoding native CD28 encode the mature of naturally occurring human CD28. In a specific embodiment, the nucleic acids do not encode native mouse CD28.

As used herein, the term "native CTLA-4" in the context of proteins or polypeptides refers to any naturally occurring CTLA-4 amino acid sequences, including immature or pre- CTLA-4 polypeptide is also known as Cytotoxic T-lymphocyte-associated antigen 4 and CD52. At least one isoform of human CTLA-4 polypeptide is 223 amino acids in length and has been reported to contain the following: a signal sequence, an immunoglobulin-like (Ig-like) V-type domain, an extracellular domain, a transmembrane domain, and a cytoplasmic domain. In particular, a human CTLA-4 isoform has been reported to contain the following: a signal sequence at amino acid residues 1 to 35 of the sequence at Accession No. P16410-1, an Ig-like V-type domain at amino acid residues 39 to 140 of the sequence at Accession No. P16410-1, an extracellular domain at amino acid residues 36 to 161 of the sequence at Accession No. P16410-1, a transmembrane domain at amino acid residues 162 to 182 of the sequence at Accession No. P16410-1, and a cytoplasmic domain at amino acid residues 183 to 223 of the sequence at Accession No. P16410-1.

As used herein, the term "native CTLA-4" in the context of nucleic acids refers to any naturally occurring nucleic acid sequences encoding CTLA-4, including the immature or precursor and mature forms. Non-limiting examples of Accession Nos. for the nucleotide sequence of various species of native mammalian CTLA-4 include: AF414120.1 (GI: 15778585; *homo sapiens*), X05719.1 (GI:50592; mouse), and X93305.1 (GI:1369935; bovine). A representative nucleotide sequence encoding the immature/precursor form of native human CTLA-4, which comprises the nucleotide sequence encoding the signal peptide (underlined) and the nucleotide sequence encoding the mature human native CTLA-4 (italicized), is provided:

(SEQ ID NO: 10)
```
   1 cttctgtgtg tgcacatgtg taatacatat ctgggatcaa agctatctat ataaagtcct
  61 tgattctgtg tgggttcaaa cacatttcaa agcttcagga tcctgaaagg ttttgctcta
 121 cttcctgaag acctgaacac cgctcccata aagccatggc ttgccttgga tttcagcggc
 181 acaaggctca gctgaacctg gctaccagga cctggccctg cactctcctg tttttcttc
 241 tcttcatccc tgtcttctgc aaagcaatgc acgtggccca gcctgctgtg gtactggcca
 301 gcagccgagg catcgccagc tttgtgtgtg agtatgcatc tccaggcaaa gccactgagg
 361 tccgggtgac agtgcttcgg caggctgaca gccaggtgac tgaagtctgt gcggcaacct
 421 acatgatggg gaatgagttg accttcctag atgattccat ctgcacgggc acctccagtg
 481 gaaatcaagt gaacctcact atccaaggac tgagggccat ggacacggga ctctacatct
 541 gcaaggtgga gctcatgtac ccaccgccat actacctggg cataggcaac ggaacccaga
 601 tttatgtaat tgatccagaa ccgtgcccag attctgactt cctcctctgg atccttgcag
 661 cagttagttc ggggttgttt ttttatagct ttctcctcac agctgtttct ttgagcaaaa
 721 tgctaaagaa aagaagccct cttacaacag gggtctatgt gaaaatgccc ccaacagagc
 781 cagaatgtga aaagcaattt cagccttatt ttattcccat caattgagaa accattatga
 841 agaagagagt ccatatttca atttccaaga gctgaggcaa ttctaacttt tttgctatcc
 901 agctatttt atttgtttgt gcatttgggg ggaattcatc tctctttaat ataaagttgg
 961 atgcggaacc caaattacgt gtactacaat ttaaagcaaa ggagtagaaa gacagagctg
1021 ggatgtttct gtcacatcag ctccactttc agtgaaagca tcacttggga ttaatatggg
1081 gatgcagcat tatgatgtgg gtcaaggaat taagttaggg aatggcacag cccaaagaag
1141 gaaaaggcag ggagcgaggg agaagactat attgtacaca ccttatattt acgtatgaga
1201 cgtttatagc cgaaatgatc ttttcaagtt aaatttatg ccttttattt cttaaacaaa
1261 tgtatgatta catcaaggct tcaaaaatac tcacatggct atgttttagc cagtgatgct
1321 aaaggttgta ttgcatatat acatatatat atatatatat atatatatat atatatatat
1381 atatatatat tttaatttga tagtattgtg catagagcca cgtatgtttt tgtgtatttg
1441 ttaatggttt gaatataaac actatatggc agtgtctttc caccttgggt cccagggaag
1501 ttttgtggag gagctcagga cactaataca ccaggtagaa cacaaggtca tttgctaact
1561 agcttggaaa ctgatgagg tcatagcagt gcttgattgc gtggaattgt gctgagttgg
1621 tgttgacatg tgctttgggg cttttacacc agttcctttc aatggtttgc aaggaagcca
1681 cagctggtgg tatctgagtt gacttgacag aacactgtct tgaagacaat ggcttactcc
1741 aggagaccca caggtatgac cttctaggaa gctccagttc gatgggccca attcttacaa
1801 acatgtggtt aatgccatgg acagaagaag gcagcaggtg gcagaatggg gtgcatgaag
1861 gtttctgaaa attaacactg cttgtgtttt taactcaata ttttccatga aaatgcaaca
1921 acatgtataa tattttttaat taaataaaaa tctgtggtgg tcgtttaaa aaaaaaaaa
1981 aaaaaaaaaa aaaaaaaaaa aaaaaaaaaa aaaaaaaaaa aaaaa.
```

In a specific embodiment, the nucleic acid is an isolated or purified nucleic acid. In some embodiments, nucleic acids encode the immature or precursor form of a naturally occurring mammalian CTLA-4. In other embodiments, nucleic acids encode the mature form of a naturally occurring mammalian CTLA-4. In a specific embodiment, nucleic acids encoding native CTLA-4 encode the precursor form of naturally occurring human CTLA-4. In another embodiment, nucleic acids encoding native CTLA-4 encode the mature of naturally occurring human CTLA-4.

As used herein, the term "native ICOS" in the context of proteins or polypeptides refers to any naturally occurring ICOS amino acid sequences, including immature or precursor and mature forms. Non-limiting examples of Accession Nos. for the amino acid sequence of various species of native mammalian ICOS include: Q9Y6W8-1 (*homo sapiens*), Q9Y6W8-1 (*homo sapiens*), NP_036224.1 (GI:15029518; *homo sapiens*), Q9WVS0-1 (mouse), NP_059508.2 (GI:224809335; mouse), Q9R1T7-1 (rat), Q9R1T7-2 (rat), Q58DF9-1 (bovine), and NP_001029447.1 (GI:77735505; bovine). A representative amino acid sequence of a first isoform the immature/precursor of native human ICOS, which comprises the signal peptide (underlined) and the mature human native ICOS (italicized), is provided:

(SEQ ID NO: 11)
MKSGLWYFFL FCLRIKVLTG EINGSANYEM FIFHNGGVQI

LCKYPDIVQQ FKMQLLKGGQ ILCDLTKTKG SGNTVSIKSL

KFCHSQLSNN SVSFFLYNLD HSHANYYFCN LSIFDPPPFK

VTLTGGYLHI YESQLCCQLK FWLPIGCAAF VVVCILGCIL

ICWLTKKKYS SSVHDPNGEY MFMRAVNTAK KSRLTDVTL.

mature form of naturally occurring human ICOS. In one embodiment, the native ICOS protein/polypeptide is isolated or purified.

ICOS is otherwise referred to as Inducible T-cell costimulator, Activation-inducible lymphocyte immunomediatory molecule, and CD278 in the literature. At least one isoform of human ICOS polypeptide is 199 amino acids in length and has been reported to contain the following: a signal sequence, an immunoglobulin-like (Ig-like) V-type domain, an extracellular domain, a transmembrane domain, and a cytoplasmic domain. A human ICOS isoform has been reported to contain the following: a signal sequence at amino acid residues 1 to 20 of the sequence at Accession No. Q9Y6W8-1, an Ig-like V-type domain at amino acid residues 30 to 140 of the sequence at Accession No. Q9Y6W8-1, an extracellular domain at amino acid residues 21 to 140 of the sequence at Accession No. Q9Y6W8-1, a transmembrane domain at amino acid residues 141 to 160 of the sequence at Accession No. Q9Y6W8-1, and a cytoplasmic domain at amino acid residues 161 to 199.

As used herein, the term "native ICOS" in the context of nucleic acids refers to any naturally occurring nucleic acid sequences encoding ICOS, including the immature or precursor and mature forms. Non-limiting examples of Accession Nos. for the nucleotide sequence of various species of native mammalian ICOS include: AF218312.1 (GI:7963649; *homo sapiens*), AF216748.1 (GI:7288512; mouse), and BT021638.1 (GI:61553958; bovine). The nucleotide sequence encoding the immature/precursor form of native human ICOS, which comprises the nucleotide sequence encoding the signal peptide (underlined) and the nucleotide sequence encoding the mature human native ICOS (italicized), is provided:

(SEQ ID NO: 12)
1 ggcccaagct tgcc<u>atgaag tcaggacttt ggtatttctt tctcttctgc ttgcgcatta</u>

61 <u>aagttttaac aggag</u>aaatc aatggttctg ccaattatga gatgttata tttcacaacg 121 gaggtgtaca aattttatgc aaatatcctg acattgtcca gcaatttaaa atgcagttgc 181 tgaaagggg gcaaatactc tgcgatctca ctaagacaaa aggaagtgga aacacagtgt 241 ccattaagag tctgaaattc tgccattctc agttatccaa caacagtgtc tccttttttc 301 tatacaactt ggaccattct catgccaact attacttctg taacctatca attttgatc 361 ctcctccttt taaagtaact cttacaggag gatatttgca tatttatgaa tcacaactt 421 gttgccagct gaagttctgg ttacccatag gatgtgcagc ctttgttgta gtctgcattt 481 tgggatgcat acttatttgt tggcttacaa aaaagaagta ttcatccagt gtgcacgacc 541 ctaacggtga atacatgttc atgagagctg tgaataccgc taagaaatct cgcctgacag 601 acgtcacact ctgattctag a.

The amino acid sequence of a second isoform of native human ICOS differs from this first isoform in that amino acid residues 168 to 199 of SEQ ID NO:11 are as follows: KYSSSVHDPNGEYMFMRAVNTAKKSRLTDVTL (SEQ ID NO:26)→M. This second isoform is predicted to be secreted. In some embodiments, native ICOS is the immature or precursor form of a naturally occurring mammalian ICOS. In other embodiments, native ICOS is the mature form of a naturally occurring mammalian ICOS. In a specific embodiment, native ICOS is the precursor form of naturally occurring human ICOS. In another embodiment, native ICOS is the In a specific embodiment, the nucleic acid is an isolated or purified nucleic acid. In some embodiments, nucleic acids encode the immature or precursor form of a naturally occurring mammalian ICOS. In other embodiments, nucleic acids encode the mature form of a naturally occurring mammalian ICOS. In a specific embodiment, nucleic acids encoding native ICOS encode the precursor form of naturally occurring human ICOS. In another embodiment, nucleic acids encoding native ICOS encode the mature form of naturally occurring human ICOS.

As used herein, the term "native ligand" refers to any naturally occurring ligand that binds to a naturally occurring receptor. In a specific embodiment, the ligand is a mammalian ligand. In another specific embodiment, the ligand is a human ligand.

As used herein, the term "native receptor" refers to any naturally occurring receptor that binds to a naturally occurring ligand. In a specific embodiment, the receptor is a mammalian receptor. In another specific embodiment, the receptor is a human receptor.

As used herein, the terms "nucleic acid", "nucleotide" and "polynucleotide" refers to deoxyribonucleotides, deoxyribonucleic acids, ribonucleotides, and ribonucleic acids, and polymeric forms thereof, and includes either single- or double-stranded forms. Nucleic acids include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleic acid analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), locked-nucleic acids (LNAs), and the like.

As used herein, the term "premature human infant" refers to a human infant born at less than 37 weeks of gestational age.

As used herein, terms "prevent", "preventing" and "prevention" in the context of administering a therapy to a subject refers to the prophylactic effect that a subject derives from receiving a therapy. In a specific embodiment, such terms refer to the inhibition of the development or onset of a disease or a symptom associated therewith, or inhibition of the recurrence of a disease or a symptom thereof.

As used herein, the terms "purified" and "isolated" in the context of an agent (including, e.g., proteinaceous agents such as antibodies) that is chemically synthesized refers to an agent that is substantially free of chemical precursors or other chemicals when chemically synthesized, i.e., it is separated from chemical precursors or other chemicals which are involved in the synthesis of the protein. In a specific embodiment, the agent is 60%, 65%, 75%, 80%, 85%, 90%, 95%, or 99% free (by dry weight) of other, different compounds or agents.

As used herein, the terms "purified" and "isolated" when used in the context of an agent (including proteinaceous agents such as antibodies and polypeptides) that can be obtained from a natural source, e.g., cells, refers to an agent which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of an agent that has been separated from the material (e.g., cellular components of the cells) from which it is isolated. Thus, an agent that is isolated includes preparations of a compound or agent having less than about 30%, 20%, 10%, 5%, 2%, or 1% (by dry weight) of cellular materials and/or contaminating materials.

An "isolated" nucleic acid sequence or nucleotide sequence is one which is separated from other nucleic acid molecules which are present in a natural source of the nucleic acid sequence or nucleotide sequence. Moreover, an "isolated", nucleic acid sequence or nucleotide sequence, such as a cDNA molecule, can be substantially free of other cellular material or culture medium when produced by recombinant techniques, or substantially free of chemical precursors when chemically synthesized. In certain embodiments, an "isolated" nucleic acid sequence or nucleotide sequence is a nucleic acid sequence or nucleotide sequence that is recombinantly expressed in a heterologous cell.

As used herein, unless otherwise specified, the terms "protein(s)" and "polypeptide(s)" interchangeably to refer to a chain of amino acids linked together by peptide bonds. In some embodiments, the terms "protein(s)" and "polypeptide(s)" refer to a macromolecule which comprises amino acids that are linked together by peptide bonds.

As used herein, the terms "subject" and "patient" are used interchangeably and refer to an animal. In a specific embodiment, such terms refer to a mammal such as a non-primate (e.g., cows, pigs, horses, cats, dogs, rats etc.) and a primate (e.g., monkey and human), most preferably a human. In certain embodiments, such terms refer to a non-human animal (e.g., a non-human animal such as a pig, horse, cow, cat, or dog). In some embodiments, such terms refer to a pet or farm animal. In specific embodiments, such terms refer to a human.

As used herein, the term "Therapeutic Agent(s)" refers to an agent(s) that modulates one or more immune system functions or responses. In a specific embodiment, a Therapeutic Agent modulates one or more of the signal transduction pathways induced when a native ligand binds to a native receptor. In another specific embodiment, a Therapeutic Agent modulates the interaction between a native receptor and one or more of its native ligands. In another specific embodiment, a Therapeutic Agent modulates the expression of a native receptor or a native ligand. In some embodiments, a therapeutic agent is an agonist. In other embodiments, a therapeutic agent is an antagonist.

As used herein, the terms "therapies" and "therapy" can refer to any protocol(s), method(s), compositions, formulations, and/or agent(s) that can be used in the prevention, treatment, management, or amelioration of a disease, e.g., cancer, infectious disease, autoimmune disease, graft versus host disease, and transplantation rejection, or a symptom associated therewith. In certain embodiments, the terms "therapies" and "therapy" refer to drug therapy, adjuvant therapy, radiation, surgery, biological therapy, supportive therapy, and/or other therapies useful in treatment, management, prevention, or amelioration of a condition or disorder or a symptom thereof. In a specific embodiment, a therapy includes the use of a Therapeutic Agent as an adjuvant therapy. For example, using a Therapeutic Agent in conjunction with a drug therapy, biological therapy, surgery, and/or supportive therapy. In a specific embodiment, a therapy includes a Therapeutic Agent.

In one embodiment, a therapy includes an Immunostimulating Therapeutic Agent. In an alternative embodiment, a therapy includes an Inhibitory Therapeutic Agent. In another embodiment, a therapy is not an Immunostimulating Therapeutic Agent. In an alternative embodiment, a therapy is not an Inhibitory Therapeutic Agent.

As used herein, the terms "treat", "treating" and "treatment" in the context of the administration of a therapy to a subject refer to the beneficial effects that a subject derives from a therapy. In certain embodiments, treatment of a subject with a Therapeutic Agent achieves one, two, three, four, or more of the following effects: (i) reduction or amelioration the severity of disease or symptom associated therewith; (ii)

reduction in the duration of a symptom associated with a disease; (iii) prevention of the progression of a disease or symptom associated therewith; (iv) regression of a disease or symptom associated therewith; (v) prevention of the development or onset of a symptom associated with a disease; (vi) prevention of the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy.

4. DESCRIPTION OF THE TABLE & FIGURES

Table 1. List of the cDNA clone collection used in the receptor-ligand proteome. Over 1,900 human genes encoding for full length plasma membrane cDNA in mammalian expression vector are included in this proteome system for screening of receptor and ligand interactions.

FIG. 1. Schematic view of the receptor-ligand proteome. A set of ~1,900 plasmids encoding human transmembrane genes are placed individually into five 384-well plates and transfected into 293T cells by lipofectamine. A target fusion protein and a secondary fluorescence-labeled antibody are subsequently added to the transfected cells after eight hours. Twenty-four hours later, the Applied Biosystem 8200 Cellular Detection System (CDS) performs the scanning on cell surface for positive wells. Individual plasmids within each well with positive hits will be picked and study further for validation.

Figure 2:
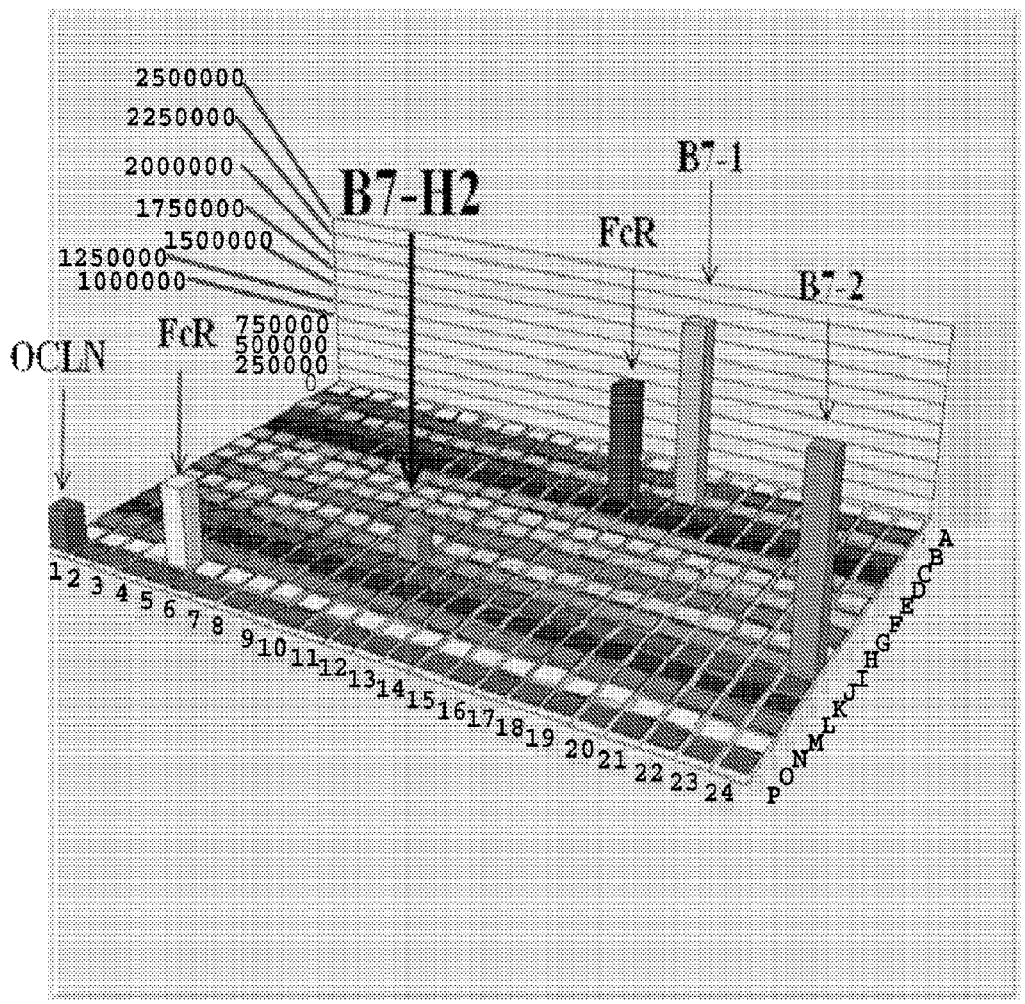

FIG. 2. Identification of B7-H2 and CD28 interaction by the receptor-ligand proteomic system. A set of ~1,900 plasmids with human transmembrane genes at 30 ng/well were placed individually into four 384-well plates, and transiently transfected into 293T cells by lipofectamine. Human CD28Ig (R&D systems, Minneapolis, Minn.) and anti-human Ig FMAT blue secondary antibody (Applied Biosystems, Foster City, Calif.) were added into the wells 8 hr after transfection. The plates were read 24 hrs after transfection by the Applied Biosystems 8200 cellular detection system and analyzed by CDS 8200 software. The 3-D illustration represents the result of a 384-well plate. The position of each well is indicated at the bottom (from 1 to 24) and at the side (from A to P) of the plate. Each bar represents the total fluorescence intensity in the FL1 gate in each well of the 384-well plate. The well transfected with human B7-H2 gene (K11) was shown to be positive in addition to B7-1 (C17) and B7-2 (K24). The Fc Receptors (D15, O5) are positive controls for transfection because they bind directly to labeled 2nd antibody. P24 is the negative control with mock-transfected 293T cells. *Occludin (P1), a tight junction adhesion molecules, was also shown positive binding to B7-H2. However, further experiments demonstrated that occludin binds the secondary antibody non-specifically.

FIGS. 3A-3K. Identification and characterization of B7-H2 as the third ligand for CD28 and CTLA-4.

(A-E) Specificity of B7-H2 bindings to CD28/CTLA-4. 293T cells were transiently transfected with human full length B7-H2 plasmids, and were stained by specific mAb to B7-H2, B7-1, B7-2 as well as ICOSIg (A), CD28Ig (B) and CTLA4Ig (C). Specific mAb to CD28 (clone CD28.6) and CTLA-4 (clone 14D3) were also included in the cultures to examine specificity of the binding. (D) CD28-transfected (D) or CTLA-4-transfected 293T cells (E) were also stained by B7-H2Ig with or without blocking mAb against B7-H2 (clone MIH12). All data were analyzed by a FACScan flow cytometry.

(F) Binding affinity of B7-H2 to ICOS, CD28 and CTLA-4. ICOSIg and CD28Ig at the indicated concentrations were injected into flow cells that were coated with B7-H2Ig at 500RUs and the responses were determined by Surface Plasmon Resonance. Similarly, CTLA4Ig at the indicated concentration were injected into a flow cell coated with B7-H2Ig at 5000RUs. In all experiments, injections of these fusion proteins into uncoated control flow cells were served as the control. Binding data were overlaid with the fit of 1:1 interaction model with drifting baseline.

(G-I) Interactions between B7-H2/ICOS and B7/CD28 pathways. To examine the interactions of B7-H2 and other ligands of CD28/CTLA-4, 293T cells were transiently transfected with full length human B7-H2 plasmids. CD28Ig and CTLA4Ig were used to stain the transfectants, and analyzed by flow cytometry. Isotype-matched human Ig (control Ig) was included as controls (upper panels). For competitive binding, CD28Ig and CTLA4Ig at 10 µg/ml were pre-incubated with excessive amount of B7-1Ig (middle panels) or B7-2Ig (lower panels) at 40 µg/ml for 15 minutes before staining B7-H2+293T cells. To determine the interactions of B7-H2 with CD28/CTLA-4 vs. ICOS, CD28 (H) or CTLA-4 (I) transfected 293T cells were stained by B7-H2Ig at 10 µg/ml, and excess amount of ICOSIg at 20 µg/ml was included to compete the binding. All data were analyzed by a FACScan flow cytometry.

(J, K) Costimulation of human T cells through B7-H2/CD28 interaction. (J) Peripheral blood T cells from healthy donor were negatively selected and purified by Pan T cell isolation kit on affinity column. Purified CD3+ T cells at $3 \times 10^5$ cells/well were stimulated with immobilized anti-human CD3 mAb (OKT3) at the indicated concentrations and 5 µg/ml B7-H2Ig or control Ig (ctl Ig). For blocking experiments, blocking mAb against ICOS (clone C398.4A) and/or CD28 (clone CD28.6) at 10 µg/ml were included in soluble form at the beginning of the culture for three days. 3HTdR was added during the final six hours of culture, and the incorporation of 3HTdR was determined by a scintillation counter. (K) Purified CD3+ T cells at $2.5 \times 10^5$ cells/wells were stimulated by CD3 mAb/B7-H2Ig as described in (J). B7-H2 mAb (clone MIH12 or 9F.8A4) or control Ig (ctl Ig) at 10 µg/ml was included to block coated B7-H2Ig for 1 hr and unbound mAbs were subsequently washed away by media before addition of T cells.

Figure 4:
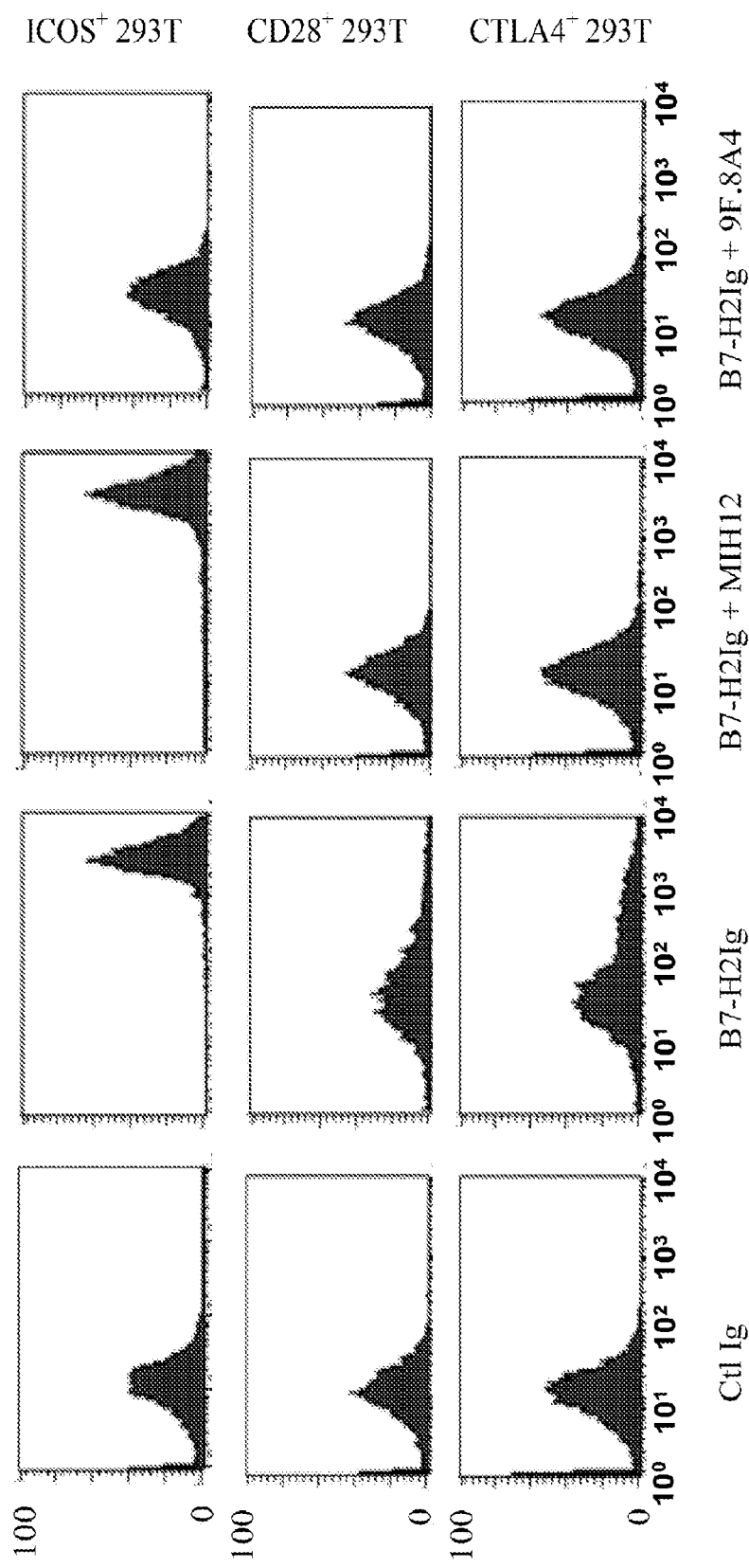

FIG. 4. Comparison of binding affinities of B7-H2 to ICOS, CD28 and CTLA-4. Human B7-H2-GFP plasmids were transiently transfected into 293T cell. GFP high population was gated and assessed for binding of ICOS, CD28 and CTLA4 fusion proteins at 10 µg/ml and analyzed by flow cytometry.

Figure 5A:
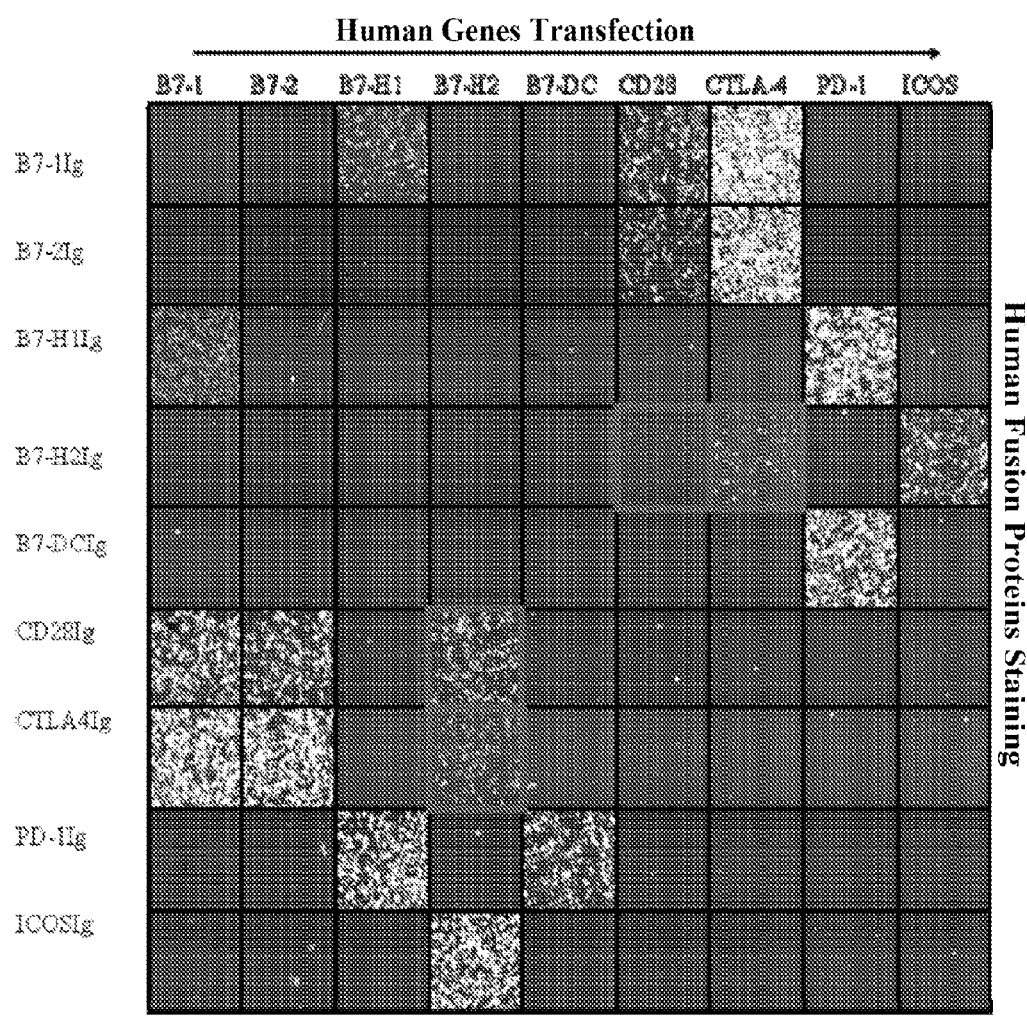
Figure 5B:
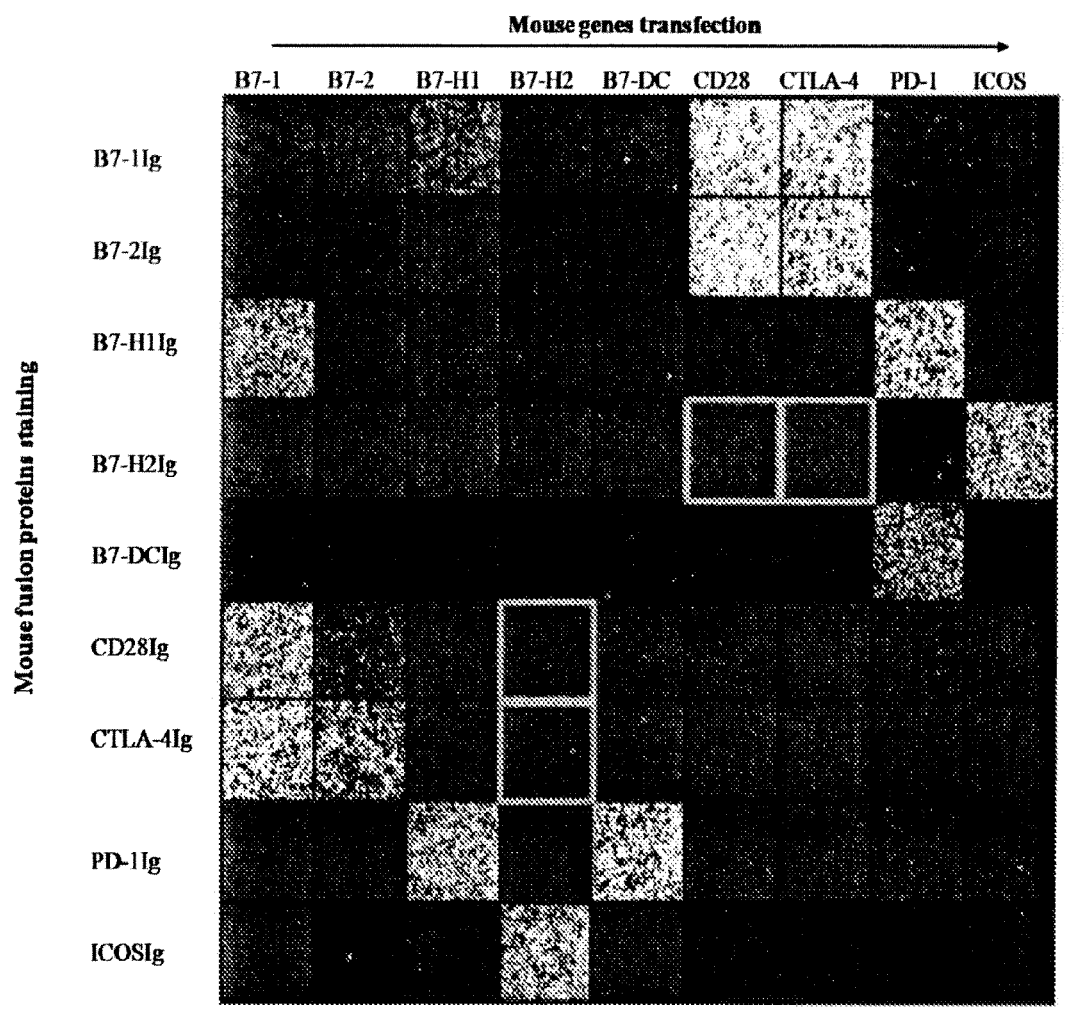

FIGS. 5A-5B. Interactions of the B7-CD28 family molecules. 293T cells were transfected with full length human (A) or mouse (B) B7-CD28 family genes as indicated on the X axis. Human (A) or mouse (B) fusion proteins were added to the culture as indicated on the Y axis to evaluate their bindings to the transfectants by CDS. Graphic view of individual wells is captured by 8200 CDS software.

Figures 6A, 6B:
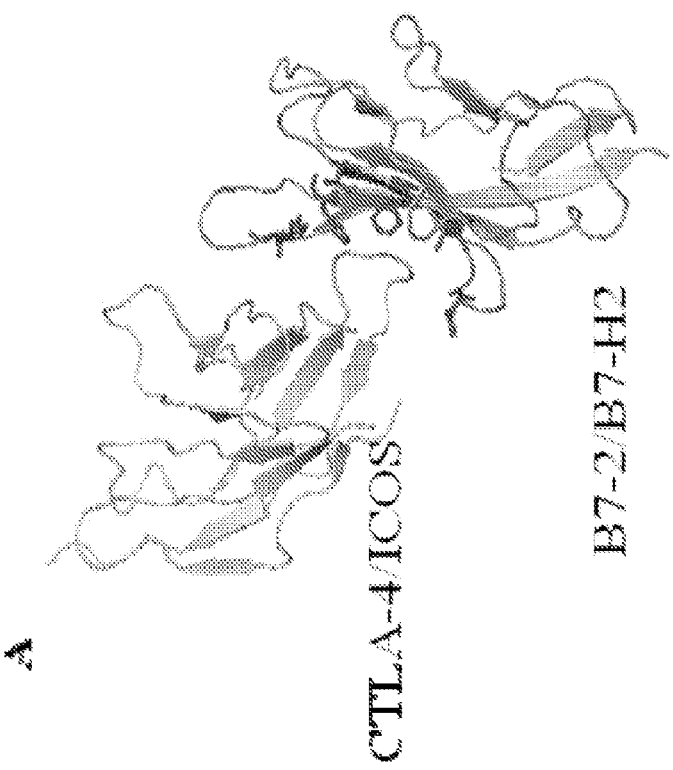

FIGS. 6A-6B. B7-H2 interacts with ICOS, CD28 and CTLA4 through overlapping domains. (A) Cartoon illustration of B7-H2-ICOS interaction is modeled using crystal structure of B7-2-CTLA4 (RCSB PDB 1i85), and generated by Pymol software (DeLano Scientific LLC.). (B) Binding site analysis of B7-H2 with its receptors by site-directed mutagenesis. Human B7-H2 full length gene was cloned into pcDNA3.1 so that the gene as fused with C terminal GFP tag. Single point mutations were introduced into B7-H2-GFP plasmid at residues buried at ligand-receptor interacting interface (shown in purple in cartoon). B7-H2 plasmids (wild-type and mutants) were then transiently transfected into 293T cells and the expression of B7-H2 was confirmed by anti-B7-H2 staining. Binding of human ICOS, CD28, CTLA4 fusion proteins to B7-H2 mutant-GFP plasmids were measured by flow cytometry and normalized against 293T cells expressing wild-type B7-H2-GFP (100%) and vector control (0%). Binding percentages relative to wild type B7-H2 (100%) and vector control (0%) are positive and negative controls.

Figure 7:
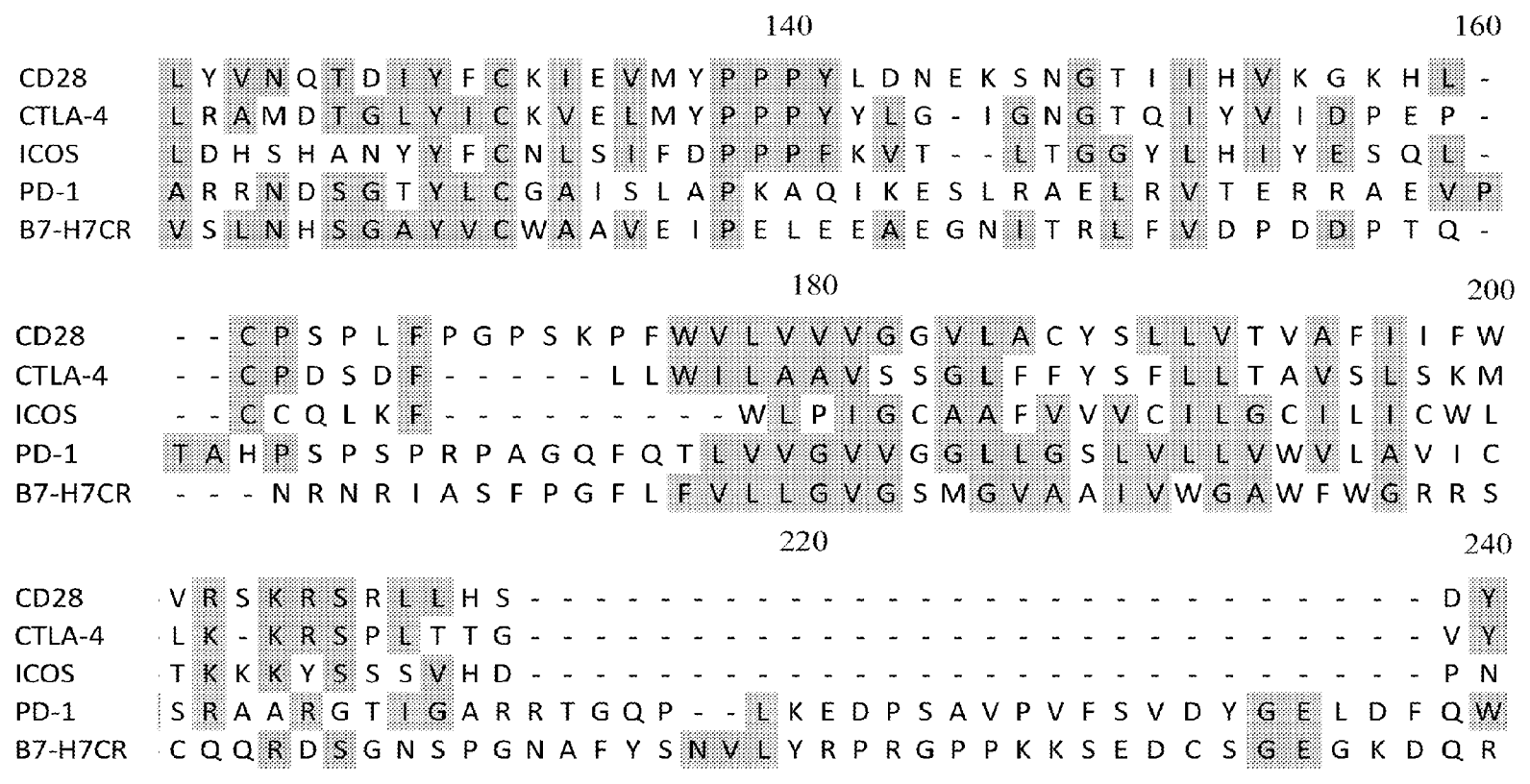

FIG. 7. B7-H7 sequence homology to previously described B7 family molecules. Human B7-H7 protein sequence was aligned by ClustalW program with other B7 ligand family members including B7-1, B7-2, B7-H1, B7-DC, B7-H3 and B7-H4.

Figure 8:
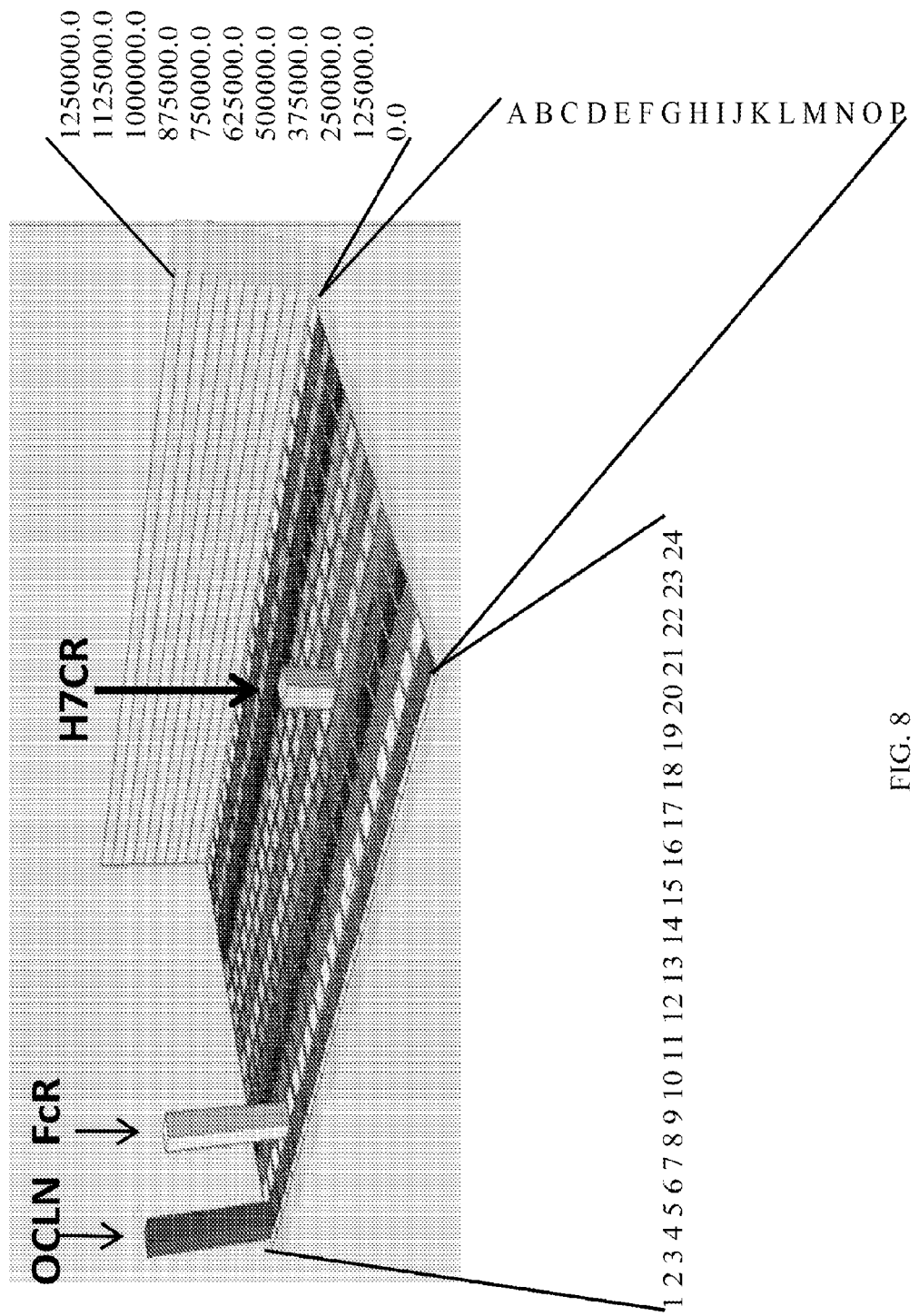

FIG. 8. Identification of B7-H7 and B7-H7R interaction by the CDS system. Using the identical procedure as described in FIG. 2, B7-H7Ig and anti-mIg FMAT blue secondary antibody were added to the 384-well plates 8 hours after transfection. The plates were read by the Applied Biosystems 8200 cellular detection system and analyzed by CDS 8200 software 24 hrs after transfection. Human B7-H7CR (J18) was identified as a positive hit in addition to positive controls, FcR (O5) and OLN (P1).

Figure 9:
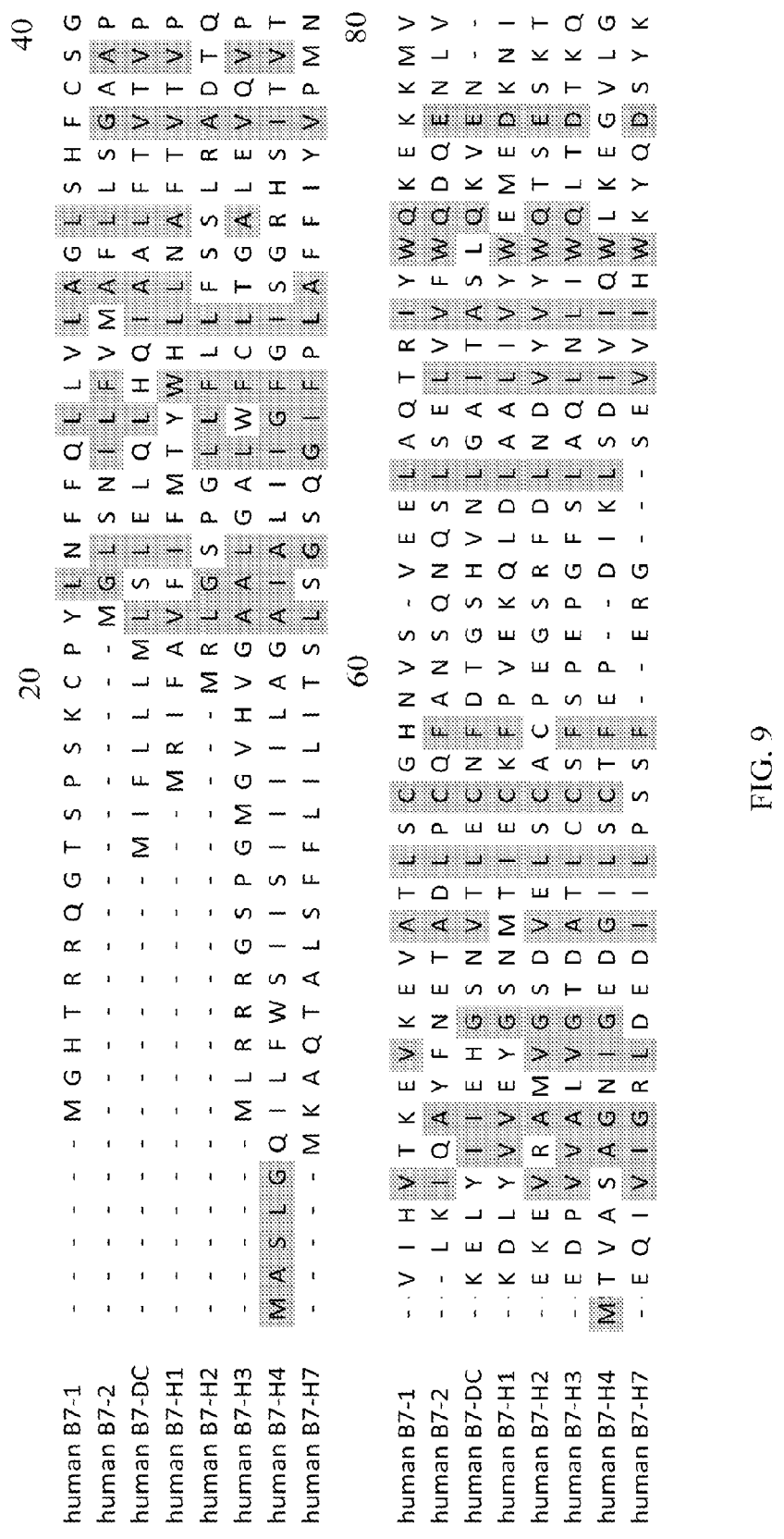
Figure 9:
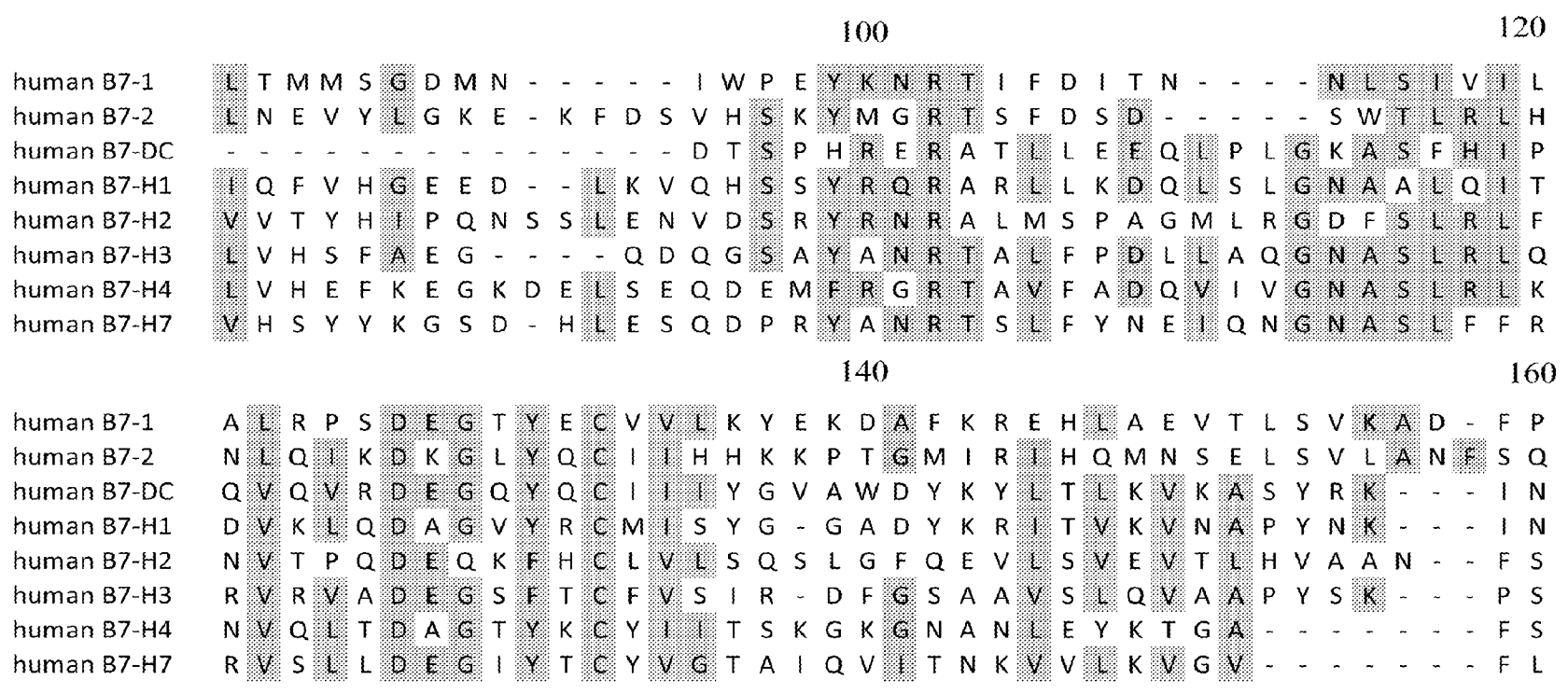
Figure 9:
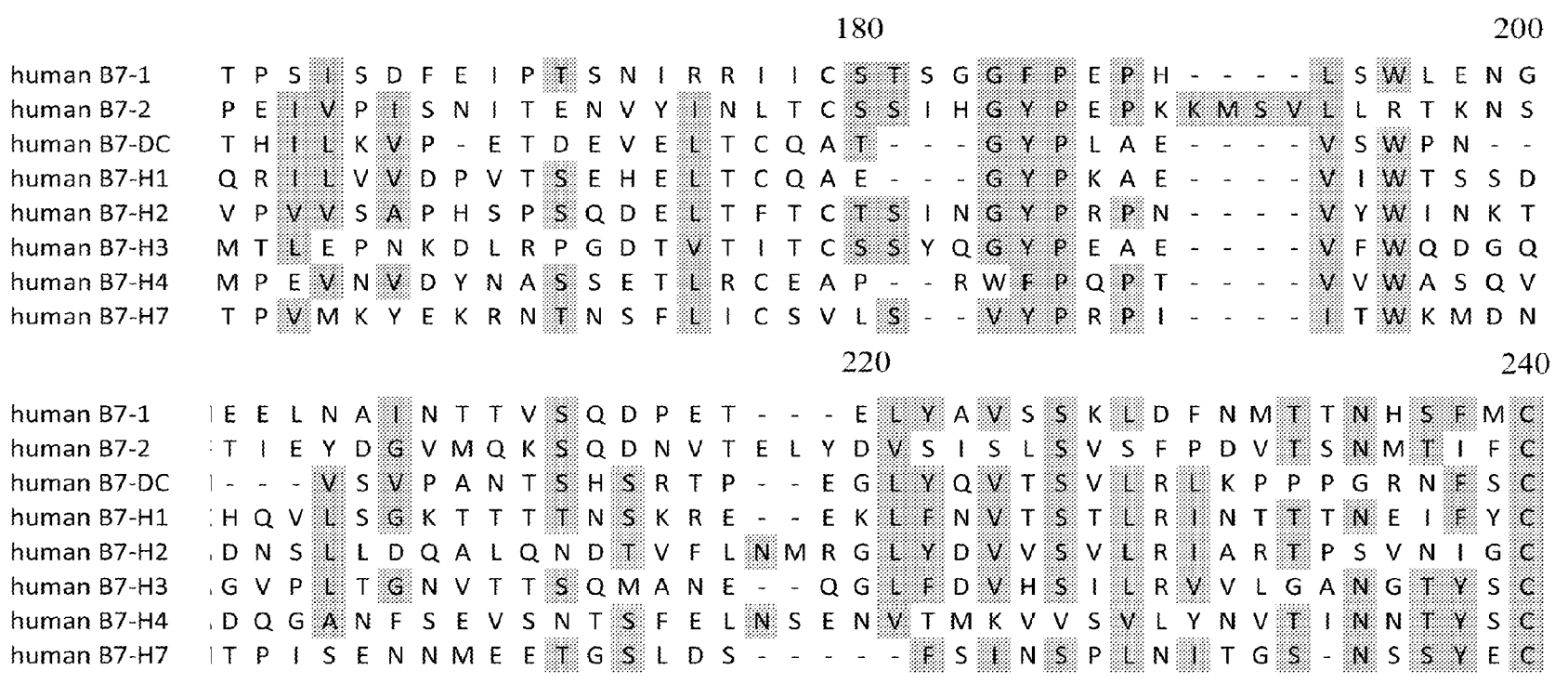
Figure 9:
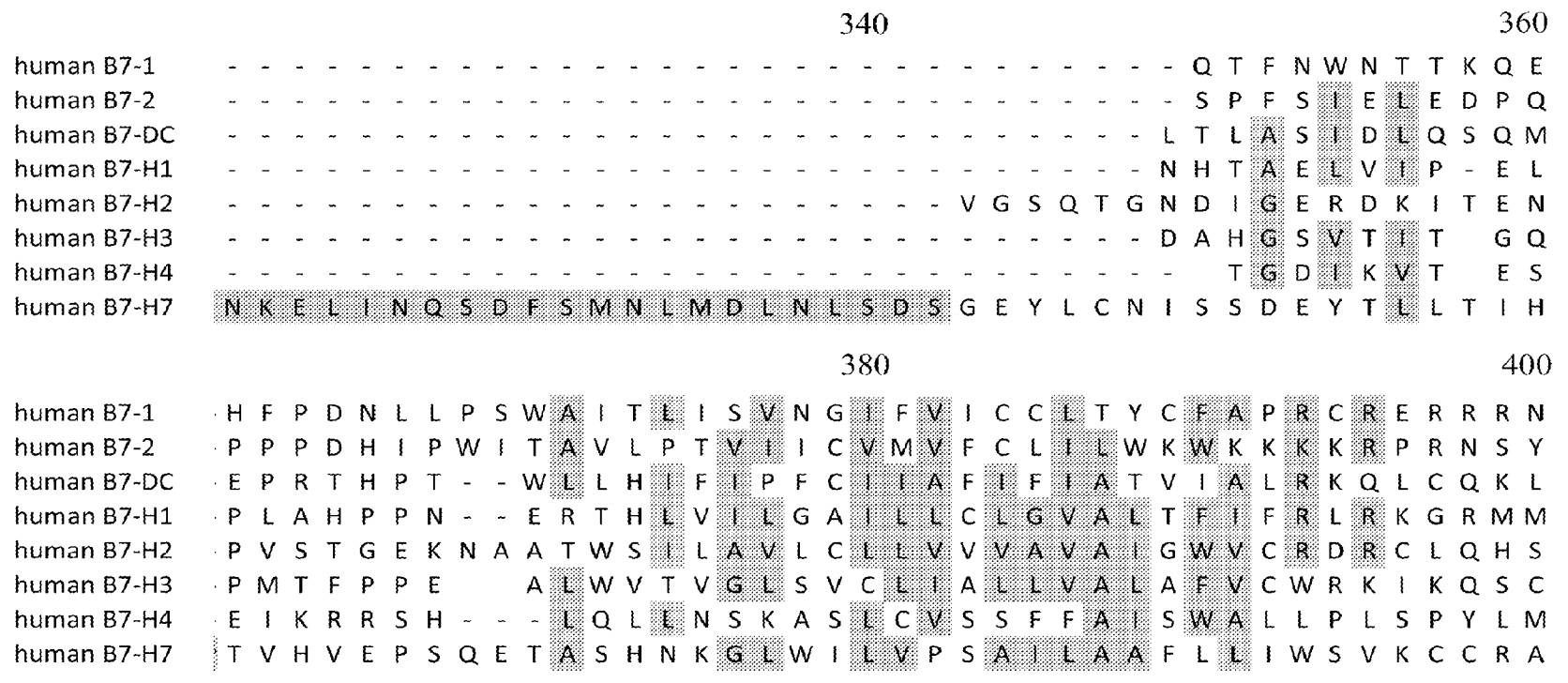

FIG. 9. B7-H7CR sequence homology to previously described CD28 family members. Human B7-H7CR protein sequence was aligned by ClustalW program with other CD28 family members including CD28, CTLA-4, PD-1 and ICOS.

FIGS. 10A-10F. Identification and characterization of a novel T cell costimulatory pathway through B7-H7 and B7-H7CR interaction.

(A) Binding of B7-H7CR by B7-H7Ig on transfected cells. 293T cells were transiently transfected with the plasmid containing human B7-H7CR cDNA or vector plasmid, and were subsequently stained by specific mAb to B7-H7CR (clone 4-5, upper panels) or B7-H7Ig (lower panels). Data were analyzed by a FACScan flow cytometry.

(B) Constitutive and inducible expression of B7-H7 on macrophages and dendritic cells. Human monocytes were purified from blood of healthy donors and cultured in vitro for one week at the presence of GM-CSF or GM-CSF+IL-4 to differentiate into macrophages (M) or dendritic cells (DC), respectively. Cells were also treated without (None) or with IFN-γ, poly I:C or heat-killed *Listeria monocytogenes* (HKLM) for 24 hrs and subsequently stained by a anti-B7-H7 mAb (clone 2D3). Data were analyzed by a FACScan flow cytometry.

(C) Constitutive and inducible expression of B7-H7CR on lymphocytes. Human peripheral blood mononuclear cells were purified and stained by specific mAb against CD3, CD19, CD56 and CD16 together with anti-B7-H7CR mAb (clone 4-5). Data were analyzed by a FACScan flow cytometry.

(D) B7-H7Ig costimulates CD4+ T cell proliferation and cytokine production. Peripheral blood CD4+ T cells from healthy donor were negatively selected and purified by affinity column. Purified CD4+ T cells at $2.5 \times 10^5$ cells/well were stimulated with immobilized anti-human CD3 mAb (OKT3) at the indicated concentrations and 5 μg/ml B7-H7Ig or control Ig (ctl Ig). 3HTdR was added during the final six hours of culture and the incorporation of 3HTdR was determined by a scintillation counter. In a parallel experiment, culture supernatants were collected and cytokines were measured by sandwich ELISA kits with specific pairs of mAb.

(E, F) Costimulation of CD4+ T cell proliferation by agonistic B7-H7CR mAb. (E) CD4+ T cells were purified and stimulated as described in (D). Instead of B7-H7Ig, an anti-B7-H7CR mAb (clone 4-5) was co-immobilized with anti-CD3 mAb in the plate (left panel). To test the synergistic effect with CD28 costimulation, a CD28 mAb (clone CD28.2, 1 μg/ml) was added to the culture together with B7-H7CR mAb (right panel). (F) Human CD4+ T cells were costimulated with plate-immobilized B7-H7Ig and anti-CD3 mAb as described in (E) in the presence of 10 μg/ml soluble B7-H7 mAb or B7-H7CRIg. 3HTdR was added during the final six hours of culture and the incorporation of 3HTdR was determined by a scintillation counter.

Figure 11:
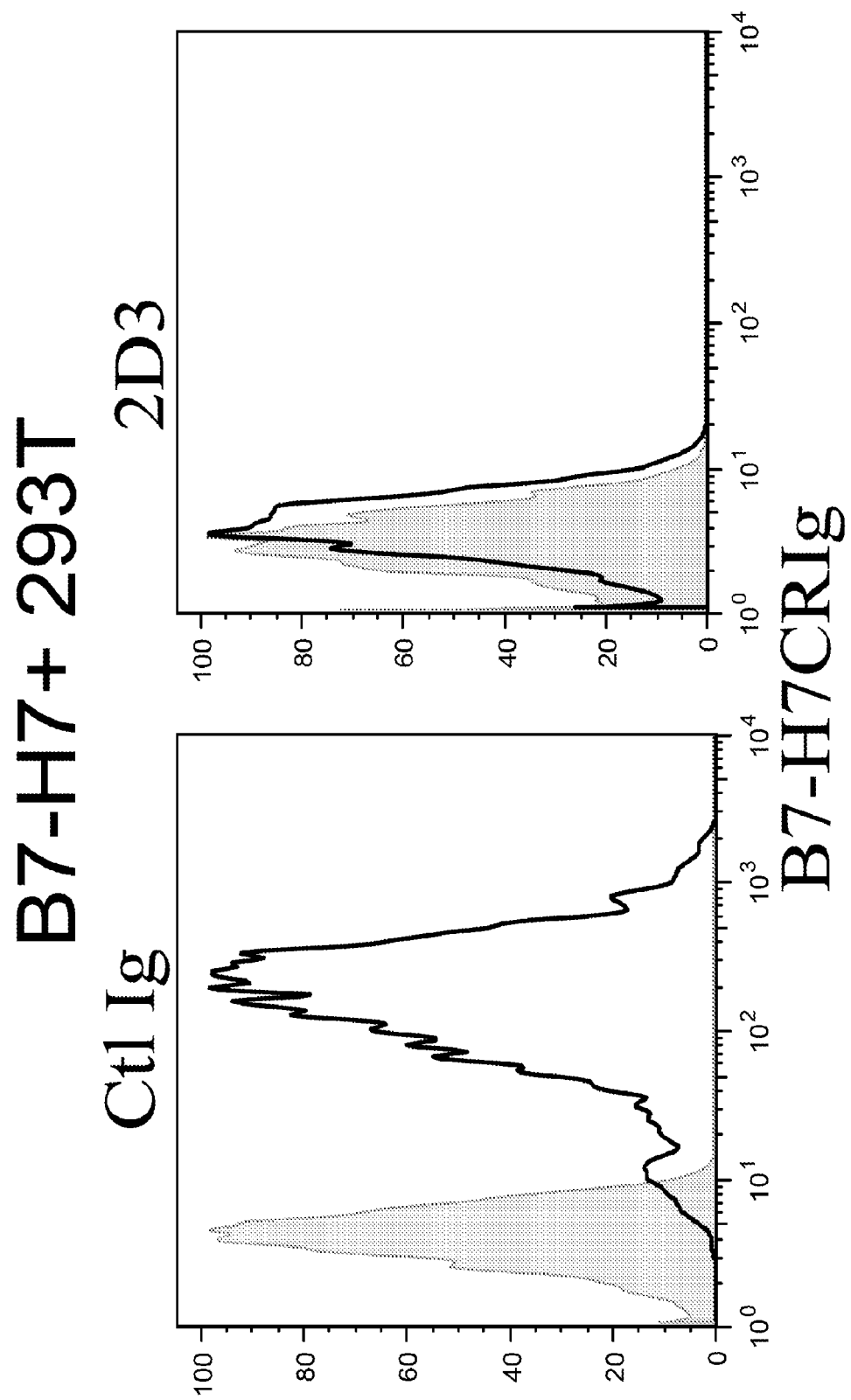

FIG. 11. B7-H7 mAb 2D3 completely blocks the binding of B7-H7CR to B7-H7+ cells. CHO cells were transfected with the plasmid encoding human B7-H7 and subsequently stained by 10 μg/ml B7-H7CRIg without (left panel) or with (right panel) a B7-H7 mAb (clone 2D3) at 20 μg/ml as described previously.

Figure 12:
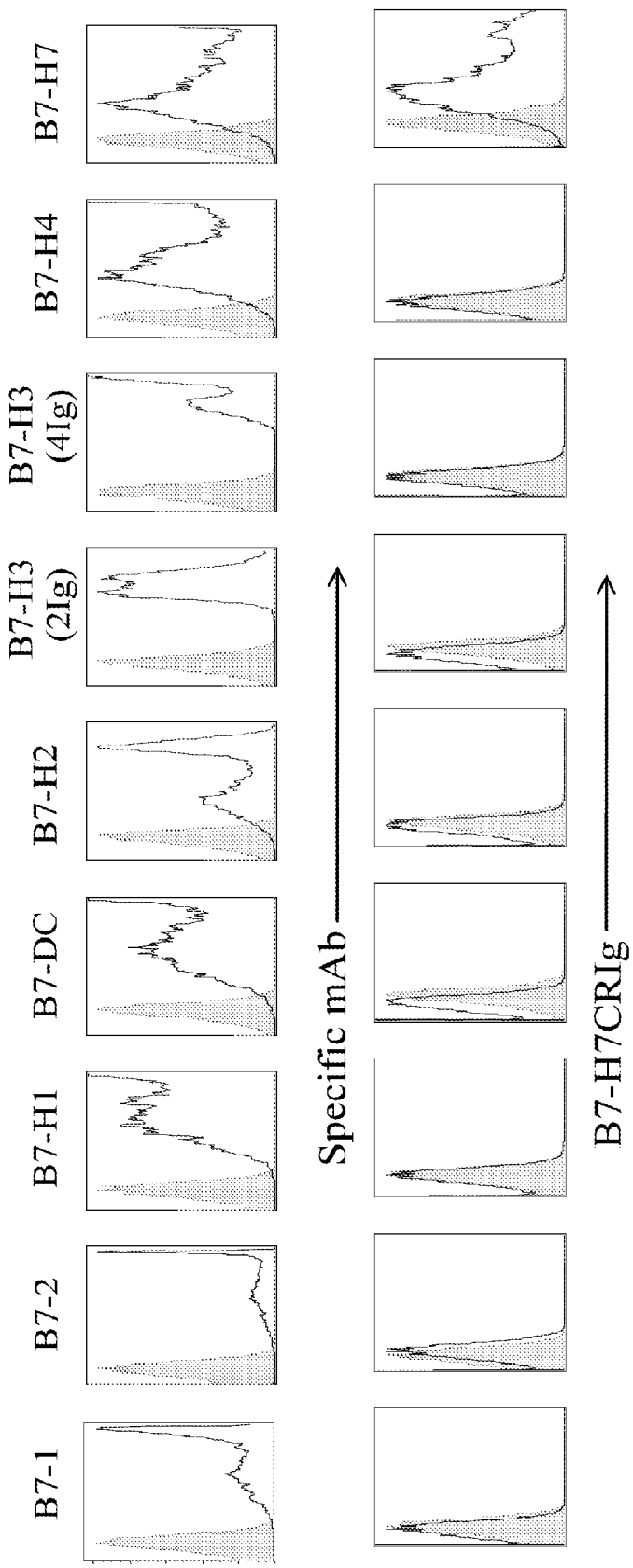

FIG. 12. B7-H7CR specifically binds B7-H7 but not other B7 family members. 293T cells were transfected with individual B7 family members including B7-1, B7-2, B7-H1, B7-DC, B7-H2, B7-H3 (both 2Ig and 4Ig forms) and B7-H4. After staining with B7-H7CRIg at 10 μg/ml and fluorescence-labeled secondary mAb, cells were analyzed by flow cytometry and the data is shown as density of fluorescence.

Figure 13:
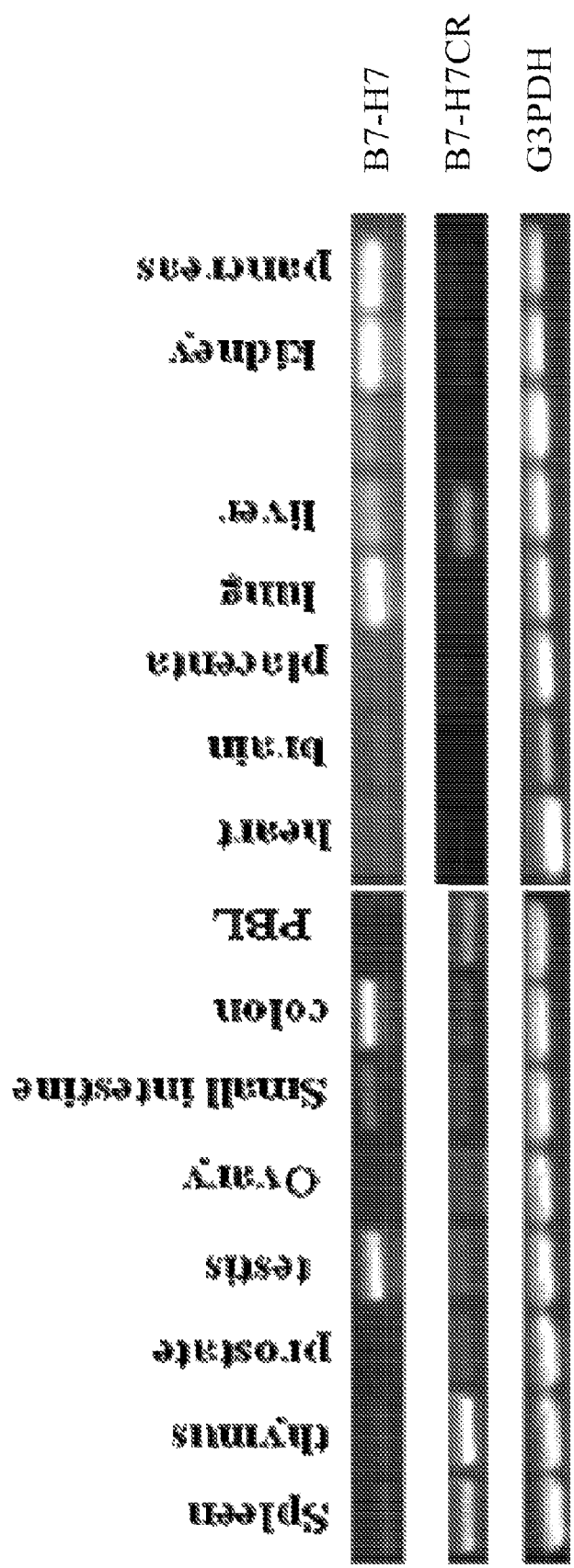

FIG. 13. Detection of human B7-H7 and B7-H7CR mRNA in tissues. Human tissue cDNA arrays (Clontech) were used as templates with B7-H7 and B7-H7CR specific primer pairs, respectively, to perform RT-PCR. G3PDH primer pairs serve as controls.

Figure 14:
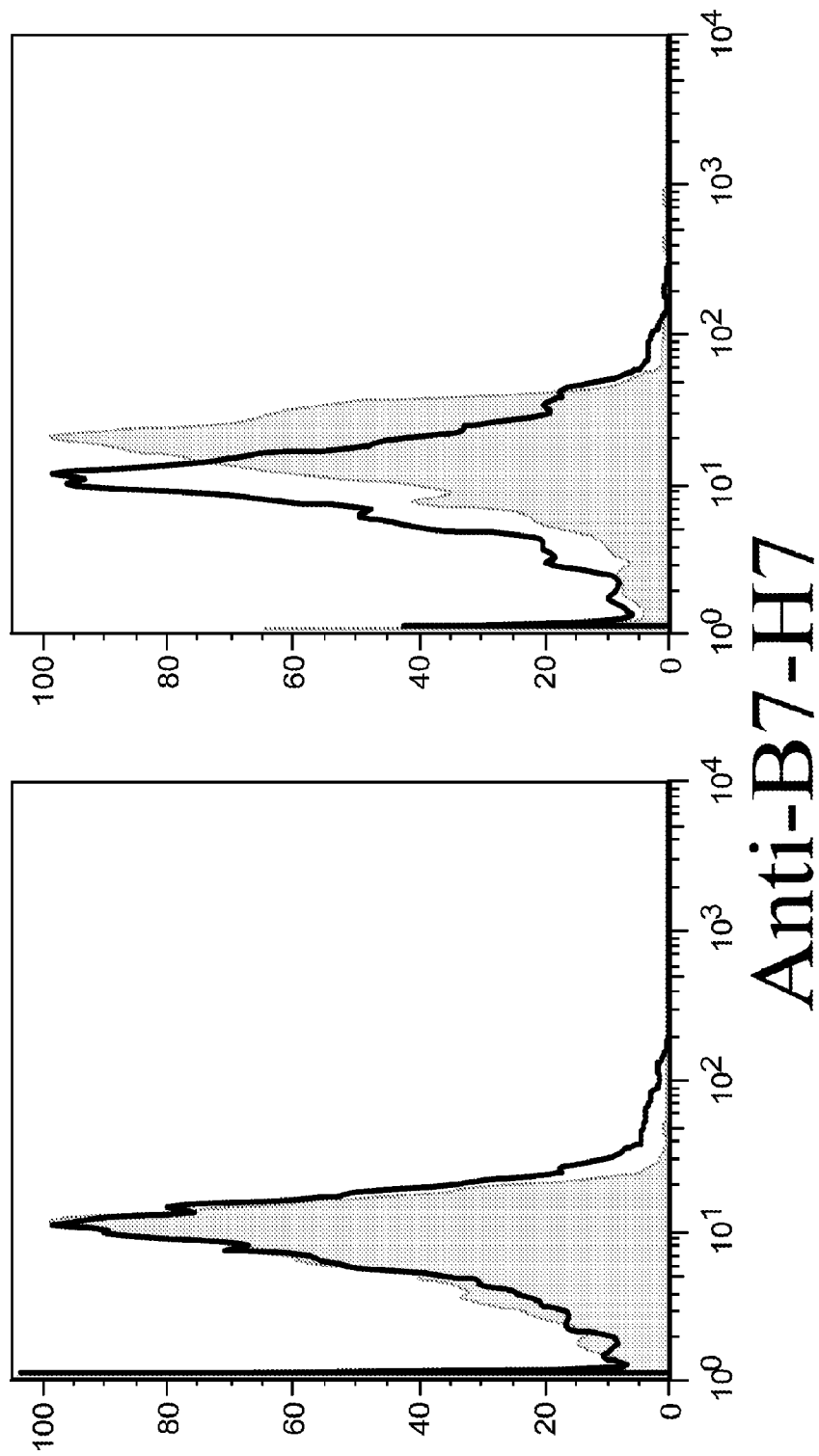
Figure 14:
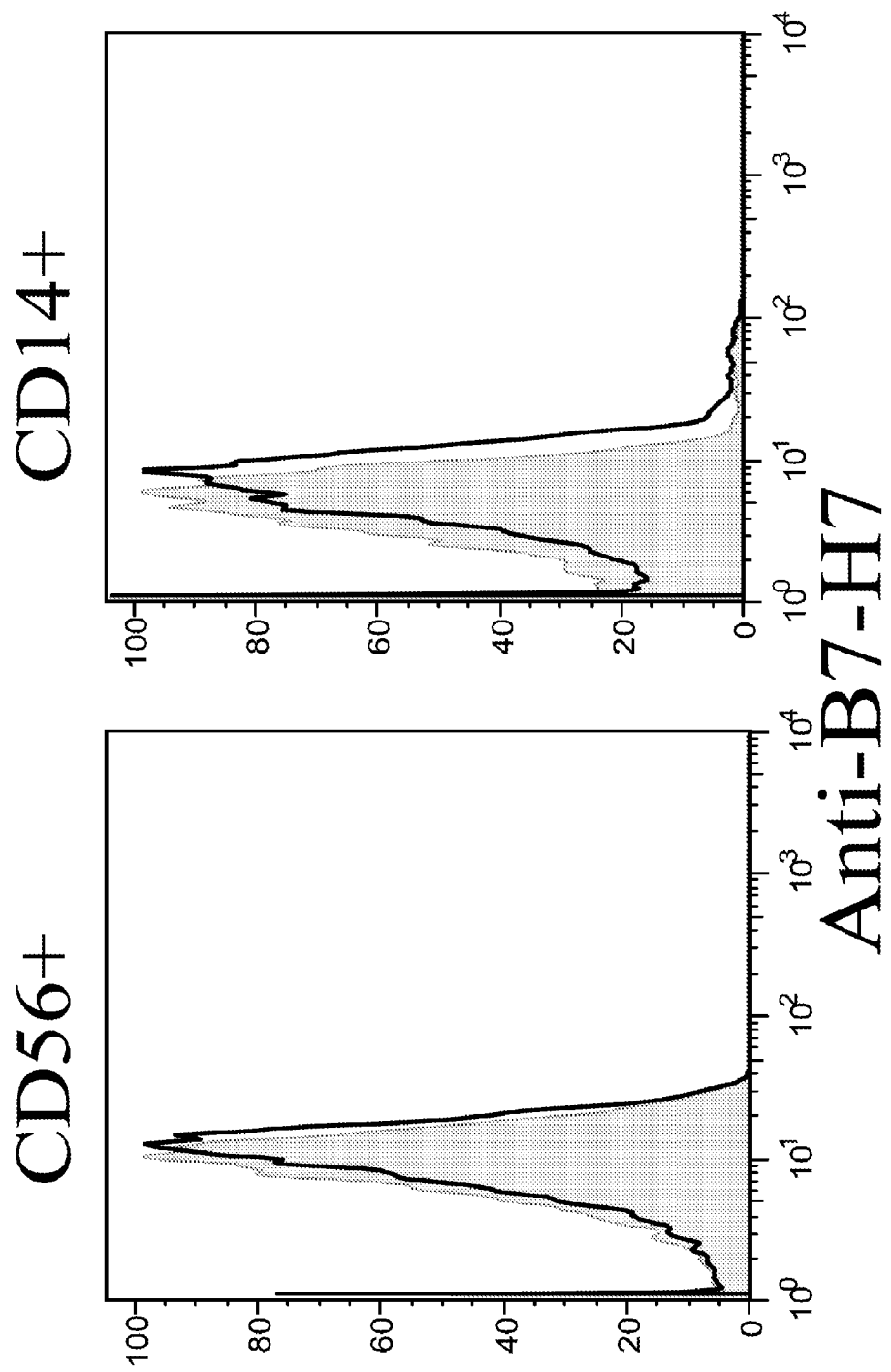

FIG. 14. Failure to detect cell surface B7-H7 on T, B, NK cells and monocytes. Human peripheral blood mononuclear cells were purified and co-stained with anti-B7-H7 mAb and cell type specific antibody against T cells (CD3), B cells (CD19), NK cells (CD56) and monocytes (CD14). After staining, cells were analyzed by flow cytometry and the data is shown as density of fluorescence.

Figure 15A:
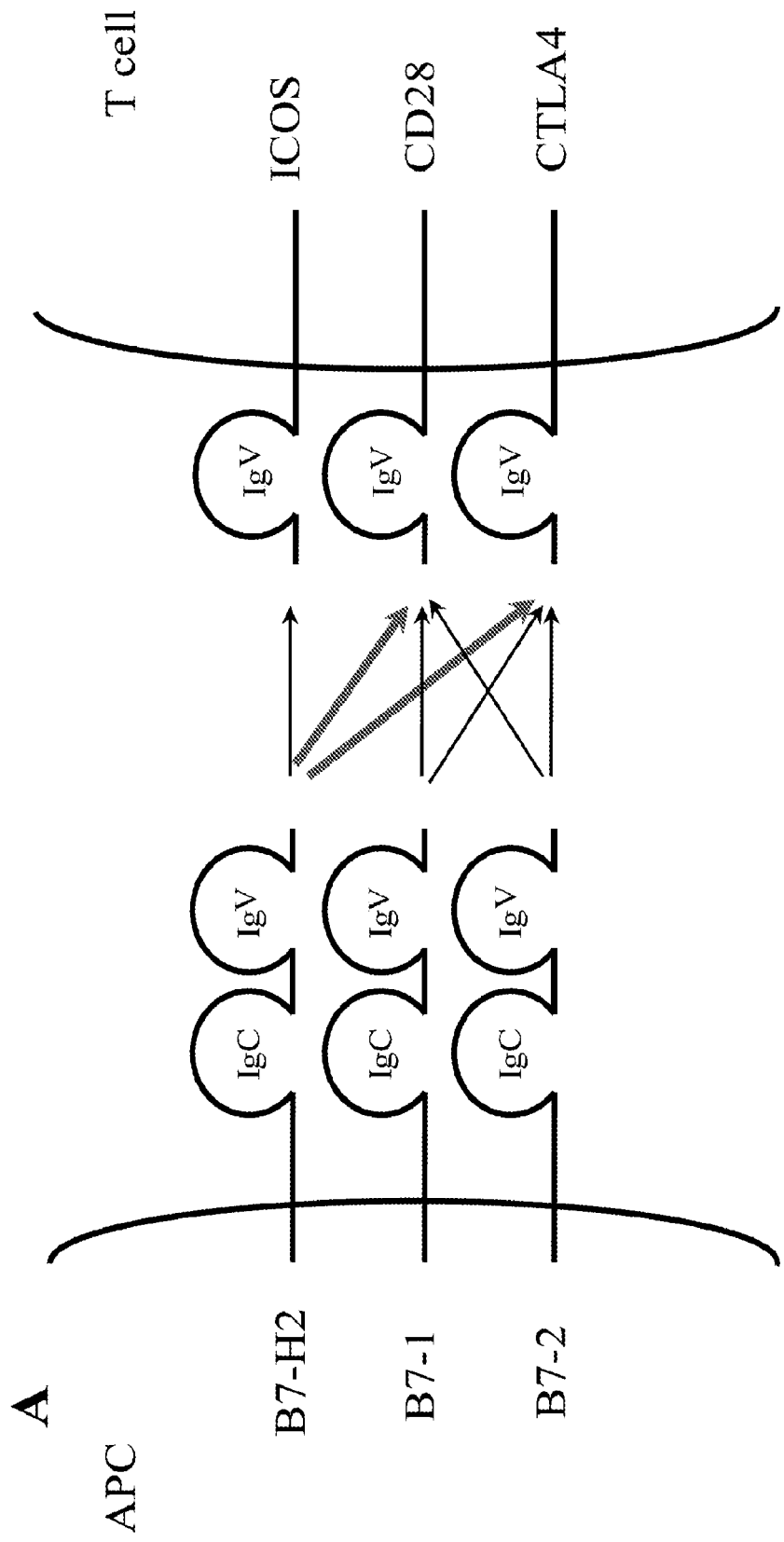
Figure 15B:
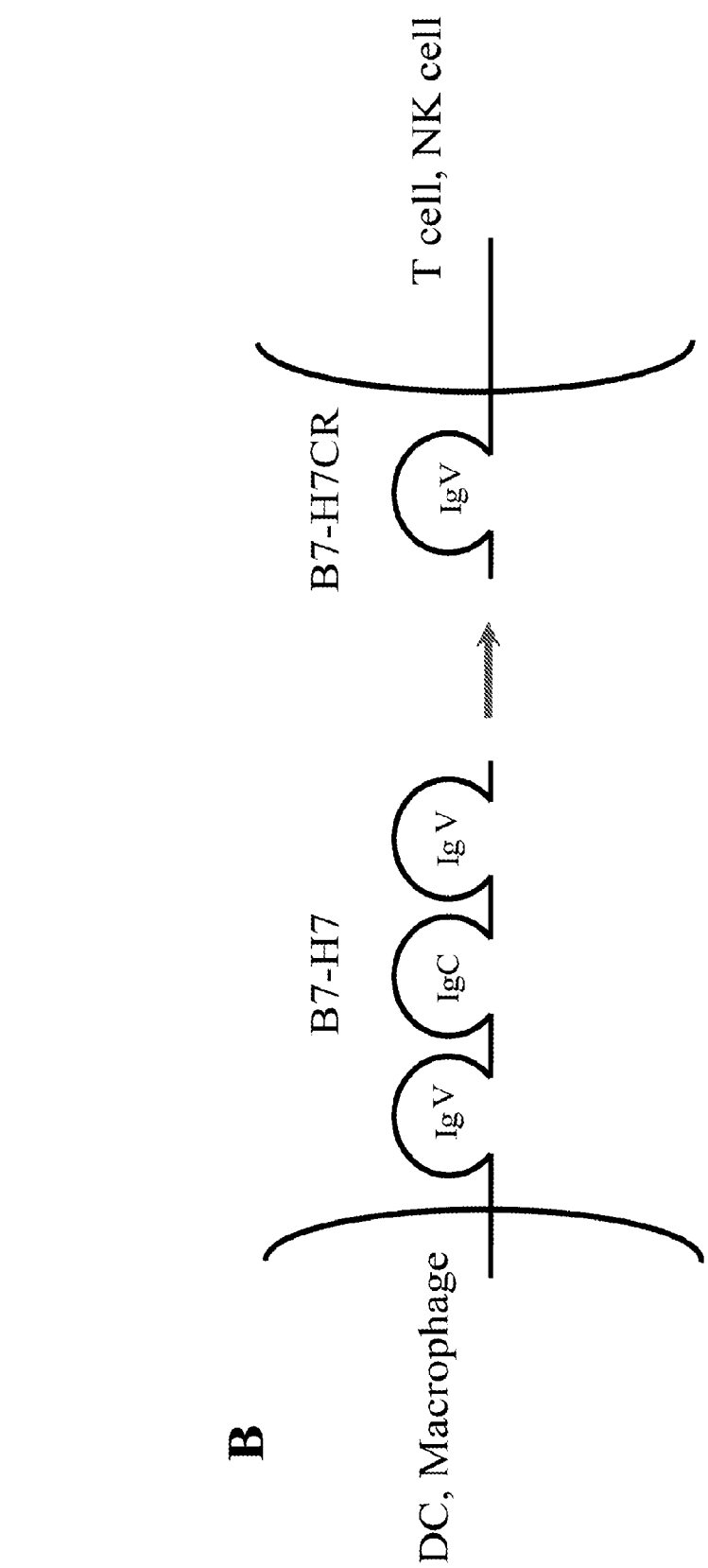

FIGS. 15A-15B. Illustration of new costimulatory pathways. (A) Intersection between the B7-CD28 and B7-H2/ICOS pathways. Previously described interactions are indicated in black lines and newly described interactions are shown in bold. (B) Newly described interactions between B7-H7 and B7-H7CR.

FIGS. 16A-16D.

(A-C) Specificity of B7-H2 bindings to CD28 and CTLA-4. 293T cells were transiently transfected with human full length B7-H2 (a), CD28 (b) or CTLA-4 (c) plasmids, and were subsequently stained by the indicated specific mAb or fusion proteins. In some experiments, mAb or fusion proteins were also included with other agents to examine specificity of the binding. Cells were analyzed using FACScan flow cytometry.

(D) Binding affinity of B7-H2 to ICOS, CD28 and CTLA-4. ICOSIg (left panel) and CD28Ig (middle panel) at the indicated concentrations were injected into flow cells that were coated with B7-H2Ig at 500RUs and the responses were determined by Surface Plasmon Resonance. Similarly, CTLA-4Ig (right panel) at the indicated concentration was injected into a flow cell coated with B7-H2Ig at 5000RUs. For all experiments, the same fusion proteins were injected into uncoated control flow cells to serve as the control. Binding data was overlaid with the fit of 1:1 interaction model.

(E) Interactions of CD28/CTLA-4 with their three ligands. To examine the relationship of B7-H2, B7-1 and B7-2 for their binding to CD28/CTLA-4, 293T cells were transiently transfected with full length human B7-H2 plasmids. CD28Ig and CTLA-4Ig were used to stain the transfectants, and then analyzed by flow cytometry. Isotype-matched human Ig (control Ig) was included as controls (upper panels). For competitive binding, CD28Ig and CTLA-4Ig at 10 µg/ml were pre-incubated with excessive amount of B7-1Ig (middle panels) or B7-2Ig (lower panels) at 40 µg/ml for 15 minutes before staining.

Figure 17A:
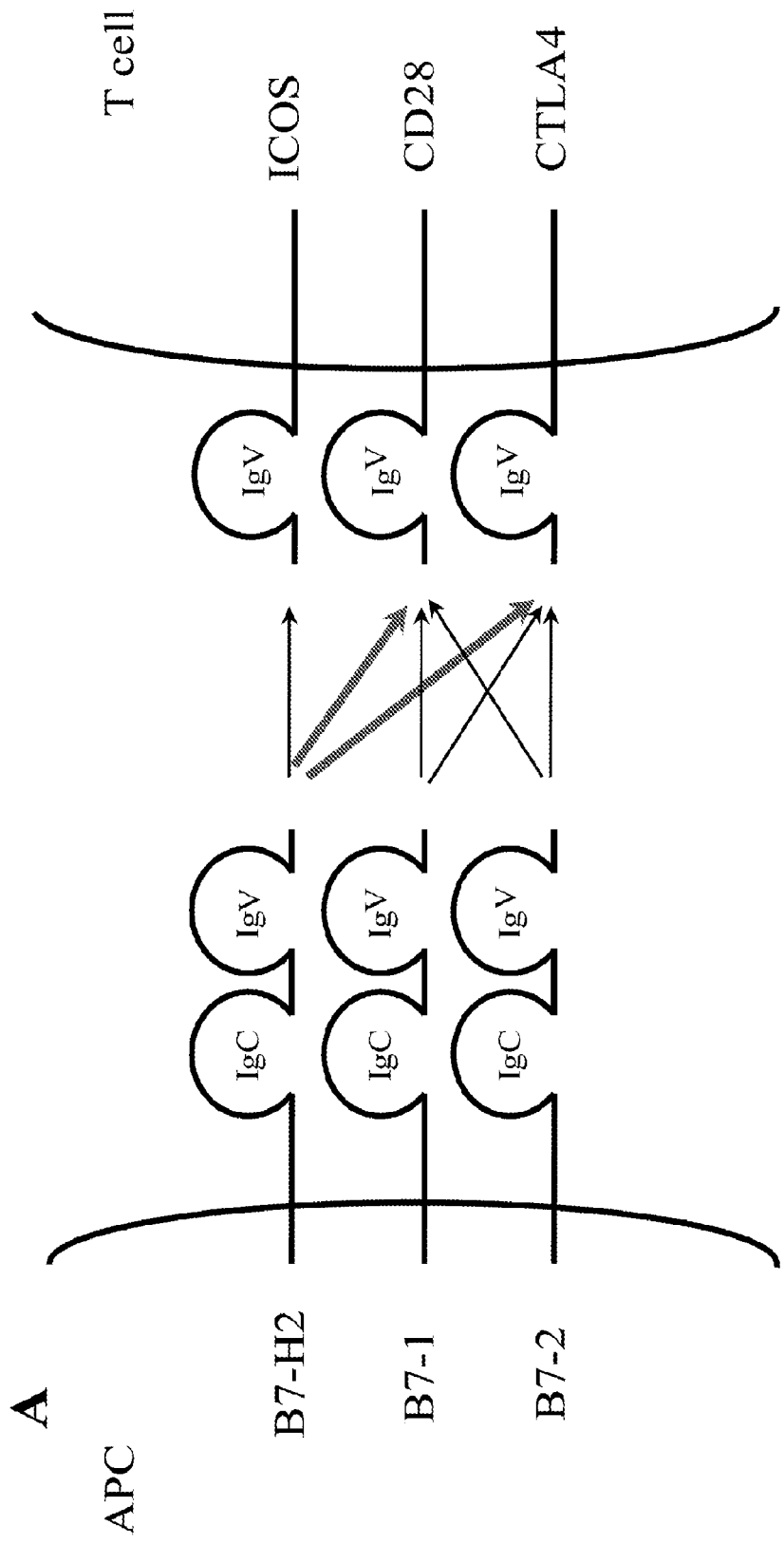
Figure 17B:
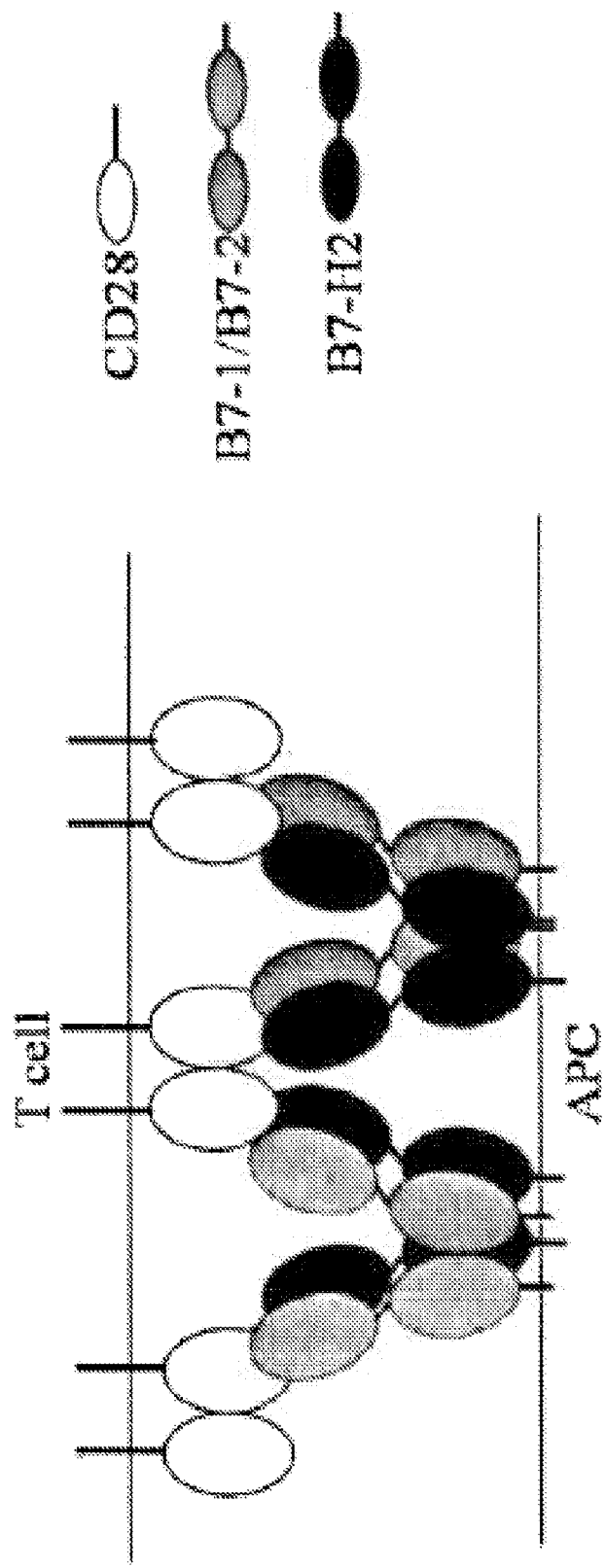

FIGS. 17A-17B. Illustration of the new costimulatory pathways. (A) Intersection between the B7-CD28 and B7-H2/ICOS pathways. Previously described interactions are indicated in black lines and newly described interactions are shown in bold. (B) The model of CD28 interaction with its three ligands on cell surface.

Figure 18:
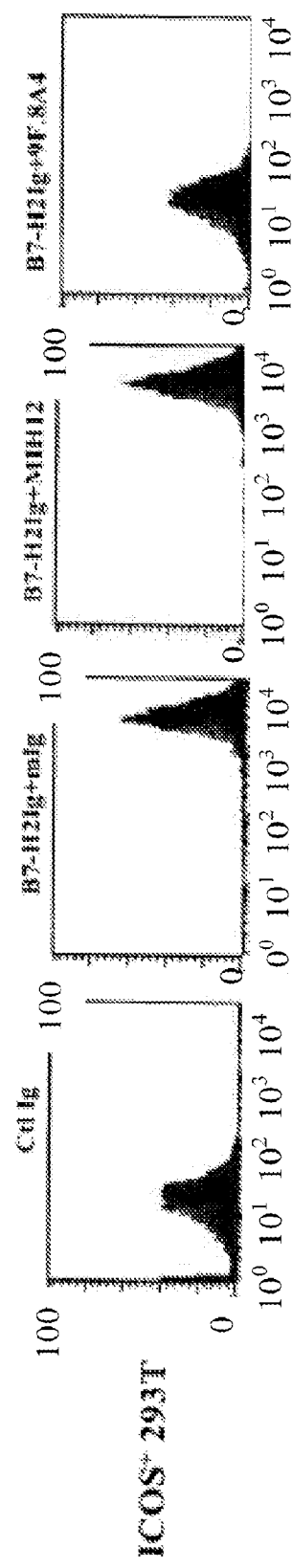
Figure 18:
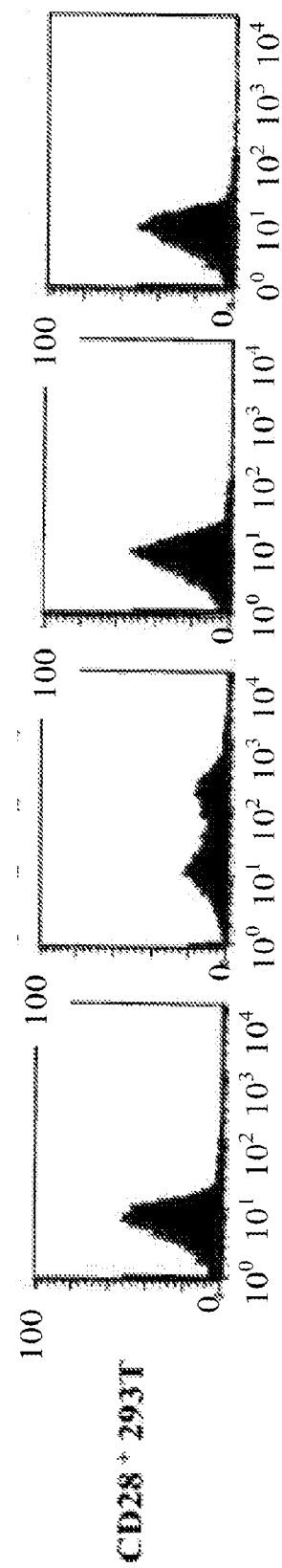
Figure 18:
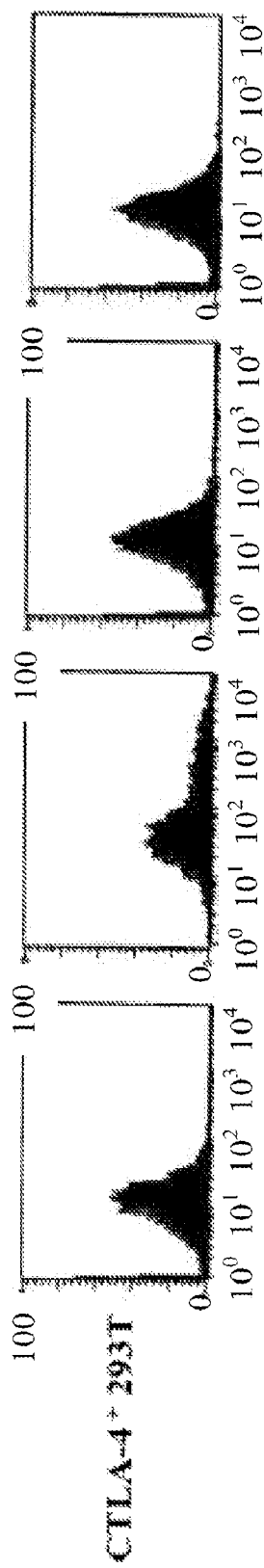

FIG. 18. Identification of mAbs that differentially abrogate B7-H2/CD28 and B7-H2/ICOS interactions. 293T cells were transiently transfected with human full length ICOS (ICOS+ 293T), CD28 (CD28+293T) or CTLA-4 (CTLA-4+293T) plasmids, and were stained by B7-H2Ig or control (ctl) Ig. Specific mAbs to B7-H2, clone MIH12 or 9F.8A4 as well as control mouse Ig, were included in the cultures to examine their blocking effects of B7-H2Ig binding. Cells were analyzed by flow cytometry.

FIGS. 19A-19B. Mouse B7-H2 does not interact with mouse CD28 and CTLA-4. (A) 293T cells were transiently transfected with mouse full length B7-H2 plasmids, and were stained by mouse ICOSIg, CD28Ig and CTLA-4Ig. (B) A mouse B7-H2/hB7-H2IgV chimera construct was made by replacing mouse B7-H2 Ig V region (Met1-Val149) with the human corresponding region (Met1-Gln123) in the mouse B7-H2 full length gene. 293T cells were transiently transfected to express this chimera gene, and were stained by mouse ICOSIg, CD28Ig and CTLA-4Ig. The results were analyzed by flow cytometry.

FIGS. 20A-20E. B7-H2 costimulation of human T cells through CD28.

(A) B7-H2/CD28 interaction costimulates human T cell proliferation. Peripheral blood T cells from a healthy donor were negatively selected and purified using a Pan T cell isolation kit (Miltenyi). Purified CD3$^+$ T cells at $2.5 \times 10^5$/well were stimulated with immobilized anti-human CD3 mAb (OKT3) at the indicated concentrations and 5 µg/ml of immobilized B7-H2Ig or control Ig (ctl Ig). B7-H2 mAb (clone MIH12 or 9F.8A4) or control mouse Ig (ctl Ig) at 10 µg/ml was included in soluble form to block coated B7-H2Ig for 1 hr and unbound mAbs were subsequently washed away by media before addition of T cells. $^3$HTdR was added during the final six hours of culture, and the incorporation of $^3$HTdR was determined by a scintillation counter.

(B) B7-H2 costimulates cytokine production from human T cells through CD28. Purified CD4$^+$ T cells at $2.5 \times 10^5$/wells were stimulated by immobilized CD3 mAb and B7-H2Ig as described in (a). MIH12, 9F.8A4 or control mouse Ig (ctl Ig) at 10 µm/ml was used in soluble form to block B7-H2Ig interaction with its receptors. Supernatants were collected daily up to three days. Cytokine levels were measured by BD Cytometric Bead Array (CBA) human Th1/Th2 cytokine kit and CBA IL-17A Flex set, and analyzed by FCAP Array software. Each data point is an average of triplicates with standard deviation.

(C & D) B7-H2/CD28 interaction enhances response of tetanus toxoid-specific memory T cells. (C) Monocyte-derived dendritic cells at $2.5 \times 10^4$/well and purified autologous T cells at $3 \times 10^5$/well were mixed together and incubated with tetanus toxoid at indicated concentration for five days. Blocking mAbs against CD28 (clone CD28.6), B7-H2 (clone MIH12 and 9F.8A4) or control mouse Ig at 10 µg/ml was included in soluble form at the beginning of the culture. $^3$HTdR was added during the final sixteen hours of culture, and the incorporation of $^3$HTdR was determined by a scintillation counter. (D) Interferon gamma concentration was measured in day 5 supernatants by BD (CBA) Human Th1/Th2 cytokine kit and analyzed by FCAP Array software. Each data point is an average of triplicates with standard deviation.

(E) B7-H2/CD28 interaction promotes IFN-gamma release in allogeneic T cell response. Monocyte derived dendritic cells at $2.5 \times 10^4$/well and purified allogeneic T cells at $3 \times 10^5$/well were mixed together. Blocking mAbs against CD28 (clone CD28.6), B7-H2 (clone MIH12 and 9F.8A4) or control mouse Ig at 10 µg/ml was included in soluble form at the beginning of the culture for five days. Interferon gamma concentration was measured in day 5 supernatants by BD (CBA) Human Th1/Th2 cytokine kit and analyzed by FCAP Array software. Each data point is an average of triplicates with standard deviation.

Figure 21:
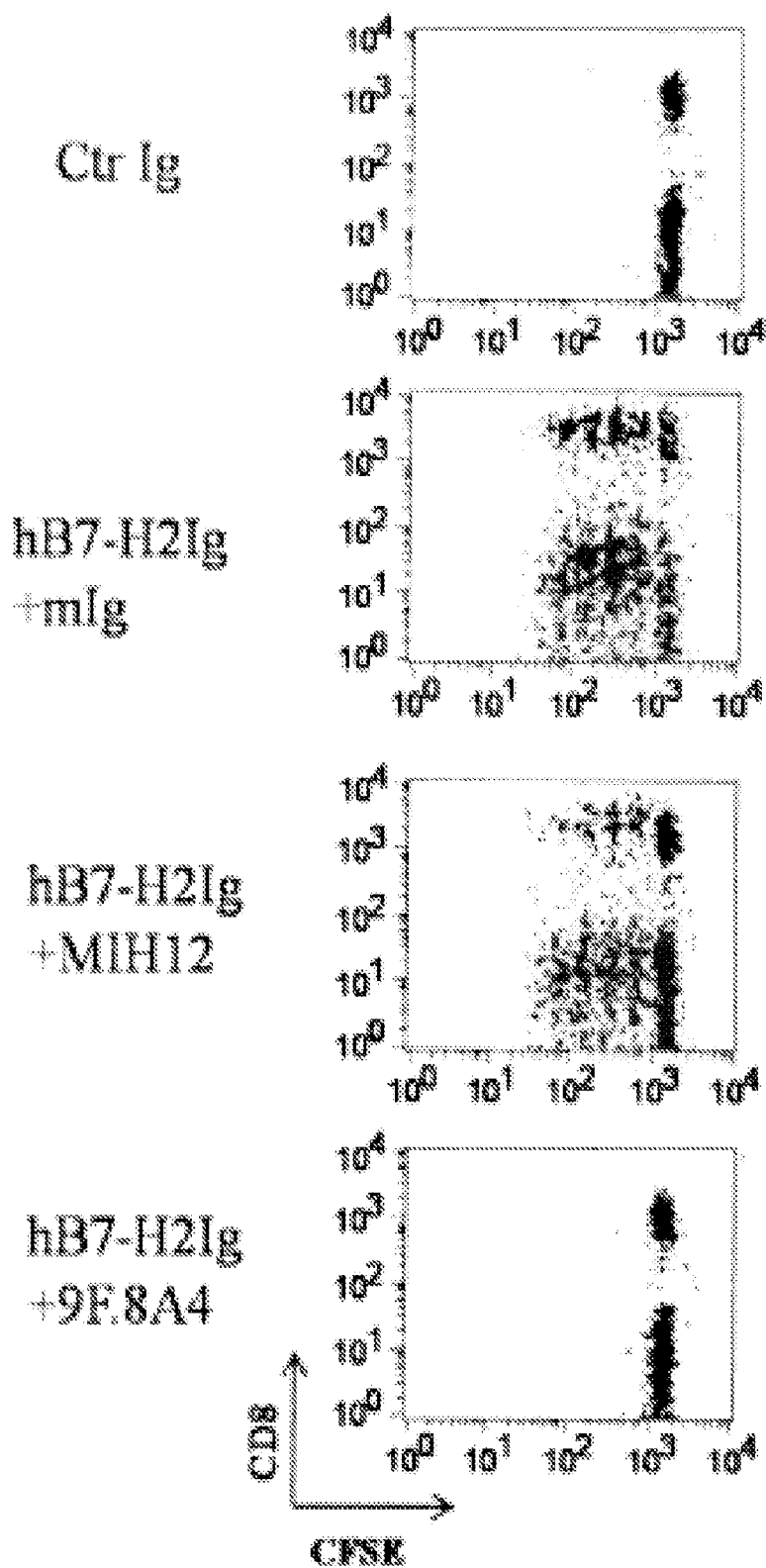
Figure 21:
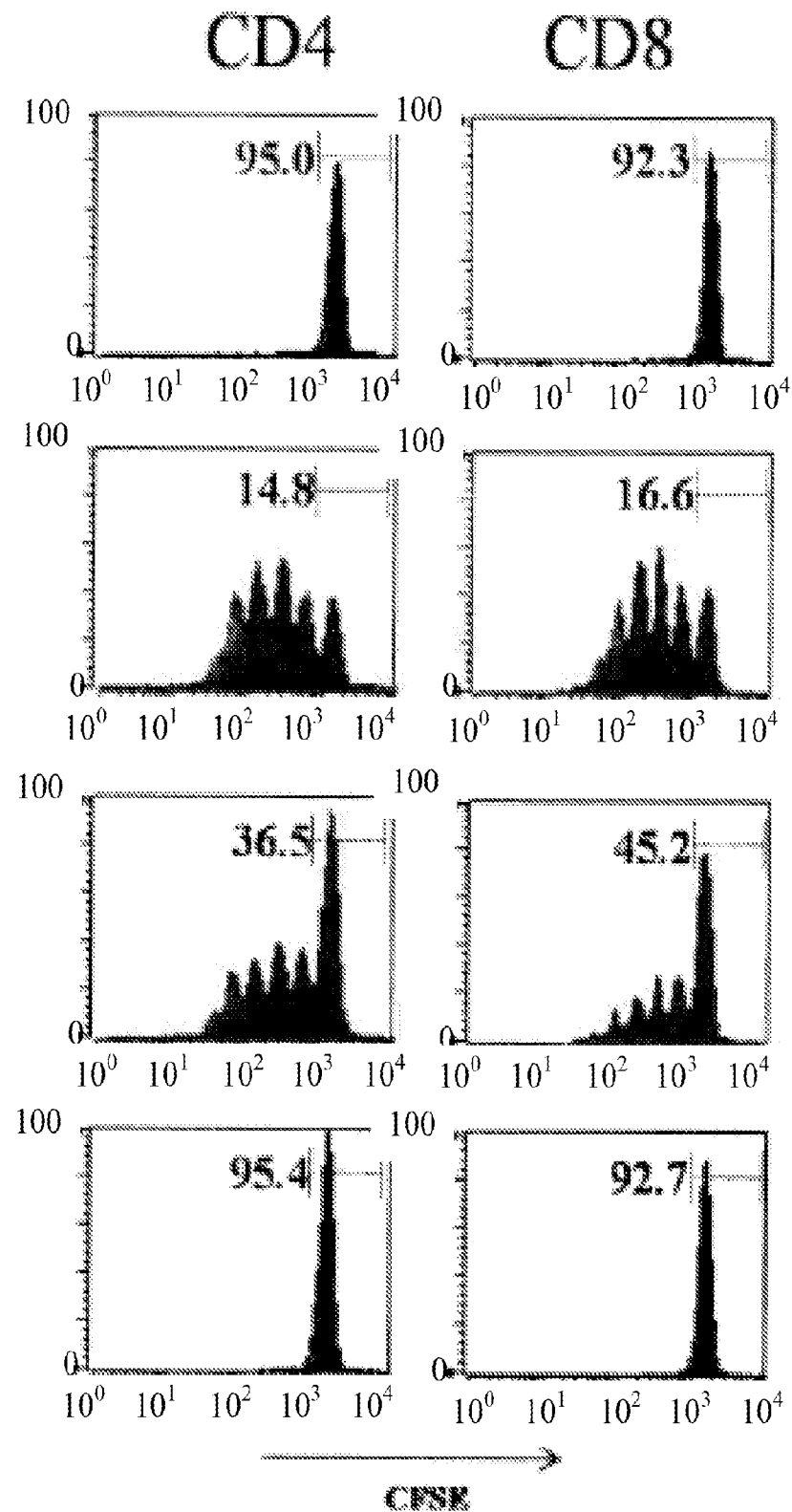

FIG. 21. B7-H2/CD28 interaction promotes division of human T cells. Peripheral blood T cells from a healthy donor were negatively selected and purified by Pan T cell isolation kit on affinity column. Purified CD3$^+$ T cells were labeled with 5 µM CSFE. Labeled human T cells at $2.5 \times 10^5$ cells/well were stimulated with immobilized anti-human CD3 mAB (OKT3) at the indicated concentrations and 5 µg/ml B7-H2Ig or control Ig (ctl Ig). B7-H2 mAB (clone MIH12 or 9F.8A4) or control Ig (ctl Ig) at 10 µg/ml was included to block coated B7-H2Ig for 1 hour and unbound mAbs were subsequently washed away by media before addition of T cells. T cells were collected on day 4 and analyzed by FACScan flow cytometry.

Figure 22:
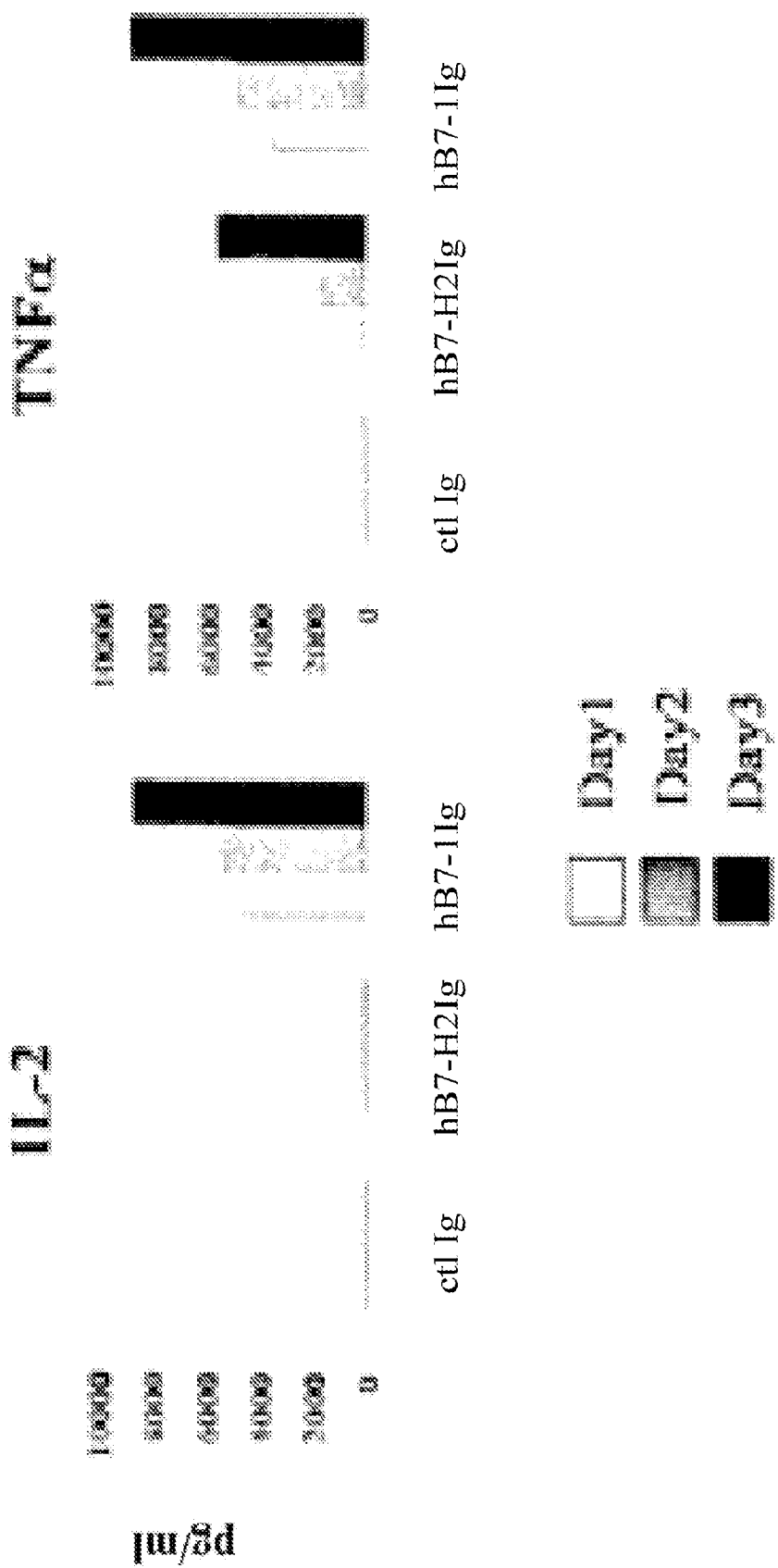
Figure 22:
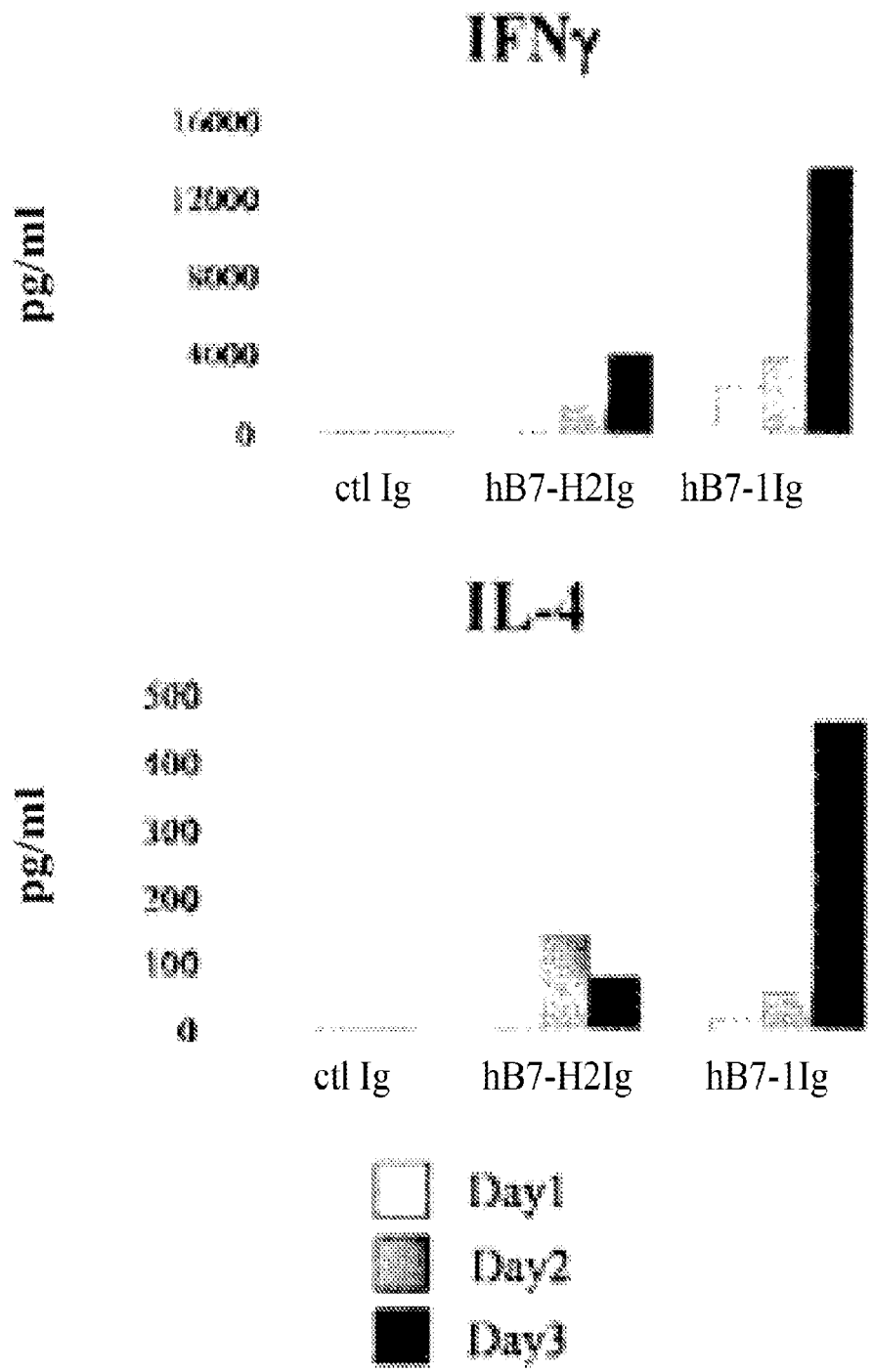
Figure 22:
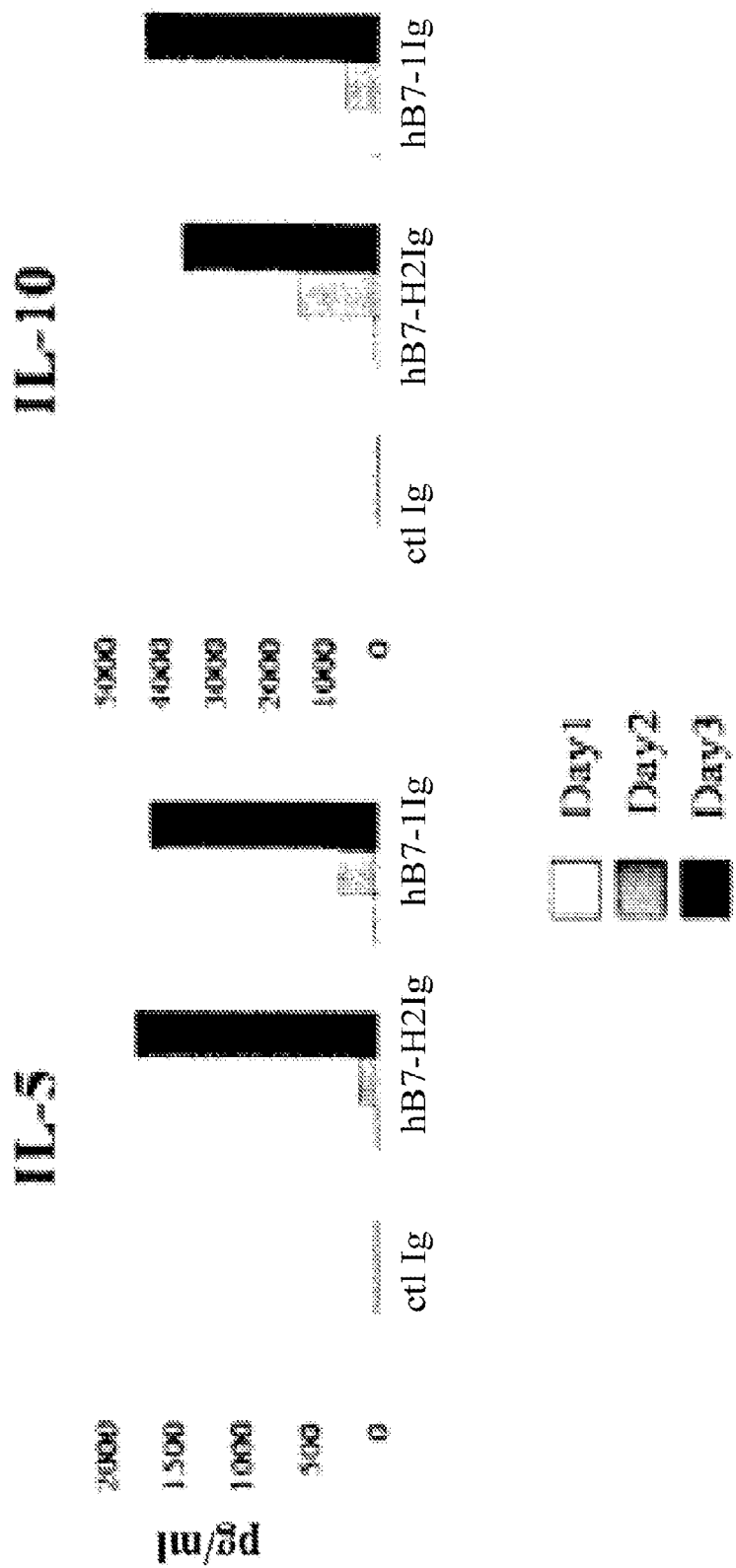
Figure 22:
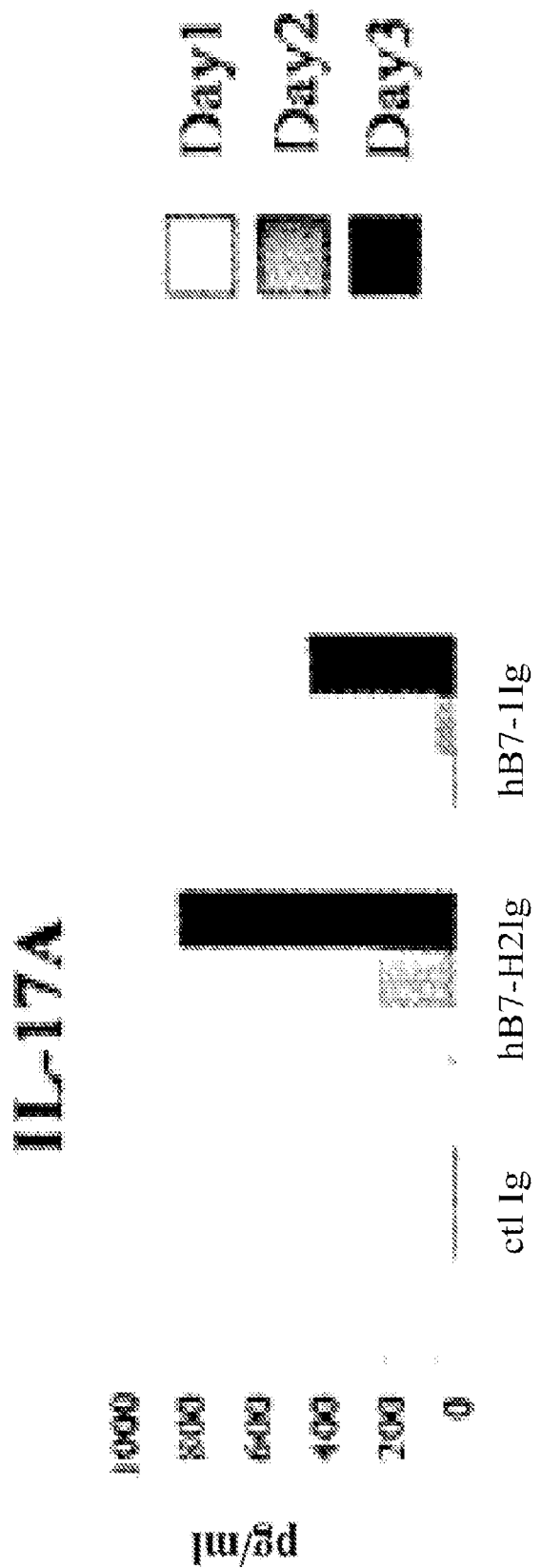

FIG. 22. Comparison of cytokine production induced by B7-1 and B7-2 costimulation. Purified CD4$^+$ T cells from PBMC of a healthy donor at $2.5 \times 10^5$ cells/well were stimulated by immobilized CD3 mAb and B7-1Ig or B7-2Ig. Supernatants were collected daily up to three days. Cytokine levels were measured by BD Cytometric Bead Array (CBA) Human Th1/Th2 cytokine kit and CBA IL-17A Flex set, and analyzed by FCAP Array software. Each data point is an average of triplicates.

FIG. 23. An alignment of amino acid sequences of representative native human B7-H7, native *pan troglodytes* B7-H7, and native *macaca mulatta* B7-H7.

FIG. 24. An alignment of the amino acid sequences of representative native human B7-H7CR, native *pan troglodytes* B7-H7CR, and native *bos taurus* B7-H7CR.

FIG. 25. An alignment of the nucleic acid sequences of representative native human B7-H7CR, native *pan troglodytes* B7-H7CR, and native *bos taurus* B7-H7CR.

5. DETAILED DESCRIPTION

In one aspect, described herein is the discovery of B7-H7CR as a co-stimulatory receptor and the modulation of one or more signal transduction pathways mediated by B7-H7CR to one or more of its ligands (e.g., B7-H7). In another aspect, described herein are antibodies that specifically bind to B7-H7, B7-H7CR, or the complex of B7-H7 and B7-HCR. In another aspect, described herein are Therapeutic Agents that modulate the interaction between certain co-stimulatory receptors and one or more of their ligands, and the use of such Therapeutic Agents for modulating one or more immune system functions. The Therapeutic Agents described herein are based, in part, on the discovery of new co-stimulatory receptor-ligand interactions. The Therapeutic Agents can be used in cell culture to modulate immune cell functions (e.g., lymphocyte proliferation, cytokine production, or antibody production). In particular, a cell may be contacted with a Therapeutic Agent to modulate one or more immune cell functions. In addition, a Therapeutic Agent can be administered to a subject to prevent, treat or manage certain diseases, such as cancer, an infectious disease, an autoimmune disease, and an inflammatory disease.

In another aspect, described herein are methods of identifying receptor-ligand interactions. Such methods can be used to identify interactions between costimulatory ligands and costimulatory receptors.

5.1 ANTIBODIES SPECIFIC FOR B7-H70R B7-H7CR

In one aspect, presented herein are antibodies that specifically bind to a B7-H7 polypeptide. In a specific embodiment, presented herein are antibodies that specifically bind to a human B7-H7 polypeptide. In another specific embodiment, presented herein are antibodies that specifically bind to a native B7-H7 polypeptide (e.g., a native human B7-H7 polypeptide) and inhibit or reduce the binding of the native B7-H7 polypeptide to one or more B7-H7 receptors (e.g., a native B7-H7CR polypeptide). In a more specific embodiment, presented herein are antibodies that specifically bind to a native B7-H7 polypeptide (e.g., a native human B7-H7 polypeptide) and inhibit or reduce the binding of native B7-H7 polypeptide (e.g., a native human B7-H7 polypeptide) to a native B7-H7CR polypeptide (e.g., a native human B7-H7CR polypeptide). Such antibodies, in accordance with this embodiments, may block (sterically or non-sterically) the binding of the B7-H7 polypeptide to B7-H7CR polypeptide. In a specific embodiment, an antibody reduces the binding of the B7-H7 polypeptide to B7-H7CR polypeptide by at least 10%, 15%, 25%, 30%, 40%, 50%, 75%, 80%, 85%, 90%, 95%, 98% or 99%, or in the range of between 10% to 25%, 10% to 50%, 10% to 75%, 25% to 50%, 25% to 75%, 25% to 98%, 50% to 98%, or 75% to 100% relative to a negative control (e.g., binding of the B7-H7 polypeptide to B7-H7CR polypeptide in the absence of the antibody or in the presence of a negative control antibody that is known not to bind to B7-H7) as determined by methods well known in the art, e.g., ELISA, cell-based assays including flow cytometry, KinEx A assay, and plasmon surface resonance assay (e.g., BIAcore® assay).

In another aspect, presented herein are antibodies that specifically bind to a B7-H7CR polypeptide. In a specific embodiment, presented herein are antibodies that specifically bind to a human B7-H7CR polypeptide. In another specific embodiment, presented herein are antibodies that specifically bind to a native B7-H7CR polypeptide (e.g., a native human B7-H7CR) and inhibits or reduces the binding of the native B7-H7CR to one or more B7-H7CR ligands (e.g., a native B7-H7 polypeptide). In a more specific embodiment, presented herein are antibodies that specifically bind to a native B7-H7CR polypeptide (e.g., a native human B7-H7CR polypeptide) and inhibit or reduce the binding of a native B7-H7CR polypeptide (e.g., a native human B7-H7CR polypeptide) to a native B7-H7 polypeptide (e.g., native human B7-H7 polypeptide). Such antibodies, in accordance with this embodiments, may block (sterically or non-sterically) the binding of the B7-H7 polypeptide to B7-H7CR polypeptide. In a specific embodiment, an antibody reduces the binding of the B7-H7 to B7-H7CR by at least 10%, 15%, 25%, 30%, 40%, 50%, 75%, 80%, 85%, 90%, 95%, 98% or 99%, or in the range of between 10% to 25%, 10% to 50%, 10% to 75%, 25% to 50%, 25% to 75%, 25% to 98%, 50% to 98%, or 75% to 100% relative to a negative control (e.g., binding of the B7-H7 polypeptide to B7-H7CR polypeptide in the absence of the antibody or in the presence of a negative control antibody that is known not to bind to B7-H7) as determined by methods well known in the art, e.g., ELISA, cell-based assays including flow cytometry, KinEx A assay, and plasmon surface resonance assay (e.g., BIAcore® assay). In certain embodiments, the antibody that specifically binds to a B7-H7CR polypeptide is an agonist. In other embodiments, the antibody that specifically binds to a B7-H7CR polypeptide is an antagonist.

In another aspect, presented herein are antibodies that specifically bind to B7-H7CR/B7-H7 complex. In a specific embodiment, presented herein are antibodies that specifically bind to human B7-H7CR/human B7-H7 complex. In another specific embodiment, presented herein are antibodies that specifically bind to a native B7-H7CR/native B7-H7 complex (e.g., a native human B7-H7CR/native human B7-H7 complex) and inhibit or reduce the binding of a native B7-H7CR polypeptide to one or more B7-H7CR ligands. Such antibodies, in accordance with this embodiment, may block (sterically or non-sterically) the native B7-H7CR to one or more B7-H7CR ligands. In a specific embodiment, the antibody reduces the binding of the native B7-H7CR polypeptide to one or more native B7-H7CR ligands by at least 10%, 15%, 25%, 30%, 40%, 50%, 75%, 80%, 85%, 90%, 95%, 98% or 99%, or in the range of between 10% to 25%, 10% to 50%, 10% to 75%, 25% to 50%, 25% to 75%, 25% to 98%, 50% to 98%, or 75% to 100% relative to a negative control (e.g., binding of the native B7-H7CR polypeptide to one or more native B7-H7CR ligands in the absence of the antibody or in the presence of a negative control antibody that is known not to bind to B7-H7) as determined by methods well known in the art, e.g., ELISA, cell-based assays including flow cytometry, KinEx A assay, and plasmon surface resonance assay (e.g., BIAcore® assay). In certain embodiments, an antibody that specifically binds to a B7-H7CR/B7-H7 complex inhibits or reduces the binding of native B7-H7 to one or more of its receptors. Such antibodies may block (sterically or non-sterically) the binding of native B7-H7 to one or more its receptors.

In another aspect, presented herein are antibodies that bind to B7-H7 and neutralize B7-H7. In another aspect, presented herein are antibodies that bind to B7-H7CR and neutralize B7-H7CR.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

In some aspects, presented herein are antibodies that bind B7-H7 and increase degradation.

Antibodies that specifically bind to the B7-H7 polypeptide, B7-H7CR polypeptide, or the B7-H7/B7-H7CR complex can be produced by any method well known in the art, e.g., as described in U.S. Pat. Nos. 5,807,715, 6,331,415, and 6,818,216; U.S. Patent Application Publication Nos. US 2002/0098189, US 2004/0028685, US 2005/0019330, US 2006/0115485, and US 2007/0086943; International Publication Nos. WO 02/46237 and WO 04/010935; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties).

In a specific embodiment, presented herein is the monoclonal antibody designated 2D3. This antibody as discussed in the example section below was generated from a hybridoma derived from the fusion of SP2 myeloma with B cells from a mouse immunized with human B7-H7-Ig. In another specific embodiment, presented herein is the monoclonal antibody designated 4-5. This antibody as discussed in the example section was generated from a hybridoma derived from the fusion of SP2 myeloma with B cells from a hamster immunized with human B7-H7CR-Ig. Encompassed herein are antigen-binding fragments (e.g., Fab fragments, F(ab') fragments, F(ab')₂ fragments) of the antibody designated 2D3 or 4-5.

In another aspect, presented herein are antibodies (such as monoclonal antibodies) that compete with the 2D3 antibody or the 4-5 antibody for binding to a native B7-H7 polypeptide or a native B7-H7CR polypeptide, respectively. Competition assays known to one of skill in the art may be used to assess the competition of the 2D3 antibody or the 4-5 antibody for binding to native B7-H7 polypeptide or native B7-H7CR polypeptide, respectively. For example, an immunoassay (e.g., an ELISA) in a competitive format may be used.

In another aspect, presented herein are antibodies that specifically bind to B7-H7 polypeptide comprising a variable light (VL) chain and/or a variable heavy (VH) chain of the antibody 2D3. In one embodiment, an antibody that specifically binds to B7-H7 polypeptide comprises the VL chain or VH chain of the antibody 2D3. In another embodiment, an antibody that specifically binds to B7-H7 polypeptide comprises the VL chain of the antibody 2D3 and the VH chain of another antibody. In another embodiment, an antibody that specifically binds to B7-H7 polypeptide comprises the VH chain of the antibody 2D3 and the VL chain of another antibody. In a specific embodiment, an antibody that specifically binds to B7-H7 polypeptide comprises the VL chain of the antibody 2D3 and the VH chain of the antibody 2D3.

In another aspect, presented herein are antibodies that specifically bind to B7-H7 polypeptide comprising a VL domain and/or a VH domain of the antibody 2D3. In one embodiment, an antibody that specifically binds to B7-H7 polypeptide comprises the VL domain or VH domain of the antibody 2D3. In another embodiment, an antibody that specifically binds to B7-H7 polypeptide comprises the VL domain of the antibody 2D3 and the VH domain of another antibody. In another embodiment, an antibody that specifically binds to B7-H7 polypeptide comprises the VH domain of the antibody 2D3 and the VL domain of another antibody. In a specific embodiment, an antibody that specifically binds to B7-H7 polypeptide comprises the VL domain of the antibody 2D3 and the VH domain of the antibody 2D3.

In another aspect, presented herein are antibodies specifically that bind to B7-H7CR polypeptide comprising a VL chain and/or a VH chain of the antibody 4-5. In one embodiment, an antibody that specifically binds to B7-H7CR polypeptide comprises the VL chain or VH chain of the antibody 4-5. In another embodiment, an antibody that specifically binds to B7-H7CR polypeptide comprises the VL chain of the antibody 4-5 and the VH chain of another antibody. In another embodiment, an antibody that specifically binds to B7-H7CR polypeptide comprises the VH chain of the antibody 4-5 and the VL chain of another antibody. In a specific embodiment, an antibody that specifically binds to B7-H7CR polypeptide comprises the VL chain of the antibody 4-5 and the VH chain of the antibody 4-5.

In another aspect, presented herein are antibodies specifically that bind to B7-H7CR polypeptide comprising a VL domain and/or a VH domain of the antibody 4-5. In one embodiment, an antibody that specifically binds to B7-H7CR polypeptide comprises the VL domain or VH domain of the antibody 4-5. In another embodiment, an antibody that specifically binds to B7-H7CR polypeptide comprises the VL domain of the antibody 4-5 and the VH domain of another antibody. In another embodiment, an antibody that specifically binds to B7-H7CR polypeptide comprises the VH domain of the antibody 4-5 and the VL domain of another antibody. In a specific embodiment, an antibody that specifically binds to B7-H7CR polypeptide comprises the VL domain of the antibody 4-5 and the VH domain of the antibody 4-5.

In another aspect, presented herein are antibodies that specifically bind to B7-H7 comprising one, two or three complementarity determining regions (CDRs) of the variable heavy chain (VH CDRs) of the antibody 2D3 and/or one, two or three CDRs of the variable light chain (VL CDRs) of the antibody 2D3. In certain embodiments, an antibody that specifically binds to B7-H7, comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR1, a VH CDR2, a VH CDR3, a VL CDR1 and a VL CDR2; a VH CDR1, a VH CDR2, a VH CDR3, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs of the antibody 2D3.

In another aspect, presented herein are antibodies that specifically bind to B7-H7CR polypeptide comprising one, two or three complementarity determining regions (CDRs) of the variable heavy chain (VH CDRs) of the antibody 4-5 and/or one, two or three CDRs of the variable light chain (VL CDRs) of the antibody 4-5. In certain embodiments, an antibody that specifically binds to B7-H7CR, comprises (or alternatively, consists of) a VH CDR1 and a VL CDR1; a VH CDR1 and a VL CDR2; a VH CDR1 and a VL CDR3; a VH CDR2 and a VL CDR1; VH CDR2 and a VL CDR2; a VH CDR2 and a VL CDR3; a VH CDR3 and a VL CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1; a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs of the antibody 4-5.

The sequences of the antibody 2D3 and 4-5 can be determined using standard techniques known to one skilled in the art and the VH chain, VL chain, VH domain, VL domain, VH CDRs, and VL CDRs can be determined using, e.g., the Kabat numbering system (such as the EU index in Kabat).

The antibodies presented herein include derivatives that are chemically modified by, e.g., the covalent or non-covalent attachment of any type of molecule to the antibody. Antibody derivatives also include antibodies that have been chemically modified by, e.g., glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies provided herein presented herein can comprise a framework region known to those of skill in the art (e.g., a human or non-human fragment). The framework region may be naturally occurring or consensus framework regions.

In another aspect, presented herein are nucleic acids encoding the antibodies presented herein. In some embodiments, a nucleic acid molecule(s) encoding an antibody presented herein is isolated. In other embodiments, a nucleic acid(s) encoding an antibody presented herein or generated in accordance with the methods provided herein is not isolated. In yet other embodiments, a nucleic acid(s) encoding an antibody presented herein is integrated, e.g., into chromosomal DNA or an expression vector. In a specific embodiment, a nucleic acid(s) presented herein encodes for the antibody 2D3, the antibody 4-5 or a fragment thereof (in particular, an antigen-binding fragment thereof).

The antibodies described herein can be affinity matured using techniques known to one of skill in the art. The monoclonal antibodies described herein can be chimerized using techniques known to one of skill in the art. A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

The monoclonal antibodies described herein can be humanized. A humanized antibody is an antibody which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework (FR) and CDR sequences, more often 90%, and most preferably greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.)

5.1.1 Increased Half-Life

In one aspect, antibodies presented herein are modified to have an extended (or increased) half-life in vivo. In one embodiment, presented herein are antibodies which have a half-life in a subject, preferably a mammal and most preferably a human, of from about 3 days to about 180 days (or more), and in some embodiments greater than 3 days, greater than 7 days, greater than 10 days, greater than 15 days, greater than 20 days, greater than 25 days, greater than 30 days, greater than 35 days, greater than 40 days, greater than 45 days, greater than 50 days, at least about 60 days, greater than 75 days, greater than 90 days, greater than 105 days, greater than 120 days, greater than 135 days, greater than 150 days, greater than 165 days, or greater than 180 days.

In a specific embodiment, modified antibodies having an increased half-life in vivo are generated by introducing one or more amino acid modifications (i.e., substitutions, insertions or deletions) into an IgG constant domain, or FcRn-binding fragment thereof (preferably a Fc or hinge-Fc domain fragment). See, e.g., International Publication Nos. WO 02/060919; WO 98/23289; and WO 97/34631; and U.S. Pat. No. 6,277,375; each of which is incorporated herein by reference in its entirety. In a specific embodiment, the antibodies may have one or more amino acid modifications in the second constant domain (i.e., the CH2 domain at, e.g., residues 231-340 of human IgG1) and/or the third constant domain (i.e., the CH3 domain at, e.g., residues 341-447 of human IgG1), with numbering according to the Kabat numbering system (e.g., the EU index in Kabat).

In some embodiments, to prolong the in vivo serum circulation of antibodies, inert polymer molecules such as high molecular weight polyethyleneglycol (PEG) are attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

In another embodiment, antibodies are conjugated to albumin in order to make the antibody more stable in vivo or have a longer half-life in vivo. The techniques are well-known in the art, see, e.g., International Publication Nos. WO 93/15199, WO 93/15200, and WO 01/77137; and European Patent No. EP 413,622, all of which are incorporated herein by reference.

5.1.2 Antibody Conjugates

In some embodiments, antibodies are conjugated or recombinantly fused to a diagnostic, detectable or therapeutic agent or any other molecule. When in vivo half-life is desired to be increased, said antibodies can be modified. The conjugated or recombinantly fused antibodies can be useful, e.g., in detecting tissues or cells that express B7-H7 polypeptide or B7-H7CR polypeptide. In a specific embodiment, a method for detecting B7-H7 expressing cells or tissue, comprises contacting an antibody that specifically binds to B7-H7 with cells or tissues of a subject and detecting the cells or tissues to which the antibody binds. In a specific embodiment, a method for detecting B7-H7CR expressing cells or tissue, comprises contacting an antibody that specifically binds to B7-H7CR with cells or tissues of subject and detecting the cells or tissues to which the antibody binds. In accordance with such embodiments, the antibody can be conjugated to a detectable moiety and the binding of an antibody to cells or tissues can be detected by detecting the presence of the detectably moiety. Alternatively, the binding of the antibody to cells or tissues can be detected by detecting using a labeled secondary antibody that binds to the antibody and detecting the presence of the labeled secondary antibody. In certain embodiments, after cells or tissue are incubated with the appropriate antibody, unbound antibody is removed by one or more washes prior to detecting the cells or tissue to which the antibody is bound. In some embodiments, the methods for detecting B7-H7- or B7-H7CR-expressing cells or tissues includes the use of positive and/or negative controls. For example, cells or tissues known to express B7-H7 or B7-H7CR can be used in the methods as a positive control and cells or tissues known not to express B7-H7 or B7-H7CR can be used in the methods as a negative control. Examples of detectable moieties include, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and acquorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In) technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Encompassed herein are antibodies recombinantly fused or chemically conjugated (including both covalent and non-covalent conjugations) to a heterologous protein or polypeptide (or fragment thereof, preferably to a polypeptide of about 5, about 10, about 20, about 30, about 40, about 50, about 60, about 70, about 80, about 90 or about 100 amino acids) to generate fusion proteins. In particular, provided herein are fusion proteins comprising an antigen-binding fragment of a monoclonal antibody (e.g., a Fab fragment, Fd fragment, Fv fragment, F(ab)$_2$ fragment, a VH domain, a VH CDR, a VL domain or a VL CDR) and a heterologous protein, polypeptide, or peptide. In a specific embodiment, the heterologous protein, polypeptide, or peptide that the antibody is fused to is useful for targeting the antibody to a particular cell type.

Encompassed herein are uses of the antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a peptide or polypeptide possessing a desired biological activity. Such proteins may include, for example, interferon-γ, interferon-β, interferon-α, interleukin-2 ("IL-2"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), granulocyte colony stimulating factor ("G-CSF")), or a growth factor. The therapeutic moiety or drug conjugated or recombinantly fused to an antibody should be chosen to achieve the desired prophylactic or therapeutic effect(s). A clinician or other medical personnel should consider the following when deciding on which therapeutic moiety or drug to conjugate or recombinantly fuse to an antibody: the nature of the disease, the severity of the disease, and the condition of the subject.

Moreover, antibodies can be fused to marker sequences, such as a peptide to facilitate purification. In preferred embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the Influenza hemagglutinin protein (Wilson et al., 1984, Cell 37:767), and the "flag" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; International publication Nos. WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; which are incorporated herein by reference in their entireties.

In particular, fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the monoclonal antibodies described herein or generated in accordance with the methods provided herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding a monoclonal antibody described herein or generated in accordance with the methods provided herein may be recombined with one or more components, motifs, sections, parts, domains, fragments, etc. of one or more heterologous molecules.

An antibody can also be conjugated to a second antibody to form an antibody heteroconjugate as described by Segal in U.S. Pat. No. 4,676,980, which is incorporated herein by reference in its entirety.

An antibody can also be linked to two, three, or more antibodies to form a bispecific or multispecific antibody.

An antibody can also be attached to solid supports, which are particularly useful for immunoassays or purification of an antigen. Such solid supports include, but are not limited to, glass, cellulose, polyacrylamide, nylon, polystyrene, polyvinyl chloride or polypropylene.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

5.2 THERAPEUTIC AGENTS THAT MODULATE THE B7-H7 & B7-H7CR INTERACTION

In one aspect, presented herein are Therapeutic Agents that modulate one or more of the signal transduction pathways mediated by a native B7-H7 polypeptide binding to one or more of its ligands (e.g., B7-H7CR). In another aspect, presented herein are Therapeutic Agents that modulate one or more of the signal transduction pathways mediated by a native B7-H7CR binding to one or more of its ligands (e.g., B7-H7). In a specific embodiment, presented herein are Therapeutic Agents that modulate one or more of the signal transduction pathways induced when a native B7-H7 polypeptide binds to a native B7-H7CR polypeptide. In another specific embodiment, a Therapeutic Agent modulates the interaction between a native B7-H7CR polypeptide and a native B7-H7 polypeptide. In another aspect, presented herein are Therapeutic Agents that modulate the expression of a native B7-H7CR polypeptide or a native B7-H7 polypeptide. In a specific embodiment, a Therapeutic Agent selectively modulates the expression of a native B7-H7CR polypeptide or a native B7-H7 polypeptide. See Sections 5.2.1 to 5.2.6, infra, for specific examples of Therapeutic Agents.

In a specific embodiment, one or more signal transduction pathways are modulated by contacting a Therapeutic Agent with an immune cell or a population of immune cells. In another embodiment, the interaction between B7-H7 and one or more of its receptors (e.g., B7-H7CR) is modulated by contacting a Therapeutic Agent with an immune cell or a population of immune cells. In another embodiment, the interaction between B7-H7CR and its ligands (e.g., B7-H7) is modulated by contacting a Therapeutic Agent with an immune cell or a population of immune cells. In another embodiment, the expression of B7-H7 or B7-H7CR is modulated by contacting a Therapeutic Agent with an immune cell or a population of immune cells expressing B7-H7 or B7-HCR, respectively.

In a specific embodiment, a Therapeutic Agent modulates one or more of the signal transduction pathways induced by B7-H7 binding to B7-H7CR. In certain embodiments, a Therapeutic Agent selectively modulates one or more signal transduction pathways induced by B7-H7 binding to B7-H7CR. In certain embodiments, a Therapeutic Agent selectively induces one or more of the signal transduction pathways induced by the binding of B7-H7 to B7-H7CR. In specific embodiments, a Therapeutic Agent induces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent. In specific embodiments, a Therapeutic Agent: (i) induces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not induce, or induces one or more of the signal transduction pathways induced by the binding of B7-H7CR to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H7CR to such one or more other ligands in the absence of the Therapeutic Agent.

In specific embodiments, a Therapeutic Agent: (i) induces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not induce, or induces one or more of the signal transduction pathways induced by the binding of B7-H7 to one or more other receptors by less than 20%, 15%, 10%, 5%, or 2%, or in the mage of between 2% to 5%, 2% to 10%, 5% to 10%, 5% to 15%, 5% to 20%, 10% to 15%, or 15% to 20% relative to the one or more signal transduction pathways induced by the binding of B7-H7 to such one or more other receptors in the absence of the Therapeutic Agent.

In certain embodiments, a Therapeutic Agent selectively activates or enhances one or more of the signal transduction pathways induced by the binding of B7-H7 to B7-H7CR. In specific embodiments, a Therapeutic Agent activates or enhances one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent. In specific embodiments, a Therapeutic Agent: (i) activates or enhances one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not activate or enhance, or activates or enhances one or more of the signal transduction pathways induced by the binding of B7-H7 to one or more other receptors by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H7 to such one or more other receptors in the absence of the Therapeutic Agent.

In specific embodiments, a Therapeutic Agent: (i) activates or enhances one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not activate or enhance, or activates or enhances one or more of the signal transduction pathways induced by the binding of B7-H7CR to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H7CR to such one or more other ligands in the absence of the Therapeutic Agent.

In some embodiments, a Therapeutic Agent selectively inhibits or reduces one or more of the signal transduction pathways induced by the binding of B7-H7 to B7-H7CR. In specific embodiments, a Therapeutic Agent inhibits or reduces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent. In specific embodiments, a Therapeutic Agent: (i) inhibits or reduces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not inhibit or reduce, or inhibits or reduces one or more of the signal transduction pathways induced by the binding of B7-H7 to one or more other receptors by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H7 to such one or more other receptors in the absence of the Therapeutic Agent.

In specific embodiments, a Therapeutic Agent: (i) inhibits or reduces one or more of the signal transduction pathways induced by the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H7 to B7-H7CR in the absence of the Therapeutic Agent; and (ii) does not inhibit or reduce, or inhibits or reduces one or more of the signal transduction pathways induced by the binding of B7-H7CR to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H7CR to such one or more other ligands in the absence of the Therapeutic Agent.

In another embodiment, a Therapeutic Agent modulates the B7-H7 polypeptide and B7-H7CR polypeptide interaction. In certain embodiments, the Therapeutic Agent selectively modulates the B7-H7 and B7-H7CR interaction. In another embodiment, a Therapeutic Agent inhibits or reduces the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H7 to B7-H7CR in the absence of the Therapeutic Agent. In another embodiment, a Therapeutic Agent: (i) inhibits or reduces the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H7 to B7-H7CR in the absence of the Therapeutic Agent, and (ii) does not inhibit or reduce, or inhibits or reduces the binding of B7-H7 to one or more other receptors by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H7 to such one or more other receptors in the absence of the Therapeutic Agent.

In another embodiment, a Therapeutic Agent: (i) inhibits or reduces the binding of B7-H7 to B7-H7CR by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H7 to B7-H7CR in the absence of the Therapeutic Agent, and (ii) does not inhibit or reduce, or inhibits or reduces the binding of B7-H7CR to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H7CR to such one or more other ligands in the absence of the Therapeutic Agent.

In certain embodiments, the Therapeutic Agents induce, activate or enhance one or more immune functions or responses (i.e., the agents are Immunostimulating Therapeutic Agents). In other embodiments, the Therapeutic Agents suppress or reduce one or more immune functions or responses (i.e., the agents are Inhibitory Therapeutic Agents). The modulation of one or more immune functions or responses can be in the form of, e.g., an antibody response (humoral response) or a cellular immune response, e.g., cytokine secretion (e.g., interferon-gamma), helper activity or cellular cytotoxicity. In one embodiment, cytokine secretion, antibody production, effector function, T cell proliferation, and/or NK cell proliferation is modulated following contact with a Therapeutic Agent. In a specific embodiment, one or more immune functions or responses is modulated by contacting a Therapeutic Agent with an immune cell or a population of immune cells.

5.2.1 Antibodies Specific for B7-H7 or B7-H7CR

In one aspect, the Therapeutic Agent is an antibody that specifically binds to a native B7-H7 polypeptide and modulates one or more of the signal transduction pathways mediated by the binding of the native B7-H7 polypeptide to one or more of its ligands (e.g., B7-H7CR). In another aspect, the Therapeutic Agent is an antibody that specifically binds to a native B7-H7CR polypeptide and modulates one or more of the signal transduction pathways mediated by the native B7-H7CR polypeptide binding to one or more of its ligands (e.g., B7-H7). In some embodiments, the Therapeutic Agent activates, enhances, or induces one or more of the signal transduction pathways. In other embodiments, the Therapeutic Agent inhibits or reduces one or more of the signal transduction pathways. In another aspect, the Therapeutic Agent is an antibody that modulates one or more of the signal transduction pathways induced by the B7-H7 polypeptide and B7-H7CR polypeptide interaction. In a specific embodiment, a Therapeutic Agent is an antibody that modulates the interaction between B7-H7CR and B7-H7. In a specific embodiment, the Therapeutic Agent is an antibody that specifically binds to B7-H7 polypeptide and inhibits or reduces the binding of B7-H7 polypeptide to B7-H7CR polypeptide. In another specific embodiment, the Therapeutic Agent is an antibody that specifically binds to B7-H7 polypeptide and inhibits or reduces the binding of B7-H7CR polypeptide to B7-H7 polypeptide. See Section 5.1 et seq., supra, for antibodies and conjugates or fusion thereof that modulate the B7-H7 polypeptide and B7-H7CR polypeptide interaction. In some embodiments, such antibodies are Immunostimulating Therapeutic Agents. In other embodiments, such antibodies are Inhibitory Therapeutic Agents.

In some embodiments, an antibody that modulates the B7-H7 polypeptide and B7-H7CR polypeptide interaction induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% one or more of the signal transduction pathways induced when a native mammalian B7-H7 polypeptide binds to a native receptor of B7-H7 polypeptide (e.g., a native B7-H7CR polypeptide), as measured by assays well-known in the art. In some embodiments, an antibody that modulates the B7-H7 polypeptide and B7-H7CR polypeptide interaction activates or enhances by at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% one or more of the signal transduction pathways induced when a native mammalian B7-H7 polypeptide binds to a native receptor of B7-H7 polypeptide (e.g., a native B7-H7CR polypeptide), as measured by assays well-known in the art. In other embodiments, an antibody that modulates the B7-H7 polypeptide and B7-H7CR polypeptide interaction does not induce or induces less than 20%, 15%, 10%, 5% or 2%, or in the range of between 2% to 20%, 2% to 15%, 2% to 10%, or 2% to 5% of one or more of the signal transduction pathways induced when a native mammalian B7-H7 polypeptide binds to a receptor of B7-H7 polypeptide (e.g., a native B7-H7CR polypeptide), as measured by assays well-known in the art. The one or more signal transduction pathways induced by the binding of a native receptor of B7-H7 (e.g., B7-H7CR polypeptide) to a B7-H7 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In certain embodiments, a Therapeutic Agent is the antibody designated 2D3, or an antigen-binding fragment thereof, or a human or humanized for thereof. In some embodiments, a Therapeutic Agent is the antibody designated 4-5, or an antigen-binding fragment thereof, or a human or humanized for thereof.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

5.2.2 Polypeptides & Derivatives
5.2.2.1 B7-H7 Polypeptides & Derivatives In one aspect, a Therapeutic Agent is a B7-H7 polypeptide. In one embodiment, such a Therapeutic Agent modulates one or more of the signal transduction pathways mediated by B7-H7CR. In one embodiment, the B7-H7 protein binds to and agonizes signal transduction through B7-H7CR. In another embodiment, the B7-H7 protein binds to B7-H7CR and antagonizes signal transduction by blocking binding of a native ligand (e.g., B7-H7). In a specific embodiment, such a Therapeutic Agent modulates one or more of the signal transduction pathways induced by B7-H7 binding to B7-H7CR. In another specific embodiment, such a Therapeutic Agent modulates the B7-H7 polypeptide and B7-H7CR polypeptide interaction.

In another aspect, a Therapeutic Agent is a B7-H7 derivative. In one embodiment, a Therapeutic Agent is a B7-H7 derivative that modulates one or more signal transduction pathways mediated by B7-H7CR. In a specific embodiment, a Therapeutic Agent is a B7-H7 derivative that modulates one or more of the signal transduction pathways induced by B7-H7 binding to B7-H7CR. In another embodiment, a Therapeutic Agent is a B7-H7 derivative that modulates the B7-H7 polypeptide and B7-H7CR polypeptide interaction. In certain embodiments, the B7-H7 derivative is an Immunostimulating Therapeutic Agent. In other embodiments, the B7-H7 derivative is an Inhibitory Therapeutic Agent.

In specific embodiments, a B7-H7 derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native mammalian B7-H7 polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native mammalian B7-H7 polypeptide; (c) a polypeptide that contains 1, 2, 3, 4, 5, 6, 7, 8, 9, 10, 11, 12, 13, 14, 15, 16, 17, 18, 19, 20 or more or 2 to 5, 2 to 10, 5 to 10, 5 to 15, 5 to 20, 10 to 15, or 15 to 20 amino acid mutations (i.e., additions, deletions and/or substitutions) relative to a native mammalian B7-H7 polypeptide; (d) a polypeptide encoded by nucleic acids can hybridize under high, moderate or typical stringency hybridization conditions to nucleic acids encoding a native mammalian B7-H7 polypeptide; (e) a polypeptide encoded by a nucleic acid sequence that can hybridize under high, moderate or typical stringency hybridization conditions to a nucleic acid sequence encoding a fragment of a native mammalian B7-H7 polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native mammalian B7-H7 polypeptide. B7-H7 derivatives also include a polypeptide that comprises the amino acid sequence of a naturally occurring mature form of a mammalian B7-H7 polypeptide and a heterologous signal peptide amino acid sequence.

In one embodiment, a B7-H7 derivative is a derivative of a native human B7-H7 polypeptide. In another embodiment, a B7-H7 derivative is a derivative of an immature or precursor form of naturally occurring human B7-H7 polypeptide. In another embodiment, a B7-H7 derivative is a derivative of a mature form of naturally occurring human B7-H7 polypeptide. In a specific embodiment, a B7-H7 derivative is isolated or purified.

In another embodiment, a B7-H7 derivative comprises (or consists) of the amino acid sequence of native B7-H7 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, 25 to 75 mutations (e.g., amino acid substitutions, insertions and/or deletions). In certain embodiments, a B7-H7 derivative comprises one or more mutations that increase the affinity of B7-H7 for one or more of its receptors, e.g., B7-H7CR (in particular, native B7-H7CR). In other embodiments, a B7-H7 derivative comprises one or more mutations that decrease the affinity of B7-H7 for one or more of its receptors, e.g., B7-H7CR (in particular, native B7-H7CR). In some embodiments, a B7-H7 derivative comprises one or more mutations in one or more of the Ig-like V-type domains and/or Ig-like C-1 type domains of native B7-H7 and such mutations change (e.g., increase) the affinity of B7-H7 for B7-H7CR. In some embodiments, a B7-H7 derivative comprises one or more mutations at one or more of the following amino acid residues of native B7-H7: 141-144, 156, 158, 160, 162, 193-196, 198, 200, 201, 224, and/or 225. In certain embodiments, a B7-H7 derivative comprises one or more mutations at one or more of the following amino acid residues which are predicted to be N-linked glycosylation sites: 90, 103, and/or 127. Mutations can be introduced at specific positions with native B7-H7 using, e.g., site-directed mutagenesis techniques and/or PCR-mediated mutagenesis techniques. Mutations can also be introduced randomly along all or part of the coding sequence using, e.g., saturation mutagenesis techniques. In specific embodiments, the mutations are conservative amino acid substitutions.

In another embodiment, a B7-H7 derivative comprises (or consists) of the amino acid sequence of native B7-H7 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues. A conservative amino acid substitution is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment, a B7-H7 derivative comprises (or consists of) one or more mutations in the Ig-like V-type 2 domain. In another embodiment, a B7-H7 derivative comprises (or consists) of the amino acid sequence of native B7-H7 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions in the Ig-like V-type 2 domain. In another embodiment, a B7-H7 derivative comprises (or consists of) one or more mutations in the Ig-like C-type 1 domain. In another embodiment, a B7-H7 derivative comprises (or consists) of the amino acid sequence of native B7-H7 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions in the Ig-like C-type 1 domain.

In another embodiment, a B7-H7 derivative comprises a fragment of native B7-H7. In certain embodiments, a B7-H7 derivative comprises (or consists of) amino acid residues 23 to 280, 23 to 275, 23 to 250, 23 to 225, 23 to 200, 23 to 175, 23 to 150, 23 to 125, 23 to 100, 23 to 95, 23 to 75, 23 to 70, 23 to 65, 23 to 60, 23 to 50, 15 to 30 or 5 to 25 of native B7-H7 of the sequence found at Accession No. O9UM44-1 (UniParc).

In one embodiment, a B7-H7 derivative is a soluble form of B7-H7. In a specific embodiment, a B7-H7 derivative comprises (or consists of) the extracellular domain of native B7-H7, or the extracellular domain of native B7-H7 containing 1, 2, 3, 4, 5, 6, 7, 8, 9, 10, 12, 15, 20 or more amino acid substitutions, deletions, and/or additions. In a specific embodiment, a B7-H7 derivative comprises (or consists of) amino acid residues 23 to 344 of the sequence found at Accession No. O9UM44-1 (UniParc). In another embodiment, a B7-H7 derivative comprises (or consists of) a fragment of the extracellular domain of native B7-H7, or a fragment of the extracellular domain of native B7-H7 containing 1, 2, 3, 4, 5, 6, 7, 8, 9, 10, 12, 15, 20 or more mutations (e.g., amino acid substitutions, deletions, and/or additions). In specific embodiments, a B7-H7 derivative comprises (or consists of) at least 25, 50, 75, 100, 125, 150, 175, 200, 225, 250, 275, 300 or 325 amino acids of the extracellular domain of native B7-H7. In certain embodiments, a B7-H7 derivative comprises (or consists of) amino acid residues 23 to 340, 23 to 325, 23 to 300, 23 to 275, 23 to 250, 23 to 225, 23 to 200, 23 to 175, 23 to 150, 23 to 125, 23 to 100, 23 to 75, or 23 to 50 of native B7-H7. In specific embodiments, a B7-H7 derivative comprises (or consists of) amino acid residues 23 to 375, 23 to 350, 23 to 23 to 340, 23 to 325, 23 to 300, 23 to 275, 23 to 250, 23 to 225, 23 to 200, 23 to 175, 23 to 150, 23 to 125, 23 to 100, 23 to 75, 23 to 50, 15 to 30 or 5 to 25 of the sequence found at Accession No. O9UM44-1 (UniParc).

In another embodiment, a B7-H7 derivative comprises (or consists of) the Ig-like V-type 1 domain of native B7-H7. In a specific embodiment, a B7-H7 derivative comprises (or consists of) amino acid residues 61 to 131 or 61 to 122 of the sequence found at Accession No. O9UM44-1 (UniParc). In another embodiment, a B7-H7 derivative comprises (or consists of) the Ig-like C-1 type domain of native B7-H7. In a specific embodiment, a B7-H7 derivative comprises (or consists of) amino acid residues 138 to 222 or 140 to 225 of the sequence found at Accession No. O9UM44-1 (UniParc). In another embodiment, a B7-H7 derivative comprises (or consists of) the Ig-like V-type 2 domain of native B7-H7. In a specific embodiment, a B7-H7 derivative comprises (or consists of) amino acid residues 235 to 328 or 239 to 317 of the sequence found at Accession No. O9UM44-1 (UniParc). In a specific embodiment, a B7-H7 derivative comprises (or consists of) amino acid residues 140 to 222 of native B7-H7.

In another embodiment, a B7-H7 derivative comprises (or consists of) the Ig-like V-type 1 and Ig-like C-1 type domains of native B7-H7. In a specific embodiment, a B7-H7 derivative comprises (or consists of) amino acid residues 61 to 222 or 61 to 225 of the sequence found at Accession No. O9UM44-1 (UniParc). In another embodiment, a B7-H7 derivative comprises (or consists of) the Ig-like C-1 type and Ig-like V-type 2 domains of the extracellular domain of native B7-H7. In a specific embodiment, a B7-H7 derivative comprises (or consists of) amino acid residues 138 to 328 or 140 to 317 of the sequence found at Accession No. O9UM44-1 (UniParc). In another embodiment, a B7-H7 derivative comprises (or consists of the Ig-like V-type 1 and Ig-like V-type 2 of the extracellular domain of native B7-H7. In another embodiment, a B7-H7 derivative comprises (or consists of) the Ig-like V-type 1, Ig-like C-1 type, and Ig-like V-type 2 domains of the extracellular domain of native B7-H7. In a specific embodiment, a B7-H7 derivative comprises (or consists of) amino acid residues 61 to 317 or 61 to 328 of the sequence found at Accession No. O9UM44-1 (UniParc).

In certain embodiments, a B7-H7 derivative comprises an amino acid substitution at one, two, or more of the following positions: 159, 210, 243, or 317 of native B7-H7 (e.g., native human B7-H7).

In another embodiment, a B7-H7 derivative comprises (or consists of) the extracellular and cytoplasmic domains of native B7-H7 or fragments thereof. In another embodiment, a B7-H7 derivative comprises (or consists of) the extracellular and cytoplasmic domains of native B7-H7 or fragments thereof containing 1, 2, 3, 4, 5, 6, 7, 8, 9, 10, 12, 15, or more or 5 to 15, 5 to 20, 2 to 10, or 2 to 5 amino acid substitutions, deletions, and/or additions. In another embodiment, a B7-H7 derivative comprises (or consists) a fragment of the extracellular domain of native B7-H7 and the cytoplasmic domain of native B7-H7 or a fragment thereof. In another embodiment, a B7-H7 derivative comprises (or consists of) the extracellular domain of native B7-H7 and a fragment of the cytoplasmic domain of native B7-H7. In another embodiment, a B7-H7 derivative lacks the transmembrane domain of native B7-H7 or a fragment thereof. In certain embodiments, a B7-H7 derivative comprises a heterologous transmembrane domain in place of the transmembrane domain of native B7-H7. In another embodiment, a B7-H7 derivative comprises (or consists of) the extracellular domain of native B7-H7 or a fragment thereof and the transmembrane domain of native B7-H7 or a fragment thereof.

The biological activity of B7-H7 derivatives can be assessed using techniques known to those skilled in the art, or described herein. For example, the ability of a B7-H7 derivative to bind to one or more receptors may be assessed using techniques described herein, or known to those skilled in the art. More specifically, the ability of a B7-H7 derivative to bind to B7-H7CR may be assessed. In addition, the ability of a B7-H7 derivative to bind to one or more receptors and induce one or more of the signal transduction pathways induced by native B7-H7 binding to the one or more receptors may be assessed using techniques described herein, or known to those skilled in the art. More specifically, the ability of a B7-H7 derivative to bind to B7-H7CR and induce one or more of the signal transduction pathways induced by native B7-H7 binding to native B7-H7CR may be assessed.

In certain embodiments, a B7-H7 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7 polypeptide to bind to a native receptor of B7-H7 (e.g., B7-H7CR), as measured by assays/techniques well known in the art, e.g., ELISA, Biacore, or co-immunoprecipitation. In a specific embodiment, a B7-H7 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7 polypeptide to bind to B7-H7CR.

In certain embodiments, a B7-H7 derivative binds to a native receptor of B7-H7 (e.g., B7-H7CR) with a higher affinity than the native B7-H7 binds to the same receptor, as measured by assays/techniques well known in the art, e.g., ELISA, cell-based assays including flow cytometry, KinEx A assay, plasmon surface resonance assay (e.g., Biacore® assay), or co-immunoprecipitation. In one embodiment, a B7-H7 derivative binds to a native receptor of B7-H7 (e.g., B7-H7CR) with a 50%, 75%, 80%, 85%, 90%, 95%, or 98%, or 25% to 50%, 25% to 75%, 50% to 95%, or 75% to 95% higher affinity than the native B7-H7 binds to the same receptor as measured by well-known assays/techniques. In a specific embodiment, a B7-H7 derivative binds to a native receptor of B7-H7 (e.g., B7-H7CR) with 0.5 log, 1 log, 1.5 log, 2 log, 2.5 log, or 3 log higher affinity than the native B7-H7 binds to the same receptor, as measured by assays/techniques well known in the art, e.g., ELISA, Biacore, or co-immunoprecipitation.

In some embodiments, a B7-H7 derivative binds to a native receptor of B7-H7 (e.g., B7-H7CR) with a lower affinity than the native B7-H7 binds to the same receptor, as measured by assays/techniques well known in the art. In one embodiment, a B7-H7 derivative binds to a native receptor of B7-H7 (e.g., B7-H7CR) with a 50%, 75%, 80%, 85%, 90%, 95%, or 98%, or 25% to 50%, 25% to 75%, 50% to 95%, or 75% to 95% lower affinity than the native B7-H7 binds to the same receptor as measured by assays/techniques known in the art. In another embodiment, a B7-H7 derivative binds to a native receptor of B7-H7 (e.g., B7-H7CR) with a 0.5 log, 1 log, 1.5 log, 2 log, 2.5 log, or 3 log lower affinity than the native B7-H7 binds to the same receptor, as measured by assays/techniques well known in the art.

In certain other embodiments, a B7-H7 derivative retains less than 20%, 15%, 10%, 5% or 2%, or in the range of between 2% to 20%, 2% to 15%, 2% to 10%, or 2% to 5% of the function of a native B7-H7 polypeptide to bind to a native receptor of B7-H7 (e.g., B7-H7CR), as measured by assays/techniques well known in the art, e.g., ELISA, cell-based assays including flow cytometry, KinEx A assay, plasmon surface resonance assay (e.g., Biacore® assay), or co-immunoprecipitation. In a specific embodiment, a B7-H7 derivative retains less than 20%, 15%, 10%, 5% or 2%, or in the range of between 2% to 20%, 2% to 15%, 2% to 10%, or 2% to 5% of the function of a native B7-H7 polypeptide to bind to B7-H7CR.

In some embodiments, a B7-H7 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native B7-H7 polypeptide binds to a native receptor of B7-H7 (e.g., B7-H7CR), as measured by assays well-known in the art. The one or more signal transduction pathways induced by the binding of a native receptor of B7-H7 (e.g., B7-H7CR) to a B7-H7 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays. In a specific embodiment, a B7-H7 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H7 polypeptide to B7-H7CR.

In certain embodiments, a B7-H7 derivative binds to its native receptor (e.g., native B7-H7CR) and induces a higher level of activity than native B7-H7 binding to the native receptor as assessed by, e.g., the induction of one or more signal transduction molecules. In specific embodiments, a B7-H7 derivative binds to native B7-H7CR and induces a higher level of activity than native B7-H7 binding to native B7-H7CR as assessed by, e.g., the activation or induction of one or more signal transduction molecules. In some embodiments, a B7-H7 derivative binds to native B7-H7CR and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 100% higher level of activity than native B7-H7 binding to native B7-H7CR as assessed by, e.g., the activation or induction of one or more signal transduction molecules.

In some other embodiments, a B7-H7 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native B7-H7 polypeptide binds to a receptor of B7-H7 (e.g., B7-H7CR), as measured by assays well-known in the art. In a specific embodiment, a B7-H7 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H7 polypeptide to B7-H7CR.

5.2.2.2 B7-H7CR Polypeptides & Derivatives

In one aspect, a Therapeutic Agent is a B7-H7CR polypeptide. In one embodiment, a Therapeutic Agent is a B7-H7CR polypeptide that modulates one or more of the signal transduction pathways mediated by B7-H7. In one embodiment the B7-H7CR protein binds to and agonizes signal transduction through the B7-H7. In another embodiment the B7-H7CR protein binds to B7-H7 and blocks binding to B7-H7CR. In a specific embodiment, a Therapeutic Agent is a B7-H7CR polypeptide that modulates one or more of the signal transduction pathways induced by B7-H7 binding to B7-H7CR. In another specific embodiment, a Therapeutic Agent is a B7-H7CR polypeptide that modulates the B7-H7 polypeptide and B7-H7CR polypeptide interaction.

In another aspect, a Therapeutic Agent is a B7-H7CR derivative. In one embodiment, a Therapeutic Agent is a B7-H7CR derivative that modulates one or more of the signal transduction pathways mediated by B7-H7. In a specific embodiment, a Therapeutic Agent is a B7-H7CR derivative that modulates one or more of the signal transduction pathways induced by B7-H7 binding to B7-H7CR. In another embodiment, such a Therapeutic Agent modulates the B7-H7 polypeptide and B7-H7CR polypeptide interaction. In certain embodiments, the B7-H7 derivative is an Immunostimulating Therapeutic Agent. In other embodiments, the B7-H7 derivative is an Inhibitory Therapeutic Agent.

In specific embodiments, a B7-H7CR derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native B7-H7CR polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native B7-H7CR polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native B7-H7CR polypeptide; (d) a polypeptide encoded by nucleic acids can hybridize under high, moderate or typical stringency hybridization conditions to nucleic acids encoding a native B7-H7CR polypeptide; (e) a polypeptide encoded by a nucleic acid sequence that can hybridize under high, moderate or typical stringency hybridization conditions to a nucleic acid sequence encoding a fragment of a native B7-H7CR polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native B7-H7CR polypeptide. B7-H7CR derivatives also include a polypeptide that comprises the amino acid sequence of a naturally occurring mature form of a mammalian B7-H7CR polypeptide and a heterologous signal peptide amino acid sequence. In a specific embodiment, a B7-H7CR derivative is a derivative of a native human B7-H7CR polypeptide. In another embodiment, a B7-H7CR derivative is a derivative of an immature or precursor form of naturally occurring human B7-H7CR polypeptide. In another embodiment, a B7-H7CR derivative is a derivative of a mature form of naturally occurring human B7-H7CR polypeptide. In one embodiment, a B7-H7CR derivative is isolated or purified.

In another embodiment, a B7-H7CR derivative comprises (or consists) of the amino acid sequence of native B7-H7CR with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, to 75 mutations (e.g., amino acid substitutions, insertions and/or deletions). In certain embodiments, a B7-H7CR derivative comprises one or more mutations that increase the affinity of B7-H7CR for one or more of its ligands, e.g., B7-H7 (in particular, native B7-H7). In other embodiments, a B7-H7CR derivative comprises one or more mutations that decrease the affinity of B7-H7CR for one or more of its ligands, e.g., B7-H7 (in particular, native B7-H7). In specific embodiments, a B7-H7CR derivative comprises one or more mutations in the Ig-like V-type domain of native B7-H7CR and such mutations increase the affinity of B7-H7CR for B7-H7. Mutations can be introduced at specific positions with native B7-H7CR using, e.g., site-directed mutagenesis techniques and/or PCR-mediated mutagenesis techniques. Mutations can also be introduced randomly along all or part of the coding sequence using, e.g., saturation mutagenesis techniques.

In another embodiment, a B7-H7CR derivative comprises (or consists) of the amino acid sequence of native B7-H7CR with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues.

In another embodiment, a B7-H7CR derivative comprises a fragment of native B7-H7CR. In certain embodiments, a B7-H7CR derivative comprises (or consists of) amino acid residues 23 to 280, 23 to 275, 23 to 250, 23 to 225, 23 to 200, 23 to 175, 23 to 150, 23 to 125, 23 to 100, 23 to 95, 23 to 75, 23 to 70, 23 to 65, 23 to 60, 23 to 50, 15 to 30 or 5 to 25 of native B7-H7CR of the sequence found at Accession No. Q96BF3-1 (UniParc). In certain embodiments, a B7-H7CR derivative has one or more mutations in amino acid residues 227-277. In some embodiments, a B7-H7CR derivative has one or more mutations at the N-linked glycosylation sites (amino acid residues 73, 105, and 127). In certain embodiments, a B7-H7CR derivative has a mutation (e.g., a substitution) at the serine residue 220.

In one embodiment, a B7-H7CR derivative is a soluble form of B7-H7CR. In a specific embodiment, a B7-H7CR derivative comprises (or consists of) the extracellular domain of native B7-H7CR, or the extracellular domain of native B7-H7CR containing 1, 2, 3, 4, 5, 6, 7, 8, 9, 10, 12, 15, 20 or more or 2 to 5, 5 to 10, 5 to 15, or 10 to 20 amino acid substitutions, deletions, and/or additions. In a specific embodiment, a B7-H7CR derivative comprises (or consists of) amino acid residues 23 to 150 of the sequence found at Accession No. Q9BF3-1 (UniParc). In another embodiment, a B7-H7CR derivative comprises (or consists of) a fragment of the extracellular domain of native B7-H7CR, or a fragment of the extracellular domain of native B7-H7CR containing 1, 2, 3, 4, 5, 6, 7, 8, 9, 10, 12, 15, 20 or more mutations (e.g., amino acid substitutions, deletions, and/or additions). In specific embodiments, a B7-H7CR derivative comprises (or consists of) at least 25, 50, 75, 100, or 125 amino acids of the extracellular domain of native B7-H7CR. In certain embodiments, a B7-H7CR derivative comprises (or consists of) amino acid residues 23 to 145, 23 to 140, 23 to 130, 23 to 125, 23 to 100, 23 to 95, 23 to 75, 23 to 70, 23 to 65, 23 to 60, or 23 to 50 of native B7-H7CR. In specific embodiments, a B7-H7CR derivative comprises (or consists of) 23 to 145, 23 to 140, 23 to 130, 23 to 125, 23 to 100, 23 to 95, 23 to 75, 23 to 70, 23 to 65, 23 to 60, or 23 to 50 amino acid residues of the sequence found at Accession No. Q96BF3-1 (UniParc). In another embodiment, a B7-H7CR derivative comprises (or consists of) the Ig-like domain of native B7-H7CR. In a specific embodiment, a B7-H7CR derivative comprises (or consists of) amino acid residues 23 to 129 of the sequence found at Accession No. Q96BF3-1 (UniParc). In another embodiment, a B7-H7CR derivative comprises (or consists of) amino acid residues 23 to 129, 23 to 150, or 129 to 150 of the sequence Q96BF3-1.

In certain embodiments, a B7-H7CR derivative comprises an amino acid substitution at one, two, or more of the following positions: 44, 67, 81, 112, 192, 197, or 222 of native B7-H7CR (e.g., native human B7-H7CR).

In another embodiment, a B7-H7CR derivative comprises (or consists of) the extracellular and cytoplasmic domains of native B7-H7CR or fragments thereof. In another embodiment, a B7-H7CR derivative comprises (or consists of) the extracellular and cytoplasmic domains of native B7-H7CR or fragments thereof containing 1, 2, 3, 4, 5, 6, 7, 8, 9, 10, 12, 15, 20 or more, or 2 to 5, 5 to 10, 5 to 15, 5 to 20, or 10 to 20 amino acid substitutions, deletions, and/or additions. In another embodiment, a B7-H7CR derivative comprises (or consists) a fragment of the extracellular domain of native B7-H7CR and the cytoplasmic domain of native B7-H7CR or a fragment thereof. In another embodiment, a B7-H7CR derivative comprises (or consists of) the extracellular domain of native B7-H7CR and a fragment of the cytoplasmic domain of native B7-H7CR. In another embodiment, a B7-H7CR derivative lacks the transmembrane domain of native B7-H7CR or a fragment thereof. In certain embodiments, a B7-H7CR derivative comprises a heterologous transmembrane domain in place of the transmembrane domain of native B7-H7CR. In another embodiment, a B7-H7CR derivative comprises (or consists of) the extracellular domain of native B7-H7CR or a fragment thereof and the transmembrane domain of native B7-H7CR or a fragment thereof.

The biological activity of B7-H7CR derivatives can be assessed using techniques known to those skilled in the art, or described herein. For example, the ability of a B7-H7CR derivative to bind to one or more ligands may be assessed using techniques described herein, or known to those skilled in the art. More specifically, the ability of a B7-H7CR derivative to bind to B7-H7 may be assessed. In addition, the ability of a B7-H7CR derivative to bind to one or more ligands and induce one or more of the signal transduction pathways induced by native B7-H7CR binding to the one or more ligands may be assessed using techniques described herein, or known to those skilled in the art. More specifically, the ability of a B7-H7CR derivative to bind to B7-H7 and induce one or more of the signal transduction pathways induced by native B7-H7 binding to native B7-H7CR may be assessed.

In certain embodiments, a B7-H7CR derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7CR polypeptide to bind to a native ligand of B7-H7CR (e.g., B7-H7), as measured by assays/techniques well known in the art, e.g., ELISA, Biacore, or co-immunoprecipitation. In a specific embodiment, a B7-H7CR derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7CR polypeptide to bind to B7-H7.

In certain embodiments, a B7-H7CR derivative binds to a native ligand of B7-H7CR (e.g., B7-H7) with a higher affinity than native B7-H7CR binds to the same ligand, as measured by assays/techniques well known in the art, e.g., ELISA, Biacore, or co-immunoprecipitation. In one embodiment, a B7-H7CR derivative binds to a native ligand of B7-H7CR (e.g., B7-H7) with a 25%, 50%, 75%, 80%, 85%, 90%, 95%, or 25% to 50%, 25% to 75%, 50% to 95%, or 75% to 95% higher affinity than the native B7-H7CR binds to the same ligand, as measured by known assays/techniques. In a specific embodiment, a B7-H7CR derivative binds to a native ligand of B7-H7CR (e.g., B7-H7) with 0.5 logs, 1 log, 1.5 logs, 2 logs, 2.5 logs, or 3 logs higher affinity than the native B7-H7CR binds to the same ligand, as measured by assays/techniques well known in the art, e.g., ELISA, Biacore, or co-immunoprecipitation.

In certain embodiments, a B7-H7CR derivative binds to a native ligand of B7-H7CR with a lower affinity than the native B7-H7CR binds to the same ligand, as measured by well-known assays/techniques. In one embodiment, a B7-H7CR derivative binds to a native ligand of B7-H7CR with 25%, 50%, 75%, 80%, 85%, 90%, 95%, 25% to 50%, 25% to 75%, 50% to 75%, 50% to 95%, or 75% to 95% lower affinity than the native B7-H7CR binds to the same ligand, as measured by well-known assays/techniques. In another embodiment, a B7-H7CR derivative binds to a native ligand of B7-H7CR with 0.5 logs, 1 log, 1.5 logs, 2 logs, 2.5 logs, or 3 logs lower affinity than the native B7-H7CR binds to the same ligand, as measured by well-known assays/techniques.

In certain other embodiments, a B7-H7CR derivative retains less than 20%, 15%, 10%, 5% or 2%, or in the range of between 2% to 20%, 2% to 15%, 2% to 10%, or 2% to 5% of the function of a native B7-H7CR polypeptide to bind to a native ligand of B7-H7CR (e.g., B7-H7), as measured by assays/techniques well known in the art, e.g., ELISA, Biacore, or co-immunoprecipitation. In a specific embodiment, a B7-H7CR derivative retains less than 20%, 15%, 10%, 5% or 2%, or in the range of between 2% to 20%, 2% to 15%, 2% to 10%, or 2% to 5% of the function of a native B7-H7CR polypeptide to bind to B7-H7.

In some embodiments, a B7-H7CR derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of B7-H7CR (e.g., B7-H7) binds to a native B7-H7CR polypeptide (e.g., a native mammalian B7-H7CR polypeptide), as measured by assays well-known in the art. The one or more signal transduction pathways induced by the binding of a native ligand of B7-H7CR to a B7-H7CR polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays. In a specific embodiment, a B7-H7CR derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H7 to a native B7-H7CR polypeptide.

In certain embodiments, a B7-H7CR derivative binds to its native ligand (e.g., native B7-H7) and induces a higher level of activity than native B7-H7CR binding to the native ligand as assessed by, e.g., the induction of one or more signal transduction molecules. In specific embodiments, a B7-H7CR derivative binds to native B7-H7 and induces a higher level of activity than native B7-H7CR binding to native B7-H7 as assessed by, e.g., the induction of one or more signal transduction molecules. In some embodiments, a B7-H7CR derivative binds to B7-H7 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H7CR binding to native B7-H7 as assessed by, e.g., the induction of one or more signal transduction molecules.

In some other embodiments, a B7-H7CR derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand (e.g., B7-H7) binds to a native B7-H7CR polypeptide (e.g., a native mammalian B7-H7CR polypeptide), as measured by assays well-known in the art. In a specific embodiment, a B7-H7CR derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H7 to a native B7-H7CR polypeptide.

5.2.3 Fusion Proteins

In one aspect, a Therapeutic Agent is a protein comprising B7-H7 polypeptide and a heterologous molecule (e.g., a heterologous amino acid sequence). In one embodiment, such a Therapeutic Agent modulates one or more of the signal transduction pathways mediated B7-H7CR. In one embodiment the Therapeutic Agent binds to and agonizes signal transduction through the B7-H7CR receptor. In another embodiment the Therapeutic Agent binds to B7-H7CR and antagonizes signal transduction by blocking binding of a native ligand (e.g. B7-H7). In a specific embodiment, such a Therapeutic Agent modulates one or more of the signal transduction pathways induced by the binding of B7-H7 to B7-H7CR. In another specific embodiment, such a Therapeutic Agent modulates the B7-H7 polypeptide and B7-H7CR polypeptide interaction. In one embodiment, a Therapeutic Agent comprises native B7-H7 and a heterologous molecule. In another embodiment, a Therapeutic Agent comprises a B7-H7 derivative and a heterologous amino acid sequence. See Section 5.2.2.1, supra, for B7-H7 derivatives. In some embodiments, such Therapeutic Agents are Immunostimulating Therapeutic Agents. In other embodiments, such Therapeutic Agents are Inhibitory Therapeutic Agents.

In a specific embodiment, a Therapeutic Agent is a fusion protein comprising B7-H7 polypeptide and a heterologous amino acid sequence. In one embodiment, a Therapeutic Agent is a fusion protein comprising a B7-H7 polypeptide and a constant region of an immunoglobulin or a fragment thereof (e.g., CH1, CH2, and/or CH3). Fc regions from, e.g., native IgG1, IgG2, or IgG4 can be used to produce such a fusion protein. In addition, hybrid IgG1/IgG4 Fc domains can be used to produce such a fusion protein as can modified IgG1 Fc domains (e.g., IgG1 modified to improve binding to certain Fc gamma receptors; IgG1 modified to minimize effector function; IgG1 with altered/no glycan; and IgG1 with altered pH-dependent binding to FcRn) and modified IgG4 Fc domains (e.g., IgG4 modified to prevent binding to Fc gamma receptors and/or complement). Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470. In a specific embodiment, a Therapeutic Agent is the B7-H7-Ig fusion protein described in Example 6, infra. In some embodiments, such Therapeutic Agents are Immunostimulating Therapeutic Agents. In other embodiments, such Therapeutic Agents are Inhibitory Therapeutic Agents.

In certain embodiments, a Therapeutic Agent is a fusion protein or a conjugate comprising a B7-H7 polypeptide and an organic molecule of interest. In accordance with these embodiments, the B7-H7 polypeptide can be used as a targeting moiety to target the organic molecule to which it is fused or conjugated to particular organs or tissues (e.g., lymphoid organs or tissues). The Examples below provide information regarding the organs and tissues expressing B7-H7. In specific embodiments, the B7-H7 polypeptide comprises the extracellular domain of native B7-H7 or a fragment thereof that retains the ability to bind to one or more receptors of B7-H7 (e.g., B7-H7CR). In certain embodiments, the B7-H7 polypeptide is a derivative of native B7-H7. The organic molecule fused or conjugated to the B7-H7 polypeptide may be a molecule that one skilled in the art is interested in targeting to a particular organ(s) or tissue(s) (e.g., lymphoid organs or tissues) (e.g., a cytokine, drug, marker, etc.).

In another aspect, a Therapeutic Agent is a protein comprising B7-H7CR polypeptide and a heterologous molecule. In one embodiment, such a Therapeutic Agent modulates one or more signal transduction pathways mediated by B7-H7. In one embodiment the Therapeutic Agent binds to and agonizes signal transduction through the B7-H7. In another embodiment the Therapeutic Agent binds to native B7-H7 and blocks binding to B7-H7CR. In a specific embodiment, such a Therapeutic Agent modulates the B7-H7 and B7-H7CR interaction. In one embodiment, a Therapeutic Agent comprises native B7-H7CR and a heterologous molecule. In another embodiment, a Therapeutic Agent comprises a B7-H7CR derivative and a heterologous amino acid sequence. See Section 5.2.2.2, supra, for B7-H7CR derivatives. In some embodiments, such Therapeutic Agents are Immunostimulating Therapeutic Agents. In other embodiments, such Therapeutic Agents are Inhibitory Therapeutic Agents.

In a specific embodiment, a Therapeutic Agent is a fusion protein comprising B7-H7CR and a heterologous molecule. In one embodiment, a Therapeutic Agent is a fusion protein comprising a B7-H7 polypeptide and a constant region of an immunoglobulin or a fragment thereof (e.g., CH1, CH2, and/or CH3). Fc regions from, e.g., native IgG1, IgG2, or IgG4 can be used to produce such a fusion protein. In addition, hybrid IgG1/IgG4 Fc domains can be used to produce such a fusion protein as can modified IgG1 Fc domains (e.g., IgG1 modified to improve binding to certain Fc gamma receptors; IgG1 modified to minimize effector function; IgG1 with altered/no glycan; and IgG1 with altered pH-dependent binding to FcRn) and modified IgG4 Fc domains (e.g., IgG4 modified to prevent binding to Fc gamma receptors and/or complement). Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470. In a specific embodiment, a Therapeutic Agent is the B7-H7CR-Ig fusion protein described in Example 6, infra. In some embodiments, such Therapeutic Agents are Immunostimulating Therapeutic Agents. In other embodiments, such Therapeutic Agents are Inhibitory Therapeutic Agents.

In certain embodiments, a Therapeutic Agent is a fusion protein or a conjugate comprising B7-H7CR polypeptide and an organic molecule. In accordance with these embodiments, the B7-H7CR polypeptide can be used as a targeting moiety to target the organic molecule to which it is fused or conjugated to particular organs or tissues (e.g., lymphoid organs or tissues). The examples below provide information regarding organs and tissues expressing. B7-H7CR. In specific embodiments, the B7-H7CR polypeptide comprises the extracellular domain of native B7-HCR or a fragment thereof that retains the ability to bind to one or more ligands of B7-H7CR (e.g., B7-H7). In certain embodiments, the B7-H7CR polypeptide is a derivative of native B7-H7CR. The organic molecule fused or conjugated to the B7-H7CR polypeptide may be any molecule that one skilled in the art is interested in targeting to particular organs or tissues (e.g., testis, colon, lung, kidney, pancreas, small intestine, liver, or skeletal muscle) (e.g., a cytokine, drug, marker, etc.).

The B7-H7 polypeptide or B7-H7CR polypeptide may be covalently or non-covalently linked to a heterologous molecule. In certain embodiments, B7-H7 polypeptide or B7-H7CR polypeptide is covalently or non-covalently linked directly to a heterologous molecule (e.g., by combining amino acid sequences via peptide bonds). In other embodiments, B7-H7 polypeptide or B7-H7CR polypeptide is linked to a heterologous molecule using one or more linkers. Linkers suitable for conjugating B7-H7 polypeptide or B7-H7CR polypeptide to a heterologous molecule comprise peptides, alkyl groups, chemically substituted alkyl groups, polymers, or any other covalently-bonded or non-covalently bonded chemical substance capable of binding together two or more components. Polymer linkers comprise any polymers known in the art, including polyethylene glycol ("PEG"). In some embodiments, the linker is a peptide that is 1, 2, 3, 4, 5, 6, 7, 8, 9, 10, 11, 12, 13, 14, 15, 16, 17, 18, 19, 20 or more amino acids long. In a specific embodiment, the linker is long enough to preserve the ability of B7-H7 polypeptide to bind to B7-H7CR polypeptide. In other embodiments, the linker is long enough to preserve the ability of the B7-H7 polypeptide to bind to B7-H7CR polypeptide and to induce one or more signal transduction pathways induced by the interaction between native B7-H7 polypeptide and native B7-H7CR polypeptide. In specific embodiments, the linker preserves the formation of disulphide bonds.

In some embodiments, the heterologous molecule is the Fc domain of an IgG immunoglobulin or a fragment thereof. In certain embodiments, the heterologous molecule is polyethylene glycol (PEG). In some embodiments, the heterologous molecule is a therapeutic moiety possessing a desired biological activity. In certain embodiments, the heterologous molecule is interferon-γ, interferon-β, interferon-α, interleukin-2 ("IL-2"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), granulocyte colony stimulating factor ("G-CSF")), or a growth factor.

In some embodiments, the heterologous molecule increases protein stability. Non-limiting examples of such molecules include polyethylene glycol (PEG), Fc domain of an IgG immunoglobulin, a fragment thereof or modified form thereof, or albumin that increase the half-life of B7-H7 or B7-H7CR in vivo. See, e.g., Section 5.1.1 for a discussion regarding modified Fc domains. In certain embodiments, the heterologous molecules is not an Fc domain of an immunoglobulin molecule or a fragment thereof. In other embodiments, the heterologous molecules reduce binding to Fc receptors, e.g., the heterologous molecule is an Fc domain of an immunoglobulin or a fragment thereof with reduced affinity for an Fc receptor (e.g., FcRn).

In some embodiments, the heterologous molecule is a detectable moiety. Non-limiting examples of detectable moieties include various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In,) technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

In some embodiments, the heterologous molecule is a marker amino acid sequence or a penetrating peptide. Marker amino acid sequences may facilitate purification of a protein. Examples of marker amino acid sequences include, but are not limited to, a hexa-histidine peptide (such as the tag provided in a pQE vector (QIAGEN, Inc.)), a hemagglutinin ("HA") tag (which corresponds to an epitope derived from the Influenza hemagglutinin protein (Wilson et al., 1984, Cell 37:767)), the Fc domain of an immunoglobulin, and the "flag" tag.

5.2.4 Nucleic Acids
5.2.4.1 B7-H7Nucleic Acids

In one aspect, presented herein are Therapeutic Agents that are nucleic acids encoding B7-H7. In one embodiment, the B7-H7 encoded by the nucleic acid is capable of binding to one or more receptors of native B7-H7 (e.g., B7-H7CR). In a specific embodiment, the B7-H7 encoded by the nucleic acids is capable of binding to B7-H7CR. In specific embodiments, the B7-H7 encoded by the nucleic acids are Immunostimulating Therapeutic Agents. In other specific embodiments, the B7-H7 encoded by the nucleic acids are Inhibitory Therapeutic Agents.

Nucleic acid sequences encoding native B7-H7 are known in the art and have been described in the literature. For example, the nucleic acid sequences encoding native B7-H7 can be found in publicly available publications and databases, e.g., National Center for Biotechnology Information website at ncbi.nlm.nih.gov. Cloning techniques well known in the art can be used to generate nucleic acids encoding B7-H7. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native B7-H7. In another embodiment, the Therapeutic Agent comprises nucleic acids that encode a fusion protein described in Section 5.2.3, supra. In another embodiment, the Therapeutic Agent comprises nucleic acids that encode a B7-H7 derivative. See Section 5.2.2.1, supra, for B7-H7 derivatives that the nucleic acids might encode.

In specific embodiments, nucleic acids encoding B7-H7 include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native B7-H7 polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native B7-H7 polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native B7-H7 polypeptide; (d) a nucleic acid sequence that hybridizes under high, moderate or typical stringency hybridization conditions to a naturally occurring nucleic acid sequence encoding a native B7-H7 polypeptide; (e) a nucleic acid sequence that hybridizes under high, moderate or typical stringency hybridization conditions to a fragment of a naturally occurring nucleic acid sequence encoding a native B7-H7 polypeptide; and (f) a nucleic acid sequence encoding a fragment of a naturally occurring nucleic acid sequence encoding a native B7-H7 polypeptide.

In a specific embodiment, a nucleic acid sequence encoding a B7-H7 polypeptide is a derivative of a naturally occurring nucleic acid sequence encoding a native human B7-H7 polypeptide. In another embodiment, a nucleic acid sequence encoding a B7-H7 polypeptide is a derivative of a naturally occurring nucleic acid sequence encoding an immature or precursor form of a native human B7-H7 polypeptide. In another embodiment, a nucleic acid sequence encoding a B7-H7 polypeptide is a derivative of a naturally occurring nucleic acid sequence encoding a mature form of a native human B7-H7 polypeptide. In another embodiment, a nucleic acid sequence encodes a B7-H7 derivative described in Section 5.2.2.1, supra. In certain embodiments, the nucleic acid sequence encoding a B7-H7 polypeptide includes non-naturally occurring residues.

In certain embodiments, nucleic acid sequences include codon-optimized nucleic acid sequences that encode native B7-H7 polypeptide, including mature and immature forms of B7-H7 polypeptide. In other embodiments, nucleic acid sequences include nucleic acids that encode B7-H7 RNA transcripts containing mutations that eliminate potential splice sites and instability elements (e.g., A/T or A/U rich elements) without affecting the amino acid sequence to increase the stability of the B7-H7 RNA transcripts.

In certain embodiments, nucleic acid sequences encode a B7-H7 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7 polypeptide to bind to a native receptor of B7-H7 polypeptide (e.g., B7-H7CR), as measured by assays well known in the art, e.g., ELISA, Biacore, or co-immunoprecipitation. In a specific embodiment, nucleic acid sequences encode a B7-H7 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7 polypeptide to bind to B7-H7CR.

In certain embodiments, nucleic acid sequences encode a B7-H7 polypeptide that has a higher affinity for a native receptor of B7-H7 (e.g., native B7-H7CR) than native B7-H7 for the same receptor, as measured by assays/techniques well known in the art, e.g., ELISA, Biacore, or co-immunoprecipitation. In one embodiment, nucleic acid sequences encode a B7-H7 polypeptide that binds to a native receptor of B7-H7 (e.g., B7-H7CR) with 25%, 50%, 75%, 80%, 85%, 85%, 90%, 95%, or 25% to 50%, 50% to 75%, 75% to 95%, or 50% to 95% higher affinity than native B7-H7 for the same receptor, as measured by known assays/techniques. In a specific embodiment, nucleic acid sequences encode a B7-H7 polypeptide that binds to a native receptor of B7-H7 (e.g., B7-H7CR) with 0.5 logs, 1 log, 1.5 logs, 2 logs, 2.5 logs, or 3 logs higher affinity than the native B7-H7 binds to the same receptor, as measured by assays/techniques well known in the art, e.g., ELISA, Biacore, or co-immunoprecipitation.

In certain embodiments, nucleic acid sequences encode a B7-H7 polypeptide that binds to a native receptor of B7-H7 with a lower affinity than the native B7-H7 binds to the same receptor, as measured by well-known assays/techniques. In one embodiment, nucleic acid sequences encode a B7-H7 polypeptide that binds to a native receptor of B7-H7 with 25%, 50%, 75%, 80%, 85%, 90%, 95%, 25% to 50%, 25% to 75%, 50% to 75%, 50% to 95%, or 75% to 95% lower affinity than the native B7-H7 binds to the same receptor, as measured by well-known assays/techniques. In another embodiment, nucleic acid sequences encode a B7-H7 polypeptide that binds to a native receptor of B7-H7 with 0.5 logs, 1 log, 1.5 logs, 2 logs, 2.5 logs, or 3 logs lower affinity than the native B7-H7 binds to the same receptor, as measured by well-known assays/techniques.

In certain other embodiments, nucleic acid sequences encode a B7-H7 polypeptide that retains less than 20%, 15%, 10%, 5% or 2%, or in the range of between 2% to 20%, 2% to 15%, 2% to 10%, or 2% to 5% of the function of a native B7-H7 polypeptide to bind to a native receptor of B7-H7 (e.g., B7-H7CR), as measured by assays well known in the art, e.g., ELISA, Biacore, or co-immunoprecipitation. In a specific embodiment, nucleic acid sequences encode a B7-H7 polypeptide that retains less than 20%, 15%, 10%, 5% or 2%, or in the range of between 2% to 20%, 2% to 15%, 2% to 10%, or 2% to 5% of the function of a native B7-H7 polypeptide to bind to B7-H7CR.

In some embodiments, nucleic acid sequences encode a B7-H7 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native receptor of B7-H7 (e.g., B7-H7CR) binds to a native B7-H7 polypeptide, as measured by assays well-known in the art. The one or more signal transduction pathways induced by the binding of a B7-H7 polypeptide to a receptor of B7-H7 (e.g., B7-H7CR) can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, 11-5, IL-10, IL-17, interferon-gamma, or tumor necrosis factor-alpha) using techniques such as ELISAs, Western blots, electromobility shift assays, and other immunoassays. In a specific embodiment, nucleic acid sequences encode a B7-H7 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H7 polypeptide to B7-H7CR.

In certain embodiments, nucleic acid sequences encode a B7-H7 polypeptide that binds to its native receptor (e.g., native B7-H7CR) and induces a higher level of activity than native B7-H7 binding to the native receptor as assessed by, e.g., the activation or induction of one or more signal transduction molecules. In specific embodiments, nucleic acid sequences encode a B7-H7 polypeptide that binds to B7-H7CR and induces a higher level of activity than native B7-H7 binding to native B7-H7CR as assessed by, e.g., the activation or induction of one or more signal transduction molecules. In some embodiments, nucleic acid sequences encode a B7-H7 polypeptide that binds to B7-H7CR and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H7 binding to native B7-H7CR as assessed by, e.g., the activation or induction of one or more signal transduction molecules.

In some other embodiments, nucleic acid sequences encode a B7-H7 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native B7-H7 polypeptide binds to a receptor of a native receptor of B7-H7 (e.g., B7-H7CR, as measured by assays well-known in the art. In a specific embodiment, nucleic acid sequences encode a B7-H7 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H7 polypeptide to B7-H7CR.

5.2.4.2 B7-H7CR Nucleic Acids

In one aspect, presented herein are Therapeutic Agents that are nucleic acids encoding B7-H7CR. In one embodiment, the B7-H7CR encoded by the nucleic acids is capable of binding to one or more ligands of native B7-H7CR (e.g., B7-H7). In a specific embodiment, the B7-H7CR encoded by the nucleic acids is capable of binding to B7-H7. In specific embodiments, the B7-H7CR encoded by the nucleic acids are Immunostimulating Therapeutic Agents. In other specific embodiments, the B7-H7CR encoded by the nucleic acids are Inhibitory Therapeutic Agents.

Nucleic acid sequences encoding native B7-H7CR are known in the art and have been described in the literature. For example, the nucleic acid sequences encoding native B7-H7CR can be found in publicly available publications and databases, e.g., National Center for Biotechnology Information website at ncbi.nlm.nih.gov. Cloning techniques well known in the art can be used to generate nucleic acids encoding B7-H7CR. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native B7-H7CR. In another embodiment, the Therapeutic Agent comprises nucleic acids that encode a fusion protein described in Section 5.2.3, supra. In another embodiment, the Therapeutic Agent comprises nucleic acids that encode a B7-H7CR derivative. See Section 5.2.2.2, supra, for B7-H7CR derivatives that the nucleic acids might encode.

In specific embodiments, nucleic acids encoding B7-H7CR include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native B7-H7CR polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native B7-H7CR polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native B7-H7CR polypeptide; (d) a nucleic acid sequence that hybridizes under high, moderate or typical stringency hybridization conditions to a naturally occurring nucleic acid sequence encoding a native B7-H7CR polypeptide; (e) a nucleic acid sequence that hybridizes under high, moderate or typical stringency hybridization conditions to a fragment of a naturally occurring nucleic acid sequence encoding a native B7-H7CR polypeptide; and (f) a nucleic acid sequence encoding a fragment of a naturally occurring nucleic acid sequence encoding a native B7-H7CR polypeptide.

In a specific embodiment, a B7-H7CR derivative in the context of nucleic acids is a derivative of a naturally occurring nucleic acid sequence encoding a human B7-H7CR polypeptide. In another embodiment, a B7-H7CR derivative in the context of nucleic acids is a derivative of a naturally occurring nucleic acid sequence encoding an immature or precursor form of a native human B7-H7CR polypeptide. In another embodiment, a B7-H7CR derivative in the context of nucleic acids is a derivative of a naturally occurring nucleic acid sequence encoding a mature form of a native human B7-H7CR polypeptide.

In a specific embodiment, a nucleic acid sequence encoding a B7-H7CR polypeptide is a derivative of a naturally occurring nucleic acid sequence encoding a native human B7-H7CR polypeptide. In another embodiment, a nucleic acid sequence encoding a B7-H7CR polypeptide is a derivative of a naturally occurring nucleic acid sequence encoding an immature or precursor form of a native human B7-H7CR polypeptide. In another embodiment, a nucleic acid sequence encoding a B7-H7CR polypeptide is a derivative of a naturally occurring nucleic acid sequence encoding a mature form of a native human B7-H7 polypeptide. In another embodiment, a nucleic acid sequence encodes a B7-H7CR derivative described in Section 5.2.2.2, supra. In certain embodiments, the nucleic acid sequence encoding a B7-H7CR polypeptide includes non-naturally occurring residues.

In certain embodiments, nucleic acid sequences include codon-optimized nucleic acid sequences that encode native B7-H7CR polypeptide, including mature and immature forms of B7-H7CR polypeptide. In other embodiments, nucleic acid sequences include nucleic acids that encode B7-H7CR RNA transcripts containing mutations that eliminate potential splice sites and instability elements (e.g., A/T or A/U rich elements) without affecting the amino acid sequence to increase the stability of the mammalian B7-H7CR RNA transcripts.

In certain embodiments, nucleic acid sequences encode a B7-H7CR polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7CR polypeptide to bind to a native ligand of B7-H7CR (e.g., B7-H7), as measured by assays well known in the art, e.g., ELISA, Biacore, or co-immunoprecipitation. In a specific embodiment, nucleic acid sequences encode a B7-H7CR polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H7CR polypeptide to bind to B7-H7.

In certain embodiments, nucleic acid sequences encode a B7-H7CR polypeptide that has a higher affinity for a native ligand of B7-H7CR (e.g., native B7-H7) than native B7-H7CR for the same ligand, as measured by assays/techniques well known in the art, e.g., ELISA, Biacore, or co-immunoprecipitation. In one embodiment, nucleic acid sequences encode a B7-H7CR polypeptide that binds to a native ligand of B7-H7CR (e.g., B7-H7) with 25%, 50%, 75%, 80%, 85%, 85%, 90%, 95%, or 25% to 50%, 50% to 75%, 75% to 95%, or 50% to 95% higher affinity than native B7-H7CR for the same ligand, as measured by known assays/techniques. In a specific embodiment, nucleic acid sequences encode a B7-H7CR polypeptide that binds to a native ligand of B7-H7CR (e.g., B7-H7) with 0.5 logs, 1 log, 1.5 logs, 2 logs, 2.5 logs, or 3 logs higher affinity than the native B7-H7CR binds to the same ligand, as measured by assays/techniques well known in the art, e.g., ELISA, Biacore, or co-immunoprecipitation.

In certain embodiments, nucleic acid sequences encode a B7-H7CR polypeptide that binds to a native ligand of B7-H7CR with a lower affinity than the native B7-H7CR binds to the same ligand, as measured by well-known assays/techniques. In one embodiment, nucleic acid sequences encode a B7-H7CR polypeptide that binds to a native ligand of B7-H7CR with 25%, 50%, 75%, 80%, 85%, 90%, 95%, 25% to 50%, 25% to 75%, 50% to 75%, 50% to 95%, or 75% to 95% lower affinity than the native B7-H7CR binds to the same ligand, as measured by well-known assays/techniques. In another embodiment, nucleic acid sequences encode a B7-H7CR polypeptide that binds to a native ligand of B7-H7CR with 0.5 logs, 1 log, 1.5 logs, 2 logs, 2.5 logs, or 3 logs lower affinity than the native B7-H7CR binds to the same ligand, as measured by well-known assays/techniques.

In certain other embodiments, nucleic acid sequences encode a B7-H7CR polypeptide that retains less than 20%, 15%, 10%, 5% or 2%, or in the range of between 2% to 20%, 2% to 15%, 2% to 10%, or 2% to 5% of the function of a native B7-H7CR polypeptide to bind to a native ligand of B7-H7CR (e.g., B7-H7), as measured by assays well known in the art, e.g., ELISA, Biacore, or co-immunoprecipitation. In a specific embodiment, nucleic acid sequences encode a B7-H7CR polypeptide that retains less than 20%, 15%, 10%, 5% or 2%, or in the range of between 2% to 20%, 2% to 15%, 2% to 10%, or 2% to 5% of the function of a native B7-H7CR polypeptide to bind to B7-H7.

In some embodiments, nucleic acid sequences encode a B7-H7CR polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of B7-H7CR (e.g., B7-H7) binds to a native B7-H7CR polypeptide, as measured by assays well-known in the art. The one or more signal transduction pathways induced by the binding of a ligand of B7-H7CR polypeptide to a B7-H7CR polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, 11-5, IL-10, IL-17, interferon-gamma, or tumor necrosis factor-alpha) using techniques such as ELISAs, Western blots, electromobility shift assays, and other immunoassays. In a specific embodiment, B7-H7CR derivative nucleic acid sequences encode a protein or polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H7 to a native B7-H7CR polypeptide.

In certain embodiments, nucleic acid sequences encode a B7-H7CR polypeptide that binds to its native ligand (e.g., native B7-H7) and induces a higher level of activity than native B7-H7CR binding to the native ligand as assessed by, e.g., the induction of one or more signal transduction molecules. In specific embodiments, nucleic acid sequences encode a B7-H7CR polypeptide that binds to B7-H7 and induces a higher level of activity than native B7-H7CR binding to native B7-H7 as assessed by, e.g., the induction of one or more signal transduction molecules. In some embodiments, nucleic acid sequences encode a B7-H7CR polypeptide that binds to B7-H7 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H7CR binding to native B7-H7 as assessed by, e.g., the induction of one or more signal transduction molecules.

In some other embodiments, nucleic acid sequences encode a B7-H7CR polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand (e.g., B7-H7) binds to a native B7-H7CR polypeptide, as measured by assays well-known in the art. In a specific embodiment, nucleic acid sequences encode a B7-H7CR polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H7 to a native B7-H7CR polypeptide.

5.2.4.3 Nucleic Acids Encoding Antibodies

In one aspect, a Therapeutic Agent is a nucleic acid sequence encoding an antibody that modulates the interaction between B7-H7 and one or more of its receptors (e.g., B7-H7CR). In another aspect, a Therapeutic Agent is a nucleic acid sequence encoding an antibody that modulates the interaction between B7-H7CR and one or more of its ligands (e.g., B7-H7). In a specific embodiment, a Therapeutic Agent is a nucleic acid sequence encoding an antibody that modulates the B7-H7 polypeptide and B7-H7CR polypeptide interaction. In a specific embodiment, the Therapeutic Agent is a nucleic acid sequence encoding an antibody that specifically binds to B7-H7 polypeptide and inhibits or reduces the binding of B7-H7 polypeptide to B7-H7CR polypeptide. In another specific embodiment, a Therapeutic Agent is a nucleic acid sequence encoding an antibody that specifically binds to B7-H7CR polypeptide and inhibits or reduces the binding of B7-H7CR polypeptide to B7-H7 polypeptide. In specific embodiments, a Therapeutic Agent is antibody (including antibody conjugates or fusion proteins) described in Section 5.1, supra or Section 5.2.1, supra. In some embodiments, antibodies encoded by the nucleic acid sequences are Immunostimulating Therapeutic Agents. In other embodiments, antibodies encoded by the nucleic acid sequences are Inhibitory Therapeutic Agents.

5.2.4.4 Constructs & Recombinant Expression

The nucleic acids encoding a protein can be inserted into nucleic acid constructs for expression in mammalian cells, non-mammalian animal cells, insect cells, plant cells, bacteria, fungus, yeast, and viruses.

Nucleic acid constructs may comprise one or more transcriptional regulatory element(s) operably linked to the coding sequence of a protein. The transcriptional regulatory elements are typically 5' to the coding sequence and direct the transcription of the nucleic acids encoding a protein. In some embodiments, one or more of the transcriptional regulatory elements that are found in nature to regulate the transcription of the native gene are used to control transcription. In other embodiments, one or more transcriptional regulatory elements that are heterologous to the native gene are used to control transcription. Any transcriptional regulatory element(s) known to one of skill in the art may be used. Non-limiting examples of the types of transcriptional regulatory element(s) include a constitutive promoter, a tissue-specific promoter, and an inducible promoter. In a specific embodiment, transcription is controlled, at least in part, by a mammalian (in some embodiments, human) transcriptional regulatory element(s). In a specific embodiment, transcription is controlled, at least in part, by a strong promoter, e.g., CMV.

Specific examples of promoters which may be used to control transcription include, but are not limited to, the SV40 early promoter region (Bernoist & Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); adenovirus (ADV), cytomegalovirus (CMV), bovine papilloma virus (BPV), parovirus B19p6 promoter, prokaryotic expression vectors such as the .beta.-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378). In other aspects, an inducible promoter can be used.

Nucleic acid constructs also may comprise one or more post-transcriptional regulatory element(s) operably linked to the coding sequence of a protein. The post-transcriptional regulatory elements can be 5' and/or 3' to the coding sequence and direct the post-transcriptional regulation of the translation of RNA transcripts encoding a protein.

In another aspect, the nucleic acid construct can be a gene targeting vector that replaces a gene's existing regulatory region with a regulatory sequence isolated from a different gene or a novel regulatory sequence as described, e.g., in International Publication Nos. WO 94/12650 and WO 01/68882, which are incorporated by reference herein in their entireties.

The nucleic acid construct chosen will depend upon a variety of factors, including, without limitation, the strength of the transcriptional regulatory elements and the cell to be used to express a protein. The nucleic acid constructs can be a plasmid, phagemid, cosmid, viral vector, phage, artificial chromosome, and the like. In one aspect, the vectors can be episomal, non-homologously, or homologously integrating vectors, which can be introduced into the appropriate cells by any suitable means (transformation, transfection, conjugation, protoplast fusion, electroporation, calcium phosphate-precipitation, direct microinjection, etc.) to transform them.

The nucleic acid constructs can be a plasmid or a stable integration vector for transient or stable expression of a protein in cells. For stable expression, the vector can mediate chromosomal integration at a target site or a random chromosomal site. Non-limiting examples of cell-vector systems that may be used to express a protein include mammalian cell systems infected with virus (e.g., vaccinia virus, adenovirus, retroviruses, lentiviruses, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. In some embodiments, the nucleic acid constructs include a selectable marker gene including, but not limited to, neo, gpt, dhfr, ada, pac, hyg, CAD and hisD.

The nucleic acid constructs can be monocistronic or multicistronic. A multicistronic nucleic acid construct may encode 2, 3, 4, 5, 6, 7, 8, 9, 10 or more, or in the range of 2-5, 5-10 or 10-20 genes/nucleotide sequences. For example, a bicistronic nucleic acid construct may comprise in the following order a promoter, a first gene and a second gene. In such a nucleic acid construct, the transcription of both genes is driven by the promoter, whereas the translation of the mRNA from the first gene is by a cap-dependent scanning mechanism and the translation of the mRNA from the second gene is by a cap-independent mechanism, e.g., by an IRES.

Techniques for practicing aspects of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

Nucleic acid constructs comprising nucleic acids encoding a protein can be administered in vivo to a mammal or transfected into primary or immortalized cells in culture. In certain aspects, nucleic acid constructs comprising nucleic acids encoding a protein are administered to a mammal for recombinant expression of a protein in vivo. In other aspects, cells transfected with the nucleic acid constructs ex vivo are transplanted or implanted in a subject. Thus, in certain embodiments, a nucleic acid construct is a Therapeutic Agent. In other embodiments, cells transplanted with a nucleic acid construct are the Therapeutic Agent.

In another aspect, the nucleic acids encoding a protein can be used to generate mammalian cells that recombinantly express a protein in high amounts for the isolation and purification. Recombinant protein production and purification are well known in the art, e.g., see International Publication No. WO 07/070,488, which is incorporated by reference herein in its entirety. Briefly, the polypeptide can be produced intracellularly, in the periplasmic space, or directly secreted into the medium. Cell lysate or supernatant comprising the polypeptide can be purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™ (gel filtration substance; Pharmacia Inc., Piscataway, N.J.) chromatography on an anion or cation exchange resin (such as a polyaspartic acid column), chromatofocusing, SDS-PAGE, and ammonium sulfate precipitation are also available.

5.2.5 Cells

Cells can be engineered to express the protein(s) encoded by the nucleic acids and nucleic acid constructs described in Section 5.2.4, supra (e.g., Section 5.2.4.4, supra). In one embodiment, such cells express amounts of protein that are at least 1 fold, 2 fold, 3 fold, 4 fold, 5 fold, 6 fold, 7 fold, 8 fold, 9 fold, 10 fold, 20 fold, 30 fold, 40 fold, 50 fold or more than 50 fold higher than amounts of protein expressed endogenously by control cells (e.g., cells that have not been genetically engineered to recombinantly express protein, or cells comprising an empty vector). In addition, cells can be engineered to express the antibodies described in Sections 5.1 and 5.2.1 supra, using techniques well-known to one of skill in the art, see, e.g., U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties). The cells chosen for expression of nucleic acids will depend upon the intended use of the cells. Factors such as whether a cell glycosylates similar to cells that endogenously express a protein may be considered in selecting the cells.

Non-limiting examples of cells that can be used to express the protein(s) encoded by the nucleic acid constructs described in Section 5.2.4.4, supra, or the antibodies described in Sections 5.1 and 5.2.1, supra, include mammalian cells, non-mammalian animal cells, bacterial cells, fungal cells, yeast cells, primary cells, immortalized cells, plant cells, and insect cells. In a specific embodiment, the cells are a mammalian cell line. Examples of mammalian cell lines include, but are not limited to, COS, CHO, HeLa, NIH3T3, HepG2, MCF7, HEK, 293T, RD, PC12, hybridomas, pre-B cells, 293, 293H, K562, SkBr3, BT474, A204, M07Sb, Raji, Jurkat, MOLT-4, CTLL-2, MC-IXC, SK-N-MC, SK-N-MC, SK-N-DZ, SH-SY5Y, C127, NO, and BE(2)-C cells. Other mammalian cell lines available as hosts for expression are known in the art and include many immortalized cell lines available from the American Type Culture Collection (ATCC). In another embodiment, the cells are immortalized cell lines derived from a subject. In another embodiment, the cells are primary or secondary cells from a subject. In a particular embodiment, the cells are cancer cells. In another embodiment, the cells are fetal/embryonic cells. In some embodiments, the cells are progenitor cells. In some embodiments, the cells are lymphocytes (e.g., T cells and B cells). In another embodiment, the cells are stem cells. In yet another embodiment, the cells engineered to express the nucleic acid constructs of Section 5.2.4.4, supra, are from an adult.

In a specific embodiment, reference to a cell transfected with nucleic acids includes the particular subject cell transfected with the nucleic acids and the progeny or potential progeny of such a cell. Progeny of such a cell may not be identical to the parent cell transfected with the nucleic acid molecule due to mutations or environmental influences that may occur in succeeding generations or integration of the nucleic acid molecule into the cell genome.

In some embodiments, isolated cells are utilized herein. In a specific embodiment, the isolated cells are at least 80%, 90%, 95% or 98% free of a different cell type as measured by a technique known to one of skill in the art, such as flow cytometry. In other words, at least 80%, 90%, 95% or 98% of the isolated cells are of the same cell type.

Any techniques known to one of skill in the art can be used to transfect or transduce cells with nucleic acids including, e.g., transformation, transfection, conjugation, protoplast fusion, electroporation, calcium phosphate-precipitation, direct microinjection, and infection with viruses, including but not limited to adenoviruses, lentiviruses, and retroviruses. In one embodiment, the cells are transiently transfected with nucleic acids. In another embodiment, the cells are stably transfected with nucleic acids.

For long-term, high-yield production of a recombinant of a protein, stable cell lines can be generated. For example, cell lines can be transformed using the nucleic acid constructs of Section 5.2.4.4 which may contain a selectable marker gene on the same or on a separate nucleic acid construct. The selectable marker gene can be introduced into the same cell by co-transfection. Following the introduction of the vector, cells are allowed to grow for 1-2 days in an enriched media before they are switched to selective media to allow growth and recovery of cells that successfully express the introduced nucleic acids. Resistant clones of stably transformed cells may be proliferated using tissue culture techniques well known in the art that are appropriate to the cell type. In a particular embodiment, the cell line has been adapted to grow in serum-free medium. In one embodiment, the cell line has been adapted to grow in serum-free medium in shaker flasks. In one embodiment, the cell line has been adapted to grow in stir or rotating flasks. In certain embodiments, the cell line is cultured in suspension.

In a specific embodiment, a particularly preferred method of high-yield production of a recombinant polypeptide of the present invention is through the use of dihydro folate reductase (DHFR) amplification in DHFR-deficient CHO cells, by the use of successively increasing levels of methotrexate as described in U.S. Pat. No. 4,889,803, which is incorporated by reference herein in its entirety. The polypeptide obtained from such cells may be in a glycosylated form.

In a specific embodiment, the nucleic acid constructs are suitable for introduction and expression in primary cells isolated from a subject. The primary cells are engineered to express a protein. In a specific embodiment, the primary cells isolated from a subject are further engineered to recombinantly express another therapeutic polypeptide, e.g., a cytokine (e.g., IL-1, IL-2, IL-6, IL-11, IL-12, IL-13, TNF-alpha, GM-CSF, interferon-α, interferon-β, or interferon-γ), CD3, a growth factor or a fragment or derivative thereof. In a specific embodiment, the primary cells isolated from a subject are further engineered to recombinantly express an antigen of a cancer.

In certain embodiments, cells engineered to express a protein are used as a Therapeutic Agent and are implanted or transplanted into a subject to prevent, treat or manage a disease.

5.2.6 Compounds

In another aspect, a Therapeutic Agent is a compound (e.g., a small molecule). In some embodiments, a Therapeutic Agent is a compound that modulates the interaction between B7-H7 and one or more of its receptors (e.g., B7-H7CR). In certain embodiments, a Therapeutic Agent is a compound that modulates the interaction between B7-H7CR and one or more of its ligands (e.g., B7-H7). In some embodiments, a Therapeutic Agent is a compound that modulates the interaction between B7-H7 and B7-H7CR. In other embodiments, a Therapeutic Agent is a compound that modulates the expression of B7-H7 or B7-H7CR. In specific embodiments, a Therapeutic Agent is an Immunostimulating Therapeutic Agent. In other specific embodiments, a Therapeutic Agent is an Inhibitory Therapeutic Agent. Examples of compounds include, but are not limited to, peptides; proteins; peptoids; random biooligomers; diversomers such as hydantoins, benzodiazepines, dipeptides; vinylogous polypeptides; nonpeptidal peptidomimetics; oligocarbamates; peptidyl phosphonates; nucleic acids (e.g., RNAi, antisense, and microRNA); antibodies; and carbohydrates. In a specific embodiment, a Therapeutic Agent is a small molecule.

In certain embodiments, a Therapeutic Agent is an antisense nucleic acid molecule that inhibits or reduces the expression of B7-H7 or B7-H7CR. An antisense molecule can hydrogen bond to a sense nucleic acid. The antisense nucleic acid can be complementary to an entire coding strand, or to only a fragment thereof, e.g., all or part of the protein coding region (or open reading frame). An antisense nucleic acid molecule can be antisense to all or part of a non-coding region of the coding strand of a nucleotide sequence encoding a protein. The non-coding regions ("5' and 3' untranslated regions") are the 5' and 3' sequences which flank the coding region and are not translated into amino acids.

An antisense nucleic acid molecule can be, for example, about 5, 10, 15, 20, 25, 30, 35, 40, 45, or 50, or 5 to 25, 5 to 50, 10 to 25, 10 to 50, 15 to 25, 15 to 50, 20 to 30, 20 to 40, 20 to 50, 25 to 40, or 25 to 50 nucleotides or more in length. An antisense nucleic acid molecule can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid molecule include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Techniques for generating antisense nucleic acid molecules are known to those skilled in the art.

In some embodiments, a Therapeutic Agent is a ribozyme that is specific for B7-H7 or B7-H7CR nucleic acids. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) Nature 334:585-591)) can be used to catalytically cleave mRNA transcripts to thereby inhibit translation of the protein encoded by the mRNA. A ribozyme having specificity for a nucleic acid molecule encoding a polypeptide can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987, 071; and Cech et al. U.S. Pat. No. 5,116,742. Alternatively, an mRNA encoding a polypeptide can be used to select a catalytic RNA having a specific ribonuclease activity from a pool of RNA molecules. See, e.g., Bartel and Szostak (1993) Science 261:1411-1418.

In some embodiments, a Therapeutic Agent is a small interfering RNA (siRNA) that inhibits or reduces the expression of B7-H7 or B7-H7CR. Techniques for generating and using siRNA are known in the art. See, e.g., U.S. Pat. Nos. 7,651,541, 7,608,707, and 7,056,704; Lopez-Fraga et al., 2009, BioDrugs 23(5): 305-332; Hajeri et al., 2009, Drug Discov Today 14(17-18):851-8; and Tilesi et al., 2009, Curr Opin Mol. Ther. 11(2):156-64 for information concerning siRNA.

5.3 THERAPEUTIC AGENTS THAT MODULATE THE INTERACTION BETWEEN B7-H2 AND ITS RECEPTORS

In one aspect, presented herein are Therapeutic Agents that modulate one or more of the signal transduction pathways induced when a native B7-H2 polypeptide binds to either a native ICOS polypeptide, native CD28 polypeptide, or native CTLA-4 polypeptide. In a specific embodiment, a Therapeutic Agent selectively modulates one or more of the signal transduction pathways induced when a native B7-H2 binds to either a native ICOS polypeptide, native CD28 polypeptide, or a native CTLA-4 polypeptide. In some embodiments, a Therapeutic Agent modulates the interaction between a native B7-H2 polypeptide and a native ICOS polypeptide, native CD28 polypeptide, or native CTLA-4 polypeptide. In certain embodiments, a Therapeutic Agent selectively modulates the interaction between either a native B7-H2 polypeptide and a native ICOS polypeptide, native CD28 polypeptide, or native CTLA-4 polypeptide.

In another aspect, presented herein are Therapeutic Agents that modulate the expression of a native B7-H2 polypeptide, native ICOS polypeptide, native CD28 polypeptide, or native CTLA-4 polypeptide. In a specific embodiment, a Therapeutic Agent selectively modulates the expression of a native B7-H2 polypeptide, native ICOS polypeptide, native CD28 polypeptide, or native CTLA-4 polypeptide. See Sections 5.3.1 to 5.3.6, infra, for specific examples of Therapeutic Agents.

In a specific embodiment, one or more signal transduction pathways mediated by B7-H2 binding to one or more of its receptors are modulated by contacting a Therapeutic Agent with an immune cell or a population of immune cells. In another embodiment, the interaction between B7-H2 and one or more of its receptors (e.g., ICOS, CD28 or CTLA-4) is modulated by contacting a Therapeutic Agent with an immune cell or a population of immune cells. In another embodiment, the expression of B7-H2, ICOS, CD28 or CTLA-4 is modulated by contacting a Therapeutic Agent with an immune cell or a population of immune cells expressing B7-H2, ICOS, CD28 or CTLA-4, respectively.

In a specific embodiment, a Therapeutic Agent modulates one or more of the signal transduction pathways induced by B7-H2 binding to ICOS. In certain embodiments, a Therapeutic Agent selectively modulates one or more signal transduction pathways induced by B7-H2 binding to ICOS. In certain embodiments, a Therapeutic Agent selectively activates or enhances one or more of the signal transduction pathways induced by the binding of B7-H2 to ICOS. In specific embodiments, a Therapeutic Agent activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent. In specific embodiments, a Therapeutic Agent: (i) activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not activate or enhance, or activates or enhances one or more of the signal transduction pathways induced by the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent.

In specific embodiments, a Therapeutic Agent: (i) activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not activate or enhance, or activates or enhances one or more of the signal transduction pathways induced by the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of ICOS to such one or more other ligands in the absence of the Therapeutic Agent.

In certain embodiments, a Therapeutic Agent selectively induces one or more of the signal transduction pathways induced by the binding of B7-H2 to ICOS. In specific embodiments, a Therapeutic Agent induces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent. In specific embodiments, a Therapeutic Agent: (i) induces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not induce, or induces one or more of the signal transduction pathways induced by the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent. In specific embodiments, a Therapeutic Agent: (i) induces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not induce, or induces one or more of the signal transduction pathways induced by the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of ICOS to such one or more other ligands in the absence of the Therapeutic Agent.

In some embodiments, a Therapeutic Agent selectively inhibits or reduces one or more of the signal transduction pathways induced by the binding of B7-H2 to ICOS. In specific embodiments, a Therapeutic Agent inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent. In specific embodiments, a Therapeutic Agent: (i) inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not inhibit or reduce, or inhibits or reduces one or more of the signal transduction pathways induced by the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent.

In specific embodiments, a Therapeutic Agent inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent. In specific embodiments, a Therapeutic Agent: (i) inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the Therapeutic Agent; and (ii) does not inhibit or reduce, or inhibits or reduces one or more of the signal transduction pathways induced by the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of ICOS to such one or more other ligands in the absence of the Therapeutic Agent.

In another embodiment, a Therapeutic Agent modulates the B7-H2 polypeptide and ICOS polypeptide interaction. In certain embodiments, the Therapeutic Agent selectively modulates the B7-H2 and ICOS interaction. In another embodiment, a Therapeutic Agent inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the Therapeutic Agent. In another embodiment, a Therapeutic Agent: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the Therapeutic Agent, and (ii) does not inhibit or reduce, or inhibits or reduces the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the Therapeutic Agent.

In another embodiment, a Therapeutic Agent: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the Therapeutic Agent, and (ii) does not inhibit or reduce, or inhibits or reduces the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of ICOS to such one or more other ligands in the absence of the Therapeutic Agent.

In a specific embodiment, a Therapeutic Agent modulates one or more of the signal transduction pathways induced by B7-H2 binding to CD28. In certain embodiments, a Therapeutic Agent selectively modulates one or more signal transduction pathways induced by B7-H2 binding to CD28. In certain embodiments, a Therapeutic Agent selectively activates or enhances one or more of the signal transduction pathways induced by the binding of B7-H2 to CD28. In specific embodiments, a Therapeutic Agent activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent. In specific embodiments, a Therapeutic Agent: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not activate or enhance, or activates or enhances one or more of the signal transduction pathways induced by the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent.

In specific embodiments, a Therapeutic Agent: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not activate or enhance, or activates or enhances one or more of the signal transduction pathways induced by the binding of CD28 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CD28 to such one or more other ligands in the absence of the Therapeutic Agent.

In certain embodiments, a Therapeutic Agent selectively induces one or more of the signal transduction pathways induced by the binding of B7-H2 to CD28. In specific embodiments, a Therapeutic Agent induces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent. In specific embodiments, a Therapeutic Agent: (i) induces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not induce, or induces one or more of the signal transduction pathways induced by the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent. In specific embodiments, a Therapeutic Agent: (i) induces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not induce, or induces one or more of the signal transduction pathways induced by the binding of CD28 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CD28 to such one or more other ligands in the absence of the Therapeutic Agent.

In some embodiments, a Therapeutic Agent selectively inhibits or reduces one or more of the signal transduction pathways induced by the binding of B7-H2 to CD28. In specific embodiments, a Therapeutic Agent inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent. In specific embodiments, a Therapeutic Agent: (i)inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not inhibit or reduce, or inhibits or reduces one or more of the signal transduction pathways induced by the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent. In specific embodiments, a Therapeutic Agent: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the Therapeutic Agent; and (ii) does not inhibit or reduce, or inhibits or reduces one or more of the signal transduction pathways induced by the binding of CD28 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CD28 to such one or more other ligands in the absence of the Therapeutic Agent.

In another embodiment, a Therapeutic Agent modulates the B7-H2 polypeptide and CD28 polypeptide interaction. In certain embodiments, the Therapeutic Agent selectively modulates the B7-H2 and CD28 interaction. In another embodiment, a Therapeutic Agent inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the Therapeutic Agent. In another embodiment, a Therapeutic Agent: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the Therapeutic Agent, and (ii) does not inhibit or reduce, or inhibits or reduces the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the Therapeutic Agent. In another embodiment, a Therapeutic Agent: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the Therapeutic Agent, and (ii) does not inhibit or reduce, or inhibits or reduces the binding of CD28 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of CD28 to such one or more other ligands in the absence of the Therapeutic Agent.

In a specific embodiment, a Therapeutic Agent modulates one or more of the signal transduction pathways induced by B7-H2 binding to CTLA-4. In certain embodiments, a Therapeutic Agent selectively modulates one or more signal transduction pathways induced by B7-H2 binding to CTLA-4. In certain embodiments, a Therapeutic Agent selectively activates or enhances one or more of the signal transduction pathways induced by the binding of B7-H2 to CTLA-4. In specific embodiments, a Therapeutic Agent activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent. In specific embodiments, a Therapeutic Agent: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not activate or enhance, or activates or enhances one or more of the signal transduction pathways induced by the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent.

In specific embodiments, a Therapeutic Agent: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not activate or enhance, or activates or enhances one or more of the signal transduction pathways induced by the binding of CTLA-4 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CTLA-4 to such one or more other ligands in the absence of the Therapeutic Agent.

In certain embodiments, a Therapeutic Agent selectively induces one or more of the signal transduction pathways induced by the binding of B7-H2 to CTLA-4. In specific embodiments, a Therapeutic Agent induces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent. In specific embodiments, a Therapeutic Agent: (i) induces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not induce, or induces one or more of the signal transduction pathways induced by the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent. In specific embodiments, a Therapeutic Agent: (i) induces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not induce, or induces one or more of the signal transduction pathways induced by the binding of CTLA-4 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CTLA-4 to such one or more other ligands in the absence of the Therapeutic Agent.

In some embodiments, a Therapeutic Agent selectively inhibits or reduces one or more of the signal transduction pathways induced by the binding of B7-H2 to CTLA-4. In specific embodiments, a Therapeutic Agent inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent. In specific embodiments, a Therapeutic Agent: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not inhibit or reduce, or inhibits or reduces one or more of the signal transduction pathways induced by the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the Therapeutic Agent.

In specific embodiments, a Therapeutic Agent: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the Therapeutic Agent; and (ii) does not inhibit or reduce, or inhibits or reduces one or more of the signal transduction pathways induced by the binding of CTLA-4 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CTLA-4 to such one or more other ligands in the absence of the Therapeutic Agent.

In another embodiment, a Therapeutic Agent modulates the B7-H2 polypeptide and CTLA-4 polypeptide interaction. In certain embodiments, the Therapeutic Agent selectively modulates the B7-H2 and CTLA-4 interaction. In another embodiment, a Therapeutic Agent inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the Therapeutic Agent. In another embodiment, a Therapeutic Agent: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the Therapeutic Agent, and (ii) does not inhibit or reduce, or inhibits or reduces the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the Therapeutic Agent. In another embodiment, a Therapeutic Agent: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the Therapeutic Agent, and (ii) does not inhibit or reduce, or inhibits or reduces the binding of CTLA-4 to one or more other ligands (e.g., B7-1 and/or B7-2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of CTLA-4 to such one or more other ligands in the absence of the Therapeutic Agent.

In a specific embodiment, a Therapeutic Agent modulates one or more of the signal transduction pathways induced by B7-H2 binding to CD28 and CTLA-4. In some embodiments, a Therapeutic Agent activates or enhances one or more of the signal transduction pathways induced by the binding of B7-H2 to CD28 and CTLA-4. In specific embodiments, a Therapeutic Agent activates or enhances one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent. In specific embodiments, a Therapeutic Agent: (i) activates or enhances one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent; and (ii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the Therapeutic Agent.

In some embodiments, a Therapeutic Agent induces one or more of the signal transduction pathways induced by the binding of B7-H2 to CD28 and CTLA-4. In specific embodiments, a Therapeutic Agent induces one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent. In specific embodiments, a Therapeutic Agent: (i) induces one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent; and (ii) does not induce, or induces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the Therapeutic Agent.

In some embodiments, a Therapeutic Agent inhibits or reduces one or more of the signal transduction pathways induced by the binding of B7-H2 to CD28 and CTLA-4. In specific embodiments, a Therapeutic Agent inhibits or reduces one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent. In specific embodiments, a Therapeutic Agent: (i) inhibits or reduces one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the Therapeutic Agent; and (ii) does not inhibit or reduce, or inhibits or reduces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the Therapeutic Agent.

In another embodiment, a Therapeutic Agent modulates the interactions between B7-H2 and CD28 and B7-H2 and CTLA-4. In another embodiment, a Therapeutic Agent inhibits or reduces the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and CTLA-4 in the absence of the Therapeutic Agent. In another embodiment, a Therapeutic Agent: (i) inhibits or reduces the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and CTLA-4 in the absence of the Therapeutic Agent, and (ii) does not inhibit or reduce, or inhibits or reduces the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS in the absence of the Therapeutic Agent.

In a specific embodiment, a Therapeutic Agent modulates one or more of the signal transduction pathways induced by B7-H2 binding to CD28 and ICOS. In some embodiments, a Therapeutic Agent activates or enhances one or more of the signal transduction pathways induced by the binding of B7-H2 to CD28 and ICOS. In specific embodiments, a Therapeutic Agent activates or enhances one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent. In specific embodiments, a Therapeutic Agent: (i) activates or enhances one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent; and (ii) does not activate or enhance, or activates or enhances one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the Therapeutic Agent.

In some embodiments, a Therapeutic Agent induces one or more of the signal transduction pathways induced by the binding of B7-H2 to CD28 and ICOS. In specific embodiments, a Therapeutic Agent induces one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent. In specific embodiments, a Therapeutic Agent: (i) induces one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent; and (ii) does not induce, or induces one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the Therapeutic Agent.

In some embodiments, a Therapeutic Agent inhibits or reduces one or more of the signal transduction pathways induced by the binding of B7-H2 to CD28 and ICOS. In specific embodiments, a Therapeutic Agent inhibits or reduces one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent. In specific embodiments, a Therapeutic Agent: (i) inhibits or reduces one or more of the signal transduction pathways induced by the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and ICOS in the absence of the Therapeutic Agent; and (ii) does not inhibit or reduce, or inhibits or reduces one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the Therapeutic Agent.

In another embodiment, a Therapeutic Agent modulates the interactions between B7-H2 and CD28 and B7-H2 and ICOS. In another embodiment, a Therapeutic Agent inhibits or reduces the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and ICOS in the absence of the Therapeutic Agent. In another embodiment, a Therapeutic Agent: (i) inhibits or reduces the binding of B7-H2 to CD28 and ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and ICOS in the absence of the Therapeutic Agent, and (ii) does not inhibit or reduce, or inhibits or reduces the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CTLA-4 in the absence of the Therapeutic Agent.

In a specific embodiment, a Therapeutic Agent modulates one or more of the signal transduction pathways induced by B7-H2 binding to ICOS and CTLA-4. In some embodiments, a Therapeutic Agent activates or enhances one or more of the signal transduction pathways induced by the binding of B7-H2 to ICOS and CTLA-4. In specific embodiments, a Therapeutic Agent activates or enhances one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent. In specific embodiments, a Therapeutic Agent: (i) activates or enhances one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent; and (ii) does not activate or enhance, or activates or enhances one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the Therapeutic Agent.

In some embodiments, a Therapeutic Agent induces one or more of the signal transduction pathways induced by the binding of B7-H2 to ICOS and CTLA-4. In specific embodiments, a Therapeutic Agent induces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent. In specific embodiments, a Therapeutic Agent: (i) induces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent; and (ii) does not induce, or induces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the Therapeutic Agent.

In some embodiments, a Therapeutic Agent inhibits or reduces one or more of the signal transduction pathways induced by the binding of B7-H2 to ICOS and CTLA-4. In specific embodiments, a Therapeutic Agent inhibits or reduces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent. In specific embodiments, a Therapeutic Agent: (i) inhibits or reduces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the Therapeutic Agent; and (ii) does not inhibit or reduce, or inhibits or reduces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the Therapeutic Agent.

In another embodiment, a Therapeutic Agent modulates the interactions between B7-H2 and ICOS and B7-H2 and CTLA-4. In another embodiment, a Therapeutic Agent inhibits or reduces the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CTLA-4 in the absence of the Therapeutic Agent. In another embodiment, a Therapeutic Agent: (i) inhibits or reduces the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CTLA-4 in the absence of the Therapeutic Agent, and (ii) does not inhibit or reduce, or inhibits or reduces the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CD28 in the absence of the Therapeutic Agent.

In a specific embodiment, a Therapeutic Agent modulates one or more of the signal transduction pathways induced by B7-H2 binding to CD28, CTLA-4 and ICOS. In some embodiments, a Therapeutic Agent activates or enhances one or more of the signal transduction pathways induced by the binding of B7-H2 to CD28, CTLA-4 and ICOS. In some embodiments, a Therapeutic Agent induces one or more of the signal transduction pathways induced by the binding of B7-H2 to CD28, CTLA-4 and ICOS. In some embodiments, a Therapeutic Agent inhibits or reduces one or more of the signal transduction pathways induced by the binding of B7-H2 to CD28, CTLA-4 and ICOS. In certain embodiments, a Therapeutic Agent modulates the interactions between B7-H2 and CD28, B7-H2 and CTLA-4, and B7-H2 and ICOS.

In certain embodiments, the Therapeutic Agents are agonists. In other embodiments, the Therapeutic Agents are antagonists.

In certain embodiments, the Therapeutic Agents induce, activate or enhance one or more immune functions or responses (i.e., the agents are Immunostimulating Therapeutic Agents). In other embodiments, the Therapeutic Agents suppress or reduce one or more immune functions or responses (i.e., the agents are Inhibitory Therapeutic Agents). The modulation of one or more immune functions or responses can be in the form of, e.g., an antibody response (humoral response) or a cellular immune response, e.g., cytokine secretion (e.g., interferon-gamma), helper activity or cellular cytotoxicity. In one embodiment, cytokine secretion, antibody production, effector function, T cell proliferation, and/or NK cell proliferation is modulated following contact with a Therapeutic Agent. In a specific embodiment, one or more immune functions or responses is modulated by contacting an immune cell or a population of immune cells with a Therapeutic Agent.

5.3.1 Antibodies

In certain embodiments, the antibodies described in this section are commercially or publicly available. In other embodiments, the antibodies described in this section can produced by any method well known in the art, e.g., as described in U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties).

5.3.1.1 Anti-B7-H2 Antibodies

In one aspect, a Therapeutic Agent is an antibody that specifically binds to B7-H2 and modulates one or more of the signal transduction pathways induced by B7-H2 binding to one or more of the following receptors: ICOS, CD28, or CTLA-4. The modulation of one or more signal transduction pathways can be measured by assessing the phosphorylation of certain subunits, the kinase activity of certain molecules (e.g., MAP kinase), the activity of certain transcription factors, or the translocation of certain transcription factors from the cytoplasm to the nucleus, cytokine production (e.g., IL-2, IL-4, IL-5, IL-10, IFN-alpha, IFN-beta, or IFN-gamma), antibody production, cellular proliferation (e.g., lymphocyte proliferation) using techniques known to those skilled in the art or described herein, e.g., ELISAs, Western Blots, electromobility shift assays or other immunoassays. In a specific embodiment, the Therapeutic Agent modulates the interaction between B7-H2 and one or more of the following receptors: ICOS, CD28 or CTLA-4. Methods well known in the art or described herein, e.g., ELISA, cell-based assays including flow cytometry, KinEx A assay, and plasmon surface resonance assay (e.g., BIAcore® assay), may be used to assess binding of B7-H2 to one or more of the following receptors: ICOS, CD28 or CTLA-4. Antibodies that modulate the interaction between B7-H2 and ICOS, CD28 or CTLA-4 may do so sterically or non-sterically.

As discussed in Examples 6 and 7 infra, the mouse anti-human B7-H2 monoclonal antibody 9F.8A4 (BioLegend; San Diego, Calif.) abrogates binding of B7-H2 to CD28, CTLA-4 and ICOS. Accordingly, in some embodiments, the Therapeutic Agent is 9F.8A4 or a fragment thereof (e.g., an antigen-binding fragment thereof). In another embodiment, the Therapeutic Agent is a chimeric or humanized form of 9F.8A4. In other embodiments, the Therapeutic Agent is not 9F.8A4, or a fragment thereof, or a chimeric or humanized form thereof. In certain embodiments, the Therapeutic Agent is an antibody that specifically binds to B7-H2 and competes with 9F.8A4 for binding to B7-H2.

In a specific embodiment, the Therapeutic Agent is an antibody that specifically binds to B7-H2 and selectively modulates one or more of the signal transduction pathways induced by the binding of B7-H2 to ICOS. In certain embodiments, the Therapeutic Agent is an antibody that specifically binds to B7-H2 and selectively activates or enhances one or more of the signal transduction pathways induced by the binding of B7-H2 to ICOS. In specific embodiments, the Therapeutic Agent is an antibody that specifically binds to B7-H2 and activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the antibody. In specific embodiments, the Therapeutic Agent is an antibody that specifically binds to B7-H2 and the antibody: (i) activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the antibody; and (ii) does not activate or enhance, or activates or enhances one or more of the signal transduction pathways induced by the binding of B7-H2 to either CD28, CTLA-4 or both by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to either CD28, CTLA-4 or both in the absence of the antibody.

In some embodiments, the Therapeutic Agent is an antibody that specifically binds to B7-H2 and selectively inhibits or reduces one or more of the signal transduction pathways induced by the binding of B7-H2 to ICOS. In specific embodiments, the Therapeutic Agent is an antibody that specifically binds to B7-H2 and inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the antibody. In specific embodiments, the Therapeutic Agent is an antibody that specifically binds to B7-H2 and the antibody: (i) inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the antibody; and (ii) does not inhibit or reduce, or inhibits or reduces one or more of the signal transduction pathways induced by the binding of B7-H2 to either CD28, CTLA-4 or both by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to either CD28, CTLA-4 or both in the absence of the antibody.

In a specific embodiment, the Therapeutic Agent is an antibody that specifically binds to B7-H2 and selectively inhibits or reduces the binding of B7-H2 to ICOS. In another embodiment, the Therapeutic Agent is an antibody that specifically binds to B7-H2 and inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the antibody. In another embodiment, the Therapeutic Agent is an antibody that specifically binds to B7-H2 and the antibody: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the antibody, and (ii) does not inhibit or reduce, or inhibits or reduces the binding of B7-H2 to either CD28, CTLA-4 or both by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to either CD28, CTLA-4 or both in the absence of the antibody.

In a specific embodiment, the Therapeutic Agent is an antibody that specifically binds to B7-H2 and selectively modulates one or more of the signal transduction pathways induced by the binding of B7-H2 to either CD28, CTLA-4 or both. In certain embodiments, the Therapeutic Agent is an antibody that specifically binds to B7-H2 and selectively activates or enhances one or more of the signal transduction pathways induced by the binding of B7-H2 to either CD28, CTLA-4 or both.

In a specific embodiment, the Therapeutic Agent is an antibody that specifically binds to B7-H2 and modulates one or more of the signal transduction pathways induced by the binding of B7-H2 to CD28 as well as one or more of the signal transduction pathways induced by the binding of B7-H2 to CTLA-4. In certain embodiments, the Therapeutic Agent is an antibody that specifically binds to B7-H2 and selectively activates or enhances: (i) one or more of the signal transduction pathways induced by the binding of B7-H2 to CD28, and (ii) one or more of the signal transduction pathways induced by the binding of B7-H2 to CTLA-4.

In specific embodiments, the Therapeutic Agent is an antibody that specifically binds to B7-H2 and the antibody: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) activates or enhances, or activates or enhances one or more of the signal transduction pathways induced by the binding of B7-H2 to CTLA-4 or both by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody.

In specific embodiments, the Therapeutic Agent is an antibody that specifically binds to B7-H2 and the antibody: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; (ii) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (iii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In some embodiments, the Therapeutic Agent is an antibody that specifically binds to B7-H2 and inhibits or reduces one or more of the signal transduction pathways induced by the binding of B7-H2 to CD28 as well one or more of the signal transduction pathways induced by the binding of B7-H2 to CTLA-4. In specific embodiments, the Therapeutic Agent is an antibody that specifically binds to B7-H2 and the antibody: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody.

In specific embodiments, the Therapeutic Agent is an antibody that specifically binds to B7-H2 and the antibody: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; (ii) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (iii) does not inhibit or reduce, or inhibits or reduces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In a specific embodiment, the Therapeutic Agent is an antibody that specifically binds to B7-H2 and inhibits or reduces the binding of B7-H2 to CD28 as well as the binding of B7-H2 to CTLA-4. In another embodiment, the Therapeutic Agent is an antibody that specifically binds to B7-H2 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody; and (ii) inhibits or reduces the binding of B7-H2 to CTLA-4 by at least 25%, 30%, 40%, 50%, 60%, 75%, 80%, 85%, 90%, 95%, 98% or 100%, or in the range of between 25% to 50%, 25% to 75%, 50% to 75%, 50% to 95%, 75% to 95%, or 75% to 100% relative to the binding of B7-H2 to CTLA-4 in the absence of the antibody.

In another embodiment, the Therapeutic Agent is an antibody that specifically binds to B7-H2 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody; (ii) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the antibody; and (iii) does not inhibit or reduce, or inhibits or reduces the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS in the absence of the antibody.

As discussed in Examples 6 and 7 infra, the mouse anti-human B7-H2 monoclonal antibody MIH12 (eBioscience; San Diego, Calif.) selectively blocks binding of B7-H2 to CD28 and CTLA-4. In other words, the antibody blocks binding of B7-H2 to CD28 and CTLA-4 without blocking binding to ICOS. Accordingly, in some embodiments, the Therapeutic Agent is MIH12 or a fragment thereof. In another embodiment, the Therapeutic Agent is a chimeric or humanized form of MIH12. In other embodiments, the Therapeutic Agent is not MIH12, or a fragment thereof, or a chimeric or humanized form thereof. In certain embodiments, the Therapeutic Agent is an antibody that specifically binds to B7-H2 and competes with MIH12 for binding to B7-H2.

In a specific embodiment, the Therapeutic Agent is an antibody that specifically binds to B7-H2 and selectively activates or enhances one or more of the signal transduction pathways induced by the binding of B7-H2 to CD28. In certain embodiments, the Therapeutic Agent is an antibody that specifically binds to B7-H2 and activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody. In specific embodiments, the Therapeutic Agent is an antibody that specifically binds to B7-H2 and the antibody: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS or both in the absence of the antibody.

In certain embodiments, the Therapeutic Agent is an antibody that specifically binds to B7-H2 and the antibody: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not activate or enhance, or activates or enhances one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the antibody. In certain embodiments, the Therapeutic Agent is an antibody that specifically binds to B7-H2 and the antibody: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not activate or enhance, or activates or enhances one or more of the signal transduction pathways induced by the binding of B7-H2 to ICOS or CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS or CTLA-4 in the absence of the antibody.

In some embodiments, the Therapeutic Agent is an antibody that specifically binds to B7-H2 and selectively inhibits or reduces one or more of the signal transduction pathways induced by the binding of B7-H2 to CD28. In specific embodiments, the Therapeutic Agent is an antibody that specifically binds to B7-H2 and inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody. In specific embodiments, the Therapeutic Agent is an antibody that specifically binds to B7-H2 and the antibody: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not inhibit or reduce, or inhibits or reduces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In certain embodiments, the Therapeutic Agent is an antibody that specifically binds to B7-H2 and the antibody: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not inhibit or reduce, or inhibits or reduces one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the antibody. In some embodiments, the Therapeutic Agent is an antibody that specifically binds to B7-H2 and the antibody: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the antibody; and (ii) does not inhibit or reduce, or inhibits or reduces one or more of the signal transduction pathways induced by the binding of B7-H2 to ICOS or CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS or CTLA-4 in the absence of the antibody.

In a specific embodiment, the Therapeutic Agent is an antibody that specifically binds to B7-H2 and selectively inhibits or reduces the binding of B7-H2 to CD28. In another embodiment, the Therapeutic Agent is an antibody that specifically binds to B7-H2 and inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody. In another embodiment, the Therapeutic Agent is an antibody that specifically binds to B7-H2 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody, and (ii) does not inhibit or reduce, or inhibits or reduces the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS in the absence of the antibody. In another embodiment, the Therapeutic Agent is an antibody that specifically binds to B7-H2 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody, and (ii) does not inhibit or reduce, or inhibits or reduces the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CTLA-4 in the absence of the antibody.

In another embodiment, the Therapeutic Agent is an antibody that specifically binds to B7-H2 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody, and (ii) does not inhibit or reduce, or inhibits or reduces the binding of B7-H2 to ICOS or CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS or CTLA-4 in the absence of the antibody.

In a specific embodiment, the Therapeutic Agent is an antibody that specifically binds to B7-H2 and selectively activates or enhances one or more of the signal transduction pathways induced by the binding of B7-H2 to CTLA-4. In certain embodiments, the Therapeutic Agent is an antibody that specifically binds to B7-H2 and activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody. In specific embodiments, the Therapeutic Agent is an antibody that specifically binds to B7-H2 and the antibody: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In certain embodiments, the Therapeutic Agent is an antibody that specifically binds to B7-H2 and the antibody: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not activate or enhance, or activates or enhances one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the antibody.

In certain embodiments, the Therapeutic Agent is an antibody that specifically binds to B7-H2 and the antibody: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In certain embodiments, the Therapeutic Agent is an antibody that specifically binds to B7-H2 and the antibody: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not activate or enhance, or activates or enhances one or more of the signal transduction pathways induced by the binding of B7-H2 to ICOS or CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS or CD28 in the absence of the antibody.

In some embodiments, the Therapeutic Agent is an antibody that specifically binds to B7-H2 and selectively inhibits or reduces one or more of the signal transduction pathways induced by the binding of B7-H2 to CTLA-4. In specific embodiments, the Therapeutic Agent is an antibody that specifically binds to B7-H2 and inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody. In specific embodiments, the Therapeutic Agent is an antibody that specifically binds to B7-H2 and the antibody: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not inhibit or reduce, or inhibits or reduces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the antibody.

In certain embodiments, the Therapeutic Agent is an antibody that specifically binds to B7-H2 and the antibody: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not inhibit or reduce, or inhibits or reduces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the antibody.

In some embodiments, the Therapeutic Agent is an antibody that specifically binds to B7-H2 and the antibody: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the antibody; and (ii) does not inhibit or reduce, or inhibits or reduces one or more of the signal transduction pathways induced by the binding of B7-H2 to ICOS or CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS or CD28 in the absence of the antibody.

In a specific embodiment, the Therapeutic Agent is an antibody that specifically binds to B7-H2 and selectively inhibits or reduces the binding of B7-H2 to CTLA-4. In another embodiment, the Therapeutic Agent is an antibody that specifically binds to B7-H2 and inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the antibody. In another embodiment, the Therapeutic Agent is an antibody that specifically binds to B7-H2 and the antibody: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the antibody, and (ii) does not inhibit or reduce, or inhibits or reduces the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS in the absence of the antibody. In another embodiment, the Therapeutic Agent is an antibody that specifically binds to B7-H2 and the antibody: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the antibody, and (ii) does not inhibit or reduce, or inhibits or reduces the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CD28 in the absence of the antibody. In another embodiment, the Therapeutic Agent is an antibody that specifically binds to B7-H2 and the antibody: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the antibody, and (ii) does not inhibit or reduce, or inhibits or reduces the binding of B7-H2 to ICOS or CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS or CD28 in the absence of the antibody.

In certain embodiments, an antibody specifically binds to an epitope comprising amino acid residues 116 to 122 of native human B7-H2. In some embodiments, an antibody specifically binds to an epitope comprising one or more of amino acid residues 51, 53, 116, and 122 of native human B7-H2.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

5.3.1.2 Anti-Complex Antibodies

In another aspect, presented herein are antibodies that specifically bind to a complex of either B7-H2 and ICOS, B7-H2 and CD28 or B7-H2 and CTLA-4. In certain embodiments, such antibodies modulate one or more of the signal transduction pathways induced by B7-H2 binding to one or more of the following receptors: ICOS, CD28 or CTLA-4. In some embodiments, such antibodies modulate the interaction between B7-H2 and one or more of the following receptors:

ICOS, CD28 or CTLA-4. Antibodies that modulate the interaction between B7-H2 and ICOS, CD28 or CTLA-4 may do so sterically or non-sterically.

In one embodiment, a Therapeutic Agent is an antibody that specifically binds to a a B7-H2/ICOS complex. In a specific embodiment, a Therapeutic Agent is an antibody that specifically binds to a B7-H2/ICOS complex and modulates one or more of the signal transduction pathways induced by B7-H2 binding to ICOS. In another embodiment, a Therapeutic Agent is an antibody that specifically binds to a B7-H2/ICOS complex and modulates the interaction between B7-H2 and ICOS.

In another embodiment, a Therapeutic Agent is an antibody that specifically binds to a B7-H2/CD28 complex. In a specific embodiment, a Therapeutic Agent is an antibody that specifically binds to a B7-H2/CD28 complex and modulates one or more of the signal transduction pathways induced by B7-H2 binding to CD28. In another embodiment, a Therapeutic Agent is an antibody that specifically binds to a B7-H2/CD28 complex and modulates the interaction between B7-H2 and CD28.

In another embodiment, a Therapeutic Agent is an antibody that specifically binds to a B7-H7/CTLA-4 complex. In a specific embodiment, a Therapeutic Agent is an antibody that specifically binds to a B7-H2/CTLA-4 complex and modulates one or more of the signal transduction pathways induced by B7-H2 binding to CTLA-4. In another embodiment, a Therapeutic Agent is an antibody that specifically binds to a B7-H2/CTLA-4 complex and modulates the interaction between B7-H2 and CTLA-4.

In some embodiments, an antibody that specifically binds to a complex of either B7-H2 and ICOS, B7-H2 and CD28 or B7-H2 and CTLA-4 induces one or more signal transduction pathways induced by the binding of B7-H2 to ICOS, B7-H2 to CD28, or B7-H2 to CTLA-4. In certain embodiments, an antibody that specifically binds to a complex of either B7-H2 and ICOS, B7-H2 and CD28 or B7-H2 and CTLA-4 induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 50% to 98% of one or more of the signal transduction pathways induced when a native B7-H2 polypeptide (e.g., a native mammalian B7-H2 polypeptide) binds to a native receptor of B7-H2 polypeptide (e.g., CD28, ICOS, or CTLA-4), as measured by assays well-known in the art. In other embodiments, an antibody that specifically binds to a complex of either B7-H2 and ICOS, B7-H2 and CD28, or B7-H2 and CTLA-4 inhibits or reduces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 50% to 98% of one or more of the signal transduction pathways induced when a native B7-H2 polypeptide binds to a native receptor of B7-H2 as measured by assays well-known in the art.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

5.3.1.3 Anti-Receptor Antibodies

In another aspect, presented herein are antibodies that specifically bind to an ICOS, CD28 or CTLA-4. In certain embodiments, such antibodies modulate one or more of the signal transduction pathways induced by B7-H2 binding to one or more of the following receptors: ICOS, CD28 or CTLA-4. In some embodiments, such antibodies modulate the interaction between B7-H2 and one or more of the following receptors: ICOS, CD28 or CTLA-4. Antibodies that modulate the interaction between B7-H2 and ICOS, CD28 or CTLA-4 may do so sterically or non-sterically.

In a specific embodiment, a Therapeutic Agent is an antibody that specifically binds to ICOS and modulates one or more of the signal transduction pathways induced by B7-H2 binding to ICOS. In another embodiment, a Therapeutic Agent is an antibody that specifically binds to ICOS and modulates the interaction between B7-H2 and ICOS.

In specific embodiments, a Therapeutic Agent is an antibody that specifically binds to ICOS and inhibits or reduces one or more signal transduction pathways induced by the binding of B7-H2 to ICOS without inhibiting or reducing one or more signal transduction pathways induced by the binding of ICOS to other ligands. In certain embodiments, a Therapeutic Agent is an antibody that specifically binds to ICOS and the antibody inhibits or reduces one or more signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of ICOS to B7-H2 in the absence of the antibody. In some specific embodiments, a Therapeutic Agent is an antibody that specifically binds to ICOS and the antibody: (i) inhibits or reduces one or more signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to ICOS in the absence of the antibody; and (ii) does not inhibit or reduce, or inhibits or reduces one or more signal transduction pathways induced by the binding of one or more other ligands of ICOS by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to ICOS in the absence of the antibody.

In specific embodiments, a Therapeutic Agent is an antibody that specifically binds to ICOS and activates or enhances one or more signal transduction pathways induced by the binding of B7-H2 to ICOS without inhibiting or reducing one or more signal transduction pathways induced by the binding of ICOS to other ligands. In certain embodiments, a Therapeutic Agent is an antibody that specifically binds to ICOS and the antibody activates or enhances one or more signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of ICOS to B7-H2 in the absence of the antibody. In some specific embodiments, a Therapeutic Agent is an antibody that specifically binds to ICOS and the antibody: (i) activates or enhances one or more signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to ICOS in the absence of the antibody; and (ii) does not activate or enhance, or activates or enhances one or more signal transduction pathways induced by the binding of one or more other ligands of ICOS by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to ICOS in the absence of the antibody.

In certain embodiments, a Therapeutic Agent is an antibody that specifically binds to ICOS and selectively modulates the interaction between B7-H2 and ICOS. In specific embodiments, a Therapeutic Agent is an antibody that specifically binds to ICOS and inhibits or reduces the binding of B7-H2 to ICOS without inhibiting or reducing the binding of ICOS to other ligands. In certain embodiments, a Therapeutic Agent is an antibody that specifically binds to ICOS and antibody inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to ICOS in the absence of the antibody. In some specific embodiments, a Therapeutic Agent is an antibody that specifically binds to ICOS and the antibody: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to ICOS in the absence of the antibody; and (ii) does not inhibit or reduce, or inhibits or reduces the binding of one or more other ligands of ICOS by less than 20%, 15%, 10%, 5%, or 2%, or in the range of between 5% to 20%, 5% to 15%, 5% to 10% or 2% to 5% relative to the binding of such one or more other ligands to ICOS in the absence of antibody.

In some embodiments, a Therapeutic Agent is the mouse anti-human ICOS monoclonal antibody C398.4 (BioLegend; San Diego, Calif.) or a fragment thereof. In other embodiments, a Therapeutic Agent is a chimeric or humanized form of the mouse anti-ICOS monoclonal antibody C398.4. In certain embodiments, a Therapeutic Agent is not the mouse anti-ICOS monoclonal antibody C398.4, or a fragment thereof, or a humanized or chimeric form thereof.

In another embodiment, a Therapeutic Agent is an antibody that specifically binds to CD28 and modulates one or more of the signal transduction pathways induced by B7-H2 binding to CD28. In specific embodiments, a Therapeutic Agent is an antibody that specifically binds to CD28 and inhibits or reduces one or more signal transduction pathways induced by the binding of B7-H2 to CD28 without inhibiting or reducing one or more signal transduction pathways induced by the binding of CD28 to other ligands (e.g., B7-1 or B7-2). In certain embodiments, a Therapeutic Agent is an antibody that specifically binds to CD28 and the antibody inhibits or reduces one or more signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of CD28 to B7-H2 in the absence of the antibody. In some specific embodiments, a Therapeutic Agent is an antibody that specifically binds to CD28 and the antibody: (i) inhibits or reduces one or more signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to CD28 in the absence of the antibody; and (ii) does not inhibit or reduce, or inhibits or reduces one or more signal transduction pathways induced by the binding of one or more other ligands of CD28 (e.g., B7-1 or B7-2) by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to CD28 in the absence of antibody.

In specific embodiments, a Therapeutic Agent is an antibody that specifically binds to CD28 and activates or enhances one or more signal transduction pathways induced by the binding of B7-H2 to CD28 without inhibiting or reducing one or more signal transduction pathways induced by the binding of CD28 to other ligands (e.g., B7-1 or B7-2). In certain embodiments, a Therapeutic Agent is an antibody that specifically binds to CD28 and antibody activates or enhances one or more signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of CD28 to B7-H2 in the absence of the antibody. In some specific embodiments, a Therapeutic Agent is an antibody that specifically binds to CD28 and the antibody: (i) activates or enhances one or more signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to CD28 in the absence of the antibody; and (ii) does not activate or enhance, or activates or enhances one or more signal transduction pathways induced by the binding of one or more other ligands of CD28 (e.g., B7-1 or B7-2) by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to CD28 in the absence of antibody.

In another embodiment, a Therapeutic Agent is an antibody that specifically binds to CD28 and modulates the interaction between B7-H2 and CD28. In certain embodiments, a Therapeutic Agent is an antibody that specifically binds to CD28 and selectively modulates the interaction between B7-H2 and CD28. In specific embodiments, a Therapeutic Agent is an antibody that specifically binds to CD28 and inhibits or reduces the binding of B7-H2 to CD28 without inhibiting or reducing the binding of CD28 to other ligands (e.g., B1-1 or B7-2). In certain embodiments, a Therapeutic Agent is an antibody that specifically binds to CD28 and the antibody inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to CD28 in the absence of the antibody. In some specific embodiments, a Therapeutic Agent is an antibody that specifically binds to CD28 and the antibody: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to CD28 in the absence of the antibody; and (ii) does not inhibit or reduce, or inhibits or reduces the binding of one or more other ligands of CD28 (e.g., B7-1 or B7-2) by less than 20%, 15%, 10%, 5%, or 2%, or in the range of between 5% to 20%, 5% to 15%, 5% to 10% or 2% to 5% relative to the binding of such one or more other ligands to CD28 in the absence of the antibody.

In some embodiments, a Therapeutic Agent is the mouse anti-human CD28 monoclonal antibody CD28.6 (blocking) or CD28.2 (costimulatory) (eBioscience; San Diego, Calif.) or a fragment thereof. In other embodiments, a Therapeutic Agent is a chimeric or humanized form of the mouse anti-CD28 monoclonal antibody CD28.6 or CD28.2. In certain embodiments, a Therapeutic Agent is not the mouse anti-CD28 monoclonal antibody CD28.2, or a fragment thereof, or a humanized or chimeric form thereof. In some embodiments, a Therapeutic Agent is not the mouse anti-CD28 monoclonal antibody CD28.6, or a fragment thereof, or a humanized or chimeric form thereof.

In another embodiment, a Therapeutic Agent is an antibody that specifically binds to CTLA-4 and modulates one or more of the signal transduction pathways induced by B7-H2 binding to CTLA-4. In specific embodiments, a Therapeutic Agent is an antibody that specifically binds to CTLA-4 and inhibits or reduces one or more signal transduction pathways induced by the binding of B7-H2 to CTLA-4 without inhibiting or reducing one or more signal transduction pathways induced by the binding of CTLA-4 to other ligands (e.g., B7-1 or B7-2). In certain embodiments, a Therapeutic Agent is an antibody that specifically binds to CTLA-4 and the antibody inhibits or reduces one or more signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of CTLA-4 to B7-H2 in the absence of the antibody. In some specific embodiments, a Therapeutic Agent is an antibody that specifically binds to CTLA-4 and the antibody: (i) inhibits or reduces one or more signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to CTLA-4 in the absence of the antibody; and (ii) does not inhibit or reduce, or inhibits or reduces one or more signal transduction pathways induced by the binding of one or more other ligands of CTLA-4 (e.g., B7-1 or B7-2) by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to CTLA-4 in the absence of antibody.

In specific embodiments, a Therapeutic Agent is an antibody that specifically binds to CTLA-4 and activates or enhances one or more signal transduction pathways induced by the binding of B7-H2 to CTLA-4 without inhibiting or reducing one or more signal transduction pathways induced by the binding of CTLA-4 to other ligands (e.g., B7-1 or B7-2). In certain embodiments, a Therapeutic Agent is an antibody that specifically binds to CTLA-4 and the antibody activates or enhances one or more signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the one or more signal transduction induced by the binding of CTLA-4 to B7-H2 in the absence of the antibody. In some specific embodiments, a Therapeutic Agent is an antibody that specifically binds to CTLA-4 and the antibody: (i) activates or enhances one or more signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to one or more signal transduction pathways induced by the binding of B7-H2 to CTLA-4 in the absence of the antibody; and (ii) does not activate or enhance, or activates or enhances one or more signal transduction pathways induced by the binding of one or more other ligands of CTLA-4 (e.g., B7-1 or B7-2) by less than 20%, 15%, 10%, 5%, or 2%, or in the range of between 5% to 20%, 5% to 15%, 5% to 10% or 2% to 5% relative to one or more signal transduction pathways induced by the binding of such one or more other ligands to CTLA-4 in the absence of antibody In another embodiment, a Therapeutic Agent is an antibody that specifically binds to a CTLA-4 and modulates the interaction between B7-H2 and CTLA-4. In another embodiment, a Therapeutic Agent is an antibody that specifically binds to CTLA-4 and modulates the interaction between B7-H2 and CTLA-4. In certain embodiments, a Therapeutic Agent is an antibody that specifically binds to CTLA-4 and selectively modulates the interaction between B7-H2 and CTLA-4. In specific embodiments, a Therapeutic Agent is an antibody that specifically binds to CTLA-4 and inhibits or reduces the binding of B7-H2 to CTLA-4 without inhibiting or reducing the binding of CTLA-4 to other ligands (e.g., B7-1 or B7-2). In certain embodiments, a Therapeutic Agent is an antibody that specifically binds to CTLA-4 and the antibody inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to CTLA-4 in the absence of the antibody. In some specific embodiments, a Therapeutic Agent is an antibody that specifically binds to CTLA-4 and antibody: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, or 75% to 100% relative to the binding of B7-H2 to CTLA-4 in the absence of the antibody; and (ii) does not inhibit or reduce, or inhibits or reduces the binding of one or more other ligands of CTLA-4 (e.g., B7-1 or B7-2) by less than 20%, 15%, 10%, 5%, or 2%, or in the range of between 5% to 20%, 5% to 15%, 5% to 10% or 2% to 5% relative to the binding of such one or more other ligands to CTLA-4 in the absence of antibody.

In some embodiments, a Therapeutic Agent is the mouse anti-human CTLA-4 monoclonal antibody 14D3 (eBioscience; San Diego, Calif.) or a fragment thereof. In other embodiments, a Therapeutic Agent is a chimeric or humanized form of the mouse anti-CTLA-4 monoclonal antibody 14D3. In certain embodiments, a Therapeutic Agent is not the mouse anti-CTLA-4 monoclonal antibody 14D3, or a fragment thereof, or a humanized or chimeric form thereof.

In some embodiments, an antibody that specifically binds to ICOS, CD28 or CTLA-4 induces one or more signal transduction pathways induced by the binding of B7-H2 to ICOS, B7-H2 to CD28, or B7-H2 to CTLA-4. In certain embodiments, an antibody that specifically binds to ICOS, CD28 or CTLA-4 induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 50% to 98% of one or more of the signal transduction pathways induced when a native B7-H2 polypeptide (e.g., a native mammalian B7-H2 polypeptide) binds to a native receptor of B7-H2 polypeptide (e.g., CD28, CTLA-4, or ICOS), as measured by assays well-known in the art. In other embodiments, an antibody that specifically binds to ICOS, CD28, or CTLA-4 inhibits or reduces by at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 50% to 98% one or more of the signal transduction pathways induced when a native B7-H2 polypeptide binds to a native receptor of B7-H2 polypeptide (e.g., CD28, ICOS, or CTLA-4), as measured by assays well-known in the art.

In certain embodiments, an antibody that specifically binds to an epitope comprising amino acid residues 116 to 122 of native human B7-H2 can be used to generate an anti-idiotypic antibody. In some embodiments, such an anti-idiotypic antibody can be used to disrupt binding of B7-H2 to either CD28, CTLA-4 or both.

In certain embodiments, an antibody described in this section comprises a modified Fc domain. Exemplary Fc domain modifications are described in Mueller et al., 1997, Molecular Immunology 34(6):441-452; Swann et al., 2008, Current Opinion in Immunology 20:493-499; and Presta, 2008, Current Opinion in Immunology 20:460-470.

5.3.1.4 Antibody Conjugates

In some embodiments, the antibodies described in this Section 5.3.1 et seq. are conjugated or recombinantly fused to a diagnostic, detectable or therapeutic agent or any other molecule. See Section 5.1.2 for a description of antibody conjugates. The embodiments described in Sections 5.1.1 and 5.1.2 are applicable to the antibodies described in this section too.

5.3.2 Polypeptides & Derivatives 5.3.2.1 B7-H2 Polypeptides & Derivatives

In one aspect, a Therapeutic Agent is a B7-H2 polypeptide. In a specific embodiment, such a Therapeutic Agent modulates one or more of the signal transduction pathways induced by B7-H2 binding to one or more of the following receptors: ICOS, CD28 or CTLA-4. In another specific embodiment, such a Therapeutic Agent modulates the interaction between B7-H2 polypeptide and one or more of the following receptors: ICOS, CD28 or CTLA-4. In certain embodiments, such Therapeutic Agents are Immunostimulating Therapeutic Agents. In other embodiments, such Therapeutic Agents are Inhibitory Therapeutic Agents.

In another aspect, a Therapeutic Agent is a B7-H2 derivative. In a specific embodiment, such a Therapeutic Agent modulates one or more of the signal transduction pathways induced by B7-H2 binding to one or more of the following receptors: ICOS, CD28 or CTLA-4. In another specific embodiment, such a Therapeutic Agent modulates the interaction between B7-H2 polypeptide and one or more of the following receptors: ICOS, CD28 or CTLA-4. In certain embodiments, a B7-H2 derivative is an Immunostimulating Therapeutic Agent. In other embodiments, a B7-H2 derivative is an Inhibitory Therapeutic Agent.

In a specific embodiment, a B7-H2 derivative modulates one or more of the signal transduction pathways induced by B7-H2 binding to ICOS. In certain embodiments, a B7-H2 derivative modulates one or more of the signal transduction pathways induced by B7-H2 binding to ICOS without modulating one or more signal transduction pathways induced by B7-H2 binding to either CD28, CTLA-4 or both. In certain embodiments, a B7-H2 derivative selectively modulates one or more signal transduction pathways induced by B7-H2 binding to ICOS. In certain embodiments, a B7-H2 derivative selectively activates or enhances one or more of the signal transduction pathways induced by the binding of B7-H2 to ICOS. In specific embodiments, a B7-H2 derivative activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative. In specific embodiments, a B7-H2 derivative: (i) activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative; and (ii) does not activate or enhance, or activates or enhances one or more of the signal transduction pathways induced by the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In certain embodiments, a B7-H2 derivative binds to native ICOS and induces a higher level of activity than native B7-H2 binding to native ICOS as assessed by, e.g., the induction of one or more signal transduction molecules. In some embodiments, a B7-H2 derivative binds to native ICOS and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H2 binding to native ICOS as assessed by, e.g., the induction of one or more signal transduction molecules.

In some embodiments, a B7-H2 derivative selectively inhibits or reduces one or more of the signal transduction pathways induced by the binding of B7-H2 to ICOS. In specific embodiments, a B7-H2 derivative inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative. In specific embodiments, a B7-H2 derivative: (i) inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 98%, or 75% to 100% relative to the one or more signal transduction pathways induced by the binding of B7-H2 to ICOS in the absence of the derivative; and (ii) does not inhibit or reduce, or inhibits or reduces one or more of the signal transduction pathways induced by the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In another embodiment, a B7-H2 derivative modulates the B7-H2 polypeptide and ICOS polypeptide interaction. In some embodiments, a B7-H2 derivative modulates the B7-H2 polypeptide and ICOS polypeptide interaction, but does not modulate the interaction between B7-H2 polypeptide and either CD28, CTLA-4 or both. In certain embodiments, the B7-H2 derivative selectively modulates the B7-H2 and ICOS interaction. In another embodiment, a B7-H2 derivative inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the derivative. In another embodiment, a B7-H2 derivative: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the derivative, and (ii) does not inhibit or reduce or inhibits or reduces the binding of B7-H2 to one or more other receptors (e.g., CTLA-4 or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the derivative.

In certain embodiments, a B7-H2 derivative binds to a native ICOS with a higher affinity than native B7-H2 binds to native ICOS, as measured by assays/techniques well known in the art, e.g., ELISA, Biacore, or co-immunoprecipitation. In one embodiment, a B7-H2 derivative binds to a native ICOS with a 50%, 75%, 80%, 85%, 90%, 95%, or 98%, or 25% to 50%, 25% to 75%, 50% to 95%, or 75% to 95% higher affinity than the native B7-H2 binds to native ICOS, as measured by techniques well-known in the art. In a specific embodiment, a B7-H2 derivative binds to a native ICOS with 0.5 logs, 1 log, 1.5 logs, 2 logs, 2.5 logs, or 3 logs higher affinity than the native B7-H2 binds to native ICOS, as measured by assays/techniques well known in the art, e.g., ELISA, Biacore, or co-immunoprecipitation.

In certain embodiments, a B7-H2 derivative binds to native ICOS with a lower affinity than the native B7-H2 binds to native ICOS, as measured by well-known assays/techniques. In one embodiment, a B7-H2 derivative binds to a native ICOS with 25%, 50%, 75%, 80%, 85%, 90%, 95%, or 98%, or 25% to 50%, 25% to 75%, 50% to 75%, 50% to 95%, or 75% to 95% lower affinity than the native B7-H2 binds to the native ICOS, as measured by well-known assays/techniques. In another embodiment, a B7-H2 derivative binds to a native ICOS with 0.5 logs, 1 log, 1.5 logs, 2 logs, 2.5 logs, or 3 logs lower affinity than the native B7-H2 binds to the native ICOS, as measured by well-known assays/techniques.

In a specific embodiment, a B7-H2 derivative modulates one or more of the signal transduction pathways induced by B7-H2 binding to CD28. In certain embodiments, a B7-H2 derivative selectively modulates one or more signal transduction pathways induced by B7-H2 binding to CD28. In certain embodiments, a B7-H2 derivative selectively activates or enhances one or more of the signal transduction pathways induced by the binding of B7-H2 to CD28. In specific embodiments, a B7-H2 derivative activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative. In specific embodiments, a B7-H2 derivative: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative; and (ii) does not activate or enhance, or activates or enhances one or more of the signal transduction pathways induced by the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In certain embodiments, a B7-H2 derivative binds to native CD28 and induces a higher level of activity than native B7-H2 binding to native CD28 as assessed by, e.g., the activation or induction of one or more signal transduction molecules. In some embodiments, a B7-H2 derivative binds to native CD28 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H2 binding to native CD28 as assessed by, e.g., the activation or induction of one or more signal transduction molecules.

In some embodiments, a B7-H2 derivative selectively inhibits or reduces one or more of the signal transduction pathways induced by the binding of B7-H2 to CD28. In specific embodiments, a B7-H2 derivative inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative. In specific embodiments, a B7-H2 derivative: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative; and (ii) does not inhibit or reduce, or inhibits or reduces one or more of the signal transduction pathways induced by the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In another embodiment, a B7-H2 derivative modulates the B7-H2 polypeptide and CD28 polypeptide interaction. In certain embodiments, the B7-H2 derivative selectively modulates the B7-H2 and CD28 interaction. In another embodiment, a B7-H2 derivative inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the derivative. In another embodiment, a B7-H2 derivative: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the derivative, and (ii) does not inhibit or reduce or inhibits or reduces the binding of B7-H2 to one or more other receptors (e.g., ICOS or CTLA-4) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the derivative.

In certain embodiments, a B7-H2 derivative binds to a native CD28 with a higher affinity than native B7-H2 binds to native CD28, as measured by assays/techniques well known in the art, e.g., ELISA, Biacore, or co-immunoprecipitation. In one embodiment, a B7-H2 derivative binds to a native CD28 with a 50%, 75%, 80%, 85%, 90%, 95%, or 98%, or 25% to 50%, 25% to 75%, 50% to 95%, or 75% to 95% higher affinity than the native B7-H2 binds to native CD28, as measured by techniques well-known in the art. In a specific embodiment, a B7-H2 derivative binds to a native CD28 with 0.5 logs, 1 log, 1.5 logs, 2 logs, 2.5 logs, or 3 logs higher affinity than the native B7-H2 binds to native CD28, as measured by assays/techniques well known in the art, e.g., ELISA, Biacore, or co-immunoprecipitation.

In certain embodiments, a B7-H2 derivative binds to native CD28 with a lower affinity than the native B7-H2 binds to native CD28, as measured by well-known assays/techniques. In one embodiment, a B7-H2 derivative binds to a native CD28 with 25%, 50%, 75%, 80%, 85%, 90%, 95%, or 98%, or 25% to 50%, 25% to 75%, 50% to 75%, 50% to 95%, or 75% to 95% lower affinity than the native B7-H2 binds to the native CD28, as measured by well-known assays/techniques. In another embodiment, a B7-H2 derivative binds to a native ICOS with 0.5 logs, 1 log, 1.5 logs, 2 logs, 2.5 logs, or 3 logs lower affinity than the native B7-H2 binds to the native CD28, as measured by well-known assays/techniques.

In a specific embodiment, a B7-H2 derivative modulates one or more of the signal transduction pathways induced by B7-H2 binding to CTLA-4. In certain embodiments, a B7-H2 derivative selectively modulates one or more signal transduction pathways induced by B7-H2 binding to CTLA-4. In certain embodiments, a B7-H2 derivative selectively activates or enhances one or more of the signal transduction pathways induced by the binding of B7-H2 to CTLA-4. In specific embodiments, a B7-H2 derivative activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative. In specific embodiments, a B7-H2 derivative: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative; and (ii) does not activate or enhance, or activates or enhances one or more of the signal transduction pathways induced by the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In certain embodiments, a B7-H2 derivative binds to native CTLA-4 and induces a higher level of activity than native B7-H2 binding to native CTLA-4 as assessed by, e.g., the activation or induction of one or more signal transduction molecules. In some embodiments, a B7-H2 derivative binds to native CTLA-4 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H2 binding to native CTLA-4 as assessed by, e.g., the activation or induction of one or more signal transduction molecules.

In some embodiments, a B7-H2 derivative selectively inhibits or reduces one or more of the signal transduction pathways induced by the binding of B7-H2 to CTLA-4. In specific embodiments, a B7-H2 derivative inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative. In specific embodiments, a B7-H2 derivative: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative; and (ii) does not inhibit or reduce, or inhibits or reduces one or more of the signal transduction pathways induced by the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to such one or more other receptors in the absence of the derivative.

In another embodiment, a B7-H2 derivative modulates the B7-H2 polypeptide and CTLA-4 polypeptide interaction. In certain embodiments, the B7-H2 derivative selectively modulates the B7-H2 and CTLA-4 interaction. In another embodiment, a B7-H2 derivative inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the derivative. In another embodiment, a B7-H2 derivative: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the derivative, and (ii) does not inhibit or reduce or inhibits or reduces the binding of B7-H2 to one or more other receptors (e.g., ICOS or CD28) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to such one or more other receptors in the absence of the derivative.

In certain embodiments, a B7-H2 derivative binds to a native CTLA-4 with a higher affinity than native B7-H2 binds to native CTLA-4, as measured by assays/techniques well known in the art, e.g., ELISA, Biacore, or co-immunoprecipitation. In one embodiment, a B7-H2 derivative binds to a native CTLA-4 with 25%, 50%, 75%, 80%, 85%, 90%, 95%, or 98%, or 25% to 50%, 25% to 75%, 50% to 75%, 50% to 95%, or 75% to 95% lower affinity than the native B7-H2 binds to the native CTLA-4, as measured by well-known assays/techniques. In a specific embodiment, a B7-H2 derivative binds to a native CTLA-4 with 0.5 logs, 1 log, 1.5 logs, 2 logs, 2.5 logs, or 3 logs higher affinity than native B7-H2 binds to native CTLA-4, as measured by assays/techniques well known in the art, e.g., ELISA, Biacore, or co-immunoprecipitation.

In certain embodiments, a B7-H2 derivative binds to native CTLA-4 with a lower affinity than the native B7-H2 binds to native CTLA-4, as measured by well-known assays/techniques. In one embodiment, a B7-H2 derivative binds to a native CTLA-4 with 25%, 50%, 75%, 80%, 85%, 90%, 95%, or 98% or 25% to 50%, 25% to 75%, 50% to 75%, 50% to 95%, or 75% to 95% lower affinity than the native B7-H2 binds to the native CTLA-4, as measured by well-known assays/techniques. In another embodiment, a B7-H2 derivative binds to a native CTLA-4 with 0.5 logs, 1 log, 1.5 logs, 2 logs, 2.5 logs, or 3 logs lower affinity than the native B7-H2 binds to the native CTLA-4, as measured by well-known assays/techniques.

In a specific embodiment, a B7-H2 derivative modulates one or more of the signal transduction pathways induced by B7-H2 binding to CD28 and CTLA-4. In some embodiments, a B7-H2 derivative activates or enhances one or more of the signal transduction pathways induced by the binding of B7-H2 to CD28 and CTLA-4. In specific embodiments, a B7-H2 derivative activates or enhances one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the derivative. In specific embodiments, a B7-H2 derivative: (i) activates or enhances one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the derivative; and (ii) does not activate or enhance, or activates or enhances one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the derivative.

In some embodiments, a B7-H2 derivative inhibits or reduces one or more of the signal transduction pathways induced by the binding of B7-H2 to CD28 and CTLA-4. In specific embodiments, a B7-H2 derivative inhibits or reduces one or more of the signal transduction pathways induced by the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 and CTLA-4 in the absence of the derivative. In specific embodiments, a B7-H2 derivative: (i) inhibits or reduces one or more of the signal transduction pathways induced by the binding of B7-H2 to CD28 and CTLA-4 by at least 25%, 30%, 40%, 50%, 60%, 75%, 80%, 85%, 90%, 95%, or 98%, or in the range of between 25% to 50%, 25% to 75%, 50% to 75%, 50% to 95%, 75% to 95%, or 75% to 98% relative to the one or more signal transduction pathways induced by the binding of B7-H2 to CD28 and CTLA-4 in the absence of the derivative; and (ii) does not inhibit or reduce, or inhibits or reduces one or more of the signal transduction pathways induced by the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to ICOS in the absence of the derivative.

In another embodiment, a B7-H2 derivative modulates the interactions between B7-H2 and CD28 and B7-H2 and CTLA-4 interactions. In another embodiment, a B7-H2 derivative inhibits or reduces the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and CTLA-4 in the absence of the derivative. In another embodiment, a B7-H2 derivative: (i) inhibits or reduces the binding of B7-H2 to CD28 and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 and CTLA-4 in the absence of the derivative, and (ii) does not inhibit or reduce or inhibits or reduces the binding of B7-H2 to ICOS by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to ICOS in the absence of the derivative.

In a specific embodiment, a B7-H2 derivative modulates one or more of the signal transduction pathways induced by B7-H2 binding to ICOS and CD28. In some embodiments, a B7-H2 derivative activates or enhances one or more of the signal transduction pathways induced by the binding of B7-H2 to ICOS and CD28. In specific embodiments, a B7-H2 derivative activates or enhances one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative. In specific embodiments, a B7-H2 derivative: (i) activates or enhances one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative; and (ii) does not activate or enhance, or activates or enhances one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the B7-H2 derivative.

In some embodiments, a B7-H2 derivative induces one or more of the signal transduction pathways induced by the binding of B7-H2 to ICOS and CD28. In specific embodiments, a B7-H2 derivative induces one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative. In specific embodiments, a B7-H2 derivative: (i) induces one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative; and (ii) does not induce, or induces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the B7-H2 derivative.

In some embodiments, a B7-H2 derivative inhibits or reduces one or more of the signal transduction pathways induced by the binding of B7-H2 to ICOS and CD28. In specific embodiments, a B7-H2 derivative inhibits or reduces one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative. In specific embodiments, a B7-H2 derivative: (i) inhibits or reduces one or more of the signal transduction pathways induced by the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CD28 in the absence of the B7-H2 derivative; and (ii) does not inhibit or reduce, or inhibits or reduces one or more of the signal transduction pathways induced by the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CTLA-4 in the absence of the B7-H2 derivative.

In another embodiment, a B7-H2 derivative modulates the interactions between B7-H2 and ICOS and B7-H2 and CD28. In another embodiment, a B7-H2 derivative inhibits or reduces the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CTLA-4 in the absence of the B7-H2 derivative. In another embodiment, a B7-H2 derivative: (i) inhibits or reduces the binding of B7-H2 to ICOS and CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CD28 in the absence of the B7-H2 derivative, and (ii) does not inhibit or reduce, or inhibits or reduces the binding of B7-H2 to CTLA-4 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CTLA-4 in the absence of the B7-H2 derivative.

In a specific embodiment, a B7-H2 derivative modulates one or more of the signal transduction pathways induced by B7-H2 binding to ICOS and CTLA-4. In some embodiments, a B7-H2 derivative activates or enhances one or more of the signal transduction pathways induced by the binding of B7-H2 to ICOS and CTLA-4. In specific embodiments, a B7-H2 derivative activates or enhances one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative. In specific embodiments, a B7-H2 derivative: (i) activates or enhances one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative; and (ii) does not activate or enhance, or activates or enhances one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the B7-H2 derivative.

In some embodiments, a B7-H2 derivative induces one or more of the signal transduction pathways induced by the binding of B7-H2 to ICOS and CTLA-4. In specific embodiments, a B7-H2 derivative induces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative. In specific embodiments, a B7-H2 derivative: (i) induces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative; and (ii) does not induce, or induces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the B7-H2 derivative.

In some embodiments, a B7-H2 derivative inhibits or reduces one or more of the signal transduction pathways induced by the binding of B7-H2 to ICOS and CTLA-4. In specific embodiments, a B7-H2 derivative inhibits or reduces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative. In specific embodiments, a B7-H2 derivative: (i) inhibits or reduces one or more of the signal transduction pathways induced by the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS and CTLA-4 in the absence of the B7-H2 derivative; and (ii) does not inhibit or reduce, or inhibits or reduces one or more of the signal transduction pathways induced by the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of B7-H2 to CD28 in the absence of the B7-H2 derivative.

In another embodiment, a B7-H2 derivative modulates the interactions between B7-H2 and ICOS and B7-H2 and CTLA-4. In another embodiment, a B7-H2 derivative inhibits or reduces the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CTLA-4 in the absence of the B7-H2 derivative. In another embodiment, a B7-H2 derivative: (i) inhibits or reduces the binding of B7-H2 to ICOS and CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS and CTLA-4 in the absence of the B7-H2 derivative, and (ii) does not inhibit or reduce, or inhibits or reduces the binding of B7-H2 to CD28 by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of B7-H2 to CD28 in the absence of the B7-H2 derivative.

In specific embodiments, a B7-H2 derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native B7-H2 polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native B7-H2 polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native B7-H2 polypeptide; (d) a polypeptide encoded by nucleic acids can hybridize under high, moderate or typical stringency hybridization conditions to nucleic acids encoding a native B7-H2 polypeptide; (e) a polypeptide encoded by a nucleic acid sequence that can hybridize under high, moderate or typical stringency hybridization conditions to a nucleic acid sequence encoding a fragment of a native B7-H2 polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids, or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native B7-H2 polypeptide. B7-H2 derivatives also include a polypeptide that comprises the amino acid sequence of a naturally occurring mature form of a mammalian B7-H2 polypeptide and a heterologous signal peptide amino acid sequence.

In a specific embodiment, a B7-H2 derivative is a derivative of a native human B7-H2 polypeptide. In another embodiment, a B7-H2 derivative is a derivative of an immature or precursor form of naturally occurring human B7-H2 polypeptide. In another embodiment, a B7-H2 derivative is a derivative of a mature form of naturally occurring human B7-H2 polypeptide. In one embodiment, a B7-H2 derivative is isolated or purified.

In another embodiment, a B7-H2 derivative comprises (or consists) of the amino acid sequence of native B7-H2 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, 25 to 75 mutations (e.g., amino acid substitutions, insertions and/or deletions). In certain embodiments, a B7-H2 derivative comprises one or more mutations that increase the affinity of B7-H2 for one or more of the following receptors: ICOS, CD28 or CTLA-4. In a specific embodiment, a B7-H2 derivative comprises one or more mutations that selectively increase the affinity of B7-H2 for ICOS. In another specific embodiment, a B7-H2 derivative comprises one or more mutations that selectively increase the affinity of B7-H2 for CD28. In another specific embodiment, a B7-H2 derivative comprises one or more mutations that selectively increase the affinity of B7-H2 for CTLA-4. Mutations can be introduced at specific positions with native B7-H2 using, e.g., site-directed mutagenesis techniques and/or PCR-mediated mutagenesis techniques. Mutations can also be introduced randomly along all or part of the coding sequence using, e.g., saturation mutagenesis techniques.

In some embodiments, a B7-H2 derivative comprises one or more mutations that decrease the affinity of B7-H2 for one or more of the following receptors: ICOS, CD28, or CTLA-4. In a specific embodiment, a B7-H2 derivative comprises one or more mutations that selectively decrease the affinity of B7-H2 for ICOS. In another specific embodiment, a B7-H2 derivative comprises one or more mutations that selectively decrease the affinity of B7-H2 for CD28. In another specific embodiment, a B7-H2 derivative comprises one or more mutations that selectively decrease the affinity of B7-H2 for CTLA-4.

In another embodiment, a B7-H2 derivative comprises (or consists) of the amino acid sequence of native B7-H2 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues. A conservative amino acid substitution is one in which the amino acid residue is replaced with an amino acid residue having a side chain with a similar charge.

In specific embodiments, a B7-H2 derivative comprises an amino acid substitution at either position 116, position 122 or both. In some embodiments, a B7-H2 derivative comprises an amino acid substitution at positions 116 to 122 and/or 53. In accordance with such embodiments, the B7-H2 derivative retains the ability to bind to ICOS but does not bind to CD28 or CTLA-4. In other embodiments, a B7-H2 derivative does not comprise an amino acid substitution at either position 116, position 122 or both. In some embodiments, a B7-H2 derivative does not comprise an amino acid substitution at positions 116 to 122 and/or 53. In a particular embodiment, the B7-H2 derivative is the B7-H2 (L116A) mutant or B7-H2 (F122A) mutant described in Examples 6 and 7, infra. In certain embodiments, the B7-H2 derivative is not the B7-H2 (L116A) mutant or B7-H2 (F122A) mutant described in Examples 6 and 7, infra.

In specific embodiments, a B7-H2 derivative comprises an amino acid substitution at either position 51, position 53 or both. In other embodiments, a B7-H2 derivative does not comprise an amino acid substitution at either position 51, position 53 or both. In a particular embodiment, the B7-H2 derivative is the B7-H2 (Y51A) mutant or B7-H2 (Y53A) mutant described in Examples 6 and 7, infra. In certain embodiments, the B7-H2 derivative is not the B7-H2 (Y51A) mutant or B7-H2 (Y53A) mutant described in Examples 6 and 7, infra In certain embodiments, a B7-H2 derivative comprises an amino acid substitution at two, three or all of the following positions: position 51, position 53, position 116, or position 122. In other embodiments, a B7-H2 derivative does not comprise an amino acid substitution at two, three or all of the following positions: position 51, position 53, position 116, or position 122. In certain embodiments, a B7-H2 derivative comprises an amino acid substitution at one, two, or three or all of positions: 51, 53, and 116 to 122. In other embodiments, a B7-H2 derivative does not comprise an amino acid substitution at one, two, or three or all of positions: 51, 53, and 116 to 122.

The data discussed in Example 7 infra indicates that the Ig-like V-type domain of B7-H2 is relevant to B7-H2 binding to ICOS, CD28 and CTLA-4. Accordingly, in specific embodiments, a B7-H2 derivative comprises 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions) in the Ig-like V-type domain of B7-H2. In certain embodiments, a B7-H2 derivative comprises (or consists of) native B7-H2 or a fragment thereof containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions) in the Ig-like V-type domain. In some embodiments, a B7-H2 derivative comprises (or consists of) the extracellular domain of native B7-H2 containing 1, 2, 3, 4, 5, 6, 7, 8, 9, 10, 12, 15, 20 or more mutations (e.g., amino acid substitutions, deletions, and/or additions) in the Ig-like V-type domain.

In another embodiment, a B7-H2 derivative comprises a fragment of native B7-H2. In certain embodiments, a B7-H72 derivative comprises (or consists of) amino acid residues 19 to 300, 19 to 300, 19 to 275, 19 to 256, 19 to 250, 19 to 225, 19 to 200, 19 to 175, 19 to 150, 19 to 129, 19 to 125, 19 to 100, 19 to 95, 19 to 75, 19 to 70, 19 to 65, 19 to 60, 19 to 50, 15 to 30 or 5 to 25, or 141 to 227 of native B7-H2 of the sequence found at Accession No. O75144-1 (UniParc).

In one embodiment, a B7-H2 derivative is a soluble form of B7-H2. In a specific embodiment, a B7-H2 derivative comprises (or consists of) the extracellular domain of native B7-H2, or the extracellular domain of native B7-H2 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions). In a specific embodiment, a B7-H2 derivative comprises (or consists of) amino acid residues 19 to 256 of the sequence found at Accession No. O75144-1 (UniParc). In another embodiment, a B7-H2 derivative comprises (or consists of) a fragment of the extracellular domain of native B7-H2, or a fragment of the extracellular domain of native B7-H2 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions). In specific embodiments, a B7-H2 derivative comprises (or consists of) at least 25, 50, 75, 100, 125, 150, 175, 200, 225, or 240 amino acids of the extracellular domain of native B7-H2. In certain embodiments, a B7-H2 derivative comprises (or consists of) amino acid residues 19 to 240, 19 to 225, 19 to 200, 19 to 175, 19 to 150, 19 to 125, 19 to 100, 19 to 75, 19 to 50, or 19 to 25 of native B7-H2. In specific embodiments, a B7-H2 derivative comprises (or consists of) amino acid residues 19 to 240, 19 to 225, 19 to 200, 19 to 175, 19 to 150, 19 to 125, 19 to 100, 19 to 75, 19 to 50, or 19 to 25 of the sequence found at Accession No. O75144-1 (UniParc).

In another embodiment, a B7-H2 derivative comprises (or consists of) the Ig-like V-type domain of native B7-H2. In a specific embodiment, a B7-H2 derivative comprises (or consists of) amino acid residues 19 to 129 of the sequence found at Accession No. O75144-1 (UniParc). In another embodiment, a B7-H2 derivative comprises (or consists of) the Ig-like C-2 type domain of native B7-H2. In a specific embodiment, a B7-H2 derivative comprises (or consists of) amino acid residues 141 to 227 of the sequence found at Accession No. O75144-1 (UniParc). In another embodiment, a B7-H2 derivative comprises (or consists of) the Ig-like V-type and Ig-like C-2 type domains of native B7-H7. In a specific embodiment, a B7-H2 derivative comprises (or consists of) amino acid residues 19 to 141 of the sequence found at Accession No. O75144-1 (UniParc).

In another embodiment, a B7-H2 derivative comprises (or consists of) the extracellular and cytoplasmic domains of native B7-H2 or fragments thereof. In another embodiment, a B7-H2 derivative comprises (or consists of) the extracellular and cytoplasmic domains of native B7-H2 or fragments thereof containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In another embodiment, a B7-H2 derivative comprises (or consists) a fragment of the extracellular domain of native B7-H2 and the cytoplasmic domain of native B7-H2 or a fragment thereof. In another embodiment, a B7-H2 derivative comprises (or consists of) the extracellular domain of native B7-H2 and a fragment of the cytoplasmic domain of native B7-H2. In another embodiment, a B7-H2 derivative lacks the transmembrane domain of native B7-H2 or a fragment thereof. In certain embodiments, a B7-H2 derivative comprises a heterologous transmembrane domain in place of the transmembrane domain of native B7-H2. In another embodiment, a B7-H2 derivative comprises (or consists of) the extracellular domain of native B7-H2 or a fragment thereof and the transmembrane domain of native B7-H2 or a fragment thereof.

In another embodiment, a B7-H2 derivative comprises (or consists of) the IgV region of native human B7-H2. In a specific embodiment, a B7-H2 derivative comprises (or consists of) the human IgV region described in Example 7, infra. In another embodiment, a B7-H2 derivative comprises (or consists of) the cysteine-cysteine region of native B7-H2.

The biological activity of B7-H2 derivatives can be assessed using techniques known to those skilled in the art, or described herein. For example, the ability of a B7-H2 derivative to bind to one or more receptors may be assessed using techniques described herein, or known to those skilled in the art. More specifically, the ability of a B7-H2 derivative to bind to one or more of the following receptors—ICOS, CD28 or CTLA-4—may be assessed. In addition, the ability of a B7-H2 derivative to bind to one or more receptors and induce one or more of the signal transduction pathways induced by native B7-H2 binding to the one or more receptors may be assessed using techniques described herein, or known to those skilled in the art. More specifically, the ability of a B7-H2 derivative to bind to one or more of the following receptors—ICOS, CD28 or CTLA-4—and induce one or more of the signal transduction pathways induced by native B7-H2 binding to native ICOS, native CD28, native CTLA-4 may be assessed.

In certain embodiments, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to a native receptor of B7-H2 (e.g., ICOS, CD28 or CTLA-4), as measured by assays/techniques well known in the art, e.g., ELISA, Biacore, or co-immunoprecipitation. In a specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to ICOS. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either CD28, CTLA-4 or both. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either CD28, ICOS or both. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either ICOS, CTLA-4, or both. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28, ICOS and CTLA-4.

In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to ICOS, but the B7-H2 derivative does not retain the function of a native B7-H2 polypeptide to bind to either CD28, CTLA-4 or both, or retains less than 20%, 15%, 10%, 5%, or 2%, or in the range of between 2% to 20%, 2% to 15%, 2% to 10% or 2% to 5% of the function of a native B7-H2 polypeptide to bind to either CD28, CTLA-4 or both. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28, but the B7-H2 derivative does not retain the function of a native B7-H2 polypeptide to bind to either ICOS, CTLA-4 or both, or retains less than 20%, 15%, 10%, 5%, or 2%, or in the range of between 2% to 20%, 2% to 15%, 2% to 10% or 2% to 5% of the function of a native B7-H2 polypeptide to bind to either ICOS, CTLA-4 or both. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28 and CTLA-4, but the B7-H2 derivative does not retain the function of a native B7-H2 polypeptide to bind to ICOS, or retains less than 20%, 15%, 10%, 5%, or 2%, or in the range of between 2% to 20%, 2% to 15%, 2% to 10% or 2% to 5% of the function of a native B7-H2 polypeptide to bind to ICOS. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28 and ICOS, but the B7-H2 derivative does not retain the function of a native B7-H2 polypeptide to bind to CTLA-4, or retains less than 20%, 15%, 10%, 5%, or 2%, or in the range of between 2% to 20%, 2% to 15%, 2% to 10% or 2% to 5% of the function of a native mammalian B7-H2 polypeptide to bind to CTLA-4. In another embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of native B7-H2 polypeptide to bind to ICOS and CTLA-4, but the B7-H2 derivative does not retain the function of a native B7-H2 polypeptide to bind to CD28, or retains less than 20%, 15%, 10%, 5%, or 2%, or in the range of between 2% to 20%, 2% to 15%, 2% to 10% or 2% to 5% of the function of a native mammalian B7-H2 polypeptide to bind to CD28.

In certain other embodiments, a B7-H2 derivative retains less than 20%, 15%, 10%, 5% or 2%, or in the range of between 2% to 20%, 2% to 15%, 2% to 10%, or 2% to 5% of the function of a native B7-H2 polypeptide to bind to a native receptor of B7-H2 (e.g., ICOS, CD28 or CTLA-4), as measured by assays/techniques well known in the art, e.g., ELISA, Biacore, or co-immunoprecipitation. In a specific embodiment, a B7-H2 derivative retains less than 20%, 15%, 10%, 5% or 2%, or in the range of between 2% to 20%, 2% to 15%, 2% to 10%, or 2% to 5% of the function of a native B7-H2 polypeptide to bind to ICOS. In another specific embodiment, a B7-H2 derivative retains less than 20%, 15%, 10%, 5% or 2%, or in the range of between 2% to 20%, 2% to 15%, 2% to 10%, or 2% to 5% of the function of a native B7-H2 polypeptide to bind to either CD28, CTLA-4 or both. In another specific embodiment, a B7-H2 derivative retains less than 20%, 15%, 10%, 5% or 2%, or in the range of between 2% to 20%, 2% to 15%, 2% to 10%, or 2% to 5% of the function of a native B7-H2 polypeptide to bind to either CD28, ICOS or both. In another embodiment, a B7-H2 derivative retains less than 20%, 15%, 10%, 5%, or 2%, or in the range of between 2% to 20%, 2% to 15%, 2% to 10% or 2% to 5% of the function of a native mammalian B7-H2 polypeptide to bind to ICOS and CTLA-4. In another specific embodiment, a B7-H2 derivative retains less than 20%, 15%, 10%, 5% or 2%, or in the range of between 2% to 20%, 2% to 15%, 2% to 10%, or 2% to 5% of the function of a native B7-H2 polypeptide to bind to CD28, ICOS and CTLA-4.

In certain embodiments, a B7-H2 derivative with a higher affinity for a native receptor of B7-H2 than native B7-H2 binds to the same receptor, as measured by well-known assays/techniques. In one embodiment, a B7-H2 derivative with a 25%, 50%, 75%, 80%, 85%, 90%, 95%, 25% to 50%, 25% to 75%, 50% to 75%, 50% to 95%, or 75% to 95% higher affinity for a native receptor of B7-H2 than the native B7-H2 binds to the same receptor, as measured by well-known assays/techniques. In another embodiment, a B7-H2 derivative with 0.5 logs, 1 log, 1.5 logs, 2 logs, 2.5 logs, or 3 logs higher affinity for a native receptor of B7-H2 than the native B7-H2 binds to the same receptor, as measured by well-known assays/techniques.

In certain embodiments, a B7-H2 derivative with a lower affinity for a native receptor of B7-H2 than native B7-H2 binds to the same receptor, as measured by well-known assays/techniques. In one embodiment, a B7-H2 derivative with a 25%, 50%, 75%, 80%, 85%, 90%, 95%, 25% to 50%, 25% to 75%, 50% to 75%, 50% to 95%, or 75% to 95% lower affinity for a native receptor of B7-H2 than the native B7-H2 binds to the same receptor, as measured by well-known assays/techniques. In another embodiment, a B7-H2 derivative with 0.5 logs, 1 log, 1.5 logs, 2 logs, 2.5 logs, or 3 logs lower affinity for a native receptor of B7-H2 than the native B7-H2 binds to the same receptor, as measured by well-known assays/techniques.

In some embodiments, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native B7-H2 polypeptide binds to a native receptor of B7-H2 (e.g., ICOS, CD28 or CTLA-4), as measured by assays well-known in the art. The one or more signal transduction pathways induced by the binding of a native receptor of B7-H2 to a B7-H2 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In a specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to ICOS. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to CD28. In another specific embodiment, a B7-H2 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to CTLA-4.

In some other embodiments, a B7-H2 derivative retains less than 20%, 15%, 10%, 5% or 2%, or in the range of between 2% to 20%, 2% to 15%, 2% to 10%, or 2% to 5% of one or more of the ability to activate or induce the signal transduction pathways induced when a native B7-H2 polypeptide binds to a receptor of B7-H2 (e.g., ICOS, CD28 or CTLA-4), as measured by assays well-known in the art. In a specific embodiment, a B7-H2 derivative retains less than 20%, 15%, 10%, 5% or 2%, or in the range of between 2% to 20%, 2% to 15%, 2% to 10%, or 2% to 5% of the ability to active or induce one or more of the signal transduction pathways induced by the binding of a native B7-H2 polypeptide to ICOS. In another specific embodiment, a B7-H2 derivative retains less than 20%, 15%, 10%, 5% or 2%, or in the range of between 2% to 20%, 2% to 15%, 2% to 10%, or 2% to 5% of one or more of the signal transduction pathways induced by the binding of a native B7-H2 polypeptide to either CD28, CTLA-4 or both. In another specific embodiment, a B7-H2 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to either CD28, ICOS or both. In another specific embodiment, a B7-H2 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to ICOS and CTLA-4. In another specific embodiment, a B7-H2 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to CD28, ICOS, and CTLA-4.

5.3.2.2 ICOS Polypeptides & Derivatives

In one aspect, a Therapeutic Agent is an ICOS polypeptide. In a specific embodiment, such a Therapeutic Agent modulates one or more of the signal transduction pathways induced by B7-H2 binding to ICOS. In another specific embodiment, such a Therapeutic Agent modulates the B7-H2 polypeptide and ICOS polypeptide interaction. In certain embodiments, such Therapeutic Agents are Immunostimulatory Therapeutic Agents. In other embodiments, such Therapeutic Agents are Inhibitory Therapeutic Agents.

In another aspect, a Therapeutic Agent is an ICOS derivative. In certain embodiments, the B7-H2 derivative is an Immunostimulating Therapeutic Agent. In other embodiments, the B7-H2 derivative is an Inhibitory Therapeutic Agent.

In a specific embodiment, an ICOS derivative modulates one or more of the signal transduction pathways induced by B7-H2 binding to ICOS. In certain embodiments, an ICOS derivative selectively modulates one or more signal transduction pathways induced by B7-H2 binding to ICOS. In certain embodiments, an ICOS derivative selectively activates or enhances one or more of the signal transduction pathways induced by the binding of B7-H2 to ICOS. In specific embodiments, an ICOS derivative activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative. In specific embodiments, an ICOS derivative: (i) activates or enhances one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative; and (ii) does not activate or enhance, or activates or enhances one or more of the signal transduction pathways induced by the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of ICOS to such one or more other ligands in the absence of the derivative.

In certain embodiments, an ICOS derivative binds to its native ligand (e.g., native B7-H2) and induces a higher level of activity than native ICOS binding to the native ligand as assessed by, e.g., the activation or induction of one or more signal transduction molecules. In specific embodiments, an ICOS derivative binds to native B7-H2 and induces a higher level of activity than native ICOS binding to native B7-H2 as assessed by, e.g., the activation or induction of one or more signal transduction molecules. In some embodiments, an ICOS derivative binds to B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native ICOS binding to native B7-H2 as assessed by, e.g., the activation or induction of one or more signal transduction molecules.

In some embodiments, an ICOS derivative selectively inhibits or reduces one or more of the signal transduction pathways induced by the binding of B7-H2 to ICOS. In specific embodiments, an ICOS derivative inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative. In specific embodiments, an ICOS derivative: (i) inhibits or reduces one or more of the signal transduction pathways induced by the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to ICOS in the absence of the derivative; and (ii) does not inhibit or reduce, or inhibits or reduces one or more of the signal transduction pathways induced by the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of ICOS to such one or more other ligands in the absence of the derivative.

In another embodiment, an ICOS derivative modulates the B7-H2 polypeptide and ICOS polypeptide interaction. In certain embodiments, the ICOS derivative selectively modulates the B7-H2 and ICOS interaction. In another embodiment, an ICOS derivative inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the derivative. In another embodiment, an ICOS derivative: (i) inhibits or reduces the binding of B7-H2 to ICOS by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to ICOS in the absence of the derivative, and (ii) does not inhibit or reduce, or inhibits or reduces the binding of ICOS to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of ICOS to such one or more other ligands in the absence of the derivative.

In certain embodiments, an ICOS derivative binds to a native B7-H2 with a higher affinity than native ICOS binds to a native ligand of ICOS (e.g., native B7-H2), as measured by assays/techniques well known in the art, e.g., ELISA, Biacore, or co-immunoprecipitation.

In one embodiment, an ICOS derivative binds to a native ligand of ICOS (e.g., native B7-H2) with a 50%, 75%, 80%, 85%, 90%, 95%, or 98%, or 25% to 50%, 25% to 75%, 50% to 95%, or 75% to 95% higher affinity than the native ICOS binds to the native ligand of ICOS (e.g., native B7-H2). In a specific embodiment, an ICOS derivative binds to a native ligand of ICOS (e.g., native B7-H2) with 0.5 logs, 1 log, 1.5 logs, 2 logs, 2.5 logs, or 3 logs higher affinity than the native ICOS binds to the native ligand of ICOS (e.g., native B7-H2), as measured by assays/techniques well known in the art, e.g., ELISA, Biacore, or co-immunoprecipitation.

In certain embodiments, an ICOS derivative binds to native B7-H2 with a lower affinity than the native ICOS binds to a native ligand of ICOS (e.g., native B7-H2), as measured by well-known assays/techniques. In one embodiment, an ICOS derivative binds to a native ligand of ICOS (e.g., native B7-H2) with 25%, 50%, 75%, 80%, 85%, 90%, 95%, 25% to 50%, 25% to 75%, 50% to 75%, 50% to 95%, or 75% to 95% lower affinity than the native ICOS binds to the native ligand of ICOS (e.g., native B7-H2), as measured by well-known assays/techniques. In another embodiment, an ICOS derivative binds to a native B 7-H2 with 0.5 logs, 1 log, 1.5 logs, 2 logs, 2.5 logs, or 3 logs lower affinity than the native ICOS binds to the native ligand of ICOS (e.g., native B7-H2), as measured by well-known assays/techniques.

In specific embodiments, an ICOS derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native ICOS polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native ICOS polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native ICOS polypeptide; (d) a polypeptide encoded by nucleic acids can hybridize under high, moderate or typical stringency hybridization conditions to nucleic acids encoding a native ICOS polypeptide; (e) a polypeptide encoded by a nucleic acid sequence that can hybridize under high, moderate or typical stringency hybridization conditions to a nucleic acid sequence encoding a fragment of a native ICOS polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids, or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native ICOS polypeptide. ICOS derivatives also include a polypeptide that comprises the amino acid sequence of a naturally occurring mature form of a native ICOS polypeptide and a heterologous signal peptide amino acid sequence. In a specific embodiment, an ICOS derivative is a derivative of a native human ICOS polypeptide. In another embodiment, an ICOS derivative is a derivative of an immature or precursor form of naturally occurring human ICOS polypeptide. In another embodiment, an ICOS derivative is a derivative of a mature form of naturally occurring human ICOS polypeptide. In one embodiment, an ICOS derivative is isolated or purified.

In another embodiment, an ICOS derivative comprises (or consists) of the amino acid sequence of native ICOS with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, 25 to 75 mutations (e.g., amino acid substitutions, insertions and/or deletions). In certain embodiments, an ICOS derivative comprises one or more mutations that increase the affinity of ICOS for B7-H2 (in particular, native B7-H2). Mutations can be introduced at specific positions with native ICOS using, e.g., site-directed mutagenesis techniques and/or PCR-mediated mutagenesis techniques. In other embodiments, an ICOS derivative comprises one or more mutations that decrease the affinity of ICOS for B7-H2 (in particular, native B7-H2) Mutations can also be introduced randomly along all or part of the coding sequence using, e.g., saturation mutagenesis techniques.

In another embodiment, an ICOS derivative comprises (or consists) of the amino acid sequence of native ICOS with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues.

In another embodiment, an ICOS derivative comprises a fragment of native ICOS. In certain embodiments, an ICOS derivative comprises (or consists of) amino acid residues 21 to 175, 21 to 150, 21 to 125, 21 to 100, 21 to 95, 21 to 75, 21 to 70, 21 to 65, 21 to 60, 21 to 50, 5 to 15, or 5 to 25 of native ICOS of the sequence found at Accession No. Q9Y6W8-1 (UniParc).

In one embodiment, an ICOS derivative is a soluble form of ICOS. In a specific embodiment, an ICOS derivative comprises (or consists of) the extracellular domain of native ICOS, or the extracellular domain of native ICOS containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In a specific embodiment, an ICOS derivative comprises (or consists of) amino acid residues 21 to 150 or 21 to 140 of the sequence found at Accession No. Q9Y6W8-1 (UniParc). In another embodiment, an ICOS derivative comprises (or consists of) a fragment of the extracellular domain of native ICOS, or a fragment of the extracellular domain of native ICOS containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions). In specific embodiments, an ICOS derivative comprises (or consists of) at least 25, 50, 75, 100, 125, or 130 amino acids of the extracellular domain of native ICOS. In certain embodiments, an ICOS derivative comprises (or consists of) amino acid residues 23 to 145, 23 to 140, 23 to 130, 23 to 125, 23 to 100, 23 to 95, 23 to 75, 23 to 70, 23 to 65, 23 to 60, or 23 to 50 of native ICOS. In specific embodiments, an ICOS derivative comprises (or consists of) 21 to 175, 21 to 150, 21 to 125, 21 to 100, 21 to 95, 21 to 75, 21 to 70, 21 to 65, 21 to 60, or 21 to 50 amino acid residues of the sequence found at Accession No. Q9Y6W8-1 (UniParc). In another embodiment, an ICOS derivative comprises (or consists of) the Ig-like domain of native ICOS. In a specific embodiment, an ICOS derivative comprises (or consists of) amino acid residues 30 to 132 or 30 to 140 of the sequence found at Accession No. Q9Y6W8-1 (UniParc).

In another embodiment, an ICOS derivative comprises (or consists of) the extracellular and cytoplasmic domains of native ICOS or fragments thereof. In another embodiment, an ICOS derivative comprises (or consists of) the extracellular and cytoplasmic domains of native ICOS or fragments thereof containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In another embodiment, an ICOS derivative comprises (or consists) a fragment of the extracellular domain of native ICOS and the cytoplasmic domain of native ICOS or a fragment thereof. In another embodiment, an ICOS derivative comprises (or consists of) the extracellular domain of native ICOS and a fragment of the cytoplasmic domain of native ICOS. In another embodiment, an ICOS derivative lacks the transmembrane domain of native ICOS or a fragment thereof. In certain embodiments, an ICOS derivative comprises a heterologous transmembrane domain in place of the transmembrane domain of native ICOS. In another embodiment, an ICOS derivative comprises (or consists of) the extracellular domain of native ICOS or a fragment thereof and the transmembrane domain of native ICOS or a fragment thereof.

The biological activity of ICOS derivatives can be assessed using techniques known to those skilled in the art, or described herein. For example, the ability of an ICOS derivative to bind to one or more ligands may be assessed using techniques described herein, or known to those skilled in the art. More specifically, the ability of an ICOS derivative to bind to B7-H2 may be assessed. In addition, the ability of an ICOS derivative to bind to one or more ligands and induce one or more of the signal transduction pathways induced by native ICOS binding to the one or more ligands may be assessed using techniques described herein, or known to those skilled in the art. More specifically, the ability of an ICOS derivative to bind to B7-H2 and induce one or more of the signal transduction pathways induced by native B7-H2 binding to native ICOS may be assessed.

In certain embodiments, an ICOS derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native ICOS polypeptide to bind to a native ligand of ICOS (e.g., B7-H2), as measured by assays/techniques well known in the art, e.g., ELISA, Biacore, or co-immunoprecipitation. In a specific embodiment, an ICOS derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native ICOS polypeptide to bind to B7-H2.

In certain other embodiments, an ICOS derivative retains less than 20%, 15%, 10%, 5% or 2%, or in the range of between 2% to 20%, 2% to 15%, 2% to 10%, or 2% to 5% of the function of a native ICOS polypeptide to bind to a native ligand of ICOS (e.g., B7-H2), as measured by assays/techniques well known in the art, e.g., ELISA, Biacore, or co-immunoprecipitation. In a specific embodiment, an ICOS derivative retains less than 20%, 15%, 10%, 5% or 2%, or in the range of between 2% to 20%, 2% to 15%, 2% to 10%, or 2% to 5% of the function of a native ICOS polypeptide to bind to B7-H2.

In some embodiments, an ICOS derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of ICOS (e.g., B7-H2) binds to an ICOS polypeptide, as measured by assays well-known in the art. The one or more signal transduction pathways induced by the binding of a native ligand of ICOS to an ICOS polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays. In a specific embodiment, an ICOS derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native ICOS polypeptide.

In some other embodiments, an ICOS derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand (e.g., B7-H2) binds to an ICOS polypeptide, as measured by assays well-known in the art. In a specific embodiment, an ICOS derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H2 to a native ICOS polypeptide.

5.3.2.3 CD28 Polypeptides & Derivatives

In one aspect, a Therapeutic Agent is a CD28 polypeptide. In a specific embodiment, such a Therapeutic Agent modulates one or more of the signal transduction pathways induced by B7-H2 binding to CD28. In another specific embodiment, such a Therapeutic Agent modulates the B7-H2 polypeptide and CD28 polypeptide interaction. In certain embodiments, such Therapeutic Agents are Immunostimulating Therapeutic Agents. In other embodiments, such Therapeutic Agents are Inhibitory Therapeutic Agents.

In another aspect, a Therapeutic Agent is a CD28 derivative. In certain embodiments, the B7-H2 derivative is an Immunostimulating Therapeutic Agent. In other embodiments, the B7-H2 derivative is an Inhibitory Therapeutic Agent.

In a specific embodiment, a CD28 derivative modulates one or more of the signal transduction pathways induced by B7-H2 binding to CD28. In certain embodiments, a CD28 derivative selectively modulates one or more signal transduction pathways induced by B7-H2 binding to CD28. In certain embodiments, a CD28 derivative activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative. In specific embodiments, a CD28 derivative: (i) activates or enhances one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative; and (ii) does not activate or enhance, or activates or enhances one or more of the signal transduction pathways induced by the binding of CD28 to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CD28 to such one or more other ligands in the absence of the derivative.

In certain embodiments, a CD28 derivative binds to its native ligand (e.g., native B7-H2) and induces a higher level of activity than native C28 binding to the native ligand as assessed by, e.g., the activation or induction of one or more signal transduction molecules. In specific embodiments, a CD28 derivative binds to B7-H2 and induces a higher level of activity than native CD28 binding to native B7-H2 as assessed by, e.g., the activation or induction of one or more signal transduction molecules. In some embodiments, a CD28 derivative binds to native B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native CD28 binding to native B7-H2 as assessed by, e.g., the activation or induction of one or more signal transduction molecules.

In some embodiments, a CD28 derivative selectively inhibits or reduces one or more of the signal transduction pathways induced by the binding of B7-H2 to CD28. In specific embodiments, a CD28 derivative inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative. In specific embodiments, a CD28 derivative: (i) inhibits or reduces one or more of the signal transduction pathways induced by the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CD28 in the absence of the derivative; and (ii) does not inhibit or reduce, or inhibits or reduces one or more of the signal transduction pathways induced by the binding of CD28 to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CD28 to such one or more other ligands in the absence of the derivative.

In another embodiment, a CD28 derivative modulates the B7-H2 polypeptide and CD28 polypeptide interaction. In certain embodiments, a CD28 derivative selectively modulates the B7-H2 and CD28 interaction. In a specific embodiment, a CD28 derivative inhibits or reduces the binding of B7-H2 to CD28. In another embodiment, a CD28 derivative inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the derivative. In another embodiment, a CD28 derivative: (i) inhibits or reduces the binding of B7-H2 to CD28 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CD28 in the absence of the derivative, and (ii) does not inhibit or reduce, or inhibits or reduces the binding of CD28 to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of CD28 to such one or more other ligands in the absence of the derivative.

In certain embodiments, a CD28 derivative binds to a native ligand of CD28 (e.g., B7-H2) with a higher affinity than native CD28 binds to the native ligand, as measured by assays/techniques well known in the art, e.g., ELISA, Biacore, or co-immunoprecipitation. In one embodiment, a CD28 derivative binds to a native ligand of CD28 (e.g., B7-H2) with a 50%, 75%, 80%, 85%, 90%, 95%, or 98%, or 25% to 50%, 25% to 75%, 50% to 95%, or 75% to 95% higher affinity than the native CD28 binds to the native ligand, as measured by well known assays/techniques. In a specific embodiment, a CD28 derivative binds to a native ligand of CD28 (e.g., B7-H2) with 0.5 logs, 1 log, 1.5 logs, 2 logs, 2.5 logs, or 3 logs higher affinity than the native CD28 binds to the native ligand, as measured by assays/techniques well known in the art, e.g., ELISA, Biacore, or co-immunoprecipitation.

In certain embodiments, a CD28 derivative binds to native ligand of CD28 (e.g., B7-H2) with a lower affinity than the native CD28 binds to the native ligand of CD28 (e.g., B7-H2), as measured by well-known assays/techniques. In one embodiment, a CD28 derivative binds to a native ligand of CD28 (e.g., B7-H2) with 25%, 50%, 75%, 80%, 85%, 90%, 95%, 25% to 50%, 25% to 75%, 50% to 75%, 50% to 95%, or 75% to 95% lower affinity than the native CD28 binds to the native ligand of CD28 (e.g., B7-H2), as measured by well-known assays/techniques. In another embodiment, a CD28 derivative binds to a native ligand of CD28 (e.g., B7-H2) with 0.5 logs, 1 log, 1.5 logs, 2 logs, 2.5 logs, or 3 logs lower affinity than the native CD28 binds to the native ligand of CD28 (e.g., B7-H2), as measured by well-known assays/techniques.

In specific embodiments, a CD28 derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native CD28 polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native CD28 polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native CD28 polypeptide; (d) a polypeptide encoded by nucleic acids can hybridize under high, moderate or typical stringency hybridization conditions to nucleic acids encoding a native CD28 polypeptide; (e) a polypeptide encoded by a nucleic acid sequence that can hybridize under high, moderate or typical stringency hybridization conditions to a nucleic acid sequence encoding a fragment of a native CD28 polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids, or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native CD28 polypeptide. CD28 derivatives also include a polypeptide that comprises the amino acid sequence of a naturally occurring mature form of a native C28 polypeptide and a heterologous signal peptide amino acid sequence. In a specific embodiment, a CD28 derivative is a derivative of a native human CD28 polypeptide. In another embodiment, a CD28 derivative is a derivative of an immature or precursor form of naturally occurring human CD28 polypeptide. In another embodiment, a CD28 derivative is a derivative of a mature form of naturally occurring human CD28 polypeptide. In one embodiment, a CD28 derivative is isolated or purified.

In another embodiment, a CD28 derivative comprises (or consists) of the amino acid sequence of native CD28 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, 25 to 75 mutations (e.g., amino acid substitutions, insertions and/or deletions). In certain embodiments, a CD28 derivative comprises one or more mutations that increase the affinity of CD28 for B7-H2 (in particular, native B7-H2). In other embodiments, a CD28 derivative comprises one or more mutations that decrease the affinity of CD28 for B7-H2 (in particular, native B7-H2). Mutations can be introduced at specific positions with native CD28 using, e.g., site-directed mutagenesis techniques and/or PCR-mediated mutagenesis techniques. Mutations can also be introduced randomly along all or part of the coding sequence using, e.g., saturation mutagenesis techniques.

In another embodiment, a CD28 derivative comprises (or consists) of the amino acid sequence of native CD28 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues.

In another embodiment, a CD28 derivative comprises a fragment of native CD28. In certain embodiments, a CD28 derivative comprises (or consists of) amino acid residues 19 to 200, 175, 19 to 150, 19 to 125, 19 to 100, 19 to 95, 19 to 75, 19 to 70, 19 to 65, 19 to 60, 19 to 50, 5 to 15, or 5 to 25 of native CD28 of the sequence found at Accession No. P10747-1 (UniParc).

In one embodiment, a CD28 derivative is a soluble form of CD28. In a specific embodiment, a CD28 derivative comprises (or consists of) the extracellular domain of native CD28, or the extracellular domain of native CD28 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In a specific embodiment, a CD28 derivative comprises (or consists of) amino acid residues 19 to 152 of the sequence found at Accession No. P10747-1 (UniParc). In another embodiment, a CD28 derivative comprises (or consists of) a fragment of the extracellular domain of native CD28, or a fragment of the extracellular domain of native CD28 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions). In specific embodiments, a CD28 derivative comprises (or consists of) at least 25, 50, 75, 100, or 125 amino acids of the extracellular domain of native CD28. In certain embodiments, a CD28 derivative comprises (or consists of) amino acid residues 19 to 200, 175, 19 to 150, 19 to 125, 19 to 100, 19 to 95, 19 to 75, 19 to 70, 19 to 65, 19 to 60, or 19 to 50 of native CD28. In specific embodiments, a CD28 derivative comprises (or consists of) 19 to 200, 175, 19 to 150, 19 to 125, 19 to 100, 19 to 95, 19 to 75, 19 to 70, 19 to 65, 19 to 60, or 19 to 50 amino acid residues of the sequence found at Accession No. P10747-1 (UniParc). In another embodiment, a CD28 derivative comprises (or consists of) the Ig-like domain of native CD28. In a specific embodiment, a CD28 derivative comprises (or consists of) amino acid residues 28 to 137 of the sequence found at Accession No. P10747-1 (UniParc).

In another embodiment, a CD28 derivative comprises (or consists of) the extracellular and cytoplasmic domains of native CD28 or fragments thereof. In another embodiment, a CD28 derivative comprises (or consists of) the extracellular and cytoplasmic domains of native CD28 or fragments thereof containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In another embodiment, a CD28 derivative comprises (or consists) a fragment of the extracellular domain of native CD28 and the cytoplasmic domain of native CD28 or a fragment thereof. In another embodiment, a CD28 derivative comprises (or consists of) the extracellular domain of native CD28 and a fragment of the cytoplasmic domain of native CD28. In another embodiment, a CD28 derivative lacks the transmembrane domain of native CD28 or a fragment thereof. In certain embodiments, a CD28 derivative comprises a heterologous transmembrane domain in place of the transmembrane domain of native CD28. In another embodiment, a CD28 derivative comprises (or consists of) the extracellular domain of native CD28 or a fragment thereof and the transmembrane domain of native CD28 or a fragment thereof.

The biological activity of CD28 derivatives can be assessed using techniques known to those skilled in the art, or described herein. For example, the ability of a CD28 derivative to bind to one or more ligands may be assessed using techniques described herein, or known to those skilled in the art. More specifically, the ability of a CD28 derivative to bind to B7-H2 may be assessed. In addition, the ability of a CD28 derivative to bind to one or more ligands and induce one or more of the signal transduction pathways induced by native CD28 binding to the one or more ligands may be assessed using techniques described herein, or known to those skilled in the art. More specifically, the ability of a CD28 derivative to bind to B7-H2 and induce one or more of the signal transduction pathways induced by native B7-H2 binding to native CD28 may be assessed.

In certain embodiments, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to a native ligand of CD28 (e.g., B7-H2, B7-1 or B7-2), as measured by assays/techniques well known in the art, e.g., ELISA, Biacore, or co-immunoprecipitation. In a specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to B7-H2. In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to B7-H2, but the CD28 derivative does not retain the function of the native CD28 polypeptide to bind to either B7-1, B7-2 or both or retains less than 20%, 15%, 10%, 5% or 2%, or in the range of between 2% to 20%, 2% to 15%, 2% to 10%, or 2% to 5% of the function of the native CD28 polypeptide to bind to either B7-1, B7-2 or both.

In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to either B7-1, B7-2 or both. In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to either B7-1, B7-2 or both, but the CD28 derivative does not retain the function of the native CD28 polypeptide to bind to B7-H2 or retains less than 20%, 15%, 10%, 5% or 2%, or in the range of between 2% to 20%, 2% to 15%, 2% to 10%, or 2% to 5% of the function of the native CD28 polypeptide to bind to B7-H2.

In certain other embodiments, a CD28 derivative retains less than 20%, 15%, 10%, 5% or 2%, or in the range of between 2% to 20%, 2% to 15%, 2% to 10%, or 2% to 5% of the function of a native CD28 polypeptide to bind to a native ligand of CD28 (e.g., B7-H2, B7-1 or B7-2), as measured by assays/techniques well known in the art, e.g., ELISA, Biacore, or co-immunoprecipitation. In a specific embodiment, a CD28 derivative retains less than 20%, 15%, 10%, 5% or 2%, or in the range of between 2% to 20%, 2% to 15%, 2% to 10%, or 2% to 5% of the function of a native CD28 polypeptide to bind to B7-H2. In another specific embodiment, a CD28 derivative retains less than 20%, 15%, 10%, 5% or 2%, or in the range of between 2% to 20%, 2% to 15%, 2% to 10%, or 2% to 5% of the function of a native CD28 polypeptide to bind to either B7-1, B7-2 or both.

In some embodiments, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of CD28 (e.g., B7-H2, B7-1 or B7-2) binds to a native CD28 polypeptide, as measured by assays well-known in the art. The one or more signal transduction pathways induced by the binding of a ligand of CD28 to a CD28 polypeptide can be measured by, e.g., assessing the activation of a signal transduction moiety (e.g., Jun kinase activation, MAP kinase activation, PKC activation), the translocation of a transcription factor (e.g., NF-kappa B or Stall), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In a specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native CD28 polypeptide. In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when B7-H2 binds a native CD28 polypeptide, but the CD28 derivative does not retain the ability to activate or induce one or more of the signal transduction pathways induced by the binding of either B7-1, B7-2 or both to the native CD28 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by either B7-1, B7-2 or both binding to the native CD28 polypeptide.

In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CD28 polypeptide. In another specific embodiment, a CD28 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of one or more of the signal transduction pathways induced by the binding of either B7-1, B7-2 or both to a native CD28 polypeptide, but the CD28 derivative does not retain the ability to activate or induce one or more of the signal transduction pathways induced by the binding of either B7-H2 to the native CD28 polypeptide, or retains less than 20%, 15%, 10%, 5% or 2%, or in the range of between 2% to 20%, 2% to 15%, 2% to 10%, or 2% to 5% of one or more of the signal transduction pathways induced by the binding of B7-H2 to the native CD28 polypeptide.

In some other embodiments, a CD28 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand of CD28 (e.g., B7-H2, B7-1 or B7-2) binds to a native CD28 polypeptide, as measured by assays well-known in the art. In a specific embodiment, a CD28 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H2 to a native CD28 polypeptide. In another specific embodiment, a CD28 derivative retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of either B7-1, B7-2 or both to a native CD28 polypeptide.

5.3.2.4 CTLA-4 Polypeptide & Derivatives

In one aspect, a Therapeutic Agent is a CTLA-4 polypeptide. In a specific embodiment, such a Therapeutic Agent modulates one or more of the signal transduction pathways induced by B7-H2 binding to CTLA-4. In another specific embodiment, such a Therapeutic Agent modulates the B7-H2 polypeptide and CTLA-4 polypeptide interaction. In certain embodiments, such Therapeutic Agents are Immunostimulatory Therapeutic Agents. In other embodiments, such Therapeutic Agents are Inhibitory Therapeutic Agents.

In another aspect, a Therapeutic Agent is a CTLA-4 derivative. In certain embodiments, the B7-H2 derivative is an Immunostimulating Therapeutic Agent. In other embodiments, the B7-H2 derivative is an Inhibitory Therapeutic Agent.

In a specific embodiment, a CTLA-4 derivative modulates one or more of the signal transduction pathways induced by B7-H2 binding to CTLA-4. In certain embodiments, a CTLA-4 derivative selectively modulates one or more signal transduction pathways induced by B7-H2 binding to CTLA-4. In certain embodiments, a CTLA-4 derivative activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative. In specific embodiments, a CTLA-4 derivative: (i) activates or enhances one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative; and (ii) does not activate or enhance, or activates or enhances one or more of the signal transduction pathways induced by the binding of CTLA-4 binding to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CTLA-4 to such one or more other ligands in the absence of the derivative.

In certain embodiments, a CTLA-4 derivative binds to its native ligand (e.g., native B7-H2) and induces a higher level of activity than native CTLA-4 binding to the native ligand as assessed by, e.g., the activation or induction of one or more signal transduction molecules. In specific embodiments, a CTLA-4 derivative binds to B7-H2 and induces a higher level of activity than native CTLA-4 binding to native B7-H2 as assessed by, e.g., the activation or induction of one or more signal transduction molecules. In some embodiments, a CTLA-4 derivative binds to native B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native CTLA-4 binding to native B7-H2 as assessed by, e.g., the activation or induction of one or more signal transduction molecules.

In some embodiments, a CTLA-4 derivative selectively inhibits or reduces one or more of the signal transduction pathways induced by the binding of B7-H2 to CTLA-4. In specific embodiments, a CTLA-4 derivative inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative. In specific embodiments, a CTLA-4 derivative: (i) inhibits or reduces one or more of the signal transduction pathways induced by the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of B7-H2 to CTLA-4 in the absence of the derivative; and (ii) does not inhibit or reduce, or inhibits or reduces one or more of the signal transduction pathways induced by the binding of CTLA-4 to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of CTLA-4 to such one or more other ligands in the absence of the derivative.

In another embodiment, a CTLA-4 derivative modulates the B7-H2 polypeptide and CTLA-4 polypeptide interaction. In certain embodiments, a CTLA-4 derivative selectively modulates the B7-H2 and CTLA-4 interaction. In a specific embodiment, a CTLA-4 derivative inhibits or reduces the binding of B7-H2 to CTLA-4. In another embodiment, a CTLA-4 derivative inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the derivative. In another embodiment, a CTLA-4 derivative: (i) inhibits or reduces the binding of B7-H2 to CTLA-4 by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the binding of B7-H2 to CTLA-4 in the absence of the derivative, and (ii) does not inhibit or reduce, or inhibits or reduces the binding of CTLA-4 to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the binding of CTLA-4 to such one or more other ligands in the absence of the derivative.

In certain embodiments, a CTLA-4 derivative binds to a native ligand of CTLA-4 (e.g., B7-H2) with a higher affinity than native CTLA-4 binds to the native ligand, as measured by assays/techniques well known in the art, e.g., ELISA, Biacore, or co-immunoprecipitation. In one embodiment, a CTLA-4 derivative binds to a native ligand of CTLA-4 (e.g., B7-H2) with a 50%, 75%, 80%, 85%, 90%, 95%, or 98%, or 25% to 50%, 25% to 75%, 50% to 95%, or 75% to 95% higher affinity than the native CTLA-4 binds to the native ligand, as measured by well known assays/techniques. In a specific embodiment, a CTLA-4 derivative binds to a native ligand of CTLA-4 (e.g., B7-H2) with 0.5 logs, 1 log, 1.5 logs, 2 logs, 2.5 logs, or 3 logs higher affinity than the native CTLA-4 binds to the native ligand, as measured by assays/techniques well known in the art, e.g., ELISA, Biacore, or co-immunoprecipitation.

In certain embodiments, a CTLA-4 derivative binds to native ligand of CTLA-4 (e.g., B7-H2) with a lower affinity than the native CTLA-4 binds to the native ligand of CTLA-4 (e.g., B7-H2), as measured by well-known assays/techniques. In one embodiment, a CTLA-4 derivative binds to a native ligand of CTLA-4 (e.g., B7-H2) with 25%, 50%, 75%, 80%, 85%, 90%, 95%, 25% to 50%, 25% to 75%, 50% to 75%, 50% to 95%, or 75% to 95% lower affinity than the native CTLA-4 binds to the native ligand of CTLA-4 (e.g., B7-H2), as measured by well-known assays/techniques. In another embodiment, a CTLA-4 derivative binds to a native ligand of CTLA-4 (e.g., B7-H2) with 0.5 logs, 1 log, 1.5 logs, 2 logs, 2.5 logs, or 3 logs lower affinity than the native CTLA-4 binds to the native ligand of CTLA-4 (e.g., B7-H2), as measured by well-known assays/techniques.

In specific embodiments, a CTLA-4 derivative is: (a) a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to a native CTLA-4 polypeptide; (b) a polypeptide encoded by a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical a nucleic acid sequence encoding a native CTLA-4 polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native CTLA-4 polypeptide; (d) a polypeptide encoded by nucleic acids can hybridize under high, moderate or typical stringency hybridization conditions to nucleic acids encoding a native CTLA-4 polypeptide; (e) a polypeptide encoded by a nucleic acid sequence that can hybridize under high, moderate or typical stringency hybridization conditions to a nucleic acid sequence encoding a fragment of a native CTLA-4 polypeptide of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids, or 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native CTLA-4 polypeptide. CTLA-4 derivatives also include a polypeptide that comprises the amino acid sequence of a naturally occurring mature form of a native CTLA-4 polypeptide and a heterologous signal peptide amino acid sequence. In a specific embodiment, a CTLA-4 derivative is a derivative of a native human CTLA-4 polypeptide. In another embodiment, a CTLA-4 derivative is a derivative of an immature or precursor form of naturally occurring human CTLA-4 polypeptide. In another embodiment, a CTLA-4 derivative is a derivative of a mature form of naturally occurring human CTLA-4 polypeptide. In one embodiment, a CTLA-4 derivative is isolated or purified.

In another embodiment, a CTLA-4 derivative comprises (or consists) of the amino acid sequence of native CTLA-4 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, 25 to 75 mutations (e.g., amino acid substitutions, insertions and/or deletions). In certain embodiments, a CTLA-4 derivative comprises one or more mutations that increase the affinity of CTLA-4 for B7-H2 (in particular, native B7-H2). See, e.g., Larsen et al., 2005, Am J. Transplant 5: 433-435 for guidance regarding mutations that increase affinity of CTLA-4 for a ligand. In other embodiments, a CTLA-4 derivative comprises one or more mutations that decrease the affinity of CTLA-4 for a ligand. Mutations can be introduced at specific positions with native CTLA-4 using, e.g., site-directed mutagenesis techniques and/or PCR-mediated mutagenesis techniques. Mutations can also be introduced randomly along all or part of the coding sequence using, e.g., saturation mutagenesis techniques.

In another embodiment, a CTLA-4 derivative comprises (or consists) of the amino acid sequence of native CTLA-4 with 1, 2, 3, 4, 5, 6, 7, 8, 9, 10, 11, 12, 13, 14, 15, 16, 17, 18, 19, 20 or more, or in the range of 1 to 5, 1 to 10, 2 to 15, 5 to 20, 5 to 30, 10 to 50, or 25 to 75 amino acid substitutions. Such amino acid substitutions can be either conservative, non-conservative, or a combination of both. In a specific embodiment, the amino acid substitutions are conservative amino acid substitutions, and in certain embodiments, introduced at one or more predicted non-essential amino acid residues.

In another embodiment, a CTLA-4 derivative comprises a fragment of native CTLA-4. In certain embodiments, a CTLA-4 derivative comprises (or consists of) amino acid residues 19 to 200, 175, 19 to 150, 19 to 125, 19 to 100, 19 to 95, 19 to 75, 19 to 70, 19 to 65, 19 to 60, 19 to 50, 5 to 20, 36 to 161, or 10 to 25 of native CTLA-4 of the sequence found at Accession No. P16410-1 (UniParc).

In one embodiment, a CTLA-4 derivative is a soluble form of CTLA-4. In a specific embodiment, a CTLA-4 derivative comprises (or consists of) the extracellular domain of native CTLA-4, or the extracellular domain of native CTLA-4 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In a specific embodiment, a CTLA-4 derivative comprises (or consists of) amino acid residues 36 to 161 of the sequence found at Accession No. P16410-1 (UniParc). In another embodiment, a CTLA-4 derivative comprises (or consists of) a fragment of the extracellular domain of native CTLA-4, or a fragment of the extracellular domain of native CTLA-4 containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 mutations (e.g., amino acid substitutions, deletions, and/or additions). In specific embodiments, a CTLA-4 derivative comprises (or consists of) at least 25, 50, 75, 100, or 125 amino acids of the extracellular domain of native CTLA-4. In certain embodiments, a CTLA-4 derivative comprises (or consists of) amino acid residues 36 to 150, 36 to 125, 36 to 100, 26 to 95, 36 to 75, 36 to 70, 36 to 65, 36 to 60, 36 to 50, 15 to 30, or 5 to 25 of native CTLA-4. In specific embodiments, a CTLA-4 derivative comprises (or consists of) 36 to 150, 36 to 125, 36 to 100, 26 to 95, 36 to 75, 36 to 70, 36 to 65, 36 to 60, 36 to 50, 15 to 30 or 5 to 25 amino acid residues of the sequence found at Accession No. P16410-1 (UniParc). In another embodiment, a CTLA-4 derivative comprises (or consists of) the Ig-like V-type domain of native CTLA-4. In a specific embodiment, a CTLA-4 derivative comprises (or consists of) amino acid residues 39 to 140 of the sequence found at Accession No. P16410-1 (UniParc).

In another embodiment, a CTLA-4 derivative comprises (or consists of) the extracellular and cytoplasmic domains of native CTLA-4 or fragments thereof. In another embodiment, a CTLA-4 derivative comprises (or consists of) the extracellular and cytoplasmic domains of native CTLA-4 or fragments thereof containing 1, 2, 3, 4, 5, 6, 7, 8, 9, 10, 12, 15, 20 or more, or 2 to 5, 2 to 10, 5 to 10, 5 to 15, 5 to 20, 10 to 15, or 15 to 20 amino acid substitutions, deletions, and/or additions. In another embodiment, a CTLA-4 derivative comprises (or consists) a fragment of the extracellular domain of native CTLA-4 and the cytoplasmic domain of native CTLA-4 or a fragment thereof. In another embodiment, a CTLA-4 derivative comprises (or consists of) the extracellular domain of native CTLA-4 and a fragment of the cytoplasmic domain of native CTLA-4. In another embodiment, a CTLA-4 derivative lacks the transmembrane domain of native CTLA-4 or a fragment thereof. In certain embodiments, a CTLA-4 derivative comprises a heterologous transmembrane domain in place of the transmembrane domain of native CTLA-4. In another embodiment, a CTLA-4 derivative comprises (or consists of) the extracellular domain of native CTLA-4 or a fragment thereof and the transmembrane domain of native CTLA-4 or a fragment thereof.

In certain embodiments, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to a native ligand of CTLA-4 (e.g., B7-H2, B7-1 or B7-2), as measured by assays/techniques well known in the art, e.g., ELISA, Biacore, or co-immunoprecipitation. In a specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to B7-H2. In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to B7-H2, but the CTLA-4 derivative does not retain the function of the native CTLA-4 polypeptide to bind to either B7-1, B7-2 or both or retains less than 20%, 15%, 10%, 5% or 2%, or in the range of between 2% to 20%, 2% to 15%, 2% to 10%, or 2% to 5% of the function of the native CTLA-4 polypeptide to bind to either B7-1, B7-2 or both.

In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to either B7-1, B7-2 or both. In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to either B7-1, B7-2 or both, but the CTLA-4 derivative does not retain the function of the native CTLA-4 polypeptide to bind to B7-H2 or retains less than 20%, 15%, 10%, 5% or 2%, or in the range of between 2% to 20%, 2% to 15%, 2% to 10%, or 2% to 5% of the function of the native CTLA-4 polypeptide to bind to B7-H2.

In certain other embodiments, a CTLA-4 derivative retains less than 20%, 15%, 10%, 5% or 2%, or in the range of between 2% to 20%, 2% to 15%, 2% to 10%, or 2% to 5% of the function of a native CTLA-4 polypeptide to bind to a native ligand of CTLA-4 (e.g., B7-H2, B7-1 or B7-2), as measured by assays/techniques well known in the art, e.g., ELISA, Biacore, or co-immunoprecipitation. In a specific embodiment, a CTLA-4 derivative retains less than 20%, 15%, 10%, 5% or 2%, or in the range of between 2% to 20%, 2% to 15%, 2% to 10%, or 2% to 5% of the function of a native CTLA-4 polypeptide to bind to B7-H2. In another specific embodiment, a CTLA-4 derivative retains less than 20%, 15%, 10%, 5% or 2%, or in the range of between 2% to 20%, 2% to 15%, 2% to 10%, or 2% to 5% of the function of a native CTLA-4 polypeptide to bind to either B7-1, B7-2 or both.

In some embodiments, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of CTLA-4 (e.g., B7-H2, B7-1 or B7-2) binds to a native CTLA-4 polypeptide, as measured by assays well-known in the art. The one or more signal transduction pathways induced by the binding of a ligand of CTLA-4 to a CTLA-4 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In a specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native CTLA-4 polypeptide. In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when B7-H2 binds a native CTLA-4 polypeptide, but the CTLA-4 derivative does not retain the ability to activate or induce one or more of the signal transduction pathways induced by the binding of either B7-1, B7-2 or both to the native CTLA-4 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by either B7-1, B7-2 or both binding to the native CTLA-4 polypeptide.

In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CTLA-4 polypeptide. In another specific embodiment, a CTLA-4 derivative retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CTLA-4 polypeptide, but the CTLA-4 derivative does not retain the ability to activate or induce one or more of the signal transduction pathways induced by the binding of B7-H2 to the native CTLA-4 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by binding B7-H2 to the native CTLA-4 polypeptide.

In some other embodiments, a CTLA-4 derivative retains less than 20%, 15%, 10%, 5% or 2%, or in the range of between 2% to 20%, 2% to 15%, 2% to 10%, or 2% to 5% of one or more of the signal transduction pathways induced when a native ligand of CTLA-4 (e.g., B7-H2, B7-1 or B7-2) binds to a native CTLA-4 polypeptide, as measured by assays well-known in the art. In a specific embodiment, a CTLA-4 derivative retains less than 20%, 15%, 10%, 5% or 2%, or in the range of between 2% to 20%, 2% to 15%, 2% to 10%, or 2% to 5% of one or more of the signal transduction pathways induced by the binding of B7-H2 to a native CTLA-4 polypeptide. In another specific embodiment, a CTLA-4 derivative retains less than 20%, 15%, 10%, 5% or 2%, or in the range of between 2% to 20%, 2% to 15%, 2% to 10%, or 2% to 5% of one or more of the signal transduction pathways induced by the binding of either B7-1, B7-2 or both to a native CTLA-4 polypeptide.

5.3.3 Fusion Proteins

In one aspect, a Therapeutic Agent is a protein comprising a B7-H2 polypeptide and a heterologous molecule (e.g., a heterologous amino acid sequence). In a specific embodiment, such a Therapeutic Agent modulates one or more of the signal transduction pathways induced by the binding of B7-H2 to one or more of the following receptors: ICOS, CD28 or CTLA-4. In another specific embodiment, such a Therapeutic Agent modulates the interaction between a B7-H2 polypeptide and one or more of the following receptors: ICOS, CD28 or CTLA-4. In a specific embodiment, such a Therapeutic Agent selectively modulates the interaction between a B7-H2 polypeptide and one or more of the following receptors: ICOS, CD28 or CTLA-4.

In one embodiment, a Therapeutic Agent comprises native B7-H2 and a heterologous molecule. In another embodiment, a Therapeutic Agent comprises a B7-H2 derivative and a heterologous amino acid sequence. See Section 5.3.2.1, supra, for B7-H2 derivatives. In some embodiments, such Therapeutic Agents are Immunostimulating Therapeutic Agents. In other embodiments, such Therapeutic Agents are Inhibitory Therapeutic Agents.

In a specific embodiment, the Therapeutic Agent is a fusion protein comprising B7-H2 polypeptide and a heterologous amino acid sequence. In some embodiments, such Therapeutic Agents are Immunostimulating Therapeutic Agents. In other embodiments, such Therapeutic Agents are Inhibitory Therapeutic Agents.

In another aspect, a Therapeutic Agent is a protein comprising ICOS polypeptide and a heterologous molecule. In a specific embodiment, such a Therapeutic Agent modulates the B7-H2 and ICOS interaction. In another specific embodiment, such a Therapeutic Agent selectively modulate the binding of B7-H2 to ICOS. In one embodiment, a Therapeutic Agent comprises native ICOS and a heterologous molecule. In another embodiment, a Therapeutic Agent comprises an ICOS derivative and a heterologous amino acid sequence. See Section 5.3.2.2, supra, for ICOS derivatives. In a specific embodiment, the Therapeutic Agent is a fusion protein comprising ICOS and a heterologous molecule.

In another aspect, a Therapeutic Agent is a protein comprising CD28 polypeptide and a heterologous molecule. In a specific embodiment, such a Therapeutic Agent modulates the B7-H2 and CD28 interaction. In another specific embodiment, such a Therapeutic Agent selectively modulates the binding of B7-H2 to CD28. In one embodiment, a Therapeutic Agent comprises native CD28 and a heterologous molecule. In another embodiment, a Therapeutic Agent comprises a CD28 derivative and a heterologous amino acid sequence. See Section 5.3.2.3, supra, for CD28 derivatives. In a specific embodiment, the Therapeutic Agent is a fusion protein comprising CD28 and a heterologous molecule.

In another aspect, a Therapeutic Agent is a protein comprising CTLA-4 polypeptide and a heterologous molecule. In a specific embodiment, such a Therapeutic Agent modulates the B7-H2 and CTLA-4 interaction. In another specific embodiment, such a Therapeutic Agent selectively modulates the binding of B7-H2 to CTLA-4. In one embodiment, a Therapeutic Agent comprises native CTLA-4 and a heterologous molecule. In another embodiment, a Therapeutic Agent comprises a CTLA-4 derivative and a heterologous amino acid sequence. See Section 5.3.2.4, supra, for CTLA-4 derivatives. In a specific embodiment, the Therapeutic Agent is a fusion protein comprising CTLA-4 and a heterologous molecule.

In a specific embodiment, a Therapeutic Agent is a fusion protein comprising an ICOS polypeptide, a CD28 polypeptide, or a CTLA-4 polypeptide and a heterologous molecule. In some embodiments, such Therapeutic Agents are Immunostimulatory Therapeutic Agents. In other embodiments, such Therapeutic Agents are Inhibitory Therapeutic Agents.

The B7-H2, ICOS, CD28 or CTLA-4 polypeptide may be covalently or non-covalently linked to a heterologous molecule. In certain embodiments, B7-H2, ICOS, CD28 or CTLA-4 polypeptide is covalently or non-covalently linked directly to a heterologous molecule (e.g., by combining amino acid sequences via peptide bonds). In other embodiments, B7-H2, ICOS, CD28 or CTLA-4 polypeptide is linked to a heterologous molecule using one or more linkers. See Section 5.2.3 regarding linkers for conjugating B7-H2, ICOS, CD28 or CTLA-4 polypeptide to a heterologous molecule.

In some embodiments, the heterologous molecule is the Fc domain of an IgG immunoglobulin or a fragment thereof. In certain embodiments, the heterologous molecule is PEG. In some embodiments, the heterologous molecule is a therapeutic moiety possessing a desired biological activity. In certain embodiments, the heterologous molecule is a cytokine or a growth factor. In some embodiments, the heterologous molecule is a small molecule.

In some embodiments, the heterologous molecule increases protein stability. See Section 5.2.3 for examples of such heterologous molecules. In a specific embodiment, the heterologous molecule is a modified Fc domain or a fragment thereof that increases the stability of the fusion protein. In other embodiments, the heterologous molecule decreases protein stability. In a specific embodiment, the heterologous molecule is a modified Fc domain that decreases the stability of the protein. In some embodiments, the heterologous molecule is a detectable moiety. See Sections 5.1.2 and 5.2.3 for examples of detectable moieties. In some embodiments, the heterologous molecule is a marker amino acid sequence or a penetrating peptide. See Section 5.2.3 for examples of marker amino acid sequences and penetrating peptides.

5.3.4 Nucleic Acids
5.3.4.1 B7-H2 Nucleic Acids

In one aspect, presented herein are Therapeutic Agents that are nucleic acids encoding B7-H2. In a specific embodiment, the B7-H2 encoded by the nucleic acids is capable of binding to one or more of the following receptors: ICOS, CD28 or CTLA-4. In certain embodiments, the B7-H2 encoded by the nucleic acids selectively binds to either ICOS, CD28 or CTLA-4. In specific embodiments, the B7-H2 encoded by the nucleic acids is an Immunostimulating Therapeutic Agent. In other specific embodiments, the B7-H2 encoded by the nucleic acids is an Inhibitory Therapeutic Agent.

Nucleic acid sequences encoding native B7-H2 are known in the art and have been described in the literature. For example, the nucleic acid sequences encoding native B7-H2 can be found in publicly available publications and databases, e.g., National Center for Biotechnology Information website at ncbi.nlm.nih.gov. Cloning techniques well known in the art can be used to generate nucleic acids encoding B7-H2. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native B7-H2. In another embodiment, the Therapeutic Agent comprises nucleic acids that encode a fusion protein described in Section 5.3.3, supra. In another embodiment, the Therapeutic Agent comprises nucleic acids that encode a B7-H2 derivative. See Section 5.3.2.1, supra, for B7-H2 derivatives that the nucleic acids might encode.

In specific embodiments, nucleic acids encoding B7-H2 include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native B7-H2 polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native B7-H2 polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native B7-H2 polypeptide; (d) a nucleic acid sequence that hybridizes under high, moderate or typical stringency hybridization conditions to a naturally occurring nucleic acid sequence encoding a native B7-H2 polypeptide; (e) a nucleic acid sequence that hybridizes under high, moderate or typical stringency hybridization conditions to a fragment of a naturally occurring nucleic acid sequence encoding a native B7-H2 polypeptide; and (f) a nucleic acid sequence encoding a fragment of a naturally occurring nucleic acid sequence encoding a native B7-H2 polypeptide. In a specific embodiment, a B7-H2 derivative in the context of nucleic acids is a derivative of a naturally occurring nucleic acid sequence encoding a human B7-H2 polypeptide. In another embodiment, a B7-H2 derivative in the context of nucleic acids is a derivative of a naturally occurring nucleic acid sequence encoding an immature or precursor form of a native human B7-H2 polypeptide. In another embodiment, a B7-H2 derivative in the context of nucleic acids is a derivative of a naturally occurring nucleic acid sequence encoding a mature form of a native human B7-H2 polypeptide.

In a specific embodiment, a nucleic acid sequence encoding a B7-H2 polypeptide is a derivative of a naturally occurring nucleic acid sequence encoding a native human B7-H2 polypeptide. In another embodiment, a nucleic acid sequence encoding a B7-H2 polypeptide is a derivative of a naturally occurring nucleic acid sequence encoding an immature or precursor form of a native human B7-H2 polypeptide. In another embodiment, a nucleic acid sequence encoding a B7-H2 polypeptide is a derivative of a naturally occurring nucleic acid sequence encoding a mature form of a native human B7-H7 polypeptide. In another embodiment, a nucleic acid sequence encodes a B7-H2 derivative described in Section 5.3.2.1, supra.

In certain embodiments, nucleic acid sequences include codon-optimized nucleic acid sequences that encode native B7-H2 polypeptide, including mature and immature forms of B7-H2 polypeptide. In other embodiments, nucleic acid sequences include nucleic acids that encode B7-H2 RNA transcripts containing mutations that eliminate potential splice sites and instability elements (e.g., A/T or A/U rich elements) without affecting the amino acid sequence to increase the stability of the mammalian B7-H2 RNA transcripts.

In certain embodiments, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to a native receptor of B7-H2 (e.g., ICOS, CD28 or CTLA-4), as measured by assays well known in the art, e.g., ELISA, Biacore, or co-immunoprecipitation. In a specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to ICOS. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either CD28, CTLA-4 or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either CD28, ICOS or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to ICOS, CTLA-4, or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to either CD28, ICOS and CTLA-4.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to ICOS, but the B7-H2 polypeptide nucleic acid sequences does not retain the function of a native B7-H2 polypeptide to bind to either CD28, CTLA-4 or both, or retains less than 20%, 15%, 10%, 5%, or 2%, or in the range of between 2% to 20%, 2% to 15%, 2% to 10% or 2% to 5% of the function of a native B7-H2 polypeptide to bind to either CD28, CTLA-4 or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28, but the B7-H2 polypeptide does not retain the function of a native B7-H2 polypeptide to bind to either ICOS, CTLA-4 or both, or retains less than 20%, 15%, 10%, 5%, or 2%, or in the range of between 2% to 20%, 2% to 15%, 2% to 10% or 2% to 5% of the function of a native B7-H2 polypeptide to bind to either ICOS, CTLA-4 or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28 and CTLA-4, but the B7-H2 polypeptide does not retain the function of a native B7-H2 polypeptide to bind to either ICOS, CD28, or both, or retains less than 20%, 15%, 10%, 5%, or 2%, or in the range of between 2% to 20%, 2% to 15%, 2% to 10% or 2% to 5% of the function of a native B7-H2 polypeptide to bind to either ICOS, CD28, or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native B7-H2 polypeptide to bind to CD28 and ICOS, but the B7-H2 polypeptide does not retain the function of a native B7-H2 polypeptide to bind to CTLA-4, or retains less than 20%, 15%, 10%, 5%, or 2%, or in the range of between 2% to 20%, 2% to 15%, 2% to 10% or 2% to 5% of the function of a native B7-H2 polypeptide to bind to CTLA-4.

In certain other embodiments, nucleic acid sequences encode a B7-H2 polypeptide that retains less than 20%, 15%, 10%, 5% or 2%, or in the range of between 2% to 20%, 2% to 15%, 2% to 10%, or 2% to 5% of the function of a native B7-H2 polypeptide to bind to a native receptor of B7-H2 (e.g., ICOS, CD28 or CTLA-4), as measured by assays well known in the art, e.g., ELISA, Biacore, or co-immunoprecipitation. In a specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the function of a native B7-H2 polypeptide to bind to ICOS. In another specific embodiment, nucleic acid sequences encode a B7-H2 polypeptide that retain less than 20%, 15%, 10%, 5% or 2%, or in the range of between 2% to 20%, 2% to 15%, 2% to 10%, or 2% to 5% of the function of a native B7-H2 polypeptide to bind to either CD28, CTLA-4 or both. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the function of a native B7-H2 polypeptide to bind to either CD28, ICOS or both. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the function of a native B7-H2 polypeptide to bind to either CTLA-4, ICOS, or both. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the function of a native B7-H2 polypeptide to bind to CD28, ICOS and CTLA-4.

In some embodiments, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native receptor of B7-H2 (e.g., ICOS, CD28 or CTLA-4) binds to a native B7-H2 polypeptide, as measured by assays well-known in the art. The one or more signal transduction pathways induced by the binding of a B7-H2 polypeptide to a receptor of B7-H2 can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, 11-5, IL-10, IL-17, interferon-gamma, or tumor necrosis factor-alpha) using techniques such as ELISAs, Western blots, electromobility shift assays, and other immunoassays. In a specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to ICOS. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to either CD28, CTLA-4 or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to either CD28, ICOS or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to either ICOS, CTLA-4, or both. In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of a native B7-H2 polypeptide to CD28, ICOS and CTLA-4.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to ICOS, but the B7-H2 polypeptide does not retain the ability to activate or induce one or more of the signal transduction pathways induced by the binding of a native B7-H2 polypeptide to either CD28, CTLA-4 or both, or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to either CD28, CTLA-4 or both.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to CD28, but the B7-H2 polypeptide does not retain the ability to activate or induce one or more of the signal transduction pathways induced by the binding of a native B7-H2 polypeptide to either ICOS, CTLA-4 or both, or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to either ICOS, CTLA-4 or both.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to CD28 and CTLA-4, but the B7-H2 polypeptide does not retain the ability to activate or induce one or more of the signal transduction pathways induced by the binding of a native B7-H2 polypeptide to ICOS, or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to ICOS.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to CD28 and ICOS, but the B7-H2 polypeptide does not retain the ability to activate or induce one or more of the signal transduction pathways induced by the binding of a native B7-H2 polypeptide to CTLA-4, or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to CTLA-4.

In another embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to ICOS, but the B7-H2 polypeptide does not retain the ability to activate or induce one or more of the signal transduction pathways induced by the binding of a native B7-H2 polypeptide to either CD28, CTLA-4, or both, or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to either CD28, CTLA-4, or both.

In another specific embodiment, nucleic acid sequences encode a B7-H2 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more signal transduction pathways induced by the binding of a native B7-H2 polypeptide to bind to CTLA-4, but the B7-H2 polypeptide does not retain the ability to activate or induce one or more of the signal transduction pathways induced by the binding of a native B7-H2 polypeptide to either CD28, ICOS, or both or retains less than 20%, 15%, 10%, 5%, or 2%, or in the range of between 2% to 20%, 2% to 15%, 2% to 10% or 2% to 5% of the ability to activate or induce one or more of the signal transduction pathways induced by the binding of a native B7-H2 polypeptide to either CD28, ICOS, or both.

In certain embodiments, nucleic acid sequences encode a B7-H2 polypeptide that binds to native ICOS and induces a higher level of activity than native B7-H2 binding to the native ICOS as assessed by, e.g., the activation or induction of one or more signal transduction molecules. In some embodiments, nucleic acid sequences encode a B7-H7 polypeptide that binds to ICOS and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native B7-H2 binding to native ICOS as assessed by, e.g., the activation or induction of one or more signal transduction molecules.

In some other embodiments, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native B7-H2 polypeptide binds to a native receptor of B7-H2 (e.g., ICOS, CD28 or CTLA-4), as measured by assays well-known in the art. In a specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to ICOS. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to either CD28, CTLA-4 or both. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to either ICOS, CD28 or both. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to ICOS and CTLA-4. In another specific embodiment, nucleic acid sequences encode a B7-H2 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of a native B7-H2 polypeptide to ICOS, CD28 and CTLA-4.

5.3.4.2 ICOS Nucleic Acids

In one aspect, presented herein are Therapeutic Agents that are nucleic acids encoding ICOS. In a specific embodiment, the ICOS encoded by the nucleic acids is capable of binding to B7-H2. In particular embodiments, the ICOS encoded by the nucleic acids selectively binds to B7-H2 and does not bind to other ligands. In specific embodiments, the ICOS encoded by the nucleic acids is an Immunostimulating Therapeutic Agent. In other specific embodiments, the ICOS encoded by the nucleic acids is an Inhibitory Therapeutic Agent.

Nucleic acid sequences encoding native ICOS are known in the art and have been described in the literature. For example, the nucleic acid sequences encoding native ICOS can be found in publicly available publications and databases, e.g., National Center for Biotechnology Information website at ncbi.nlm.nih.gov. Cloning techniques well known in the art can be used to generate nucleic acids encoding ICOS. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native ICOS. In another embodiment, the Therapeutic Agent comprises nucleic acids that encode a fusion protein described in Section 5.3.3, supra. In another embodiment, the Therapeutic Agent comprises nucleic acids that encode an ICOS derivative. See Section 5.3.2.2, supra, for ICOS derivatives that the nucleic acids might encode.

In specific embodiments, nucleic acids encoding ICOS include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native ICOS polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native ICOS polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native ICOS polypeptide; (d) a nucleic acid sequence that hybridizes under high, moderate or typical stringency hybridization conditions to a naturally occurring nucleic acid sequence encoding a native ICOS polypeptide; (e) a nucleic acid sequence that hybridizes under high, moderate or typical stringency hybridization conditions to a fragment of a naturally occurring nucleic acid sequence encoding a native ICOS polypeptide; and (f) a nucleic acid sequence encoding a fragment of a naturally occurring nucleic acid sequence encoding a native ICOS polypeptide. In a specific embodiment, an ICOS derivative in the context of nucleic acids is a derivative of a naturally occurring nucleic acid sequence encoding a human ICOS polypeptide. In another embodiment, an ICOS derivative in the context of nucleic acids is a derivative of a naturally occurring nucleic acid sequence encoding an immature or precursor form of a native human ICOS polypeptide. In another embodiment, an ICOS derivative in the context of nucleic acids is a derivative of a naturally occurring nucleic acid sequence encoding a mature form of a native human ICOS polypeptide.

In a specific embodiment, a nucleic acid sequence encoding an ICOS polypeptide is a derivative of a naturally occurring nucleic acid sequence encoding a native human ICOS polypeptide. In another embodiment, a nucleic acid sequence encoding an ICOS polypeptide is a derivative of a naturally occurring nucleic acid sequence encoding an immature or precursor form of a native human ICOS polypeptide. In another embodiment, a nucleic acid sequence encoding an ICOS polypeptide is a derivative of a naturally occurring nucleic acid sequence encoding a mature form of a native human B7-H7 polypeptide.

In certain embodiments, nucleic acid sequences include codon-optimized nucleic acid sequences that encode native ICOS polypeptide, including mature and immature forms of ICOS polypeptide as well as fragments thereof. In other embodiments, nucleic acid sequences include nucleic acids that encode ICOS RNA transcripts containing mutations that eliminate potential splice sites and instability elements (e.g., A/T or A/U rich elements) without affecting the amino acid sequence to increase the stability of the mammalian ICOS RNA transcripts.

In certain embodiments, nucleic acid sequences encoded an ICOS polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native ICOS polypeptide to bind a native ligand of ICOS (e.g., B7-H2), as measured by assays well known in the art, e.g., ELISA, Biacore, or co-immunoprecipitation. In a specific embodiment, nucleic acid sequence encode an ICOS polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native ICOS polypeptide to bind B7-H2.

In certain other embodiments, nucleic acid sequences encode an ICOS polypeptide that retains less than 20%, 15%, 10%, 5% or 2%, or in the range of between 2% to 20%, 2% to 15%, 2% to 10%, or 2% to 5% of the function of a native ICOS polypeptide to bind a native ligand of ICOS (e.g., B7-H2), as measured by assays well known in the art, e.g., ELISA, Biacore, or co-immunoprecipitation. In a specific embodiment, nucleic acid sequences encode an ICOS derivative that retains less than 20%, 15%, 10%, 5% or 2%, or in the range of between 2% to 20%, 2% to 15%, 2% to 10%, or 2% to 5% of the function of a native ICOS polypeptide to bind B7-H2.

In certain embodiments, nucleic acid sequences encode an ICOS polypeptide with a higher affinity for a native ligand of ICOS than native ICOS binds to the same ligand, as measured by well-known assays/techniques. In one embodiment, nucleic acid sequences encode an ICOS polypeptide with a 25%, 50%, 75%, 80%, 85%, 90%, 95%, 25% to 50%, 25% to 75%, 50% to 75%, 50% to 95%, or 75% to 95% higher affinity for a native ligand of ICOS than the native ICOS binds to the same ligand, as measured by well-known assays/techniques. In another embodiment, nucleic acid sequences encode an ICOS polypeptide with 0.5 logs, 1 log, 1.5 logs, 2 logs, 2.5 logs, or 3 logs higher affinity for a native ligand of ICOS than the native ICOS binds to the same ligand, as measured by well-known assays/techniques.

In certain embodiments, nucleic acid sequences encode an ICOS polypeptide with a lower affinity for a native ligand of ICOS than native ICOS binds to the same ligand, as measured by well-known assays/techniques. In one embodiment, nucleic acid sequences encode an ICOS polypeptide with a 25%, 50%, 75%, 80%, 85%, 90%, 95%, 25% to 50%, 25% to 75%, 50% to 75%, 50% to 95%, or 75% to 95% lower affinity for a native ligand of ICOS than the native ICOS binds to the same ligand, as measured by well-known assays/techniques. In another embodiment, nucleic acid sequences encode an ICOS polypeptide with 0.5 logs, 1 log, 1.5 logs, 2 logs, 2.5 logs, or 3 logs lower affinity for a native ligand of ICOS than the native ICOS binds to the same ligand, as measured by well-known assays/techniques.

In some embodiments, nucleic acid sequences encode an ICOS polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of ICOS (e.g., B7-H2) binds to a native ICOS polypeptide, as measured by assays well-known in the art. The one or more signal transduction pathways induced by the binding of a ligand of ICOS to an ICOS polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays. In a specific embodiment, nucleic acid sequences encode an ICOS polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native ICOS polypeptide.

In certain embodiments, nucleic acid sequences encode an ICOS polypeptide that binds to its native ligand (e.g., native B7-1, B7-2 or B7-H2) and induces a higher level of activity than native ICOS binding to the native ligand as assessed by, e.g., the activation or induction of one or more signal transduction molecules. In some embodiments, nucleic acid sequences encode an ICOS polypeptide that binds to B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native ICOS binding to native B7-H2 as assessed by, e.g., the activation or induction of one or more signal transduction molecules.

In some other embodiments, nucleic acid sequences encode an ICOS polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand of ICOS (e.g., B7-H2) binds to a native ICOS polypeptide, as measured by assays well-known in the art. In a specific embodiment, nucleic acid sequences encode an ICOS polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H2 to a native ICOS polypeptide.

5.3.4.3 CD28 Nucleic Acids

In one aspect, presented herein are Therapeutic Agents that are nucleic acids encoding CD28. In a specific embodiment, the CD28 encoded by the nucleic acids is capable of binding to B7-H2. In particular embodiments, the CD28 encoded by the nucleic acids selectively binds to B7-H2 and does not bind to other ligands (e.g., B7-1 and/or B7-2). In specific embodiments, the CD28 encoded by the nucleic acids is an Immunostimulating Therapeutic Agent. In other specific embodiments, the CD28 encoded by the nucleic acids is an Inhibitory Therapeutic Agent.

Nucleic acid sequences encoding native CD28 are known in the art and have been described in the literature. For example, the nucleic acid sequences encoding native CD28 can be found in publicly available publications and databases, e.g., National Center for Biotechnology Information website at ncbi.nlm.nih.gov. Cloning techniques well known in the art can be used to generate nucleic acids encoding CD28. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native CD28. In another embodiment, the Therapeutic Agent comprises nucleic acids that encode a fusion protein described in Section 5.3.3, supra. In another embodiment, the Therapeutic Agent comprises nucleic acids that encode a CD28 derivative. See Section 5.3.2.3, supra, for CD28 derivatives that the nucleic acids might encode.

In specific embodiments, nucleic acids encoding CD28 include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native CD28 polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native CD28 polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native CD28 polypeptide; (d) a nucleic acid sequence that hybridizes under high, moderate or typical stringency hybridization conditions to a naturally occurring nucleic acid sequence encoding a native CD28 polypeptide; (e) a nucleic acid sequence that hybridizes under high, moderate or typical stringency hybridization conditions to a fragment of a naturally occurring nucleic acid sequence encoding a native CD28 polypeptide; and (f) a nucleic acid sequence encoding a fragment of a naturally occurring nucleic acid sequence encoding a native CD28 polypeptide. In a specific embodiment, a CD28 derivative in the context of nucleic acids is a derivative of a naturally occurring nucleic acid sequence encoding a human CD28 polypeptide. In another embodiment, a CD28 derivative in the context of nucleic acids is a derivative of a naturally occurring nucleic acid sequence encoding an immature or precursor form of a native human CD28 polypeptide. In another embodiment, a CD28 derivative in the context of nucleic acids is a derivative of a naturally occurring nucleic acid sequence encoding a mature form of a native human CD28 polypeptide.

In a specific embodiment, a nucleic acid sequence encoding a CD28 polypeptide is a derivative of a naturally occurring nucleic acid sequence encoding a native human CD28 polypeptide. In another embodiment, a nucleic acid sequence encoding a CD28 polypeptide is a derivative of a naturally occurring nucleic acid sequence encoding an immature or precursor form of a native human CD28 polypeptide. In another embodiment, a nucleic acid sequence encoding a CD28 polypeptide is a derivative of a naturally occurring nucleic acid sequence encoding a mature form of a native human B7-H7 polypeptide.

In certain embodiments, nucleic acid sequences include codon-optimized nucleic acid sequences that encode native CD28 polypeptide, including mature and immature forms of CD28 polypeptide as well as fragments thereof. In other embodiments, nucleic acid sequences include nucleic acids that encode CD28 RNA transcripts containing mutations that eliminate potential splice sites and instability elements (e.g., A/T or A/U rich elements) without affecting the amino acid sequence to increase the stability of the mammalian CD28 RNA transcripts.

In certain embodiments, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to a native ligand of CD28 (e.g., B7-H2, B7-1 or B7-2), as measured by assays well known in the art, e.g., ELISA, Biacore, or co-immunoprecipitation. In a specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to B7-H2. In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 50% to 98% of the function of a native CD28 polypeptide to bind to B7-H2, but the CD28 polypeptide encoded by the nucleic acid sequences does not retain the function of the native CD28 polypeptide to bind to either B7-1, B7-2 or both, or retains less than 20%, 15%, 10%, 5% or 2%, or in the range of between 2% to 20%, 2% to 15%, 2% to 10%, or 2% to 5% of the function of the native CD28 polypeptide to bind to either B7-1, B7-2 or both.

In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to either B7-1, B7-2 or both. In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CD28 polypeptide to bind to either B7-1, B7-2 or both, but the CD28 polypeptide encoded by the nucleic acid sequences does not retain the function of the native CD28 polypeptide to bind to B7-H2, or retains less than 20%, 15%, 10%, 5% or 2%, or in the range of between 2% to 20%, 2% to 15%, 2% to 10%, or 2% to 5% of the function of the native CD28 polypeptide to bind to B7-H2.

In certain other embodiments, nucleic acid sequences encode a CD28 polypeptide that retains less than 20%, 15%, 10%, 5% or 2%, or in the range of between 2% to 20%, 2% to 15%, 2% to 10%, or 2% to 5% of the function of a native CD28 polypeptide to bind to a native ligand of CD28 (e.g., B7-H2, B7-1 or B7-2), as measured by assays well known in the art, e.g., ELISA, Biacore, or co-immunoprecipitation. In a specific embodiment, nucleic acid sequences encode a CD28 polypeptide that retains less than 20%, 15%, 10%, 5% or 2%, or in the range of between 2% to 20%, 2% to 15%, 2% to 10%, or 2% to 5% of the function of a native CD28 polypeptide to bind to B7-H2. In another specific embodiment, nucleic acid sequences encode a CD28 polypeptide that retains less than 20%, 15%, 10%, 5% or 2%, or in the range of between 2% to 20%, 2% to 15%, 2% to 10%, or 2% to 5% of the function of a native CD28 polypeptide to bind to either B7-1, B7-2 or both.

In certain embodiments, nucleic acid sequences encode a CD28 polypeptide that has a higher affinity for a native ligand of CD28 (e.g., native B7-H2) than native CD28 for the same receptor, as measured by assays/techniques well known in the art, e.g., ELISA, Biacore, or co-immunoprecipitation. In one embodiment, nucleic acid sequences encode a CD28 polypeptide that binds to a native ligand of CD28 (e.g., B7-H2) with a 50%, 75%, 80%, 85%, 90%, 95%, or 98%, or 25% to 50%, 25% to 75%, 50% to 95%, or 75% to 95% higher affinity than the native CD28 binds to the native ligand, as measured by well known assays/techniques. In a specific embodiment, nucleic acid sequences encode a CD28 polypeptide that binds to a native ligand of CD28 (e.g., B7-H2) with 0.5 logs, 1 log, 1.5 logs, 2 logs, 2.5 logs, or 3 logs higher affinity than the native CD28 binds to the same ligand, as measured by assays/techniques well known in the art, e.g., ELISA, Biacore, or co-immunoprecipitation.

In certain embodiments, nucleic acid sequences encode a CD28 polypeptide with a lower affinity for a native ligand of CD28 than native CD28 binds to the same ligand, as measured by well-known assays/techniques. In one embodiment, nucleic acid sequences encode a CD28 polypeptide with a 25%, 50%, 75%, 80%, 85%, 90%, 95%, 25% to 50%, 25% to 75%, 50% to 75%, 50% to 95%, or 75% to 95% lower affinity for a native ligand of CD28 than the native CD28 binds to the same ligand, as measured by well-known assays/techniques. In another embodiment, nucleic acid sequences encode a CD28 polypeptide with 0.5 logs, 1 log, 1.5 logs, 2 logs, 2.5 logs, or 3 logs lower affinity for a native ligand of CD28 than the native CD28 binds to the same ligand, as measured by well-known assays/techniques.

In some embodiments, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when a native ligand of CD28 (e.g., B7-H2, B7-1 or B7-2) binds to a native CD28 polypeptide, as measured by assays well-known in the art. The one or more signal transduction pathways induced by the binding of a ligand of CD28 to a CD28 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In a specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native CD28 polypeptide. In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 75% of the ability to activate or induce one or more of the signal transduction pathways induced when B7-H2 binds a native CD28 polypeptide, but the CD28 polypeptide encoded by the nucleic acid sequences does not retain the ability to activate or induce one or more of the signal transduction pathways induced by the binding of either B7-1, B7-2 or both to the native CD28 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by either B7-1, B7-2 or both binding to the native CD28 polypeptide.

In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CD28 polypeptide. In another specific embodiment, nucleic acid sequences encode a CD28 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CD28 polypeptide, but the CD28 polypeptide encoded by the nucleic acid sequences does not retain the ability to activate or induce one or more of the signal transduction pathways induced by the binding of either B7-H2 to the native CD28 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by binding B7-H2 to the native CD28 polypeptide.

In certain embodiments, nucleic acid sequences encode a CD28 polypeptide that binds to its native ligand (e.g., native B7-1, B7-2 or B7-H2) and induces a higher level of activity than native CD28 binding to the native ligand as assessed by, e.g., the activation or induction of one or more signal transduction molecules. In some embodiments, nucleic acid sequences encode a CD28 polypeptide that binds to B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native CD28 binding to native B7-H2 as assessed by, e.g., the activation or induction of one or more signal transduction molecules.

In some other embodiments, nucleic acid sequences encode a CD28 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand of CD28 (e.g., B7-H2, B7-1 or B7-2) binds to a native CD28 polypeptide, as measured by assays well-known in the art. In a specific embodiment, nucleic acid sequences encode a CD28 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H2 to a native CD28 polypeptide. In another specific embodiment, nucleic acid sequences encode a CD28 polypeptide that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of either B7-1, B7-2 or both to a native CD28 polypeptide.

5.3.4.4 CTLA-4 Nucleic Acids

In one aspect, presented herein are Therapeutic Agents that are nucleic acids encoding CTLA-4. In a specific embodiment, the CTLA-4 encoded by the nucleic acids is capable of binding to B7-H2. In particular embodiments, the CTLA-4 encoded by the nucleic acids selectively binds to B7-H2 and does not bind to other ligands (e.g., B7-1 and/or B7-2). In specific embodiments, the CTLA-4 encoded by the nucleic acids is an Immunostimulating Therapeutic Agent. In other specific embodiments, the CTLA-4 encoded by the nucleic acids is an Inhibitory Therapeutic Agent.

Nucleic acid sequences encoding native CTLA-4 are known in the art and have been described in the literature. For example, the nucleic acid sequences encoding native CTLA-4 can be found in publicly available publications and databases, e.g., National Center for Biotechnology Information website at ncbi.nlm.nih.gov. Cloning techniques well known in the art can be used to generate nucleic acids encoding CTLA-4. See, e.g., Ausubel et al., Current Protocols in Molecular Biology, John Wiley and Sons, Inc. (1995); Sambrook et al., Molecular Cloning, A Laboratory Manual (2d ed.), Cold Spring Harbor Press, Cold Spring Harbor, N.Y. (1989); Birren et al., Genome Analysis: A Laboratory Manual, volumes 1 through 4, Cold Spring Harbor Press, Cold Spring Harbor, N.Y. (1997-1999).

In one embodiment, the Therapeutic Agent comprises nucleic acids that encode native CTLA-4. In another embodiment, the Therapeutic Agent comprises nucleic acids that encode a fusion protein described in Section 5.3.3, supra. In another embodiment, the Therapeutic Agent comprises nucleic acids that encode a CTLA-4 derivative. See Section 5.3.2.4, supra, for CTLA-4 derivatives that the nucleic acids might encode.

In specific embodiments, nucleic acids encoding CTLA-4 include: (a) a nucleic acid sequence that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical to the naturally occurring nucleic acid sequence encoding a native CTLA-4 polypeptide; (b) a nucleic acid sequence encoding a polypeptide that is at least 40%, 45%, 50%, 55%, 60%, 65%, 70%, 75%, 80%, 85%, 90%, 95%, 98%, or 99% or is 40% to 65%, 50% to 90%, 65% to 90%, 70% to 90%, 75% to 95%, 80% to 95%, or 85% to 99% identical the amino acid sequence of a native CTLA-4 polypeptide; (c) a nucleic acid sequence that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 nucleic acid base mutations (e.g., additions, deletions and/or substitutions) relative to the naturally occurring nucleic acid sequence encoding a native CTLA-4 polypeptide; (d) a nucleic acid sequence that hybridizes under high, moderate or typical stringency hybridization conditions to a naturally occurring nucleic acid sequence encoding a native CTLA-4 polypeptide; (e) a nucleic acid sequence that hybridizes under high, moderate or typical stringency hybridization conditions to a fragment of a naturally occurring nucleic acid sequence encoding a native CTLA-4 polypeptide; and (f) a nucleic acid sequence encoding a fragment of a naturally occurring nucleic acid sequence encoding a native CTLA-4 polypeptide. In a specific embodiment, a CTLA-4 derivative in the context of nucleic acids is a derivative of a naturally occurring nucleic acid sequence encoding a human CTLA-4 polypeptide. In another embodiment, a CTLA-4 derivative in the context of nucleic acids is a derivative of a naturally occurring nucleic acid sequence encoding an immature or precursor form of a native human CTLA-4 polypeptide. In another embodiment, a CTLA-4 derivative in the context of nucleic acids is a derivative of a naturally occurring nucleic acid sequence encoding a mature form of a native human CTLA-4 polypeptide.

In a specific embodiment, a nucleic acid sequence encoding a CTLA-4 polypeptide is a derivative of a naturally occurring nucleic acid sequence encoding a native human CTLA-4 polypeptide. In another embodiment, a nucleic acid sequence encoding a CTLA-4 polypeptide is a derivative of a naturally occurring nucleic acid sequence encoding an immature or precursor form of a native human CTLA-4 polypeptide. In another embodiment, a nucleic acid sequence encoding a CTLA-4 polypeptide is a derivative of a naturally occurring nucleic acid sequence encoding a mature form of a native human B7-H7 polypeptide.

In certain embodiments, nucleic acid sequences include codon-optimized nucleic acid sequences that encode native CTLA-4 polypeptide, including mature and immature forms of CTLA-4 polypeptide as well as fragments thereof. In other embodiments, nucleic acid sequences include nucleic acids that encode CTLA-4 RNA transcripts containing mutations that eliminate potential splice sites and instability elements (e.g., A/T or A/U rich elements) without affecting the amino acid sequence to increase the stability of the mammalian CTLA-4 RNA transcripts.

In certain embodiments, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to a native ligand of CTLA-4 (e.g., B7-H2, B7-1 or B7-2), as measured by assays well known in the art, e.g., ELISA, Biacore, or co-immunoprecipitation. In a specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to B7-H2. In another specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to B7-H2, but the CTLA-4 derivative nucleic acid sequences does not retain the function of the native CTLA-4 polypeptide to bind to either B7-1, B7-2 or both, or retains less than 20%, 15%, 10%, 5% or 2%, or in the range of between 2% to 20%, 2% to 15%, 2% to 10%, or 2% to 5% of the function of the native CTLA-4 polypeptide to bind to either B7-1, B7-2 or both.

In another specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to either B7-1, B7-2 or both. In another specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the function of a native CTLA-4 polypeptide to bind to either B7-1, B7-2 or both, but the CTLA-4 derivative nucleic acid sequences do not retain the function of the native CTLA-4 polypeptide to bind to B7-H2, or retains less than 20%, 15%, 10%, 5% or 2%, or in the range of between 2% to 20%, 2% to 15%, 2% to 10%, or 2% to 5% of the function of the native CTLA-4 polypeptide to bind to B7-H2.

In certain other embodiments, nucleic acid sequences encode a CTLA-4 that retains less than 20%, 15%, 10%, 5% or 2%, or in the range of between 2% to 20%, 2% to 15%, 2% to 10%, or 2% to 5% of the function of a native CTLA-4 polypeptide to bind to a native ligand of CTLA-4 (e.g., B7-H2, B7-1 or B7-2), as measured by assays well known in the art, e.g., ELISA, Biacore, or co-immunoprecipitation. In a specific embodiment, nucleic acid sequences encode a CTLA-4 that retains less than 20%, 15%, 10%, 5% or 2%, or in the range of between 2% to 20%, 2% to 15%, 2% to 10%, or 2% to 5% of the function of a native CTLA-4 polypeptide to bind to B7-H2. In another specific embodiment, nucleic acid sequences encode a CTLA-4 that retains less than 20%, 15%, 10%, 5% or 2%, or in the range of between 2% to 20%, 2% to 15%, 2% to 10%, or 2% to 5% of the function of a native CTLA-4 polypeptide to bind to either B7-1, B7-2 or both.

In certain embodiments, nucleic acid sequences encode a CTLA-4 that has a higher affinity for a native ligand of CTLA-4 (e.g., native B7-H2) than native CTLA-4 for the same ligand, as measured by assays/techniques well known in the art, e.g., ELISA, Biacore, or co-immunoprecipitation. In one embodiment, nucleic acid sequences encode a CTLA-4 polypeptide that binds to a native ligand of CTLA-4 (e.g., B7-H2) with a 50%, 75%, 80%, 85%, 90%, 95%, or 98%, or 25% to 50%, 25% to 75%, 50% to 95%, or 75% to 95% higher affinity than the native CTLA-4 binds to the native ligand, as measured by well known assays/techniques. In a specific embodiment, nucleic acid sequences encode a CTLA-4 that binds to a native ligand of CTLA-4 (e.g., B7-H2) with 0.5 logs, 1 log, 1.5 logs, 2 logs, 2.5 logs, or 3 logs higher affinity than the native CLTA-4 binds to the same ligand, as measured by assays/techniques well known in the art, e.g., ELISA, Biacore, or co-immunoprecipitation.

In certain embodiments, nucleic acid sequences encode a CTLA-4 polypeptide with a lower affinity for a native ligand of CTLA-4 than native CTLA-4 binds to the same ligand, as measured by well-known assays/techniques. In one embodiment, nucleic acid sequences encode a CTLA-4 polypeptide with a 25%, 50%, 75%, 80%, 85%, 90%, 95%, 25% to 50%, 25% to 75%, 50% to 75%, 50% to 95%, or 75% to 95% lower affinity for a native ligand of CTLA-4 than the native CTLA-4 binds to the same ligand, as measured by well-known assays/techniques. In another embodiment, nucleic acid sequences encode a CTLA-4 polypeptide with 0.5 logs, 1 log, 1.5 logs, 2 logs, 2.5 logs, or 3 logs lower affinity for a native ligand of CTLA-4 than the native CTLA-4 binds to the same ligand, as measured by well-known assays/techniques.

In some embodiments, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of one or more of the signal transduction pathways induced when a native ligand of CTLA-4 (e.g., B7-H2, B7-1 or B7-2) binds to a native CTLA-4 polypeptide, as measured by assays well-known in the art. The one or more signal transduction pathways induced by the binding of a ligand of CTLA-4 to a CTLA-4 polypeptide can be measured by, e.g., assessing the activation of a signal transduction moiety (e.g., Jun kinase activation, MAP kinase activation, PKC activation), the translocation of a transcription factor (e.g., NF-kappa B or Stat1), and cytokine production (e.g., IL-2, IL-4, IL-5, IL-10, IL-17, interferon-gamma, or tumor necrosis factor-alpha) using techniques such as ELISAs, Western blots, electromobility shift assays, and other immunoassays.

In a specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of B7-H2 to a native CTLA-4 polypeptide. In another specific embodiment, nucleic acid sequences encode CTLA-4 polypeptide that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced when B7-H2 binds a native CTLA-4 polypeptide, but the CTLA-4 polypeptide encoded by the nucleic acid sequences does not retain the ability to activate or induce one or more of the signal transduction pathways induced by the binding of either B7-1, B7-2 or both to the native CTLA-4 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by either B7-1, B7-2 or both binding to the native CTLA-4 polypeptide.

In another specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CTLA-4 polypeptide. In another specific embodiment, nucleic acid sequences encode a CTLA-4 that retains at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, or 75% to 100% of the ability to activate or induce one or more of the signal transduction pathways induced by the binding of either B7-1, B7-2 or both to a native CTLA-4 polypeptide, but the CTLA-4 polypeptide encoded by the nucleic acid sequences does not retain the ability to activate or induce one or more of the signal transduction pathways induced by the binding of either B7-H2 to the native CTLA-4 polypeptide, or retains less than 20%, 15%, 10%, 5% or 2%, or in the range of between 2% to 20%, 2% to 15%, 2% to 10%, or 2% to 5% of the ability to activate or induce one or more of the signal transduction pathways induced by binding B7-H2 to the native CTLA-4 polypeptide.

In certain embodiments, nucleic acid sequences encode a CTLA-4 that binds to its native ligand (e.g., native B7-H2) and induces a higher level of activity than native CTLA-4 binding to the native ligand as assessed by, e.g., the activation or induction of one or more signal transduction molecules. In some embodiments, nucleic acid sequences encode a CTLA-4 that binds to B7-H2 and induces at least 25%, 30%, 35%, 40%, 45%, 50%, 55%, 60%, 65%, 70%, 75%, 80%, 85%, 90%, 95%, 98% or 99%, or in the range of between 25% to 50%, 25% to 75%, 25% to 98%, 50% to 75%, 50% to 98%, or 75% to 90% higher level of activity than native CTLA-4 binding to native B7-H2 as assessed by, e.g., the activation or induction of one or more signal transduction molecules.

In some other embodiments, nucleic acid sequences encode a CTLA-4 that retains less than 20%, 15%, 10%, 5% or 2%, or in the range of between 2% to 20%, 2% to 15%, 2% to 10%, or 2% to 5% of the ability to activate or induce one or more of the signal transduction pathways induced when a native ligand of CTLA-4 (e.g., B7-H2, B7-1 or B7-2) binds to a native CTLA-4 polypeptide, as measured by assays well-known in the art. In a specific embodiment, nucleic acid sequences encode a CTLA-4 that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of B7-H2 to a native CTLA-4 polypeptide. In another specific embodiment, nucleic acid sequences encode a CTLA-4 that retains less than 20%, 15%, 10%, 5% or 2%, or in the range of between 2% to 20%, 2% to 15%, 2% to 10%, or 2% to 5% of the ability to activate or induce one or more of the signal transduction pathways induced by the binding of either B7-1, B7-2 or both to a native CTLA-4 polypeptide.

5.3.4.5 Nucleic Acids Encoding Antibodies

In one aspect, a Therapeutic Agent is a nucleic acid sequence encoding an antibody described in Section 5.3.1, supra (including antibody conjugate or fusion proteins). In some embodiments, antibodies encoded by the nucleic acid sequences are Immunostimulating Therapeutic Agents. In other embodiments, antibodies encoded by the nucleic acid sequences are Inhibitory Therapeutic Agents.

5.3.4.6 Constructs & Recombinant Expression

The nucleic acids encoding a protein can be inserted into nucleic acid constructs for expression in mammalian cells, bacteria, yeast, and viruses. See Section 5.2.4.4 regarding information relating to constructs for expression of nucleic acids. The embodiments described in that section are applicable here too.

5.3.5 Cells

Cells can be engineered to express the protein(s) encoded by the nucleic acid constructs described in Section 5.2.5, supra. In one embodiment, such cells express amounts of protein that are at least 1 fold, 2 fold, 3 fold, 4 fold, 5 fold, 6 fold, 7 fold, 8 fold, 9 fold, 10 fold, 20 fold, 30 fold, 40 fold, 50 fold or more than 50 fold higher than amounts of protein expressed endogenously by control cells (e.g., cells that have not been genetically engineered to recombinantly express protein, or cells comprising an empty vector). In addition, cells can be engineered to express the antibodies described in Section 5.3.1 et seq., supra, using techniques well-known to one of skill in the art, see, e.g., U.S. Pat. Nos. 5,807,715, 6,331,415, and 6,818,216; U.S. Patent Application Publication Nos. US 2002/0098189, US 2004/0028685, US 2005/0019330, and US 2007/0086943; International Publication No. WO 02/46237; and Harlow et al., Antibodies. A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references are incorporated by reference herein in their entireties). The cells chosen for expression of nucleic acids will depend upon the intended use of the cells. Factors such as whether a cell glycosylates similar to cells that endogenously express a protein may be considered in selecting the cells. See Section 5.2.5 supra for information regarding cells genetically engineered to recombinantly express a protein. The embodiments described in that section is applicable here too.

5.3.6 Compounds

In another aspect, a Therapeutic Agent is a compound (e.g., a small molecule). In certain embodiments, a Therapeutic Agent is a compound that modulates one or more of the signal transduction pathways induced by B7-H2 binding to one or more of the following receptors: ICOS, CD28 or CTLA-4. In some embodiments, a Therapeutic Agent is a compound that modulates the interaction between B7-H2 and one or more of the following: ICOS, CD28 or CTLA-4. In certain embodiments, a Therapeutic Agent is a compound that modulates the expression of B7-H2, ICOS, CD28 or CTLA-4. In specific embodiments, a Therapeutic Agent selectively modulates: (i) one or more signal transduction pathways induced by B7-H2 binding to ICOS, CD28 or CTLA-4; (ii) the interaction between B7-H2 and ICOS, CD28 or CTLA-4; and/or (iii) the expression of B7-H2, ICOS, CD28 or CTLA-4. Examples of compounds include, but are not limited to, peptides; proteins; peptoids; random biooligomers; diversomers such as hydantoins, benzodiazepines, dipeptides; vinylogous polypeptides; nonpeptidal peptidomimetics; oligocarbamates; peptidyl phosphonates; nucleic acids (e.g., RNAi, antisense, and microRNA); antibodies; and carbohydrates. In a specific embodiment, a Therapeutic Agent is a small molecule.

In certain embodiments, a Therapeutic Agent is an antisense nucleic acid molecule that inhibits or reduces the expression of B7-H2, ICOS, CD28 or CTLA-4. See Section 5.2.6, supra, for information relating antisense molecules.

In some embodiments, a Therapeutic Agent is a ribozyme that is specific for B7-H2, ICOS, CD28 or CTLA-4 nucleic acids. In certain embodiments, a Therapeutic Agent is a small interfering RNA (siRNA) that inhibits or reduces the expression of B7-H2, ICOS, CD28 or CTLA-4. See Section 5.2.6, supra, for information relating to ribozymes and siRNA.

5.4 COMPOSITIONS

Presented herein are compositions comprising one or more Therapeutic Agents, including Immunostimulating Therapeutic Agents and Inhibitory Therapeutic Agents. The compositions include bulk drug compositions useful in the manufacture of compositions (e.g., impure or non-sterile compositions) and pharmaceutical compositions (i.e., compositions that are suitable for administration to a subject or patient) which can be used in the preparation of unit dosage forms. The compositions comprise an effective amount of a Therapeutic Agent or a combination of Therapeutic Agents and a pharmaceutically acceptable carrier. In specific embodiments, the compositions comprise an effective amount of one or more Therapeutic Agents and a pharmaceutically acceptable carrier. In specific embodiments, a pharmaceutical composition comprises an amount of a Therapeutic Agent that is effective to achieve the desired effect (e.g., modulation of T lymphocyte proliferation, modulation of immune function, or prevention, treatment or management of disease). In some embodiments, the composition further comprises an additional therapy/therapeutic, e.g., anti-cancer agent, anti-viral agent, anti-inflammatory agent, adjuvant. Non-limiting examples of such therapies/therapeutics are provided in Section 5.7 et seq., infra.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete) or, more preferably, MF59C.1 adjuvant available from Chiron, Emeryville, Calif.), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In one embodiment, water is a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Pharmaceutical compositions for use in accordance with the methods described herein may be formulated in any conventional manner using one or more pharmaceutically acceptable carriers or excipients.

Generally, the components of the pharmaceutical compositions comprising Therapeutic Agents are supplied either separately or mixed together in unit dosage form, for example, as a dry lyophilized powder or water free concentrate in a hermetically sealed container such as an ampoule or sachette indicating the quantity of active agent. Where the Therapeutic Agent is to be administered by infusion, it can be dispensed with an infusion bottle containing sterile pharmaceutical grade water or saline (e.g., PBS). Where the Therapeutic Agent is administered by injection, an ampoule of sterile water for injection or saline can be provided so that the ingredients may be mixed prior to administration.

In some embodiments, Therapeutic Agents may be formulated for administration by any method known to one of skill in the art, including but not limited to, inhalation, insufflation (either through the mouth or the nose), oral, intradermal, transdermal, intraparenteral, intravenous, subcutaneous, intramuscular, intratumoral, and mucosal (such as buccal, vaginal, rectal, sublingual) administration.

In a specific embodiment, the Therapeutic Agents are formulated for local or systemic parenteral administration. In one embodiment, the Therapeutic Agents are formulated in a pharmaceutically compatible solution.

For oral administration, the pharmaceutical compositions comprising Therapeutic Agents that are polypeptides or nucleic acids may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the Therapeutic Agent or compositions thereof. For buccal administration the compositions may take the form of tablets or lozenges formulated in conventional manner.

For administration by inhalation, the Therapeutic Agents are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The Therapeutic Agents can be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the Therapeutic Agent may be in powder form for constitution with a suitable vehicle, e.g., sterile pyrogen-free water, before use.

The Therapeutic Agents may also be formulated in rectal compositions such as suppositories or retention enemas, e.g., containing conventional suppository bases such as cocoa butter or other glycerides.

In addition to the formulations described previously, the Therapeutic Agents may also be formulated for implantation (for example subcutaneously or intramuscularly) or by intramuscular injection.

In a specific embodiment, the formulation and administration of various chemotherapeutic, biological/immunotherapeutic and hormonal therapeutic agents for use in combination with Therapeutic Agents are known in the art and described in the Physician's Desk Reference, 63rd ed. (2009). In some embodiments, the Therapeutic Agents are formulated with other therapies, such as those described in Section 5.7 et seq. below. In some embodiments, Therapeutic Agents comprising cells recombinantly expressing B7-H7, B7-H7CR, B7-H2, ICOS, CD28 or CTLA-4 are formulated as pharmaceutical compositions.

5.5 PROPHYLACTIC AND THERAPEUTIC USES OF THERAPEUTIC AGENTS THAT ENHANCE IMMUNE FUNCTION 5.5.1 Enhancing Immune Function In one aspect, presented herein are methods for enhancing one or more immune functions or responses in a subject, comprising administering to a subject in need thereof an Immunostimulating Therapeutic Agent or a composition thereof. In a specific embodiment, presented herein are methods for preventing, treating, and/or managing diseases in which it is desirable to activate or enhance one or more immune functions or responses, comprising administering to a subject in need thereof an Immunostimulating Therapeutic Agent or a composition thereof. In other specific embodiments, the method comprises combination therapy, wherein the Immunostimulating Therapeutic Agent is administered to a subject in combination with another therapy, such as those described below, to activate or enhance one or more immune functions or responses. In certain embodiments, the Immunostimulating Therapeutic Agent is administered as an adjuvant in combination with an antigenic composition. In a particular embodiment, the Immunostimulating Therapeutic Agent is administered in combination with a vaccine composition to induce or activate or enhance the immune response elicited by the vaccine composition.

Non-limiting examples of diseases that can be prevented, treated, or managed by an enhancement of immune function include, but are not limited to, cancer, infectious diseases, diseases characterized by infiltrating macrophages, or atherosclerosis. Various cancers and infectious diseases are described below. In a specific embodiment, an Immunostimulating Therapeutic Agent described herein can be used to treat or manage a condition associated with cancer or a condition resulting from the administration of an anti-cancer therapy (such as, e.g., chemotherapy or radiation). In a particular embodiment, an Immunostimulating Therapeutic Agent can be used to treat or manage lymphocytopenia. In another embodiment, an Immunostimulating Therapeutic Agent is administered to a patient diagnosed with cancer to increase the proliferation and/or effector function of one or more immune cell populations in the patient.

In a specific embodiment, an Immunostimulating Therapeutic Agent activates or enhances or induces one or more immune functions or responses in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the Immunostimulating Therapeutic Agent using assays well known in the art, e.g., ELISPOT, ELISA, and cell proliferation assays. In a specific embodiment, the immune function is cytokine release (e.g., interferon-gamma, IL-2, IL-5, IL-10, IL-12, or transforming growth factor (TGF)-beta). In one embodiment, the immune function is NK cell proliferation, which can be assayed, e.g., by flow cytometry to detect the number of cells expressing markers of NK cells (e.g., CD56). In one embodiment, the immune function is T cell proliferation, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a Th17 response. In another embodiment, the immune function is a Th22 response. In another embodiment, the immune function is a memory response.

In specific embodiments, non-limiting examples of immune functions that may be enhanced by the Immunostimulating Therapeutic Agent are proliferation/expansion of lymphocytes (e.g., increase in the number of lymphocytes), inhibition of apoptosis of lymphocytes, activation of dendritic cells (or antigen presenting cells), and antigen presentation. In particular embodiments, an immune function enhanced by the Immunostimulating Therapeutic Agent is proliferation/expansion in the number of or activation of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells). In one embodiment, the Immunostimulating Therapeutic Agent activates or enhances the proliferation/expansion or number of lymphocyte progenitors. In certain embodiments, the Immunostimulating Therapeutic Agent reduces the proliferation/expansion of Tregs. In some embodiments, an Immunostimulating Therapeutic Agent increases the number of $CD4^+$ T cells (e.g., Th1 and Th2 helper T cells), $CD8^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, $CD122^+$ T cells, or natural killer cells (NK cells) by approximately at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an Immunostimulating Therapeutic Agent).

In certain embodiments, an Immunostimulating Therapeutic Agent inhibits or reduces one or more signal transduction pathways mediated by CTLA-4 binding to one or more of its ligands (e.g., B7-1, B7-2, or B7-H2). In some embodiments, an Immunostimulatory Therapeutic Agent inhibits or reduces the binding of native CTLA-4 to one or more of its ligands (e.g., B7-1, B7-2, or B7-H2). In a specific embodiment, an Immunostimulatory Therapeutic Agent is a B7-H2-Ig polypeptide or derivative thereof or other CTLA-4 inhibitor described herein. In certain embodiments, a chronic disease (e.g., HIV or HCV infection, cancer, etc.) is treated or managed by administering such an Immunostimulatory Therapeutic Agent.

In certain embodiments, an Immunostimulatory Therapeutic Agent enhances, activates or induces one or more signal transduction pathways mediated by CD28 binding to one or more of its ligands (e.g., B7-1, B7-2 or B7-H2). In a specific embodiment, an Immunostimulatory Therapeutic Agent is a B7-H2Ig or another agonist described herein. In certain embodiments, an acute disease (e.g., an acute infection) is treated or managed by administering such an Immunostimulatory Therapeutic Agent.

In certain embodiments, an Immunostimulatory Therapeutic Agent enhances, activates or induces one or more signal transduction pathways mediated by ICOS binding to one or more of its ligands (e.g., B7-H2). In certain embodiments, an chronic disease (e.g., a chronic viral infection) is treated or managed by administering such an Immunostimulatory Therapeutic Agent.

The immunostimulatory molecules, B7-1 and B7-2, which bind to the inducible inhibitory CTLA-4 receptor with higher affinity than the constitutive stimulatory CD28 receptor. Therefore, B7-1 and B7-2 initially stimulate immune responses via CD28 but later inhibit of immune responses via CTLA-4, which prevents over-stimulation of the immune system. In contrast, B7-H2 has a relatively low affinity for CTLA-4 compared to CD28 and ICOS. Therefore, an agonistic B7-H2 polypeptide or fusion thereof (e.g. B7-H2-Ig) may be very useful for producing sustained immune responses through CD28 (a constitutive receptor) and ICOS (an inducible receptor) for treating chronic cancers and infections, and to help generate memory responses. In addition, an agonistic B7-H2 polypeptide or fusion thereof (e.g. B7-H2-Ig) maybe a very good 'adjuvant' for other therapeutics relying on immune stimulation, such as vaccines against cancers and infectious disease. The effects may be enhanced in combination of CTLA4 inhibitors e.g. anti-CTLA4.

5.5.1.1 Cancer

In a specific aspect, presented herein are methods for preventing, treating, and/or managing cancer, comprising administering to a subject in need thereof an effective amount of an Immunostimulating Therapeutic Agent or a composition thereof. In a specific embodiment, an Immunostimulating Therapeutic Agent or a composition thereof is the only active agent administered to a subject (i.e., monotherapy).

The effect of an Immunostimulating Therapeutic Agent on proliferation of cancer cells can be detected by routine assays, such as by assays that measure the uptake of radiolabeled thymidine. Alternatively, cell viability can be measured by assays that measure lactate dehydrogenase (LDH), a stable cytosolic enzyme that is released upon cell lysis, or by the release of [$^{51}$Cr] upon cell lysis. In one embodiment, necrosis measured by the ability or inability of a cell to take up a dye such as neutral red, trypan blue, or ALAMAR™ blue (Page et al., 1993, Intl. J. of Oncology 3:473 476). In such an assay, the cells are incubated in media containing the dye, the cells are washed, and the remaining dye, reflecting cellular uptake of the dye, is measured spectrophotometrically.

In another embodiment, the dye is sulforhodamine B (SRB), whose binding to proteins can be used as a measure of cytotoxicity (Skehan et al., 1990, J. Nat'l Cancer Inst. 82:1107 12). In yet another embodiment, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55 63).

In other embodiments, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (see, e.g., Piazza et al., 1995, Cancer Research 55:3110 16). Features of this method include collecting both floating and attached cells, identification of the optimal treatment times and dose range for observing apoptosis, and identification of optimal cell culture conditions.

In another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals). In yet another embodiment, apoptosis can be observed morphologically.

Cancer cell lines on which such assays can be performed are well known to those of skill in the art. Apoptosis, necrosis and proliferation assays can also be performed on primary cells, e.g., a tissue explant.

In a specific embodiment, the proliferation or viability of cancer cells contacted with an Immunostimulating Therapeutic Agent or a composition comprising an Immunostimulating Therapeutic Agent is inhibited or reduced by at least 2 fold, preferably at least 2.5 fold, at least 3 fold, at least 4 fold, at least 5 fold, at least 7 fold, or at least 10 fold, or 2 to 5 fold, 2 to 10 fold, 4 to 7 fold, 4 to 10 fold, or 7 to 10 fold relative to the proliferation of the cancer cells when contacted with a negative control (e.g., PBS) as measured using assays well known in the art, e.g., cell proliferation assays using CSFE, BrdU, and $^3$H-Thymidine incorporation. In another embodiment, the proliferation of cancer cells contacted with an Immunostimulating Therapeutic Agent or a composition comprising an Immunostimulating Therapeutic Agent is inhibited or reduced by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or 25% to 65%, 40% to 65%, 50% to 90%, 65% to 90%, 70% to 90%, 75% to 95%, 80% to 95%, or 85% to 99% relative to cancer cells contacted with a negative control (e.g., PBS) as measured using assays well known in the art, e.g., cell proliferation assays using CSFE, BrdU, and $^3$H-Thymidine incorporation, or those assays described above.

In specific embodiments, the administration of an Immunostimulating Therapeutic Agent or a composition thereof to a subject with cancer (in some embodiments, an animal model for cancer) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) an increase in the survival rate of patients; (xiii) a decrease in hospitalization rate; (ix) the prevention of the development or onset of one or more symptoms associated with cancer; (x) the reduction in the number of symptoms associated with cancer; (xi) an increase in symptom-free survival of cancer patients; (xii) improvement in quality of life as assessed by methods well known in the art; (xiii) the prevention in the recurrence of a tumor; (xiv) the regression of tumors and/or one or more symptoms associated therewith;

(xvii) the inhibition of the progression of tumors and/or one or more symptoms associated therewith; (xviii) a reduction in the growth of a tumor; (xix) a decrease in tumor size (e.g., volume or diameter); (xx) a reduction in the formation of a newly formed tumor; (xxi) eradication, removal, or control of primary, regional and/or metastatic tumors; (xxii) a decrease in the number or size of metastases; (xxiii) a reduction in mortality; (xxiv) an increase in the tumor-free survival rate of patients; (xxv) an increase in relapse free survival; (xxvi) an increase in the number of patients in remission; (xxvii) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxviii) an increase in the length of remission in patients.

In a specific embodiment, the administration of an Immunostimulating Therapeutic Agent or a composition thereof to a subject with cancer (in some embodiments, an animal model for cancer) inhibits or reduces the growth of a tumor by at least 2 fold, preferably at least 2.5 fold, at least 3 fold, at least 4 fold, at least 5 fold, at least 7 fold, or at least 10 fold or 2 to 5 fold, 2 to 10 fold, 4 to 7 fold, 4 to 10 fold, or 7 to 10 fold relative to the growth of a tumor in a subject with cancer (in some embodiments, in the same animal model for cancer) administered a negative control (e.g., PBS) as measured using assays well known in the art. In another embodiment, the administration of an Immunostimulating Therapeutic Agent or a composition comprising an Immunostimulating Therapeutic Agent to a subject with cancer (in some embodiments, an animal model for cancer) inhibits or reduces the growth of a tumor by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or 25% to 65%, 40% to 65%, 50% to 90%, 65% to 90%, 70% to 90%, 75% to 95%, 80% to 95%, or 85% to 99% relative to the growth of a tumor in a subject with cancer (in some embodiments, in the same animal model for cancer) administered a negative control (e.g., PBS) as measured using assays well known in the art.

In a specific embodiment, the administration of an Immunostimulating Therapeutic Agent or a composition comprising an Immunostimulating Therapeutic Agent to a subject with cancer (in some embodiments, an animal model for cancer) reduces the size of a tumor by at least 2 fold, preferably at least 2.5 fold, at least 3 fold, at least 4 fold, at least 5 fold, at least 7 fold, or at least 10 fold, or 2 to 5 fold, 2 to 10 fold, 4 to 7 fold, 4 to 10 fold, or 7 to 10 fold relative to the growth of a tumor in a subject with cancer (in some embodiments, the same animal model for cancer) administered a negative control (e.g., PBS) as measured using assays well known in the art. In another embodiment, the administration of an Immunostimulating Therapeutic Agent or a composition comprising an Immunostimulating Therapeutic Agent to a subject with (in some embodiments, an animal model for cancer) reduces the size of a tumor by at least 10%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, or 10% to 25%, 25% to 50%, 25% to 75%, 50% to 75%, 75% to 95%, 75% to 100% relative to the growth of a tumor in a subject with cancer (in some embodiments, the same animal model for cancer) administered a negative control (e.g., PBS) as measured using assays well known in the art.

In certain embodiments, two or more different Immunostimulating Therapeutic Agents are administered to a subject. In some embodiments, an Immunostimulating Therapeutic Agent is administered to a subject in combination with one or more other therapies, e.g., anti-cancer agents, cytokines, cellular vaccines or anti-hormonal agents, to treat and/or manage cancer. Non-limiting examples of other therapies is provided in Section 5.7 et seq., infra. In one embodiment, the combination of an Immunostimulating Therapeutic Agent and one or more other therapies provides an additive therapeutic effect relative to the therapeutic effects of the Immunostimulating Therapeutic Agent alone or the one or more other therapies alone. In one embodiment, the combination of an Immunostimulating Therapeutic Agent and one or more other therapies provides more than an additive therapeutic effect relative to the therapeutic effects of the Immunostimulating Therapeutic Agent alone or the one or more other therapies alone. In one embodiment, the combination of an Immunostimulating Therapeutic Agent and one or more other therapies provides a synergistic therapeutic effect relative to the therapeutic effects of the Immunostimulating Therapeutic Agent alone or the one or more other therapies alone.

In a specific embodiment, an Immunostimulating Therapeutic Agent is administered in combination with radiation therapy comprising, e.g., the use of x-rays, gamma rays and other sources of radiation to destroy the cancer cells. In specific embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass. In one aspect, the Immunostimulating Therapeutic Agent can activate or enhance the immune function for response in a cancer patient with a compromised immune system due to anti-cancer therapy. In another embodiment, an Immunostimulating Therapeutic Agent is administered to a subject in combination with chemotherapy. In an embodiment, an Immunostimulating Therapeutic Agent can be used before, during or after radiation therapy or chemotherapy. In another embodiment, an Immunostimulating Therapeutic Agent can be used before, during or after surgery. In another embodiment, an Immunostimulating Therapeutic Agent is administered to a subject in combination with one or more other therapies that target different immunostimulatory pathways. In one embodiment the Immunostimulating Therapeutic Agent is administered to a subject in combination with B7-DC-Ig (e.g., Amp-224 (Amplimmune, Rockville, Md.)), anti-PD-1, anti-B7-1, anti-B7-2, or anti-CTLA4 (Ipilimumab or Tremelimumab). In another embodiment, an Immunostimulating Therapeutic Agent is administered to a subject in combination with agonistic anti-CD28 (TGN1412). In another embodiment, an Immunostimulating Therapeutic Agent is administered to a subject in combination with cyclophosphamide or a derivative thereof. In a specific embodiment, an Immunostimulating Therapeutic Agent is administered to a subject in combination with low dose TGN1412. In another embodiment, an Immunostimulating Therapeutic Agent is administered to a subject in combination with an anti-hormonal agent, an aromatase inhibitor, a ribozyme, a vaccine, etc.

Non-limiting examples of anti-cancer agents that can be administered to a subject in combination with an Immunostimulating Therapeutic Agent are anti-hormonal agents that act to regulate or inhibit hormone action on tumors, such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN®V exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELX® rmRH; Vinorelbine and Esperamicins (see U.S. Pat. No. 4,675,187), and pharmaceutically acceptable salts, acids or derivatives of any of the above. Other anti-cancer agents include cyclophosphamide. Cyclophosphamide (CTX, Cytoxan®, or Neosar®) is an oxazaphosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety. In other embodiments, the anti-cancer agent reduces the activity and/or number of regulatory T lymphocytes (T-regs), preferably Sunitinib (SUTENT®), anti-TGFβ or Imatinib (GLEEVAC®). Useful anti-cancer agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16), anthracyclines, oxaliplatin, doxorubicin, TLR4 antagonists, and IL-18 antagonists.

5.5.1.1.1 Types of Cancers

Cancers and related disorders that can be prevented, treated, or managed in accordance with the methods described herein include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, and chronic lymphocytic leukemia, hairy cell leukemia; polycythemia vera; lymphomas such as but not limited to Hodgkin's disease, and non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytoma and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungaling (polyploid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma; gallbladder cancers including but not limited to, adenocarcinoma; cholangiocarcinomas including but not limited to, papillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, semi noma, anaplastic, spermatocytic, nonseminoma, embryonal carcinoma, teratoma carcinoma, choriocarcinoma (yolk-sac tumor); prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, and superficial spreading melanoma, nodular melanoma, lentigo malignant melanoma, acral lentiginous melanoma; kidney cancers including but not limited to, renal cell cancer, renal cancer, adenocarcinoma, hypernephroma, fibrosarcoma, and transitional cell cancer (renal pelvis and/or uterer); Wilms' tumor; bladder cancers including but not limited to, transitional cell carcinoma, squamous cell cancer, adenocarcinoma, and carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In one embodiment, the cancer is benign, e.g., polyps and benign lesions. In other embodiments, the cancer is metastatic. The Immunostimulating Therapeutic Agents can be used in the treatment of pre-malignant as well as malignant conditions. Pre-malignant conditions include hyperplasia, metaplasia, and dysplasia. Treatment of malignant conditions includes the treatment of primary as well as metastatic tumors. In a specific embodiment the cancer is melanoma, colon cancer, lung cancer, breast cancer, prostate cancer, cervical cancer, liver cancer, testicular cancer, brain cancer, pancreatic cancer, or renal cancer.

5.5.1.1.2 Patient Population

In some embodiments, Immunostimulating Therapeutic Agents, compositions comprising Immunostimulating Therapeutic Agents, or combination therapies are administered to a subject suffering from or diagnosed with cancer. In other embodiments, Immunostimulating Therapeutic Agents, compositions comprising Immunostimulating Therapeutic Agents, or combination therapies are administered to a subject predisposed or susceptible to developing cancer. In some embodiments, Immunostimulating Therapeutic Agents, compositions comprising Immunostimulating Therapeutic Agents, or combination therapies are administered to a subject that lives in a region where there is a high occurrence rate of cancer. In a specific embodiment, the cancer is characterized by a pre-malignant tumor or a malignant tumor.

In some embodiments, an Immunostimulating Therapeutic Agent, composition comprising an Immunostimulating Therapeutic Agent, or a combination therapy is administered to a mammal. In certain embodiments, an Immunostimulating Therapeutic Agent, composition comprising an Immunostimulating Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an Immunostimulating Therapeutic Agent, composition comprising an Immunostimulating Therapeutic Agent, or a combination therapy is administered to a pet, e.g., a dog or cat. In certain embodiments, an Immunostimulating Therapeutic Agent, composition comprising an Immunostimulating Therapeutic Agent, or a combination therapy is administered to a farm animal or livestock, e.g., pig, cows, horses, chickens, etc.

In certain embodiments, an Immunostimulating Therapeutic Agent, composition comprising an Immunostimulating Therapeutic Agent, or a combination therapy is administered to a human at risk developing cancer. In certain embodiments, an Immunostimulating Therapeutic Agent, composition comprising an Immunostimulating Therapeutic Agent, or a combination therapy is administered to a human with cancer. In certain embodiments, an Immunostimulating Therapeutic Agent, composition comprising an Immunostimulating Therapeutic Agent, or a combination therapy is administered to a human diagnosed with cancer. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Immunostimulating Therapeutic Agent, composition comprising an Immunostimulating Therapeutic Agent, or a combination therapy is administered to a human infant or a premature human infant. In other embodiments, an Immunostimulating Therapeutic Agent, composition comprising an Immunostimulating Therapeutic Agent, or a combination therapy is administered to a human child. In other embodiments, an Immunostimulating Therapeutic Agent, composition comprising an Immunostimulating Therapeutic Agent, or a combination therapy is administered to a human adult. In yet other embodiments, an Immunostimulating Therapeutic Agent, composition comprising an Immunostimulating Therapeutic Agent, or a combination therapy is administered to an elderly human.

In certain embodiments, an Immunostimulating Therapeutic Agent, composition comprising an Immunostimulating Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Immunostimulating Therapeutic Agent, composition comprising an Immunostimulating Therapeutic Agent, or a combination therapy is administered to a subject receiving or recovering from immunosuppressive therapy. In certain embodiments, an Immunostimulating Therapeutic Agent, composition comprising an Immunostimulating Therapeutic Agent, or a combination therapy is administered to a subject that has or is at risk of getting AIDS, a viral infection, or a bacterial infection. In certain embodiments, a subject that is, will or has undergone surgery, chemotherapy and/or radiation therapy. In some embodiments, an Immunostimulating Therapeutic Agent, composition comprising an Immunostimulating Therapeutic Agent, or a combination therapy is administered to a subject that lives in a nursing home, a group home (i.e., a home for 10 or more subjects), or a prison.

In certain embodiments, an Immunostimulating Therapeutic Agent, composition comprising an Immunostimulating Therapeutic Agent, or a combination therapy is administered to a subject that has abnormal levels of expression of one or more of the following: B7-H2, ICOS, CD28, or CTLA-4. In some embodiments, an Immunostimulating Therapeutic Agent, composition comprising an Immunostimulating Therapeutic Agent, or a combination therapy is administered to a subject that has abnormal levels of expression of either B7-H7, B7-H7CR or both.

In some embodiments, a patient is administered an Immunostimulating Therapeutic Agent, composition comprising an Immunostimulating Therapeutic Agent, or a combination therapy is before any adverse effects or intolerance to therapies other than Immunostimulating Therapeutic Agents develops. In some embodiments, Immunostimulating Therapeutic Agents, compositions comprising Immunostimulating Therapeutic Agents, or combination therapies are administered to refractory patients. In a certain embodiment, refractory patient is a patient refractory to a standard anti-cancer therapy. In certain embodiments, a patient with cancer, is refractory to a therapy when the cancer has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with cancer is refractory when a cancerous tumor has not decreased or has increased.

In some embodiments, Immunostimulating Therapeutic Agents, compositions comprising Immunostimulating Therapeutic Agents, or combination therapies are administered to a patient to prevent the onset or reoccurrence of cancer in a patient at risk of developing such cancer. In some embodiments, Immunostimulating Therapeutic Agents, compositions comprising Immunostimulating Therapeutic Agents, or combination therapies are administered to a patient who is susceptible to adverse reactions to conventional therapies.

In some embodiments, one or more Immunostimulating Therapeutic Agents, compositions comprising Immunostimulating Therapeutic Agents, or combination therapies are administered to a patient who has proven refractory to therapies other than Immunostimulating Therapeutic Agents, but are no longer on these therapies. In certain embodiments, the patients being managed or treated in accordance with the methods described herein are patients already being treated with antibiotics, anti-cancer agents, or other biological therapy/immunotherapy. Among these patients are refractory patients, patients who are too young for conventional therapies, and patients with reoccurring viral infections despite management or treatment with existing therapies.

In some embodiments, the subject being administered one or more Immunostimulating Therapeutic Agents, compositions comprising Immunostimulating Therapeutic Agents, or combination therapies has not received a therapy prior to the administration of the Immunostimulating Therapeutic Agents, compositions comprising Immunostimulating Therapeutic Agents, or combination therapies. In other embodiments, one or more Immunostimulating Therapeutic Agents, compositions comprising Immunostimulating Therapeutic Agents, or combination therapies are administered to a subject who has received a therapy prior to administration of one or more Immunostimulating Therapeutic Agents, compositions comprising Immunostimulating Therapeutic Agents, or combination therapies. In some embodiments, the subject administered an Immunostimulating Therapeutic Agent or a composition comprising an Immunostimulating Therapeutic Agent was refractory to a prior therapy or experienced adverse side effects to the prior therapy or the prior therapy was discontinued due to unacceptable levels of toxicity to the subject.

5.5.1.2 Infectious Diseases

In a specific aspect, presented herein are methods for preventing, treating, and/or managing an infectious disease, comprising administering to a subject in need thereof an effective amount of an Immunostimulating Therapeutic Agent or a composition thereof. In a specific embodiment, an Immunostimulating Therapeutic Agent or a composition thereof is the only active agent administered to a subject.

Infectious diseases that can be treated, prevented, and/or managed by Immunostimulating Therapeutic Agents are caused by infectious agents including but not limited to bacteria, fungi, protozae, and viruses. Viral diseases that can be prevented, treated and/or managed in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented, treated and/or managed in accordance with the methods described herein include, but are not limited to, mycobacteria *rickettsia*, mycoplasma, *neisseria, S. pneumonia, Borrelia burgdorferi* (Lyme disease), *Bacillus antracis* (anthrax), tetanus, *streptococcus, staphylococcus*, mycobacterium, pertissus, cholera, plague, diptheria, chlamydia, *S. aureus* and *legionella*.

Protozoal diseases caused by protozoa that can be prevented, treated and/or managed in accordance with the methods described herein include, but are not limited to, *leishmania, kokzidioa, trypanosoma schistosoma* or malaria. Parasitic diseases caused by parasites that can be prevented, treated and/or managed in accordance with the methods described herein include, but are not limited to, chlamydia and *rickettsia*.

Fungal infections that can be prevented, treated and/or managed in accordance with the methods described herein include, but are not limited to, *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Crypto-*

*coccus neoformans* infection, fungal peritonitis, *Curvularia geniculata* infection, staphylococcal endophthalmitis, sporotrichosis, and dermatophytosis.

In certain embodiments, administering an Immunostimulating Therapeutic Agent or a composition thereof to a subject (in some embodiments, an animal model) achieves one, two, three, four, or more of the following effects: (i) reduction or amelioration the severity of an infectious disease or symptom associated therewith; (ii) reduction in the duration of an infectious disease or symptom associated therewith; (iii) prevention of the progression of an infectious disease or symptom associated therewith; (iv) regression of an infectious disease or symptom associated therewith; (v) prevention of the development or onset of an infectious disease or symptom associated therewith; (vi) prevention of the recurrence of an infectious disease or symptom associated therewith; (vii) reduction or prevention of the spread of an infectious agent from one cell to another cell, one tissue to another tissue, or one organ to another organ; (viii) prevention or reduction of the spread/transmission of an infectious agent from one subject to another subject; (ix) reduction in organ failure associated with an infectious disease; (x) reduction in the hospitalization of a subject; (xi) reduction in the hospitalization length; (xii) an increase in the survival of a subject with an infectious disease; (xiii) elimination of an infectious disease; (xiii) inhibition or reduction in replication of an infectious agent; (xiv) inhibition or reduction in the entry of an infectious agent into a cell(s); (xv) inhibition or reduction of replication of the genome of an infectious agent; (xvi) inhibition or reduction in the synthesis of infectious agent proteins; (xvii) inhibition or reduction in the assembly of infectious agents; (xviii) inhibition or reduction in the release of infectious agents from a cell(s); (xviii) reduction in the number or titer of an infectious agent; (xix) the reduction in the number of symptoms associated with an infectious disease; (xx) enhancement, improvement, supplementation, complementation, or augmentation of the prophylactic or therapeutic effect(s) of another therapy; and (xxi) prevention of the onset or progression of a secondary infection associated with an infectious disease.

In certain embodiments, administering an Immunostimulating Therapeutic Agent or a composition comprising an Immunostimulating Therapeutic Agent to a subject (in some embodiments, an animal model) infected with an infectious agent inhibits or reduces replication of the infectious agent by at least 20%, 25%, 30%, 35%, 40%, 45%, 50%, 55%, 60%, 65%, 70%, 75%, 80%, 85%, 90%, or 95%, or 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control (e.g., PBS) as determined using an assay described herein or others known to one of skill in the art. In some embodiments, administering an Immunostimulating Therapeutic Agent or a composition comprising an Immunostimulating Therapeutic Agent to a subject (in some embodiments, an animal model) infected with an infectious agent inhibits or reduces replication of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control (e.g., PBS) as determined using an assay described herein or others known to one of skill in the art. In other embodiments, administering an Immunostimulating Therapeutic Agent or a composition comprising an Immunostimulating Therapeutic Agent to a subject (in some embodiments, an animal model) infected with an infectious agent inhibits or reduces replication of the infectious agent by 1 log, 1.5 logs, 2 logs, 2.5 logs, 3 logs, 3.5 logs, 4 logs, 5 logs or more relative to a negative control (e.g., PBS) as determined using an assay described herein or others known to one of skill in the art.

In certain embodiments, administering an Immunostimulating Therapeutic Agent or a composition comprising an Immunostimulating Therapeutic Agent to a subject (in some embodiments, an animal model) infected with an infectious agent reduces the titer of the infectious agent by at least 20%, 25%, 30%, 35%, 40%, 45%, 50%, 55%, 60%, 65%, 70%, 75%, 80%, 85%, 90%, or 95%, or 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control (e.g., PBS) as determined using an assay described herein or others known to one of skill in the art. In some embodiments, administering an Immunostimulating Therapeutic Agent or a composition comprising an Immunostimulating Therapeutic Agent to a subject (in some embodiments, an animal model) infected with an infectious agent reduces the titer of the infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control (e.g., PBS) as determined using an assay described herein or others known to one of skill in the art. In other embodiments, administering an Immunostimulating Therapeutic Agent or a composition comprising an Immunostimulating Therapeutic Agent to a subject (in some embodiments, an animal model) infected with an infectious agent reduces the titer of the infectious agent by 1 log, 1.5 logs, 2 logs, 2.5 logs, 3 logs, 3.5 logs, 4 logs, 5 logs or more relative to a negative control (e.g., PBS) as determined using an assay described herein or others known to one of skill in the art.

In certain embodiments, two or more different Immunostimulating Therapeutic Agents are administered to a subject. In some embodiments, an Immunostimulating Therapeutic Agent is administered to a subject in combination with one or more other therapies. Non-limiting examples of other therapies that can be used in combination with Immunostimulating Therapeutic Agents are described in Sections 5.7 et seq. In one embodiment, the combination of an Immunostimulating Therapeutic Agent and one or more other therapies provides an additive therapeutic effect relative to the therapeutic effects of the Immunostimulating Therapeutic Agent alone or the one or more other therapies alone. In one embodiment, the combination of an Immunostimulating Therapeutic Agent and one or more other therapies provides more than an additive therapeutic effect relative to the therapeutic effects of the Immunostimulating Therapeutic Agent alone or the one or more other therapies alone. In one embodiment, the combination of an Immunostimulating Therapeutic Agent and one or more other therapies provides a synergistic therapeutic effect relative to the therapeutic effect of the Immunostimulating Therapeutic Agent alone or the one or more other therapies alone.

In a specific embodiment, an Immunostimulating Therapeutic Agent is administered to a subject in combination with one or more antibiotics. In another embodiment, an Immunostimulating Therapeutic Agent is administered in combination with one or more anti-virals. In another embodiment, an Immunostimulating Therapeutic Agent is administered in combination with one or more anti-fungals. In another embodiment, an Immunostimulating Therapeutic Agent is administered in combination with B7-DC Ig, (e.g., Amp-224 (Amplimmune; Rockville, Md.)).

5.5.1.2.1 Patient Population

In some embodiments, Immunostimulating Therapeutic Agents, compositions comprising Immunostimulating Therapeutic Agents, or combination therapies are administered to a subject suffering from an infectious disease caused by infectious agents including, but not limited to bacteria, fungi, protozae, and viruses. In certain embodiments, Immunostimulating Therapeutic Agents, compositions comprising Immunostimulating Therapeutic Agents, or combination therapies are administered to a subject diagnosed as having an infectious disease caused by infectious agents including, but not limited to bacteria, fungi, protozae, and viruses. In other embodiments, Immunostimulating Therapeutic Agents, compositions comprising Immunostimulating Therapeutic Agents, or combination therapies are administered to a subject predisposed or susceptible to an infectious disease. In some embodiments, Immunostimulating Therapeutic Agents, compositions comprising Immunostimulating Therapeutic Agents, or combination therapies are administered to a subject that lives in a region where there has been or might be an outbreak with infections by infectious agents. In some embodiments, the infection is a latent infection. In other embodiments, the infection by the infectious agent is an active infection. In certain embodiments, the infection by the infectious agent is an acute infection. In yet other embodiments, the infection by the infectious agent is a chronic infection.

In some embodiments, an Immunostimulating Therapeutic Agent, composition comprising an Immunostimulating Therapeutic Agent, or a combination therapy is administered to a mammal. In certain embodiments, an Immunostimulating Therapeutic Agent, composition comprising an Immunostimulating Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In certain embodiments, an Immunostimulating Therapeutic Agent, composition comprising an Immunostimulating Therapeutic Agent, or a combination therapy is administered to a pet, e.g., a dog or cat. In certain embodiments, an Immunostimulating Therapeutic Agent, composition comprising an Immunostimulating Therapeutic Agent, or a combination therapy is administered to a farm animal or livestock, e.g., pig, cows, horses, chickens, etc. In certain embodiments, an Immunostimulating Therapeutic Agent, composition comprising an Immunostimulating Therapeutic Agent, or a combination therapy is administered to a bird, e.g., ducks or chicken.

In certain embodiments, an Immunostimulating Therapeutic Agent, composition comprising an Immunostimulating Therapeutic Agent, or a combination therapy is administered to a human at risk of an infectious disease. In certain embodiments, an Immunostimulating Therapeutic Agent, composition comprising an Immunostimulating Therapeutic Agent, or a combination therapy is administered to a human with an infectious disease. In some embodiments, an Immunostimulating Therapeutic Agent, composition comprising an Immunostimulating Therapeutic Agent, or a combination therapy is administered to a human diagnosed as having an infectious disease. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Immunostimulating Therapeutic Agent, composition comprising an Immunostimulating Therapeutic Agent, or a combination therapy is administered to a human infant or premature human infant. In other embodiments, an Immunostimulating Therapeutic Agent, composition comprising an Immunostimulating Therapeutic Agent, or a combination therapy is administered to a human child. In other embodiments, an Immunostimulating Therapeutic Agent, composition comprising an Immunostimulating Therapeutic Agent, or a combination therapy is administered to a human adult. In yet other embodiments, an Immunostimulating Therapeutic Agent, composition comprising an Immunostimulating Therapeutic Agent, or a combination therapy is administered to an elderly human.

In certain embodiments, an Immunostimulating Therapeutic Agent, composition comprising an Immunostimulating Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Immunostimulating Therapeutic Agent, composition comprising an Immunostimulating Therapeutic Agent, or a combination therapy is administered to a subject receiving or recovering from immunosuppressive therapy. In certain embodiments, an Immunostimulating Therapeutic Agent, composition comprising an Immunostimulating Therapeutic Agent, or a combination therapy is administered to a subject that has or is at risk of getting cancer, AIDS, another infection, or a bacterial infection. In certain embodiments, a subject that is, will or has undergone surgery, chemotherapy and/or radiation therapy. In certain embodiments, an Immunostimulating Therapeutic Agent, composition comprising an Immunostimulating Therapeutic Agent, or a combination therapy is administered to a subject that has cystic fibrosis, pulmonary fibrosis, or another disease which makes the subject susceptible to an infection. In certain embodiments, an Immunostimulating Therapeutic Agent, composition comprising an Immunostimulating Therapeutic Agent, or a combination therapy is administered to a subject that has, will have or had a tissue transplant. In some embodiments, an Immunostimulating Therapeutic Agent, composition comprising an Immunostimulating Therapeutic Agent, or a combination therapy is administered to a subject that lives in a nursing home, a group home (i.e., a home for 10 or more subjects), or a prison. In some embodiments, an Immunostimulating Therapeutic Agent, composition comprising an Immunostimulating Therapeutic Agent, or a combination therapy is administered to a subject that attends school (e.g., elementary school, middle school, junior high school, high school or university) or daycare. In some embodiments, an Immunostimulating Therapeutic Agent, composition comprising an Immunostimulating Therapeutic Agent, or a combination therapy is administered to a subject that works in the healthcare area, such as a doctor or a nurse, or in a hospital. In certain embodiments, an Immunostimulating Therapeutic Agent, composition comprising an Immunostimulating Therapeutic Agent, or a combination therapy is administered to a subject that is pregnant or will become pregnant.

In certain embodiments, an Immunostimulating Therapeutic Agent, composition comprising an Immunostimulating Therapeutic Agent, or a combination therapy is administered to a subject that has abnormal levels of expression of one or more of the following: B7-H2, ICOS, CD28, or CTLA-4. In some embodiments, an Immunostimulating Therapeutic Agent, composition comprising an Immunostimulating Therapeutic Agent, or a combination therapy is administered to a subject that has abnormal levels of expression of either B7-H7, B7-H7CR or both.

In some embodiments, a patient is administered an Immunostimulating Therapeutic Agent, composition comprising an Immunostimulating Therapeutic Agent, or a combination therapy before any adverse effects or intolerance to therapies other than Immunostimulating Therapeutic Agents develops. In some embodiments, Immunostimulating Therapeutic Agents, compositions comprising Immunostimulating Therapeutic Agents, or combination therapies are administered to refractory patients. In a certain embodiment, refractory patient is a patient refractory to a standard therapy. In certain embodiments, a patient with an infectious disease is refractory to a therapy when the infectious disease has not significantly been eradicated and/or the symptoms have not been significantly alleviated. The determination of whether a patient is refractory can be made either in vivo or in vitro by any method known in the art for assaying the effectiveness of a treatment of an infectious disease, using art-accepted meanings of "refractory" in such a context. In various embodiments, a patient with an infection is refractory when replication of the infectious agent has not decreased or has increased.

In some embodiments, Immunostimulating Therapeutic Agents, compositions comprising Immunostimulating Therapeutic Agents, or combination therapies are administered to a patient to prevent the onset or reoccurrence of an infectious disease in a patient at risk of developing such a disease. In some embodiments, Immunostimulating Therapeutic Agents, compositions comprising Immunostimulating Therapeutic Agents, or combination therapies are administered to a patient who are susceptible to adverse reactions to conventional therapies.

In some embodiments, one or more Immunostimulating Therapeutic Agents, compositions comprising Immunostimulating Therapeutic Agents, or combination therapies are administered to a patient who has proven refractory to therapies other than Immunostimulating Therapeutic Agents, but are no longer on these therapies. In certain embodiments, the patients being managed or treated in accordance with the methods of this invention are patients already being treated with antibiotics, anti-virals, anti-fungals, or other biological therapy/immunotherapy. Among these patients are refractory patients, patients who are too young for conventional therapies, and patients with reoccurring viral infections despite management or treatment with existing therapies.

In some embodiments, the subject being administered one or more Immunostimulating Therapeutic Agents, compositions comprising Immunostimulating Therapeutic Agents, or combination therapies has not received a therapy prior to the administration of the Immunostimulating Therapeutic Agents, compositions comprising Immunostimulating Therapeutic Agents, or combination therapies. In other embodiments, one or more Immunostimulating Therapeutic Agents, compositions comprising Immunostimulating Therapeutic Agents, or combination therapies are administered to a subject who has received a therapy prior to administration of one or more Immunostimulating Therapeutic Agents or compositions comprising one or more Immunostimulating Therapeutic Agents, or combination therapies. In some embodiments, the subject administered an Immunostimulating Therapeutic Agent or a composition comprising an Immunostimulating Therapeutic Agent was refractory to a prior therapy or experienced adverse side effects to the prior therapy or the prior therapy was discontinued due to unacceptable levels of toxicity to the subject.

5.6 PROPHYLACTIC AND THERAPEUTIC USES OF THERAPEUTIC AGENTS THAT SUPPRESS IMMUNE FUNCTION

5.6.1 Suppressing Immune Function

In one aspect, presented herein are methods for suppressing one or more immune system functions or responses in a subject function in a subject, comprising administering to a subject in need thereof an Inhibitory Therapeutic Agent or a composition thereof. In a specific embodiment, presented herein are methods for preventing, treating, and/or managing diseases in which it is desirable to suppress immune function, comprising administering to a subject in need thereof an Inhibitory Therapeutic Agent or a composition thereof. In specific embodiments, an Inhibitory Therapeutic Agent can be administered to a subject in combination with one or more other therapies to suppress immune function or response.

Non-limiting examples of diseases that can be prevented, treated, or managed by suppressing immune function include, but are not limited to, autoimmune disease, inflammatory disorders, graft versus host disease, and transplant rejection.

In a specific embodiment, an Inhibitory Therapeutic Agent suppresses one or more immune functions or responses in a subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the immune function in a subject not administered the Immunostimulating Therapeutic Agent using assays well known in the art, e.g., ELISPOT, ELISA, and cell proliferation assays. In a specific embodiment, the immune function is cytokine release (e.g., interferon-gamma, IL-2, IL-5, or IL-12). In one embodiment, the immune function is NK cell proliferation, which can be assayed, e.g., by flow cytometry to detect the number of cells expressing markers of NK cells (e.g., CD56). In one embodiment, the immune function is T cell proliferation, which can be assayed, e.g., by flow cytometry to detect the number of cells expressing markers of T cells (e.g., CD3, CD4, or CD8). In another embodiment, the immune function is antibody production, which can be assayed, e.g., by ELISA. In some embodiments, the immune function is effector function, which can be assayed, e.g., by a cytotoxicity assay or other assays well known in the art. In another embodiment, the immune function is a Th1 response. In another embodiment, the immune function is a Th2 response. In another embodiment, the immune function is a Th17 response. In another embodiment, the immune function is a Th22 response. In another embodiment, the immune function is a Treg response.

In specific embodiments, non-limiting examples of immune functions that may be suppressed by the Inhibitory Therapeutic Agent are proliferation/expansion of lymphocytes (e.g., increase in the number of lymphocytes), inhibition of apoptosis of lymphocytes, activation of dendritic cells (or antigen presenting cells), and antigen presentation. In particular embodiments, an immune function suppressed by the Inhibitory Therapeutic Agent is proliferation/expansion in the number of or activation of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, CD122$^+$ T cells, Tregs, or natural killer cells (NK cells). In one embodiment, the Inhibitory Therapeutic Agent suppresses the proliferation/expansion or number of lymphocyte progenitors. In some embodiments, an Inhibitory Therapeutic Agent decreases the number of CD4$^+$ T cells (e.g., Th1 and Th2 helper T cells), CD8$^+$ T cells (e.g., cytotoxic T lymphocytes, alpha/beta T cells, and gamma/delta T cells), B cells (e.g., plasma cells), memory T cells, memory B cells, dendritic cells (immature or mature), antigen presenting cells, macrophages, mast cells, natural killer T cells (NKT cells), tumor-resident T cells, CD122$^+$ T cells, or natural killer cells (NK cells) by approximately at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative a negative control (e.g., number of the respective cells not treated, cultured, or contacted with an Inhibitory Therapeutic Agent).

In certain embodiments, some functions of the immune system, such as Treg proliferation or activity, are increased when the immune response is decreased.

Various autoimmune and inflammatory diseases that can be prevented, treated and/or managed are provided below.

In certain embodiments, an Inhibitory Therapeutic Agent enhances, activates or induces one or more signal transduction pathways mediated by CTLA-4 binding to one or more of its ligands (e.g., B7-1, B7-2, or B7-H2). In some embodiments, an Inhibitory Therapeutic Agent inhibits or reduces the binding of native CTLA-4 to one or more of its ligands (e.g., B7-1, B7-2, or B7-H2) as described herein. In a specific embodiment, an Inhibitory Therapeutic Agent is an agonistic B7-H2-Ig polypeptide or derivative thereof described herein.

In certain embodiments, an Inhibitory Therapeutic Agent inhibits or reduces one or more signal transduction pathways mediated by CD28 binding to one or more of its ligands (e.g., B7-1, B7-2 or B7-H2). In some embodiments, an Inhibitory Therapeutic Agent inhibits or reduces the binding of native CD28 to one or more of its ligands (e.g., B7-1, B7-2, or B7-H2) as described herein. In a specific embodiment, an Inhibitory Therapeutic Agent is an antagonistic B7-H2-Ig polypeptide or derivative thereof described herein.

In certain embodiments, an Inhibitory Therapeutic Agent inhibits or reduces one or more signal transduction pathways mediated by ICOS binding to one or more of its ligands (e.g., B7-H2). In some embodiments, an Inhibitory Therapeutic Agent inhibits or reduces the binding of native ICOS to one or more of its ligands (e.g., B7-H2) as described herein. In a specific embodiment, an Inhibitory Therapeutic Agent is an antagonistic B7-H2-Ig polypeptide or derivative thereof described herein.

5.6.1.1 Autoimmune and Inflammatory Disorders

In a specific embodiment, presented herein is a method for treating, preventing and/or managing an autoimmune disorder or inflammatory disorder in a subject, comprising administering to a subject in need thereof an effective amount of an Inhibitory Therapeutic Agent or a composition thereof. In another embodiment, presented herein is a method for reducing inflammation in a subject, comprising administering to a subject in need thereof an effective amount of an Inhibitory Therapeutic Agent or a composition thereof. Non-limiting examples of autoimmune disorders and inflammatory disorders include transplant rejection and graft versus host disease (GVHD). GVHD occurs when a donor's immune cells (e.g., donor's T cells) attack cells in the recipient subject's body. Transplant rejection occurs when a transplanted organ or tissue fails to be accepted by the body of the transplant recipient. In general, the transplant rejection is due to the immune system of the recipient (e.g., recipient's T cells) attacking the transplanted organ or tissue.

In certain embodiments, administering an Inhibitory Therapeutic Agent or a composition thereof to a subject (in some embodiments, an animal model) achieves one, two, three, four, or more of the following effects: (i) reduction or amelioration the severity of an autoimmune or inflammatory disorder or symptom associated therewith; (ii) reduction in the duration of a symptom associated with an autoimmune or inflammatory disorder; (iii) prevention of the progression of an autoimmune or inflammatory disorder, or symptom associated therewith; (iv) regression of an autoimmune or inflammatory disorder, or symptom associated therewith; (v) prevention of the development or onset of a symptom associated with an autoimmune or inflammatory disorder; (vi) prevention of the recurrence of a symptom associated with an autoimmune or inflammatory disorder; (vii) reduction in organ failure associated with an autoimmune or inflammatory disorder; (viii) reduction in the hospitalization of a subject; (ix) reduction in the hospitalization length; (x) an increase in the survival of a subject with an autoimmune or inflammatory disorder; (xi) a reduction in the number of symptoms associated with an autoimmune or inflammatory disorder; (xii) a reduction in inflammation of inflammatory cells; (xiii) a reduction in inflammatory cytokines; (xiv) a reduction in inflammation associated with an autoimmune or inflammatory disorder; (xv) improve life expectancy; (xvi) increase symptom-free survival; (xvii) increase the length of symptom-free remission; and/or (xviii) an enhancement, improvement, supplementation, complementation, or augmentation of the prophylactic or therapeutic effect(s) of another therapy.

In a specific embodiment, administering an Inhibitory Therapeutic Agent or composition comprising an Inhibitory Therapeutic Agent to a subject (in some embodiments, an animal model) reduces the inflammation in an subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to the inflammation in an subject not administered the Inhibitory Therapeutic Agent using methods known in the art. For example, reduction in inflammation can be measured by the reduction in cytokine secretion (e.g., tumor necrosis factor alpha, interferon gamma). In a specific embodiment, administering an Inhibitory Therapeutic Agent or composition comprising an Inhibitory Therapeutic Agent to a subject (in some embodiments, an animal model) reduces inflammatory cytokine production and/or secretion in an subject by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10%, or in the range of between 10% to 25%, 25% to 50%, 50% to 75%, or 75% to 95% relative to inflammatory cytokine production and/or secretion in an subject not administered the Inhibitory Therapeutic Agent using methods known in the art.

In other embodiments, an Inhibitory Therapeutic Agent can be administered in combination with one or more other therapies to suppress immune function or response in a subject. In certain embodiments, two or more different Immunostimulating Therapeutic Agents are administered to a subject. In some embodiments, an Immunostimulating Therapeutic Agent is administered to a subject in combination with one or more other therapies. Various anti-inflammatory agents known in the art can be used in combination with Inhibitory Therapeutic Agents. See Section 5.7 et seq. for examples of therapies. In certain embodiments, an Inhibitory Therapeutic Agent is administered in combination with CTLA-4-Ig (e.g., abatacept, belatacept), an anti-TNF alpha antibody (e.g., Remicade), or TNFR-Ig (e.g., Enbrel).

5.6.1.1.1 Types of Diseases

Examples of autoimmune disorders that can be prevented, treated and/or managed in accordance with the methods described herein include, but are not limited to, celiac (coeliac disease), alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections. Some autoimmune disorders are associated with an inflammatory condition. Thus, there is overlap between what is considered an autoimmune disorder and an inflammatory disorder. Therefore, some autoimmune disorders may also be characterized as inflammatory disorders.

5.6.1.1.2 Patient Population

In some embodiments, Inhibitory Therapeutic Agents, compositions comprising Inhibitory Therapeutic Agents, or combination therapies are administered to a subject suffering from an autoimmune disease or inflammatory disorder. In other embodiments, Inhibitory Therapeutic Agents, compositions comprising Inhibitory Therapeutic Agents, or combination therapies are administered to a subject predisposed or susceptible to developing an autoimmune disease or inflammatory disorder.

In certain embodiments, an Inhibitory Therapeutic Agent, composition comprising an Inhibitory Therapeutic Agent, or a combination therapy is administered to a mammal. In specific embodiments, an Inhibitory Therapeutic Agent, composition comprising an Inhibitory Therapeutic Agent, or a combination therapy is administered to a mammal which is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In certain embodiments, an Inhibitory Therapeutic Agent, composition comprising an Inhibitory Therapeutic Agent, or a combination therapy is administered to a human at risk developing an autoimmune disease or inflammatory disorder. In certain embodiments, an Inhibitory Therapeutic Agent, composition comprising an Inhibitory Therapeutic Agent, or a combination therapy is administered to a human with an autoimmune disease or inflammatory disorder. In certain embodiments, an Inhibitory Therapeutic Agent, composition comprising an Inhibitory Therapeutic Agent, or a combination therapy is administered to a human diagnosed has having an autoimmune disease or inflammatory disorder. In certain embodiments, the patient is a human 0 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, an Inhibitory Therapeutic Agent, composition comprising an Inhibitory Therapeutic Agent, or a combination therapy is administered to a human infant or premature human infant. In other embodiments, an Inhibitory Therapeutic Agent, composition comprising an Inhibitory Therapeutic Agent, or a combination therapy is administered to a human child. In other embodiments, an Inhibitory Therapeutic Agent, composition comprising an Inhibitory Therapeutic Agent, or a combination therapy is administered to a human adult. In yet other embodiments, an Inhibitory Therapeutic Agent, composition comprising an Inhibitory Therapeutic Agent, or a combination therapy is administered to an elderly human.

In certain embodiments, an Inhibitory Therapeutic Agent, composition comprising an Inhibitory Therapeutic Agent, or a combination therapy is administered to a pet, e.g., a dog or cat. In certain embodiments, an Inhibitory Therapeutic Agent, composition comprising an Inhibitory Therapeutic Agent, or a combination therapy is administered to a farm animal or livestock, e.g., pig, cows, horses, chickens, etc.

In certain embodiments, an Inhibitory Therapeutic Agent, composition comprising an Inhibitory Therapeutic Agent, or a combination therapy is administered to a primate, preferably a human, or another mammal, such as a pig, cow, horse, sheep, goat, dog, cat and rodent, in an immunocompromised state or immunosuppressed state or at risk for becoming immunocompromised or immunosuppressed. In certain embodiments, an Inhibitory Therapeutic Agent, composition comprising an Inhibitory Therapeutic Agent, or a combination therapy is administered to a subject receiving or recovering from immunosuppressive therapy. In certain embodiments, an Inhibitory Therapeutic Agent, composition comprising an Inhibitory Therapeutic Agent, or a combination therapy is administered to a subject that has or is at risk of getting AIDS, a viral infection, or a bacterial infection. In certain embodiments, a subject that is, will or has undergone surgery, chemotherapy and/or radiation therapy.

In certain embodiments, an Inhibitory Therapeutic Agent, composition comprising an Inhibitory Therapeutic Agent, or a combination therapy is administered to a subject that has abnormal levels of expression of one or more of the following: B7-H2, ICOS, CD28, or CTLA-4. In some embodiments, an Inhibitory Therapeutic Agent, composition comprising an Inhibitory Therapeutic Agent, or a combination therapy is administered to a subject that has abnormal levels of expression of either B7-H7, B7-H7CR or both.

In some embodiments, a patient is administered an Inhibitory Therapeutic Agent, composition comprising an Inhibitory Therapeutic Agent, or a combination therapy before any adverse effects or intolerance to therapies other than Inhibitory Therapeutic Agents develops. In some embodiments, Inhibitory Therapeutic Agents, compositions comprising Inhibitory Therapeutic Agents, or combination therapies are administered to refractory patients. In a certain embodiment, refractory patient is a patient refractory to a standard therapy. In certain embodiments, a patient with an autoimmune disease or inflammatory disorder, is refractory to a therapy when the autoimmune disease or inflammatory disorder, respectively, has not significantly been eradicated and/or the symptoms have not been significantly alleviated. The determination of whether a patient is refractory can be made either in vivo or in vitro by any method known in the art for assaying the effectiveness of a treatment, using art-accepted meanings of "refractory" in such a context. In various embodiments, a patient with a inflammatory disorder is refractory when inflammation has not decreased or has increased.

In some embodiments, Inhibitory Therapeutic Agents, compositions comprising Inhibitory Therapeutic Agents, or combination therapies are administered to a patient who are susceptible to adverse reactions to conventional therapies.

In some embodiments, one or more Inhibitory Therapeutic Agents, compositions comprising Inhibitory Therapeutic Agents, or combination therapies are administered to a patient who has proven refractory to therapies other than Inhibitory Therapeutic Agents, but are no longer on these therapies. In certain embodiments, the patients being managed or treated in accordance with the methods described herein are patients already being treated with antibiotics, anti-cancer agents, anti-inflammatory agents, or other biological therapy/immunotherapy. Among these patients are refractory patients, patients who are too young for conventional therapies.

In some embodiments, the subject being administered one or more Inhibitory Therapeutic Agents, compositions comprising Inhibitory Therapeutic Agents, or combination therapies has not received a therapy prior to the administration of the Inhibitory Therapeutic Agents, compositions comprising Inhibitory Therapeutic Agents, or combination therapies. In other embodiments, one or more Inhibitory Therapeutic Agents, compositions comprising Inhibitory Therapeutic Agents, or combination therapies are administered to a subject who has received a therapy prior to administration of one or more Inhibitory Therapeutic Agents, compositions comprising Inhibitory Therapeutic Agents, or combination therapies. In some embodiments, the subject administered an Inhibitory Therapeutic Agent or a composition comprising an Inhibitory Therapeutic Agent was refractory to a prior therapy or experienced adverse side effects to the prior therapy or the prior therapy was discontinued due to unacceptable levels of toxicity to the subject.

5.7 COMBINATION THERAPIES

Other therapies that can be used in combination with Therapeutic Agents (i.e., Immunostimulating Therapeutic Agents and/or Inhibitory Therapeutic Agents) for the prevention, treatment and/or management of a disease that is affected by immune function or response, e.g., cancer, infectious disease, autoimmune and inflammatory disease, and transplant rejection, include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. Specific examples of such therapies include, but are not limited to, immunomodulatory agents (e.g., interferon), anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steriods, and non-steriodal anti-inflammatory drugs (e.g., aspirin, ibuprofen, diclofenac, and COX-2 inhibitors), pain relievers, leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anti-PD1 antibodies, PD1 inhibitors, anti-B7-H1, anti-CTLA-4, CTLA-4-Ig anticholinergic agents (e.g., ipratropium bromide and oxitropium bromide), sulphasalazine, penicillamine, dapsone, antihistamines, anti-malarial agents (e.g., hydroxychloroquine), anti-viral agents (e.g., nucleoside analogs (e.g., zidovudine, acyclovir, gancyclovir, vidarabine, idoxuridine, trifluridine, and ribavirin), foscarnet, amantadine, rimantadine, saquinavir, indinavir, ritonavir, and AZT) and antibiotics (e.g., dactinomycin (formerly actinomycin), bleomycin, erythromycin, penicillin, mithramycin, and anthramycin (AMC)).

In certain embodiments, anti-TNF alpha antibodies (e.g., Remicade), CTLA-4-Ig (e.g., orencia), and/or TNFR-Ig (e.g., Enbrel) are used in combination with a Therapeutic Agent to prevent, treat, and/or manage an autoimmune disease, inflammatory disease, rheumatoid arthritis, and/or transplant rejection.

Any therapy which is known to be useful, or which has been used or is currently being used for the prevention, management, and/or treatment of a disease that is affected by immune function or response can be used in combination with Therapeutic Agents. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996, and Physicians' Desk Reference (61st ed. 2007) for information regarding therapies (e.g., prophylactic or therapeutic agents) which have been or are currently being used for preventing, treating and/or managing disease or disorder.

5.7.1 Anti-Cancer Agents/Immunomodulatory Agents

Non-limiting examples of one or more other therapies that can be used in combination with a Therapeutic Agent include immunomodulatory agents, such as but not limited to, chemotherapeutic agents and non-chemotherapeutic immunomodulatory agents. Non-limiting examples of chemotherapeutic agents include cyclophosphamide, methotrexate, cyclosporin A, leflunomide, cisplatin, ifosfamide, taxanes such as taxol and paclitaxol, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, cytochalasin B, gramicidin D, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin homologs, and cytoxan. Examples of non-chemotherapeutic immunomodulatory agents include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos. WO 02/098370 and WO 02/069904), anti-CD11a antibodies (e.g., Xanelim (Genentech)), and anti-B7 antibodies (e.g., IDEC-114) (IDEC)); anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-alpha antibodies, anti-IL-1alpha antibodies, anti-IL-6 antibodies, anti-IL-8 antibodies (e.g., ABX-IL-8 (Abgenix)), anti-IL-12 antibodies and anti-IL-23 antibodies)); CTLA4-immunoglobulin; LFA-3TIP (Biogen, International Publication No. WO 93/08656 and U.S. Pat. No. 6,162,432); soluble cytokine receptors (e.g., the extracellular domain of a TNF-alpha receptor or a fragment thereof, the extracellular domain of an IL-1 alpha receptor or a fragment thereof, and the extracellular domain of an IL-6 receptor or a fragment thereof); cytokines or fragments thereof (e.g., interleukin (IL)-2, IL-3, IL-4, IL-5, IL-6, IL-7, IL-8, IL-9, IL-10, IL-11, IL-12, IL-15, IL-23, TNF-alpha, TNF-beta, interferon (IFN)-alpha, IFN-beta, IFN-gamma, and GM-CSF); and anti-cytokine antibodies (e.g., anti-IL-2 antibodies, anti-IL-4 antibodies, anti-IL-6 antibodies, anti-IL-10 antibodies, anti-IL-12 antibodies, anti-IL-15 antibodies, anti-TNF-alpha antibodies, and anti-IFN-gamma antibodies), and antibodies that immunospecifically bind to tumor-associated antigens (e.g., Herceptin®). In certain embodiments, an immunomodulatory agent is an immunomodulatory agent other than a chemotherapeutic agent. In other embodiments an immunomodulatory agent is an immunomodulatory agent other than a cytokine or hemopoietic such as IL-1, IL-2, IL-4, IL-12, IL-15, TNF, IFN-alpha, IFN-beta, IFN-gamma, M-CSF, G-CSF, IL-3 or erythropoietin. In yet other embodiments, an immunomodulatory agent is an agent other than a chemotherapeutic agent and a cytokine or hemopoietic factor.

Non-limiting examples of anti-cancer agents that can be used as therapies in combination with Therapeutic Agents, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-aletheine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins;

chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+mycobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In specific embodiments, a anti-cancer agent is not a chemotherapeutic agent.

In certain embodiments, certain of the therapies described in this section 5.7.1 are used in combination with a Therapeutic Agent to prevent, treat, or manage an autoimmune disease, inflammatory disease, and/or transplant rejection.

5.7.2 Antiviral Agents

Antiviral agents that can be used in combination with Therapeutic Agents include, but are not limited to, non-nucleoside reverse transcriptase inhibitors, nucleoside reverse transcriptase inhibitors, protease inhibitors, and fusion inhibitors. In one embodiment, the antiviral agent is selected from the group consisting of amantadine, oseltamivir phosphate, rimantadine, and zanamivir. In another embodiment, the antiviral agent is a non-nucleoside reverse transcriptase inhibitor selected from the group consisting of delavirdine, efavirenz, and nevirapine. In another embodiment, the antiviral agent is a nucleoside reverse transcriptase inhibitor selected from the group consisting of abacavir, didanosine, emtricitabine, emtricitabine, lamivudine, stavudine, tenofovir DF, zalcitabine, and zidovudine. In another embodiment, the antiviral agent is a protease inhibitor selected from the group consisting of amprenavir, atazanavir, fosamprenav, indinavir, lopinavir, nelfinavir, ritonavir, and saquinavir. In another embodiment, the antiviral agent is a fusion inhibitor such as enfuvirtide.

Additional, non-limiting examples of antiviral agents for use in combination with Therapeutic Agents include the following: rifampicin, nucleoside reverse transcriptase inhibitors (e.g., AZT, ddI, ddC, 3TC, d4T), non-nucleoside reverse transcriptase inhibitors (e.g., delavirdine efavirenz, nevirapine), protease inhibitors (e.g., aprenavir, indinavir, ritonavir, and saquinavir), idoxuridine, cidofovir, acyclovir, ganciclovir, zanamivir, amantadine, and palivizumab. Other examples of anti-viral agents include but are not limited to acemannan; acyclovir; acyclovir sodium; adefovir; alovudine; alvircept sudotox; amantadine hydrochloride (SYMMETREL™); aranotin; arildone; atevirdine mesylate; pyridine; cidofovir; cipamfylline; cytarabine hydrochloride; delavirdine mesylate; desciclovir; didanosine; disoxaril; edoxudine; enviradene; enviroxime; famciclovir; famotine hydrochloride; fiacitabine; fialuridine; fosarilate; foscamet sodium; fosfonet sodium; ganciclovir; ganciclovir sodium; idoxuridine; kethoxal; lamivudine; lobucavir; memotine hydrochloride; methisazone; nevirapine; oseltamivir phosphate (TAMIFLU™); penciclovir; pirodavir; ribavirin; rimantadine hydrochloride (FLUMADINE™); saquinavir mesylate; somantadine hydrochloride; sorivudine; statolon; stavudine; tilorone hydrochloride; trifluridine; valacyclovir hydrochloride; vidarabine; vidarabine phosphate; vidarabine sodium phosphate; viroxime; zalcitabine; zanamivir (RELENZA™); zidovudine; and zinviroxime.

5.7.3 Antibacterial Aunts

Antibacterial agents, including antibiotics, that can be used in combination with Therapeutic Agents include, but are not limited to, aminoglycoside antibiotics, glycopeptides, amphenicol antibiotics, ansamycin antibiotics, cephalosporins, cephamycins oxazolidinones, penicillins, quinolones, streptogamins, tetracyclins, and analogs thereof. In some embodiments, antibiotics are administered in combination with a Therapeutic Agent to prevent and/or treat a bacterial infection.

In a specific embodiment, Therapeutic Agents are used in combination with other protein synthesis inhibitors, including but not limited to, streptomycin, neomycin, erythromycin, carbomycin, and spiramycin.

In one embodiment, the antibacterial agent is selected from the group consisting of ampicillin, amoxicillin, ciprofloxacin, gentamycin, kanamycin, neomycin, penicillin G, streptomycin, sulfanilamide, and vancomycin. In another embodiment, the antibacterial agent is s elected from the group consisting of azithromycin, cefonicid, cefotetan, cephalothin, cephamycin, chlortetracycline, clarithromycin, clindamycin, cycloserine, dalfopristin, doxycycline, erythromycin, linezolid, mupirocin, oxytetracycline, quinupristin, rifampin, spectinomycin, and trimethoprim.

Additional, non-limiting examples of antibacterial agents for use in combination with Therapeutic Agents include the following: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), folic acid analogs (e.g., trimethoprim), glycopeptides (e.g., vancomycin), lincosamides (e.g., clindamycin, and lincomycin), macrolides (e.g., azithromycin, carbomycin, clarithomycin, dirithromycin, erythromycin, and erythromycin acistrate), monobactams (e.g., aztreonam, carumonam, and tigemonam), nitrofurans (e.g., furaltadone, and furazolium chloride), oxacephems (e.g., flomoxef, and moxalactam), oxazolidinones (e.g., linezolid), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o benethamine, penicillin 0, penicillin V, penicillin V benzathine, penicillin V hydrabamine, penimepicycline, and phencihicillin potassium), quinolones and analogs thereof (e.g., cinoxacin, ciprofloxacin, clinafloxacin, flumequine, grepagloxacin, levofloxacin, and moxifloxacin), streptogramins (e.g., quinupristin and dalfopristin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), and tetracyclines (e.g., apicycline, chlortetracycline, clomocycline, and demeclocycline). Additional examples include cycloserine, mupirocin, tuberin amphomycin, bacitracin, capreomycin, colistin, enduracidin, enviomycin, and 2,4 diaminopyrimidines (e.g., brodimoprim).

5.8 ADMINISTRATION & DOSAGE OF THERAPEUTIC AGENTS

5.8.1 Mode of Administration of Therapeutic Agents

Therapeutic Agents can be administered via any route known in the art. Therapeutic Agents or compositions thereof can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to deliver the Therapeutic Agents or compositions thereof and pharmaceutically acceptable salts thereof.

Methods of administration include but are not limited to parenteral, intradermal, intramuscular, intraperitoneal, intravenous, subcutaneous, intranasal, epidural, oral, sublingual, intranasal, intracerebral, intravaginal, transdermal, rectally, by inhalation, intratumorally, or topically, particularly to the ears, nose, eyes, or skin. The mode of administration is left to the discretion of the practitioner. In some embodiments, administration will result in the release of a Therapeutic Agent into the bloodstream.

In specific embodiments, it may be desirable to administer a Therapeutic Agent locally. This may be achieved, for example, and not by way of limitation, by local infusion, topical application, e.g., in conjunction with a wound dressing, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce a Therapeutic Agent into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In certain embodiments, a Therapeutic Agent is formulated as a suppository, with traditional binders and vehicles such as triglycerides.

For viral infections or melanoma with cutaneous manifestations, the Therapeutic Agent can be administered topically.

In another embodiment, a Therapeutic Agent is delivered in a vesicle, in particular a liposome (See Langer, 1990, Science 249:1527 1533; Treat et al., in Liposomes in the Therapy of Infectious Disease and Bacterial infection, Lopez-Berestein and Fidler (eds.), Liss, New York, pp. 353 365 (1989); Lopez Berestein, ibid., pp. 317 327).

In another embodiment, a Therapeutic Agent is delivered in a controlled release system (See, e.g., Goodson, in Medical Applications of Controlled Release, supra, vol. 2, pp. 115 138 (1984)). Examples of controlled-release systems are discussed in the review by Langer, 1990, Science 249:1527 1533 may be used. In one embodiment, a pump may be used (See Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (See Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; See also Levy et al., 1985, Science 228:190; During et al., 1989, Ann. Neurol. 25:351; Howard et al., 1989, J. Neurosurg. 71:105). In a specific embodiment, a controlled-release system comprising a Therapeutic Agent is placed in close proximity to the tissue affected by the disease to be prevented, treated and/or managed. In accordance with this embodiment, the close proximity of the controlled-release system to the affected tissue may result in only a fraction of the dose of the Therapeutic Agent required if it is systemically administered.

5.8.2 Dosage of Therapeutic Agents

The amount of a Therapeutic Agent, or the amount of a composition comprising a Therapeutic Agent, that will be effective in the prevention, treatment and/or management of a disease can be determined by standard clinical techniques. In vitro or in vivo assays may optionally be employed to help identify optimal dosage ranges. The precise dose to be employed will also depend, e.g., on the route of administration, the type of symptoms, and the seriousness of the symptoms, and should be decided according to the judgment of the practitioner and each patient's or subject's circumstances.

In some embodiments, the dosage of a Therapeutic Agent or compositions thereof is determined by extrapolating from the no observed adverse effective level (NOAEL), as determined in animal studies. This extrapolated dosage is useful in determining the maximum recommended starting dose for human clinical trials. For instance, the NOAELs can be extrapolated to determine human equivalent dosages (HED). Typically, HED is extrapolated from a non-human animal dosage based on the doses that are normalized to body surface area (i.e., mg/m2). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, See Guidance for Industry Estimating the Maximum Safe Starting Dose in Initial Clinical Trials for Therapeutics in Adult Healthy Volunteers, U.S. Department of Health and Human Services Food and Drug Administration Center for Drug Evaluation and Research (CDER), Pharmacology and Toxicology, July 2005. In one embodiment, a Therapeutic Agent or composition thereof is administered at a dose that is lower than the human equivalent dosage (HED) of the NOAEL over a period of 1 week, 2 weeks, 3 weeks, 1 month, 2 months, three months, four months, six months, nine months, 1 year, 2 years, 3 years, 4 years or more.

In certain embodiments, a dosage regime for a human subject can be extrapolated from animal model studies using the dose at which 10% of the animals die (LD10). In general the starting dose of a Phase I clinical trial is based on preclinical testing. A standard measure of toxicity of a drug in preclinical testing is the percentage of animals that die because of treatment. It is well within the skill of the art to correlate the LD10 in an animal study with the maximal-tolerated dose (MTD) in humans, adjusted for body surface area, as a basis to extrapolate a starting human dose. In some embodiments, the interrelationship of dosages for one animal model can be converted for use in another animal, including humans, using conversion factors (based on milligrams per meter squared of body surface) as described, e.g., in Freireich et al., Cancer Chemother. Rep., 1966, 50:219-244. Body surface area may be approximately determined from height and weight of the patient. See, e.g., Scientific Tables, Geigy Pharmaceuticals, Ardley, N.Y., 1970, 537. In certain embodiments, the adjustment for body surface area includes host factors such as, for example, surface area, weight, metabolism, tissue distribution, absorption rate, and excretion rate. In addition, the route of administration, excipient usage, and the specific disease or virus to target are also factors to consider. In one embodiment, the standard conservative starting dose is about $1/10$ the murine LD10, although it may be even lower if other species (i.e., dogs) were more sensitive to the Therapeutic Agent. In other embodiments, the standard conservative starting dose is about $1/100$, $1/95$, $1/90$, $1/85$, $1/80$, $1/75$, $1/70$, $1/65$, $1/60$, $1/55$, $1/50$, $1/45$, $1/40$, $1/35$, $1/30$, $1/25$, $1/20$, $1/15$, $2/10$, $3/10$, $4/10$, or $5/10$ of the murine LD10. In other embodiments, an starting dose amount of a Therapeutic Agent in a human is lower than the dose extrapolated from animal model studies. In another embodiment, an starting dose amount of a Therapeutic Agent in a human is higher than the dose extrapolated from animal model studies. It is well within the skill of the art to start doses of the active composition at relatively low levels, and increase or decrease the dosage as necessary to achieve the desired effect with minimal toxicity.

Exemplary doses of Therapeutic Agents comprising polypeptides or antibodies or compositions thereof include milligram or microgram amounts per kilogram of subject or sample weight (e.g., about 1 microgram per kilogram to about 500 milligrams per kilogram, about 5 micrograms per kilogram to about 100 milligrams per kilogram, or about 1 microgram per kilogram to about 50 micrograms per kilogram). In specific embodiments, a daily dose is at least 50 mg, 75 mg, 100 mg, 150 mg, 250 mg, 500 mg, 750 mg, or at least 1 g.

In one embodiment, the dosage is a concentration of 0.01 to 5000 mM, 1 to 300 mM, 10 to 100 mM and 10 mM to 1 M. In another embodiment, the dosage is a concentration of at least 5 μM, at least 10 μM, at least 50 μM, at least 100 μM, at least 500 μM, at least 1 mM, at least 5 mM, at least 10 mM, at least 50 mM, at least 100 mM, or at least 500 mM.

In one embodiment, the dosage is a concentration of 0.01 to 5000 mM, 1 to 300 mM, 10 to 100 mM and 10 mM to 1 M. In another embodiment, the dosage is a concentration of at least 5 μM, at least 10 μM, at least 50 μM, at least 100 μM, at least 500 μM, at least 1 mM, at least 5 mM, at least 10 mM, at least 50 mM, at least 100 mM, or at least 500 mM. In a specific embodiment, the dosage is 0.25 µg/kg or more, preferably 0.5 µg/kg or more, 1 µg/kg or more, 2 µg/kg or more, 3 µg/kg or more, 4 µg/kg or more, 5 µg/kg or more, 6 µg/kg or more, 7 µg/kg or more, 8 µg/kg or more, 9 µg/kg or more, or 10 µg/kg or more, 25 µg/kg or more, preferably 50 µg/kg or more, 100 µg/kg or more, 250 µg/kg or more, 500 µg/kg or more, 1 mg/kg or more, 5 mg/kg or more, 6 mg/kg or more, 7 mg/kg or more, 8 mg/kg or more, 9 mg/kg or more, or 10 mg/kg or more of a patient's body weight.

In another embodiment, the dosage is a unit dose of 1 mg, preferably 2 mg, 5 mg, 10 mg, 50 mg, 100 mg, 150 mg, 200 mg, 250 mg, 300 mg, 350 mg, 400 mg, 500 mg, 550 mg, 600 mg, 650 mg, 700 mg, 750 mg, 800 mg or more. In another embodiment, the dosage is a unit dose that ranges from about 5 mg to about 100 mg, about 100 mg to about 200 µg, about 150 mg to about 300 mg, about 150 mg to about 400 mg, 250 µg to about 500 mg, about 500 mg to about 800 mg, about 500 mg to about 1000 mg, or about 5 mg to about 1000 mg.

Exemplary doses of Therapeutic Agents comprising nucleic acids or compositions thereof include 0.1 µg, 0.5 µg, 1 µg, 1.5 µg, 2 µg, 3 µg, 4 µg, 5 µg, 6 µg, 7 µg, 8 µg, 9 µg, 10 µg, 15 µg, 20 µg, 25 µg, 30 µg, 35 µg, 40 µg, 45 µg, 50 µg, or 60 µg of nucleic acids per dose. In a specific embodiment, the dose is in the range of 10 ng to 100 mg, or 50 ng to 100 mg, or 100 ng to 100 mg of nucleic acids per dose. In some specific embodiments, the dose is in the range of 10 pg to 100 mg, or 50 pg to 100 mg, or 100 pg to 100 mg, or 100 pg to 100 ng of nucleic acids per dose.

In certain embodiments, suitable dosage ranges for oral administration are about 0.001 milligram to about 500 milligrams of a Therapeutic Agent, per kilogram body weight per day. In specific embodiments, the oral dose is about 0.01 milligram to about 100 milligrams per kilogram body weight per day, about 0.1 milligram to about 75 milligrams per kilogram body weight per day or about 0.5 milligram to 5 milligrams per kilogram body weight per day. The dosage amounts described herein refer to total amounts administered; that is, if more than one Therapeutic Agent is administered, then, in some embodiments, the dosages correspond to the total amount administered. In a specific embodiment, oral compositions contain about 10% to about 95% a Therapeutic Agent by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. In some embodiments, suitable dosage ranges for intranasal administration are about 0.01 µg/kg body weight per day to about 1 mg/kg body weight per day. Suppositories generally contain about 0.01 milligram to about 50 milligrams of a Therapeutic Agent per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 500 milligrams per kilogram of body weight per day. Suitable doses for topical administration include doses that are in the range of about 0.001 milligram to about 50 milligrams, depending on the area of administration.

In another embodiment, a subject is administered one or more doses of an effective amount of a Therapeutic Agent or a composition thereof, wherein the effective amount is not the same for each dose. In another embodiment, a subject is administered one or more doses of an effective amount of a Therapeutic Agent or a composition thereof, wherein the dose of an effective amount administered to said subject is increased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses. In another embodiment, a subject is administered one or more doses of an effective amount of a Therapeutic Agent or composition thereof, wherein the dose is decreased by, e.g., 0.01 µg/kg, 0.02 µg/kg, 0.04 µg/kg, 0.05 µg/kg, 0.06 µg/kg, 0.08 µg/kg, 0.1 µg/kg, 0.2 µg/kg, 0.25 µg/kg, 0.5 µg/kg, 0.75 µg/kg, 1 µg/kg, 1.5 µg/kg, 2 µg/kg, 4 µg/kg, 5 µg/kg, 10 µg/kg, 15 µg/kg, 20 µg/kg, 25 µg/kg, 30 µg/kg, 35 µg/kg, 40 µg/kg, 45 µg/kg, or 50 µg/kg, as treatment progresses.

For Therapeutic Agents comprising cells expressing B7-H7, B7-H7CR, B7-H2, ICOS, CD28 or CTLA-4 in high amounts, the suitable dosage range for administration by any route of administration can be at least 100, 200, 300, 400, 500, 700, 1,000, 5,000, 10,000, 25,000, 50,000, or 100,000 cells. In specific embodiments, the number of cells is at least 100, 200, 300, 400, 500 cells. In other embodiments, the number of cells is at least 300, 400, 500, 700, 1,000 cells. In yet other specific embodiments, the number of cells is at least 700, 1,000, 5,000, 10,000 cells. In some embodiments, the number of cells is at least 5,000, 10,000, 25,000, 50,000, or 100,000 cells. In yet another embodiment, the number of cells is at least 50,000, or 100,000 cells. In other embodiments, the number of cells is at least $1\times10^6$, $5\times10^6$, $1\times10^7$, $5\times10^7$, $1\times10^8$, $5\times10^8$ or more cells. In specific embodiments, the number of cells is between $1\times10^4$ to $1\times10^4$, $5\times10^4$ to $5\times10^6$, $1\times10^5$ to $1\times10^7$, $1\times10^5$ to $5\times10^8$, $1\times10^6$ to $1\times10^8$, or $1\times10^6$ to $1\times10^7$, or $1\times10^4$ to $1\times10^5$ cells.

In certain embodiments, a subject is administered a Therapeutic Agent or composition thereof in an amount effective to inhibit or reduce symptoms associated with a disease or disorder by at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% or at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments to treat, a subject is administered a Therapeutic Agent or a composition thereof in an amount effective to inhibit or reduce symptoms associated with a disease or disorder by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or other known to one of skill in the art.

In certain embodiments to treat or manage an infectious disease, a subject is administered an Immunostimulating Therapeutic Agent or composition thereof in an amount effective to inhibit or reduce replication of an infectious agent by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In certain embodiments, a subject is administered an Immunostimulating Therapeutic Agent or composition thereof in an amount effective to inhibit or reduce replication of an infectious agent by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art. In other embodiments, a subject is administered an Immunostimulating Therapeutic Agent or composition thereof in an amount effective to inhibit or reduce replication of an infectious agent by at least 1 log, 1.5 logs, 2 logs, 2.5 logs, 3 logs, 3.5 logs, 4 logs, 5 logs or more relative to a negative control as determined using an assay described herein or others known to one of skill in the art.

In certain embodiments to prevent, treat, and/or manage cancer, a subject is administered an Immunostimulating Therapeutic Agent or composition thereof in an amount effective to inhibit or reduce tumor growth or cancer cell proliferation by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Immunostimulating Therapeutic Agent or composition thereof in an amount effective to inhibit or reduce tumor growth or cancer cell proliferation by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to treat or manage autoimmune or inflammatory diseases, a subject is administered an Inhibitory Therapeutic Agent or composition thereof in an amount effective to suppress or reduce certain aspects of the immune function by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Inhibitory Therapeutic Agent or composition thereof in an amount effective to suppress or reduce certain aspects of the immune function by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered an Immunostimulating Therapeutic Agent or composition thereof in an amount effective to induce or enhance an immune response by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Immunostimulating Therapeutic Agent or composition thereof in an amount effective to induce or enhance an immune response by at least 1.5 fold, 2 fold, 2.5 fold, 3 fold, 4 fold, 5 fold, 8 fold, 10 fold, 15 fold, 20 fold, or 2 to 5 fold, 2 to 10 fold, 5 to 10 fold, or 5 to 20 fold relative to a negative control as determined using an assay described herein or others known to one of skill in the art.

In certain embodiments to, a subject is administered an Immunostimulating Therapeutic Agent or composition thereof in an amount effective to increase or enhance the number of lymphocytes (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Immunostimulating Therapeutic Agent or composition thereof in an amount effective to increase or enhance the number of lymphocytes (in some embodiments, in a specific target body compartment) by at least 1.5 fold, at least 2 fold, at least 2.5 fold, at least 3 fold, at least 4 fold, at least 5 fold, at least 8 fold, at least 10 fold, at least 15 fold, or at least 20 fold; or by approximately 2 to 5 fold, 2 to 10 fold, 5 to 10 fold, or 5 to 20 fold relative to a negative control as determined using an assay described herein or others known to one of skill in the art. In some embodiments, the specific target body compartment where the number of lymphocytes is increased or enhanced by an Immunostimulating Therapeutic Agent is the lung, stomach, heart, kidney, liver, small intestines, large intestines, breast, prostate, or bladder. In particular embodiments, the specific target body compartment where the number of lymphocytes is increased or enhanced is the body compartment affected by a disease or disorder (e.g., cancer or infectious disease). In some embodiments, the specific target body compartment where the number of lymphocytes is increased or enhanced is the lymph node, spleen, or peripheral blood.

In certain embodiments to, a subject is administered an Inhibitory Therapeutic Agent or composition thereof in an amount effective to reduce the number of lymphocytes (in some embodiments, in a specific target body compartment) by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, or up to at least 85% relative to a negative control as determined using an assay described herein or others known to one of skill in the art. In some embodiments, a subject is administered an Inhibitory Therapeutic Agent or composition thereof in an amount effective to reduce the number of lymphocytes (in some embodiments, in a specific target body compartment) by at least 1.5 fold, at least 2 fold, at least 2.5 fold, at least 3 fold, at least 4 fold, at least 5 fold, at least 8 fold, at least 10 fold, at least 15 fold, or at least 20 fold; or by approximately 2 to 5 fold, 2 to 10 fold, 5 to 10 fold, or 5 to 20 fold relative to a negative control as determined using an assay described herein or others known to one of skill in the art. In some embodiments, the specific target body compartment where the number of lymphocytes is reduced by an Inhibitory Therapeutic Agent is the lung, stomach, heart, kidney, liver, small intestines, large intestines, breast, prostate, or bladder. In particular embodiments, the specific target body compartment where the number of lymphocytes is increased or enhanced is the body compartment affected by a disease or disorder (e.g., cancer or infectious disease). In some embodiments, the specific target body compartment where the number of lymphocytes is increased or enhanced is the lymph node, spleen, or peripheral blood.

In certain embodiments, a dose of a Therapeutic Agent or composition thereof is administered to a subject every day, every other day, every couple of days, every third day, once a week, twice a week, three times a week, or once every two weeks. In other embodiments, two, three or four doses of a Therapeutic Agent or composition thereof is administered to a subject every day, every couple of days, every third day, once a week or once every two weeks. In some embodiments, a dose(s) of a Therapeutic Agent or composition thereof is administered for 2 days, 3 days, 5 days, 7 days, 14 days, or 21 days. In certain embodiments, a dose of a Therapeutic Agent or composition thereof is administered for 1 month, 1.5 months, 2 months, 2.5 months, 3 months, 4 months, 5 months, 6 months or more.

The dosages of prophylactic or therapeutic agents which have been or are currently used for the prevention, treatment and/or management of a disease or disorder, such as, e.g., cancer, infectious disease, autoimmune and inflammatory disease, and transplant rejection, can be determined using references available to a clinician such as, e.g., the Physicians' Desk Reference (63rd ed. 2009). Preferably, dosages lower than those which have been or are currently being used to prevent, treat and/or manage the disease or disorder are utilized in combination with one or more Therapeutic Agents or compositions thereof.

The above-described administration schedules are provided for illustrative purposes only and should not be considered limiting. A person of ordinary skill in the art will readily understand that all doses are within the scope of the invention.

5.9 BIOLOGICAL ASSAYS 5.9.1 Assays to Assessing the Binding Characteristics of Therapeutic Agents Therapeutic Agents that specifically bind to the B7-H7, B7-H7CR, B7-H2, ICOS, CD28, CTLA-4, or a complex of B7-H7 and B7-H7CR, or B7-H2 and either ICOS, CD28 or CTLA-4 can be assessed using any method well known in the art, e.g., ELISA, coimmunoprecipitation, Biacore assays, and KinEx A assays.

Binding assays can be used to determine the binding affinity of a Therapeutic Agent for B7-H7, B7-H7CR, B7-H2, ICOS, CD28, CTLA-4, or a complex of B7-H7 and B7-H7CR, or B7-H2 and either ICOS, CD28 or CTLA-4. Binding assays may be performed either as direct binding assays or as competition-binding assays. Binding can be detected using standard ELISA or standard Flow Cytometry assays. In a direct binding assay, a Therapeutic Agent is tested for binding to the B7-H7, B7-H7CR, B7-H2, ICOS, CD28, CTLA-4, or a complex of B7-H7 and B7-H7CR, or B7-H2 and either ICOS, CD28 or CTLA-4.

Competition-binding assays, on the other hand, assess the ability of a Therapeutic Agent to compete with a known agent (e.g., antibodies or other compound) that binds to B7-H7, B7-H7CR, B7-H2, ICOS, CD28, CTLA-4, or a complex of B7-H7 and B7-H7CR, or B7-H2 and either ICOS, CD28 or CTLA-4.

In a direct binding assay, B7-H7, B7-H7CR, B7-H2, ICOS, CD28, CTLA-4, or a complex of B7-H7 and B7-H7CR, or B7-H2 and either ICOS, CD28 or CTLA-4 is contacted with a Therapeutic Agent under conditions that allow binding of the Therapeutic Agent to the B7-H7, B7-H7CR, B7-H2, ICOS, CD28, CTLA-4, or a complex of B7-H7 and B7-H7CR, or B7-H2 and either ICOS, CD28 or CTLA-4. The binding may take place in solution or on a solid surface. Preferably, the candidate antibody is previously labeled for detection. Any detectable compound may be used for labeling, such as but not limited to, a luminescent, fluorescent, or radioactive isotope or group containing same, or a nonisotopic label, such as an enzyme or dye. After a period of incubation sufficient for binding to take place, the reaction is exposed to conditions and manipulations that remove excess or non-specifically bound antibody. Typically, it involves washing with an appropriate buffer. Finally, the presence of a Therapeutic Agent bound to B7-H7, B7-H7CR, B7-H2, ICOS, CD28, CTLA-4, or a complex of B7-H7 and B7-H7CR, or B7-H2 and either ICOS, CD28 or CTLA-4 is detected.

In a competition-binding assay, a Therapeutic Agent is evaluated for its ability to inhibit or displace the binding of a known agent (e.g., an antibody other compound) to the B7-H7, B7-H7CR, B7-H2, ICOS, CD28, CTLA-4, or a complex of B7-H7 and B7-H7CR, or B7-H2 and either ICOS, CD28 or CTLA-4. A labeled known binder of B7-H7, B7-H7CR, B7-H2, ICOS, CD28, CTLA-4, or a complex of B7-H7 and B7-H7CR, or B7-H2 and either ICOS, CD28 or CTLA-4 may be mixed, and placed under conditions in which the interaction between them would normally occur, with and without the addition of the Therapeutic Agent. The amount of labeled known binder that binds the B7-H7, B7-H7CR, B7-H2, ICOS, CD28, CTLA-4, or a complex of B7-H7 and B7-H7CR, or B7-H2 and either ICOS, CD28 or CTLA-4 may be compared to the amount bound in the presence or absence of the Therapeutic Agent.

In one embodiment, the binding assay is carried out with one or more components immobilized on a solid surface to facilitate antibody antigen complex formation and detection. In various embodiments, the solid support could be, but is not restricted to, polycarbonate, polystyrene, polypropylene, polyethylene, glass, nitrocellulose, dextran, nylon, polyacrylamide and agarose. The support configuration can include beads, membranes, microparticles, the interior surface of a reaction vessel such as a microtiter plate, test tube or other reaction vessel. The immobilization of B7-H7, B7-H7CR, B7-H2, ICOS, CD28, CTLA-4, or a complex of B7-H7 and B7-H7CR, or B7-H2 and either ICOS, CD28 or CTLA-4, or other component, can be achieved through covalent or non-covalent attachments. In one embodiment, the attachment may be indirect, i.e., through an attached antibody. In another embodiment, the B7-H7, B7-H7CR, B7-H2, ICOS, CD28, CTLA-4, or a complex of B7-H7 and B7-H7CR, or B7-H2 and either ICOS, CD28 or CTLA-4 and negative controls are tagged with an epitope, such as glutathione S-transferase (GST) so that the attachment to the solid surface can be mediated by a commercially available antibody such as anti-GST (Santa Cruz Biotechnology).

For example, such an affinity binding assay may be performed using the B7-H7, B7-H7CR, B7-H2, ICOS, CD28, CTLA-4, or a complex of B7-H7 and B7-H7CR, or B7-H2 and either ICOS, CD28 or CTLA-4 which is immobilized to a solid support. Typically, the non-mobilized component of the binding reaction, in this case the Therapeutic Agent, is labeled to enable detection. A variety of labeling methods are available and may be used, such as luminescent, chromophore, fluorescent, or radioactive isotope or group containing same, and nonisotopic labels, such as enzymes or dyes. In one embodiment, the Therapeutic Agent is labeled with a fluorophore such as fluorescein isothiocyanate (FITC, available from Sigma Chemicals, St. Louis). Such an affinity binding assay may be performed using the B7-H7, B7-H7CR, B7-H2, ICOS, CD28, CTLA-4, or a complex of B7-H7 and B7-H7CR, or B7-H2 and either ICOS, CD28 or CTLA-4 immobilized on a solid surface. Therapeutic Agents are then incubated with the B7-H7, B7-H7CR, B7-H2, ICOS, CD28, CTLA-4, or a complex of B7-H7 and B7-H7CR, or B7-H2 and either ICOS, CD28 or CTLA-4 and the specific binding of Therapeutic Agents is detected by methods known in the art including, but not limited to, BiaCore Analyses, ELISA, FMET and RIA methods.

Finally, the label remaining on the solid surface may be detected by any detection method known in the art. For example, if the Therapeutic Agent is labeled with a fluorophore, a fluorimeter may be used to detect complexes.

In one embodiment, the Therapeutic Agent is added to intact cells that express B7-H7, B7-H7CR, B7-H2, ICOS, CD28, or CTLA-4, or isolated membranes containing B7-H7, B7-H7CR, B7-H2, ICOS, CD28, or CTLA-4. Thus, direct binding of Therapeutic Agent may be assayed in intact cells in culture or in animal models. A labeled Therapeutic Agent may be mixed with cells that express B7-H7, B7-H7CR, B7-H2, ICOS, CD28, or CTLA-4, or with crude extracts obtained from such cells. Isolated membranes may be used to identify Therapeutic Agents that interact with B7-H7, B7-H7CR, B7-H2, ICOS, CD28, or CTLA-4. For example, in a typical experiment using isolated membranes, cells may be genetically engineered to express B7-H7, B7-H7CR, B7-H2, ICOS, CD28, or CTLA-4. Membranes can be harvested by standard techniques and used in an in vitro binding assay. Labeled Therapeutic Agent (e.g., fluorescent labeled antibody) is bound to the membranes and assayed for specific activity; specific binding is determined by comparison with binding assays performed in the presence of excess unlabeled (cold) Therapeutic Agent. Alternatively, soluble B7-H7, B7-H7CR, B7-H2, ICOS, CD28, or CTLA-4 may be recombinantly expressed and utilized in non-cell based assays to identify Therapeutic Agents that bind to B7-H7, B7-H7CR, B7-H2, ICOS, CD28, or CTLA-4.

Alternatively, the binding reaction may be carried out in solution. In this assay, the labeled component is allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner and so on.

Various methods described above or known in the art can be adapted to assay the binding affinity of a Therapeutic Agent for B7-H7, B7-H7CR, B7-H2, ICOS, CD28, CTLA-4, or a complex of B7-H7 and B7-H7CR, or B7-H2 and either ICOS, CD28 or CTLA-4.

5.9.2 Assays for Assessing the Function of the Therapeutic Agents

Various assays known in the art can be used to assess whether a Therapeutic Agent activates, enhances, suppresses or reduces immune function. In one aspect, the Therapeutic Agent increases an immune response that can be, e.g., an antibody response (humoral response) or a cellular immune response, e.g., cytokine secretion (e.g., interferon-gamma), helper activity or cellular cytotoxicity. In one embodiment, the increased immune response is increased cytokine secretion, antibody production, effector function, T cell proliferation, and/or NK cell proliferation. In another aspect, the Therapeutic Agent suppresses an immune response that can be, e.g., an antibody response (humoral response) or a cellular immune response, e.g., cytokine secretion (e.g., interferon-gamma), helper activity or cellular cytotoxicity. In one embodiment, the decreased immune response is decreased cytokine secretion, antibody production, effector function, T cell proliferation, and/or NK cell proliferation. Various assays to measure such activities are well known in the art, and exemplary descriptions of such assays are provided below.

Proliferation of certain immune cells may assessed by $^3$H-thymidine incorporation. The "tetramer staining" assay (Altman et al., 1996, Science 274: 94-96) may be used to identify antigen-specific T-cells and to assess how Therapeutic Agents modulate (e.g., activate, enhance, reduce or suppress) antigen-specific T cell responses. For example, an MHC molecule containing a specific peptide antigen, such as a tumor-specific antigen, is multimerized to make soluble peptide tetramers and labeled, for example, by complexing to streptavidin. The MHC-peptide antigen complex is then mixed with a population of T cells obtained from a subject administered with an immunogenic composition alone or in combination with a Therapeutic Agent. Biotin is then used to stain T cells which express the tumor-specific antigen of interest.

Furthermore, using the mixed lymphocyte target culture assay, the cytotoxicity of T cells can be tested in a $^{51}$Cr-release assay as described, e.g., in Palladino et al., 1987, Cancer Res. 47:5074-5079. Briefly, the mixed lymphocyte culture is added to a target cell suspension to give different effector: target (E:T) ratios (usually 1:1 to 40:1). The target cells are pre-labeled by incubating $1\times10^6$ target cells in culture medium containing 500 µCi of $^{51}$Cr per ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

An ELISPOT assay can be used to measure cytokine release in vitro by T cells after administration of an effective amount of a Therapeutic Agent to a subject. Cytokine release is detected by antibodies which are specific for a particular cytokine, e.g., interleukin-2, tumor necrosis factor-α or interferon-γ (see, e.g., Scheibenbogen et al., 1997, Int. J. Cancer 71:932-936). The assay is carried out in a microtitre plate which has been pre-coated with an antibody specific for a cytokine of interest which captures the cytokine secreted by T cells. After incubation of T cells for 24-48 hours in the coated wells, the T cells are removed and replaced with a second labeled antibody that recognizes a different epitope on the cytokine. After extensive washing to remove unbound antibody, an enzyme substrate which produces a colored reaction product is added to the plate. The number of cytokine-producing cells is counted under a microscope. This method has the advantages of short assay time, and sensitivity without the need of a large number of cytotoxic T cells.

In specific embodiments, the assays described in Examples 6 and 7, infra, may be used to assess the affect of a Therapeutic Agent on immune function. For example, the affect of a Therapeutic Agent on immune function can be assessed using the T cell costimulation assay described in Examples 6 and 7 infra.

Enzyme-linked immunosorbent assays (ELISA) are well known in the art and are described, e.g., in Section 2.1 of Current Protocols in Immunology, Coligan et al. (eds.), John Wiley and Sons, Inc. 1997.

In some aspects, the immune response induced or enhanced by an Immunostimulating Therapeutic Agent is enhanced or increased by at least at least 10%, 15%, 20%, 25%, 30%, 40%, 50%, 60%, 70%, 75%, 80%, 90%. 95%, 98% or 99%, or in the range of between 10% to 25%, 10% to 50%, 25% to 50%, 25% to 75%, 50% to 75%, 50% to 90%, 75% to 90%, 75% to 100% relative to an immune response elicited by a negative control as determined by any known assay in the art. In certain embodiments, the immune response induced by the Immunostimulating Therapeutic Agent is enhanced by at least 0.5-2 times, at least 2-5 times, at least 5-10 times, at least 10-50 times, at least 50-100 times, at least 100-200 times, at least 200-300 times, at least 300-400 times or at least 400-500 times relative to the immune response induced by a negative control as assayed by any known method in the art. In specific embodiments, the assay used to assess immune response measures the level of antibody production, cytokine production, or cellular cytotoxicity, and such assays are well known in the art. In some embodiments, the assay used to measure the immune response is an enzyme-linked immunosorbent assay (ELISA) that determines antibody or cytokine levels, an ELISPOT assay that determines cytokine release, or a 51Cr release assay that determines cellular cytotoxicity.

In specific embodiments, the Immunostimulating Therapeutic Agent induces or enhances an immune response in a subject that is measured by antibody titer in the serum of the subject, and the antibody titer is at least 0.2 to 5 times, 5 to 20 times, 10 to 30 times, 20 to 50 times, 50 to 200 times, 100 to 500, 200 to 1000 times, or 500 to 2,000 times higher as compared to the antibody titer in the serum of a subject administered a negative control. In specific embodiments, the mean serum antibody titer against the antigen in the subject administered the Immunostimulating Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum antibody titer in the subject administered a negative control as determined by methods well known in the art.

In another specific embodiment, presented herein are methods of administering Immunostimulating Therapeutic Agents to modulate the level of cytokine production or secretion as compared to the level of cytokine production or secretion in a negative control sample.

In a specific embodiment, presented herein are methods of administering Immunostimulating Therapeutic Agents to induce or enhance the level of cytokine production or secretion, e.g., interferon-γ, (that may be 0.5 to 500 times higher) as compared to the level of cytokine production or secretion in a negative control sample. In specific embodiments, the Immunostimulating Therapeutic Agent induces or enhances an immune response that is measured by increased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the cytokine concentration of a negative control. In specific embodiments, the mean serum cytokine concentration of samples obtained from a subject administered the Immunostimulating Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Immunostimulating Therapeutic Agent.

In a specific embodiment, presented herein are methods of administering Immunostimulating Therapeutic Agents to decrease the level of cytokine production or secretion as compared to the level of cytokine production or secretion in a negative control sample. In specific embodiments, the Immunostimulating Therapeutic Agent induces or enhances an immune response that is measured by decreased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times lower as compared to the cytokine concentration of a negative control. In specific embodiments, the mean serum cytokine concentration of samples obtained from a subject administered the Immunostimulating Therapeutic Agent is decreased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Immunostimulating Therapeutic Agent.

In specific embodiments, the Immunostimulating Therapeutic Agent induces or enhances NK cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to NK cell proliferation in a negative control. In specific embodiments, the Agnostic Therapeutic Agent induces or enhances T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, 3H-thymidine incorporation.

The increase in antibody (humoral) or cellular immune response induced by an effective amount of the Therapeutic Agent can be assessed using various methods well known in the art.

In some aspects, the immune response suppressed by an Inhibitory Therapeutic Agent is reduced by at least 10%, 15%, 20%, 25%, 30%, 40%, 50%, 60%, 70%, 75%, 80%, 90%. 95%, 98% or 99%, or in the range of between 10% to 25%, 10% to 50%, 25% to 50%, 25% to 75%, 50% to 75%, 50% to 90%, 75% to 90%, 75% to 100% relative to an immune response elicited by a negative control as determined by any known assay in the art. In certain embodiments, the immune response reduced by the Inhibitory Therapeutic Agent is enhanced by at least 0.5-2 times, at least 2-5 times, at least 5-10 times, at least 10-50 times, at least 50-100 times, at least 100-200 times, at least 200-300 times, at least 300-400 times or at least 400-500 times relative to the immune response induced by a negative control as assayed by any known method in the art. In specific embodiments, the assay used to assess immune response measures the level of antibody production, cytokine production, or cellular cytotoxicity, and such assays are well known in the art. In some embodiments, the assay used to measure the immune response is an enzyme-linked immunosorbent assay (ELISA) that determines antibody or cytokine levels, an ELISPOT assay that determines cytokine release, or a 51Cr release assay that determines cellular cytotoxicity.

In specific embodiments, the Inhibitory Therapeutic Agent reduces an immune response in a subject that is measured by antibody titer in the serum of the subject, and the antibody titer is at least 0.2 to 5 times, 5 to 20 times, 10 to 30 times, 20 to 50 times, 50 to 200 times, 100 to 500, 200 to 1000 times, or 500 to 2,000 times higher as compared to the antibody titer in the serum of a subject administered a negative control. In specific embodiments, the mean serum antibody titer against the antigen in the subject administered the Inhibitory Therapeutic Agent is decreased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum antibody titer in the subject administered a negative control as determined by methods well known in the art.

In another specific embodiment, presented herein are methods of administering Inhibitory Therapeutic Agents to modulate the level of cytokine production or secretion as compared to the level of cytokine production or secretion in a negative control sample.

In another specific embodiment, presented herein are methods of administering Inhibitory Therapeutic Agents to decreases the level of cytokine production or secretion, e.g., interferon-γ, (that may be 0.5 to 500 times higher) as compared to the level of cytokine production or secretion in a negative control sample. In specific embodiments, the Inhibitory Therapeutic Agent reduces an immune response that is measured by decreased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times lower as compared to the cytokine concentration of a negative control. In specific embodiments, the mean serum cytokine concentration of samples obtained from a subject administered the Inhibitory Therapeutic Agent is decreased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Inhibitory Therapeutic Agent.

In another specific embodiment, presented herein are methods of administering Inhibitory Therapeutic Agents to induce or enhance the level of cytokine production or secretion as compared to the level of cytokine production or secretion in a negative control sample. In specific embodiments, the Inhibitory Therapeutic Agent induces or enhances an immune response that is measured by increased cytokine release, and the cytokine concentration is at least 0.2 to 5 times, 5 to 20 times, 10 to 30 times, 20 to 50 times, 50 to 200 times, 100 to 500, 200 to 1000 times, or 500 to 2,000 times higher as compared to the cytokine concentration of a negative control. In specific embodiments, the mean serum cytokine concentration of samples obtained from a subject administered the Inhibitory Therapeutic Agent is increased by at least 0.5-2 times, at least 2-5 times, at least 5-10 times, at least 10-50 times, at least 50-100 times, at least 100-200 times, at least 200-300 times, at least 300-400 times or at least 400-500 times relative to the mean serum cytokine concentration of samples obtained from a subject administered a negative control as determined by methods well known in the art. In some embodiments, the negative control can be samples from the subject prior to administration of the Inhibitory Therapeutic Agent.

In specific embodiments, the Inhibitory Therapeutic Agent reduces NK cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to NK cell proliferation in a negative control. In specific embodiments, the Inhibitory Therapeutic Agent reduces T cell proliferation in a subject that by at least 0.2 to 5 times, 5 to 20 times, 10 to 30 times, 20 to 50 times, 50 to 200 times, 100 to 500, 200 to 1000 times, or 500 to 2,000 times higher relative to T cell proliferation in a negative control as determined by methods well known in the art, e.g., flow cytometry, CSFE staining, 3H-thymidine incorporation.

5.9.3 Cytotoxicity Assays

The toxicity and/or efficacy of the therapies described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred. While therapies that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the ED50 with little or no toxicity. The dosage may vary within this range depending upon the dosage form employed and the route of administration utilized. For any therapy used in the method, e.g., as described herein, the therapeutically effective dose can be estimated initially from cell culture assays. A dose may be formulated in animal models to achieve a circulating plasma concentration range that includes the IC50 (i.e., the concentration of the Therapeutic Agent that achieves a half-maximal inhibition of symptoms) as determined in cell culture. Such information can be used to more accurately determine useful doses in humans. Levels in plasma may be measured, for example, by high performance liquid chromatography.

In certain embodiments, the cytotoxicity of a Therapeutic Agent can be determined by measuring the level of apoptosis of cells in a cell culture exposed to the Therapeutic Agent. In one embodiment, apoptosis can be quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34 37 (Roche Molecular Biochemicals). In yet another embodiment, apoptosis can be observed morphologically.

Cell lines on which such assays can be performed are well known to those of skill in the art. Apoptosis, necrosis and proliferation assays can also be performed on primary cells, e.g., a tissue explant.

5.9.4 Animal Models

Therapeutic Agents are preferably assayed in vivo for the desired therapeutic or prophylactic activity prior to use in humans. For example, in one embodiment, a Therapeutic Agent can be administered to the animal at the same time as the onset of a disease or disorder in the animal. In another embodiment, a Therapeutic Agent can be administered to the animal prior to the onset of a disease or disorder in the animal. In another embodiment, a Therapeutic Agent can be administered to the animal subsequent to the onset of a disease or disorder in the animal. In a specific embodiment, the Therapeutic Agent is administered to the animal more than one time. In another specific embodiment, the Therapeutic Agent is administered in combination with another therapy.

Therapeutic Agents can be tested in animal models systems including, but are not limited to, rats, mice, chicken, cows, monkeys, pigs, goats, sheep, dogs, rabbits, guinea pigs, etc. In a specific embodiment, Therapeutic Agents are tested in a mouse model system. Such model systems are widely used and well-known to the skilled artisan. In a specific embodiment, Therapeutic Agents are tested in knockout animals for restoration of function. For example, a B7-H2 knockout may be used to test for restoration of certain B7-H2-related functions by certain Therapeutic Agents.

The anti-cancer activity of the Therapeutic Agent can be determined by using various experimental animal models for the study of cancer well known in the art as described in, e.g., Relevance of Tumor Models for Anticancer Drug Development (1999, eds. Fiebig and Burger); Contributions to Oncology (1999, Karger); The Nude Mouse in Oncology Research (1991, eds. Boven and Winograd); and Anticancer Drug Development Guide (1997 ed. Teicher), incorporated herein by reference in their entireties.

Animal models for cancer can be used to assess the efficacy of a Therapeutic Agent, a composition thereof, or a combination therapy comprising a Therapeutic Agent. Non-limiting examples of animal models for lung cancer include, but are not limited to, lung cancer animal models described by Zhang & Roth (1994, In vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR-ÿ and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3): 1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

For animal models of infectious diseases, the effectiveness of a Therapeutic Agent relative to a negative control can be assessed in animals infected with virus. Samples obtained from these animals (e.g., serum, urine, sputum, semen, saliva, plasma, or tissue sample) can be tested for enhancement of immune function, e.g., enhancement in cytokine release, enhancement in antibody production, T cell proliferation, NK cell proliferation, with methods well known in the art and described herein. Samples obtained from these animals (e.g., serum, urine, sputum, semen, saliva, plasma, or tissue sample) can also be tested for reduction in viral replication via well known methods in the art, e.g., those that measure altered viral replication (as determined, e.g., by plaque formation) or the production of viral proteins (as determined, e.g., by Western blot, ELISA, or flow cytometry analysis) or viral nucleic acids (as determined, e.g., by RT-PCR, northern blot analysis or southern blot). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody. Non-limiting exemplary animal models described below can be adapted for other viral systems.

Various animal models for infectious diseases that are well known in the art can be employed to assess the efficacy of Therapeutic Agents in preventing, treating, and/or managing infectious diseases, e.g.: mouse models of herpes simplex virus (HSV) are described in Crute et al., Nature Medicine, 2002, 8:386-391 and Bolger et al., Antiviral Res., 1997, 35:157-165; guinea pig models of HSV are described in Chen et al., Virol. J, 2004 Nov. 23, 1:11; animal models of mouse cytomegalovirus (MCMV) and human cytomegalovirus (HCMV) are described in Kern et al., Antimicrob. Agents Chemother., 2004, 48:4745-4753; Guinea pig models of CMV is described in Bourne et al., Antiviral Res., 2000, 47:103-109, Bravo et al., Antiviral Res., 2003, 60:41-49 and Bravo et al, J. Infectious Diseases, 2006, 193:591-597; animal models of influenza virus are described in Sidwell et al., Antiviral Res., 2000, 48:1-16; and McCauley et al., Antiviral Res., 1995, 27:179-186; mouse models of hepatitis B virus (HBV) are described in Cavanaugh et al., J. Virol., 1997, 71:3236-3243 and Guidotti et al., J. Virol., 1995, 69:6158-6169; mouse models of hepatitis C virus (HCV) are described in Zhu et al., Antimicrobial Agents and Chemother., 2006, 50:3260-3268, Bright et al., Nature, 2005, 436:973-978, Hsu et al., Nat. Biotechnol., 2003, 21:519-525, Ilan et al., J. Infect. Dis. 2002, 185:153-161, Kneteman et al., Hepatology, 2006, 43:1346-1353, Mercer et al., Nat. Med., 2001, 7:927-933, and Wu et al., Gastroenterology, 2005, 128:1416-1423; animal models of HIV are described in Ayash-Rashkovsky et al., FASEB J., 2005, 19:1149-1151, Mosier et al., Semin Immunol., 1996, 8:255-262, Mosier et al., Hosp. Pract. (Off Ed)., 1996, 31:41-48, 53-55, 59-60, Bonyhadi et al., Mol. Med. Today, 1997, 3:246-253, Jolicoeur et al., Leukemia, 1999, 13:S78-S80, Browning et al., Proc. Natl. Acad. Sci. USA, 1997, 94:14637-14641, and Sawada et al., J. Exp. Med., 1998, 187:1439-1449, and Schito et al., Curr. HIV Res., 2006, 4:379-386.

Other animal models for viral infections can also be used to assess the efficacy of a Therapeutic Agent, a composition thereof, or a combination therapy comprising a Therapeutic Agent, e.g., animal models for viral infections such as EBV-associated diseases, gammaherpesviruses, infectious mononucleosis, simian immunodeficiency virus ("SIV"), Borna disease virus infection, hepatitis, varicella virus infection, viral pneumonitis, Epstein-Barr virus pathogenesis, feline immunodeficiency virus ("Fly"), HTLV type 1 infection, human rotaviruses, and genital herpes have been developed (see, e.g., Hayashi et al., 2002, Histol Histopathol 17(4): 1293-310; Arico et al., 2002, J Interferon Cytokine Res 22(11):1081-8; Flano et al., 2002, Immunol Res 25(3):201-17; Sauermann, 2001, Curr Mol Med 1(4):515-22; Pletnikov et al., 2002, Front Biosci 7:d593-607; Engler et al., 2001, Mol Immunol 38(6):457-65; White et al., 2001, Brain Pathol 11(4):475-9; Davis & Matalon, 2001, News Physiol Sci 16:185-90; Wang, 2001, Curr Top Microbiol Immunol. 258:

201-19; Phillips et al., 2000, J Psychopharmacol. 14(3):244-50; Kazanji, 2000, AIDS Res Hum Retroviruses. 16(16): 1741-6; Saif et al., 1996, Arch Virol Suppl. 12:153-61; and Hsiung et al., 1984, Rev Infect Dis. 6(1):33-50).

Other animal models for viral respiratory infections include, but not limited to, PIV (see, e.g., Shephard et al., 2003 Res Vet Sci 74(2): 187-190; Ottolini et al., 2002 J Infect Dis 186(12): 1713-1717), and RSV (see, e.g., Culley et al., 2002 J Exp Med 196(10): 1381-1386; and Curtis et al., 2002 Exp Biol Med 227(9): 799-802).

The Therapeutic Agent, composition thereof, or combination therapy comprising the Therapeutic Agent can be tested for their ability to decrease the time course of viral infection.

Animal models for bacterial infections can also be used to assess the efficacy of a Therapeutic Agent, a composition thereof, or a combination therapy comprising a Therapeutic Agent. Animal models for bacterial infections such as *H. pylori*-infection, genital mycoplasmosis, primary sclerosing cholangitis, cholera, chronic lung infection with *Pseudomonas aeruginosa*, Legionnaires' disease, gastroduodenal ulcer disease, bacterial meningitis, gastric *Helicobacter* infection, pneumococcal otitis media, experimental allergic neuritis, leprous neuropathy, mycobacterial infection, endocarditis, *Aeromonas*-associated enteritis, *Bacteroides fragilis* infection, syphilis, streptococcal endocarditis, acute hematogenous osteomyelitis, human scrub typhus, toxic shock syndrome, anaerobic infections, *Escherichia coli* infections, and *Mycoplasma pneumoniae* infections have been developed (see, e.g., Sugiyama et al., 2002, J Gastroenterol. 37 Suppl 13:6-9; Brown et al., 2001, Am J Reprod Immunol. 46(3): 232-41; Vierling, 2001, Best Pract Res Clin Gastroenterol. 15(4):591-610; Klose, 2000, Trends Microbiol. 8(4):189-91; Stotland et al., 2000, Pediatr Pulmonol. 30(5):413-24; Brieland et al., 2000, Immunopharmacology 48(3):249-52; Lee, 2000, Baillieres Best Pract Res Clin Gastroenterol. 14(1):75-96; Koedel & Pfister, 1999, Infect Dis Clin North Am. 13(3): 549-77; Nedrud, 1999, FEMS Immunol Med Microbiol. 24(2):243-50; Prellner et al., 1999, Microb Drug Resist. 5(1): 73-82; Vriesendorp, 1997, J Infect Dis. 176 Suppl 2:S164-8; Shetty & Antia, 1996, Indian J. Lepr. 68(1):95-104; Balasubramanian et al., 1994, Immunobiology 191(4-5):395-401; Carbon et al., 1994, Int J Biomed Comput. 36(1-2):59-67; Haberberger et al., 1991, Experientia. 47(5):426-9; Onderdonk et al., 1990, Rev Infect Dis. 12 Suppl 2:S169-77; Wicher & Wicher, 1989, Crit. Rev Microbiol. 16(3):181-234; Scheld, 1987, J Antimicrob Chemother. 20 Suppl A:71-85; Emslie & Nade, 1986, Rev Infect Dis. 8(6):841-9; Ridgway et al., 1986, Lab Anim Sci. 36(5):481-5; Quimby & Nguyen, 1985, Crit Rev Microbiol. 12(1):1-44; Onderdonk et al., 1979, Rev Infect Dis. 1(2):291-301; Smith, 1976, Ciba Found Symp. (42):45-72, and Taylor-Robinson, 1976, Infection. 4(1 Suppl):4-8).

The Therapeutic Agent, composition thereof, or combination therapy comprising the Therapeutic Agent can be tested for their ability to decrease the time course of bacterial infection, e.g., a bacterial respiratory infection by at least 25%, at least 50%, at least 60%, at least 75%, at least 85%, at least 95%, or at least 99% or 25% to 65%, 40% to 65%, 50% to 90%, 65% to 90%, 70% to 90%, 75% to 95%, 80% to 95%, or 85% to 99% relative to a negative control using methods well known in the art.

The efficacy of Therapeutic Agents, compositions thereof, or combination therapies comprising Therapeutic Agents for the prevention, treatment and/or management of a fungal infection can be assessed in animal models for such infections. Animal models for fungal infections such as *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis have been developed (see, e.g., Arendrup et al., 2002, Infection 30(5):286-91; Kamei, 2001, Mycopathologia 152(1):5-13; Guhad et al., 2000, FEMS Microbiol Lett. 192(1):27-31; Yamagata et al., 2000, J Clin Microbiol. 38(9):32606; Andrutis et al., 2000, J Clin Microbiol. 38(6):2317-23; Cock et al., 2000, Rev Inst Med Trop Sao Paulo 42(2):59-66; Shibuya et al., 1999, Microb Pathog. 27(3):123-31; Beers et al., 1999, J Lab Clin Med. 133(5):423-33; Najvar et al., 1999, Antimicrob Agents Chemother. 43(2):413-4; Williams et al., 1988, J Infect Dis. 178(4):1217-21; Yoshida, 1988, Kansenshogaku Zasshi. 1998 June; 72(6):621-30; Alexandrakis et al., 1998, Br J Ophthalmol. 82(3):306-11; Chakrabarti et al., 1997, J Med Vet Mycol. 35(4):295-7; Martin et al., 1997, Antimicrob Agents Chemother. 41(1):13-6; Chu et al., 1996, Avian Dis. 40(3):715-9; Fidel et al., 1996, J Infect Dis. 173(2):425-31; Cole et al., 1995, FEMS Microbiol Lett. 15; 126(2):177-80; Pollock et al., 1995, Nat Genet. 9(2):202-9; Uchida et al., 1994, Jpn J Antibiot. 47(10):1407-12; Maebashi et al., 1994, J Med Vet Mycol. 32(5):349-59; Jensen & Schonheyder, 1993, J Exp Anim Sci. 35(4):155-60; Gokaslan & Anaissie, 1992, Infect Immun 60(8):3339-44; Kurup et al., 1992, J Immunol. 148(12):3783-8; Singh et al., 1990, Mycopathologia. 112(3):127-37; Salkowski & Balish, 1990, Infect Immun. 58(10):3300-6; Ahmad et al., 1986, Am J Kidney Dis. 7(2):153-6; Alture-Werber E, Edberg S C, 1985, Mycopathologia. 89(2):69-73; Kane et al., 1981, Antimicrob Agents Chemother. 20(5):595-9; Barbee et al., 1977, Am J Pathol. 86(1):281-4; and Maestrone et al., 1973, Am J Vet Res. 34(6):833-6). Animal models for fungal respiratory infections such as *Candida albicans, Aspergillus fumigatus*, invasive pulmonary aspergillosis, *Pneumocystis carinii*, pulmonary cryptococcosis, *Pseudomonas aeruginosa, Cunninghamella bertholletia* (see, e.g., Aratani et al., 2002 Med Mycol 40(6):557-563; Bozza et al., 2002 Microbes Infect 4(13): 1281-1290; Kurup et al., 2002 Int Arch Allergy Immunol 129(2):129-137; Hori et al., 2002 Eur J Immuno 32(5): 1282-1291; Rivera et al., 2002 J Immuno 168(7): 3419-3427; Vassallo et al., 2001, Am J Respir Cell Mol Biol 25(2): 203-211; Wilder et al., 2002 Am J Cell Mol Biol 26(3): 304-314; Yonezawa et al., 2000 J Infect Chemother 6(3): 155-161; Cacciapuoti et al., 2000 Antimicrob Agents Chemother 44(8): 2017-2022; and Honda et al., 1998 Mycopathologia 144(3): 141-146).

The Therapeutic Agents, compositions thereof, or combination therapies comprising Therapeutic Agents can be tested for their ability to decrease the time course of fungal infection (e.g., a fungal respiratory infection) by at least 25%, at least 50%, at least 60%, at least 75%, at least 85%, at least 95%, or at least 99% or 25% to 65%, 40% to 65%, 50% to 90%, 65% to 90%, 70% to 90%, 75% to 95%, 80% to 95%, or 85% to 99% relative to a negative control (e.g., PBS) as measured using assays well known in the art. Techniques known to those of skill in the art can be used to analyze the function of the Therapeutic Agents, compositions thereof, or combination therapies comprising Therapeutic Agents in vivo.

Animal models for autoimmune disorders can also be used to assess the efficacy of a Therapeutic Agent, composition thereof, or combination therapy comprising a Therapeutic Agent. Animal models for autoimmune disorders such as type 1 diabetes, thyroid autoimmunity, systemic lupus erythematosus, and glomerulonephritis have been developed (Flanders et al., 1999, Autoimmunity 29:235-246; Krogh et al., 1999, Biochimie 81:511-515; Foster, 1999, Semin Nephrol. 19:12-24).

Efficacy in preventing, treating and/or managing an autoimmune disorder may be demonstrated, e.g., by detecting the ability of a Therapeutic Agent, a composition, or a combination therapy described herein to reduce one or more symptoms of the autoimmune disorder, to reduce mean absolute lymphocyte counts, to decrease T cell activation, to decrease T cell proliferation, to reduce cytokine production, or to modulate one or more particular cytokine profiles. Efficacy in preventing or treating psoriasis may be demonstrated, e.g., by detecting the ability of a Therapeutic Agent or composition thereof to reduce one or more symptoms of psoriasis, to reduce mean absolute lymphocyte counts, to reduce cytokine production, to modulate one or more particular cytokine profiles, to decrease scaling, to decrease erythema, to decrease plaque elevation, to decrease T cell activation in the dermis or epidermis of an affected area, to decrease T cell infiltration to the dermis or epidermis of an affected area, to reduce PASI, to improve the physician's global assessment score, or to improve quality of life.

The anti-inflammatory activity of a Therapeutic Agent, a composition thereof, or a combination therapy comprising a Therapeutic Agent can be determined by using various experimental animal models of inflammatory arthritis known in the art and described in Crofford L. J. and Wilder R. L., "Arthritis and Autoimmunity in Animals," in Arthritis and Allied Conditions: A Textbook of Rheumatology, McCarty (eds.), Chapter 30 (Lee and Febiger, 1993). Experimental and spontaneous animal models of inflammatory arthritis and autoimmune rheumatic diseases can also be used to assess the anti-inflammatory activity of the Therapeutic Agents, compositions thereof, or combination therapies comprising Therapeutic Agents.

The anti-inflammatory activity of a Therapeutic Agent, a composition thereof, or a combination therapy comprising a Therapeutic Agent can also be assessed by measuring the inhibition of carrageenan-induced paw edema in the rat, using a modification of the method described in Winter C. A. et al., "Carrageenan Induced Edema in Hind Paw of the Rat as an Assay for Anti-inflammatory Drugs" Proc. Soc. Exp. Biol Med. 111, 544-547, (1962). This assay has been used as a primary in vivo screen for the anti-inflammatory activity of most NSAIDs, and is considered predictive of human efficacy. The anti-inflammatory activity of the test therapies (e.g., The Therapeutic Agents, compositions thereof, or combination therapies comprising Therapeutic Agents) is expressed as the percent inhibition of the increase in hind paw weight of the test group relative to the vehicle dosed control group.

In a specific embodiment where the experimental animal model used is adjuvant-induced arthritis rat model, body weight can be measured relative to a control group to determine the anti-inflammatory activity of a Therapeutic Agent, a composition thereof, or a combination therapy.

Animal models for allergies and asthma are known in the art, such as constant-flow inflation with end-inspiratory occlusion described in Ewart et al., 1995 J Appl Physiol 79(2):560-566 and other assays described in, e.g., Komai et al., 2003 Br J Pharmacol 138(5): 912-920; Kenyon et al., 2003 Toxicol Appl Pharmacol 186(2): 90-100; Path et al., 2002 Am J Resp & Critical Care Med 166(6): 818-826; Martins et al., 1990 Crit Care Med 19:515-519; Nicolaides et al., 1997 Proc Natl Acad Sci USA 94:13175-13180; McLane et al., 1998 19:713-720; and Temann et al., 1998 J Exp Med 188(7): 1307-1320. For example, the murine adoptive transfer model is an animal model used to assess the efficacy a Therapeutic Agent, a composition thereof, or a combination therapy for the prevention, treatment, and/or management, of asthma include. In the murine adoptive transfer model, aeroallergen provocation of TH1 or TH2 recipient mice results in TH effector cell migration to the airways and is associated with an intense neutrophilic (TH1) and eosinophilic (TH2) lung mucosal inflammatory response (Cohn et al., 1997, J. Exp. Med. 1861737-1747). Airway hypersensitivity can be induced in mice by ovalbumin (Tomkinson et al., 2001, J. Immunol. 166:5792-5800) or *Schistosoma mansoni* egg antigen (Tesciuba et al., 2001, J. Immunol. 167:1996-2003).

Efficacy in preventing or treating an inflammatory disorder may be demonstrated, e.g., by detecting the ability of a Therapeutic Agent, a composition thereof, or a combination therapy comprising a Therapeutic Agent to reduce one or more symptoms of the inflammatory disorder, to decrease T cell activation, to decrease T cell proliferation, to modulate one or more cytokine profiles, to reduce cytokine production, to reduce inflammation of a joint, organ or tissue or to improve quality of life.

Changes in inflammatory disease activity may also be assessed through tender and swollen joint counts, patient and physician global scores for pain and disease activity, and the ESR/CRP. Progression of structural joint damage may be assessed by quantitative scoring of X-rays of hands, wrists, and feet (Sharp method). Changes in functional status in humans with inflammatory disorders may be evaluated using the Health Assessment Questionnaire (HAQ), and quality of life changes are assessed with the SF.

The efficacy of a Therapeutic Agent, a composition thereof, or a combination therapy comprising a Therapeutic Agent in preventing, treating and/or managing Type I allergic reaction may be assessed by its ability to induce anti-IgE antibodies that inhibit IgE from binding to is receptor on mast cells or basophils in vitro. IgE levels can be assayed by immunoassays, gel electrophoresis followed by visualization, radioimmunosorbent test (RIST), radioallergosorbent test (RAST), or any other method known to those skilled in the art.

5.10 KITS

Provided herein is a pharmaceutical pack or kit comprising one or more containers filled with one or more of the ingredients of the compositions described herein, such as one or more antibodies provided herein, or one or more Therapeutic Agents provided herein. Optionally associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical pack or kit may include instructions for use of an antibody or Therapeutic Agent described herein.

The kits encompassed herein can be used in the above methods. In one embodiment, a kit comprises an antibody described herein, preferably an isolated antibody, in one or more containers. In another embodiment, a kit comprises a Therapeutic Agent described herein, in one or more containers.

In certain embodiments, encompassed herein are diagnostic kits for assessing the level of expression of a native receptor or native ligand. In some embodiments, one or more of the Therapeutic Agents described herein may be used to assess the level of expression of a native receptor or native ligand. Accordingly, provided herein are diagnostic kits comprising a Therapeutic Agent described, in a container. In some embodiments, instructions for how to use to the Therapeutic Agent to assess the level of expression of a native receptor or native ligand is included with the kit. In particular, the instructions included can describe contacting a patient sample (e.g., cells, fluids, etc.) with a Therapeutic Agent and detecting the Therapeutic Agent bound to the sample. The Therapeutic Agent might be labeled with a detectable moiety or a labeled secondary agent that recognizes the Therapeutic Agent might be used (and thus, can be included in the kit).

5.11 SCREENING ASSAY TO IDENTIFY RECEPTOR/LIGAND INTERACTIONS

In one aspect, presented herein are methods for identifying a receptor-ligand interaction. In one embodiment, presented herein is a method for identifying a receptor-ligand interaction, comprising: (a) contacting a fusion protein or conjugate with a cell engineered to express or expressing a protein of interest under conditions that permit the fusion protein or conjugate and the protein of interest to form a complex, wherein the fusion protein comprises a target protein or a fragment thereof and a peptide tag or other polypeptide marker, a penetrating peptide, or small molecule other than an organic molecule; and (b) detecting the presence of a fusion protein-protein of interest complex or conjugate-protein of interest complex, wherein the presence of a fusion protein-protein of interest complex or conjugate-protein of interest complex indicates that the target protein and the protein of interest have a receptor-ligand interaction. In another embodiment, presented herein is a method for identifying a receptor-ligand interaction, comprising: (a) contacting a fusion protein or conjugate with a cell engineered to express or expressing 2, 4, 6, 8, 10, 12 or more proteins of interest, or between 2 to 5, 2 to 8, 5 to 8, 5 to 10, or 10 to 12 proteins of interest under conditions that permit the fusion or conjugate protein and a protein of interest to form a complex, wherein the fusion protein or conjugate comprises a target protein or a fragment thereof and a peptide tag or other polypeptide marker, a penetrating peptide, or small molecule other than an organic molecule; and (b) detecting the presence of a fusion protein-protein of interest complex or conjugate-protein of interest complex, wherein the presence of a fusion protein-protein of interest complex or conjugate-protein of interest complex indicates that the target protein and the protein of interest have a receptor-ligand interaction.

In another embodiment, presented herein is a method for identifying a receptor-ligand interaction, comprising: (a) contacting a library of fusion proteins or a library of conjugates with a cell engineered to express or expressing a protein of interest under conditions that permit a fusion protein or conjugate and the protein of interest to form a complex, wherein the fusion protein or conjugate comprises a target protein or a fragment thereof and a peptide tag or other polypeptide marker, a penetrating peptide, or a small molecule other than an organic molecule; and (b) detecting the presence of a fusion protein-protein of interest complex or conjugate-protein of interest complex, wherein the presence of a fusion protein-protein of interest complex or conjugate-protein of interest complex indicates that the target protein and the protein of interest have a receptor-ligand interaction. In another embodiment, presented herein is a method for identifying a receptor-ligand interaction, comprising: (a) contacting a fusion protein or conjugate with a library of cells engineered to express or expressing a different protein of interest under conditions that permit the fusion protein or conjugate and a protein of interest to form a complex, wherein the fusion protein or conjugate comprises a target protein or a fragment thereof and a peptide tag or other polypeptide marker, a penetrating peptide, or small molecule other than an organic molecule; and (b) detecting the presence of a fusion protein-protein of interest complex or conjugate-protein of interest complex, wherein the presence of a fusion protein-protein of interest complex or conjugate-protein of interest complex indicates that the target protein and the protein of interest have a receptor-ligand interaction.

In certain embodiments, the target protein is expressed by a mammalian cell. In a specific embodiment the target protein is expressed by a hematopoietic cell. In another embodiment, the target protein is expressed by a muscle cell. In another embodiment the target protein expressed by a fibroblast. In another embodiment, the target protein is expressed by a epithelial cell. In another embodiment, the target protein is expressed by an endothelial cell. In another embodiment, the target protein is expressed by a lymphocyte. In another embodiment, the target protein is expressed by a macrophage or a fragment thereof. In another embodiment, the target protein is expressed by a dendritic cell. In another embodiment, the target protein is a co-stimulatory molecule (e.g., a co-stimulatory receptor or ligand). In another embodiment, the target protein is a cytokine or cytokine receptor. In a specific embodiment, the target protein is a human protein. In another specific embodiment, the target protein is a full length transmembrane protein. In another embodiment, the target protein is an orphan receptor or orphan ligand.

Non-limiting examples of peptide tags and other polypeptide markers include: a hexa-histidine peptide, an HA tag, a flag tag, the Fc domain of an antibody (e.g., an IgG antibody such as IgG1 or IgG2) and a region of the Fc domain of an antibody (e.g. an IgG antibody). In certain embodiments, a fusion protein comprises both a peptide tag or other polypeptide marker and a penetrating peptide.

Standard molecular biology techniques can be used to generate nucleic acids encoding a fusion protein, express the fusion protein, and isolate or purify it from cell culture. Nucleic acids encoding the extracellular domain of a target protein or a fragment thereof as well as nucleic acids encoding peptide tags or other polypeptide markers, or penetrating peptides may be publicly or commercially available. Nucleic acids can be engineered into constructs using standard molecular biology techniques. See Sections 5.2.4 and 5.3.4, supra, relating to nucleic acids. The nucleic acid constructs described in that section can also be used to produce nucleic acid constructs for transfection into cells for use in the methods described in this section.

In certain embodiments, the protein of interest is a protein expressed by a mammalian cell. In a specific embodiment the protein of interest is a protein expressed by a hematopoietic cell. In another embodiment, the protein of interest is a protein expressed by a muscle cell. In another embodiment the protein of interest is a protein expressed by a fibroblast. In another embodiment, the protein of interest is a protein expressed by a epithelial cell. In another embodiment, the protein of interest is a protein expressed by a endothelial cell. In another embodiment, the protein of interest is a protein expressed by a lymphocyte. In another embodiment, the protein of interest is a protein expressed by a dendritic cell. In another embodiment, the protein of interest is a protein is a co-stimulatory molecule (e.g., a co-stimulatory receptor or ligand). In another embodiment, the protein of interest is a cytokine or cytokine receptor. In a specific embodiment, the protein of interest is a human protein. In another specific embodiment, the protein of interest is a full length transmembrane protein. In another embodiment, the protein of interest is an orphan receptor or orphan ligand. See Table 1 non-limiting examples of proteins of interest.

Nucleic acids encoding a protein of interest or a fragment thereof may be publicly or commercially available. Nucleic acids can be engineered into constructs using standard molecular biology techniques. See Sections 5.2.4 and 5.3.4, supra, relating to nucleic acids. The nucleic acid constructs described in that section can also be used to produce nucleic acid constructs for transfection into cells for use in the methods described in this section.

Cells may be transfected stably or transiently with a nucleic acid sequence encoding a protein of interest or a nucleic acid construct comprising a nucleic acid sequence encoding a protein of interest. See Section 5.3.5 supra for methods for transfecting cells with nucleic acid sequences. Non-limiting examples of cells that can be used to express the fusion protein(s) include mammalian cells, bacterial cells, yeast cells, primary cells, immortalized cells, and insect cells. In certain embodiments, the cells are a mammalian cell line.

Examples of mammalian cell lines include, but are not limited to, COS, CHO, HeLa, NIH3T3, HepG2, MCF7, HEK, 293T, RD, PC12, hybridomas, pre-B cells, 293, 293H, K562, SkBr3, BT474, A204, M07Sb, TFÿ, Raji, Jurkat, MOLT-4, CTLL-2, MC-IXC, SK-N-MC, SK-N-MC, SK-N-DZ, SH-SY5Y, C127, NO, and BE(2)-C cells. Other mammalian cell lines available as hosts for expression are known in the art and include many immortalized cell lines available from the American Type Culture Collection (ATCC). In another embodiment, the cells are immortalized cell lines derived from a subject. In another embodiment, the cells are primary or secondary cells from a subject. In a particular embodiment, the cells are cancer cells. In another embodiment, the cells are fetal/embryonic cells. In some embodiments, the cells are progenitor cells. In some embodiments, the cells are lymphocytes (e.g., T cells and B cells). In another embodiment, the cells are stem cells. In a specific embodiment, the cells are 293T cells.

In specific embodiments, cells transfected with nucleic acids encoding a protein of interest have a high level of expression.

In certain embodiments, a fusion protein or conjugate is contacted with a cell expressing a protein of interest in a well of plate. In particular embodiments, a fusion protein or conjugate is contacted with a cell expressing a protein of interest in a microtiter plate. In a specific embodiment, microtiter plate is a 12 well, 96, well, or 384 well microtiter plate.

In certain embodiments, a cell expressing a protein of interest is incubated with a fusion protein or conjugate under physiological conditions. In some embodiments, a cell expressing a protein of interest is incubated with a fusion protein or conjugate at about 22° C., 25° C., 32° C., or 37° C., or about 22° C. to about 25° C., about 22° C. to about 27° C., about 25° C. to about 27° C., about 32° C. to about 35° C., or 32° C. to about 37° C. In certain embodiments, a cell expressing a protein of interest is contacted with a fusion protein or conjugate for about 5 minutes, 10 minutes, 15 minutes, 30 minutes, 45 minutes, 1 hour, 2 hours, 4 hours, 6 hours, 8 hours, 10 hours, 12 hours, 16 hours, 18 hours, 1 day, 2 days or more. In some embodiments, after contacting the fusion protein or conjugate with a protein of interest, one or more wash steps may be performed to remove unbound fusion protein or unbound conjugate. In alternative embodiments, no wash steps may be performed to remove unbound fusion protein or unbound conjugate.

In some embodiments, an antibody that specifically binds to a peptide tag or other polypeptide marker, or a penetrating peptide is used to detect a fusion protein-protein of interest complex or conjugate-protein of interest complex. In some embodiments, the antibody is contacted with the cells at about 22° C., 25° C., 32° C., or 37° C., or about 22° C. to about 25° C., about 22° C. to about 27° C., about 25° C. to about 27° C., about 32° C. to about 35° C., or 32° C. to about 37° C. In some embodiments, the antibody is contacted with the cells for about 15 minutes, 30 minutes, 45 minutes, 1 hour, 2 hours, 4 hours, 6 hours, 8 hours, 10 hours, 12 hours, 16 hours, 18 hours, 1 day, 2 days or more. In some embodiments, after contacting the antibody with the cells, one or more wash steps may be performed to remove unbound antibody. In alternative embodiments, no wash steps may be performed to remove unbound antibody.

In specific embodiments, an antibody that specifically binds to a peptide tag or other polypeptide marker, or a penetrating peptide is labeled with a detectable moiety. Non-limiting examples of detectable moities can be found in Section 5.1.2 and 5.2.3, supra. In a specific embodiment, the antibody is labeled with a fluorescent moiety. In certain embodiments, the Applied BioSystem 8200 Cellular Detection System (CDS) can be used to detect the fluorescence of the antibody bound to the fusion protein-protein of interest complex. In a specific embodiment, the CDS scans the well of a microtiter plate at a depth of about 75 µm, about 90 µm, about 95 µm, about 100 µm, about 105 µm, about 110 µm, about 115 µm, or about 120 µm. In some embodiments, fluorescence polarization is used to detect a fusion protein-protein of interest complex.

Once a receptor-ligand interaction has been identified using a method described this section, the receptor-ligand interaction may be assessed using another biological assay described herein (e.g., binding affinity, a proliferation assay, etc.).

The assays described in this section can be applied to identify an interaction between a small molecule and another organic molecule, such as a peptide comprising certain residues of interest from a particular protein (e.g., tyrosine residues).

6. EXAMPLE

Identification of Lymphocyte Co-Stimulatory Interactions by a Human Receptor Proteome The following example is offered by way of illustration, and not by way of limitation.

6.1 MATERIALS & METHODS 6.1.1 Plasmids, Fusion Proteins and Monoclonal Antibodies Human full length plasma membrane cDNA set (MHS5007) was purchased from the Open Biosystems Inc. (Huntsville, Ala.), and ~800 genes from the set which is on mammalian expression vector pCMV-SPORT6 were included. Approximately 1,000 genes in non-mammalian expression vector pcDNA3.2/V5-DEST or pcDNA6.2/V5-DEST plasmids were cloned into pcDNA3 vector using the Gateway Cloning System based on homologous recombination (Invitrogen, Carlsbad, Calif.). Other genes are cloned into pcDNA3 plasmid by standard RT-PCR cloning technique and the cDNA sequences were validated by the sequencing.

Human CD28Ig, CTLA4Ig, ICOSIg, PD-1Ig, B7-1Ig, B7-2Ig, B7-H1Ig, B7-DCIg and B7-H2Ig fusion proteins were purchased from R&D systems (Minneapolis, Minn.). CTLA4Ig (Orencia) was purchased from the Bristol-Myers Squibb (New York, N.Y.). B7-H7Ig, B7-H67CRIg and FLAG-Ig fusion proteins were made by transiently transfecting 293T cells with the constructs in pMIgV or pHIgV plasmids, and were purified by protein A columns as described previously (1).

Mouse anti-human CD3 mAb OKT3, mouse anti-human CD28 mAb CD28.6 (blocking), mouse anti-human CD28 mAb CD28.2 (costimulatory), mouse anti-human CTLA-4 mAb 14D3 and mouse anti-human B7-H2 mAb MIH12 were purchased from eBioscience (San Diego, Calif.). Mouse anti-human ICOS mAb C398.4A and mouse anti-human B7-H2 mAb 9F.8A4 were purchased from BioLegend (San Diego, Calif.). Anti-human Ig and anti-mouse Ig FMAT blue antibody were purchased from Applied Biosystems (Foster City, Calif.). Control human IgG (Synagis®) was purchased from MedImmune (Rockville, Md.). Control hamster IgG, hamster anti-mouse TNP was purchased from eBioscience. Mouse anti-human B7-H7 mAb was generated from a hybridoma derived from the fusion of SP2 myeloma with B cells from a mouse immunized with human B7-H7Ig. Hamster anti-human B7-H7CR mAb was generated from a hybridoma derived by fusion of SP2 myeloma with B cells from a hamster immunized with human B7-H7CRIg as described elsewhere (2). All other antibodies used in flow cytometry were purchased from BD Bioscience (San Jose, Calif.) or eBioscience.

6.1.2 High-Throughput Transfection and Screening

Plasmids with human transmembrane genes were diluted by OPTI-MEM media and placed individually into five 384-well plates at 30 ng/well. Lipofectamine 2000 was added to each well and mix with plasmids for 30 minutes. Ten thousand 293T cells were added subsequently to the wells to perform transient transfection. Eight hours after transfection, human CD28Ig and anti-human Ig FMAT blue secondary antibody, or human B7-H7CRIg and anti-mouse Ig FMAT blue secondary antibody were added into the wells. The plates were read twenty-four hours after transfection by the Applied Biosystems 8200 cellular detection system and analyzed by CDS 8200 software. The plasmids in positive wells were picked and subsequently transfected into 293T cells for further validation.

6.1.3 Surface Plasmon Resonance

Protein interactions were measured and analyzed on a BIAcore 3000 instrument (BIAcore AB, Uppsala, Sweden) performed at 25° C. as described previously (3). 0.1 M Hepes, pH 7.4, containing 0.15 M NaCl, 0.005% surfactant P20 (HBS) was used as running buffer. Human B7-H2Ig, CD28Ig and CTLA-4Ig were purchase from R&D systems. All other reagents were purchased from BIAcore. The B7-H2Ig was covalently coupled to a CM5 sensor chip (BIAcore AB) by crosslinking primary amine groups to the carboxymethylated dextran matrix. A flow cell on the CM5 chip was activated with 1:1 N-ethyl-N-dimethylaminopropyl carbodiimide (EDC) and N-hydroxysuccinimide (NHS) mixture, followed by injection of 20 μg/ml B7-H2Ig diluted in 10 mM sodium acetate buffer, pH 5.0, until desired response units (RU) were achieved. Another activated flow cell on the same chip, which did not receive any fusion protein, was used as a control sensor surface. The remaining activated carboxyl groups were blocked with 1 M ethanolamine (pH 8.5). Subsequently, the flow cells were extensively washed with HBS to generate a stable baseline. Analytes, ICOSIg, CD28Ig and CTLA4Ig, in serial dilutions were injected over the sensor surface in triplicates at a flow rate of 20-30 μl/min for 3 min, and then the dissociation was allowed for 5 min. The flow cells were regenerated by two consecutive 10-second pulse with 10 mM NaOH. Data was analyzed by BIAevaluation software 4.1 (BIAcore).

6.1.4 T Cell Costimulation Assay

OKT mAb (anti-human CD3) was pre-coated in the 96-well plates at the indicated concentrations. B7-H2Ig, B7-H7Ig, anti-B7-H7CR or control Ig at 5 μg/ml were also immobilized in the wells. Human peripheral blood T cells were negatively selected and purified by a human pan-T cell selection kit or a human CD4 T cell selection kit (Miltenyi Biotec, Auburn, Calif.). Naïve human T cells were added into each well at $2.5-3 \times 10^5$ cells/well and cultured for three days. In some experiments, costimulatory anti-human CD28 or blocking anti-human CD28 and anti-human ICOS were added at the beginning of the culture. 3HTdR was added during the final six hours of culture. 3H-TdR incorporation was counted with a MicroBeta Trilux liquid scintillation counter (Wallac).

6.1.5 Human Monocyte-Drived Macrophates and Dendritic Cells

Human PBMC were isolated by density-gradient centrifugation. Fifty million PBMCs were adhered on 100 mm tissue culture dish for 45 min in a 37 degree incubator. Adherent cells at $0.5 \times 10^6$ cells/ml were cultured in 10 ml 10% complete RPMI media. The media was supplemented with 1,000 U/ml GM-CSF for macrophage generation, or 500 U/ml IL-4 and 1000 U/ml GM-CSF for dendritic cell differentiation. On day 2, 4 and 6, half of the media was taken out and changed with fresh media with cytokines. On day 7, macrophages and immature dendritic cells were harvested.

6.1.6 Elisa

Supernatants from T cell costimulation assay were collected. Human IFN-γ, IL-2 and IL-10 were detected by sandwich ELISA methods according to the manufacturer instructions (BD PharMingen or eBioscience).

6.2 RESULTS

Plasma membrane receptors on immune cells are evolved to mediate broad biological functions including detection of pathogens, cell adhesion, antigen recognition and transmission of extracellular signals into cells. Therefore, interactions between immune receptors and their ligands (or counter-receptor) are pivotal for cell communication and integration leading to execution of immune responses. By searching human genome databases, more than 3,000 unique DNA sequences, which encode hydrophilic extracellular domain and hydrophobic transmembrane domain, are predicted to be capable of encoding cell membrane proteins (4, 5). However, less than 500 proteins have been identified as counter-receptors and this is largely due to limitation of sensitive methods. Many cell surface proteins or their mRNA are in low abundance and their expressions varies according to environmental cues. In addition, the majority of cell surface molecular interactions are in fast-on-and-fast-off mode with weak affinity. While this feature allows maximal control of signaling and their effect in immune responses, it increases the difficulty to identify the interactions by current methods including expression cloning and protein micro-sequencing.

Over 1,900 full length human transmembrane genes have been obtained based on their expression on hematopoietic cells (Table 1). These genes include the molecules from immunoglobulin superfamily (IgSF), tumor necrosis factor superfamily (TNFRSF), C-type lectin superfamily, G protein coupled receptor (GPCR) superfamily, as well as the majority of lectins, integrins and scavenger receptors. By transfection of individual plasmids into 293T cells in 384-well plates, high level expression of genes in 50-70% of 293T cells from randomly selected samples in this proteome was demonstrated. High level expression of individual proteins on the cell surface increases avidity of interaction with their counter-receptors. For screening of an unknown counter-receptor of a target protein, the extracellular domain of the target gene is genetically fused to a tag gene (mouse IgG2a Fc, human IgG1 Fc, FLAG or 6×HIS), and the recombinant fusion protein, which is generated by transient transfection of the plasmid into 293T cells, is used for detection by binding to the proteome. Fluorescence-labeled secondary antibody against the tag is applied to detect the binding of target protein to the proteome. The Applied Biosystem 8200 Cellular Detection System (CDS) was adapted for rapid screening of binding fluorescence activity (FIG. 1). The CDS allows scanning of only the bottom of a microplate well at a depth of 100 μm so as to ignore non-binding secondary antibody, resulting in a high signal to noise ratio eliminating all washing steps. Combining increased avidity interaction and a highly sensitive detection system, enables the identification receptor-ligand interactions which are undetectable on primary cells by other methods such as flow cytometry.

Molecules in the B7-CD28 family are found to modulate T cell receptor signals and play essential roles in the control of T cell-mediated immune responses in positive and negative fashions (6-8). CD28 was selected as a target protein to test the proteome system. CD28 delivers a costimulatory signal to naive T cells upon engaging one of two counter-receptors B7-1 or B7-2, on professional antigen presenting cells including dendritic cells, B cells and macrophages (9). As expected, recombinant human CD28Ig fusion proteins bound 293T cells which were transfected to express B7-1 (CD80) or B7-2 (CD86, B70) genes. The cells expressing Fc receptors were also positively stained due to human IgG1 Fc tag on CD28Ig. Unexpectedly, CD28Ig was also found to bind 293T cells transfected with B7-H2 gene (FIG. 2). B7-H2 (ICOSL, CD275, B7RP-1) is a B7 family molecule and was previously shown to be the ligand for inducible costimulator (ICOS) (7). ICOS is a CD28-like molecule on activated T cells and is costimulatory for T cells upon binding B7-H2 to preferentially elicit Th2-mediated immune responses (10, 11). This binding was validated by flow cytometry analysis with positive staining of CD28Ig to B7-H2+293 cells (FIGS. 3A and 3B) and vice versa with B7-H2Ig staining of CD28+ cells (FIG. 3D) Importantly, the binding of CD28Ig to B7-H2+ 293T cells could be selectively blocked by the inclusion of monoclonal antibody (mAb) against CD28 (clone CD28.6) (FIG. 3B) and mAb against B7-H2 (clone MIH12) (data not shown). Interestingly, while a B7-H2 mAb (clone 9F.8A4) could block binding of B7-H2Ig to both ICOS and CD28, another mAb (clone MIH12) selectively abrogated the B7-H2/CD28 but not B7-H2/ICOS interactions (FIGS. 3D and 4), indicating that B7-H2 utilizes non-overlapping binding sites to interact with CD28 and ICOS. The results thus demonstrate the specificity of B7-H2/CD28 binding. Affinity comparison of B7-H2 to ICOS vs. CD28 by surface plasmon resonance (SPR) analysis shows that B7-H2/CD28 interaction has a significantly slow association (Ka) and a faster dissociation constants (Kd) to B7-H2/ICOS (FIG. 3F), indicating that ICOS has higher affinity than CD28 for binding B7-H2. CD28 is constitutively expressed on naive T cells while ICOS is inducible upon antigen stimulation (11). These findings implicate a role of B7-H2 in the costimulation of naive T cells in addition to activated T cells.

Figures 3D, 3E:
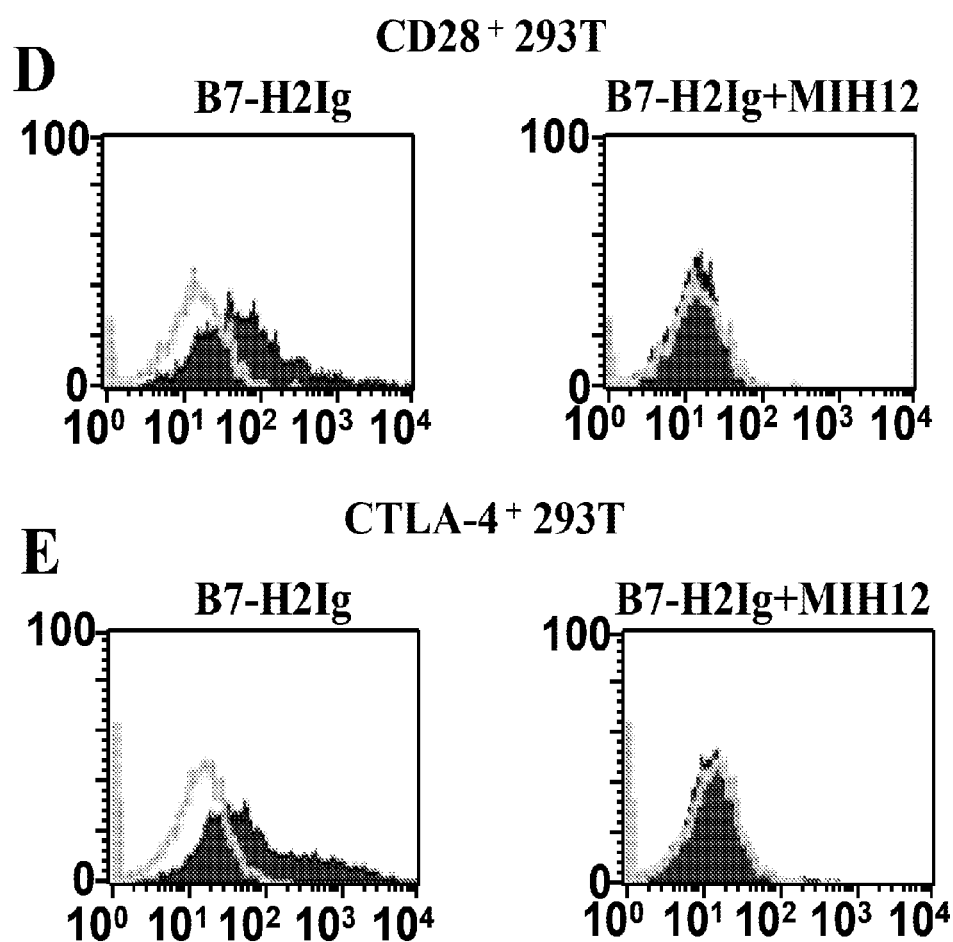
Figure 3F:
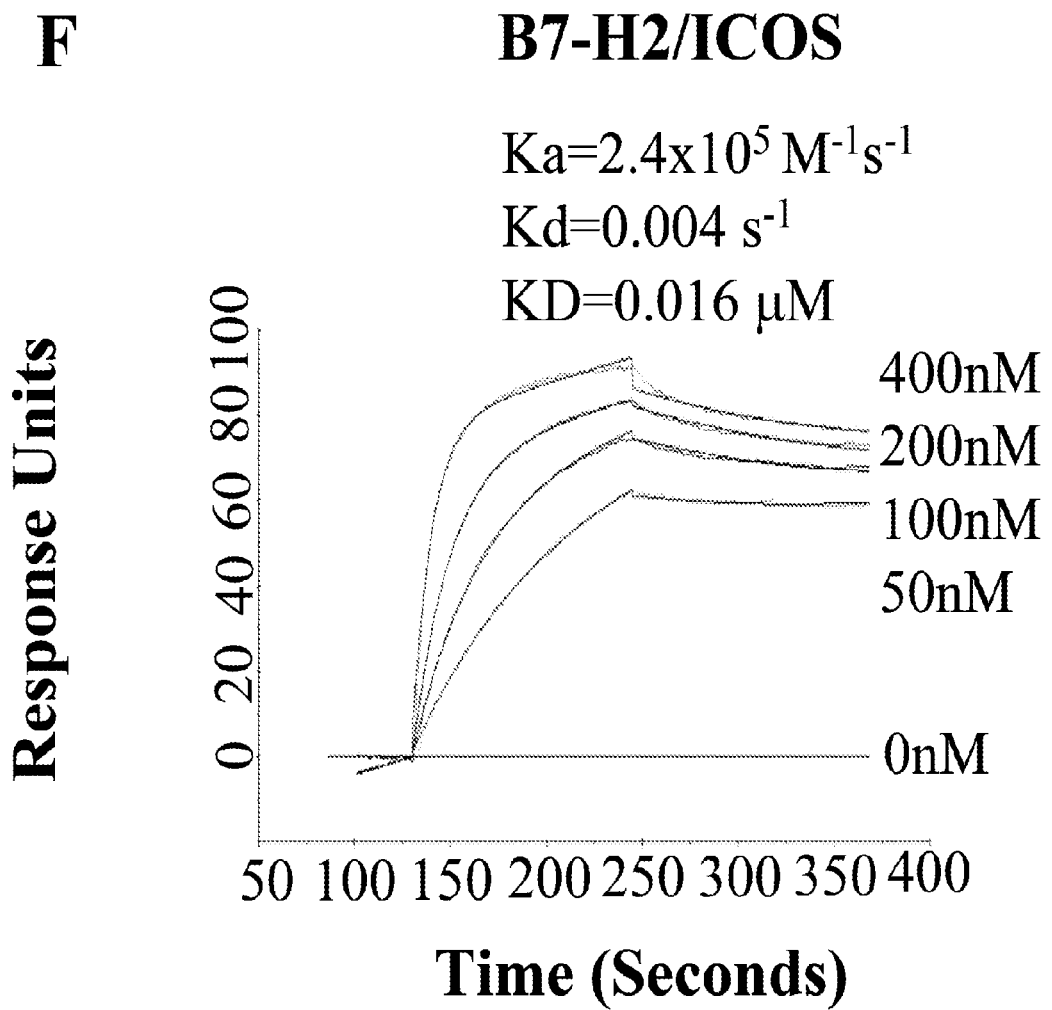
Figure 3F:
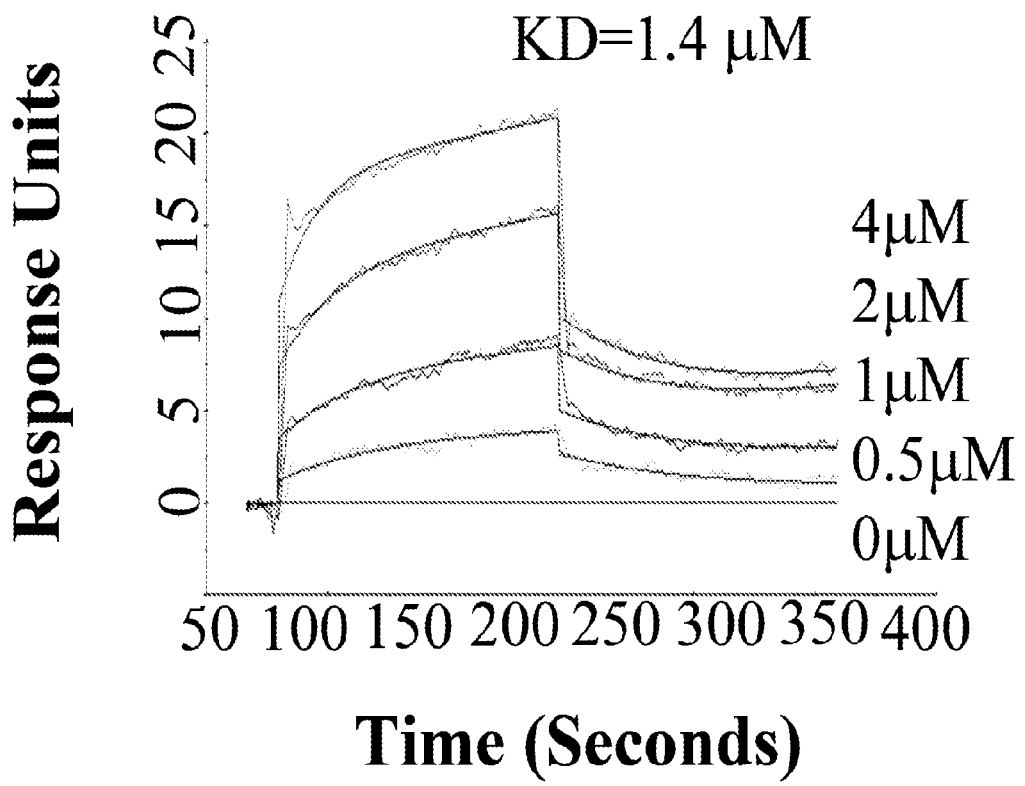
Figure 3F:
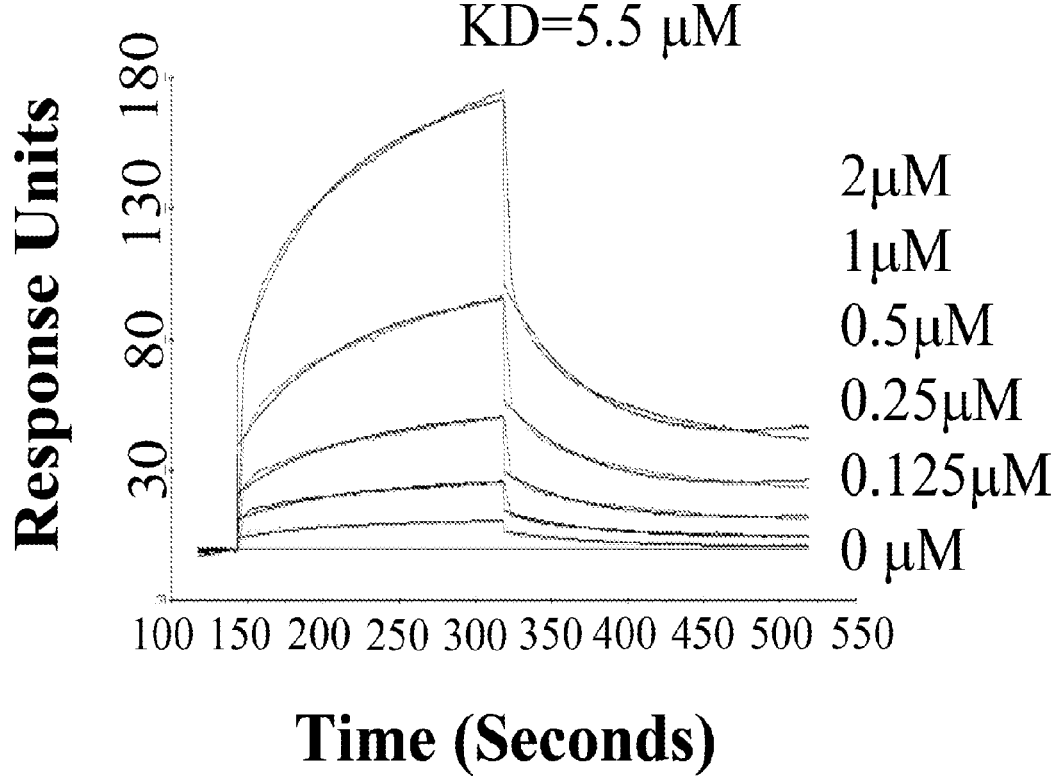

CTLA-4, homologue of CD28 and similar to ICOS, can be induced on T cells upon activation. Engagements of CTLA-4 by B7-1 and B7-2 are thought to deliver an inhibitory signal to down-regulate T cell response to antigen (12). CTLA4Ig was shown to also bind B7-H2+293 cells (FIG. 3C) and the binding was largely eliminated by inclusion of a CTLA-4 mAb (clone 14D3) (FIG. 3C) which showed to block CTLA-4 and its ligands (13). Conversely, B7-H2Ig bound CTLA-4+293T cells and two B7-H2 mAbs (clone MIH12 and 9F.8A4), which block B7-H2/CD28 binding, also abrogated this binding (FIGS. 3D, 3E and 4). In comparison with B7-H2/ICOS, B7-H2/CTLA-4 interaction has a much slower association and a faster dissociation (FIG. 3F). These results indicate that B7-H2 will preferentially interact with ICOS. Both ICOS and CTLA-4 are inducible receptors with similar expression kinetics upon activation (11). This finding predicts that the major effect of B7-H2 on activated T cells will be those related to ICOS rather than CTLA-4. To determine if there are other interactions in currently discovered molecules of the B7-CD28 family, the binding of these receptors and their counter-receptors were screened using the proteomic system. As summarized in FIG. 5A, there are no additional interactions except further confirmation of B7-H2 binding to both CD28 and CTLA-4.

Figure 3G:
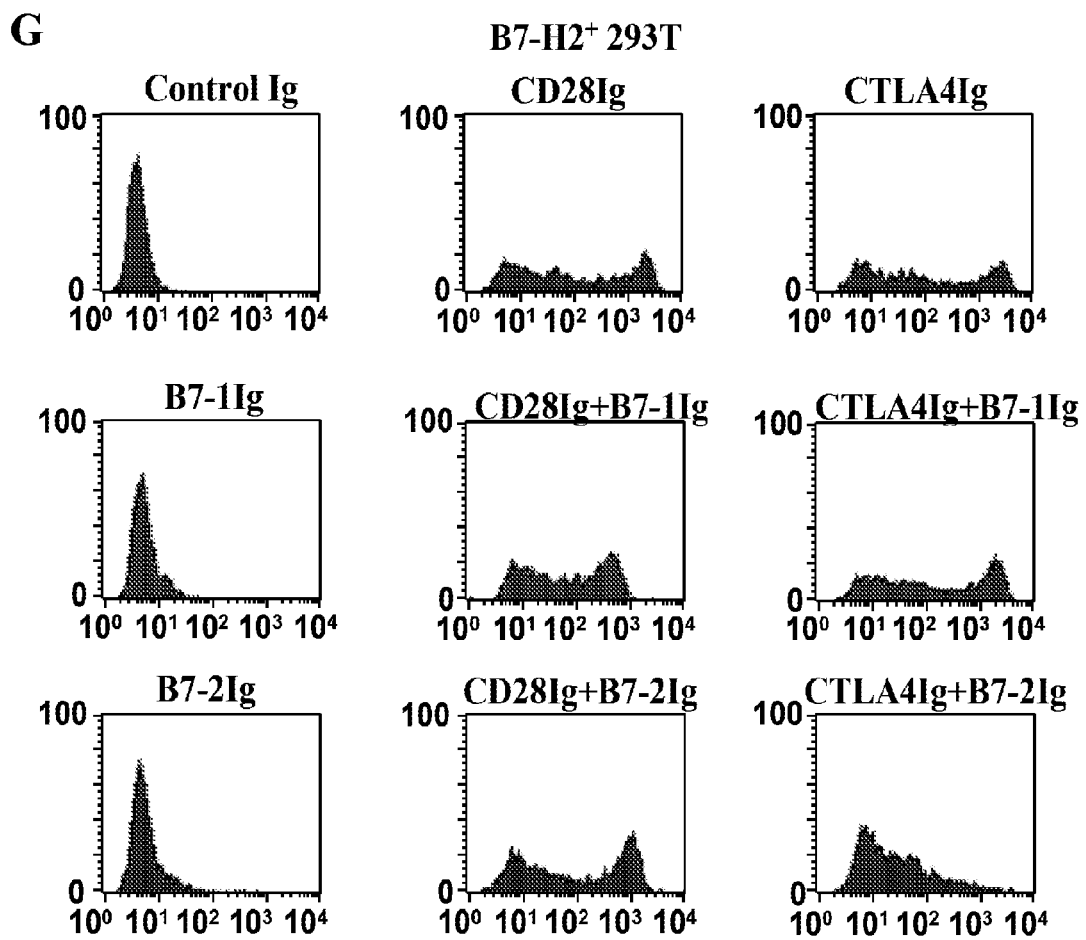

Comparison of binding B7-H2 to CTLA-4 vs. CD28 by SPR analysis indicates that B7-H2/CTLA-4 interaction has ~4 fold less association (Ka) but similar dissociation rate (Kd) to B7-H2/CD28 (FIG. 3F), indicating that B7-H2 has higher affinity to CD28 than CTLA-4 (FIG. 3F). This observation is in sharp contrast to B7-1 and B7-2 which bind CTLA-4 with much higher affinity (>10 folds) than CD28 (14), implicating that B7-H2 is a non-redundant ligand to B7-1/B7-2. To test this, the ability of the B7-H2/CD28 interaction to be interfered by B7-1/B7-2 was determined. By flow cytometry, saturated doses of B7-1Ig and B7-2Ig had only minimal effect on the binding of CD28Ig to B7-H2+293T cells, supporting that B7-H2 interacts with a non-overlapping site vs. B7-1/B7-2 on CD28 molecule (FIG. 3G). In contrast, B7-1 and B7-2 are largely redundant in term of their interaction with CD28 and could compete each other for binding CD28 (15). These findings implicate a new feature of costimulation: more than one structure on a costimulatory receptor is available for ligands to interact, and this finding suggests that B7-H2 could costimulate naive T cells in synergy with B7-1/B7-2.

To further understand architecture of interactions between B7-H2 and its three receptors, site-directed mutagenesis was conducted to identify critical residues for these interactions. Selection of residues for mutation was based on their locations in the interfaces of B7-H2/ICOS interaction as predicted from crystal structure analysis (16) as shown in ribbon diagram (FIG. 6A). These residues were all converted to alanine, a small aromatic amino acid, to avoid a large overall structure modulation (16). Wild type and mutated B7-H2 full length genes were transfected into 293 cells and the binding of these cells by CD28Ig, CTLA-4Ig and ICOSIg were determined by flow cytometry analysis. All mutants, which lost their binding to CD28, also do not interact with CTLA-4, indicating that B7-H2 binding sites for CD28 and CTLA-4 are largely overlapped, i.e. CD28 and CTLA-4 should compete for the binding to B7-H2. Two mutants (Y51A, Y53A) that lose their binding to ICOS, also show significant decrease in their binding to CD28 and CTLA-4 (FIG. 6B). Interestingly, two mutants (L116A and F122A), which largely retain the ability to bind ICOS, have only minimal binding capacity to CD28 and CTLA-4. In the context of the finding that MIH12 mAb selectively blocked B7-H2 binding to CD28 and CTLA-4 but not ICOS (FIG. 4), these results support the notion that B7-H2 uses non-identical but overlapping binding sites for interacting with ICOS and CD28/CTLA-4.

Figure 3J:
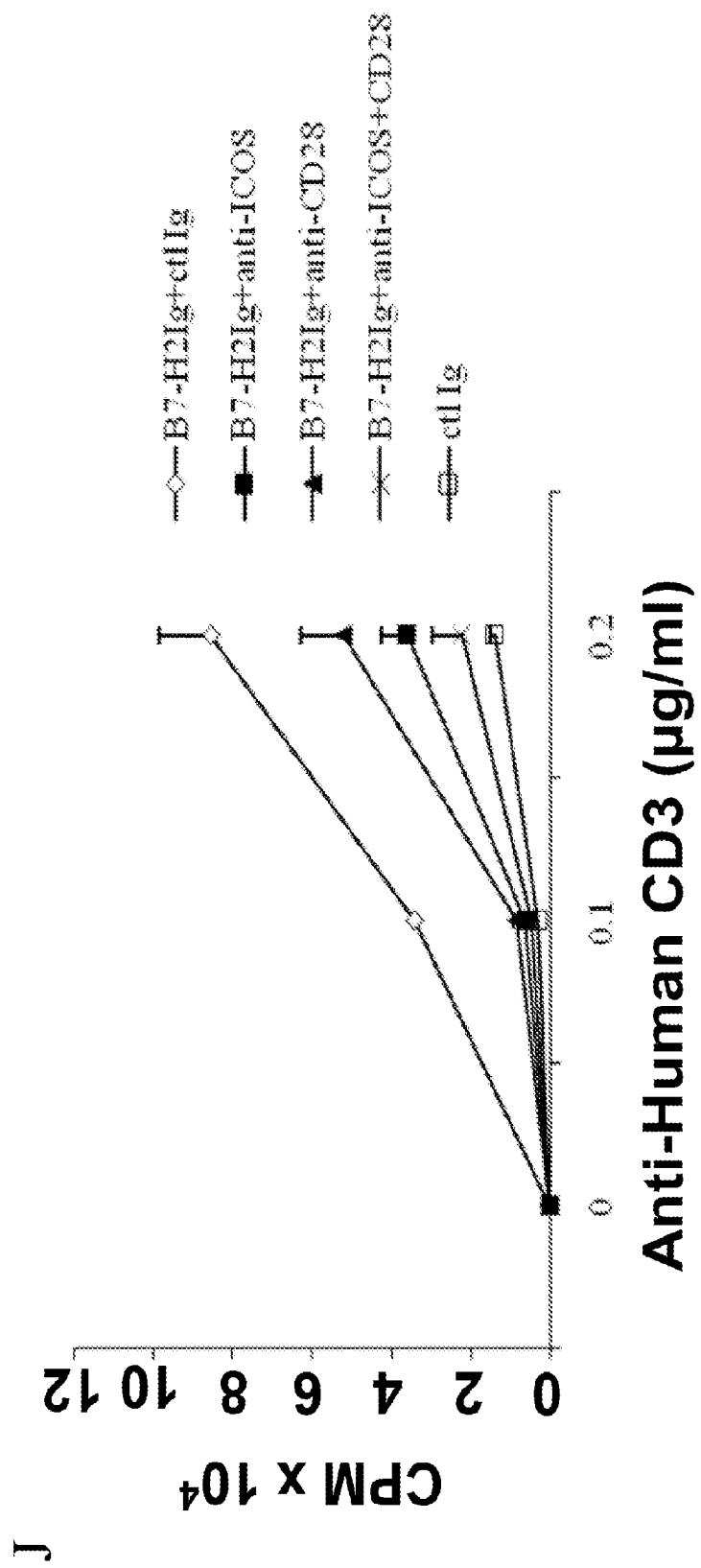
Figure 3K:
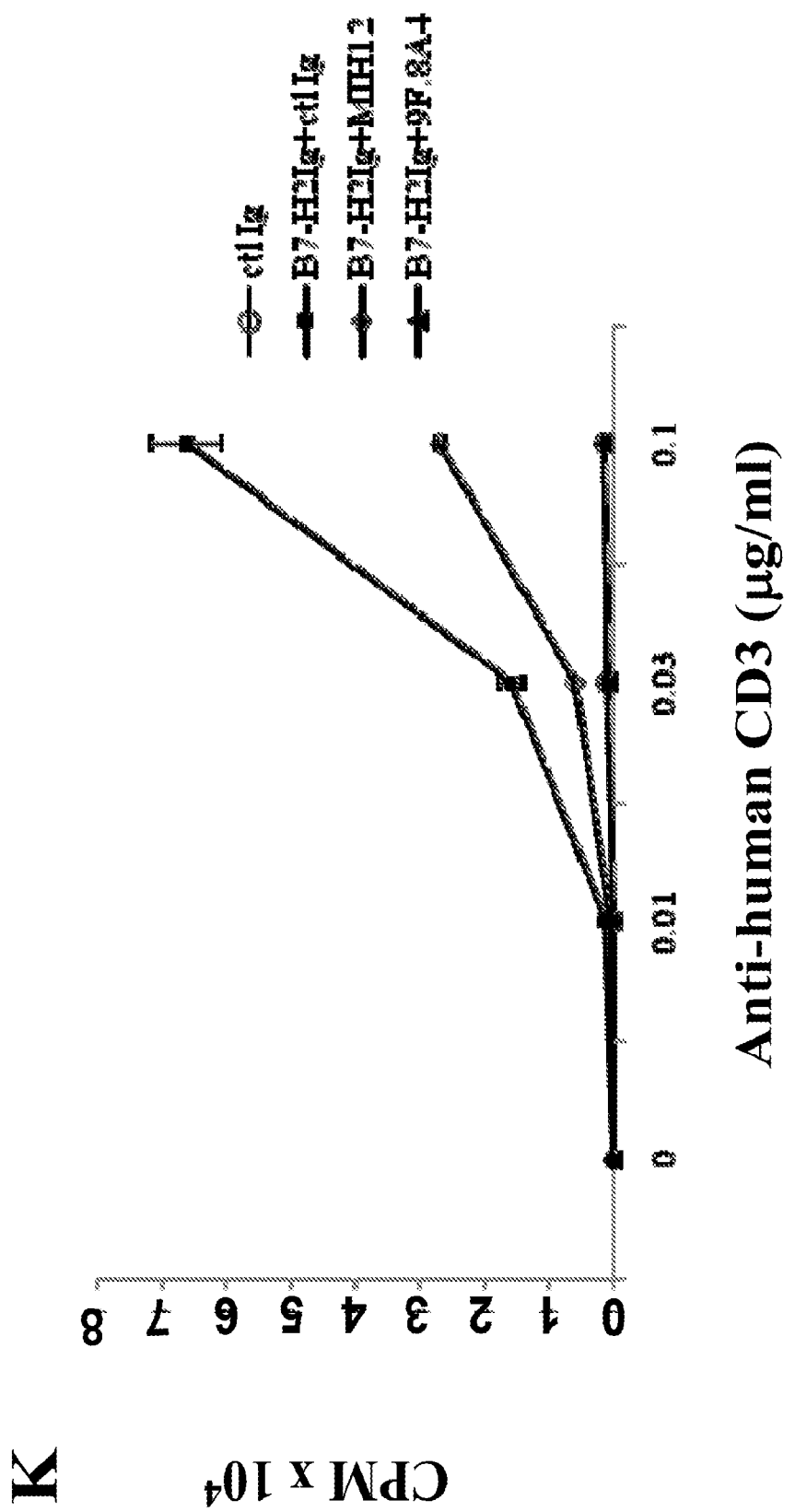

To demonstrate that the interaction of B7-H2 and CD28 is functional, an in vitro costimulation assay was utilized in which suboptimal concentrations of plate-bound human CD3 mAb were used as mimicry of a T cell receptor signal and B7-H2Ig was co-immobilized in the same well to provide costimulation for purified human T cells. B7-H2Ig potently costimulated proliferation of naïve human T cells in this assay (FIG. 3J). Inclusion of blocking mAb either to CD28 (clone CD28.6, non-costimulatory) or ICOS (clone C398.4A, non-costimulatory) partially but significantly reduced T cell proliferation, whereas blockade of both ICOS and CD28 negated the majority of B7-H2 costimulatory effect (FIG. 3J), This result indicates that the effect of B7-H2-mediated costimulation of T cells requires CD28 in addition to ICOS in this in vitro T cell proliferation assay. To exclude possible costimulation from B7-1 and B7-2 that could be upregulated on T cells, both B7-1 and B7-2 were blocked by specific mAb in this assay. B7-H2Ig-mediated costimulation was not affected by mAb to B7-1/B7-2 while this treatment inhibited T cell costimulation by B7-1Ig and B7-2Ig (data not shown). The effect of B7-H2 specific mAb MIH12 is shown to selectively eliminate B7-H2 binding to CD28/CTLA-4 but not to ICOS (FIG. 4). This treatment partially suppressed the B7-H2Ig-mediated costimulation. Furthermore, mAb 9F.8A4, which blocks B7-H2 binding to all three receptors, completely abolished the effect of B7-H2Ig (FIG. 3K). All together, these results support that B7-H2 is capable of costimulating T cell growth via CD28.

B7-H2-CD28/CTLA4 interactions add another layer of complexity to T cell costimulation. The non-overlapping expression patterns of B7-H2 with B7-1 and B7-2 in the peripheral organs make it possible that three ligands could affect T cell responses through CD28/CTLA4 in spatially and timely divergent settings. Discovery of B7-H2-CD28 and B7-H2-CTLA4 interactions thus validated this proteomic system as a tool to discover novel interactions even among well-studied molecules.

The use of this proteome system to identify the receptor for orphan ligands using B7-H7 as an example was explored. B7-H7 was previously described as human endogenous retrovirus-H long terminal repeat-associating protein 2 (HHLA2) without identified biological function (17), though it was noted as a potential B7 family member by homolog search (18). By comparison of its nucleotide and protein sequences, its homology to other known human B7 members including B7-1, B7-2, B7-H1, B7-DC, B7-H2, B7-H3 and B7-H4, with the highest homology to B7-H4 was demonstrated (FIG. 7). Therefore, assigned the gene name B7-H7 was assigned. The gene is located in chromosome 3q13.13, immediately adjacent to B7-1 and B7-2, and encodes a 414 amino-acid-long type I transmembrane protein with predicted molecular mass ~45 KD. B7-H7 has 3 signature immunoglobulin (Ig) sets (IgV-IgC-IgV) in its extracellular domain and shares ~20% homology in protein sequence with other B7 family molecules. B7-H7 also has an irregular intracellular domain without any significant homology to other B7 family molecules and no obvious motifs for signal transduction, a signature of the B7 family molecules.

Figure 10A:
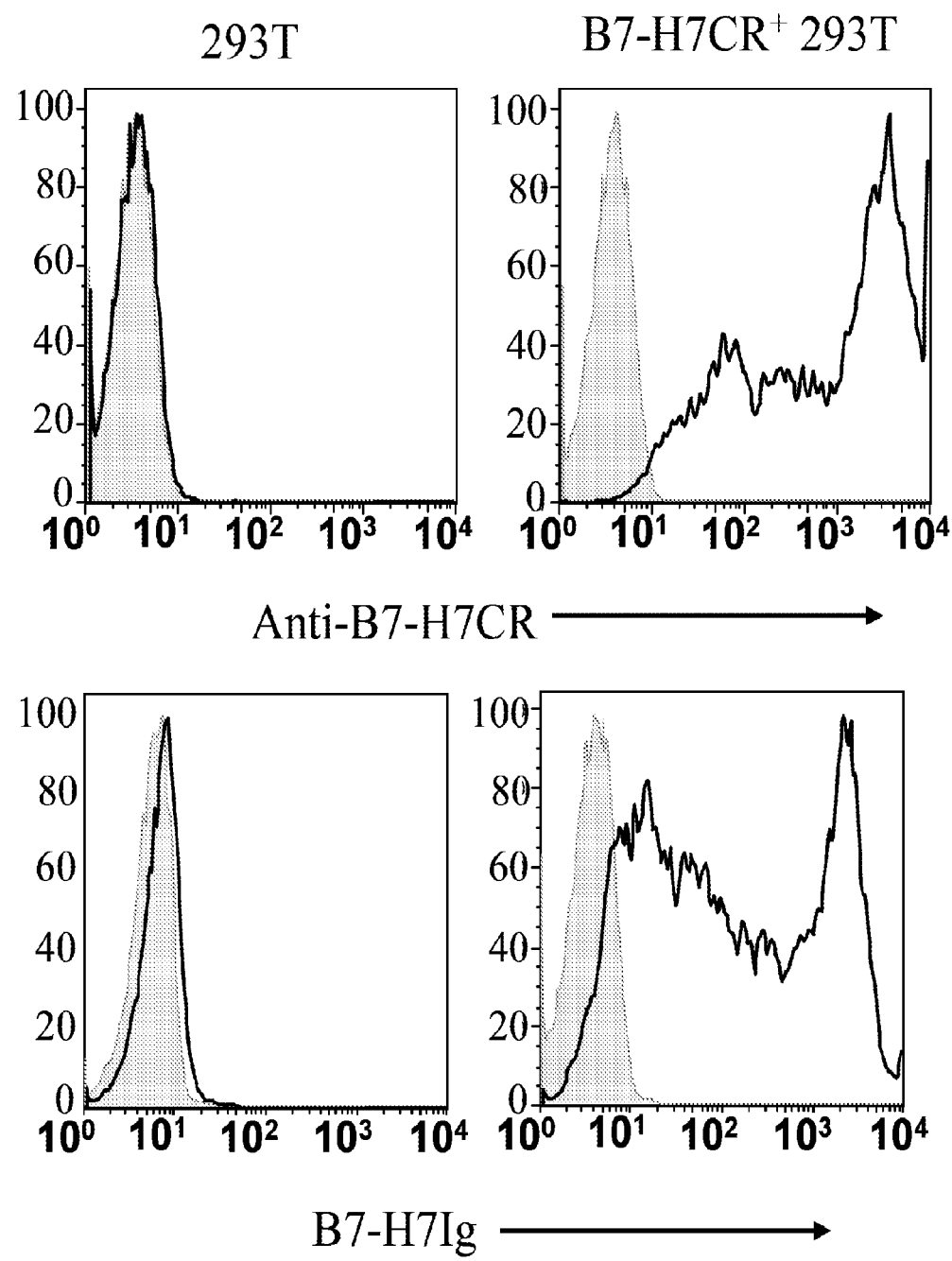

By screening the receptor-ligand proteome with B7-H7Ig, a B7-H7 binding partner called transmembrane and immunoglobulin domain containing 2 (TMIGD2) (gene ID 126259) was identified (FIG. 8). Similar to B7-H7, no function has been assigned for this gene. Herein this gene product was renamed the counter-receptor for B7-H7 (B7-H7CR). B7-H7CR is located in chromosome 19p13.3 and encodes a transmembrane protein with a single extracellular IgV domain and a long intracellular domain, which is structurally similar to other known B7 family receptors. Notably, the intracellular domain of B7-H7CR also contains three tyrosine residues, which are potentially docking sites for signaling transduction. Overall, B7-H7CR shares about 10% protein sequence homology with CD28, CTLA-4, ICOS and PD-1 (FIG. 9). mAb specific to both human B7-H7 and B7-H7CR was generated. By transfection of 293T cells with B7-H7CR gene, the expression of cell surface B7-H7CR by staining with anti-B7-H7CR mAb (clone 4-5) in flow cytometry analysis was demonstrated. B7-H7Ig strongly bound B7-H7CR+293T cells but not mock-transfected cells (FIG. 10A). Similarly, B7-H7CRIg also bound cells which were transfected with B7-H7 gene, but not mock-transfected cells. Inclusion of B7-H7 mAb (clone 2D3) completely blocked this interaction (FIG. 11). The potential cross-reactivity between B7-H7CR to other known B7 family ligands was excluded by B7-H7CRIg staining of 293T cells transfected with human B7-1, B7-2, B7-H1, B7-DC, B7-H2, B7-H3 (both 2Ig and 4Ig forms) and B7-H4 (FIG. 12). These results thus indicate that B7-H7 specifically binds B7-H7CR and may represent a new pair in the B7-CD28 family.

Figure 10B:
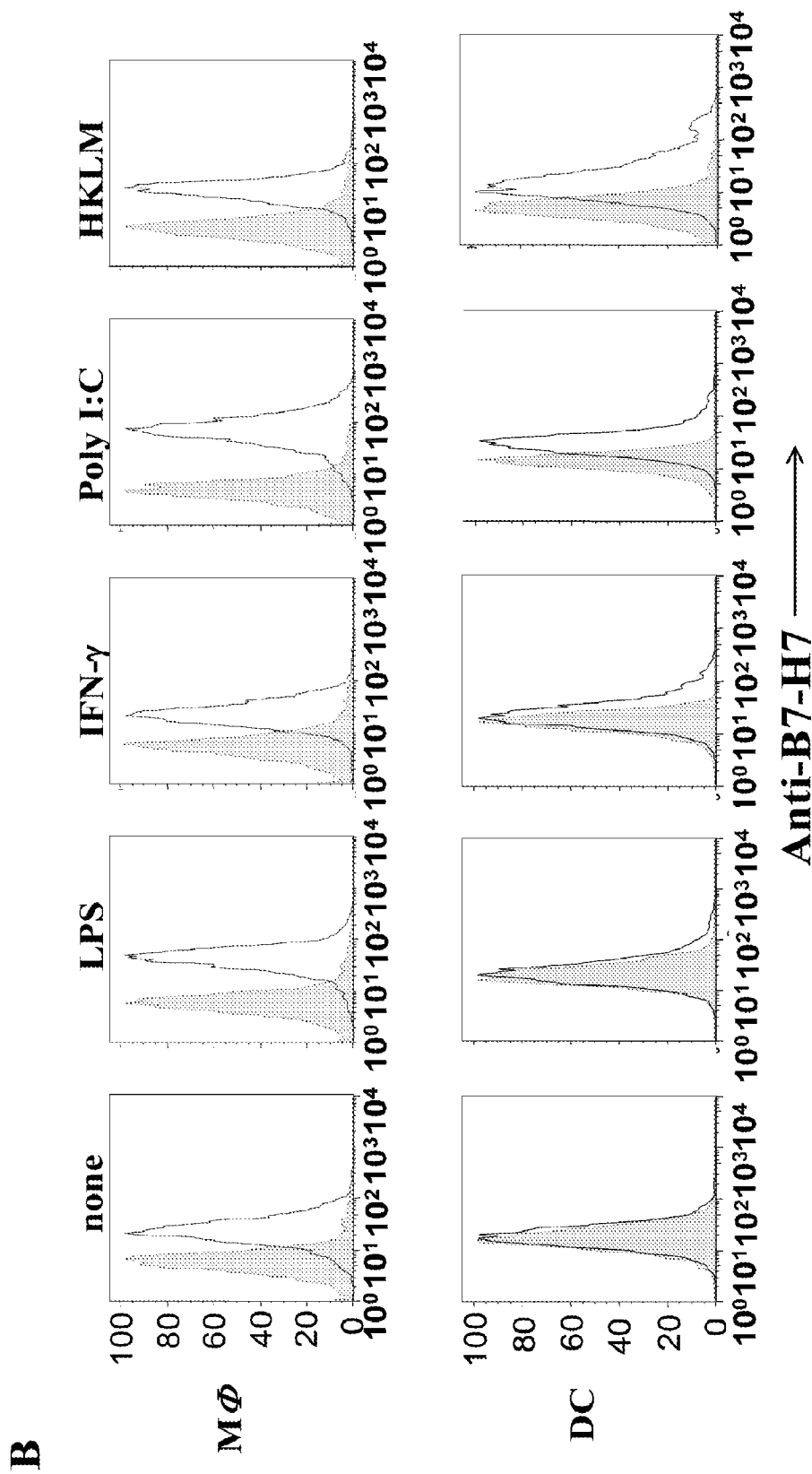
Figure 10C:
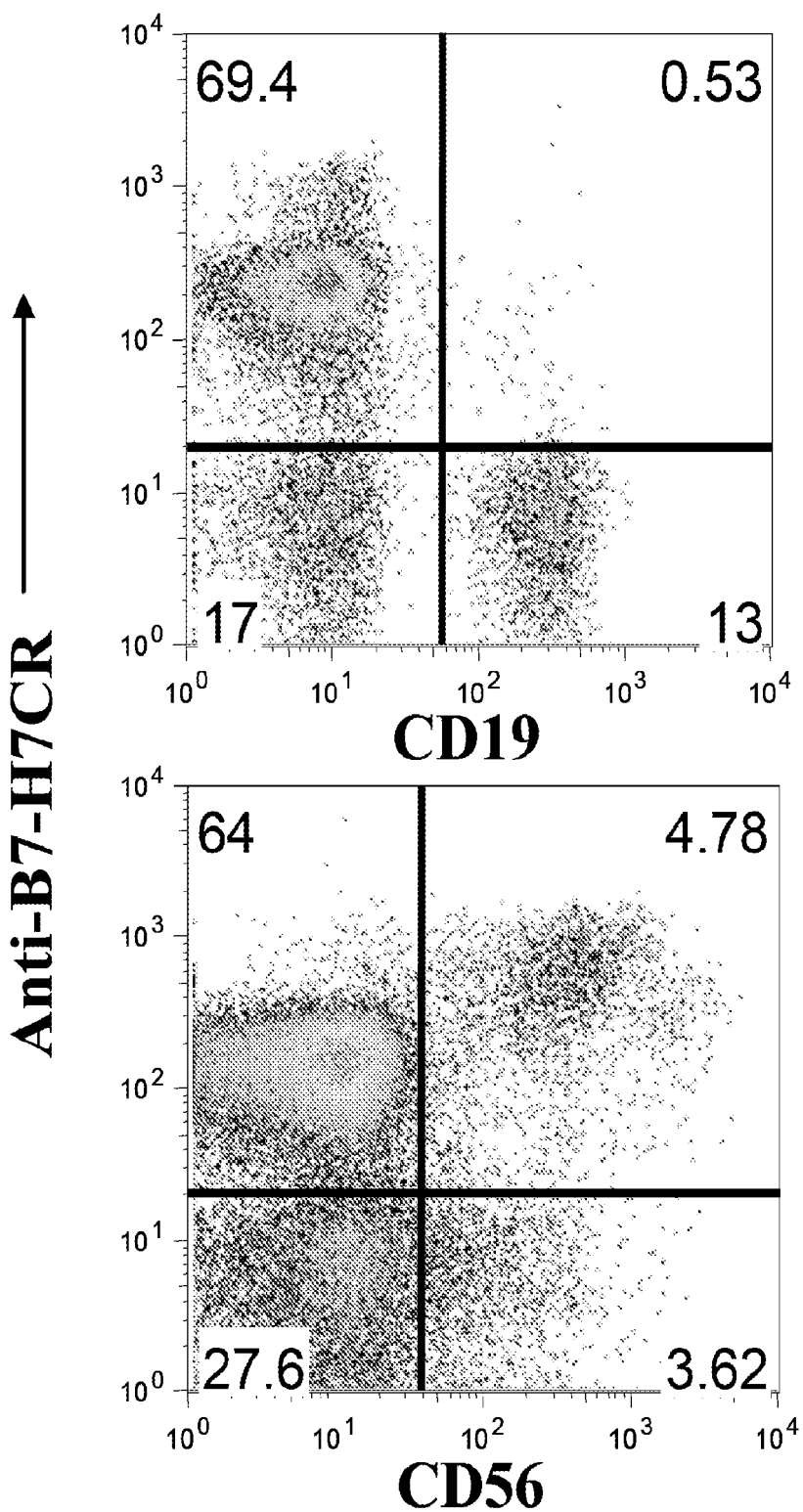
Figure 10C:
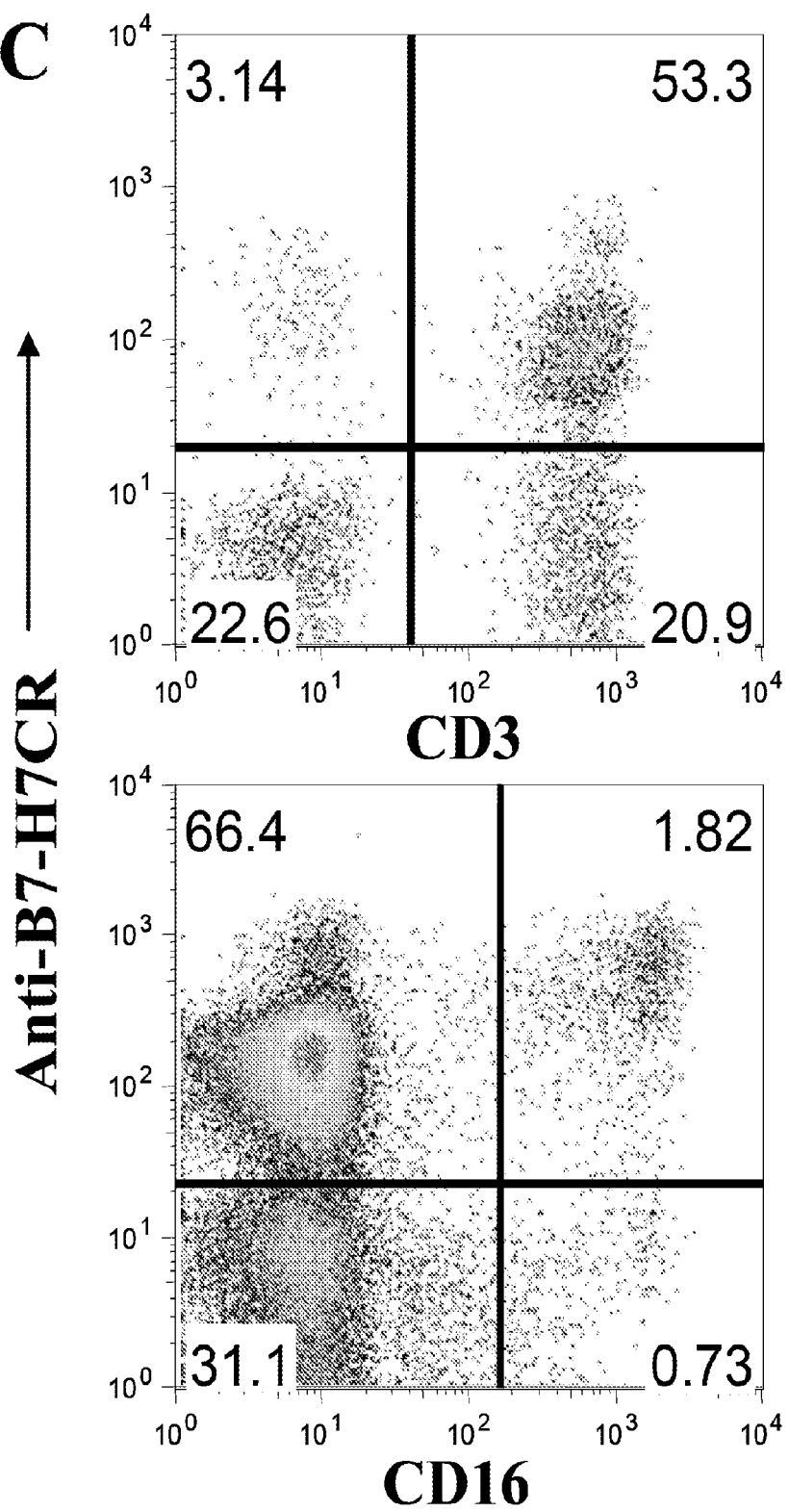

B7-H7 mRNA is abundant in testis, colon, lung, kidney and pancreas while it shows low levels in small intestine, liver and skeletal muscle. In contrast, B7-H7CR mRNA was mainly found in lymphoid organs (FIG. 13); thymus and spleen are the most abundant, with peripheral blood lymphocyte (PBL) and liver showing second. Consistent to these findings, no cell surface B7-H7 was detected by specific mAb on T, B, NK cells or neutrophils in human PBL (FIG. 14). However, macrophages derived from monocytes constantly expressed B7-H7, and activation of macrophages with LPS, poly I:C, heat-killed *Listeria monocytogenes* (HKLM) or interferon-gamma further upregulated the expression (FIG. 10B). Monocyte-derived immature dendritic cells (DC) could also be induced by poly I:C or HKLM to express B7-H7. On the other hand, B7-H7CR is constitutively expressed on the majority of T and NK cells, but not on B cells (FIG. 10C). Taken together, the expression patterns of B7-H7 and its counter-receptor suggest their roles in the interaction of professional antigen-presenting cells with T and NK cells.

Figure 10D:
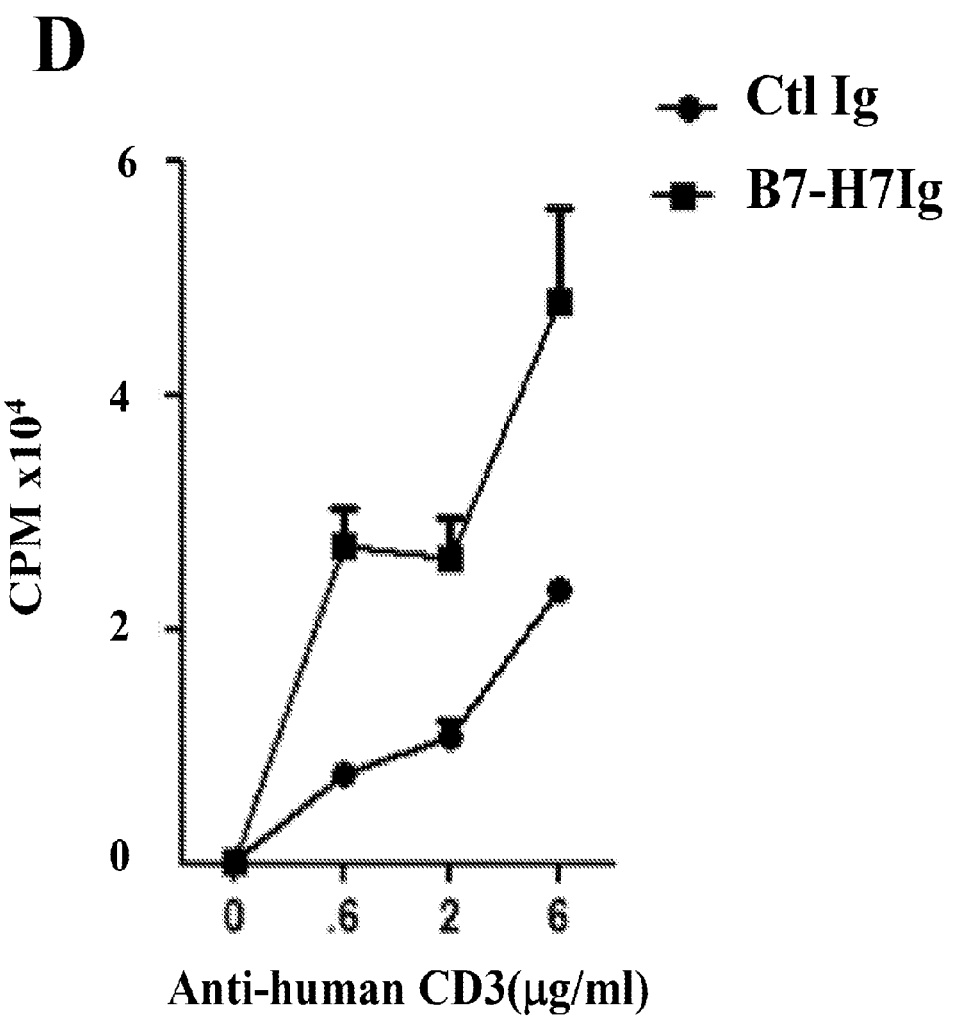
Figure 10D:
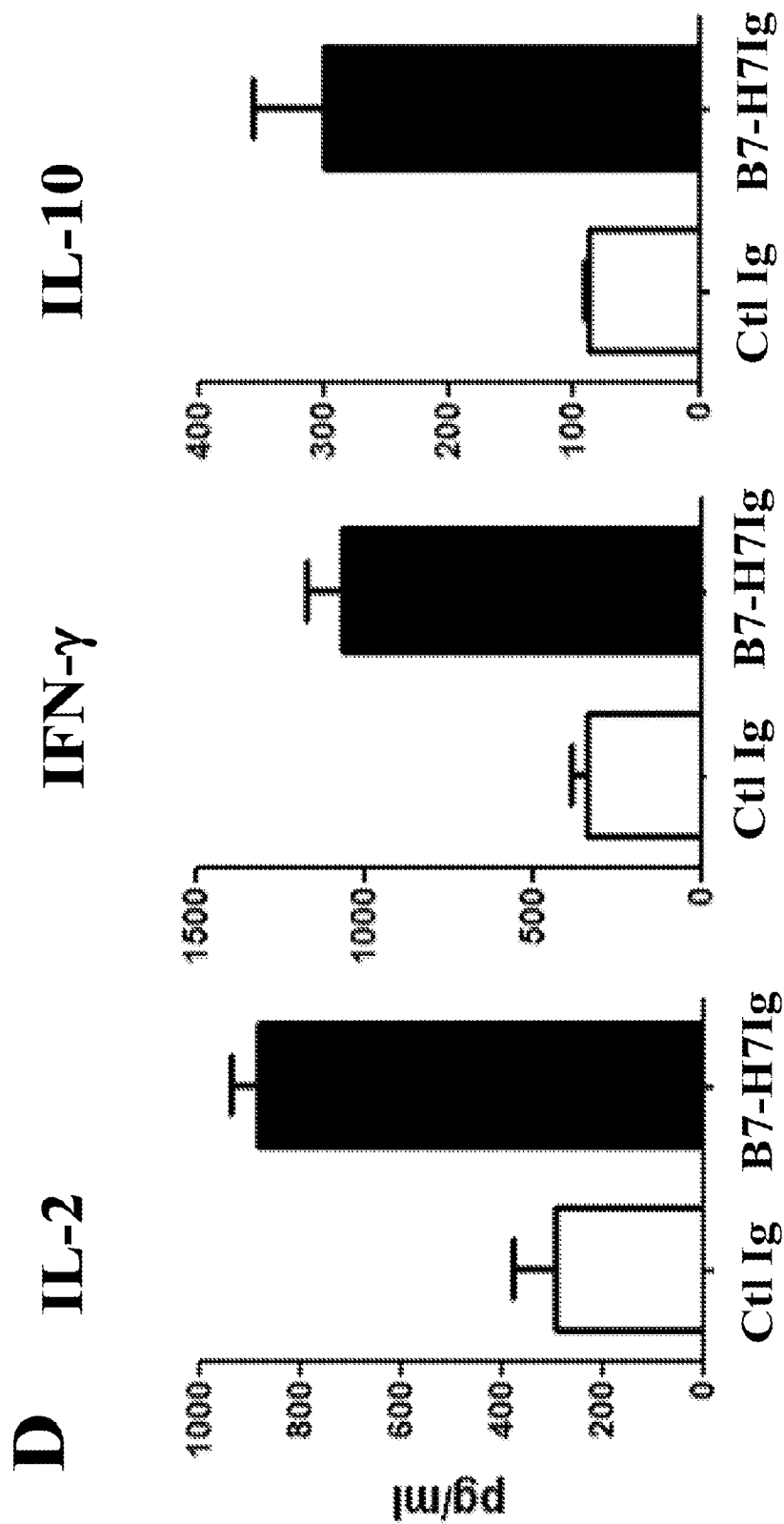
Figure 10E:
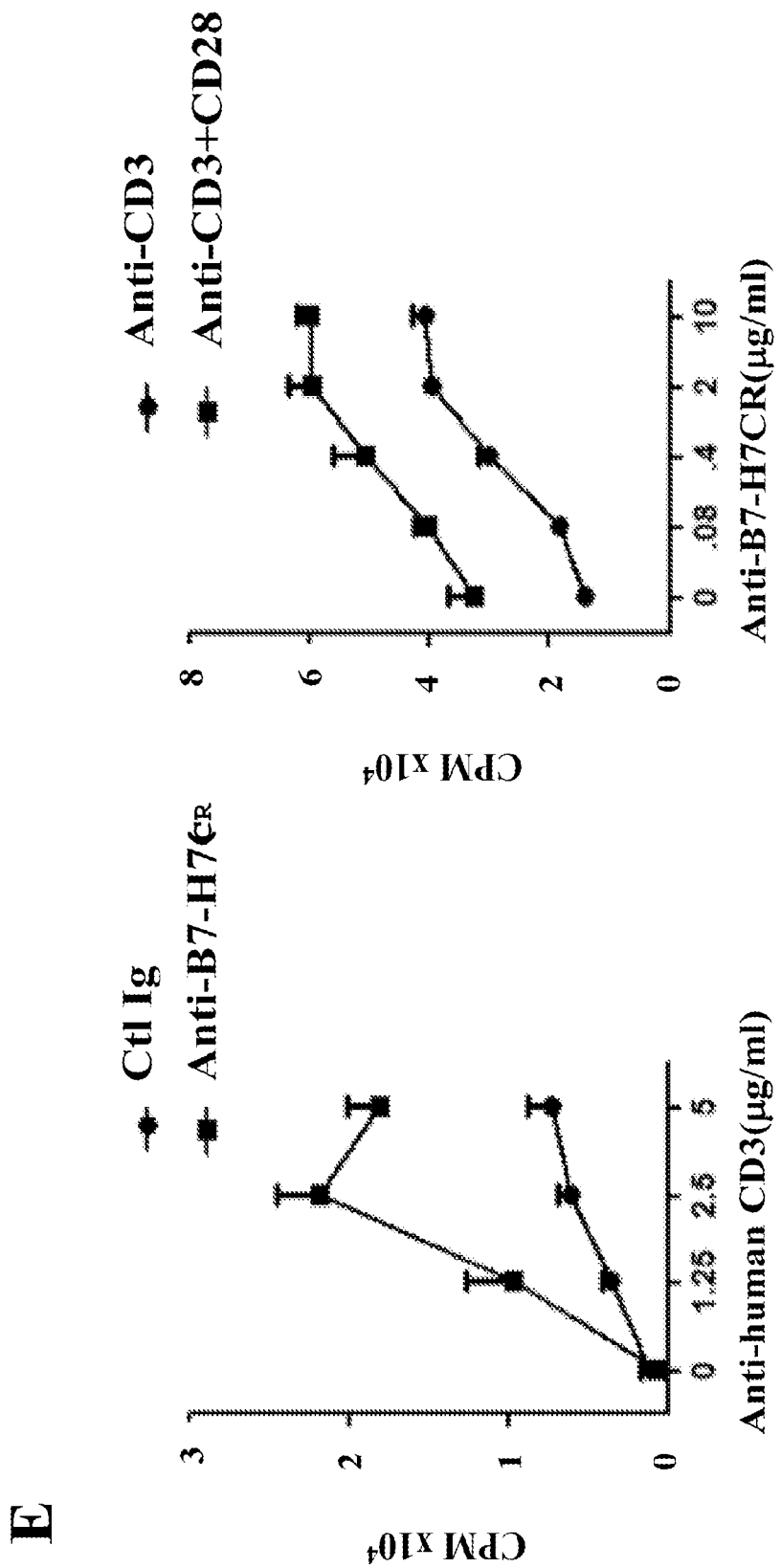
Figure 10F:
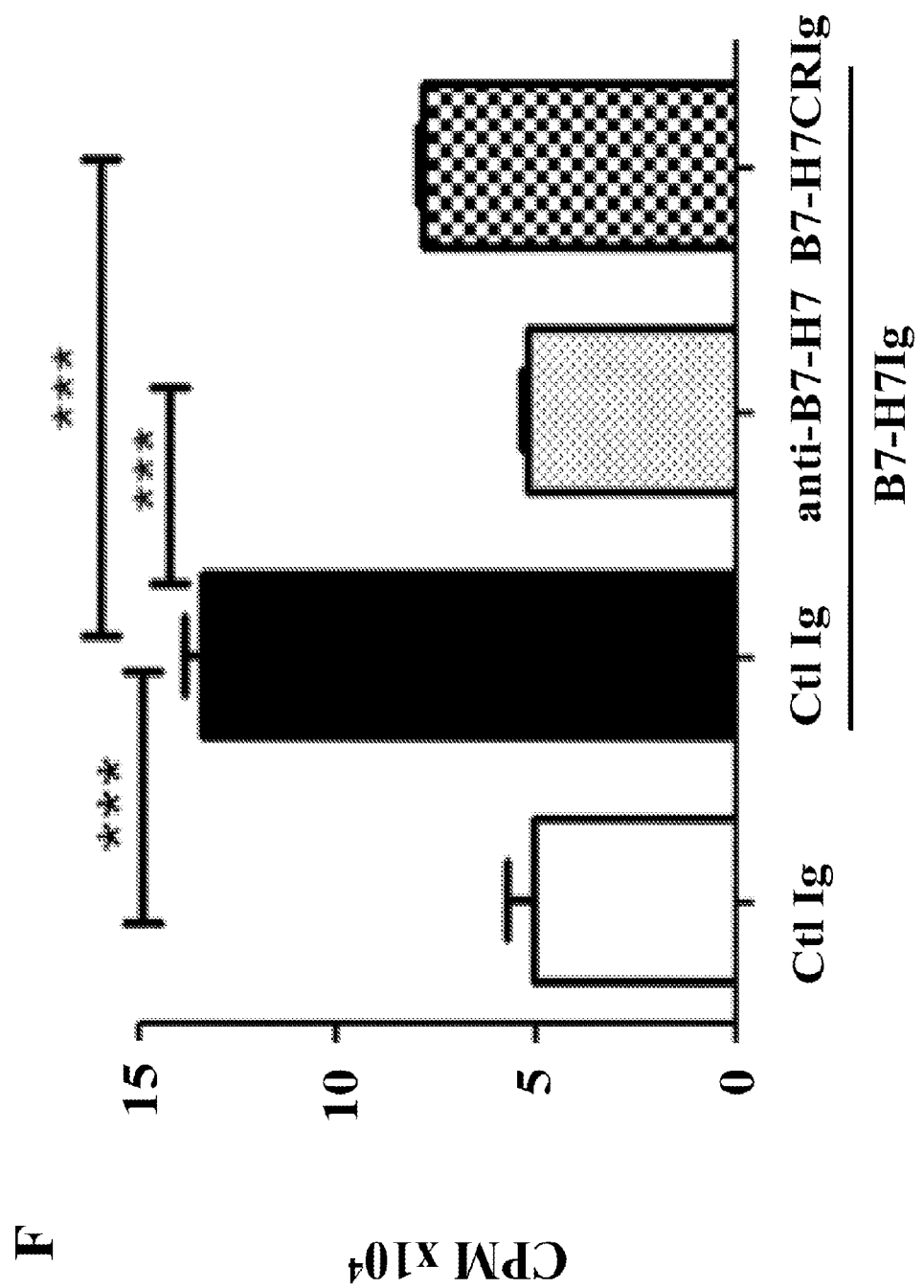

A hallmark of the B7 family molecules is their capability to costimulate or coinhibit T cell responses in the presence of antigen (6). The plate-coated B7-H7Ig strongly promoted CD4+ T cell proliferation as well as production of IL-2, IFN-γ and IL-10 in the presence of suboptimal doses of anti-CD3 mAb (OKT3) (FIG. 10D). In addition, the B7-H7CR mAb in immobilized form could mimic the role of B7-H7 to enhance T cell proliferation either alone or in synergy with CD28 mAb (FIG. 10E), suggesting an agonistic feature of this B7-H7CR mAb. Furthermore, inclusion of soluble B7-H7 mAb (2D3) or B7-H7CRIg abrogated the costimulatory effect of B7-H7 (FIG. 10F). Combined together, these results support that B7-H7 and B7-H7CR interaction represents a novel T cell costimulatory pathway which promotes human T cell growth.

The mechanisms of these newly described costimulatory pairs in the regulation of immune responses is yet to be elucidated (FIG. 15), especially in the context of other costimulatory and coinhibitory pathways previously described. However, this receptor-ligand proteomic system represents a promising approach to discover new molecular interactions on cell surface. With the expansion of proteome to include all plasma membrane proteins, this system could be utilized to identify any cell surface receptor-ligand pair in question and there the significance should be well beyond mere understanding the immune system.

6.3 REFERENCES

Below is the list of references cited in Section 6.
1. Dong, H., Zhu, G., Tamada, K., and Chen, L. 1999. B7-H1, a third member of the B7 family, co-stimulates T-cell proliferation and interleukin-10 secretion. Nat Med 5:1365-1369.
2. Tamura, H., Dong, H., Zhu, G., Sica, G. L., Flies, D. B., Tamada, K., and Chen, L. 2001. B7-H1 costimulation preferentially enhances CD28-independent T-helper cell function. Blood 97:1809-1816.
3. Wang, S., Bajorath, J., Flies, D. B., Dong, H., Honjo, T., and Chen, L. 2003. Molecular modeling and functional mapping of B7-H1 and B7-DC uncouple costimulatory function from PD-1 interaction. J Exp Med 197:1083-1091.
4. Lander, E. S., Linton, L. M., Birren, B., Nusbaum, C., Zody, M. C., Baldwin, J., Devon, K., Dewar, K., Doyle, M., FitzHugh, W., et al. 2001. Initial sequencing and analysis of the human genome. Nature 409:860-921.
5. Venter, J. C., Adams, M. D., Myers, E. W., Li, P. W., Mural, R. J., Sutton, G. G., Smith, H. O., Yandell, M., Evans, C. A., Holt, R. A., et al. 2001. The sequence of the human genome. Science 291:1304-1351.
6. Chen, L. 2003. The B7-CD28 family molecules. New York, N.Y.: Landes Bioscience/Eurekah.com; Kluwer Academic/Plenum. 141 pp.
7. Chen, L. 2004. Co-inhibitory molecules of the B7-CD28 family in the control of T-cell immunity. Nat Rev Immunol 4:336-347.
8. Sharpe, A. H., and Freeman, G. J. 2002. The B7-CD28 superfamily. Nat Rev Immunol 2:116-126.
9. Linsley, P. S., Clark, E. A., and Ledbetter, J. A. 1990. T-cell antigen CD28 mediates adhesion with B cells by interacting with activation antigen B7/BB-1. Proc Natl Acad Sci USA 87:5031-5035.
10. Yoshinaga, S. K., Whoriskey, J. S., Khare, S. D., Sarmiento, U., Guo, J., Horan, T., Shih, G., Zhang, M., Coccia, M. A., Kohno, T., et al. 1999. T-cell co-stimulation through B7RP-1 and ICOS. Nature 402:827-832.
11. Hutloff, A., Dittrich, A.M., Beier, K. C., Eljaschewitsch, B., Kraft, R., Anagnostopoulos, I., and Kroczek, R. A. 1999. ICOS is an inducible T-cell co-stimulator structurally and functionally related to CD28. Nature 397:263-266.
12. Krummel, M. F., and Allison, J. P. 1995. CD28 and CTLA-4 have opposing effects on the response of T cells to stimulation. J Exp Med 182:459-465.
13. Walunas, T. L., Lenschow, D. J., Bakker, C. Y., Linsley, P. S., Freeman, G. J., Green, J. M., Thompson, C. B., and Bluestone, J. A. 1994. CTLA-4 can function as a negative regulator of T cell activation. Immunity 1:405-413.
14. van der Merwe, P. A., Bodian, D. L., Daenke, S., Linsley, P., and Davis, S. J. 1997. CD80 (B7-1) binds both CD28 and CTLA-4 with a low affinity and very fast kinetics. J Exp Med 185:393-403.
15. Freeman, G. J., Gribben, J. G., Boussiotis, V. A., Ng, J. W., Restivo, V. A., Jr., Lombard, L. A., Gray, G. S., and Nadler, L. M. 1993. Cloning of B7-2: a CTLA-4 counter-receptor that costimulates human T cell proliferation. Science 262:909-911.
16. Chattopadhyay, K., Bhatia, S., Fiser, A., Almo, S. C., and Nathenson, S. G. 2006. Structural basis of inducible costimulator ligand costimulatory function: determination of the cell surface oligomeric state and functional mapping of the receptor binding site of the protein. J Immunol 177:3920-3929.
17. Carreno, B. M., and Collins, M. 2002. The B7 family of ligands and its receptors: new pathways for costimulation and inhibition of immune responses. Annu Rev Immunol 20:29-53.
18. Fahrer, A. M., Bazan, J. F., Papathanasiou, P., Nelms, K. A., and Goodnow, C. C. 2001. A genomic view of immunology. Nature 409:836-838.

7. EXAMPLE

Molecular Basis of Functional Redundancy in CD28 and ICOS Costimulatory Pathways The following example is offered by way of illustration, and not by way of limitation.

7.1 MATERIALS & METHODS

Plasmids, fusion proteins and monoclonal antibodies. Human full length plasma membrane cDNA set (MHS5007) was purchased from Open Biosystems Inc. (Huntsville, Ala.). About 800 genes from the set which is on mammalian expression vector pCMV-SPORT6 were selected. Over 1,000 genes were cloned into mammalian expression vector pcDNA3.2/V5-DEST, pcDNA6.2/V5-DEST or pLP-CMVneo vectors using Gateway Cloning System (Invitrogen, Carlsbad, Calif.) and Creator Cloning Kit (BD Biosciences, San Jose, Calif.). Other genes were cloned into pcDNA3.1(−) plasmid by standard RT-PCR cloning technique. All plasmids were validated by sequencing.

Human and mouse CD28, CTLA4, ICOS, PD-1, B7-1, B7-2, B7-H1, B7-DC and B7-H2 Ig fusion proteins were purchased from R&D systems (Minneapolis, Minn.). Wild type and mutant Human B7-H2 Ig were made by transiently transfecting 293T cells with the constructs in pHIgV plasmids, and were purified by protein A columns as described previously 19.

Mouse anti-human CD3 mAb OKT3, mouse anti-human CD28 mAb CD28.6 (blocking), mouse anti-human CTLA-4 mAb 14D3 and mouse anti-human B7-H2 mAb MIH12 were purchased from eBioscience (San Diego, Calif.). Mouse anti-human B7-H2 mAb 9F.8A4 was purchased from BioLegend (San Diego, Calif.). Anti-human Ig FMAT blue antibody was purchased from Applied Biosystems (Foster City, Calif.). Control human IgG (Synagis) was purchased from MedImmune (Rockville, Md.). All other antibodies used in flow cytometry were purchased from BD Biosciences or eBioscience.

Surface Plasmon Resonance.

Protein interactions were measured and analyzed on a BIAcore 3000 instrument (BIAcore AB, Uppsala, Sweden) performed at 25° C. as described previously 20. 0.1 M Hepes, pH 7.4, containing 0.15 M NaCl, 0.005% surfactant P20 (HBS) was used as running buffer. Human B7-H2Ig, CD28Ig and CTLA-4Ig were purchased from R&D systems. All other reagents were purchased from BIAcore. The B7-H2Ig was covalently coupled to a CM5 sensor chip (BIAcore AB) by crosslinking primary amine groups to the carboxymethylated dextran matrix. A flow cell on the CM5 chip was activated with 1:1 N-ethyl-N-dimethylaminopropyl carbodiimide (EDC) and N-hydroxysuccinimide (NHS) mixture, followed by injection of 20 μg/ml B7-H2Ig diluted in 10 mM sodium acetate buffer, pH 5.0, until desired response units (RU) were achieved. Another activated flow cell on the same chip, which did not receive any fusion protein, was used as a control sensor surface. The remaining activated carboxyl groups were blocked with 1 M ethanolamine (pH 8.5). Subsequently, the flow cells were extensively washed with HBS to generate a stable baseline. ICOSIg, CD28Ig and CTLA4Ig, in serial dilutions were injected over the sensor surface in triplicates at a flow rate of 20-30 µl/min for 3 min, and then the dissociation was allowed for 5 min. The flow cells were regenerated by two consecutive 10-second pulses with 10 mM NaOH. Data was analyzed by BIAevaluation software 4.1 (BIAcore).

T Cell Costimulation Assay.

OKT3 mAb (anti-human CD3) was pre-coated in 96-well plates at the indicated concentrations. B7-H2Ig or isotype-matched control Ig at 5 µg/ml was also immobilized in the wells. T cells from human peripheral mononuclear cells (PBMCs) were negatively selected and purified by a human pan-T cell selection kit or a human CD4 T cell selection kit (Miltenyi Biotec, Auburn, Calif.). Purified human T cells were added into each well at $2.5 \times 10^5$/well and cultured for three days. In some experiments, anti-B7-H2 mAb, MIH12 or 9F.8A4 was added at the beginning of culture, and unbound mAbs were washed away by media before addition of T cells. 3HTdR was added during the final six hours of culture. 3H-TdR incorporation was counted with a MicroBeta Trilux liquid scintillation counter (PerkinElmer, Waltham, Mass.).

Human Monocyte-Derived Dendritic Cells.

Human PBMCs were isolated by density-gradient centrifugation. Fifty million PBMCs were adhered on a 100 mm tissue culture dish for 45 min in a 37 degree incubator. Adherent cells at $0.5 \times 10^6$/ml were cultured in 10 ml complete RPMI media containing 10% human AB serum. The media was supplemented with 500 U/ml recombinant human interleukin-4 (BD Biosciences) and 1000 U/ml recombinant human granulocyte-monocyte growth factor for dendritic cell differentiation. On day 2, 4 and 6, half of the media was replaced with fresh media and cytokines. On day 7, dendritic cells were harvested.

7.2 RESULTS

Using the receptor-ligand proteome approach described in Example 6, we demonstrated that recombinant human CD28Ig fusion proteins bound to 293T cells expressing B7-1, B7-2 and B7-H2. A lower level of CD28Ig bound to cells expressing B7-H2 than cells expressing B7-1 and B7-2 (FIGS. 16 and 5A). A binding activity to occuldin (OCLN) molecule was also found but later this interaction was demonstrated to be non-specific (data not shown). There was no additional binding activity by CD28Ig in our receptor-ligand proteome (FIG. 2). Therefore, CD28 and ICOS may share a common ligand, B7-H2.

Figure 16B:
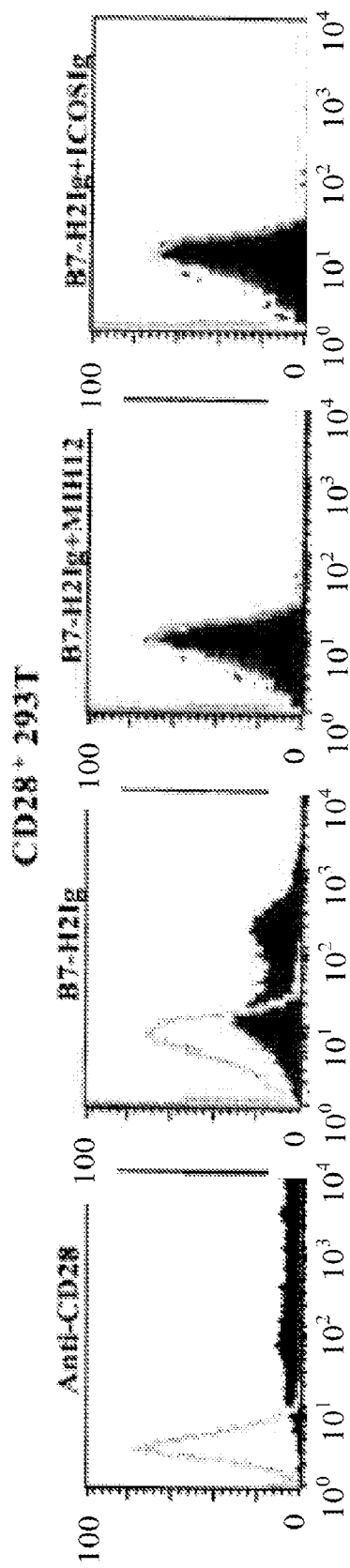
Figure 16C:
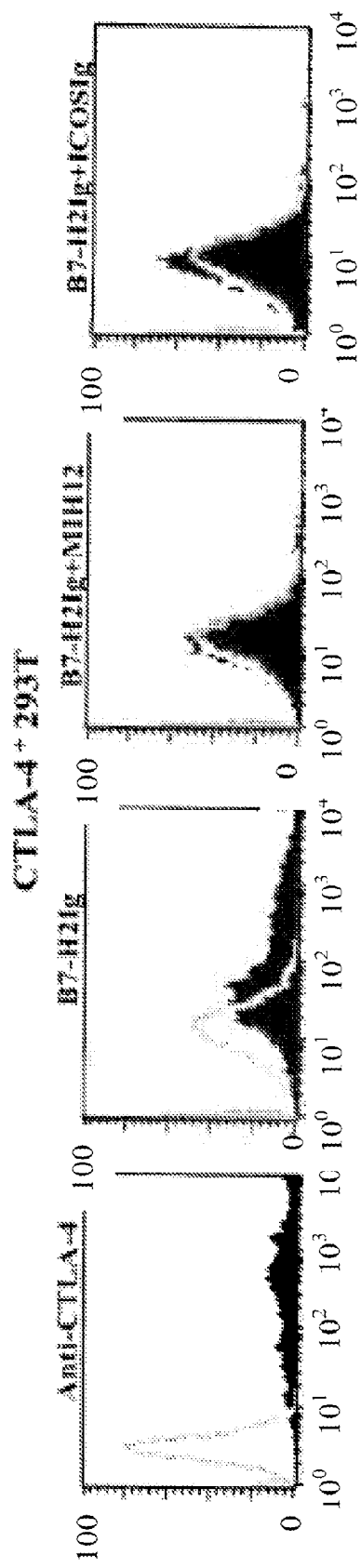

This binding was first validated by staining of CD28Ig to B7-H2$^+$293T cells with optimized transient transfection protocol. High B7-H2 expression was verified by positive anti-B7-H2 monoclonal antibody (mAb) staining and negative anti-B7-1 and anti-B7-2 staining by flow cytometry analysis (FIG. 16A). Under this condition, a significant fraction of cells also stained positively with ICOSIg, demonstrating the specific expression of B7-H2 on 293T cells. Importantly, CD28Ig showed significant binding to B7-H2$^+$293T cells, and this binding could be completely blocked by the inclusion of a mAb against CD28 (clone CD28.6). Interestingly, CTLA4Ig could also bind B7-H2$^+$293T transfectant and the binding was largely blocked by a mAb against CTLA-4 (clone 14D3) (FIG. 16A), suggesting B7-H2, similar to B7-1 and B7-2, binds both CD28 and CTLA-4. To further validate these interactions, 293T cells were transiently transfected to express high level CD28 or CTLA4, as shown by positive mAbs staining. Binding of these cells by B7-H2Ig demonstrated a significant staining. The binding could be completely abrogated by inclusion of a mAb against B7-H2 (Clone MIH12) or by ICOSIg (FIGS. 16B and 16C). These results support the specificity of interactions between B7-H2 and CD28/CTLA-4 and an overlapping binding site on B7-H2 for interacting with CD28, CTLA-4 and ICOS.

Figure 16D:
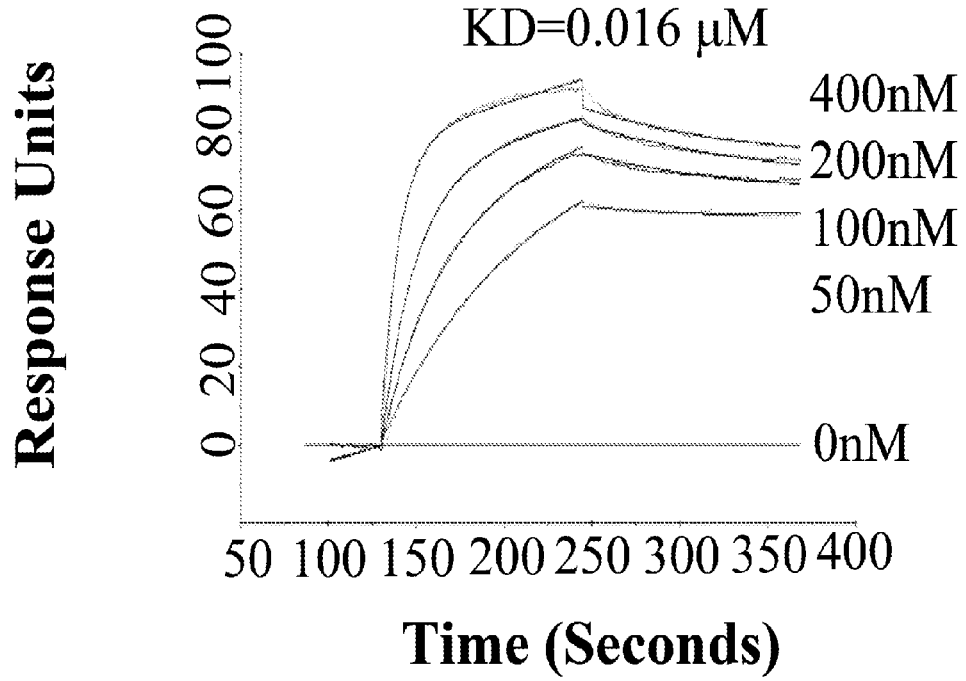
Figure 16D:
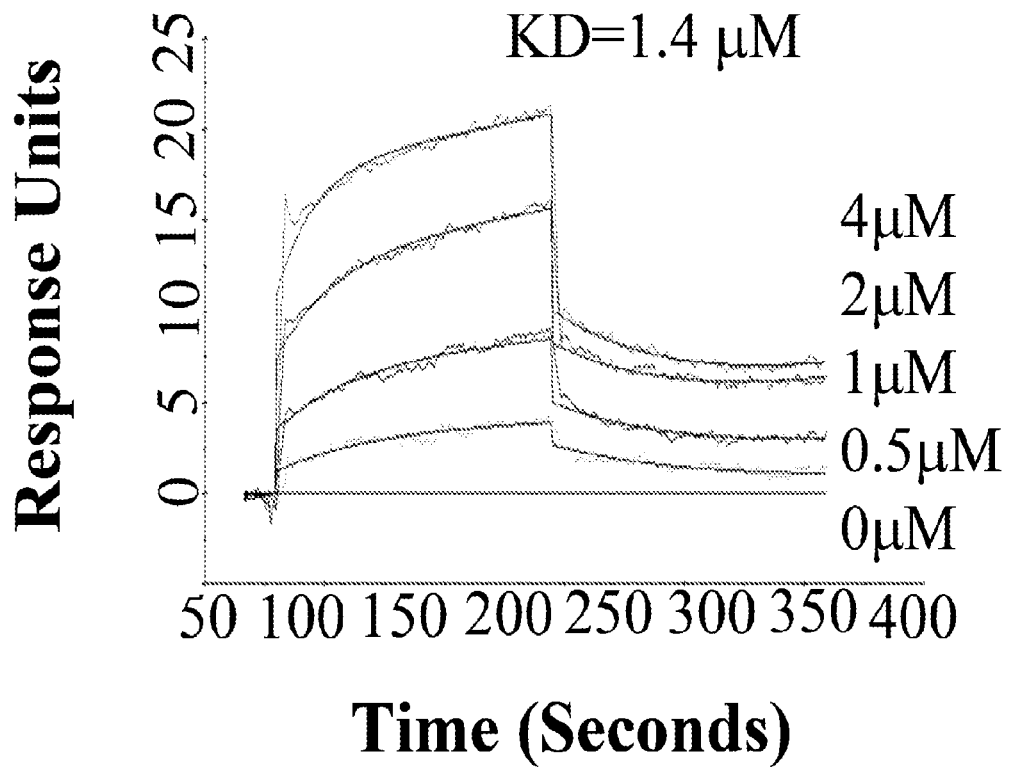
Figure 16D:
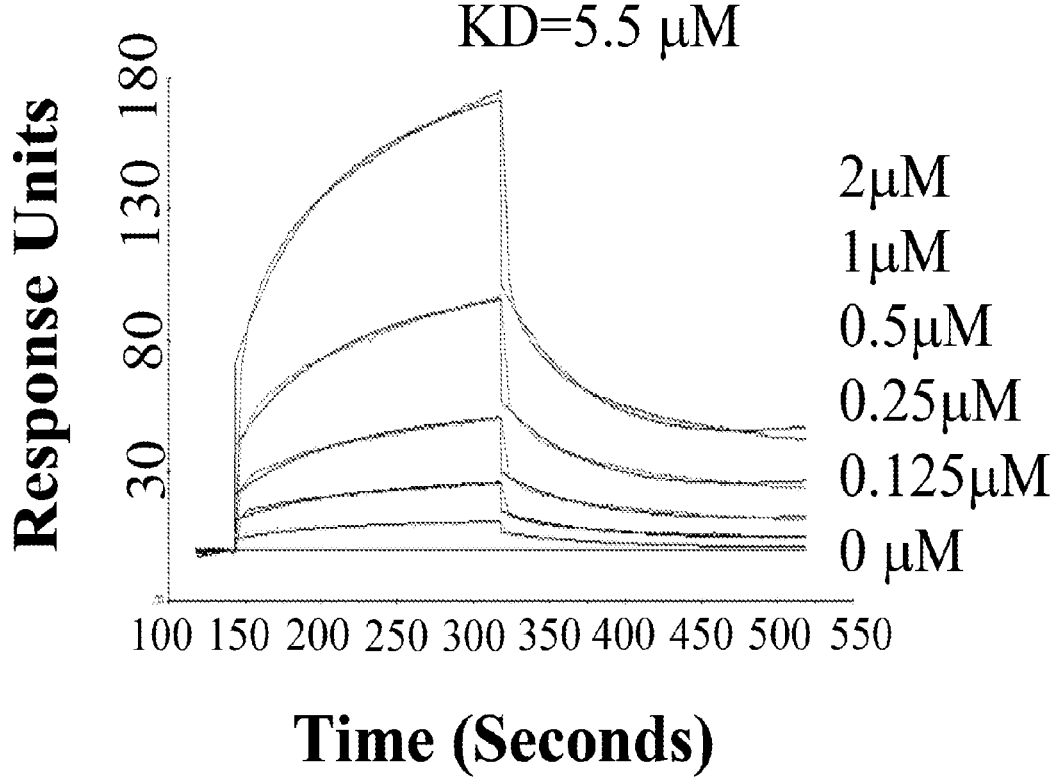

Next, the binding affinity of B7-H2 to ICOS, CD28 and CTLA-4 was compared by surface plasmon resonance (SPR) analysis (FIG. 16D). B7-H2/CD28 interaction had a significantly slower association constant ($K_{ON}=1.2\times10^4$ M$^{-1}$s$^{-1}$) and a faster dissociation constant ($K_{OFF}=0.017$ s$^{-1}$) compared to B7-H2/ICOS ($K_{ON}=2.4\times10^5$ M$^{-1}$s$^{-1}$; $K_{OFF}=0.004$ s$^{-1}$), indicating that ICOS has a much higher affinity (~100 folds) than CD28 for binding B7-H2. Meanwhile, B7-H2/CTLA-4 had slightly lower affinity (~4 folds) than B7-H2/CD28 interaction (FIG. 16D). When compared with the published affinity of B7-1/CD28 interaction (KD=4 µM) (14), the affinity of B7-H2/CD28(KD=1.4 µM) and B7-H2/CTLA4 (KD=5.5 µM) is in a similar range.

While these results reveal B7-H2 as a potential ligand for both CD28 and CTLA-4, there are several fundamental differences between these and previously identified interactions. CTLA-4 has at least a 10 fold higher affinity than CD28 to interact with B7s(14), whereas B7-H2 has similar affinity for these two receptors. CD28 is constitutively expressed on naive T cells while ICOS and CTLA4 are inducible upon antigen stimulation (3). Because B7-H2 is constitutively expressed by hematopoietic and non-hematopoietic cells, these findings implicate a role of B7-H2 in the costimulation of naive T cells through CD28. The role of B7-H2 in the inhibition of activated T cells via CTLA-4 may be minimal because B7-H2 has a much lower affinity for CTLA-4 than ICOS.

Figure 16E:
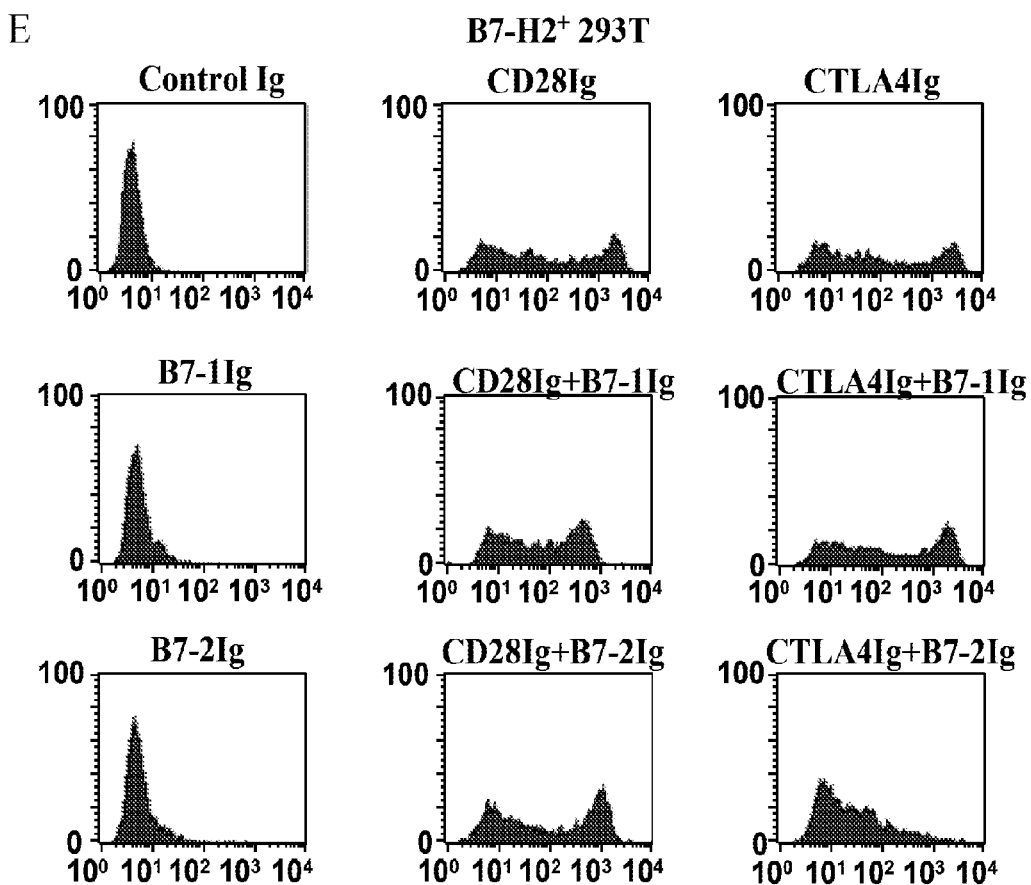

Next, the B7-H2/CD28 interaction was examined to see if it could compete with other CD28 ligands, B7-1 and B7-2. By flow cytometry analysis, saturated doses of B7-1Ig and B7-2Ig had only minimal effect on the binding of CD28Ig to B7-H2$^+$293T cells, supporting that CD28 interacts with B7-H2 through a different interface than B7-1/B7-2 (FIG. 16E). Interestingly, B7-2Ig but not B7-1Ig appears to partially compete for the binding of CTLA-4Ig to B7-H2, indicating that the binding sites on CTLA-4 for B7-H2 and B7-2 may be partially overlapped (FIG. 16E). In contrast, B7-1 and B7-2 are largely redundant in terms of their interaction with CD28 and CTLA-4 and could compete with each other for binding (1). These findings implicate a new feature of CD28 costimulation: more than one interface on a costimulatory receptor is available for different ligands to engage. These finding also suggest that B7-H2 could costimulate naive T cells through CD28 in synergy with B7-1/B7-2.

To understand the architecture of the interactions between B7-H2 and its three receptors, site-directed mutagenesis on B7-H2 was conducted to identify critical residues for these interactions. Selection of residues for mutation was based on their locations in the binding interfaces of B7-H2 and three receptors predicted from the crystal structure of B7-2/CTLA4 (15, 16) (FIG. 6A). These residues were all converted to alanine, a small aromatic amino acid with neutral charge, to avoid a large overall structure modulation (16). Wild type (wt) and mutated B7-H2 full length genes were expressed on the surface of 293T cells and confirmed by anti-B7-H2 mAb staining. The binding of these cells by CD28Ig, CTLA-4Ig and ICOSIg were determined by flow cytometry analysis and relative binding capacity of these recombinant fusion proteins to B7-H2 mutants were compared to wt B7-H2 (FIG. 6B). All mutants, which lost their binding to CD28 (Y51A, Y53A, L116A and F122A), also did not interact with CTLA-4, indicating that B7-H2 binding sites for CD28 and CTLA-4 are largely overlapped, i.e., CD28 and CTLA-4 should compete for the binding to B7-H2. Two mutants (Y51A, Y53A) that lost their binding to ICOS, also show no binding to CD28 and CTLA-4. Interestingly, two mutants (L116A and F122A), which largely retained the ability to bind ICOS, have only minimal binding capacity to CD28 and CTLA-4. These results support the notion that B7-H2 uses non-identical but overlapping binding sites for interacting with ICOS versus CD28/CTLA-4, whereas B7-H2 may use similar, if not identical binding sites to interact with CD28 and CTLA-4.

The finding that B7-H2 might utilize differential binding sites to interact with ICOS versus CD28/CTLA-4 encouraged the seeking of mAbs that selectively block individual interactions to facilitate functional analysis. By screening available mAbs against B7-H2, the MIH12 was demonstrated to selectively blocked B7-H2 binding to CD28/CTLA-4 but not to ICOS, whereas 9F.8A4 abrogated B7-H2Ig binding to all three receptors by flow cytometry analysis (FIG. 4).

Figure 19:
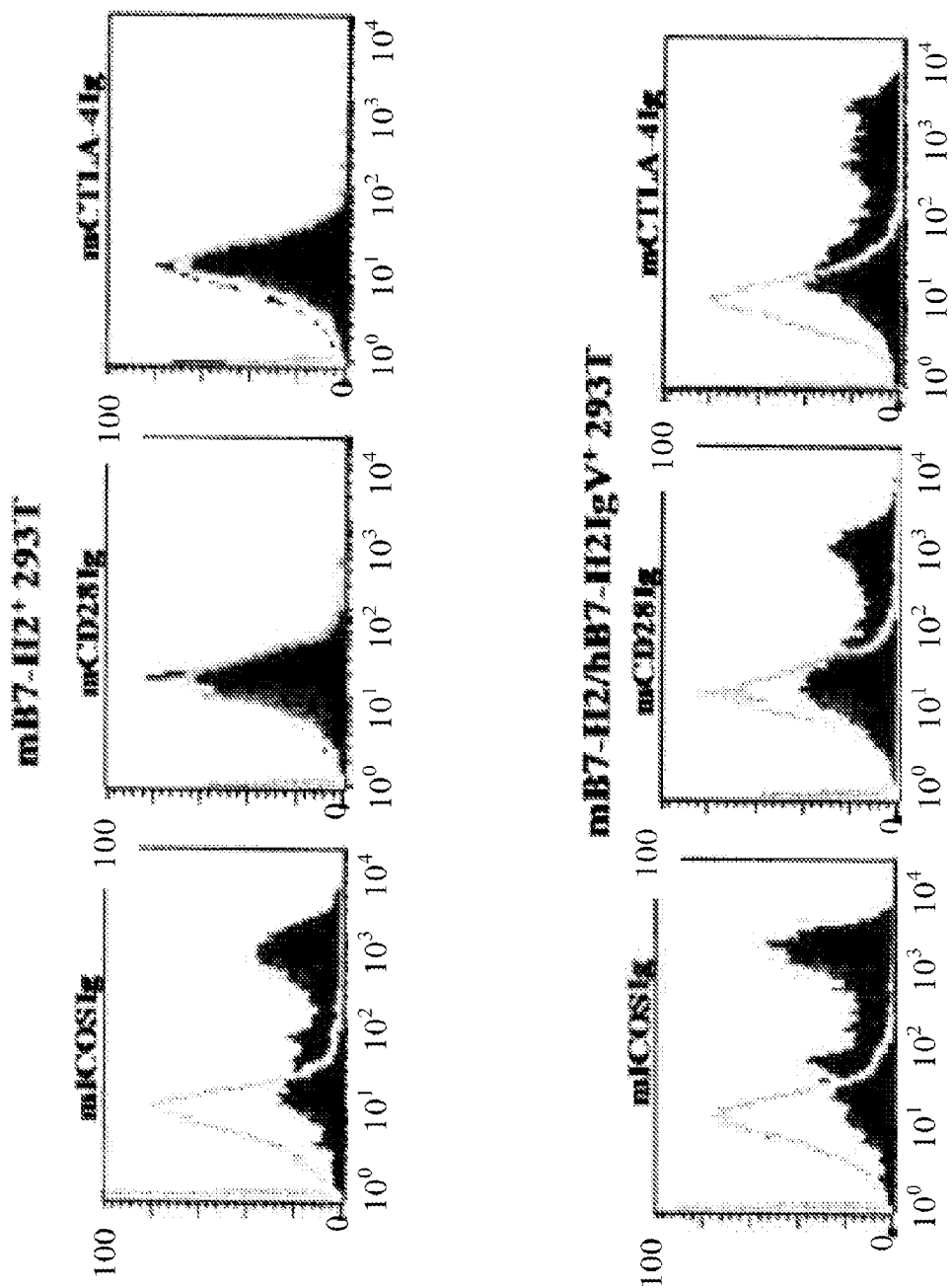

Consistent with previous reports (4, 17), we demonstrated that mouse B7-H2 did not interact with mouse CD28 and CTLA-4 (FIGS. 5B and 19). Interestingly, when mouse B7-H2 IgV region (Met1-Val149) was replaced with its corresponding human counterpart (Met1-Gln123), this chimeric gene product was capable of binding mouse CD28Ig and CTLA-4Ig (FIG. 19), indicating that mouse and human B7-H2 might have divergent evolutions from a common ancestor.

To demonstrate that the interaction of B7-H2 and CD28 is functional, an in vitro costimulation assay was utilized in which suboptimal concentrations of human CD3 mAb were immobilized in the wells of a 96-well plate as a mimicry of T cell receptor (TCR) signaling. B7-H2Ig was co-immobilized in the same well to provide a costimulatory signal for purified human T cells. While suboptimal concentrations of CD3 mAb up to 0.1 µg/ml did not stimulate significant proliferation of T cells, inclusion of B7-H2Ig induced a high level proliferation of T cells as evidenced by increased incorporation of tritiated thymidine (FIG. 20A). The effect of B7-H2 was dependent on TCR signaling because B7-H2Ig itself in the absence of CD3 mAb did not stimulate any detectable proliferation (data not shown). Inclusion of MIH12 mAb, which specifically blocks B7-H2 binding to CD28/CTLA-4, suppressed about 50% of B7-H2Ig-mediated costimulation. The 9F.8A4 mAb, which blocks B7-H2 binding to all three receptors, completely abolished the effect of B7-H2Ig (FIG. 20A). Using carboxyl fluorescent succinimidyl ester (CFSE)-labeled human T cells to monitor cell division, blockade of B7-H2/CD28 interaction with MIH12 had a partial inhibitory effect on the division of both CD4 and CD8 T cells whereas 9F.8A4 completely suppressed T cell division (FIG. 21). Activated T cells in this setting expressed high level ICOS in addition to CD28 (data not shown). These results suggest that both CD28 and ICOS on T cells independently contribute to the costimulatory effect of B7-H2. CTLA-4 was also upregulated on T cells with similar kinetics as ICOS in our experimental setting (data not shown). However, the predominant effect of B7-H2Ig in this system is enhancement of T cell growth. This is likely due to the low affinity of B7-H2/CTLA-4 interaction (FIG. 16). All together, these results support that B7-H2 is capable of costimulating T cell growth via engaging CD28.

One characteristic feature of CD4$^+$ T cell costimulation by CD28 and ICOS is that both of them induce high amounts of cytokines, whereas TCR engagement alone produce minimal (3). Cytokine production mediated by immobilized human B7-1Ig and B7-H2Ig in the same concentration was compared (FIG. 22). Consistent with previous finding using CD28 and ICOS agonist mAbs (6), costimulation through B7-1 and B7-H2 induce a overlapping spectrum of T cell-derived cytokines including TNFα, IFNγ, IL-4, IL-5, IL-10 and IL-17, with one major difference that only B7-1Ig stimulated large amount of IL-2 (3). B7-1 also appears to elicit higher level of TNFα and IFNγ, while B7-H2 induces higher level IL-17A (18). Both B7-1 and B7-H2 induced similar levels of other cytokines with small differences observed in different experiments (data not shown). A major difference in comparison with previously published results using agonist mAb (3), it was found that B7-H2 did not preferentially stimulate IL-10 production (FIG. 22).

In the context of this generally overlapping cytokine profiles induced by B7-1 and B7-H2, the relative contribution of B7-H2/CD28 vs. B7-H2/ICOS to the overall B7-H2-mediated cytokine production by antibody blockade was evaluated (FIG. 20B). As expected, blockade by 9F.8A4 reduced all cytokine productions to background level, indicating that cytokine production is dependent on all three receptors of B7-H2. However, selective blockade of B7-H2/CD28 interaction by MIH12 partially decreased the production of the majority of cytokines, with more profound effects on IL-4, IL-5, IL-10 and IL-17 but less effective on IL-2, TNFα and IFNγ (FIG. 20B). These results indicate a significant portion of CD28-mediated Th2 and IL-17 cytokine production might be attributed to B7-H2 binding instead of exclusively to B7-1/B7-2 engagement.

Figure 20C:
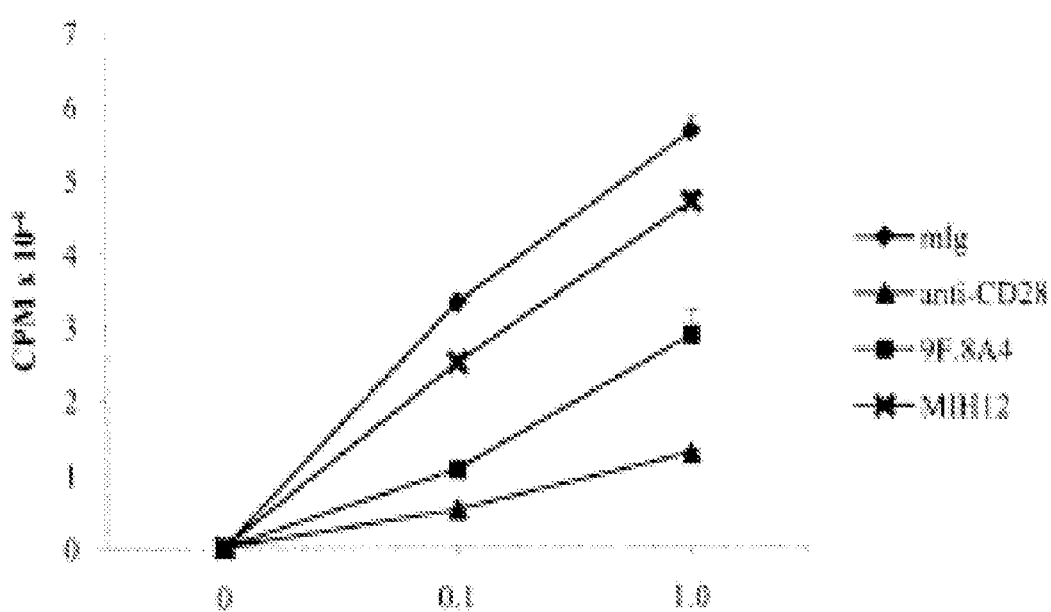
Figure 20D:
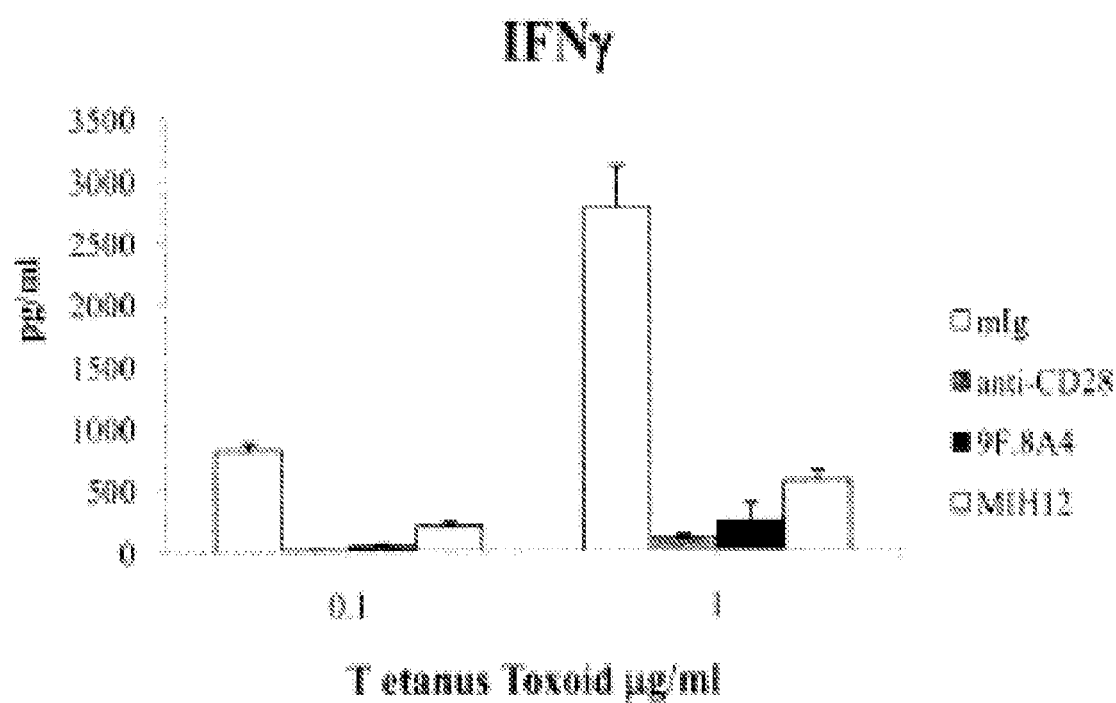

The observation that B7-H2/CD28 interaction is not conserved in mouse prevents us to evaluate this pathway in vivo. Next, the role of B7-H2/CD28 interaction in more physiologically relevant models in vitro, including antigen-specific memory T cell recall response and primary T cell responses to allogeneic antigens, was evaluated. In the first model, monocyte-derived dendritic cells were incubated with tetanus toxoid (TT) to stimulate autologous peripheral T cells from an adult individual who was immunized previously with tetanus vaccine. The proliferation and IFNγ production of polyclonal long-term memory T cells in response to TT antigen were examined in the presence of selected mAbs. MIH12 reduced TT antigen-elicited proliferation by approximately 20%, a small but significant inhibition (P<0.05) (FIG. 20C). However, this treatment had a profound effect on IFNγ production: over 80% IFNγ production was suppressed (FIG. 20D). Addition of a CD28 blocking mAb (clone CD28.6, non-costimulatory) or 9F.8A4 achieved>50% inhibition on proliferation and >90% on IFNγ production (FIGS. 20C and 20D). These findings indicate that both CD28 and ICOS pathways are required for the proliferation and IFNγ production of memory T cells in this setting. B7-H2/CD28 interaction, albeit plays a minor role in the growth of memory T cells, is critical for TT-induced IFNγ production from memory T cells.

Figure 20E:
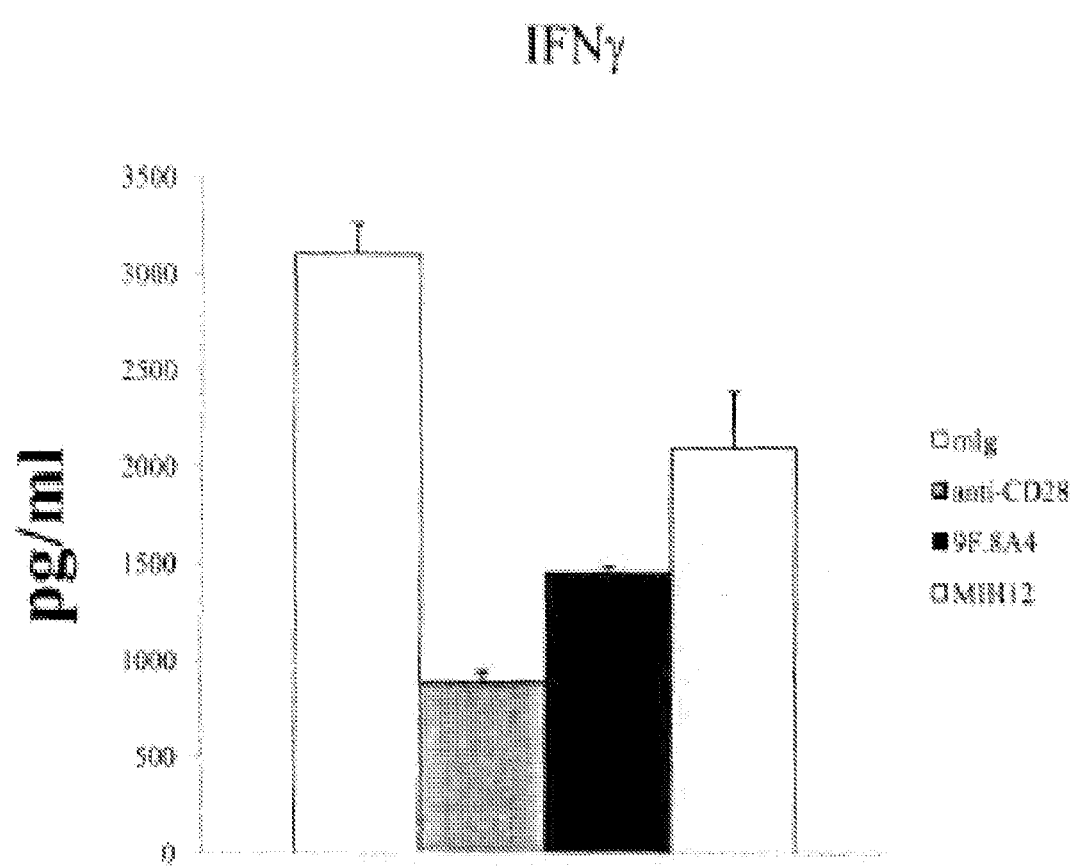

In the second model, monocyte-derived dendritic cells were used for stimulation of allogeneic T cells from peripheral blood. In this culture system, MIH12 also significantly suppressed IFNγ production from allogeneic T cells (P<0.05) (FIG. 20E). Similar to TT antigen-elicited memory T cell response, MIH12 was mainly effective on IFNγ production but less effective on T cell growth (data not shown). These findings may be related to the weak ability of B7-H2/CD28 to stimulate IL-2 production (FIG. 22). These results demonstrate that endogenous B7-H2/CD28 interaction plays critical roles in promoting T cell activation and cytokine production.

These findings demonstrate that B7-H2 is the third ligand for CD28 (FIG. 17A). B7-H2 is expressed constitutively by hematopoietic and non-hematopoietic cells in peripheral organs, whereas B7-1 and B7-2 are largely inducible molecules on selective antigen-presenting cells. This distinct and non-overlapping expression pattern of these three ligands may regulate T cell responses through CD28/CTLA-4 in spatially and temporally divergent settings. Constitutive B7-H2 expression may allow CD28 costimulation to be sustained in peripheral organs for effector or memory T cells. It is yet to be determined whether B7-H2 provides a completely overlapping signal as B7-1 and B7-2. The non-competing nature of B7-H2/CD28 and B7s/CD28 interactions also make it possible that B7-1/B7-2 and B7-H2 could bind CD28 simultaneously, delivering synergistic costimulatory signals in lymphoid organs (FIG. 17B). These finding also warrant re-evaluation of CD28 and ICOS pathways as targets for immunotherapeutic manipulation. For example, the effect of CTLA-4Ig (abatacept) as an immunosuppressive drug could be interpreted at least partially as interference of B7-H2/CD28 interaction, since CTLA-4 and CD28 share the same binding interface with B7-H2.

7.3 REFERENCES

Below is the list of references cited in Section 7.
1. Lenschow, D. J., Walunas, T. L. & Bluestone, J. A. CD28/B7 system of T cell costimulation. Annu Rev Immunol 14, 233-58 (1996).
2. Linsley, P. S., Clark, E. A. & Ledbetter, J. A. T-cell antigen CD28 mediates adhesion with B cells by interacting with activation antigen B7/BB-1. Proc Natl Acad Sci USA 87, 5031-5 (1990).
3. Hutloff, A. et al. ICOS is an inducible T-cell co-stimulator structurally and functionally related to CD28. Nature 397, 263-6 (1999).
4. Yoshinaga, S. K. et al. T-cell co-stimulation through B7RP-1 and ICOS. Nature 402, 827-32 (1999).
5. Wang, S. et al. Costimulation of T cells by B7-H2, a B7-like molecule that binds ICOS. Blood 96, 2808-13 (2000).
6. Riley, J. L. et al. Modulation of TCR-induced transcriptional profiles by ligation of CD28, ICOS, and CTLA-4 receptors. Proc Natl Acad Sci USA 99, 11790-5 (2002).
7. Krummel, M. F. & Allison, J. P. CD28 and CTLA-4 have opposing effects on the response of T cells to stimulation. J Exp Med 182, 459-65 (1995).
8. Walunas, T. L. et al. CTLA-4 can function as a negative regulator of T cell activation. Immunity 1, 405-13 (1994).
9. Ling, V. et al. Assembly and annotation of human chromosome 2q33 sequence containing the CD28, CTLA4, and ICOS gene cluster: analysis by computational, comparative, and microarray approaches. Genomics 78, 155-68 (2001).
10. Dong, C. et al. ICOS co-stimulatory receptor is essential for T-cell activation and function. Nature 409, 97-101 (2001).
11. McAdam, A. J. et al. ICOS is critical for CD40-mediated antibody class switching. Nature 409, 102-5 (2001).
12. Tafuri, A. et al. ICOS is essential for effective T-helper-cell responses. Nature 409, 105-9 (2001).
13. Linterman, M. A. et al. Roquin differentiates the specialized functions of duplicated T cell costimulatory receptor genes CD28 and ICOS. Immunity 30, 228-41 (2009).
14. van der Merwe, P. A., Bodian, D. L., Daenke, S., Linsley, P. & Davis, S. J. CD80 (B7-1) binds both CD28 and CTLA-4 with a low affinity and very fast kinetics. J Exp Med 185, 393-403 (1997).
15. Schwartz, J. C., Zhang, X., Fedorov, A. A., Nathenson, S. G. & Almo, S. C. Structural basis for co-stimulation by the human CTLA-4/B7-2 complex. Nature 410, 604-8 (2001).
16. Chattopadhyay, K., Bhatia, S., Fiser, A., Almo, S. C. & Nathenson, S. G. Structural basis of inducible costimulator ligand costimulatory function: determination of the cell surface oligomeric state and functional mapping of the receptor binding site of the protein. J Immunol 177, 3920-9 (2006).
17. Swallow, M. M., Wallin, J. J. & Sha, W. C. B7h, a novel costimulatory homolog of B7.1 and B7.2, is induced by TNFalpha. Immunity 11, 423-32 (1999).
18. Bauquet, A. T. et al. The costimulatory molecule ICOS regulates the expression of c-Maf and IL-21 in the development of follicular T helper cells and TH-17 cells. Nat Immunol 10, 167-75 (2009).
19. Dong, H., Zhu, G., Tamada, K. & Chen, L. B7-H1, a third member of the B7 family, co-stimulates T-cell proliferation and interleukin-10 secretion. Nat Med 5, 1365-9 (1999).
20. Wang, S. et al. Molecular modeling and functional mapping of B7-H1 and B7-DC uncouple costimulatory function from PD-1 interaction. J Exp Med 197, 1083-91 (2003).

The foregoing is not to be limited in scope by the specific embodiments described herein. Indeed, various modifications of the antibodies and methods provided herein and their equivalents, in addition to those described herein will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

TABLE 1

List of cDNA clones used in the receptor-ligand proteome.

| No. | Gene List |
|---|---|
| 1 | ABCA1 |
| 2 | ABCA3 |
| 3 | ABCC4 |
| 4 | ABCD3 |
| 5 | ABCG1 |
| 6 | ABCG2 |
| 7 | ABI1 |
| 8 | ACCN4 |
| 9 | ACE |
| 10 | ACE2 |
| 11 | ACSL3 |
| 12 | ACTL6A |
| 13 | ACTN1 |
| 14 | ACTN2 |
| 15 | ACVR1 |
| 16 | ACVR1B |
| 17 | ACVRL1 |
| 18 | ACY3 |
| 19 | ADAM10 |
| 20 | ADAM17 |
| 21 | ADAM2 |
| 22 | ADAM23 |
| 23 | ADAM8 |
| 24 | ADCY7 |
| 25 | ADD1 |
| 26 | ADD2 |
| 27 | ADD3 |
| 28 | ADI1 |
| 29 | ADORA2A |
| 30 | ADORA2B |
| 31 | ADORA3 |

TABLE 1-continued

List of cDNA clones used in the receptor-ligand proteome.

| No. | Gene List |
|---|---|
| 32 | ADRA2A |
| 33 | ADRB2 |
| 34 | ADRM1 |
| 35 | AGER |
| 36 | AGPAT3 |
| 37 | AGPAT5 |
| 38 | AGTRL1 |
| 39 | AHCY |
| 40 | AIFM3 |
| 41 | AIG1 |
| 42 | AKAP7 |
| 43 | AKR1A1 |
| 44 | AKT1 |
| 45 | AKTIP |
| 46 | ALCAM |
| 47 | ALDH3A2 |
| 48 | ALEX1 |
| 49 | ALG5 |
| 50 | ALOX15 |
| 51 | ALPL |
| 52 | ALPP |
| 53 | ALPPL2 |
| 54 | AMBP |
| 55 | AMD |
| 56 | AMFR |
| 57 | AMICA1 |
| 58 | AMIGO1 |
| 59 | AMIGO2 |
| 60 | AMIGO3 |
| 61 | AMOTL2 |
| 62 | AMPH |
| 63 | ANK1 |
| 64 | ANKH |
| 65 | ANPEP |
| 66 | ANTXR2 |
| 67 | ANXA1 |
| 68 | ANXA2 |
| 69 | AOC3 |
| 70 | AP1G1 |
| 71 | AP1G2 |
| 72 | AP1M1 |
| 73 | AP1M2 |
| 74 | AP1S1 |
| 75 | AP1S2 |
| 76 | AP1S3 |
| 77 | AP2A1 |
| 78 | AP2A2 |
| 79 | AP2B1 |
| 80 | AP2M1 |
| 81 | AP2S1 |
| 82 | AP3B1 |
| 83 | AP4B1 |
| 84 | AP4M1 |
| 85 | AP4S1 |
| 86 | APBB1IP |
| 87 | APH1A |
| 88 | APLP1 |
| 89 | APLP2 |
| 90 | APOE |
| 91 | APOM |
| 92 | APP |
| 93 | APR-3 |
| 94 | AQP3 |
| 95 | AQP4 |
| 96 | AQP7 |
| 97 | AQP8 |
| 98 | AQP9 |
| 99 | ARC |
| 100 | ARF1 |
| 101 | ARF5 |
| 102 | ARF6 |
| 103 | ARFIP2 |
| 104 | ARHGAP1 |
| 105 | ARHGAP17 |
| 106 | ARHGEF1 |
| 107 | ARRB1 |
| 108 | ARRB2 |
| 109 | ARSA |
| 110 | ART3 |
| 111 | ART4 |
| 112 | ASAM |
| 113 | ASGR1 |
| 114 | ASGR2 |
| 115 | AT1G16170 |
| 116 | ATF4 |
| 117 | ATP12A |
| 118 | ATP1A1 |
| 119 | ATP1A2 |
| 120 | ATP1A3 |
| 121 | ATP1A4 |
| 122 | ATP1B1 |
| 123 | ATP1B2 |
| 124 | ATP1B3 |
| 125 | ATP2A2 |
| 126 | ATP2A3 |
| 127 | ATP2B4 |
| 128 | ATP5G1 |
| 129 | ATP6AP2 |
| 130 | ATP6V0B |
| 131 | ATP6V0C |
| 132 | ATP6V1A |
| 133 | ATP6V1B1 |
| 134 | ATP6V1E1 |
| 135 | AUP1 |
| 136 | AXIN1 |
| 137 | AXL |
| 138 | AZGP1 |
| 139 | B2M |
| 140 | B3GALT2 |
| 141 | B3GALT3 |
| 142 | B3GAT1 |
| 143 | B3GAT3 |
| 144 | B3GNT1 |
| 145 | B3GNT3 |
| 146 | B4GALT4 |
| 147 | B7-DC |
| 148 | B7-H1 |
| 149 | B7-H2 |
| 150 | B7-H3 |
| 151 | B7-H4 |
| 152 | bA16L21.2.1 |
| 153 | BACE1 |
| 154 | BAIAP2 |
| 155 | BASP1 |
| 156 | BBP |
| 157 | BBS2 |
| 158 | BCAM |
| 159 | BCAN |
| 160 | BCAP31 |
| 161 | BCAR1 |
| 162 | BCL10 |
| 163 | BDKRB1 |
| 164 | BEST1 |
| 165 | BEST3 |
| 166 | BFAR |
| 167 | BLCAP |
| 168 | BMPR1B |
| 169 | BMPR2 |
| 170 | BNIP3 |
| 171 | BNIP3L |
| 172 | BOC |
| 173 | BPI |
| 174 | BRI3 |
| 175 | BSG |
| 176 | BST1 |
| 177 | BST2 |
| 178 | BTBD10 |
| 179 | BTLA |
| 180 | BTN1A1 |
| 181 | BTN2A1 |
| 182 | BTN2A2 |
| 183 | BTN2A3 |

TABLE 1-continued

List of cDNA clones used in the receptor-ligand proteome.

| No. | Gene List |
|---|---|
| 184 | BTN3A1 |
| 185 | BTN3A2 |
| 186 | BTN3A3 |
| 187 | BTNL2 |
| 188 | BTNL3 |
| 189 | BTNL8 |
| 190 | BTNL9 |
| 191 | BZRP |
| 192 | C11orf90 |
| 193 | C14orf100 |
| 194 | C18orf1 |
| 195 | C18orf55 |
| 196 | C1orf27 |
| 197 | C1QBP |
| 198 | C22orf29 |
| 199 | C2orf63 |
| 200 | C3HC4 |
| 201 | C5AR1 |
| 202 | C5orf15 |
| 203 | C9 |
| 204 | C9orf58 |
| 205 | CA12 |
| 206 | CA9 |
| 207 | CABP1 |
| 208 | CACNA1G |
| 209 | CACNG3 |
| 210 | CACNG4 |
| 211 | CACNG6 |
| 212 | CADM1 |
| 213 | CADM2 |
| 214 | CADM3 |
| 215 | CADM4 |
| 216 | CADPS |
| 217 | CALCYON |
| 218 | CALM1 |
| 219 | CALM2 |
| 220 | CALM3 |
| 221 | CALR |
| 222 | CALY |
| 223 | CAMK1G |
| 224 | CANX |
| 225 | CAP1 |
| 226 | CAP2 |
| 227 | CAPN1 |
| 228 | CAPN2 |
| 229 | CAPNS1 |
| 230 | CAPNS2 |
| 231 | CAPRIN1 |
| 232 | CARD14 |
| 233 | CARKD |
| 234 | CAV1 |
| 235 | CAV2 |
| 236 | CCBP2 |
| 237 | CCDC8 |
| 238 | CCKBR |
| 239 | CCL14 |
| 240 | CCNB1IP1 |
| 241 | CCR1 |
| 242 | CCR2 |
| 243 | CCR3 |
| 244 | CCR4 |
| 245 | CCR5 |
| 246 | CCR6 |
| 247 | CCR7 |
| 248 | CCR8 |
| 249 | CCR9 |
| 250 | CD14 |
| 251 | CD151 |
| 252 | CD160 |
| 253 | CD163 |
| 254 | CD163L1 |
| 255 | CD164 |
| 256 | CD177 |
| 257 | CD180 |
| 258 | CD19 |
| 259 | CD1A |
| 260 | CD1B |
| 261 | CD1C |
| 262 | CD1D |
| 263 | CD1E |
| 264 | CD2 |
| 265 | CD200 |
| 266 | CD200R1 |
| 267 | CD207 |
| 268 | CD209 |
| 269 | CD22 |
| 270 | CD226 |
| 271 | CD24 |
| 272 | CD244 |
| 273 | CD247 |
| 274 | CD248 |
| 275 | CD28 |
| 276 | CD300A |
| 277 | CD300C |
| 278 | CD300LB |
| 279 | CD300LD |
| 280 | CD300LE |
| 281 | CD300LF |
| 282 | CD300LG |
| 283 | CD302 |
| 284 | CD33 |
| 285 | CD34 |
| 286 | CD36 |
| 287 | CD37 |
| 288 | CD38 |
| 289 | CD3D |
| 290 | CD3E |
| 291 | CD3G |
| 292 | CD4 |
| 293 | CD44 |
| 294 | CD45 |
| 295 | CD47 |
| 296 | CD48 |
| 297 | CD5 |
| 298 | CD52 |
| 299 | CD53 |
| 300 | CD55 |
| 301 | CD58 |
| 302 | CD59 |
| 303 | CD5L |
| 304 | CD6 |
| 305 | CD63 |
| 306 | CD68 |
| 307 | CD69 |
| 308 | CD7 |
| 309 | CD72 |
| 310 | CD74 |
| 311 | CD79A |
| 312 | CD79B |
| 313 | CD80 |
| 314 | CD81 |
| 315 | CD82 |
| 316 | CD83 |
| 317 | CD84 |
| 318 | CD86 |
| 319 | CD8A |
| 320 | CD8B |
| 321 | CD9 |
| 322 | CD90 |
| 323 | CD93 |
| 324 | CD96 |
| 325 | CD97 |
| 326 | CD99 |
| 327 | CDC42 |
| 328 | CDC42EP2 |
| 329 | CDC42EP5 |
| 330 | CDC42SE1 |
| 331 | CDCP1 |
| 332 | CDH1 |
| 333 | CDH11 |
| 334 | CDH12 |
| 335 | CDH15 |

TABLE 1-continued

List of cDNA clones used in the receptor-ligand proteome.

| No. | Gene List |
|---|---|
| 336 | CDH16 |
| 337 | CDH18 |
| 338 | CDH19 |
| 339 | CDH2 |
| 340 | CDH23 |
| 341 | CDH24 |
| 342 | CDH3 |
| 343 | CDH5 |
| 344 | CDH6 |
| 345 | CDH7 |
| 346 | CDH8 |
| 347 | CDH9 |
| 348 | CDIPT |
| 349 | CDON |
| 350 | CDS1 |
| 351 | CDSN |
| 352 | CEACAM1 |
| 353 | CEACAM19 |
| 354 | CEACAM21 |
| 355 | CEACAM3 |
| 356 | CEACAM4 |
| 357 | CEACAM5 |
| 358 | CEACAM6 |
| 359 | CEACAM7 |
| 360 | CEACAM8 |
| 361 | CECR1 |
| 362 | CENTA1 |
| 363 | CENTA2 |
| 364 | CENTD3 |
| 365 | CERCAM |
| 366 | CHAF1B |
| 367 | CHIC2 |
| 368 | CHL1 |
| 369 | CHRM1 |
| 370 | CHRM3 |
| 371 | CHRNA1 |
| 372 | CHRNA3 |
| 373 | CHRNA5 |
| 374 | CHRNA6 |
| 375 | CHRNA7 |
| 376 | CHRNB1 |
| 377 | CHST10 |
| 378 | CILP1 |
| 379 | CISH |
| 380 | CKLFSF6 |
| 381 | CLCA2 |
| 382 | CLCN2 |
| 383 | CLCN7 |
| 384 | CLCNKA |
| 385 | CLCNKB |
| 386 | CLDN1 |
| 387 | CLDN10 |
| 388 | CLDN11 |
| 389 | CLDN14 |
| 390 | CLDN15 |
| 391 | CLDN19 |
| 392 | CLDN2 |
| 393 | CLDN3 |
| 394 | CLDN4 |
| 395 | CLDN5 |
| 396 | CLDN6 |
| 397 | CLDN7 |
| 398 | CLDN8 |
| 399 | CLDN9 |
| 400 | CLEC10A |
| 401 | CLEC12A |
| 402 | CLEC1A |
| 403 | CLEC2B |
| 404 | CLEC2D |
| 405 | CLEC4C |
| 406 | CLEC4M |
| 407 | CLEC9A |
| 408 | CLIC1 |
| 409 | CLIC2 |
| 410 | CLIC4 |
| 411 | CLMN |
| 412 | CLN3 |
| 413 | CLPTM1 |
| 414 | CLSTN3 |
| 415 | CLTA |
| 416 | CLTB |
| 417 | CLTC |
| 418 | CNIH |
| 419 | CNKSR1 |
| 420 | CNN2 |
| 421 | CNNM3 |
| 422 | CNPY2 |
| 423 | CNTFR |
| 424 | CNTFR |
| 425 | CNTN1 |
| 426 | CNTN2 |
| 427 | CNTN4 |
| 428 | CNTN6 |
| 429 | COMT |
| 430 | COX10 |
| 431 | COX4I1 |
| 432 | COX6C |
| 433 | COX7A2L |
| 434 | CPE |
| 435 | CPEB1 |
| 436 | CPM |
| 437 | CPR8 |
| 438 | CR2 |
| 439 | CRB3 |
| 440 | CREG |
| 441 | CRIPT |
| 442 | CRK |
| 443 | CRLF1 |
| 444 | CRTAC1 |
| 445 | CRTAM |
| 446 | CSF1 |
| 447 | CSF1R |
| 448 | CSF2RA |
| 449 | CSF2RB |
| 450 | CSF3R |
| 451 | CSK |
| 452 | CSNK2A1 |
| 453 | CTGF |
| 454 | CTLA4 |
| 455 | CTNNA1 |
| 456 | CTNNA2 |
| 457 | CTNNA3 |
| 458 | CTNNAL1 |
| 459 | CTNNB1 |
| 460 | CTNND1 |
| 461 | CTNS |
| 462 | CTSB |
| 463 | CUTL1 |
| 464 | CUX1 |
| 465 | CX3CL1 |
| 466 | CX3CR1 |
| 467 | CXADR |
| 468 | CXCL16 |
| 469 | CXCR3 |
| 470 | CXCR4 |
| 471 | CXCR5 |
| 472 | CXCR6 |
| 473 | CXorf61 |
| 474 | CYB561 |
| 475 | CYB5R1 |
| 476 | CYBB |
| 477 | CYFIP1 |
| 478 | CYFIP2 |
| 479 | CYP2J2 |
| 480 | CYP39A1 |
| 481 | CYSLTR1 |
| 482 | DAB2 |
| 483 | DAD1 |
| 484 | DAG1 |
| 485 | DARC |
| 486 | DCBLD2 |
| 487 | DDR1 |

TABLE 1-continued

List of cDNA clones used in the receptor-ligand proteome.

| No. | Gene List |
|---|---|
| 488 | DEAF1 |
| 489 | DEF6 |
| 490 | DEGS1 |
| 491 | DES |
| 492 | DGKA |
| 493 | DHCR7 |
| 494 | DIAPH1 |
| 495 | DIO3 |
| 496 | DIRAS2 |
| 497 | DIXDC1 |
| 498 | DKFZp686O24166 |
| 499 | DKK1 |
| 500 | DLG2 |
| 501 | DLG5 |
| 502 | DLGAP1 |
| 503 | DNAJD1 |
| 504 | DNM1 |
| 505 | DNM2 |
| 506 | DOC2A |
| 507 | Dok2 |
| 508 | DPAGT1 |
| 509 | DPEP1 |
| 510 | DPP4 |
| 511 | DRD2 |
| 512 | DRD5 |
| 513 | DTNA |
| 514 | DTNBP1 |
| 515 | DUSP15 |
| 516 | EBI2 |
| 517 | EBI3 |
| 518 | ECEL1 |
| 519 | ECRG4 |
| 520 | EDAR |
| 521 | EDG1 |
| 522 | EDNRB |
| 523 | EEF1A2 |
| 524 | EFNA1 |
| 525 | EFNA3 |
| 526 | EFNA5 |
| 527 | EFNB1 |
| 528 | EFNB3 |
| 529 | EHD2 |
| 530 | EI24 |
| 531 | EIF2B1 |
| 532 | ELMO1 |
| 533 | ELTD1 |
| 534 | EMB |
| 535 | EMCN |
| 536 | EMP1 |
| 537 | EMR2 |
| 538 | ENAH |
| 539 | ENDOGL1 |
| 540 | ENG |
| 541 | ENO1 |
| 542 | ENO1P |
| 543 | ENO2 |
| 544 | ENOX2 |
| 545 | ENPEP |
| 546 | ENPP4 |
| 547 | ENPP5 |
| 548 | ENTPD1 |
| 549 | ENTPD3 |
| 550 | ENTPD8 |
| 551 | EPB41 |
| 552 | EPB41L2 |
| 553 | EPB41L3 |
| 554 | EPHA10 |
| 555 | EPHA2 |
| 556 | EPHA4 |
| 557 | EPHA8 |
| 558 | EPHB3 |
| 559 | EPHB4 |
| 560 | EPN1 |
| 561 | ERBB2 |
| 562 | ERBB3 |
| 563 | ERMAP |
| 564 | ESAM |
| 565 | EVI2A |
| 566 | EVI2B |
| 567 | EVL |
| 568 | EXOC7 |
| 569 | EXTL1 |
| 570 | F2R |
| 571 | F2RL1 |
| 572 | F3 |
| 573 | FACL5 |
| 574 | FADS2 |
| 575 | FAF1 |
| 576 | FAIM2 |
| 577 | FAIM3 |
| 578 | FAM118B |
| 579 | FAM127A |
| 580 | FAM20B |
| 581 | FAM57A |
| 582 | FAM62B |
| 583 | FBLIM1 |
| 584 | FBXW7 |
| 585 | FCAR |
| 586 | FCER1A |
| 587 | FCER1G |
| 588 | FCER2 |
| 589 | FCG3A |
| 590 | FCGR1A |
| 591 | FCGR2A |
| 592 | FCGR2B |
| 593 | FCGR3A |
| 594 | FCGR3B |
| 595 | FCGRT |
| 596 | FCRL1 |
| 597 | FCRL2 |
| 598 | FCRL3 |
| 599 | FCRL4 |
| 600 | FCRL5 |
| 601 | FCRLA |
| 602 | FERMT1 |
| 603 | FEZ1 |
| 604 | FFAR3 |
| 605 | FGFBP1 |
| 606 | FGFR1 |
| 607 | FGFR1 |
| 608 | FGFR2 |
| 609 | FGFR4 |
| 610 | FGRL1 |
| 611 | FLOT1 |
| 612 | FLOT2 |
| 613 | FLRT1 |
| 614 | FLRT3 |
| 615 | FLT1 |
| 616 | FLT3 |
| 617 | FLT3LG |
| 618 | FLVCR1 |
| 619 | FLVCR2 |
| 620 | FNBP1 |
| 621 | FOLH1 |
| 622 | FOLR1 |
| 623 | FPR1 |
| 624 | FPR2 |
| 625 | FRAS1 |
| 626 | FRS2 |
| 627 | FTH1 |
| 628 | FURIN |
| 629 | FUT3 |
| 630 | FUT9 |
| 631 | FXYD1 |
| 632 | FXYD2 |
| 633 | FXYD3 |
| 634 | FXYD5 |
| 635 | FXYD6 |
| 636 | FYN |
| 637 | FZD6 |
| 638 | FZD7 |
| 639 | G3BP1 |

TABLE 1-continued

List of cDNA clones used in the receptor-ligand proteome.

| No. | Gene List |
|---|---|
| 640 | GABARAPL1 |
| 641 | GABARAPL2 |
| 642 | GABBR1 |
| 643 | GABRA1 |
| 644 | GABRA5 |
| 645 | GABRB3 |
| 646 | GABRD |
| 647 | GABRG2 |
| 648 | GAK |
| 649 | GAL3ST1 |
| 650 | GAP43 |
| 651 | GAPDH |
| 652 | GBA2 |
| 653 | GBAS |
| 654 | GBP1 |
| 655 | GBP2 |
| 656 | GBP5 |
| 657 | GCA |
| 658 | GDPD2 |
| 659 | GFRA1 |
| 660 | GFRA2 |
| 661 | GFRA3 |
| 662 | GI24 |
| 663 | GJA4 |
| 664 | GJA5 |
| 665 | GJB1 |
| 666 | GJB2 |
| 667 | GJB3 |
| 668 | GJB4 |
| 669 | GJB5 |
| 670 | GJB6 |
| 671 | GLRA2 |
| 672 | GLRB |
| 673 | GM2A |
| 674 | GNA11 |
| 675 | GNA14 |
| 676 | GNA15 |
| 677 | GNAS |
| 678 | GNAT2 |
| 679 | GNAZ |
| 680 | GNB1 |
| 681 | GNB1L |
| 682 | GNB2 |
| 683 | GNB2L1 |
| 684 | GNB3 |
| 685 | GNB4 |
| 686 | GNB5 |
| 687 | GNG10 |
| 688 | GNG11 |
| 689 | GNG12 |
| 690 | GNG3 |
| 691 | GNG5 |
| 692 | GNG7 |
| 693 | GNGT1 |
| 694 | GNGT2 |
| 695 | GOLGA5 |
| 696 | GOLM1 |
| 697 | GOPC |
| 698 | GOT2 |
| 699 | GP1BA |
| 700 | GP2 |
| 701 | GP6 |
| 702 | GP9 |
| 703 | GPA33 |
| 704 | GPAA1 |
| 705 | GPBAR1 |
| 706 | GPC1 |
| 707 | GPC2 |
| 708 | GPC3 |
| 709 | GPC4 |
| 710 | GPC5 |
| 711 | GPD2 |
| 712 | GPER |
| 713 | GPLD1 |
| 714 | GPNMB |
| 715 | GPR1 |
| 716 | GPR109A |
| 717 | GPR109B |
| 718 | GPR114 |
| 719 | GPR132 |
| 720 | GPR137B |
| 721 | GPR146 |
| 722 | GPR153 |
| 723 | GPR157 |
| 724 | GPR160 |
| 725 | GPR161 |
| 726 | GPR162 |
| 727 | GPR17 |
| 728 | GPR171 |
| 729 | GPR173 |
| 730 | GPR176 |
| 731 | GPR18 |
| 732 | GPR182 |
| 733 | GPR21 |
| 734 | GPR3 |
| 735 | GPR32 |
| 736 | GPR34 |
| 737 | GPR37 |
| 738 | GPR39 |
| 739 | GPR4 |
| 740 | GPR45 |
| 741 | GPR52 |
| 742 | GPR55 |
| 743 | GPR56 |
| 744 | GPR61 |
| 745 | GPR63 |
| 746 | GPR64 |
| 747 | GPR65 |
| 748 | GPR75 |
| 749 | GPR77 |
| 750 | GPR82 |
| 751 | GPR83 |
| 752 | GPR87 |
| 753 | GPR97 |
| 754 | GPRC5A |
| 755 | GPRC5C |
| 756 | GRASP |
| 757 | GRB10 |
| 758 | GRIA2 |
| 759 | GRIK2 |
| 760 | GYPA |
| 761 | GYPB |
| 762 | GYPC |
| 763 | GZMA |
| 764 | GZMB |
| 765 | HAPLN1 |
| 766 | HAPLN2 |
| 767 | HAPLN3 |
| 768 | HAS1 |
| 769 | HAS3 |
| 770 | HBEGF |
| 771 | HDAC11 |
| 772 | HDLBP |
| 773 | HEPACAM |
| 774 | HEPACAM2 |
| 775 | HEXB |
| 776 | HFE2 |
| 777 | HHAT |
| 778 | HHIP |
| 779 | HHLA2 |
| 780 | HIG1 |
| 781 | HIGD1A |
| 782 | HIP1R |
| 783 | HLA-A |
| 784 | HLA-B |
| 785 | HLA-C |
| 786 | HLA-DMA |
| 787 | HLA-DMB |
| 788 | HLA-DOA |
| 789 | HLA-DOB |
| 790 | HLA-DPA1 |
| 791 | HLA-DPB1 |

TABLE 1-continued

List of cDNA clones used in the receptor-ligand proteome.

| No. | Gene List |
|---|---|
| 792 | HLA-DQA1 |
| 793 | HLA-DQB1 |
| 794 | HLA-DQB2 |
| 795 | HLA-DQB3 |
| 796 | HLA-DRA |
| 797 | HLA-DRB1 |
| 798 | HLA-DRB3 |
| 799 | HLA-E |
| 800 | HLA-F |
| 801 | HLA-G |
| 802 | HMOX1 |
| 803 | HMOX2 |
| 804 | HNRNPM |
| 805 | HNT |
| 806 | HOMER1 |
| 807 | HOMER2 |
| 808 | HOMER3 |
| 809 | HPN |
| 810 | HPS1 |
| 811 | HRAS |
| 812 | HRH2 |
| 813 | HSD11B1 |
| 814 | HSD17B10 |
| 815 | HSP90B1 |
| 816 | HSPC154 |
| 817 | HT017 |
| 818 | HTGN29 |
| 819 | HTR1D |
| 820 | HTR2A |
| 821 | HTR2B |
| 822 | HTR3A |
| 823 | HYAL2 |
| 824 | I11RA |
| 825 | ICAM1 |
| 826 | ICAM2 |
| 827 | ICAM3 |
| 828 | ICAM4 |
| 829 | ICAM5 |
| 830 | ICOS |
| 831 | IFITM3 |
| 832 | IFNAR1 |
| 833 | IFNAR2 |
| 834 | IFNGR1 |
| 835 | IFT140 |
| 836 | IGDCC3 |
| 837 | IGF1R |
| 838 | IGHA1 |
| 839 | IGLL1 |
| 840 | IGSF1 |
| 841 | IGSF2 |
| 842 | IGSF3 |
| 843 | IGSF6 |
| 844 | IGSF8 |
| 845 | IGSF9 |
| 846 | IL10RA |
| 847 | IL10RB |
| 848 | IL11RA |
| 849 | IL12RB1 |
| 850 | IL13RA1 |
| 851 | IL15 |
| 852 | IL17RA |
| 853 | IL17RB |
| 854 | IL17RC |
| 855 | IL18R1 |
| 856 | IL1R1 |
| 857 | IL1R2 |
| 858 | IL1RAP |
| 859 | IL1RAPL1 |
| 860 | IL1RAPL2 |
| 861 | IL1RL1 |
| 862 | IL1RL2 |
| 863 | IL27RA |
| 864 | IL2RA |
| 865 | IL2RB |
| 866 | IL2RG |
| 867 | IL3RA |
| 868 | IL5RA |
| 869 | IL6R |
| 870 | IL6RB |
| 871 | IL7R |
| 872 | IL8RA |
| 873 | IL8RB |
| 874 | IL9R |
| 875 | ILK |
| 876 | INSIG1 |
| 877 | IRAK1 |
| 878 | ISLR |
| 879 | ISLR2 |
| 880 | ISY1 |
| 881 | ITFG1 |
| 882 | ITFG2 |
| 883 | ITFG3 |
| 884 | ITGA2B |
| 885 | ITGA3 |
| 886 | ITGA5 |
| 887 | ITGA7 |
| 888 | ITGA9 |
| 889 | ITGAE |
| 890 | ITGAM |
| 891 | ITGAX |
| 892 | ITGB1 |
| 893 | ITGB2 |
| 894 | ITGB3 |
| 895 | ITGB5 |
| 896 | ITGB6 |
| 897 | ITGB7 |
| 898 | ITGB8 |
| 899 | ITGBL1 |
| 900 | ITM2A |
| 901 | ITM2B |
| 902 | JAG1 |
| 903 | JAM1 |
| 904 | JAM2 |
| 905 | JAM3 |
| 906 | JM4 |
| 907 | JMJD6 |
| 908 | JPH3 |
| 909 | JTB |
| 910 | JUB |
| 911 | JUP |
| 912 | KAZALD1 |
| 913 | KCNA2 |
| 914 | KCND2 |
| 915 | KCNE1 |
| 916 | KCNE1L |
| 917 | KCNE3 |
| 918 | KCNG1 |
| 919 | KCNG4 |
| 920 | KCNH2 |
| 921 | KCNIP1 |
| 922 | KCNIP2 |
| 923 | KCNIP3 |
| 924 | KCNIP4 |
| 925 | KCNJ11 |
| 926 | KCNJ12 |
| 927 | KCNJ14 |
| 928 | KCNJ15 |
| 929 | KCNJ8 |
| 930 | KCNK1 |
| 931 | KCNK6 |
| 932 | KCNMB1 |
| 933 | KCNMB2 |
| 934 | KCNMB4 |
| 935 | KCNN3 |
| 936 | KCNN4 |
| 937 | KCNQ2 |
| 938 | KCNRG |
| 939 | KCNS2 |
| 940 | KCNS3 |
| 941 | KCTD10 |
| 942 | KCTD11 |
| 943 | KCTD12 |

TABLE 1-continued

List of cDNA clones used in the receptor-ligand proteome.

| No. | Gene List |
|---|---|
| 944 | KCTD15 |
| 945 | KCTD17 |
| 946 | KCTD20 |
| 947 | KCTD5 |
| 948 | KCTD6 |
| 949 | KCTD9 |
| 950 | KDELC1 |
| 951 | KDELR2 |
| 952 | KDR |
| 953 | KDSR |
| 954 | KEL |
| 955 | KIR2DL1 |
| 956 | KIR2DL3 |
| 957 | KIR2DL4 |
| 958 | KIR2DS2 |
| 959 | KIR2DS4 |
| 960 | KIR3DL1 |
| 961 | KIRREL |
| 962 | KIRREL2 |
| 963 | KIRREL3 |
| 964 | KISS1R |
| 965 | KIT |
| 966 | KITLG |
| 967 | KLRB1 |
| 968 | KLRC1 |
| 969 | KLRD1 |
| 970 | KLRK1 |
| 971 | KRAS |
| 972 | KRT19 |
| 973 | KRT8 |
| 974 | L1CAM |
| 975 | LAG3 |
| 976 | LAIR1 |
| 977 | LAIR2 |
| 978 | LAMP1 |
| 979 | LAMP2 |
| 980 | LAPTM5 |
| 981 | LAT |
| 982 | LAT2 |
| 983 | LBR |
| 984 | LCK |
| 985 | LCP1 |
| 986 | LDLRAP1 |
| 987 | LEPR |
| 988 | LEPROT |
| 989 | LEPROTL1 |
| 990 | LETM1 |
| 991 | LETMD1 |
| 992 | LFA3 |
| 993 | LGALS3 |
| 994 | LGALS4 |
| 995 | LGR6 |
| 996 | LILRA1 |
| 997 | LILRA2 |
| 998 | LILRA3 |
| 999 | LILRA4 |
| 1000 | LILRA5 |
| 1001 | LILRB1 |
| 1002 | LILRB2 |
| 1003 | LILRB3 |
| 1004 | LILRB4 |
| 1005 | LILRB5 |
| 1006 | LIMA1 |
| 1007 | LIME1 |
| 1008 | LIMS1 |
| 1009 | LIMS2 |
| 1010 | LIN7C |
| 1011 | LINGO1 |
| 1012 | LINGO2 |
| 1013 | LINGO4 |
| 1014 | LMBR1L |
| 1015 | LOC100128783 |
| 1016 | LOC51233 |
| 1017 | LOC552891 |
| 1018 | LOC727811 |
| 1019 | LPAR1 |
| 1020 | LPAR2 |
| 1021 | LPAR4 |
| 1022 | LPAR5 |
| 1023 | LPHN1 |
| 1024 | LPL |
| 1025 | LR8 |
| 1026 | LRFN1 |
| 1027 | LRFN2 |
| 1028 | LRFN3 |
| 1029 | LRFN4 |
| 1030 | LRFN5 |
| 1031 | LRIG1 |
| 1032 | LRIG2 |
| 1033 | LRIG3 |
| 1034 | LRIT1 |
| 1035 | LRIT3 |
| 1036 | LRMP |
| 1037 | LRP10 |
| 1038 | LRP12 |
| 1039 | LRP3 |
| 1040 | LRRC4 |
| 1041 | LRRC4C |
| 1042 | LRRC5 |
| 1043 | LRRC59 |
| 1044 | LRRN1 |
| 1045 | LRRN2 |
| 1046 | LRRN3 |
| 1047 | LRRN4 |
| 1048 | LRRTM2 |
| 1049 | LSAMP |
| 1050 | LSP1 |
| 1051 | LSR |
| 1052 | LST1 |
| 1053 | LTB |
| 1054 | LTB4R |
| 1055 | LY6D |
| 1056 | LY6G6F |
| 1057 | LY6H |
| 1058 | LY86 |
| 1059 | LY9 |
| 1060 | LY96 |
| 1061 | LYNX1 |
| 1062 | LYPD1 |
| 1063 | LYVE1 |
| 1064 | M6PR |
| 1065 | MADCAM1 |
| 1066 | MAEA |
| 1067 | MAG |
| 1068 | MAGEA1 |
| 1069 | MAGED1 |
| 1070 | MAGEE1 |
| 1071 | MAGEH1 |
| 1072 | MAL |
| 1073 | MAL2 |
| 1074 | MALL |
| 1075 | MAMC1 |
| 1076 | MAOB |
| 1077 | MAP4K2 |
| 1078 | MAP7 |
| 1079 | MARCKS |
| 1080 | MARCKSL1 |
| 1081 | MARK2 |
| 1082 | MARVELD2 |
| 1083 | MAST1 |
| 1084 | MBP |
| 1085 | MC1R |
| 1086 | MC2R |
| 1087 | MCAM |
| 1088 | MCF2L |
| 1089 | MCHR1 |
| 1090 | MCL1 |
| 1091 | MCOLN1 |
| 1092 | MDK |
| 1093 | MDS032 |
| 1094 | MEGF10 |
| 1095 | MERTK |

TABLE 1-continued

List of cDNA clones used in the receptor-ligand proteome.

| No. | Gene List |
|---|---|
| 1096 | MEST |
| 1097 | MF12 |
| 1098 | MFA3L |
| 1099 | MFAP3 |
| 1100 | MGAT4B |
| 1101 | MGC31957 |
| 1102 | MGEA6 |
| 1103 | MICA |
| 1104 | MICB |
| 1105 | MIR16 |
| 1106 | MLANA |
| 1107 | MMD |
| 1108 | MME |
| 1109 | MMP14 |
| 1110 | MMP15 |
| 1111 | MOG |
| 1112 | MPP1 |
| 1113 | MPP2 |
| 1114 | MPP3 |
| 1115 | MPP6 |
| 1116 | MPV17 |
| 1117 | MPZ |
| 1118 | MPZL1 |
| 1119 | MPZL2 |
| 1120 | MPZL3 |
| 1121 | MR1 |
| 1122 | MRAP |
| 1123 | MRAS |
| 1124 | MRC2 |
| 1125 | MRGPRF |
| 1126 | MRGPRX2 |
| 1127 | MRGPRX3 |
| 1128 | MS4A1 |
| 1129 | MSLN |
| 1130 | MSR1 |
| 1131 | MTFR1 |
| 1132 | MTUS1 |
| 1133 | MUC1 |
| 1134 | MUC18 |
| 1135 | MUC20 |
| 1136 | MUPCDH |
| 1137 | MUSK |
| 1138 | MXRA8 |
| 1139 | MYCBP |
| 1140 | MYH9 |
| 1141 | MYO1C |
| 1142 | N2DL1 |
| 1143 | N2DL2 |
| 1144 | NAE1 |
| 1145 | NCAM1 |
| 1146 | NCAM2 |
| 1147 | NCF4 |
| 1148 | NCKAP1 |
| 1149 | NCKAP1L |
| 1150 | NCR1 |
| 1151 | NCR2 |
| 1152 | NCR3 |
| 1153 | NDRG1 |
| 1154 | NDUFA3 |
| 1155 | NDUFA4 |
| 1156 | NDUFB1 |
| 1157 | NDUFB6 |
| 1158 | NDUFB8 |
| 1159 | NECAP1 |
| 1160 | NECAP2 |
| 1161 | NEGR1 |
| 1162 | NELF |
| 1163 | NELL2 |
| 1164 | NEO1 |
| 1165 | NEU1 |
| 1166 | NF2 |
| 1167 | NFAM1 |
| 1168 | NFE2L3 |
| 1169 | NINJ2 |
| 1170 | NKD1 |
| 1171 | NKD2 |
| 1172 | NKG2C |
| 1173 | NKG2D |
| 1174 | NKG7 |
| 1175 | NLE1 |
| 1176 | NLGN1 |
| 1177 | NLGN4Y |
| 1178 | NMUR1 |
| 1179 | NMUR2 |
| 1180 | NOSTRIN |
| 1181 | NOTCH2NL |
| 1182 | NOTCH4 |
| 1183 | NOX4 |
| 1184 | NOXA1 |
| 1185 | NOXO1 |
| 1186 | NPBWR2 |
| 1187 | NPC1 |
| 1188 | NPHP1 |
| 1189 | NPHS2 |
| 1190 | NPTN |
| 1191 | NPY1R |
| 1192 | NPY5R |
| 1193 | NRAS |
| 1194 | NRCAM |
| 1195 | NRG1 |
| 1196 | NRN1 |
| 1197 | NRP1 |
| 1198 | NT5E |
| 1199 | NTM |
| 1200 | NTNG1 |
| 1201 | NTNG2 |
| 1202 | NTRK1 |
| 1203 | NTRK2 |
| 1204 | NTRK3 |
| 1205 | NTT73 |
| 1206 | NUMB |
| 1207 | NUP85 |
| 1208 | OCLN |
| 1209 | OLR1 |
| 1210 | OMG |
| 1211 | OPCML |
| 1212 | OPN3 |
| 1213 | OPRL1 |
| 1214 | OPRS1 |
| 1215 | OR2L13 |
| 1216 | OR51E1 |
| 1217 | OR51E2 |
| 1218 | OR9Q1 |
| 1219 | ORAI1 |
| 1220 | ORMDL1 |
| 1221 | OSMR |
| 1222 | OSTM1 |
| 1223 | P24B |
| 1224 | P2RX4 |
| 1225 | P2RX5 |
| 1226 | P2RX6 |
| 1227 | P2RX7 |
| 1228 | P2RY10 |
| 1229 | P2RY11 |
| 1230 | P2RY12 |
| 1231 | P2RY13 |
| 1232 | P2RY2 |
| 1233 | P2RY6 |
| 1234 | P2RY8 |
| 1235 | PACSIN3 |
| 1236 | PAG |
| 1237 | PAG1 |
| 1238 | PALM |
| 1239 | PAM |
| 1240 | PANX1 |
| 1241 | PAPLN |
| 1242 | PARD3 |
| 1243 | PARD3B |
| 1244 | PARD6A |
| 1245 | PARVA |
| 1246 | PARVB |
| 1247 | PARVG |

TABLE 1-continued

List of cDNA clones used in the receptor-ligand proteome.

| No. | Gene List |
|---|---|
| 1248 | PCDH1 |
| 1249 | PCDH12 |
| 1250 | PCDH17 |
| 1251 | PCDH20 |
| 1252 | PCDHA4 |
| 1253 | PCDHB10 |
| 1254 | PCDHB13 |
| 1255 | PCDHB15 |
| 1256 | PCDHB16 |
| 1257 | PCDHB2 |
| 1258 | PCDHB3 |
| 1259 | PCDHB4 |
| 1260 | PCDHB5 |
| 1261 | PCDHB8 |
| 1262 | PCDHGA2 |
| 1263 | PCDHGB7 |
| 1264 | PCDHGC3 |
| 1265 | PCDHGC4 |
| 1266 | PCLO |
| 1267 | PCSK1N |
| 1268 | PDCD1 |
| 1269 | PDE6A |
| 1270 | PDGFRA |
| 1271 | PDGFRB |
| 1272 | PDPK1 |
| 1273 | PDPN |
| 1274 | PDZD3 |
| 1275 | PECAM1 |
| 1276 | PERP |
| 1277 | PEX11B |
| 1278 | PEX3 |
| 1279 | PGRMC1 |
| 1280 | PGRMC2 |
| 1281 | PHB |
| 1282 | PHCA |
| 1283 | PHKA2 |
| 1284 | PHKB |
| 1285 | PI4K2A |
| 1286 | PICALM |
| 1287 | PICK1 |
| 1288 | PIGF |
| 1289 | PIGH |
| 1290 | PIGR |
| 1291 | PIGR3 |
| 1292 | PIGY |
| 1293 | PILRB |
| 1294 | PIM1 |
| 1295 | PIP4K2B |
| 1296 | PIP5K1A |
| 1297 | PIP5K1C |
| 1298 | PIP5K3 |
| 1299 | PITPNC1 |
| 1300 | PKP3 |
| 1301 | PLAUR |
| 1302 | PLD2 |
| 1303 | PLEKHA1 |
| 1304 | PLSCR1 |
| 1305 | PLSCR3 |
| 1306 | PMEPA1 |
| 1307 | PMP22 |
| 1308 | PNN |
| 1309 | PNPLA2 |
| 1310 | PODXL2 |
| 1311 | POU2F1 |
| 1312 | PP1201 |
| 1313 | PPAN |
| 1314 | PPAP2A |
| 1315 | PPAP2B |
| 1316 | PPAP2C |
| 1317 | PPFIBP1 |
| 1318 | PPP1R16A |
| 1319 | PPP2CA |
| 1320 | PPT1 |
| 1321 | PRKAR2A |
| 1322 | PRKCZ |
| 1323 | PRMT7 |
| 1324 | PRNP |
| 1325 | PROCR |
| 1326 | PROM1 |
| 1327 | PRRG2 |
| 1328 | PRSS8 |
| 1329 | PRTG |
| 1330 | PSCA |
| 1331 | PSCD1 |
| 1332 | PSCD2 |
| 1333 | PSCD3 |
| 1334 | PSD3 |
| 1335 | PSD4 |
| 1336 | PSEN1 |
| 1337 | PSEN2 |
| 1338 | PSENEN |
| 1339 | PSKH1 |
| 1340 | PSMG1 |
| 1341 | PTDSS1 |
| 1342 | PTGDR |
| 1343 | PTGER1 |
| 1344 | PTGFR |
| 1345 | PTGFRN |
| 1346 | PTGIR |
| 1347 | PTGS2 |
| 1348 | PTH2R |
| 1349 | PTHR1 |
| 1350 | PTK2 |
| 1351 | PTK2B |
| 1352 | PTK7 |
| 1353 | PTN |
| 1354 | PTOV1 |
| 1355 | PTP4A1 |
| 1356 | PTP4A2 |
| 1357 | PTP4A3 |
| 1358 | PTPNS1 |
| 1359 | PTPRA |
| 1360 | PTPRB |
| 1361 | PTPRC |
| 1362 | PTPRCAP |
| 1363 | PTPRD |
| 1364 | PTPRE |
| 1365 | PTPRF |
| 1366 | PTPRG |
| 1367 | PTPRH |
| 1368 | PTPRJ |
| 1369 | PTPRK |
| 1370 | PTPRN |
| 1371 | PTPRN2 |
| 1372 | PTPRO |
| 1373 | PTPRR |
| 1374 | PTPRS |
| 1375 | PTPRT |
| 1376 | PTPRU |
| 1377 | PTRF |
| 1378 | PVR |
| 1379 | PVRL1 |
| 1380 | PVRL2 |
| 1381 | PVRL3 |
| 1382 | PVRL4 |
| 1383 | PXK |
| 1384 | PXMP3 |
| 1385 | PXN |
| 1386 | RAB10 |
| 1387 | RAB11A |
| 1388 | RAB13 |
| 1389 | RAB14 |
| 1390 | RAB18 |
| 1391 | RAB1B |
| 1392 | RAB22A |
| 1393 | RAB23 |
| 1394 | RAB25 |
| 1395 | RAB26 |
| 1396 | RAB2B |
| 1397 | RAB30 |
| 1398 | RAB31 |
| 1399 | RAB33A |

TABLE 1-continued

List of cDNA clones used in the receptor-ligand proteome.

| No. | Gene List |
|---|---|
| 1400 | RAB35 |
| 1401 | RAB38 |
| 1402 | RAB39 |
| 1403 | RAB39B |
| 1404 | RAB3A |
| 1405 | RAB3B |
| 1406 | RAB3C |
| 1407 | RAB3D |
| 1408 | RAB43 |
| 1409 | RAB4B |
| 1410 | RAB5A |
| 1411 | RAB5B |
| 1412 | RAB5C |
| 1413 | RAB7L1 |
| 1414 | RAB8B |
| 1415 | RAB9A |
| 1416 | RABAC1 |
| 1417 | RAC1 |
| 1418 | RAGE |
| 1419 | RALA |
| 1420 | RALB |
| 1421 | RAMP1 |
| 1422 | RAMP2 |
| 1423 | RAMP3 |
| 1424 | RAP1A |
| 1425 | RAP1B |
| 1426 | RAP2B |
| 1427 | RAP2C |
| 1428 | RAPSN |
| 1429 | RASA3 |
| 1430 | RASD1 |
| 1431 | RASGRF1 |
| 1432 | RASGRP3 |
| 1433 | RASL10A |
| 1434 | RASL10B |
| 1435 | rbr-2 |
| 1436 | RCP9 |
| 1437 | RELL2 |
| 1438 | RELT |
| 1439 | REM2 |
| 1440 | RFTN2 |
| 1441 | RGMA |
| 1442 | RGR |
| 1443 | RGS1 |
| 1444 | RGS11 |
| 1445 | RGS13 |
| 1446 | RGS19 |
| 1447 | RHAG |
| 1448 | RHBG |
| 1449 | RHCE |
| 1450 | RHCG |
| 1451 | RHD |
| 1452 | RHEB |
| 1453 | RHOB |
| 1454 | RHOC |
| 1455 | RHOD |
| 1456 | RHOF |
| 1457 | RHOH |
| 1458 | RHOJ |
| 1459 | RHOQ |
| 1460 | RIMBP2 |
| 1461 | RIMS3 |
| 1462 | RIN1 |
| 1463 | RNASE1 |
| 1464 | RNASE6 |
| 1465 | RNF130 |
| 1466 | RNF139 |
| 1467 | RNF5 |
| 1468 | RNPEP |
| 1469 | ROBO1 |
| 1470 | ROBO2 |
| 1471 | ROBO3 |
| 1472 | ROBO4 |
| 1473 | ROM1 |
| 1474 | ROR1 |
| 1475 | ROR2 |
| 1476 | RP2 |
| 1477 | RPH3A |
| 1478 | RPL21 |
| 1479 | RPLP0 |
| 1480 | RPS10 |
| 1481 | RPS6KB1 |
| 1482 | RPSA |
| 1483 | RRAGC |
| 1484 | RRAS |
| 1485 | RRAS2 |
| 1486 | RTN4R |
| 1487 | RTP1 |
| 1488 | RTP2 |
| 1489 | RUNX1T1 |
| 1490 | S100A7 |
| 1491 | S1PR1 |
| 1492 | S1PR4 |
| 1493 | S1PR5 |
| 1494 | SC4MOL |
| 1495 | SC5DL |
| 1496 | SCAMP1 |
| 1497 | SCAMP3 |
| 1498 | SCAMP5 |
| 1499 | SCARB2 |
| 1500 | SCN1B |
| 1501 | SCN2B |
| 1502 | SCN3B |
| 1503 | SCNN1A |
| 1504 | SCNN1B |
| 1505 | SCNN1D |
| 1506 | SCRG1 |
| 1507 | SCTR |
| 1508 | SDC1 |
| 1509 | SDC2 |
| 1510 | SDCBP |
| 1511 | SDCBP2 |
| 1512 | SDFR1 |
| 1513 | SDPR |
| 1514 | SEC11A |
| 1515 | SEC61G |
| 1516 | SECTM1 |
| 1517 | SELE |
| 1518 | SELL |
| 1519 | SELP |
| 1520 | SELPLG |
| 1521 | SEMA3A |
| 1522 | SEMA3B |
| 1523 | SEMA3C |
| 1524 | SEMA3F |
| 1525 | SEMA4A |
| 1526 | SEMA4B |
| 1527 | SEMA4C |
| 1528 | SEMA4D |
| 1529 | SEMA4F |
| 1530 | SEMA4G |
| 1531 | SEMA5A |
| 1532 | SEMA6A |
| 1533 | SEMA6B |
| 1534 | SEMA7A |
| 1535 | SEPW1 |
| 1536 | SERINC3 |
| 1537 | SERP1 |
| 1538 | SGCA |
| 1539 | SGCB |
| 1540 | SGCD |
| 1541 | SGMS1 |
| 1542 | SH3BP4 |
| 1543 | SH3KBP1 |
| 1544 | SHC1 |
| 1545 | SIGIRR |
| 1546 | SIGLEC1 |
| 1547 | SIGLEC10 |
| 1548 | SIGLEC11 |
| 1549 | SIGLEC12 |
| 1550 | SIGLEC5 |
| 1551 | SIGLEC6 |

TABLE 1-continued

List of cDNA clones used in the receptor-ligand proteome.

| No. | Gene List |
|---|---|
| 1552 | SIGLEC7 |
| 1553 | SIGLEC8 |
| 1554 | SIGLEC9 |
| 1555 | SILV |
| 1556 | SIRPA |
| 1557 | SIRPB1 |
| 1558 | SIRPB2 |
| 1559 | SIRPD |
| 1560 | SIRPG |
| 1561 | SIVA1 |
| 1562 | SKAP2 |
| 1563 | SLA2 |
| 1564 | SLAMF1 |
| 1565 | SLAMF5 |
| 1566 | SLAMF6 |
| 1567 | SLAMF7 |
| 1568 | SLAMF8 |
| 1569 | SLAMF9 |
| 1570 | SLC11A1 |
| 1571 | SLC11A2 |
| 1572 | SLC12A1 |
| 1573 | SLC12A4 |
| 1574 | SLC12A7 |
| 1575 | SLC14A1 |
| 1576 | SLC16A14 |
| 1577 | SLC16A4 |
| 1578 | SLC16A5 |
| 1579 | SLC16A6 |
| 1580 | SLC17A5 |
| 1581 | SLC17A7 |
| 1582 | SLC18A3 |
| 1583 | SLC19A1 |
| 1584 | SLC1A2 |
| 1585 | SLC1A3 |
| 1586 | SLC1A4 |
| 1587 | SLC1A5 |
| 1588 | SLC1A6 |
| 1589 | SLC20A1 |
| 1590 | SLC20A2 |
| 1591 | SLC22A11 |
| 1592 | SLC22A12 |
| 1593 | SLC22A18 |
| 1594 | SLC22A2 |
| 1595 | SLC22A4 |
| 1596 | SLC22A5 |
| 1597 | SLC22A6 |
| 1598 | SLC22A7 |
| 1599 | SLC22A8 |
| 1600 | SLC23A1 |
| 1601 | SLC23A2 |
| 1602 | SLC25A11 |
| 1603 | SLC25A12 |
| 1604 | SLC25A13 |
| 1605 | SLC25A17 |
| 1606 | SLC25A3 |
| 1607 | SLC25A4 |
| 1608 | SLC25A5 |
| 1609 | SLC26A2 |
| 1610 | SLC26A6 |
| 1611 | SLC29A1 |
| 1612 | SLC29A2 |
| 1613 | SLC2A2 |
| 1614 | SLC2A3 |
| 1615 | SLC2A4 |
| 1616 | SLC2A5 |
| 1617 | SLC2A6 |
| 1618 | SLC2A8 |
| 1619 | SLC2A9 |
| 1620 | SLC30A5 |
| 1621 | SLC30A9 |
| 1622 | SLC31A1 |
| 1623 | SLC31A2 |
| 1624 | SLC33A1 |
| 1625 | SLC34A1 |
| 1626 | SLC35A1 |
| 1627 | SLC35E3 |
| 1628 | SLC38A1 |
| 1629 | SLC38A2 |
| 1630 | SLC38A3 |
| 1631 | SLC38A5 |
| 1632 | SLC39A1 |
| 1633 | SLC39A4 |
| 1634 | SLC39A5 |
| 1635 | SLC39A6 |
| 1636 | SLC40A1 |
| 1637 | SLC41A2 |
| 1638 | SLC41A3 |
| 1639 | SLC43A1 |
| 1640 | SLC44A1 |
| 1641 | SLC46A1 |
| 1642 | SLC46A2 |
| 1643 | SLC47A1 |
| 1644 | SLC4A1 |
| 1645 | SLC4A4 |
| 1646 | SLC5A6 |
| 1647 | SLC6A13 |
| 1648 | SLC6A15 |
| 1649 | SLC6A18 |
| 1650 | SLC6A6 |
| 1651 | SLC6A8 |
| 1652 | SLC7A1 |
| 1653 | SLC7A10 |
| 1654 | SLC7A11 |
| 1655 | SLC7A3 |
| 1656 | SLC7A5 |
| 1657 | SLC7A6 |
| 1658 | SLC7A7 |
| 1659 | SLC7A8 |
| 1660 | SLC7A9 |
| 1661 | SLC9A3R1 |
| 1662 | SLC9A3R2 |
| 1663 | SLCO2A1 |
| 1664 | SLIT1 |
| 1665 | SMAD3 |
| 1666 | SMAP1 |
| 1667 | SMBP |
| 1668 | SMPD2 |
| 1669 | SMPD3 |
| 1670 | SNAP23 |
| 1671 | SNAP25 |
| 1672 | SNAP29 |
| 1673 | SNN |
| 1674 | SNPH |
| 1675 | SNTB2 |
| 1676 | SOD1 |
| 1677 | SORBS3 |
| 1678 | SPACA4 |
| 1679 | SPC18 |
| 1680 | SPCS1 |
| 1681 | SPN |
| 1682 | SPRY2 |
| 1683 | SQLE |
| 1684 | SRD5A1 |
| 1685 | SREB3 |
| 1686 | SRI |
| 1687 | SSFA2 |
| 1688 | SSH1 |
| 1689 | SSPN |
| 1690 | SSR1 |
| 1691 | SSR2 |
| 1692 | SSTR1 |
| 1693 | SSTR2 |
| 1694 | SSX2IP |
| 1695 | ST14 |
| 1696 | ST3GAL5 |
| 1697 | ST6GAL1 |
| 1698 | ST6GALNAC6 |
| 1699 | ST7 |
| 1700 | STBD1 |
| 1701 | STCH |
| 1702 | STEAP1 |
| 1703 | STEAP4 |

TABLE 1-continued

List of cDNA clones used in the receptor-ligand proteome.

| No. | Gene List |
|---|---|
| 1704 | STIM1 |
| 1705 | STOM |
| 1706 | STOML3 |
| 1707 | STRA6 |
| 1708 | STT3A |
| 1709 | STX12 |
| 1710 | STX17 |
| 1711 | STX1A |
| 1712 | STX1B |
| 1713 | STX3 |
| 1714 | STX4 |
| 1715 | STX6 |
| 1716 | STX7 |
| 1717 | STX8 |
| 1718 | STXBP5 |
| 1719 | STYK1 |
| 1720 | SUCNR1 |
| 1721 | SV2A |
| 1722 | SVOP |
| 1723 | SWAP70 |
| 1724 | SYK |
| 1725 | SYMPK |
| 1726 | SYN2 |
| 1727 | SYNGR1 |
| 1728 | SYNGR2 |
| 1729 | SYNGR3 |
| 1730 | SYP |
| 1731 | SYPL1 |
| 1732 | SYT1 |
| 1733 | SYT11 |
| 1734 | SYT12 |
| 1735 | SYT15 |
| 1736 | SYT5 |
| 1737 | SYT6 |
| 1738 | SYT9 |
| 1739 | SYTL1 |
| 1740 | SYTL2 |
| 1741 | SYTL4 |
| 1742 | TACSTD1 |
| 1743 | TACSTD2 |
| 1744 | TAOK3 |
| 1745 | TAP2 |
| 1746 | TAPBP |
| 1747 | TAPBPL |
| 1748 | TBL2 |
| 1749 | TCIRG1 |
| 1750 | TCP10 |
| 1751 | TDGF1 |
| 1752 | TDRKH |
| 1753 | TEGT |
| 1754 | TEX101 |
| 1755 | TFG |
| 1756 | TFRC |
| 1757 | TGFA |
| 1758 | TGFB1I1 |
| 1759 | TGFBR3 |
| 1760 | TGM1 |
| 1761 | TGM2 |
| 1762 | TGOLN2 |
| 1763 | THBD |
| 1764 | THEM4 |
| 1765 | TIE1 |
| 1766 | TIE2 |
| 1767 | TIGIT |
| 1768 | TIMD1 |
| 1769 | TIMD3 |
| 1770 | TIMD4 |
| 1771 | TJAP1 |
| 1772 | TLR1 |
| 1773 | TLR2 |
| 1774 | TLR3 |
| 1775 | TLR4 |
| 1776 | TLR6 |
| 1777 | TLR9 |
| 1778 | TM4SF1 |
| 1779 | TM4SF11 |
| 1780 | TM4SF20 |
| 1781 | TM4SF4 |
| 1782 | TM7SF2 |
| 1783 | TM7SF3 |
| 1784 | TM9SF1 |
| 1785 | TM9SF2 |
| 1786 | TMBIM1 |
| 1787 | TMED1 |
| 1788 | TMED10 |
| 1789 | TMED2 |
| 1790 | TMED5 |
| 1791 | TMEM106B |
| 1792 | TMEM11 |
| 1793 | TMEM126B |
| 1794 | TMEM14A |
| 1795 | TMEM14C |
| 1796 | TMEM15 |
| 1797 | TMEM150 |
| 1798 | TMEM204 |
| 1799 | TMEM25 |
| 1800 | TMEM33 |
| 1801 | TMEM46 |
| 1802 | TMEM5 |
| 1803 | TMEM50A |
| 1804 | TMEM50B |
| 1805 | TMEM8 |
| 1806 | TMEM81 |
| 1807 | TMEM86A |
| 1808 | TMEM9 |
| 1809 | TMEPAI |
| 1810 | TMIGD1 |
| 1811 | TMIGD2 |
| 1812 | TMPRSS2 |
| 1813 | TNFAIP1 |
| 1814 | TNFRSF10A |
| 1815 | TNFRSF10B |
| 1816 | TNFRSF10C |
| 1817 | TNFRSF11A |
| 1818 | TNFRSF12A |
| 1819 | TNFRSF13B |
| 1820 | TNFRSF14 |
| 1821 | TNFRSF16 |
| 1822 | TNFRSF17 |
| 1823 | TNFRSF18 |
| 1824 | TNFRSF19 |
| 1825 | TNFRSF1A |
| 1826 | TNFRSF1B |
| 1827 | TNFRSF21 |
| 1828 | TNFRSF25 |
| 1829 | TNFRSF27 |
| 1830 | TNFRSF3 |
| 1831 | TNFRSF4 |
| 1832 | TNFRSF5 |
| 1833 | TNFRSF6 |
| 1834 | TNFRSF7 |
| 1835 | TNFRSF8 |
| 1836 | TNFRSF9 |
| 1837 | TNFSF10 |
| 1838 | TNFSF11 |
| 1839 | TNFSF12 |
| 1840 | TNFSF13 |
| 1841 | TNFSF13B |
| 1842 | TNFSF14 |
| 1843 | TNFSF15 |
| 1844 | TNFSF18 |
| 1845 | TNFSF4 |
| 1846 | TNFSF5 |
| 1847 | TNFSF6 |
| 1848 | TNFSF7 |
| 1849 | TNFSF8 |
| 1850 | TNFSF9 |
| 1851 | TNK2 |
| 1852 | TNS3 |
| 1853 | TNS4 |
| 1854 | TOLLIP |
| 1855 | TOMM20 |

TABLE 1-continued

List of cDNA clones used in the receptor-ligand proteome.

| No. | Gene List |
|---|---|
| 1856 | TOMM22 |
| 1857 | TPARL |
| 1858 | TPSB2 |
| 1859 | TRA |
| 1860 | TRAF7 |
| 1861 | TRAJ17 |
| 1862 | TRAT1 |
| 1863 | TRAV20 |
| 1864 | TRDV2 |
| 1865 | TREM1 |
| 1866 | TREM2 |
| 1867 | TREM4b |
| 1868 | TREML1 |
| 1869 | TREML2 |
| 1870 | TREML4 |
| 1871 | TRIM13 |
| 1872 | TRIM27 |
| 1873 | TRIP10 |
| 1874 | TRIP6 |
| 1875 | TRO |
| 1876 | TRPV2 |
| 1877 | TRPV5 |
| 1878 | TRPV6 |
| 1879 | TSHR |
| 1880 | TSPAN13 |
| 1881 | TSPAN15 |
| 1882 | TSPAN2 |
| 1883 | TSPAN-2 |
| 1884 | TSPAN31 |
| 1885 | TSPAN4 |
| 1886 | TSPAN7 |
| 1887 | TSPAN8 |
| 1888 | TSPAN9 |
| 1889 | TSPO |
| 1890 | TTYH1 |
| 1891 | TTYH2 |
| 1892 | TUBB3 |
| 1893 | TUBB4 |
| 1894 | TULP3 |
| 1895 | TWF2 |
| 1896 | TYRO3 |
| 1897 | TYROBP |
| 1898 | TYRP1 |
| 1899 | UBE2B |
| 1900 | UBE2J1 |
| 1901 | UBL3 |
| 1902 | UFO |
| 1903 | ULBP2 |
| 1904 | UMOD |
| 1905 | UNC5A |
| 1906 | UNC5B |
| 1907 | UNC5C |
| 1908 | UNC5CL |
| 1909 | USE1 |
| 1910 | USH1C |
| 1911 | VAMP1 |
| 1912 | VAMP2 |
| 1913 | VAMP3 |
| 1914 | VAMP5 |
| 1915 | VAPA |
| 1916 | VAPB |
| 1917 | VASP |
| 1918 | VCAM1 |
| 1919 | VCL |
| 1920 | VDAC1 |
| 1921 | VDAC2 |
| 1922 | VDAC3 |
| 1923 | VEPH1 |
| 1924 | VIP |
| 1925 | VIPR1 |
| 1926 | VIPR2 |
| 1927 | VN1R1 |
| 1928 | VPRE3 |
| 1929 | VPREB1 |
| 1930 | VSIG1 |
| 1931 | VSIG2 |
| 1932 | VSIG4 |
| 1933 | VSIG8 |
| 1934 | VSTM1 |
| 1935 | WDR5 |
| 1936 | WFIKKN2 |
| 1937 | WIBG |
| 1938 | WNT2 |
| 1939 | WRB |
| 1940 | XK |
| 1941 | XLKD1 |
| 1942 | XPR1 |
| 1943 | YIPF3 |
| 1944 | YKT6 |
| 1945 | ZAP70 |
| 1946 | ZDHHC7 |
| 1947 | ZMYND19 |
| 1948 | ZNF662 |
| 1949 | ZP2 |
| 1950 | ZYX |

I claim:

1. A pharmaceutical composition comprising:
  (a) an antibody, or fragment thereof, that specifically binds to a human B7-H7CR having an amino acid sequence of SEQ ID NO:5 or SEQ ID NO:20, in an amount effective to increase an immune response; and
  (b) a pharmaceutically acceptable carrier.

2. The pharmaceutical composition of claim 1, wherein said antibody, or fragment thereof, agonizes a function of human B7-H7CR upon specifically binding to human B7-H7CR, wherein said function of said human B7-H7CR is:
  (i) binding to human B7-H7 (SEQ ID NO:3);
  (ii) enhancement of a signal transduction pathway inducing activity of human B7-H7CR;
  (iii) enhancement of T lymphocyte proliferation; or
  (iv) enhancement of immune function.

3. A method for modulating an activity of human B7-H7CR, wherein said method comprises:
  (a) administering the pharmaceutical composition of claim 2 to a subject in need thereof; or
  (b) contacting immune cells of said subject that express or are induced to express said human B7-H7CR with said pharmaceutical composition;
  wherein said pharmaceutical composition is provided in an amount effective to increase an immune response, and said activity of said human B7-H7CR is:
    (i) binding to human B7-H7 (SEQ ID NO:3) and human B7-H7CR;
    (ii) enhancement of a signal transduction pathway inducing activity of human B7-H7CR;
    (iii) enhancement of T lymphocyte proliferation; or
    (iv) enhancement of immune function.

4. The method of claim 3, wherein said method enhances T lymphocyte proliferation.

5. The method of claim 3, wherein said method enhances immune function.

6. The method of claim 3, wherein said method enhances a signal transduction pathway inducing activity of human B7-H7CR.

7. An antibody, or fragment thereof, that specifically binds to a human B7-H7CR, said human B7-H7CR having an amino acid sequence of SEQ ID NO:5 or SEQ ID NO:20.

* * * * *

SEQUENCE LISTING

```
<160> NUMBER OF SEQ ID NOS: 26

<210> SEQ ID NO 1
<211> LENGTH: 302
<212> TYPE: PRT
<213> ORGANISM: Homo sapiens
<220> FEATURE:
<223> OTHER INFORMATION: immature/precursor form of native human B7-H2
      isoform 1

<400> SEQUENCE: 1

Met Arg Leu Gly Ser Pro Gly Leu Leu Phe Leu Leu Phe Ser Ser Leu
 1               5                  10                  15

Arg Ala Asp Thr Gln Glu Lys Glu Val Arg Ala Met Val Gly Ser Asp
             20                  25                  30

Val Glu Leu Ser Cys Ala Cys Pro Glu Gly Ser Arg Phe Asp Leu Asn
         35                  40                  45
```

```
Asp Val Tyr Val Tyr Trp Gln Thr Ser Glu Ser Lys Thr Val Thr
 50                  55                  60

Tyr His Ile Pro Gln Asn Ser Ser Leu Glu Asn Val Asp Ser Arg Tyr
 65                  70                  75                  80

Arg Asn Arg Ala Leu Met Ser Pro Ala Gly Met Leu Arg Gly Asp Phe
                 85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
            115                 120                 125

Glu Val Thr Leu His Val Ala Ala Asn Phe Ser Val Pro Val Val Ser
130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
            195                 200                 205

Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
            275                 280                 285

Ala Trp Ala Val Ser Pro Glu Thr Glu Leu Thr Gly His Val
290                 295                 300

<210> SEQ ID NO 2
<211> LENGTH: 1572
<212> TYPE: DNA
<213> ORGANISM: Homo sapiens
<220> FEATURE:
<223> OTHER INFORMATION: immature/precursor form of native human B7-H2

<400> SEQUENCE: 2
gagtagagcc gatctcccgc gccccgaggt tgctcctctc cgaggtctcc cgcggcccaa    60
gttctccgcg ccccgaggtc tccgcgcccc gaggtctccg cggcccgagg tctccgcccg   120
caccatgcgg ctgggcagtc ctggactgct cttcctgctc ttcagcagcc ttcgagctga   180
tactcaggag aaggaagtca gagcgatggt aggcagcgac gtggagctca gctgcgcttg   240
ccctgaagga agccgttttg atttaaatga tgtttacgta tattggcaaa ccagtgagtc   300
gaaaaccgtg gtgacctacc acatcccaca gaacagctcc ttggaaaacg tggacagccg   360
ctaccggaac cgagccctga tgtcaccggc cggcatgctg cggggcgact ctccctgcg    420 cttgttcaac gtcaccccc aggacgagca aagtttcac tgcctggtgt tgagccaatc   480
cctgggattc caggaggttt tgagcgttga ggttacactg catgtggcag caaacttcag   540
cgtgcccgtc gtcagcgccc ccacagccc tcccaggat gagctcacct tcacgtgtac   600
atccataaac ggctaccccca ggcccaacgt gtactggatc aataagacgg acaacagcct   660
```

-continued

```
gctggaccag gctctgcaga atgacaccgt cttcttgaac atgcgggct tgtatgacgt      720 ggtcagcgtg ctgaggatcg cacgdccccc cagcgtgaac attggctgct gcatagagaa      780
cgtgcttctg cagcagaacc tgactgtcgg cagccagaca ggaaatgaca tcggagagag      840
agacaagatc acagagaatc cagtcagtac cggcgagaaa aacgcggcca cgtggagcat      900
cctggctgtc ctgtgcctgc ttgtggtcgt ggcggtggcc ataggctggg tgtgcaggga      960
ccgatgcctc caacacagct atgcaggtgc ctgggctgtg agtccggaga cagagctcac     1020
tggccacgtt tgaccggagc tcaccgccca gagcgtggac agggcttcca tgagacgcca     1080
ccgtgagagg ccaggtggca gcttgagcat ggactccag actgcagggg agcacttggg     1140
gcagccccca gaaggaccac tgctggatcc cagggagaac ctgctggcgt ggctgtgat     1200 cctggaatga ggcccttca aaagcgtcat ccacaccaaa ggcaaatgtc cccaagtgag     1260
tgggctcccc gctgtcactg ccagtcaccc acaggaaggg actggtgatg ggctgtctct     1320
acccggagcg tgcgggattc agcaccaggc tcttcccagt accccagacc cactgtgggt     1380
cttcccgtgg gatgcgggat cctgagaccg aagggtgttt ggtttaaaaa gaagactggg     1440
cgtccgctct tccaggacgg cctctgtgct gctggggtca cgcgaggctg tttgcagggg     1500
acacggtcac aggagctctt ctgccctgaa cgcttccaac ctgctccggc cggaagccac     1560
aggacccact ca                                                          1572
```

<210> SEQ ID NO 3
<211> LENGTH: 414
<212> TYPE: PRT
<213> ORGANISM: Homo sapiens
<220> FEATURE:
<223> OTHER INFORMATION: immature/precursor form of native human B7-H7

<400> SEQUENCE: 3

```
Met Lys Ala Gln Thr Ala Leu Ser Phe Phe Leu Ile Leu Ile Thr Ser
 1               5                  10                  15

Leu Ser Gly Ser Gln Gly Ile Phe Pro Leu Ala Phe Phe Ile Tyr Val
            20                  25                  30

Pro Met Asn Glu Gln Ile Val Ile Gly Arg Leu Asp Glu Asp Ile Ile
        35                  40                  45

Leu Pro Ser Ser Phe Glu Arg Gly Ser Glu Val Val Ile His Trp Lys
    50                  55                  60

Tyr Gln Asp Ser Tyr Lys Val His Ser Tyr Tyr Lys Gly Ser Asp His
65                  70                  75                  80

Leu Glu Ser Gln Asp Pro Arg Tyr Ala Asn Arg Thr Ser Leu Phe Tyr
                85                  90                  95

Asn Glu Ile Gln Asn Gly Asn Ala Ser Leu Phe Phe Arg Arg Val Ser
            100                 105                 110

Leu Leu Asp Glu Gly Ile Tyr Thr Cys Tyr Val Gly Thr Ala Ile Gln
        115                 120                 125

Val Ile Thr Asn Lys Val Val Leu Lys Val Gly Val Phe Leu Thr Pro
    130                 135                 140

Val Met Lys Tyr Glu Lys Arg Asn Thr Asn Ser Phe Leu Ile Cys Ser
145                 150                 155                 160

Val Leu Ser Val Tyr Pro Arg Pro Ile Ile Thr Trp Lys Met Asp Asn
                165                 170                 175

Thr Pro Ile Ser Glu Asn Asn Met Glu Glu Thr Gly Ser Leu Asp Ser
            180                 185                 190
```

```
Phe Ser Ile Asn Ser Pro Leu Asn Ile Thr Gly Ser Asn Ser Ser Tyr
            195                 200                 205

Glu Cys Thr Ile Glu Asn Ser Leu Leu Lys Gln Thr Trp Thr Gly Arg
    210                 215                 220

Trp Thr Met Lys Asp Gly Leu His Lys Met Gln Ser Glu His Val Ser
225                 230                 235                 240

Leu Ser Cys Gln Pro Val Asn Asp Tyr Phe Ser Pro Asn Gln Asp Phe
                245                 250                 255

Lys Val Thr Trp Ser Arg Met Lys Ser Gly Thr Phe Ser Val Leu Ala
            260                 265                 270

Tyr Tyr Leu Ser Ser Ser Gln Asn Thr Ile Ile Asn Glu Ser Arg Phe
        275                 280                 285

Ser Trp Asn Lys Glu Leu Ile Asn Gln Ser Asp Phe Ser Met Asn Leu
    290                 295                 300

Met Asp Leu Asn Leu Ser Asp Ser Gly Glu Tyr Leu Cys Asn Ile Ser
305                 310                 315                 320

Ser Asp Glu Tyr Thr Leu Leu Thr Ile His Thr Val His Val Glu Pro
                325                 330                 335

Ser Gln Glu Thr Ala Ser His Asn Lys Gly Leu Trp Ile Leu Val Pro
            340                 345                 350

Ser Ala Ile Leu Ala Ala Phe Leu Leu Ile Trp Ser Val Lys Cys Cys
        355                 360                 365

Arg Ala Gln Leu Glu Ala Arg Arg Ser Arg His Pro Ala Asp Gly Ala
    370                 375                 380

Gln Gln Glu Arg Cys Cys Val Pro Pro Gly Arg Cys Pro Ser Ala
385                 390                 395                 400

Pro Asp Asn Gly Glu Glu Asn Val Pro Leu Ser Gly Lys Val
                405                 410

<210> SEQ ID NO 4
<211> LENGTH: 2689
<212> TYPE: DNA
<213> ORGANISM: Homo sapiens
<220> FEATURE:
<223> OTHER INFORMATION: immature/precursor form of native human B7-H7

<400> SEQUENCE: 4
agttctcttc aagtcatgta atcgactttt ttgaattagt tttcagtttc attttgtttt      60
ccctaattca agttgggaac acttcatttt ccccaattca agttgggaac acttccttgg     120
tatttccttg ctacatggac tttagcaaat gctactttac tctccttcca gctactcagg     180
aggctgaggc aggagaatcg cttgaacccg ggaggcggag gttacagtga gccttttcct     240
agttttactg ttggaagcct aactcacagg agagattatg caatacagtc ctgaagtcaa     300
ggaaggagag catgtaggag aatactaacc tgcacagat tgtgatggtg atgtggaata     360
tactaaagcc tagaacgcac ctcctctgca tgactaatat gttctgcaca agacatgaag     420
gcacagacag cactgtcttt cttcctcatt ctcataacat ctctgagtgg atctcaaggc     480
atattccctt tggctttctt catttatgtt cctatgaatg aacaaatcgt cattggaaga     540
cttgatgaag atataattct cccttcttca tttgagaggg gatccgaagt cgtaatacac     600
tggaagtatc aagatagcta aaggttcat agttactaca aaggcagtga ccatttggaa     660
agccaagatc ccagatatgc aaacaggaca tcccttttct ataatgagat tcaaaatggg     720
aatgcgtcac tattttttcag aagagtaagc cttctggacg aaggaattta cacctgctat     780
gtaggaacag caattcaagt gattacaaac aaagtggtgc taaaggtggg agttttctc     840
```

```
acacccgtga tgaagtatga aaagaggaac acaaacagct tcttaatatg cagcgtgtta    900
agtgtttatc ctcgtccaat tatcacgtgg aaaatggaca cacacctat ctctgaaaac    960
aacatggaag aaacagggtc tttggattct ttttctatta acagcccact gaatattaca   1020
ggatcaaatt catcttatga atgtacaatt gaaaattcac tgctgaagca acatggaca   1080
gggcgctgga cgatgaaaga tggccttcat aaaatgcaaa gtgaacacgt tcactctca   1140
tgtcaacctg taaatgatta ttttttcacca aaccaagact tcaaagttac ttggtccaga  1200
atgaaaagtg ggactttctc tgtcctggct tactatctga ctcctcaca aaatacaatt   1260
atcaatgaat cccgattctc atggaacaaa gagctgataa accagagtga cttctctatg  1320
aatttgatgg atcttaatct ttcagacagt ggggaatatt tatgcaatat ttcttcggat  1380
gaatatactt tacttaccat ccacacagtg catgtagaac cgagccaaga aacagcttcc  1440
cataacaaag cttatggat tttggtgccc tctgcgattt tggcagcttt tctgctgatt   1500
tggagcgtaa atgttgcag agcccagcta aagccagga ggagcagaca ccctgctgat   1560
ggagcccaac aagaaagatg ttgtgtccct cctggtgagc gctgtcccag tgcacccgat   1620
aatggcgaag aaaatgtgcc tctttcagga aagtatagg aaatgagaga agactgtgac   1680
aactcatgac ctgcatcctt aatatccagt gacttcatct cccctttctt caccacaatt   1740
ccaggcaatg gcctgtcgga ccagacaatt ctaccactgc aaagagttgt aaccattttc  1800
tggtatcaca tttatttttc aagacatact tttcaagaca tcattcactg acccactacc  1860
tgcattgagt ataaatgcct ggatgttaag gattccaatt taactttgaa aagaactgtc  1920
tcattcattt acatttctgt tacagtcagc ccaggaggtt acagtgagct ctccactaag  1980
aatctggaag aaatgcatca ctaggggttg attcccaatc tgatcaactg ataatgggtg  2040
agagagcagg taagagccaa agtcacctta gtggaaaggt taaaaaccag agcctggaaa  2100
ccaagatgat tgatttgaca aggtatttta gtctagtttt atatgaacgg ttgtatcagg  2160
gtaaccaact cgatttggga tgaatcttag ggcaccaaag actaagacag tatctttaag  2220
attgctaggg aaaagggccc tatgtgtcag gcctctgagc ccaagccaag catcgcatcc  2280
cctgtgattt gcacgtatac atccagatgg cctaaagtaa ctgaagatcc acaaaagaag  2340
taaaaatagc cttaactgat gacattccac cattgtgatt tgttcctgcc ccaccctaac  2400
tgatcaagt actttgtaat ctcccccacc cttaagaagg tactttgtaa tcttccccac  2460
ccttaagaag gttctttgta attctcccca cccttgagaa tgtactttgt gagatccacc  2520
ctgcccacaa aacattgctc ttaacttcac cgcctaaccc aaaacctata agaactaatg  2580
ataatccatc acccttcgct gactctcttt tcggactcag cccacctgca cccaggtgaa  2640
ataaacagct ttattgctca aaaaaaaaaa aaaaaaaaa aaaaaaaa                 2689
```

<210> SEQ ID NO 5
<211> LENGTH: 282
<212> TYPE: PRT
<213> ORGANISM: Homo sapiens
<220> FEATURE:
<223> OTHER INFORMATION: immature/precursor form of native human B7-H7CR

<400> SEQUENCE: 5

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

```
Gln Val Arg Gln Gly Ser Gln Ala Thr Leu Val Cys Gln Val Asp Gln
             35                  40                  45

Ala Thr Ala Trp Glu Arg Leu Arg Val Lys Trp Thr Lys Asp Gly Ala
 50                  55                  60

Ile Leu Cys Gln Pro Tyr Ile Thr Asn Gly Ser Leu Ser Leu Gly Val
 65                  70                  75                  80

Cys Gly Pro Gln Gly Arg Leu Ser Trp Gln Ala Pro Ser His Leu Thr
                 85                  90                  95

Leu Gln Leu Asp Pro Val Ser Leu Asn His Ser Gly Ala Tyr Val Cys
                100                 105                 110

Trp Ala Ala Val Glu Ile Pro Glu Leu Glu Glu Ala Glu Gly Asn Ile
            115                 120                 125

Thr Arg Leu Phe Val Asp Pro Asp Pro Thr Gln Asn Arg Asn Arg
            130                 135                 140

Ile Ala Ser Phe Pro Gly Phe Leu Phe Val Leu Leu Gly Val Gly Ser
145                 150                 155                 160

Met Gly Val Ala Ala Ile Val Trp Gly Ala Trp Phe Trp Gly Arg Arg
                165                 170                 175

Ser Cys Gln Gln Arg Asp Ser Gly Asn Ser Pro Gly Asn Ala Phe Tyr
                180                 185                 190

Ser Asn Val Leu Tyr Arg Pro Arg Gly Ala Pro Lys Lys Ser Glu Asp
            195                 200                 205

Cys Ser Gly Glu Gly Lys Asp Gln Arg Gly Gln Ser Ile Tyr Ser Thr
            210                 215                 220

Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
                260                 265                 270

Pro Lys Gly Phe Pro Lys Val Gly Glu Glu
            275                 280

<210> SEQ ID NO 6
<211> LENGTH: 1276
<212> TYPE: DNA
<213> ORGANISM: Homo sapiens
<220> FEATURE:
<223> OTHER INFORMATION: immature/precursor form of native human B7-H7CR

<400> SEQUENCE: 6
ggaagtctgt caactgggag ggggagaggg gggtgatggg ccaggaatgg ggtccccggg    60
catggtgctg ggcctcctgg tgcagatctg ggccctgcaa gaagcctcaa gcctgagcgt   120
gcagcagggg cccaacttgc tgcaggtgag gcagggcagt caggcgaccc tggtctgcca   180
ggtggaccag gccacagcct gggaacggct ccgtgttaag tggacaaagg atggggccat   240
cctgtgtcaa ccgtacatca ccaacggcag cctcagcctg ggggtctgcg ggccccaggg   300
acggctctcc tggcaggcac ccagccatct caccctgcag ctggaccctg tgagcctcaa   360
ccacagcggg gcgtacgtgt gctgggcggc cgtagagatt cctgagttgg aggaggctga   420
gggcaacata caaggctctt tgtggaccc agatgacccc acacagaaca gaaaccggat   480
cgcaagcttc ccaggattcc tcttcgtgct gctgggggtg ggaagcatgg gtgtggctgc   540
gatcgtgtgg ggtgcctggt tctggggccg ccgcagctgc cagcaaaggg actcaggtaa   600
cagcccagga aatgcattct acagcaacgt cctataccgg ccccgggggc ccccaaagaa   660
```

```
gagtgaggac tgctctggag aggggaagga ccagaggggc cagagcattt attcaacctc    720
cttcccgcaa ccggcccccc gccagccgca cctggcgtca agaccctgcc ccagcccgag    780
accctgcccc agccccaggc ccggccaccc cgtctctatg gtcagggtct ctcctagacc    840 aagcccacc cagcagccga ggccaaaagg gttccccaaa gtgggagagg agtgagagat     900
cccaggagac ctcaacagga ccccacccat aggtacacac aaaaaagggg ggatcgaggc    960
cagacacggt ggctcacgcc tgtaatccca gcagtttggg aagccgaggc gggtggaaca   1020
cttgaggtca ggggtttgag accagcctgg cttgaacctg ggaggcggag gttgcagtga   1080
gccgagattg cgccactgca ctccagcctg ggcgacagag tgagactccg tctcaaaaaa   1140
aacaaaaagc aggaggattg ggagcctgtc agccccatcc tgagaccccg tcctcatttc   1200
tgtaatgatg gatctcgctc ccactttccc ccaagaacct aataaaggct tgtgaagaaa   1260
aaaaaaaaaa aaaaaa                                                   1276

<210> SEQ ID NO 7
<211> LENGTH: 220
<212> TYPE: PRT
<213> ORGANISM: Homo sapiens
<220> FEATURE:
<223> OTHER INFORMATION: immature/precursor form of native human CD28

<400> SEQUENCE: 7

Met Leu Arg Leu Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 8
<211> LENGTH: 753
<212> TYPE: DNA
```

```
<213> ORGANISM: Homo sapiens
<220> FEATURE:
<223> OTHER INFORMATION: immature/precursor form of native human CD28

<400> SEQUENCE: 8
ggaggagggg ctggaaccct agccatcgt caggacaaag atgctcaggc tgctcttggc      60
tctcaactta ttcccttcaa ttcaagtaac aggaaacaag attttggtga agcagtcgcc    120
catgcttgta gcgtacgaca atgcggtcaa ccttagctgc aagtattcct acaatctctt    180
ctcaagggag ttccgggcat cccttcacaa aggactggat agtgctgtgg aagtctgtgt    240
tgtatatggg aattactccc agcagcttca ggtttactca aaaacggggt tcaactgtga    300
tgggaaattg ggcaatgaat cagtgacatt ctacctccag aatttgtatg ttaaccaaac    360
agatatttac ttctgcaaaa ttgaagttat gtatcctcct ccttacctag acaatgagaa    420
gagcaatgga accattatcc atgtgaaagg gaaacacctt tgtccaagtc cctatttcc    480 cggaccttct aagccctttt gggtgctggt ggtggttggt ggagtcctgg cttgctatag    540
cttgctagta acagtggcct ttattatttt ctgggtgagc agtaagagga gcaggctcct    600
gcacagtgac tacatgaaca tgactccccg ccgccccggg cccacccgca gcattacca    660 gcctatgcc ccaccacgcg acttcgcagc ctatcgctcc tgacacggac gcctatccag    720
aagccagccg gctggcagcc cccatctgct caa                                 753

<210> SEQ ID NO 9
<211> LENGTH: 223
<212> TYPE: PRT
<213> ORGANISM: Homo sapiens
<220> FEATURE:
<223> OTHER INFORMATION: immature/precursor form of native human CTLA-4

<400> SEQUENCE: 9
```

Met Ala Cys Leu Gly Phe Gln Arg His Lys Ala Gln Leu Asn Leu Ala
 1               5                  10                  15

Thr Arg Thr Trp Pro Cys Thr Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu

```
              195                 200                 205
Pro Glu Cys Glu Lys Gln Phe Gln Pro Tyr Phe Ile Pro Ile Asn
    210                 215                 220
```

<210> SEQ ID NO 10
<211> LENGTH: 2025
<212> TYPE: DNA
<213> ORGANISM: Homo sapiens
<220> FEATURE:
<223> OTHER INFORMATION: immature/precursor form of native human CTLA-4

<400> SEQUENCE: 10

```
cttctgtgtg tgcacatgtg taatacatat ctgggatcaa agctatctat ataaagtcct      60
tgattctgtg tgggttcaaa cacatttcaa agcttcagga tcctgaaagg ttttgctcta     120
cttcctgaag acctgaacac cgctcccata aagccatggc ttgccttgga tttcagcggc     180
acaaggctca gctgaacctg gctaccagga cctggccctg cactctcctg ttttttcttc     240
tcttcatccc tgtcttctgc aaagcaatgc acgtggccca gcctgctgtg gtactggcca     300
gcagccgagg catcgccagc tttgtgtgtg agtatgcatc tccaggcaaa gccactgagg     360
tccgggtgac agtgcttcgg caggctgaca gccaggtgac tgaagtctgt gcggcaacct     420
acatgatggg gaatgagttg accttcctag atgattccat ctgcacgggc acctccagtg     480
gaaatcaagt gaacctcact atccaaggac tgagggccat ggacacggga ctctacatct     540
gcaaggtgga gctcatgtac ccaccgccat actacctggg cataggcaac ggaacccaga     600
tttatgtaat tgatccagaa ccgtgcccag attctgactt cctcctctgg atccttgcag     660
cagttagttc ggggttgttt ttttatagct ttctcctcac agctgtttct tgagcaaaa      720
tgctaaagaa aagaagccct cttacaacag gggtctatgt gaaaatgccc caacagagc      780
cagaatgtga aaagcaattt cagccttatt ttattcccat caattgagaa accattatga     840
agaagagagt ccatatttca atttccaaga gctgaggcaa ttctaacttt tttgctatcc     900
agctattttt atttgtttgt gcatttgggg ggaattcatc tctctttaat ataaagttgg     960
atgcggaacc caaattacgt gtactacaat ttaaagcaaa ggagtagaaa gacagagctg    1020
ggatgttttct gtcacatcag ctccactttc agtgaaagca tcacttggga ttaatatggg    1080
gatgcagcat tatgatgtgg gtcaaggaat taagttaggg aatggcacag cccaaagaag    1140
gaaaaggcag ggagcgaggg agaagactat attgtacaca ccttatattt acgtatgaga    1200
cgtttatagc cgaaatgatc ttttcaagtt aaatttttatg ccttttatttt cttaaacaaa    1260
tgtatgatta catcaaggct tcaaaaatac tcacatggct atgttttagc cagtgatgct    1320
aaaggttgta ttgcatatat acatatatat atatatatat atatatatat atatatatat    1380
atatatatat tttaatttga tagtattgtg catagagcca cgtatgtttt tgtgtatttg    1440
ttaatggttt gaatataaac actatatggc agtgtctttc caccttgggt cccagggaag    1500
ttttgtggag gagctcagga cactaataca ccaggtagaa cacaaggtca tttgctaact    1560
agcttggaaa ctggatgagg tcatagcagt gcttgattgc gtggaattgt gctgagttgg    1620
tgttgacatg tgctttgggg cttttacacc agttcctttc aatggtttgc aaggaagcca    1680
cagctggtgg tatctgagtt gacttgacag aacactgtct tgaagacaat ggcttactcc    1740
aggagaccca caggtatgac cttctaggaa gctccagttc gatgggccca attcttacaa    1800
acatgtggtt aatgccatgg acagaagaag gcagcaggtg gcagaatggg gtgcatgaag    1860
gtttctgaaa attaacactg cttgtgtttt taactcaata ttttccatga aaatgcaaca    1920
```

```
acatgtataa tatttttaat taaataaaaa tctgtggtgg tcgttttaaa aaaaaaaaaa    1980
aaaaaaaaaa aaaaaaaaaa aaaaaaaaaa aaaaaaaaaa aaaaa                    2025
```

<210> SEQ ID NO 11
<211> LENGTH: 199
<212> TYPE: PRT
<213> ORGANISM: Homo sapiens
<220> FEATURE:
<223> OTHER INFORMATION: first isoform the immature/precursor of native
      human ICOS

<400> SEQUENCE: 11

```
Met Lys Ser Gly Leu Trp Tyr Phe Phe Leu Phe Cys Leu Arg Ile Lys
 1               5                  10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195
```

<210> SEQ ID NO 12
<211> LENGTH: 621
<212> TYPE: DNA
<213> ORGANISM: Homo sapiens
<220> FEATURE:
<223> OTHER INFORMATION: immature/precursor form of native human ICOS

<400> SEQUENCE: 12

```
ggcccaagct tgccatgaag tcaggacttt ggtatttctt tctcttctgc ttgcgcatta     60
aagttttaac aggagaaatc aatggttctg ccaattatga gatgtttata tttcacaacg    120
gaggtgtaca aattttatgc aaatatcctg acattgtcca gcaatttaaa atgcagttgc    180
tgaaaggggg gcaaatactc tgcgatctca ctaagacaaa aggaagtgga aacacagtgt    240
ccattaagag tctgaaattc tgccattctc agttatccaa caacagtgtc tcctttttc     300 tatacaactt ggaccattct catgccaact attacttctg taacctatca attttttgatc   360 ctcctccttt taagtaaact cttacaggag gatatttgca tatttatgaa tcacaacttt    420
gttgccagct gaagttctgg ttacccatag gatgtgcagc ctttgttgta gtctgcattt    480
```

| | |
|---|---|
| tgggatgcat acttatttgt tggcttacaa aaaagaagta ttcatccagt gtgcacgacc | 540 |
| ctaacggtga atacatgttc atgagagctg tgaataccgc taagaaatct cgcctgacag | 600 |
| acgtcacact ctgattctag a | 621 |

<210> SEQ ID NO 13
<211> LENGTH: 1245
<212> TYPE: DNA
<213> ORGANISM: Homo sapiens
<220> FEATURE:
<223> OTHER INFORMATION: human B7-H7

<400> SEQUENCE: 13

| | |
|---|---|
| atgaaggcac agacagcact gtctttcttc ctcattctca taacatctct gagtggatct | 60 |
| caaggcatat tccctttggc tttcttcatt tatgttccta tgaatgaaca atcgtcatt | 120 |
| ggaagacttg atgaagatat aattctccct tcttcatttg agaggggatc cgaagtcgta | 180 |
| atacactgga agtatcaaga tagctataag gttcacagtt actacaaagg cagtgaccat | 240 |
| ttggaaagcc aagatcccag atatgcaaac aggacatccc ttttctataa tgagattcaa | 300 |
| aatgggaatg cgtcgctatt tttcagaaga gtaagccttc tggacgaagg aatttacacc | 360 |
| tgctatgtag aacagcaat tcaagtgatt acaaacaaag tggtgctaaa ggtgggagtt | 420 |
| tttctcacac ccgtgatgaa gtatgaaaag gaacacaa acagcttctt aatatgcagc | 480 |
| gtgttaagtg tttatcctcg tccaattatc acgtggaaaa tggacaacac acctatctct | 540 |
| gaaaacaaca tggaagaaac agggtctttg gattctttt ctattaacag cccactgaat | 600 |
| attacaggat caaattcatc ttatgaatgt acaattgaaa attcactgct gaagcaaaca | 660 |
| tggacagggc gctggacgat gaaagatggc cttcataaaa tgcaaagtga acacgtttca | 720 |
| ctctcatgtc aacctgtaaa tgattatttt tcaccaaacc aagacttcaa agttacttgg | 780 |
| tccagaatga aaagtgggac tttctctgtc ctggcttact atctgagctc ctcacaaaat | 840 |
| acaattatca tgaatcccg attctcatgg aacaaagagc tgataaacca gagtgacttc | 900 |
| tctatgaatt tgatggatct taatctttca gacagtgggg aatattatg caatatttct | 960 |
| tcggatgaat atactttact taccatccac acagtgcatg tagaaccgag ccaagaaaca | 1020 |
| gcttcccata caaaggctt atggattttg gtgccctctg cgattttggc agcttttctg | 1080 |
| ctgatttgga gcgtaaaatg ttgcagagcc agctagaag ccaggaggag cagacaccct | 1140 |
| gctgatggag cccaacaaga aagatgttgt gtccctcctg gtgagcgctg tcccagtgca | 1200 |
| cccgataatg gcgaagaaaa tgtgaggtct gtttctggga aagtg | 1245 |

<210> SEQ ID NO 14
<211> LENGTH: 1242
<212> TYPE: DNA
<213> ORGANISM: Pan troglodytes (Common Chimpanzee)
<220> FEATURE:
<223> OTHER INFORMATION: PANTRA B7H7

<400> SEQUENCE: 14

| | |
|---|---|
| atgaaggcac agacagcact gtctttcttc ctcattctca taacatctct gagtggatct | 60 |
| caagccatat tccctatggc tttctccact tatgttcctg tgaatgaaca atcgtcatt | 120 |
| ggaagacttg atgaagatat aattctccct tcttcatttg agaggggatc ggaagtcgta | 180 |
| atacactgga agtatcaaga tagctataag gttcacagtt actacaaagg cagtgaccat | 240 |
| ttggaaagcc aagatcccag atatacaaac aggacatccc ttttctataa tgagattcaa | 300 |

```
gggaatgcgt cgctatttc cccaagagta agccttctgg acgaaggaat ttacacctgc    360
tatgtaggaa cagcaattca agtgattaca aacaaagtgg tgctaaaggt gggagttttt    420
ctcacacccg tgatgaagta tgaaaagagg aacacaaaca gcttcttaat atgcagcgtg    480
ttaagtgttt atcctcgtcc aattatcacg tggaaaatgg acaacacacc tatctctgaa    540
aacaacatgg aagaaacagg gtctttggat tcttttttcta ttaacagccc actgaatatt    600
acaggatcaa attcatctta tgaatgtaca attgaaaatt cactgctgaa gcaaacatgg    660
acagggcgct ggacaatgaa agatggcctt cataaaatgc aaagtgaaca cgtttcactc    720
tcatgtcaac ctgtaaatga ttattttca ccaaaccaag acttcaaagt tacttggtcc    780
agaatgaaaa gtgggacttt ctctatcctg gcttactatc tgagctcctc acaaaataca    840
attatcaatg aatcccgatt ctcatggaac aaagagctga taaaccagag tgacttctct    900
atgaatttga tggatcttaa tcttttcagac agtggggaat atttatgcaa tatttcttca    960
gatgaatata ctttacttac catccacaca gtgcatgtag aaccaagcca agaaacagct   1020
tcccataaca aaggcttatg gattttggtg ccctctgtga ttttggcagc tttctgctg    1080 atttggacag taaaacgttg cagagcccag ccagaagcca ggaggagcag acaccctgct   1140
gatggagccc aacaagaaag atattgtgtc cctcctggtg agcactgtcc cagtgcaccc   1200
gataatggcg aagaaaatgt gaggtctgtt tctgggaaag tg                      1242
```

<210> SEQ ID NO 15
<211> LENGTH: 1164
<212> TYPE: DNA
<213> ORGANISM: Macaca mulatta (Rhesus Monkey)
<220> FEATURE:
<223> OTHER INFORMATION: MACMU B7-H7

<400> SEQUENCE: 15

```
atgaaggcac agacgtcttt cttcctcatt ctcatatcat ctctgagtgg atctcaaggc     60
atattccttt cagcttttctt cacttacgtt cctatgaatg aacaaatcat cattggaaga    120
cttggtgaag atataattct cccttcttca tttgagaggg gatccgaagt tgtaatacac    180
tggaagtatc aagacagcta caatagctac aatgttcaca gttactacaa aggcagtggc    240
cgtttggaaa gccaagatac cagatatgca aacaggacat cccttttcta taatgagatt    300
caaaatggga atgcgtctct attttttcaga agattaagcc ttctggatga aggaattat     360 acctgctatg taggaacagc aattcaagcg attacaaaca aagtggtgct aaaggtggga    420 gttttctca cacccatgat gaagtatgaa aagaggaaca caaacagctt cttaatatgc    480
aacgtgttaa gtgtttatcc tcgtccaatt atcacgtgga aaatggacaa cacacctatc    540
tctgaaaaca atatgcaaga aacagggtct ttgggtcctt ttttcgattaa cagcacgctg   600 aatattacag gatcaaattc atcttatgaa tgtacaattg aaaattcact tctgaagcaa   660
acatggacag gcgcgtggac aatgaaagat ggccttcata aaatgcaaag tgaacatgtt    720
tcactctcat gtgaacttgt aaatgatgat ttttcaccaa accaagactt caaagttact   780
tggtccagaa tggaaagtgg gatttcctct atcctggctt actatctgag ctcctcacaa    840
aatacaactt tctatgaatc ccgattctca tggaacaaag agctgaaaaa ccagagtgac    900
ttctctatga atttgacgga tcttagtctt tcagacagtg gggaaatattt gtgcaatatt    960 tcttcggatg aatatacttt actccaccata cacgggtgc acgtagaacc aagccaagaa   1020
acagcttccg ataacaaagg cttatggatt ttggtggcca gtctgatttt ggtgctctgt   1080
ctgatttggc tgatttggaa agtaaaatgt tccacagccc aaatagaagc caggaggagc   1140
```
agataccctg ctgatggagc ccaa                                              1164

<210> SEQ ID NO 16
<211> LENGTH: 702
<212> TYPE: DNA
<213> ORGANISM: Bovine
<220> FEATURE:
<223> OTHER INFORMATION: bovine B7-H7

<400> SEQUENCE: 16

```
atgaatgagc aaatcgtcac tggaagacta ggtgaagatg tcattctccc ttgctcattt    60
gagagtggac ccaatgtcgt aattcactgg aagaaccaag ataccaatgt ttactcatac   120
tacagagaca gcgaccagtt ggaaaagcaa gatcccagat atgtaaacag gatatccctc   180
ttccatggtg agattcacaa tgggaatgcc tccctgtctt cagaagatt aacccttcag   240
gatgaaggaa tctacgtatg ctatgtggga acatcacttg gaaaaatcac aaagaaaata   300
gtcctaaaag tgggagcttt tgtcacacct gtgatgaagt atgaaaagaa taccaccaac   360
agcttcttaa tatgcaatgt gttaagtgtt tttccttatc caattatcac atggaaagtg   420
gataataata catctatctc tgaaaacaat gggaagaag ttggatcttt gggtcctttt   480
catataaaca gcagagtaaa tattacagga tcaaattcat catatcagtg tgaaattgaa   540
aacccactgc tgaagcaaac atggacagga agatggacaa ggaagataa agaaaggaat   600
acaaaaagga aggaaatgca tttgcagagt tcactagaag taaagcaaat tttttctgta   660
aatctccata cagtggactt acaatattat ttcagtataa aa                      702
```

<210> SEQ ID NO 17
<211> LENGTH: 414
<212> TYPE: PRT
<213> ORGANISM: Pan troglodytes (Common Chimpanzee)
<220> FEATURE:
<223> OTHER INFORMATION: PANTRA B7-H7

<400> SEQUENCE: 17

```
Met Lys Ala Gln Thr Ala Leu Ser Phe Phe Leu Ile Leu Ile Thr Ser
  1               5                  10                  15

Leu Ser Gly Ser Gln Ala Ile Phe Pro Met Ala Phe Ser Thr Tyr Val
             20                  25                  30

Pro Val Asn Glu Gln Ile Val Ile Gly Arg Leu Asp Glu Asp Ile Ile
         35                  40                  45

Leu Pro Ser Ser Phe Glu Arg Gly Ser Glu Val Val Ile His Trp Lys
     50                  55                  60

Tyr Gln Asp Ser Tyr Lys Val His Ser Tyr Tyr Lys Gly Ser Asp His
 65                  70                  75                  80

Leu Glu Ser Gln Asp Pro Arg Tyr Thr Asn Arg Thr Ser Leu Phe Tyr
                 85                  90                  95

Asn Glu Ile Gln Gly Asn Ala Ser Leu Phe Ser Pro Arg Val Ser Leu
            100                 105                 110

Leu Asp Glu Gly Ile Tyr Thr Cys Tyr Val Gly Thr Ala Ile Gln Val
        115                 120                 125

Ile Thr Asn Lys Val Val Leu Lys Val Gly Val Phe Leu Thr Pro Val
    130                 135                 140

Met Lys Tyr Glu Lys Arg Asn Thr Asn Ser Phe Leu Ile Cys Ser Val
145                 150                 155                 160

Leu Ser Val Tyr Pro Arg Pro Ile Ile Thr Trp Lys Met Asp Asn Thr
                165                 170                 175
```

```
Pro Ile Ser Glu Asn Asn Met Glu Glu Thr Gly Ser Leu Asp Ser Phe
            180                 185                 190

Ser Ile Asn Ser Pro Leu Asn Ile Thr Gly Ser Asn Ser Ser Tyr Glu
            195                 200                 205

Cys Thr Ile Glu Asn Ser Leu Leu Lys Gln Thr Trp Thr Gly Arg Trp
210                 215                 220

Thr Met Lys Asp Gly Leu His Lys Met Gln Ser Glu His Val Ser Leu
225                 230                 235                 240

Ser Cys Gln Pro Val Asn Asp Tyr Phe Ser Pro Asn Gln Asp Phe Lys
                245                 250                 255

Val Thr Trp Ser Arg Met Lys Ser Gly Thr Phe Ser Ile Leu Ala Tyr
            260                 265                 270

Tyr Leu Ser Ser Ser Gln Asn Thr Ile Ile Asn Glu Ser Arg Phe Ser
            275                 280                 285

Trp Asn Lys Glu Leu Ile Asn Gln Ser Asp Phe Ser Met Asn Leu Met
            290                 295                 300

Asp Leu Asn Leu Ser Asp Ser Gly Glu Tyr Leu Cys Asn Ile Ser Ser
305                 310                 315                 320

Asp Glu Tyr Thr Leu Leu Thr Ile His Thr Val His Val Glu Pro Ser
                325                 330                 335

Gln Glu Thr Ala Ser His Asn Lys Gly Leu Trp Ile Leu Val Pro Ser
            340                 345                 350

Val Ile Leu Ala Ala Phe Leu Leu Ile Trp Thr Val Lys Arg Cys Arg
            355                 360                 365

Ala Gln Pro Glu Ala Arg Arg Ser Arg His Pro Ala Asp Gly Ala Gln
            370                 375                 380

Gln Glu Arg Tyr Cys Val Pro Pro Gly Glu His Cys Pro Ser Ala Pro
385                 390                 395                 400

Asp Asn Gly Glu Glu Asn Val Arg Ser Val Ser Gly Lys Val
                405                 410

<210> SEQ ID NO 18
<211> LENGTH: 388
<212> TYPE: PRT
<213> ORGANISM: Macaca mulatta (Rhesus Monkey)
<220> FEATURE:
<223> OTHER INFORMATION: MACMU B7-H7

<400> SEQUENCE: 18

Met Lys Ala Gln Thr Ser Phe Phe Leu Ile Leu Ile Ser Ser Leu Ser
1               5                   10                  15

Gly Ser Gln Gly Ile Phe Leu Ser Ala Phe Thr Tyr Val Pro Met
            20                  25                  30

Asn Glu Gln Ile Ile Ile Gly Arg Leu Gly Glu Asp Ile Ile Leu Pro
            35                  40                  45

Ser Ser Phe Glu Arg Gly Ser Glu Val Val Ile His Trp Lys Tyr Gln
        50                  55                  60

Asp Ser Tyr Asn Ser Tyr Asn Val His Ser Tyr Tyr Lys Gly Ser Gly
65                  70                  75                  80

Arg Leu Glu Ser Gln Asp Thr Arg Tyr Ala Asn Arg Thr Ser Leu Phe
                85                  90                  95

Tyr Asn Glu Ile Gln Asn Gly Asn Ala Ser Leu Phe Phe Arg Arg Leu
            100                 105                 110

Ser Leu Leu Asp Glu Gly Ile Tyr Thr Cys Tyr Val Gly Thr Ala Ile
            115                 120                 125
```

Gln Ala Ile Thr Asn Lys Val Leu Lys Val Gly Val Phe Leu Thr
    130                 135                 140

Pro Met Met Lys Tyr Glu Lys Arg Asn Thr Asn Ser Phe Leu Ile Cys
145                 150                 155                 160

Asn Val Leu Ser Val Tyr Pro Arg Pro Ile Ile Thr Trp Lys Met Asp
                165                 170                 175

Asn Thr Pro Ile Ser Glu Asn Asn Met Gln Glu Thr Gly Ser Leu Gly
                180                 185                 190

Pro Phe Ser Ile Asn Ser Thr Leu Asn Ile Thr Gly Ser Asn Ser Ser
                195                 200                 205

Tyr Glu Cys Thr Ile Glu Asn Ser Leu Leu Lys Gln Thr Trp Thr Gly
    210                 215                 220

Arg Trp Thr Met Lys Asp Gly Leu His Lys Met Gln Ser Glu His Val
225                 230                 235                 240

Ser Leu Ser Cys Glu Leu Val Asn Asp Tyr Phe Ser Pro Asn Gln Asp
                245                 250                 255

Phe Lys Val Thr Trp Ser Arg Met Glu Ser Gly Ile Ser Ser Ile Leu
                260                 265                 270

Ala Tyr Tyr Leu Ser Ser Ser Gln Asn Thr Thr Phe Tyr Glu Ser Arg
    275                 280                 285

Phe Ser Trp Asn Lys Glu Leu Lys Asn Gln Ser Asp Phe Ser Met Asn
290                 295                 300

Leu Thr Asp Leu Ser Leu Ser Asp Ser Gly Glu Tyr Leu Cys Asn Ile
305                 310                 315                 320

Ser Ser Asp Glu Tyr Thr Leu Leu Thr Ile His Thr Val His Val Glu
                325                 330                 335

Pro Ser Gln Glu Thr Ala Ser Asp Asn Lys Gly Leu Trp Ile Leu Val
                340                 345                 350

Ala Ser Leu Ile Leu Val Leu Cys Leu Ile Trp Leu Ile Trp Lys Val
    355                 360                 365

Lys Cys Ser Thr Ala Gln Ile Glu Ala Arg Arg Ser Arg Tyr Pro Ala
370                 375                 380

Asp Gly Ala Gln
385

<210> SEQ ID NO 19
<211> LENGTH: 234
<212> TYPE: PRT
<213> ORGANISM: Bovine
<220> FEATURE:
<223> OTHER INFORMATION: bovine B7-H7 (incomplete)

<400> SEQUENCE: 19

Met Asn Glu Gln Ile Val Thr Gly Arg Leu Gly Glu Asp Val Ile Leu
 1               5                   10                  15

Pro Cys Ser Phe Glu Ser Gly Pro Asn Val Val Ile His Trp Lys Asn
                20                  25                  30

Gln Asp Thr Asn Val Tyr Ser Tyr Tyr Arg Asp Ser Asp Gln Leu Glu
                35                  40                  45

Lys Gln Asp Pro Arg Tyr Val Asn Arg Ile Ser Leu Phe His Gly Glu
    50                  55                  60

Ile His Asn Gly Asn Ala Ser Leu Ser Phe Arg Arg Leu Thr Leu Gln
65                  70                  75                  80

Asp Glu Gly Ile Tyr Val Cys Tyr Val Gly Thr Ser Leu Gly Lys Ile
                85                  90                  95

```
Thr Lys Lys Ile Val Leu Lys Val Gly Ala Phe Val Thr Pro Val Met
            100                 105                 110
Lys Tyr Glu Lys Asn Thr Thr Asn Ser Phe Leu Ile Cys Asn Val Leu
            115                 120                 125
Ser Val Phe Pro Tyr Pro Ile Ile Thr Trp Lys Val Asp Asn Asn Thr
130                 135                 140
Ser Ile Ser Glu Asn Asn Gly Lys Glu Val Gly Ser Leu Gly Pro Phe
145                 150                 155                 160
His Ile Asn Ser Arg Val Asn Ile Thr Gly Ser Asn Ser Ser Tyr Gln
                165                 170                 175
Cys Glu Ile Glu Asn Pro Leu Leu Lys Gln Thr Trp Thr Gly Arg Trp
            180                 185                 190
Thr Arg Lys Asp Lys Glu Arg Asn Thr Lys Arg Lys Glu Met His Leu
            195                 200                 205
Gln Ser Ser Leu Glu Val Lys Gln Ile Phe Ser Val Asn Leu His Thr
            210                 215                 220
Val Asp Leu Gln Tyr Tyr Phe Ser Ile Lys
225                 230

<210> SEQ ID NO 20
<211> LENGTH: 282
<212> TYPE: PRT
<213> ORGANISM: Homo sapiens
<220> FEATURE:
<223> OTHER INFORMATION: Human H7CR

<400> SEQUENCE: 20

Met Gly Ser Pro Gly Met Val Leu Gly Leu Leu Val Gln Ile Trp Ala
  1               5                  10                  15
Leu Gln Glu Ala Ser Ser Leu Ser Val Gln Gln Gly Pro Asn Leu Leu
                20                  25                  30
Gln Val Arg Gln Gly Ser Gln Ala Thr Leu Val Cys Gln Val Asp Gln
            35                  40                  45
Ala Thr Ala Trp Glu Arg Leu Arg Val Lys Trp Thr Lys Asp Gly Ala
 50                  55                  60
Ile Leu Cys Gln Pro Tyr Ile Thr Asn Gly Ser Leu Ser Leu Gly Val
 65                  70                  75                  80
Cys Gly Pro Gln Gly Arg Leu Ser Trp Gln Ala Pro Ser His Leu Thr
                85                  90                  95
Leu Gln Leu Asp Pro Val Ser Leu Asn His Ser Gly Ala Tyr Val Cys
            100                 105                 110
Trp Ala Ala Val Glu Ile Pro Glu Leu Glu Glu Ala Glu Gly Asn Ile
            115                 120                 125
Thr Arg Leu Phe Val Asp Pro Asp Pro Thr Gln Asn Arg Asn Asn Arg
130                 135                 140
Ile Ala Ser Phe Pro Gly Phe Leu Phe Val Leu Leu Gly Val Gly Ser
145                 150                 155                 160
Met Gly Val Ala Ala Ile Val Trp Gly Ala Trp Phe Trp Gly Arg Arg
                165                 170                 175
Ser Cys Gln Gln Arg Asp Ser Gly Asn Ser Pro Gly Asn Ala Phe Tyr
            180                 185                 190
Ser Asn Val Leu Tyr Arg Pro Arg Gly Pro Pro Lys Lys Ser Glu Asp
            195                 200                 205
Cys Ser Gly Glu Gly Lys Asp Gln Arg Gly Gln Ser Ile Tyr Ser Thr
            210                 215                 220
```

```
Ser Phe Pro Gln Pro Ala Pro Arg Gln Pro His Leu Ala Ser Arg Pro
225                 230                 235                 240

Cys Pro Ser Pro Arg Pro Cys Pro Ser Pro Arg Pro Gly His Pro Val
            245                 250                 255

Ser Met Val Arg Val Ser Pro Arg Pro Ser Pro Thr Gln Gln Pro Arg
            260                 265                 270

Pro Lys Gly Phe Pro Lys Val Gly Glu Glu
        275                 280

<210> SEQ ID NO 21
<211> LENGTH: 282
<212> TYPE: PRT
<213> ORGANISM: Pan troglodytes (Common Chimpanzee)
<220> FEATURE:
<223> OTHER INFORMATION: Pan troglodytes H7CR

<400> SEQUENCE: 21

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Pro Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Asn Leu Asn His Ser Gly Ala Tyr Val Cys
            100                 105                 110

Trp Ala Ala Val Glu Ile Pro Glu Leu Glu Glu Ala Glu Ser Asn Ile
        115                 120                 125

Thr Arg Leu Phe Val Asp Pro Asp Pro Thr Gln Asn Arg Asn Arg
130                 135                 140

Ile Thr Ser Phe Pro Gly Phe Leu Phe Val Leu Leu Gly Val Gly Ser
145                 150                 155                 160

Gly Ala Val Ala Ala Ile Val Leu Gly Ala Trp Phe Trp Gly Arg Arg
                165                 170                 175

Ser Cys Gln Gln Arg Asp Ser Gly Asn Ser Pro Gly Asn Ala Phe Tyr
            180                 185                 190

Ser Asn Val Leu Tyr Arg Pro Arg Gly Ala Pro Lys Lys Ser Glu Asp
        195                 200                 205

Cys Ser Gly Glu Gly Lys Asp Gln Arg Gly Gln Ser Ile Tyr Ser Thr
    210                 215                 220

Ser Phe Pro Gln Pro Ala Thr Arg Gln Pro His Leu Ala Pro Arg Pro
225                 230                 235                 240

Cys Pro Ser Pro Arg Pro Cys Pro Ser Pro Arg Pro Gly His Pro Val
                245                 250                 255

Ser Met Val Arg Val Ser Pro Arg Pro Ser Pro Thr Gln Gln Pro Arg
            260                 265                 270

Pro Lys Gly Phe Pro Lys Val Gly Glu Glu
        275                 280

<210> SEQ ID NO 22
```

<211> LENGTH: 292
<212> TYPE: PRT
<213> ORGANISM: Bos taurus (bovine)
<220> FEATURE:
<223> OTHER INFORMATION: bovine H7CR

<400> SEQUENCE: 22

```
Met Gly Ser Pro Gly Thr Val Leu Val Leu Leu Val Gln Phe Trp Val
 1               5                  10                  15

Leu Gln Gly Val Thr Gly Leu Thr Val Gln Gln Ala Pro Lys Leu Leu
            20                  25                  30

Gln Val Arg Gln Asp Ser Gln Val Thr Leu Ala Cys Gln Val Met His
        35                  40                  45

Ala Gln Ala Trp Glu Trp Leu Arg Val Glu Trp Ile Lys Asp Ala Asp
    50                  55                  60

Ile Phe Cys Gln Thr His Ile Ile Asn Gly Ser Leu Ser Lys Asp Val
65                  70                  75                  80

Cys Gly Pro Gln Gly Trp Leu Ser Trp Gln Pro Pro Gly Asn Leu Thr
                85                  90                  95

Leu Gln Leu Asn His Val Ser Leu Asn Asp Ser Gly Leu Tyr Val Cys
            100                 105                 110

Gly Ala Thr Val Glu Ile Pro Val Trp Glu Glu Ala Gln Gly Asn Gly
        115                 120                 125

Thr Gln Leu Leu Val Glu Arg Gly Val Trp Leu Gln Asp His Ser Phe
    130                 135                 140

Ser Gly Leu Tyr Phe Ala Pro Leu Val Thr Gly Ala Val Ala Val Ala
145                 150                 155                 160

Val Phe Ala Leu Gly Ala Gly Ile Trp Gly Arg Arg Cys Arg Asn
                165                 170                 175

Gly Asp Ala Gly Ser Pro Ile Tyr Ser Asn Val Leu Tyr Arg Pro Arg
            180                 185                 190

Arg Ala Ala Arg Lys Lys Ala Trp Pro Val Glu Arg Lys Val Leu Asp
        195                 200                 205

Ser Glu Asp Gln Lys Gly Gln Ser Phe Tyr Ser Ile Ser Phe Pro Gln
    210                 215                 220

Arg Pro Lys Ser His Met Ala Pro Lys Phe Cys Pro Ser Pro Arg Pro
225                 230                 235                 240

Ile His Pro Ile Ser Ala Val Arg Ile Ser Pro Gly Pro Gly Ser Ser
                245                 250                 255

Gly Gln Pro Arg Ser Arg Gly Phe Leu Glu Val Gly Arg Glu Ile Arg
            260                 265                 270

Thr Ala Gly Glu Pro Glu Lys Thr Tyr Pro Gln Arg Leu Tyr Lys Asp
        275                 280                 285

Val Thr Tyr Ser
    290
```

<210> SEQ ID NO 23
<211> LENGTH: 849
<212> TYPE: DNA
<213> ORGANISM: Homo sapiens
<220> FEATURE:
<223> OTHER INFORMATION: human H7CR

<400> SEQUENCE: 23

```
atggggtccc cgggcatggt gctgggcctc ctggtgcaga tctgggccct gcaagaagcc      60
tcaagcctga gcgtgcagca ggggcccaac ttgctgcagg tgaggcaggg cagtcaggcg     120
```

| | |
|---|---|
| acctggtct gccaggtgga ccaggccaca gcctgggaac ggctccgtgt taagtggaca | 180 |
| aaggatgggg ccatcctgtg tcaaccgtac atcaccaacg gcagcctcag cctgggggtc | 240 |
| tgcgggcccc agggacggct ctcctggcag gcacccagcc atctcaccct gcagctggac | 300 |
| cctgtgagcc tcaaccacag cggggcgtac gtgtgctggg cggccgtaga gattcctgag | 360 |
| ttggaggagg ctgagggcaa cataacaagg ctctttgtgg acccagatga ccccacacag | 420 |
| aacagaaacc ggatcgcaag cttcccagga ttcctcttcg tgctgctggg ggtgggaagc | 480 |
| atgggtgtgg ctgcgatcgt gtgggggtgcc tggttctggg gccgccgcag ctgccagcaa | 540 |
| agggactcag gtaacagccc aggaaatgca ttctacagca acgtcctata ccggccccgg | 600 |
| gggcccccaa agaagagtga ggactgctct ggagagggga aggaccagag gggccagagc | 660 |
| atttattcaa cctccttccc gcaaccggcc cccgccagc cgcacctggc gtcaagaccc | 720 |
| tgccccagcc cgagaccctg ccccagcccc aggcccggcc accccgtctc tatggtcagg | 780 |
| gtctctccta gaccaagccc cacccagcag ccgaggccaa aagggttccc caaagtggga | 840 |
| gaggagtga | 849 |

<210> SEQ ID NO 24
<211> LENGTH: 849
<212> TYPE: DNA
<213> ORGANISM: Pan troglodytes (Common Chimpanzee)
<220> FEATURE:
<223> OTHER INFORMATION: chimpanzee H7CR cDNA

<400> SEQUENCE: 24

| | |
|---|---|
| atggggtccc cggcatggt gctgggcctc ctggtgcaga tctgggccct gcaagaagcc | 60 |
| tcaagcctga gcgtgcagca ggggcccaac ttgctgcagg tgaggcaggg cagtcaggcg | 120 |
| accctggtct gccaggtgga ccaggcccca gcctgggaac ggctccgtgt taagtggaca | 180 |
| aaggatgggg ccatcctgtg tcaaccgtac atcaccaacg gcagcctcag cctgggggtc | 240 |
| tgcgggcccc agggacggct ctcctggcag gcacccagcc atctcaccct gcagctggac | 300 |
| cctgtgaacc tcaaccacag cggggcgtac gtgtgctggg cggccgtaga gattcctgag | 360 |
| ttggaggagg ctgagagcaa cataacaagg ctctttgtgg acccagatga ccccacacag | 420 |
| aacagaaacc ggatcacaag cttcccagga ttcctcttcg tgctgctggg ggtgggaagc | 480 |
| ggggctgtgg ccgcgatcgt gttgggtgcc tggttctggg gccgccgcag ctgccagcaa | 540 |
| agggactcag gtaacagccc aggaaatgca ttctacagca acgtcctata ccggccccgg | 600 |
| gggcccccaa agaagagtga ggactgctct ggagagggga aggaccagag gggccagagc | 660 |
| atttattcaa cctccttccc gcaaccggcc accgccagc cgcacctggc gccaagaccc | 720 |
| tgccccagcc cgagaccctg ccccagcccc aggcccggcc accccgtctc tatggtcagg | 780 |
| gtctctccta gaccaagccc cacccagcag ccgaggccaa aagggttccc caaagtggga | 840 |
| gaggagtaa | 849 |

<210> SEQ ID NO 25
<211> LENGTH: 879
<212> TYPE: DNA
<213> ORGANISM: Bos taurus (bovine)
<220> FEATURE:
<223> OTHER INFORMATION: bovine H7CR cDNA

<400> SEQUENCE: 25

| | |
|---|---|
| atggggtccc cggcacagt gctggtcctc ctggtgcagt tctgggtcct acaaggagtc | 60 |
| acaggcctga ctgtgcagca ggcaccgaag ttgctgcagg tgagacagga cagccaggtg | 120 |

```
actttggcct gccaggtgat gcacgcccag gcctgggagt ggctccgtgt cgagtggatc      180
aaggatgctg acatcttttg ccagacacac atcatcaatg gcagtctgag caaggatgtc      240
tgtgggcctc agggatggct atcctggcag ccgcctggca acctcaccct gcagctgaac      300
cacgtgagcc tcaatgacag tggactctat gtgtgtgggg caaccgtgga gatccctgtt      360
tgggaggagg cccagggcaa cgggacgcag ctcctggtgg agagaggtgt ctggctgcag      420
gaccacagct tctcaggcct ctacttcgcg ccgctggtga cgggggccgt ggccgttgcc      480
gttttcgctc tgggcgctgg gatctggggc cgccgccgct gccggaacgg ggatgcaggc      540
agtccaatct acagcaacgt cctataccgg ccccggagag ccgcaaggaa gaaggcatgg      600
cctgtggaaa ggaaggtgct ggacagtgag gatcagaagg gccaaagctt ctactcgatc      660
tctttccccc agcgcccaa gtcgcatatg gctcccaaat tttgcccag tcccagaccc       720 attcacccca tctctgcagt cagaatctct cctggcccag gctcctctgg gcagccaagg      780
tcaagagggt tccttgaagt gggaagagaa atcagaaccg caggagagcc agagaagacc      840 taccccagc gactatataa agatgtgact tattcctag                              879
```

<210> SEQ ID NO 26
<211> LENGTH: 32
<212> TYPE: PRT
<213> ORGANISM: Artificial Sequence
<220> FEATURE:
<223> OTHER INFORMATION: Acid residues 168 to 199 of a second isoform of native human ICOS

<400> SEQUENCE: 26

Lys Tyr Ser Ser Ser Val His Asp Pro Asn Gly Glu Tyr Met Phe Met
1               5                   10                  15

Arg Ala Val Asn Thr Ala Lys Lys Ser Arg Leu Thr Asp Val Thr Leu
            20                  25                  30